US010584103B2

(12) United States Patent
Pinkerton et al.

(10) Patent No.: US 10,584,103 B2
(45) Date of Patent: Mar. 10, 2020

(54) SMALL MOLECULE AGONISTS OF NEUROTENSIN RECEPTOR 1

(71) Applicant: Sanford Burnham Prebys Medical Discovery Institute, La Jolla, CA (US)

(72) Inventors: Anthony B. Pinkerton, La Jolla, CA (US); Paul M. Hershberger, La Jolla, CA (US); Satyamaheshwar Peddibhotla, La Jolla, CA (US); Patrick R. Maloney, La Jolla, CA (US); Michael P. Hedrick, La Jolla, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 0 days.

(21) Appl. No.: 16/140,363

(22) Filed: Sep. 24, 2018

(65) Prior Publication Data

US 2019/0023665 A1    Jan. 24, 2019

Related U.S. Application Data

(63) Continuation of application No. 15/319,329, filed as application No. PCT/US2015/037515 on Jun. 24, 2015, now Pat. No. 10,118,902.

(60) Provisional application No. 62/017,046, filed on Jun. 25, 2014.

(51) Int. Cl.
| | |
|---|---|
| C07D 239/94 | (2006.01) |
| C07D 401/14 | (2006.01) |
| C07D 401/04 | (2006.01) |
| C07D 403/12 | (2006.01) |
| C07D 401/12 | (2006.01) |
| C07D 403/04 | (2006.01) |
| C07D 409/14 | (2006.01) |
| C07D 487/10 | (2006.01) |

(52) U.S. Cl.
CPC ......... *C07D 239/94* (2013.01); *C07D 401/04* (2013.01); *C07D 401/12* (2013.01); *C07D 401/14* (2013.01); *C07D 403/04* (2013.01); *C07D 403/12* (2013.01); *C07D 409/14* (2013.01); *C07D 487/10* (2013.01)

(58) Field of Classification Search
CPC .................................................. C07D 239/94
See application file for complete search history.

(56) References Cited

U.S. PATENT DOCUMENTS

| | | | |
|---|---|---|---|
| 5,866,562 | A | 2/1999 | Schohe-Loop' et al. |
| 9,868,707 | B2 | 1/2018 | Pinkerton et al. |
| 10,118,902 | B2 | 11/2018 | Pinkerton et al. |
| 2005/0096327 | A1 | 5/2005 | Caprathe et al. |
| 2006/0217377 | A1 | 9/2006 | Gonzalez, III |
| 2009/0163545 | A1 | 6/2009 | Goldfarb |
| 2009/0259044 | A1 | 10/2009 | Kazantsev |

FOREIGN PATENT DOCUMENTS

| | | |
|---|---|---|
| CN | 102786483 A | 11/2012 |
| EP | 0638567 A1 | 2/1995 |
| JP | S58172379 A | 10/1983 |
| WO | WO-0224667 A1 | 3/2002 |
| WO | WO-2006007864 A1 | 1/2006 |
| WO | WO-2007071055 A1 | 6/2007 |
| WO | WO-2011153553 A2 | 12/2011 |
| WO | WO-2014052699 A1 | 4/2014 |
| WO | WO-2014100501 A1 | 6/2014 |
| WO | WO-2015200534 A2 | 12/2015 |

OTHER PUBLICATIONS

Allen et al. Discovery of β-arrestin-biased dopamine D2 ligands for probing signal transduction pathways essential for antipsychotic efficacy. PNAS USA 108:18488-18493 (2011).
Bridges et al. Tyrosine kinase inhibitors. 8. An unusually steep structure-activity relationship for analogues of 4-(3-bromoanilino)-6,7-dimethoxyquinazoline (PD 153035), a potent inhibitor of the epidermal growth factor receptor. J Med Chem 39(1):267-276 (1996).
Chemical Abstracts—Retrieved from STN Database Accession No. 1002177-75-4 (2008).
Chemical Abstracts—Retrieved from STN Database Accession No. 1003477-61-9 (2008).
Chemical Abstracts—Retrieved from STN Database Accession No. 1328207-13-1 (2011).
Chemical Abstracts—Retrieved from STN Database Accession No. 1338120-56-1 (2011).
Chemical Abstracts—Retrieved from STN Database Accession No. 1338170-26-5 (2011).
Chemical Abstracts—Retrieved from STN Database Accession No. 1369053-41-7 (2012).
Chemical Abstracts—Retrieved from STN Database Accession No. 496873-49-5 (2003).
Chemical Abstracts—Retrieved from STN Database Accession No. 496873-50-8 (2003).
Chemical Abstracts—Retrieved from STN Database Accession No. 496873-57-5 *496873-57-5; 496873-55-3; 496873-18-8; 496872-42-5; 496872-41-4; 496872-40-3; 496872-36-7; 496872-35-6; 496872-24-3; 496872-17-4; 496872-04-9; 496867-91-5* (12 pgs) (2003).
Chemical Abstracts—Retrieved from STN Database Accession No. 667897-12-3; *667897-12-3; 667897-00-9; 667896-98-2;667896-24-4;667896-21-1;667896-14-2; 667896-13-1; 667896-12-0* (8 pgs) (2004).
Chemical Abstracts—Retrieved from STN Database Accession No. 677748-35-5 (2004).
Chemical Abstracts—Retrieved from STN Database Accession No. 929432-71-3 (2007).
Chemical Abstracts—Retrieved from STN Database Accession No. 929455-75-4 (2007).

(Continued)

*Primary Examiner* — Paul V Ward
(74) *Attorney, Agent, or Firm* — Wilson Sonsini Goodrich & Rosati

(57) ABSTRACT

Provided herein are small molecule neurotensin receptor agonists, compositions comprising the compounds, and methods of using the compounds and compositions comprising the compounds.

20 Claims, No Drawings

(56) References Cited

OTHER PUBLICATIONS

Di Fruscia et al. The discovery of indole full agonists of the neurotensin receptor 1 (NTSR1). Bioorg Med Chem Lett. 24(16):3974-3978 (2014).
Dilly et al. Identification of a pharmacophore of SKCa channel blockers. J Enzyme Inhib Med Chem 20(6):517-523 (2005).
Fan et al. The identification of neurotensin NTS1 receptor partial agonists through a ligand-based virtual screening approach. Bioorg Med Chem Lett. 18(21):5789-5791 (2008).
Griebel et al. Neuropeptide receptor ligands as drugs for psychiatric diseases: the end of the beginning? Nat Rev Drug Discov 11(6):462-478 (2012).
Gully et al. Biochemical and pharmacological activities of SR 142948A, a new potent neurotensin receptor antagonist. J Pharmacol Exp Ther 280(2):802-812 (1997).
Gully et al. Biochemical and pharmacological profile of a potent and selective nonpeptide antagonist of the neurotensin receptor. PNAS USA 90(1):65-69 (1993).
Herschberger et al. Small Molecule Agonists for the Neurotensin 1 Receptor (NTR1 Agonists). Probe Reports from the NIH Molecular Libraries Program—NCBI Bookshelf. Available at http://www.ncbi.nlm.nih.gov/books/NBK184496 (12 pgs) (Retrieved May 13, 2016).
Marugan et al. Evaluation of quinazoline analogues as glucocerebrosidase inhibitors with chaperone activity. J Med Chem 54(4)1033-1058 (2011).
PCT/US2013/076735 International Search Report and Written Opinion dated Apr. 30, 2014.
PCT/US2015/037515 International Preliminary Report on Patentability dated Jan. 5, 2017.
PCT/US2015/037515 International Search Report and Written Opinion dated Feb. 29, 2016.
Peddibhotla et al. Discovery of ML314, a Brain Penetrant Non-Peptidic β-Arrestin Biased Agonist of the Neurotensin NTR1 Receptor. ACS Med Chem Lett 4(9):846-851 (2013).
Rajagopal et al. Teaching old receptors new tricks: biasing seven-transmembrane receptors. Nat Rev Drug Discovery 9:373-386 (2010).
Schaeffer et al. SR142948A is a potent antagonist of the cardiovascular effects of neurotensin. J Cardiovasc Pharmacol 31(4):545-550 (1998).
Sirisoma et al. Discovery of N-(4-methoxyphenyl)-N,2-dimethylquinazolin-4-amine, a potent apoptosis inducer and efficacious anticancer agent with high blood brain barrier penetration. J. Med. Chem. 42(8):2341-2351 (2009).
Thomas et al. The identification of nonpeptide neurotensin receptor partial agonists from the potent antagonist SR48692 using a calcium mobilization assay. Bioorg Med Chem Lett 19(5):1438-1441 (2009).
U.S. Appl. No. 14/652,705 Office Action dated Mar. 14, 2017.
U.S. Appl. No. 14/652,705 Office Action dated Sep. 29, 2016.
U.S. Appl. No. 15/319,329 Office Action dated Dec. 22, 2017.
Vippagunta et al. Crystalline Solids. Advanced Drug Delivery Reviews 48(2001):3-26 (2001).
Whalen et al. Therapeutic potential of β-arrestin- and G protein-biased agonists. Trends Mol Med 17(3):126-139 (2011).
White et al. Structure of the agonist-bound neurotensin receptor. Nature 490(7421):508-513 (2012).

SMALL MOLECULE AGONISTS OF NEUROTENSIN RECEPTOR 1

RELATED APPLICATIONS

This application is a continuation of U.S. patent application Ser. No. 15/319,329, filed Dec. 15, 2016, which is a U.S. National Stage entry of International Application No. PCT/US2015/037515, filed Jun. 24, 2015, which claims the benefit of U.S. Provisional Patent Application No. 62/017,046 entitled "SMALL MOLECULE AGONISTS OF NEUROTENSIN RECEPTOR 1" filed on Jun. 25, 2014, all of which are hereby incorporated by reference in their entirety.

SUMMARY OF THE INVENTION

Described herein are compounds that modulate the activity of the neurotensin 1 receptor (NTR1). The neurotensin 1 receptor is a therapeutic target for the treatment of a variety of diseases or conditions. In some embodiments, the neurotensin 1 receptor is a therapeutic target for the treatment of diseases or conditions such as, but not limited to, neurological diseases or conditions, and cancer. In some embodiments, the compounds described herein are agonists of the neurotensin 1 receptor.

In one aspect, provided herein is a compound of Formula (I), or a pharmaceutically acceptable salt, solvate, tautomer, or N-oxide thereof:

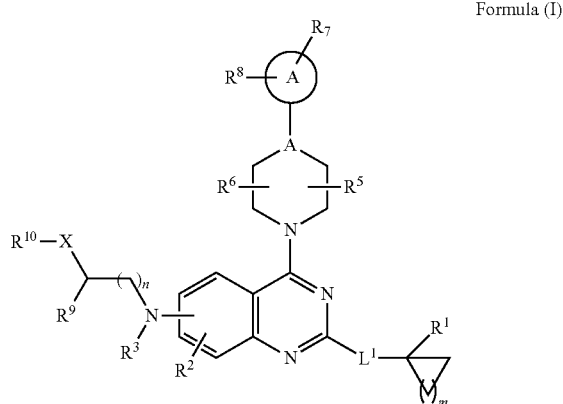

Formula (I)

wherein, ring A is $C_3$-$C_6$cycloalkyl, $C_2$-$C_6$heterocycloalkyl, phenyl or monocyclic heteroaryl;

A is N or CH;

$R^1$ is halogen, $C_1$-$C_4$alkyl, $C_1$-$C_4$alkoxy, $C_1$-$C_4$haloalkyl, $C_1$-$C_4$haloalkoxy, or —N($R^a$)$_2$; and $R^3$ is hydrogen, $C_1$-$C_4$alkyl or $C_1$-$C_4$haloalkyl;

or $R^1$ is hydrogen, halogen, $C_1$-$C_4$alkyl, $C_1$-$C_4$alkoxy, $C_1$-$C_4$haloalkyl, $C_1$-$C_4$haloalkoxy, or —N($R^a$)$_2$;

and $R^3$ and $R^9$ are taken together with the intervening atoms to form an optionally substituted $C_2$-$C_6$heterocycloalkyl;

each $R^a$ is independently selected from the group consisting of hydrogen and $C_1$-$C_4$ alkyl, —C(=O)$R^{11}$, —C(=O)—O—$R^{11}$, —S(=O)$_2R^{11}$, —C(=O)$R^{11}$, or 2 $R^a$ taken together with the nitrogen to which they are attached form an optionally substituted $C_2$-$C_6$heterocycloalkyl;

$L^1$ is absent, $C_1$-$C_4$alkylene, $C_1$-$C_4$alkenylene, $C_1$-$C_4$alkynylene, —O— or —N($R^b$)—;

$R^2$ is hydrogen, $C_1$-$C_4$alkyl or $C_1$-$C_4$haloalkyl, —C(=O)$R^{11}$, —C(=O)—O—$R^{11}$, —S(=O)$_2R^{11}$, or —C(=O)$R^{11}$;

$R^2$ is hydrogen, halogen, —CN, —OH, —NO$_2$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, and optionally substituted 5- or 6-membered heteroaryl;

$R^5$ and $R^6$ are each independently selected from hydrogen, halogen, —OH, and $C_1$-$C_4$alkyl, or when on the same carbon, $R^5$ and $R^6$ are taken together form an oxo;

$R^7$ is hydrogen, halogen, —CN, —OH, —NO$_2$, —N($R^{12}$)—$R^{13}$, —C(=O)—N($R^{12}$)—$R^{13}$, —NR$^{12}$C(=O)$R^{11}$, —C(=O)—O—$R^{11}$, —O—C(=O)—$R^{11}$, —SR$^{12}$, —S(=O)$R^{11}$, —S(=O)$_2R^{11}$, —N($R^{12}$)S(=O)$_2R^{11}$, —S(=O)$_2$—N($R^{12}$)—$R^{13}$, —C(=O)$R^{11}$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, optionally substituted 5- or 6-membered heteroaryl;

$R^8$ is hydrogen, —OH, $C_1$-$C_4$alkyl, $C_1$-$C_4$fluoroalkyl, $C_1$-$C_4$alkoxy, $C_1$-$C_4$fluoroalkoxy, or —N($R^a$)$_2$;

$R^9$ is hydrogen, $C_1$-$C_4$alkyl, or $C_1$-$C_4$fluoroalkyl;

X is —O— or —N($R^b$)—;

$R^{10}$ is hydrogen, $C_1$-$C_4$alkyl, $C_1$-$C_4$fluoroalkyl, —C(=O)$R^{11}$, —C(=O)—O—$R^{11}$, —C(=O)N($R^{12}$)$R^{13}$, —S(=O)$_2R^{11}$, or —C(=O)$R^{11}$;

each $R^{11}$ is independently selected from the group consisting of optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl;

each of $R^{12}$ and $R^{13}$ is independently selected from the group consisting of hydrogen, optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl; or $R^{12}$ and $R^{13}$, when on the same nitrogen atom, are taken together with the nitrogen atom to which they are attached to form an optionally substituted $C_2$-$C_6$heterocycloalkyl;

n is 1, 2 or 3; and m is 1, 2, 3 or 4.

In another aspect, provided herein is a compound of formula (II), or a pharmaceutically acceptable salt, solvate, prodrug, or N-oxide thereof:

Formula (II)

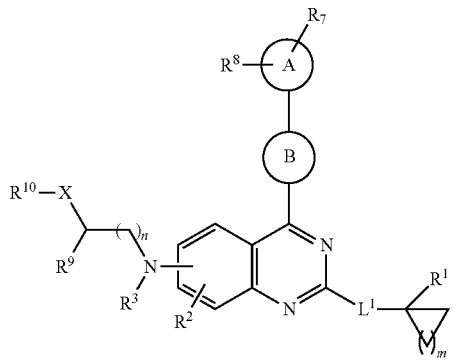

wherein,
ring A is $C_3$-$C_6$cycloalkyl, $C_2$-$C_6$heterocycloalkyl, phenyl or monocyclic heteroaryl;
ring B is an optionally substituted bicyclic heterocycloalkyl or an optionally substituted tricyclic heterocycloalkyl;
$R^1$ is hydrogen, halogen, $C_1$-$C_4$alkyl, $C_1$-$C_4$alkoxy, $C_1$-$C_4$haloalkyl, $C_1$-$C_4$haloalkoxy, or —N($R^a$)$_2$;
  each $R^a$ is independently selected from the group consisting of hydrogen and $C_1$-$C_4$ alkyl, —C(=O)$R^{11}$, —C(=O)—O—$R^{11}$, —S(=O)$_2$$R^{11}$, —C(=O)$R^{11}$, or 2 $R^a$ taken together with the nitrogen to which they are attached form an optionally substituted $C_2$-$C_6$heterocycloalkyl;
$R^2$ is hydrogen, halogen, —CN, —OH, —NO$_2$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, and optionally substituted 5- or 6-membered heteroaryl;
$R^3$ is hydrogen, $C_1$-$C_4$alkyl or $C_1$-$C_4$haloalkyl;
or
$R^3$ and $R^9$ are taken together with the intervening atoms to form an optionally substituted $C_2$-$C_6$heterocycloalkyl;
$L^1$ is absent, $C_1$-$C_4$alkylene, $C_1$-$C_4$alkenylene, $C_1$-$C_4$alkynylene, —O— or —N($R^b$)—;
  $R^b$ is hydrogen, $C_1$-$C_4$alkyl or $C_1$-$C_4$haloalkyl, —C(=O)$R^{11}$, —C(=O)—O—$R^{11}$, —S(=O)$_2$$R^{11}$, or —C(=O)$R^{11}$;
$R^5$ and $R^6$ are each independently selected from hydrogen, halogen, —OH, and $C_1$-$C_4$alkyl, or when on the same carbon, $R^5$ and $R^6$ are taken together form an oxo;
$R^7$ is hydrogen, halogen, —CN, —OH, —NO$_2$, —N($R^{12}$)—$R^{13}$, —C(=O)—N($R^{12}$)—$R^{13}$, —NR$^{12}$C(=O)$R^{11}$, —C(=O)—O—$R^{11}$, —O—C(=O)—$R^{11}$, —SR$^{12}$, —S(=O)$R^{11}$, —S(=O)$_2$$R^{11}$, —N($R^{12}$)S(=O)$_2$$R^{11}$, —S(=O)$_2$—N($R^{12}$)—$R^{13}$, —C(=O)$R^{11}$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, optionally substituted 5- or 6-membered heteroaryl;
$R^8$ is hydrogen, —OH, $C_1$-$C_4$alkyl, $C_1$-$C_4$fluoroalkyl, $C_1$-$C_4$alkoxy, $C_1$-$C_4$fluoroalkoxy, or —N($R^a$)$_2$;

$R^9$ is hydrogen or $C_1$-$C_4$alkyl, or $C_1$-$C_4$fluoroalkyl;
X is —O— or —N($R^b$)—;
$R^{10}$ is hydrogen, $C_1$-$C_4$alkyl, $C_1$-$C_4$fluoroalkyl, —C(=O)$R^{11}$, —C(=O)—O—$R^{11}$, —C(=O)N($R^{12}$)$R^{13}$, —S(=O)$_2$$R^{11}$, or —C(=O)$R^{11}$; or $R^{10}$ and $R^b$ are taken together with the N atom to which they are attached to form a $C_2$-$C_6$heterocycle;
each $R^{11}$ is independently selected from the group consisting of optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl;
each of $R^{12}$ and $R^{13}$ is independently selected from the group consisting of hydrogen, optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl; or $R^{12}$ and $R^{13}$, when on the same nitrogen atom, are taken together with the nitrogen atom to which they are attached to form an optionally substituted $C_2$-$C_6$heterocycloalkyl;
n is 1, 2 or 3; and
m is 1, 2, 3 or 4.
In another aspect, provided herein is a compound of Formula (III), or a pharmaceutically acceptable salt, solvate, prodrug, or N-oxide thereof:

Formula (III)

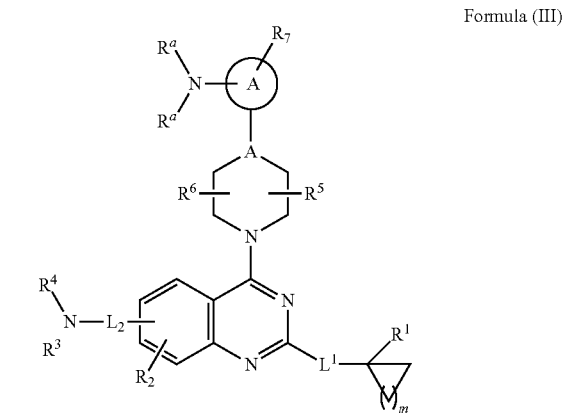

wherein
ring A is $C_3$-$C_6$cycloalkyl, $C_2$-$C_6$heterocycloalkyl, phenyl or monocyclic heteroaryl;
A is N or CH;
$L^1$ is absent, $C_1$-$C_4$alkylene, $C_1$-$C_4$alkenylene, $C_1$-$C_4$alkynylene, —O— or —N($R^b$)—;
  $R^b$ is hydrogen, $C_1$-$C_4$alkyl or $C_1$-$C_4$haloalkyl, —C(=O)$R^{11}$, —C(=O)—O—$R^{11}$, —S(=O)$_2$$R^{11}$, or —C(=O)$R^{11}$;
$L^2$ is absent or an optionally substituted $C_1$-$C_4$alkylene;
$R^1$ is hydrogen, halogen, $C_1$-$C_4$alkyl, $C_1$-$C_4$alkoxy, $C_1$-$C_4$haloalkyl, $C_1$-$C_4$haloalkoxy, or —N($R^a$)$_2$;
  each $R^a$ is independently selected from the group consisting of hydrogen and $C_1$-$C_4$alkyl, —C(=O)$R^{11}$, —C(=O)—O—$R^{11}$, —S(=O)$_2$$R^{11}$, —C(=O)$R^{11}$, or 2 $R^a$ taken together with the nitrogen to which they are attached form an optionally substituted $C_2$-$C_6$heterocycloalkyl;

$R^2$ is hydrogen, halogen, —CN, —OH, —NO$_2$, optionally substituted C$_1$-C$_4$alkyl, optionally substituted C$_1$-C$_4$alkoxy, optionally substituted C$_1$-C$_4$haloalkyl, optionally substituted C$_1$-C$_4$haloalkoxy, optionally substituted C$_3$-C$_6$cycloalkyl, optionally substituted C$_2$-C$_6$heterocycloalkyl, optionally substituted phenyl, and optionally substituted 5- or 6-membered heteroaryl;

$R^3$ is hydrogen, C$_1$-C$_4$alkyl or C$_1$-C$_4$haloalkyl;

$R^4$ is hydrogen, optionally substituted C$_1$-C$_4$ alkyl, —C$_1$-C$_4$ alkylene-C(=O)OR$^{11}$, —C$_1$-C$_4$ alkylene-OR$^{10}$, or C$_1$-C$_4$ alkylene-N(R$^b$)(R$^{10}$);

$R^{10}$ is hydrogen, C$_1$-C$_4$alkyl, C$_1$-C$_4$fluoroalkyl, —C(=O)R$^{11}$, —C(=O)—O—R$^{11}$, —C(=O)N(R$^{12}$)R$^{13}$, —S(=O)$_2$R$^{11}$, or —C(=O)R$^{11}$; or $R^{10}$ and $R^b$ are taken together with the N atom to which they are attached to form a C$_2$-C$_6$heterocycle;

or $R^3$ and $R^4$ taken together with the nitrogen to which they are attached form an optionally substituted C$_2$-C$_6$heterocycloalkyl;

$R^5$ and $R^6$ are each independently selected from hydrogen, halogen, —OH, and C$_1$-C$_4$alkyl, or when on the same carbon, $R^5$ and $R^6$ are taken together form an oxo;

$R^7$ is hydrogen, halogen, —CN, —OH, —NO$_2$, —N(R$^{12}$)—R$^{13}$, —C(=O)—N(R$^{12}$)—R$^{13}$, —NR$^{12}$C(=O)R$^{11}$, —C(=O)—O—R$^{11}$, —O—C(=O)—R$^{11}$, —SR$^{12}$, —S(=O)R$^{11}$, —S(=O)$_2$R$^{11}$, —N(R$^{12}$)S(=O)$_2$R$^{11}$, —S(=O)$_2$—N(R$^{12}$)—R$^{13}$, —C(=O)R$^{11}$, optionally substituted C$_1$-C$_4$alkyl, optionally substituted C$_1$-C$_4$alkoxy, optionally substituted C$_1$-C$_4$haloalkyl, optionally substituted C$_1$-C$_4$haloalkoxy, optionally substituted C$_3$-C$_6$cycloalkyl, optionally substituted C$_2$-C$_6$heterocycloalkyl, optionally substituted phenyl, optionally substituted 5- or 6-membered heteroaryl;

each $R^{11}$ is independently selected from the group consisting of optionally substituted C$_1$-C$_4$alkyl, optionally substituted C$_1$-C$_4$fluoroalkyl, optionally substituted C$_3$-C$_6$cycloalkyl, optionally substituted C$_2$-C$_6$heterocycloalkyl, optionally substituted phenyl, and optionally substituted 5- or 6-membered heteroaryl;

each of $R^{12}$ and $R^{13}$ is independently selected from the group consisting of hydrogen, optionally substituted C$_1$-C$_4$alkyl, optionally substituted C$_1$-C$_4$fluoroalkyl, optionally substituted C$_3$-C$_6$cycloalkyl, optionally substituted C$_2$-C$_6$heterocycloalkyl, optionally substituted phenyl, and optionally substituted 5- or 6-membered heteroaryl; or $R^{12}$ and $R^{13}$, when on the same nitrogen atom, are taken together with the nitrogen atom to which they are attached to form an optionally substituted C$_2$-C$_6$heterocycloalkyl; and m is 1, 2, 3 or 4; and provided that the compound is not 4-(4-(2-(azetidin-1-yl)phenyl)piperazin-1-yl)-2-cyclopropyl-N,N-dimethylquinazolin-6-amine, 4-(4-(2-(azetidin-1-yl)phenyl)piperazin-1-yl)-2-cyclopropyl-N-ethyl-N-methylquinazolin-6-amine, or 4-(4-(2-(azetidin-1-yl)phenyl)piperidin-1-yl)-2-cyclopropyl-N,N-dimethylquinazolin-6-amine.

In yet another aspect, provided herein is a compound of Formula (IV), or a pharmaceutically acceptable salt, solvate, prodrug, or N-oxide thereof:

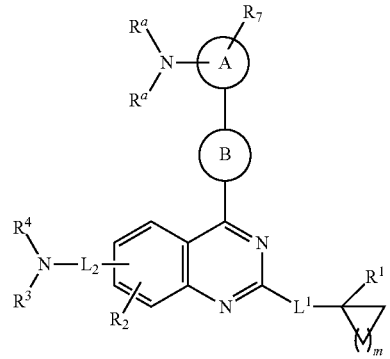

Formula (IV)

wherein, ring A is C$_3$-C$_6$cycloalkyl, C$_2$-C$_6$heterocycloalkyl, phenyl or monocyclic heteroaryl;

ring B is an optionally substituted bicyclic heterocycloalkyl or an optionally substituted tricyclic heterocycloalkyl;

$L^1$ is absent, C$_1$-C$_4$alkylene, C$_1$-C$_4$alkenylene, C$_1$-C$_4$alkynylene, —O— or —N(R$^b$)—;

$R^b$ is hydrogen, C$_1$-C$_4$alkyl or C$_1$-C$_4$haloalkyl, —C(=O)R$^{11}$, —C(=O)—O—R$^{11}$, —S(=O)$_2$R$^{11}$, or —C(=O)R$^{11}$;

$L^2$ is absent or an optionally substituted C$_1$-C$_4$alkylene;

$R^1$ is hydrogen, halogen, C$_1$-C$_4$alkyl, C$_1$-C$_4$alkoxy, C$_1$-C$_4$haloalkyl, C$_1$-C$_4$haloalkoxy, or —N(R$^a$)$_2$;

each $R^a$ is independently selected from the group consisting of hydrogen and C$_1$-C$_4$ alkyl, —C(=O)R$^{11}$, —C(=O)—O—R$^{11}$, —S(=O)$_2$R$^{11}$, —C(=O)R$^{11}$, or 2 $R^a$ taken together with the nitrogen to which they are attached form an optionally substituted C$_2$-C$_6$heterocycloalkyl;

$R^2$ is hydrogen, halogen, —CN, —OH, —NO$_2$, optionally substituted C$_1$-C$_4$alkyl, optionally substituted C$_1$-C$_4$alkoxy, optionally substituted C$_1$-C$_4$haloalkyl, optionally substituted C$_1$-C$_4$haloalkoxy, optionally substituted C$_3$-C$_6$cycloalkyl, optionally substituted C$_2$-C$_6$heterocycloalkyl, optionally substituted phenyl, and optionally substituted 5- or 6-membered heteroaryl;

$R^3$ is hydrogen, C$_1$-C$_4$alkyl or C$_1$-C$_4$haloalkyl;

$R^4$ is hydrogen, optionally substituted C$_1$-C$_4$ alkyl, —C$_1$-C$_4$ alkylene-C(=O)OR$^{11}$, —C$_1$-C$_4$ alkylene-OR$^{10}$, or —C$_1$-C$_4$ alkylene-N(R$^b$)(R$^{10}$);

$R^{10}$ is hydrogen, C$_1$-C$_4$alkyl, C$_1$-C$_4$fluoroalkyl, —C(=O)R$^{11}$, —C(=O)—O—R$^{11}$, —C(=O)N(R$^{12}$)R$^{13}$, —S(=O)$_2$R$^{11}$, or —C(=O)R$^{11}$; or $R^{10}$ and $R^b$ are taken together with the N atom to which they are attached to form a C$_2$-C$_6$heterocycle;

or $R^3$ and $R^4$ taken together with the nitrogen to which they are attached form an optionally substituted C$_2$-C$_6$heterocycloalkyl;

$R^7$ is hydrogen, halogen, —CN, —OH, —NO$_2$, —N(R$^{12}$)—R$^{13}$, —C(=O)—N(R$^{12}$)—R$^{13}$, —NR$^{12}$C(=O)R$^{11}$, —C(=O)—O—R$^{11}$, —O—C(=O)—R$^{11}$, —SR$^{12}$, —S(=O)R$^{11}$, —S(=O)$_2$R$^{11}$, —N(R$^{12}$)S(=O)$_2$R$^{11}$, —S(=O)$_2$—N(R$^{12}$)—R$^{13}$, —C(=O)R$^{11}$, optionally substituted C$_1$-C$_4$alkyl, optionally substituted C$_1$-C$_4$alkoxy, optionally substituted C$_1$-C$_4$haloalkyl, optionally substituted C$_1$-C$_4$haloalkoxy, optionally substituted C$_3$-C$_6$cycloalkyl, optionally substituted C$_2$-C$_6$heterocycloalkyl, optionally substituted phenyl, optionally substituted 5- or 6-membered heteroaryl;

each $R^{11}$ is independently selected from the group consisting of optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl;

each of $R^{12}$ and $R^{13}$ is independently selected from the group consisting of hydrogen, optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl; or $R^{12}$ and $R^{13}$, when on the same nitrogen atom, are taken together with the nitrogen atom to which they are attached to form an optionally substituted $C_2$-$C_6$heterocycloalkyl; and m is 1, 2, 3 or 4.

In another aspect, provided herein is a compound of Formula (V), or a pharmaceutically acceptable salt, solvate, prodrug, or N-oxide thereof:

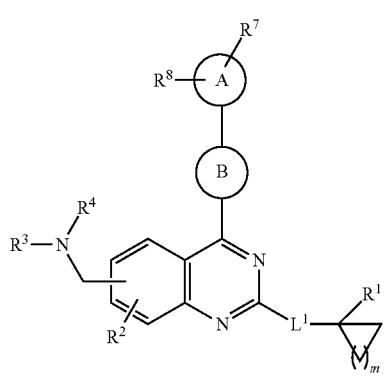

Formula (V)

wherein:
ring A is $C_3$-$C_6$cycloalkyl, $C_2$-$C_6$heterocycloalkyl, phenyl or monocyclic heteroaryl;
ring B is an optionally substituted hetereocycloalkyl, wherein if ring B is substituted then it is substituted with $R^5$ and $R^6$;
$L^1$ is absent, $C_1$-$C_4$alkylene, $C_1$-$C_4$alkenylene, $C_1$-$C_4$alkynylene, —O— or —N($R^b$)—;
$R^b$ is hydrogen, $C_1$-$C_4$alkyl or $C_1$-$C_4$haloalkyl, —C(=O)$R^{11}$, —C(=O)—O—$R^{11}$, —S(=O)$_2R^{11}$, or —C(=O)$R^{11}$;
$R^1$ is hydrogen, halogen, $C_1$-$C_4$alkyl, $C_1$-$C_4$alkoxy, $C_1$-$C_4$haloalkyl, $C_1$-$C_4$haloalkoxy, or —N($R^a$)$_2$;
each $R^a$ is independently selected from the group consisting of hydrogen and $C_1$-$C_4$ alkyl, —C(=O)$R^{11}$, —C(=O)—O—$R^{11}$, —S(=O)$_2R^{11}$, —C(=O)$R^{11}$, or 2 $R^a$ taken together with the nitrogen to which they are attached form an optionally substituted $C_2$-$C_6$heterocycloalkyl;
$R^2$ is hydrogen, halogen, —CN, —OH, —NO$_2$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, and optionally substituted 5- or 6-membered heteroaryl;
$R^3$ is hydrogen, $C_1$-$C_4$alkyl or $C_1$-$C_4$haloalkyl;

$R^4$ is hydrogen, optionally substituted $C_1$-$C_4$ alkyl, —$C_1$-$C_4$ alkylene-C(=O)$R^{11}$, —$C_1$-$C_4$ alkylene-O$R^{10}$, or —$C_1$-$C_4$ alkylene-N($R^b$)($R^{10}$);
$R^{10}$ is hydrogen, $C_1$-$C_4$alkyl, $C_1$-$C_4$fluoroalkyl, —C(=O)$R^{11}$, —C(=O)—O—$R^{11}$, —C(=O)N($R^{12}$)$R^{13}$, —S(=O)$_2R^{11}$, or —C(=O)$R^{11}$; or $R^{10}$ and $R^b$ are taken together with the N atom to which they are attached to form a $C_2$-$C_6$heterocycle;
or $R^3$ and $R^4$ taken together with the nitrogen to which they are attached form an optionally substituted $C_2$-$C_6$heterocycloalkyl;
$R^5$ and $R^6$ are each independently selected from hydrogen, halogen, —OH, and $C_1$-$C_4$alkyl, or when on the same carbon, $R^5$ and $R^6$ are taken together form an oxo;
$R^7$ is hydrogen, halogen, —CN, —OH, —NO$_2$, —N($R^{12}$)—$R^{13}$, —C(=O)—N($R^{12}$)—$R^{13}$, —N$R^{12}$C(=O)$R^{11}$, —C(=O)—O—$R^{11}$, —O—C(=O)—$R^{11}$, —S$R^{12}$, —S(=O)$R^{11}$, —S(=O)$_2R^{11}$, —N($R^{12}$)S(=O)$_2R^{11}$, —S(=O)$_2$—N($R^{12}$)—$R^{13}$, —C(=O)$R^{11}$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, optionally substituted 5- or 6-membered heteroaryl;
$R^8$ is hydrogen, —OH, $C_1$-$C_4$alkyl, $C_1$-$C_4$fluoroalkyl, $C_1$-$C_4$alkoxy, $C_1$-$C_4$fluoroalkoxy, or —N($R^a$)$_2$;
each $R^{11}$ is independently selected from the group consisting of optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl;
each of $R^{12}$ and $R^{13}$ is independently selected from the group consisting of hydrogen, optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl; or $R^{12}$ and $R^{13}$, when on the same nitrogen atom, are taken together with the nitrogen atom to which they are attached to form an optionally substituted $C_2$-$C_6$heterocycloalkyl; and m is 1, 2, 3 or 4.

In yet another aspect, provided herein is a compound of Formula (VI), or a pharmaceutically acceptable salt, solvate, prodrug, or N-oxide thereof:

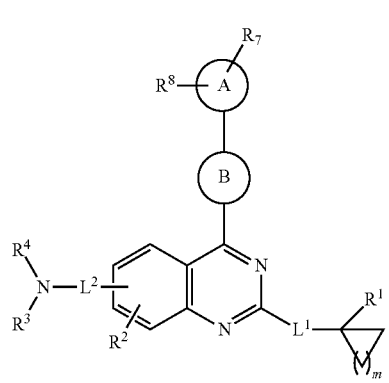

Formula (VI)

wherein:
ring A is $C_3$-$C_6$cycloalkyl, $C_2$-$C_6$heterocycloalkyl, or monocyclic heteroaryl;
ring B is an optionally substituted hetereocycloalkyl, wherein if ring B is substituted then it is substituted with $R^5$ and $R^6$;
$R^1$ is hydrogen, halogen, $C_1$-$C_4$alkyl, $C_1$-$C_4$alkoxy, $C_1$-$C_4$haloalkyl, $C_1$-$C_4$haloalkoxy, or —N($R^a$)$_2$;
  each $R^a$ is independently selected from the group consisting of hydrogen and $C_1$-$C_4$ alkyl, —C(=O)$R^{11}$, —C(=O)—O—$R^{11}$, —S(=O)$_2$$R^{11}$, —C(=O)$R^{11}$, or 2 $R^a$ taken together with the nitrogen to which they are attached form an optionally substituted $C_2$-$C_6$heterocycloalkyl;
$L^1$ is absent, $C_1$-$C_4$alkylene, $C_1$-$C_4$alkenylene, $C_1$-$C_4$alkynylene, —O— or —N($R^b$)—;
$R^b$ is hydrogen, $C_1$-$C_4$alkyl or $C_1$-$C_4$haloalkyl, —C(=O)$R^{11}$, —C(=O)—O—$R^{11}$, —S(=O)$_2$$R^{11}$, or —C(=O)$R^{11}$;
$R^2$ is hydrogen, halogen, —CN, —OH, —NO$_2$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, and optionally substituted 5- or 6-membered heteroaryl;
$L^2$ is absent or an optionally substituted $C_1$-$C_4$alkylene;
$R^3$ is hydrogen, $C_1$-$C_4$alkyl or $C_1$-$C_4$haloalkyl;
$R^4$ is hydrogen, optionally substituted $C_1$-$C_4$ alkyl, —$C_1$-$C_4$ alkylene-C(=O)O$R^{11}$, —$C_1$-$C_4$ alkylene-O$R^{10}$, or —$C_1$-$C_4$ alkylene-N($R^b$)($R^{10}$);
  $R^{10}$ is hydrogen, $C_1$-$C_4$alkyl, $C_1$-$C_4$fluoroalkyl, —C(=O)$R^{11}$, —C(=O)—O—$R^{11}$, —C(=O)N($R^{12}$)$R^{13}$, —S(=O)$_2$$R^{11}$, or —C(=O)$R^{11}$; or $R^{10}$ and $R^b$ are taken together with the N atom to which they are attached to form a $C_2$-$C_6$heterocycle;
or $R^3$ and $R^4$ taken together with the nitrogen to which they are attached form an optionally substituted $C_2$-$C_6$heterocycloalkyl;
$R^5$ and $R^6$ are each independently selected from hydrogen, halogen, —OH, and $C_1$-$C_4$alkyl, or when on the same carbon, $R^5$ and $R^6$ are taken together form an oxo;
$R^7$ is hydrogen, halogen, —CN, —OH, —NO$_2$, —N($R^{12}$)—$R^{13}$, —C(=O)—N($R^{12}$)—$R^{13}$, —N$R^{12}$C(=O)$R^{11}$, —C(=O)—O—$R^{11}$, —O—C(=O)—$R^{11}$, —S$R^{12}$, —S(=O)$R^{11}$, —S(=O)$_2$$R^{11}$, —N($R^{12}$)S(=O)$_2$$R^{11}$, —S(=O)$_2$—N($R^{12}$)—$R^{13}$, —C(=O)$R^{11}$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, optionally substituted 5- or 6-membered heteroaryl;
$R^8$ is hydrogen, —OH, $C_1$-$C_4$alkyl, $C_1$-$C_4$fluoroalkyl, $C_1$-$C_4$alkoxy, $C_1$-$C_4$fluoroalkoxy, or —N($R^a$)$_2$;
X is —O— or —N($R^b$)—;
$R^{10}$ is hydrogen, $C_1$-$C_4$alkyl, $C_1$-$C_4$fluoroalkyl, —C(=O) $R^{11}$, —C(=O)—O—$R^{11}$, —C(=O)N($R^{12}$)$R^{13}$, —S(=O)$_2$$R^{11}$, or —C(=O)$R^{11}$;
each $R^{11}$ is independently selected from the group consisting of optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl;
each of $R^{12}$ and $R^{13}$ is independently selected from the group consisting of hydrogen, optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl; or $R^{12}$ and $R^{13}$, when on the same nitrogen atom, are taken together with the nitrogen atom to which they are attached to form an optionally substituted $C_2$-$C_6$heterocycloalkyl;
n is 1, 2 or 3; and
m is 1, 2, 3 or 4.

In another aspect, provided herein is a compound of Formula (VII), or a pharmaceutically acceptable salt, solvate, prodrug, or N-oxide thereof:

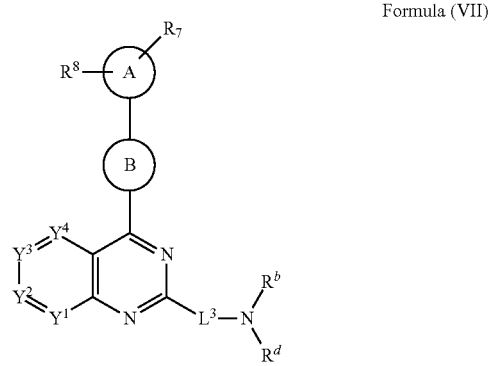

Formula (VII)

wherein:
ring A is $C_3$-$C_6$cycloalkyl, $C_2$-$C_6$heterocycloalkyl, phenyl or monocyclic heteroaryl;
ring B is an optionally substituted hetereocycloalkyl; wherein if ring B is substituted then it is substituted with $R^5$ and $R^6$;
$L^3$ is absent or an optionally substituted $C_1$-$C_4$alkylene;
$R^b$ is hydrogen, optionally substituted $C_1$-$C_4$alkyl, optionally substituted $C_1$-$C_4$haloalkyl, —C(=O)$R^{11}$, —C(=O)—O—$R^{11}$, —S(=O)$_2$$R^{11}$, or —C(=O)$R^{11}$;
$R^d$ is hydrogen, optionally substituted $C_1$-$C_4$alkyl, optionally substituted $C_1$-$C_4$haloalkyl, or optionally substituted $C_1$-$C_6$heterocycloalkyl, wherein if $R^d$ is substituted then it is substituted with $R^1$;
$R^1$ is hydrogen, halogen, $C_1$-$C_4$alkyl, $C_1$-$C_4$alkoxy, $C_1$-$C_4$haloalkyl, $C_1$-$C_4$haloalkoxy, or —N($R^a$)$_2$;
  each $R^a$ is independently selected from the group consisting of hydrogen and $C_1$-$C_4$ alkyl, —C(=O)$R^{11}$, —C(=O)—O—$R^{11}$, —S(=O)$_2$$R^{11}$, —C(=O)$R^{11}$, or 2 $R^a$ taken together with the nitrogen to which they are attached form an optionally substituted $C_2$-$C_6$heterocycloalkyl;
or $R^b$ and $R^d$ taken together with the nitrogen to which they are attached form an optionally substituted $C_2$-$C_6$heterocycloalkyl;
each $Y^1$, $Y^2$, $Y^3$, and $Y^4$ is independently selected from N and $CR^2$, provided that at least 1 of $Y^1$, $Y^2$, $Y^3$, and $Y^4$ is CR2.

11

$R^2$ is hydrogen, halogen, —CN, —OH, —NO$_2$, —N(R$^3$)—R$^4$, optionally substituted C$_1$-C$_4$alkyl, optionally substituted C$_1$-C$_4$alkoxy, optionally substituted C$_1$-C$_4$haloalkyl, optionally substituted C$_1$-C$_4$haloalkoxy, optionally substituted C$_3$-C$_6$cycloalkyl, optionally substituted C$_2$-C$_6$heterocycloalkyl, optionally substituted phenyl, and optionally substituted 5- or 6-membered heteroaryl;

$R^3$ is hydrogen, C$_1$-C$_4$alkyl or C$_1$-C$_4$haloalkyl;

$R^4$ is hydrogen, optionally substituted C$_1$-C$_4$ alkyl, —C$_1$-C$_4$ alkylene-C(=O)OR$^{11}$, —C$_1$-C$_4$ alkylene-OR$^{10}$, or —C$_1$-C$_4$ alkylene-N(R$^b$)(R$^{10}$);

$R^{10}$ is hydrogen, C$_1$-C$_4$alkyl, C$_1$-C$_4$fluoroalkyl, —C(=O)R$^{11}$, —C(=O)—O—R$^{11}$, —C(=O)N(R$^{12}$)R$^{13}$, —S(=O)$_2$R$^{11}$, or —C(=O)R$^{11}$; or R$^b$ and R$^{10}$ are taken together with the nitrogen to which they are attached form an optionally substituted C$_2$-C$_6$heterocycloalkyl;

or $R^3$ and $R^4$ taken together with the nitrogen to which they are attached form an optionally substituted C$_2$-C$_6$heterocycloalkyl;

$R^5$ and $R^6$ are each independently selected from hydrogen, halogen, —OH, and C$_1$-C$_4$alkyl, or when on the same carbon, R$^5$ and R$^6$ are taken together form an oxo;

$R^7$ is hydrogen, halogen, —CN, —OH, —NO$_2$, —N(R$^{12}$)—R$^{13}$, —C(=O)—N(R$^{12}$)—R$^{13}$, —NR$^{12}$C(=O)R$^{11}$, —C(=O)—O—R$^{11}$, —O—C(=O)—R$^{11}$, —SR$^{12}$, —S(=O)R$^{11}$, —S(=O)$_2$R$^{11}$, —N(R$^{12}$)S(=O)$_2$R$^{11}$, —S(=O)$_2$—N(R$^{12}$)—R$^{13}$, —C(=O)R$^{11}$, optionally substituted C$_1$-C$_4$alkyl, optionally substituted C$_1$-C$_4$alkoxy, optionally substituted C$_1$-C$_4$haloalkyl, optionally substituted C$_1$-C$_4$haloalkoxy, optionally substituted C$_3$-C$_6$cycloalkyl, optionally substituted C$_2$-C$_6$heterocycloalkyl, optionally substituted phenyl, optionally substituted 5- or 6-membered heteroaryl;

$R^8$ is hydrogen, —OH, C$_1$-C$_4$fluoroalkyl, C$_1$-C$_4$alkoxy, C$_1$-C$_4$fluoroalkoxy, or —N(R$^a$)$_2$;

each $R^H$ is independently selected from the group consisting of optionally substituted C$_1$-C$_4$alkyl, optionally substituted C$_1$-C$_4$fluoroalkyl, optionally substituted C$_3$-C$_6$cycloalkyl, optionally substituted C$_2$-C$_6$heterocycloalkyl, optionally substituted phenyl, and optionally substituted 5- or 6-membered heteroaryl;

each of $R^{12}$ and $R^{13}$ is independently selected from the group consisting of hydrogen, optionally substituted C$_1$-C$_4$alkyl, optionally substituted C$_1$-C$_4$fluoroalkyl, optionally substituted C$_3$-C$_6$cycloalkyl, optionally substituted C$_2$-C$_6$heterocycloalkyl, optionally substituted phenyl, and optionally substituted 5- or 6-membered heteroaryl; or R$^{12}$ and R$^{13}$, when on the same nitrogen atom, are taken together with the nitrogen atom to which they are attached to form an optionally substituted C$_2$-C$_6$heterocycloalkyl.

In yet another aspect, provided herein is a compound of Formula (VIII), or a pharmaceutically acceptable salt, solvate, prodrug, or N-oxide thereof:

12

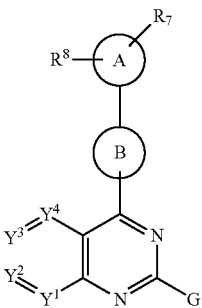

Formula (VIII)

wherein:

ring A is C$_3$-C$_6$cycloalkyl, C$_2$-C$_6$heterocycloalkyl, phenyl or monocyclic heteroaryl;

ring B is an optionally substituted hetereocycloalkyl;

each Y$^1$, Y$^2$, Y$^3$, and Y$^4$ is independently selected from N and CR$^2$, provided that at least 1 of Y$^1$, Y$^2$, Y$^d$, and Y$^4$ is N;

G is optionally substituted C$_1$-C$_4$alkyl, optionally substituted C$_1$-C$_4$haloalkyl, -L$^1$-R$^d$, or -L$^3$-N(R$^b$)—R$^d$;

L$^1$ is absent, C$_1$-C$_4$alkylene, C$_1$-C$_4$alkenylene, C$_1$-C$_4$alkynylene, —O— or —N(R$^b$)—;

L$^3$ is absent or an optionally substituted C$_1$-C$_4$alkylene;

R$^b$ is hydrogen, optionally substituted C$_1$-C$_4$alkyl, optionally substituted C$_1$-C$_4$haloalkyl, —C(=O)R$^{11}$, —C(=O)—O—R$^{11}$, —S(=O)$_2$R$^{11}$, or —C(=O)R$^{11}$;

R$^d$ is hydrogen, optionally substituted C$_1$-C$_4$alkyl, optionally substituted C$_1$-C$_4$haloalkyl, or optionally substituted C$_1$-C$_6$heterocycloalkyl, wherein if R$^d$ is substituted then it is substituted with R$^1$;

$R^1$ is hydrogen, halogen, C$_1$-C$_4$alkyl, C$_1$-C$_4$alkoxy, C$_1$-C$_4$haloalkyl, C$_1$-C$_4$haloalkoxy, or —N(R$^a$)$_2$;

each R$^a$ is independently selected from the group consisting of hydrogen and C$_1$-C$_4$ alkyl, —C(=O)R$^{11}$, —C(=O)—O—R$^{11}$, —S(=O)$_2$R$^{11}$, —C(=O)R$^{11}$, or 2 R$^a$ taken together with the nitrogen to which they are attached form an optionally substituted C$_2$-C$_6$heterocycloalkyl;

or R$^b$ and R$^d$ taken together with the nitrogen to which they are attached form an optionally substituted C$_2$-C$_6$heterocycloalkyl;

$R^2$ is hydrogen, halogen, —CN, —OH, —NO$_2$, —N(R$^3$)—R$^4$, optionally substituted C$_1$-C$_4$alkyl, optionally substituted C$_1$-C$_4$alkoxy, optionally substituted C$_1$-C$_4$haloalkyl, optionally substituted C$_1$-C$_4$haloalkoxy, optionally substituted C$_3$-C$_6$cycloalkyl, optionally substituted C$_2$-C$_6$heterocycloalkyl, optionally substituted phenyl, and optionally substituted 5- or 6-membered heteroaryl;

$R^3$ is hydrogen, C$_1$-C$_4$alkyl or C$_1$-C$_4$haloalkyl;

$R^4$ is hydrogen, optionally substituted C$_1$-C$_4$ alkyl, —C$_1$-C$_4$ alkylene-C(=O)OR$^{11}$, —C$_1$-C$_4$ alkylene-OR$^{10}$, or —C$_1$-C$_4$ alkylene-N(R$^b$)(R$^{10}$);

$R^{10}$ is hydrogen, C$_1$-C$_4$alkyl, C$_1$-C$_4$fluoroalkyl, —C(=O)R$^{11}$, —C(=O)—O—R$^{11}$, —C(=O)N(R$^{12}$)R$^{13}$, —S(=O)$_2$R$^{11}$, or —C(=O)R$^{11}$; or R$^b$ and R$^{10}$ are taken together with the nitrogen to which they are attached form an optionally substituted C$_2$-C$_6$heterocycloalkyl;

or $R^3$ and $R^4$ taken together with the nitrogen to which they are attached form an optionally substituted $C_2$-$C_6$heterocycloalkyl;

$R^7$ is hydrogen, halogen, —CN, —OH, —$NO_2$, —$N(R^{12})$—$R^{13}$, —C(=O)—$N(R^{12})$—$R^{13}$, —$NR^{12}$C(=O)$R^{11}$, —C(=O)—O—$R^{11}$, —O—C(=O)—$R^{11}$, —$SR^{12}$, —S(=O)$R^{11}$, —S(=O)$_2R^{11}$, —$N(R^{12})$S(=O)$_2R^{11}$, —S(=O)$_2$—$N(R^{12})$—$R^{13}$, —C(=O)$R^{11}$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, optionally substituted 5- or 6-membered heteroaryl;

$R^8$ is hydrogen, —OH, $C_1$-$C_4$alkyl, $C_1$-$C_4$fluoroalkyl, $C_1$-$C_4$alkoxy, $C_1$-$C_4$fluoroalkoxy, or —$N(R^a)_2$;

each $R^a$ is independently selected from the group consisting of hydrogen and $C_1$-$C_4$ alkyl, —C(=O)$R^{11}$, —C(=O)—O—$R^{11}$, —S(=O)$_2R^{11}$, —C(=O)$R^{11}$, or 2 $R^a$ taken together with the nitrogen to which they are attached form an optionally substituted $C_2$-$C_6$heterocycloalkyl;

each $R^{11}$ is independently selected from the group consisting of optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl;

each of $R^{12}$ and $R^{13}$ is independently selected from the group consisting of hydrogen, optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl; or $R^{12}$ and $R^{13}$, when on the same nitrogen atom, are taken together with the nitrogen atom to which they are attached to form an optionally substituted $C_2$-$C_6$heterocycloalkyl;

provided that the compound is not 2-cyclopropyl-6-methoxy-4-(4-(2-methoxyphenyl)piperazin-1-yl)pyrido[3,4-d]pyrimidine or 2-cyclopropyl-4-(4-(2-methoxyphenyl)piperazin-1-yl)pyrido[2,3-d]pyrimidine.

Any combination of the groups described above or below for the various variables is contemplated herein. Throughout the specification, groups and substituents thereof are chosen by one skilled in the field to provide stable moieties and compounds.

In one aspect, provided herein is a pharmaceutical composition comprising a compound of Formula (I), (II), (III), (IV), (V), (VI), (VII) or (VIII), or a pharmaceutically acceptable salt thereof, and a pharmaceutically acceptable excipient.

In some embodiments, the compound of Formula (I), (II), (III), (IV), (V), (VI), (VII) or (VIII), or a pharmaceutically acceptable salt thereof, is formulated for intravenous injection, subcutaneous injection, oral administration, inhalation, nasal administration, topical administration, ophthalmic administration or otic administration. In some embodiments, the compound of Formula (I), (II), (III), (IV), (V), (VI), (VII) or (VIII), or a pharmaceutically acceptable salt thereof, is formulated as (i.e. incorporated into) a tablet, a pill, a capsule, a liquid, an inhalant, a nasal spray solution, a suppository, a suspension, a gel, a solution, an ointment, a lotion, an eye drop or an ear drop In another aspect, described herein is a method of treating a disease, disorder or condition mediated by neurotensin and/or neurotensin receptor 1 in a subject in need thereof, which method comprises administering to the subject a therapeutically effective amount of a compound of Formula (I), (II), (III), (IV), (V), (VI), (VII) or (VIII), or a pharmaceutically acceptable salt thereof. In another aspect, described herein is a method of treating a disease in a subject mediated by neurotensin and/or neurotensin receptor 1, which method comprises administering to the subject a pharmaceutical composition comprising a compound of Formula (I), (II), (III), (IV), (V), (VI), (VII) or (VIII), or a pharmaceutically acceptable salt thereof. In some embodiments, the disease, disorder, condition is drug abuse. In some embodiments, the disease, disorder or condition is Parkinson's disease. In some embodiments, the disease is schizophrenia. In some embodiments, the disease, disorder or condition is pain.

In any of the aforementioned aspects are further embodiments in which: (a) the effective amount of the compound of Formula (I), (II), (III), (IV), (V), (VI), (VII) or (VIII), is systemically administered to the mammal; and/or (b) the effective amount of the compound is administered orally to the mammal; and/or (c) the effective amount of the compound is intravenously administered to the mammal; and/or (d) the effective amount of the compound is administered by inhalation; and/or (e) the effective amount of the compound is administered by nasal administration; or and/or (f) the effective amount of the compound is administered by injection to the mammal; and/or (g) the effective amount of the compound is administered topically to the mammal; and/or (h) the effective amount of the compound is administered by ophthalmic administration; and/or (i) the effective amount of the compound is administered rectally to the mammal; and/or (j) the effective amount is adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In any of the aforementioned aspects involving the administration of a compound of Formula (I), (II), (III), (IV), (V), (VI), (VII) or (VIII), or a pharmaceutically acceptable salt thereof, to a subject are further embodiments comprising administering at least one additional agent in addition to the administration of a compound having the structure of Formula (I), (II), (III), (IV), (V), (VI), (VII) or (VIII), or a pharmaceutically acceptable salt thereof. In various embodiments, the compound of Formula (I), (II), (III), (IV), (V), (VI), (VII) or (VIII) and the additional agent are administered in any order, including simultaneously. In some embodiments, the compound of Formula (I), (II), (III), (IV), (V), (VI), (VII) or (VIII) and the additional agent are administered to the subject in the same pharmaceutical composition or in separate pharmaceutical compositions.

In any of the embodiments disclosed herein, the subject is a human.

In some embodiments, compounds and compositions provided herein are administered to a human.

In some embodiments, compounds and compositions provided herein are orally administered.

In other embodiments, compounds provided herein are used for the formulation of a medicament for the modulation of the activity of the neurotensin 1 receptor in a subject.

Articles of manufacture, which include packaging material, a compound of Formula (I), (II), (III), (IV), (V), (VI), (VII) or (VIII), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for the treatment of diseases or conditions that would benefit from modulation of the neurotensin 1 receptor, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description

DETAILED DESCRIPTION OF THE INVENTION

Neurotensin is a 13 amino acid neuropeptide that is implicated in the regulation of luteinizing hormone and prolactin release and has significant interaction with the dopaminergic system. Neurotensin was first isolated from extracts of bovine hypothalamus based on its ability to cause a visible vasodilation in the exposed cutaneous regions of anesthetized rats. Neurotensin is distributed throughout the central nervous system, with highest levels in the hypothalamus, amygdala and nucleus accumbens. It induces a variety of effects, including: analgesia, hypothermia and increased locomotor activity. It is also involved in regulation of dopamine pathways. In the periphery, neurotensin is found in endocrine cells of the small intestine, where it leads to secretion and smooth muscle contraction Neurotensin has been implicated in the modulation of dopamine signaling, and produces a spectrum of pharmacological effects resembling those of antipsychotic drugs, leading to the suggestion that neurotensin may be an endogenous neuroleptic. Neurotensin-deficient mice display defects in responses to several antipsychotic drugs consistent with the idea that neurotensin signaling is a key component underlying at least some antipsychotic drug actions. These mice exhibit modest defects in prepulse inhibition (PPI) of the startle reflex, a model that has been widely used to investigate antipsychotic drug action in animals. Antipsychotic drug administration augments PPI under certain conditions. Comparisons between normal and neurotensin-deficient mice revealed striking differences in the ability of different antipsychotic drugs to augment PPI. While the atypical antipsychotic drug clozapine augmented PPI normally in neurotensin-deficient mice, the antipsychotic haloperidol and the antipsychotic quetiapine were ineffective in these mice, in contrast to normal mice where these drugs significantly augmented PPI. These results suggest that certain antipsychotic drugs require neurotensin for at least some of their effects. Neurotensin-deficient mice also display defects in striatal activation following haloperidol, but not clozapine administration in comparison to normal wild type mice, indicating that striatal neurotensin is required for the full spectrum of neuronal responses to a subset of antipsychotic drugs.

Neurotensin is an endogenous neuropeptide involved in thermoregulation that can induce hypothermia and neuroprotection in experimental models of cerebral ischemia.

The neurotensin receptors are transmembrane receptors that bind the neurotransmitter neurotensin. Two of the receptors encoded by the NTSR1 and NTSR2 genes contain seven transmembrane helices and are G protein coupled. The third receptor has a single transmembrane domain and is encoded by the SORT1gene.

Addiction is the continued repetition of a behavior despite adverse consequences, or a neurological impairment leading to such behaviors. Addictions can include, but are not limited to, drug abuse, exercise addiction, food addiction, sexual addiction, computer addiction and gambling. Classic hallmarks of addiction include impaired control over substances or behavior, preoccupation with substance or behavior, continued use despite consequences, and denial. Habits and patterns associated with addiction are typically characterized by immediate gratification (short-term reward), coupled with delayed deleterious effects (long-term costs). Some drugs associated with addiction include alcohol, substituted amphetamines (e.g. methamphetamine), barbiturates, benzodiazepines (particularly alprazolam, temazepam, diazepam and clonazepam), cocaine, methaqualone, and opioids.

Neurotensin (NT) receptors are expressed on dopaminergic neurological pathways associated with reward, and the neurotensin receptor 1 (NTR1) is a therapeutic target for the treatment of methamphetamine abuse. In particular, peptide-based NTR1 agonists produce behaviors that are opposite to the psychostimulant effects observed with psychoactive drugs, such as but not limited to methamphetamine, such as hyperactivity, neurotoxicity, psychotic episodes, and cognitive deficits.

NTR1 is a G protein coupled receptor (GPCR). Two distinct, interdependent paradigms are associated with GPCR signaling. In addition to the well-defined signaling cascades involving heterotrimeric G proteins, recent advances in receptor pharmacology have identified the importance of β-arrestins in regulating alternative biochemical cascades that produce their own unique biological effects. For example, in a mouse model, Allen et al developed a series of β-arrestin-2 biased agonists for the D(2)R with antipsychotic properties, and most importantly, a reduced propensity to induce catalepsy like standard neuroleptic antagonists (Allen et al. Discovery of β-Arrestin-Biased Dopamine D2 Ligands for Probing Signal Transduction Pathways Essential for Antipsychotic Efficacy. *Proc. Natl. Acad. Sci. USA*. 2011, 108, 18488-18493; Rajagopal et al. Teaching old receptors new tricks: biasing seven-transmembrane receptors. *Nat. Rev. Drug Discovery* 2010, 9, 373-386). Studies with those biased compounds illustrate how ligand directed signaling bias, in this case favoring β-arrestin, can ameliorate undesirable biological outcomes. Downstream modulators of β-arrestin/GPCR signaling are less characterized than their G protein counterparts, and, due to their potential as targets for producing new medical therapies are the subjects of increasing numbers of investigations. Recognized β-arrestin partners include the proteins Src, ERK, and Jnk. Their agonist-induced interactions with β-arrestin are associated with clathrin-compartmentalized signaling and the accumulation of ligand activated β-arrestin/GPCR complexes in clathrin coated pits. The determination as to whether a GPCR ligand is biased towards or against β-arrestin may consequently be evaluated by following these biochemical processes.

In one aspect, compounds described herein are used in the treatment of a disease or condition in a subject that is mediated by neurotensin and/or neurotensin receptor 1.

In one aspect, compounds described herein are used in the treatment of a neurological disease or condition mediated by neurotensin and/or neurotensin receptor 1. In some embodiments, the neurological disease or condition is acute stress disorder, alcohol abuse, alcohol dependence, alcohol withdrawal, alcoholic hallucinosis, alzheimer's disease, amphetamine dependence, amphetamine withdrawal psychosis, anorexia nervosa, anxiety disorder, anxiolytic-related disorders, asperger syndrome, attention deficit disorder, attention deficit hyperactivity disorder, autism, barbiturate dependence, benzodiazepine dependence, benzodiazepine misuse, benzodiazepine withdrawal, bipolar disorder, bipolar I disorder, bipolar II disorder, bulimia nervosa, cannabis dependence, catatonic disorder, catatonic schizophrenia, cocaine dependence, cocaine intoxication, cotard delusion, cyclothymia, delirium tremens, depressive disorder, generalized anxiety disorder, grandiose delusions, hallucinogen-related disorder, hallucinogen persisting perception disorder, huntington's disease, impulse control disorder, intermittent explosive disorder, major depressive disorder, major depressive episode, manic episode, minor depressive disorder, minor depressive episode, munchausen's syndrome, neuroleptic-related disorder, night eating syndrome, obsessive-compulsive disorder (OCD), opioid dependence, pain disorder, panic disorder, paranoid personality disorder, parasomnia, parkinson's disease, partner relational problem, pathological gambling, phencyclidine (or phencyclidine-like)-related disorder, residual schizophrenia, sadomasochism, schizoaffective disorder, schizoid personality disorder, schizophrenia, schizophreniform disorder, schizotypal personality disorder, social anxiety disorder, social phobia, substance-related disorder, tardive dyskinesia, or tourette syndrome.

In some embodiments, compounds described herein are useful in the treatment of amphetamine addiction. In some embodiments, the amphetamine is Methamphetamine, ethylamphetamine, propylamphetamine, isopropylamphetamine, phentermine, phenylpropanolamine (PPA), Cathine, Cathinone, Ortetamine, 2-Fluoroamphetamine (2-FA), 3-Methylamphetamine (3-MA), 3-Fluoroamphetamine (3-FA), Norfenfluramine, 4-Methylamphetamine (4-MA), para-Methoxyamphetamine (PMA), para-Ethoxyamphetamine, 4-Methylthioamphetamine (4-MTA), Norpholedrine (α-Me-TRA), para-Bromoamphetamine (PBA, 4-BA), para-Chloroamphetamine (PCA, 4-CA), para-Fluoroamphetamine (PFA, 4-FA, 4-FMP), para-Iodoamphetamine (PIA, 4-IA), Dimethylamphetamine, Benzphetamine, Selegiline, Mephentermine, Phenpentermine, Ephedrine (EPH), Pseudoephedrine (PSE), Methcathinone, Ethcathinone, Clortermine, Methoxymethylamphetamine (MMA), Fenfluramine, Dexfenfluramine, 4-Methylmethamphetamine (4-MMA), Para-methoxymethamphetamine (PMMA), para-Methoxyethylamphetamine (PMEA), Pholedrine, Chlorphentermine, para-Fluoromethamphetamine (PFMA, 4-FMA), Xylopropamine, alpha-Methyldopamine (alpha-Me-DA), Methylenedioxyamphetamine (MDA), Dimethoxyamphetamine (DMA), Nordefrin (alpha-Me-NE), Oxilofrine, Aleph, Dimethoxybromoamphetamine (DOB), Dimethoxychloroamphetamine (DOC), Dimethoxyfluoroethylamphetamine (DOEF), Dimethoxyethylamphetamine (DOET), Dimethoxyfluoroamphetamine (DOF), Dimethoxyiodoamphetamine (DOI), Dimethoxymethylamphetamine (DOM), Dimethoxynitroamphetamine (DON), Dimethoxypropylamphetamine (DOPR), Dimethoxytrifluoromethylamphetamine (DOTFM), Methylenedioxymethamphetamine (MDMA), Methylenedioxyethylamphetamine (MDEA), Methylenedioxyhydroxyamphetamine (MDOH), 2-Methyl-MDA, 5-Methyl-MDA, Methoxymethylenedioxyamphetamine (MMDA), Trimethoxyamphetamine (TMA), Dimethylcathinone, Diethylcathinone, Bupropion, Mephedrone (4-MMC), Methedrone (PMMC), Brephedrone (4-BMC), Flephedrone (4-FMC). In some embodiments, the amphetamine is methamphetamine.

In certain instances, compounds described herein are used in the treatment of stroke/cerebral ischemia. In certain instances, compounds described herein reduce infarct formation and/or brain cell death. In certain instances, compounds described herein increase patient recovery post-stroke.

In a further aspect, compounds described herein are used in the treatment of neurotensin-dependent pathologies.

In one aspect, compounds described herein are used in the treatment of neuropsychiatric disorders mediated by neurotensin and/or neurotensin receptor 1, for example substance abuse, psychosis, schizophrenia, Parkinson's disease, attention deficit hyperactivity disorder (ADHD), and pain. In some embodiments, compounds described herein are used in the treatment of schizophrenia. In some embodiments, compounds described herein are used in the treatment of Parkinson's disease. In some embodiments, compounds described herein are used in the treatment of pain. In some embodiments, the pain is acute pain or chronic pain. In some embodiments, the pain is neuropathic pain, e.g., chronic neuropathic pain.

In some embodiments, compounds described herein are used in the treatment of schizophrenia. In some embodiments, the schizophrenia is newly diagnosed or not adequately controlled or resistant to the typical and atypical anti-psychotics.

In some embodiments, the neuropsychiatric disorder is substance abuse. In some embodiments, the neuropsychiatric disorder is substance abuse and the substance of abuse is, for example an opiate (e.g., heroin, morphine, codeine), a psychomotor stimulant (e.g., amphetamine, methamphetamine (meth), ephedrine, or pseudoephedrine), a cannabinoids (e.g., tetrahydrocannabinol (THC)), alcohol, nicotine, or a hallucinogen. In some embodiments, compounds described herein are used in the treatment of alcohol addiction in subjects that have failed non-pharmacologic intervention. In some embodiments, compounds described herein are used in the treatment of psychostimulant addiction in subjects that have failed non-pharmacologic intervention.

In some embodiments, the neuropsychiatric disorder is an eating disorder such as bulimia nervosa, binge eating disorder, compulsive overeating, anxiety, sleep disorder, or bipolar disorder. In some embodiments, compounds described herein are used to reduce food intake and/or increase satiety.

In one other aspect compounds described herein are used in the treatment of a neurodegenerative disease mediated by neurotensin and/or neurotensin receptor 1, for example, Alzheimer's disease, Hungtinton's disease, or Amyotrophic Lateral Sclerosis (ALS or Lou Gehrig's disease). In some embodiments, compounds described herein are used in the treatment of a neurodegenerative disease, wherein the compound described herein alleviates one or more symptoms or side effects of the neurodegenerative disease. In some embodiments the symptoms or side effects of neurodegenerative diseases include, but are not limited to, dementia, memory loss, dyskinesias, cognitive impairment, tremors, rigidity, slowness of movement, postural instability, involuntary jerking or writhing movements (chorea), slow or abnormal eye movements, difficulty with the physical production of speech or swallowing, psychiatric disorders, muscle cramps and spasms, spasticity, constipation, fatigue, excessive salivation, excessive phlegm, pain, sleep problems, uncontrolled outbursts of laughing or crying.

In one other aspect, compounds described herein are used in the treatment of cancer. In some embodiments, the cancer is a solid tumor. In some embodiments, the cancer is bladder cancer, colon cancer, brain cancer, breast cancer, bone cancer, endometrial cancer, heart cancer, kidney cancer, lung cancer, liver cancer, uterine cancer, ovarian cancer, pancreatic cancer, prostate cancer, thyroid cancer, or skin cancer In one other aspect, compounds described herein are used in the treatment of cardiovascular disorders such as, but not limited to, hypertension, coronary artery disease, cardiomyopathy, or inflammatory heart disease.

Compounds

In one aspect, provided herein is a compound of Formula (I), or a pharmaceutically acceptable salt, solvate, tautomer, or N-oxide thereof:

Formula (I)

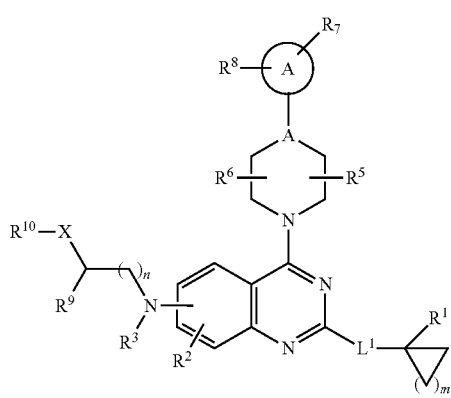

wherein, ring A is $C_3$-$C_6$cycloalkyl, $C_2$-$C_6$heterocycloalkyl, phenyl or monocyclic heteroaryl; A is N or CH;

$R^1$ is halogen, $C_1$-$C_4$alkyl, $C_1$-$C_4$alkoxy, $C_1$-$C_4$haloalkyl, $C_1$-$C_4$haloalkoxy, or —N($R^a$)$_2$; and $R^3$ is hydrogen, $C_1$-$C_4$alkyl or $C_1$-$C_4$haloalkyl;

or $R^1$ is hydrogen, halogen, $C_1$-$C_4$alkyl, $C_1$-$C_4$alkoxy, $C_1$-$C_4$haloalkyl, $C_1$-$C_4$haloalkoxy, or —N($R^a$)$_2$; and $R^3$ and $R^9$ are taken together with the intervening atoms to form an optionally substituted $C_2$-$C_6$heterocycloalkyl;

each $R^a$ is independently selected from the group consisting of hydrogen and $C_1$-$C_4$ alkyl, —C(=O)$R^{11}$, —C(=O)—O—$R^{11}$, —S(=O)$_2$$R^{11}$, —C(=O)$R^{11}$, or 2 $R^a$ taken together with the nitrogen to which they are attached form an optionally substituted $C_2$-$C_6$heterocycloalkyl;

$L^1$ is absent, $C_1$-$C_4$alkylene, $C_1$-$C_4$alkenylene, $C_1$-$C_4$alkynylene, or N($R^b$)—;

$R^b$ is hydrogen, $C_1$-$C_4$alkyl or $C_1$-$C_4$haloalkyl, —C(=O)$R^{11}$, —C(=O)—O—$R^{11}$, —S(=O)$_2$$R^{11}$, or —C(=O)$R^{11}$;

$R^2$ is hydrogen, halogen, —CN, —OH, —NO$_2$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, and optionally substituted 5- or 6-membered heteroaryl;

$R^5$ and $R^6$ are each independently selected from hydrogen, halogen, —OH, and $C_1$-$C_4$alkyl, or when on the same carbon, $R^5$ and $R^6$ are taken together form an oxo;

$R^7$ is hydrogen, halogen, —CN, —OH, —NO$_2$, —N($R^{12}$)—$R^{13}$, —C(=O)—N($R^{12}$)—$R^{13}$, —NR$^{12}$C(=O)$R^{11}$, —C(=O)—O—$R^{11}$, —O—C(=O)—$R^{11}$, —SR$^{12}$, —S(=O)$R^{11}$, —S(=O)$_2$$R^{11}$, —N($R^{12}$)S(=O)$_2$$R^{11}$, —S(=O)$_2$—N($R^{12}$)—$R^{13}$, —C(=O)$R^{11}$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, optionally substituted 5- or 6-membered heteroaryl;

$R^8$ is hydrogen, —OH, $C_1$-$C_4$alkyl, $C_1$-$C_4$fluoroalkyl, $C_1$-$C_4$alkoxy, $C_1$-$C_4$fluoroalkoxy, or —N($R^a$)$_2$;

$R^9$ is hydrogen, $C_1$-$C_4$alkyl, or $C_1$-$C_4$fluoroalkyl;

X is —O— or —N($R^b$)—;

$R^{10}$ is hydrogen, $C_1$-$C_4$alkyl, $C_1$-$C_4$fluoroalkyl, —C(=O)$R^{11}$, —C(=O)—O—$R^{11}$, —C(=O)N($R^{12}$)$R^{13}$, —S(=O)$_2$$R^{11}$, or —C(=O)$R^{11}$;

each $R^H$ is independently selected from the group consisting of optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl;

each of $R^{12}$ and $R^{13}$ is independently selected from the group consisting of hydrogen, optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl; or $R^{12}$ and $R^{13}$, when on the same nitrogen atom, are taken together with the nitrogen atom to which they are attached to form an optionally substituted $C_2$-$C_6$heterocycloalkyl;

n is 1, 2 or 3; and m is 1, 2, 3 or 4.

Any combination of the groups described above or below for the various variables is contemplated herein. For example, in some embodiments ring A is monocyclic heteroaryl. In some embodiments ring A is a monocyclic 6 membered heteroaryl. In some embodiments ring A is a monocyclic 5 membered heteroaryl. In some embodiments ring A is pyridine, pyrimidine, pyrazine, pyridazine, or thiophene. In some embodiments ring A is pyridine. In some embodiments ring A is thiophene. In some other embodi- 1ments, ring A is $C_3$-$C_6$cycloalkyl or phenyl. In some other embodiments, ring A is $C_3$-$C_6$cycloalkyl. In some embodiment ring A is cyclopropyl, cyclobutyl, cyclopentyl, cyclohexyl, or cycloheptyl. In some embodiments ring A is cyclopentyl. In some other embodiments, ring A is phenyl.

In some embodiments, the compound of Formula (I), or a pharmaceutically acceptable salt, solvate, prodrug, or N-oxide thereof has the following structure:

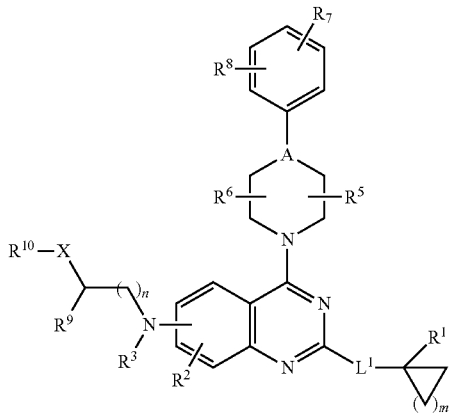

In some embodiments, $L^1$ is absent, $C_1$-$C_4$alkylene, $C_1$-$C_4$alkenylene, $C_1$-$C_4$alkynylene, or $N(R^b)$—. In some embodiments, $L^1$ is absent, $C_1$-$C_4$alkylene, $C_1$-$C_4$alkenylene, or $C_1$-$C_4$alkynylene. In some embodiments, $L^1$ is $C_1$-$C_4$alkylene. In some embodiments, $L^1$ is $C_1$-$C_4$alkenylene. In some embodiments, $L^1$ is $C_1$-$C_4$alkynylene. In some embodiments, $L^1$ is —O— or $N(R^b)$—. In some embodiments, $L^1$ is $N(R^b)$—. In some embodiments, $L^1$ is —O—.

In some embodiments, $L^1$ is absent.

In some embodiments $R^2$ is hydrogen, halogen, —CN, —OH, —$NO_2$, optionally substituted $C_1$-$C_4$alkyl, optionally substituted $C_1$-$C_4$alkoxy, optionally substituted $C_1$-$C_4$haloalkyl. In some embodiments $R^2$ is hydrogen, halogen, or methyl.

In some embodiments The compound of claim 4 or claim 5, n the compound of Formula (I), or a pharmaceutically acceptable salt, solvate, prodrug, or N-oxide thereof has the following structure of Formula (Ia):

Formula (Ia)

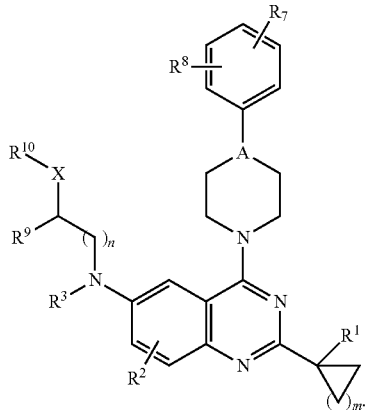

In some embodiments $R^1$ is halogen, $C_1$-$C_4$alkyl, $C_1$-$C_4$alkoxy, $C_1$-$C_4$haloalkyl, $C_1$-$C_4$haloalkoxy, or —$N(R^a)_2$; and $R^3$ is hydrogen, or $C_1$-$C_4$alkyl.

In some embodiments $R^1$ is F, $C_1$-$C_4$alkyl, or $C_1$-$C_4$fluoroalkyl. In some embodiments $R^1$ is F or $C_1$-$C_4$fluoroalkyl. In some embodiments $R^1$ is F. In some embodiments $R^1$ is methyl. In some embodiments $R^1$ is $CF_3$.

In some embodiments $R^1$ is hydrogen, halogen, $C_1$-$C_4$alkyl, $C_1$-$C_4$alkoxy, $C_1$-$C_4$haloalkyl, $C_1$-$C_4$haloalkoxy, or —$N(R^a)_2$; and $R^3$ and $R^9$ are taken together with the intervening atoms to form an optionally substituted $C_2$-$C_6$heterocycloalkyl.

In some embodiments $R^3$ and $R^9$ are taken together with the intervening atoms to form an optionally substituted $C_2$-$C_6$heterocycloalkyl, wherein the optionally substituted $C_2$-$C_6$heterocycloalkyl is an optionally substituted azetidenyl, optionally substituted pyrrolidinyl, or optionally substituted piperidinyl. In some embodiments the optionally substituted $C_2$-$C_6$heterocycloalkyl is optionally substituted pyrrolidinyl.

In some embodiments $R^1$ is hydrogen, F, $C_1$-$C_4$alkyl, or $C_1$-$C_4$fluoroalkyl. In some embodiments $R^1$ is hydrogen, methyl, or $CF_3$ and $R^3$ and $R^9$ are taken together with the intervening atoms to form an optionally substituted $C_2$-$C_6$heterocycloalkyl.

In some embodiments the compound of Formula (I), or a pharmaceutically acceptable salt, solvate, prodrug, or N-oxide thereof has the following structure of Formula (Ib):

Formula (Ib)

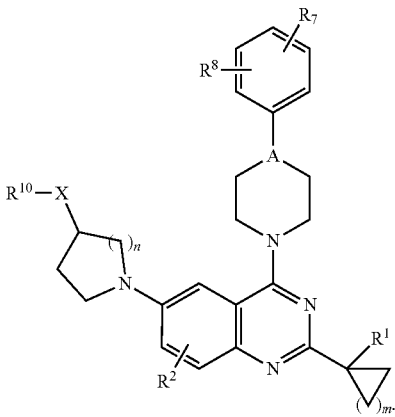

In some embodiments, the compound of Formula (Ib) has one of the following structures:

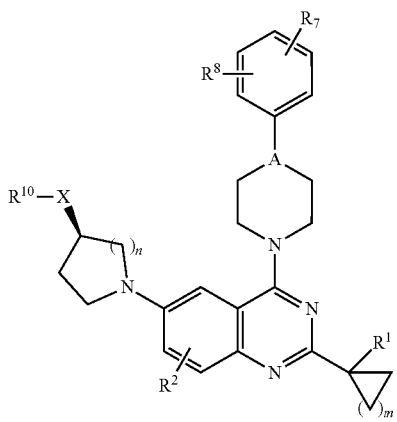

-continued

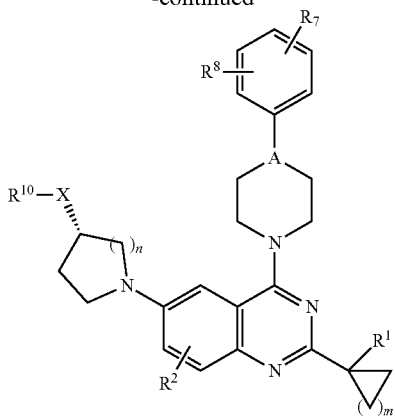

In some embodiments A is CH.
In some embodiments A is N.
In some embodiments, m is 1 or 2. In some embodiments, m is 1. In some embodiments, m is 2.
In some embodiments, n is 1 or 2. In some embodiments, n is 1. In some embodiments, n is 2.
In some embodiments, X is O. In some embodiments X—$N(R^b)$—. In some embodiments X is NH.
In some embodiments $R^{10}$ is hydrogen, or $C_1$-$C_4$alkyl. In some embodiments $R^{10}$ is hydrogen.
In some embodiments $R^8$ is $C_1$-$C_4$alkoxy, or —$N(R^a)_2$. In some embodiments $R^8$ is methoxy. In some embodiments $R^8$ is —$N(R^a)_2$. In some embodiments $R^8$ is —$N(R^a)_2$ where —$N(R^a)_2$ is dimethylamino or azetidenyl.
In some embodiments $R^7$ is hydrogen, halogen, —CN, —OH, $C_1$-$C_4$alkyl, $C_1$-$C_4$alkoxy, $C_1$-$C_4$haloalkyl, or $C_1$-$C_4$haloalkoxy. In some embodiments $R^7$ is hydrogen or halogen. In some embodiments $R^7$ is hydrogen.
In another aspect, provided herein is a compound of formula (II), or a pharmaceutically acceptable salt, solvate, prodrug, or N-oxide thereof:

Formula (II)

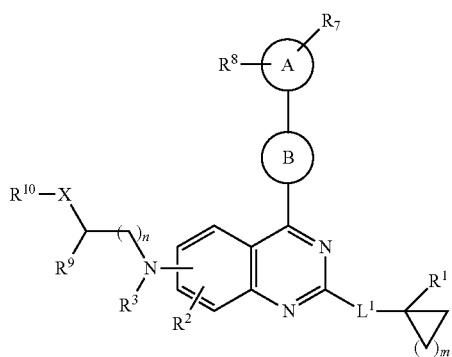

wherein,
ring A is $C_3$-$C_6$cycloalkyl, $C_2$-$C_6$heterocycloalkyl, phenyl or monocyclic heteroaryl;
ring B is an optionally substituted bicyclic heterocycloalkyl or an optionally substituted tricyclic heterocycloalkyl;
$R^1$ is hydrogen, halogen, $C_1$-$C_4$alkyl, $C_1$-$C_4$alkoxy, $C_1$-$C_4$haloalkyl, $C_1$-$C_4$haloalkoxy, or —$N(R^a)_2$;
each $R^a$ is independently selected from the group consisting of hydrogen and $C_1$-$C_4$ alkyl, —C(=O)$R^{11}$, —C(=O)—O—$R^{11}$, —S(=O)$_2R^{11}$, —C(=O)$R^{11}$, or 2 $R^a$ taken together with the nitrogen to which they are attached form an optionally substituted $C_2$-$C_6$heterocycloalkyl;
$R^2$ is hydrogen, halogen, —CN, —OH, —NO$_2$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, and optionally substituted 5- or 6-membered heteroaryl;
$R^3$ is hydrogen, $C_1$-$C_4$alkyl or $C_1$-$C_4$haloalkyl;
or
$R^3$ and $R^9$ are taken together with the intervening atoms to form an optionally substituted $C_2$-$C_6$heterocycloalkyl;
$L^1$ is absent, $C_1$-$C_4$alkylene, $C_1$-$C_4$alkenylene, $C_1$-$C_4$alkynylene, or $N(R^b)$—;
$R^b$ is hydrogen, $C_1$-$C_4$alkyl or $C_1$-$C_4$haloalkyl, —C(=O)$R^{11}$, —C(=O)—O—$R^{11}$, —S(=O)$_2R^{11}$, or —C(=O)$R^{11}$;
$R^5$ and $R^6$ are each independently selected from hydrogen, halogen, —OH, and $C_1$-$C_4$alkyl, or when on the same carbon, $R^5$ and $R^6$ are taken together form an oxo;
$R^7$ is hydrogen, halogen, —CN, —OH, —NO$_2$, —$N(R^{12})$—$R^{13}$, —C(=O)—$N(R^{12})$—$R^{13}$, —$NR^{12}$C(=O)$R^{11}$, —C(=O)—O—$R^{11}$, —O—C(=O)—$R^{11}$, —$SR^{12}$, —S(=O)$R^{11}$, —S(=O)$_2R^{11}$, —$N(R^{12})$S(=O)$_2R^{11}$, —S(=O)$_2$—$N(R^{12})$—$R^{13}$, —C(=O)$R^{11}$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, optionally substituted 5- or 6-membered heteroaryl;
$R^8$ is hydrogen, —OH, $C_1$-$C_4$alkyl, $C_1$-$C_4$fluoroalkyl, $C_1$-$C_4$alkoxy, $C_1$-$C_4$fluoroalkoxy, or —$N(R^a)_2$;
$R^9$ is hydrogen or $C_1$-$C_4$alkyl, or $C_1$-$C_4$fluoroalkyl;
X is —O— or —$N(R^b)$—;
$R^{10}$ is hydrogen, $C_1$-$C_4$alkyl, $C_1$-$C_4$fluoroalkyl, —C(=O)$R^{11}$, —C(=O)—O—$R^{11}$, —C(=O)$N(R^{12})R^{13}$, —S(=O)$_2R^{11}$, or —C(=O)$R^{11}$; or $R^{10}$ and $R^b$ are taken together with the N atom to which they are attached to form a $C_2$-$C_6$heterocycle;
each $R^{11}$ is independently selected from the group consisting of optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl;
each of $R^{12}$ and $R^{13}$ is independently selected from the group consisting of hydrogen, optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl; or $R^{12}$ and $R^{13}$, when on the same nitrogen atom, are taken together with the nitrogen atom to which they are attached to form an optionally substituted $C_2$-$C_6$heterocycloalkyl;
n is 1, 2 or 3; and
m is 1, 2, 3 or 4.
In some embodiments ring A is monocyclic heteroaryl. In some embodiments ring A is monocyclic 6-membered heteroaryl. In some embodiments ring A is monocyclic 5-membered heteroaryl. In some embodiments ring A is pyridine, pyrimidine, pyrazine, pyridazine, or thiophene. In some embodiments ring A is pyridine. In some embodiments ring A is thiophene.

In some embodiments, ring A is $C_3$-$C_6$cycloalkyl or phenyl. In some embodiments, ring A is phenyl.

In some embodiments, ring A is $C_3$-$C_6$cycloalkyl. In some embodiment ring A is cyclopropyl, cyclobutyl, cyclopentyl, cyclohexyl, or cycloheptyl. In some embodiments ring A is cyclopentyl.

In some embodiments, the compound of Formula (II), or a pharmaceutically acceptable salt, solvate, prodrug, or N-oxide thereof has the following structure:

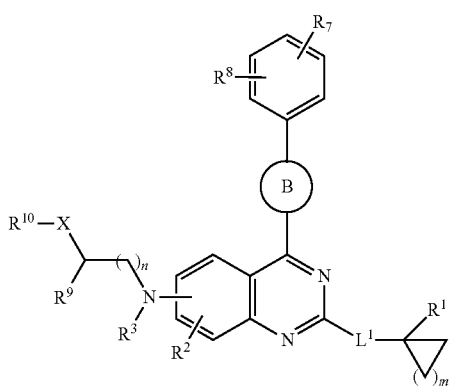

In some embodiments $L^1$ is absent.

In some embodiments $R^2$ is hydrogen, halogen, —CN, —OH, —NO$_2$, optionally substituted $C_1$-$C_4$alkyl, optionally substituted $C_1$-$C_4$alkoxy, optionally substituted $C_1$-$C_4$haloalkyl. In some embodiments $R^2$ is hydrogen, halogen, or methyl.

In some embodiments, the compound of Formula (II), or a pharmaceutically acceptable salt, solvate, prodrug, or N-oxide thereof has the following structure of Formula (IIa):

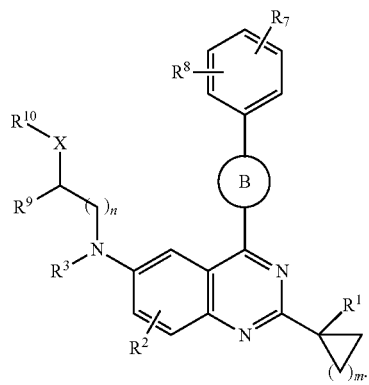

Formula (IIa)

In some embodiments $R^1$ is hydrogen, halogen, $C_1$-$C_4$alkyl, $C_1$-$C_4$alkoxy, $C_1$-$C_4$haloalkyl, $C_1$-$C_4$haloalkoxy, or —N(R$^a$)$_2$; and $R^3$ is hydrogen, or $C_1$-$C_4$alkyl. In some embodiments $R^1$ is F or $C_1$-$C_4$haloalkyl. In some embodiments $R^1$ is hydrogen, F, $C_1$-$C_4$alkyl, or $C_1$-$C_4$fluoroalkyl. In some embodiments $R^1$ is methyl or CF$_3$.

In some embodiments $R^1$ is hydrogen, halogen, $C_1$-$C_4$alkyl, $C_1$-$C_4$alkoxy, $C_1$-$C_4$haloalkyl, $C_1$-$C_4$haloalkoxy, or —N(R$^a$)$_2$; and $R^3$ and $R^9$ are taken together with the intervening atoms to form an optionally substituted $C_2$-$C_6$heterocycloalkyl.

In some embodiments $R^1$ is hydrogen, F, $C_1$-$C_4$alkyl, or $C_1$-$C_4$fluoroalkyl; and $R^3$ and $R^9$ are taken together with the intervening atoms to form an optionally substituted $C_2$-$C_6$heterocycloalkyl. In some embodiments $R^3$ and $R^9$ are taken together with the intervening atoms to form an optionally substituted $C_2$-$C_6$heterocycloalkyl, wherein the optionally substituted $C_2$-$C_6$heterocycloalkyl is optionally substituted azetidenyl, optionally substituted pyrrolidinyl, or optionally substituted piperidinyl. In some embodiments the optionally substituted $C_2$-$C_6$heterocycloalkyl is optionally substituted pyrrolidinyl.

In some embodiments $R^1$ is methyl or CF$_3$.

In some embodiments, the compound of Formula (II), or a pharmaceutically acceptable salt, solvate, prodrug, or N-oxide thereof has the following structure of Formula (IIb):

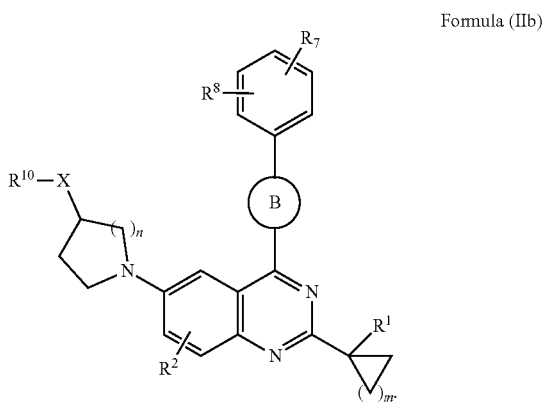

Formula (IIb)

In some embodiments, the compound of Formula (IIb) has one of the following structures:

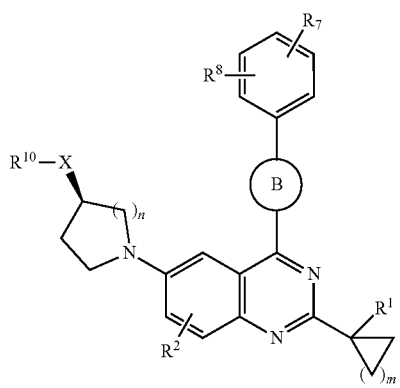

-continued

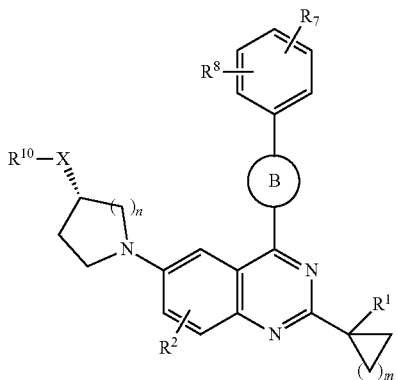

In some embodiments m is 1 or 2. In some embodiments m is 1. In some embodiments m is 2.

In some embodiments n is 1 or 2. In some embodiments n is 1. In some embodiments n is 2.

In some embodiments X is O. In some embodiments X is $N(R^b)$—. In some embodiments X is NH.

In some embodiments $R^{10}$ is hydrogen, or $C_1$-$C_4$alkyl. In some embodiments, $R^{10}$ is hydrogen.

In some embodiments $R^8$ is $C_1$-$C_4$alkoxy, or —$N(R^a)_2$. In some embodiments $R^8$ is methoxy. In some embodiments $R^8$ is —$N(R^a)_2$. In some embodiments $R^8$ is —$N(R^a)_2$, where —$N(R^a)_2$ is dimethylamino. In some embodiments $R^8$ is —$N(R^a)_2$, where —$N(R^a)_2$ is azetidenyl.

In some embodiments $R^7$ is hydrogen, halogen, —CN, —OH, $C_1$-$C_4$alkyl, $C_1$-$C_4$alkoxy, $C_1$-$C_4$haloalkyl, or $C_1$-$C_4$haloalkoxy. In some embodiments $R^7$ is hydrogen or halogen. In some embodiments $R^7$ is hydrogen.

In some embodiments ring B is an N-containing optionally substituted bicyclic heterocycloalkyl. In some embodiments ring B is an N-containing optionally substituted bicyclic heterocycloalkyl, wherein N-containing optionally substituted bicyclic heterocycloalkyl is octahydropyrrolo[3,4-c]pyrrolyl, decahydro-2,6-naphthyridinyl, decahydro-2,7-naphthyridinyl, octahydro-1H-pyrrolo[3,4-c]pyridinyl, or 2,6-diazaspiro[3.3]heptanyl.

In some embodiments ring B is an N-containing optionally substituted tricyclic heterocycloalkyl.

In some embodiments ring B is

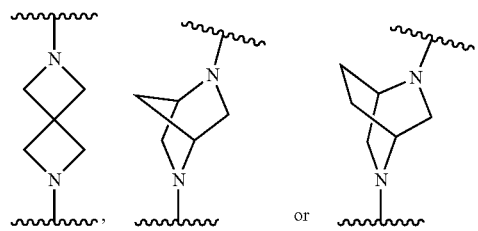

In another aspect, provided herein is a compound of Formula (III), or a pharmaceutically acceptable salt, solvate, prodrug, or N-oxide thereof:

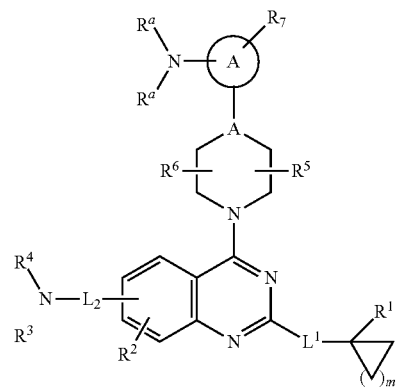

Formula (III)

wherein
ring A is $C_3$-$C_6$cycloalkyl, $C_2$-$C_6$heterocycloalkyl, phenyl or monocyclic heteroaryl;
A is N or CH;
$L^1$ is absent, $C_1$-$C_4$alkylene, $C_1$-$C_4$alkenylene, $C_1$-$C_4$alkynylene, or —$N(R^b)$—;
$R^b$ is hydrogen, $C_1$-$C_4$alkyl or $C_1$-$C_4$haloalkyl, —C(=O)$R^{11}$, —C(=O)—O—$R^{11}$, —S(=O)$_2R^{11}$, or —C(=O)$R^{11}$;
$L^2$ is absent or an optionally substituted $C_1$-$C_4$alkylene;
$R^1$ is hydrogen, halogen, $C_1$-$C_4$alkyl, $C_1$-$C_4$alkoxy, $C_1$-$C_4$haloalkyl, $C_1$-$C_4$haloalkoxy, or —$N(R^a)_2$;
each $R^a$ is independently selected from the group consisting of hydrogen and $C_1$-$C_4$alkyl, —C(=O)$R^{11}$, —C(=O)—O—$R^{11}$, —S(=O)$_2R^{11}$, —C(=O)$R^{11}$, or 2 $R^a$ taken together with the nitrogen to which they are attached form an optionally substituted $C_2$-$C_6$heterocycloalkyl;
$R^2$ is hydrogen, halogen, —CN, —OH, —NO$_2$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, and optionally substituted 5- or 6-membered heteroaryl;
$R^3$ is hydrogen, $C_1$-$C_4$alkyl or $C_1$-$C_4$haloalkyl;
$R^4$ is hydrogen, optionally substituted $C_1$-$C_4$ alkyl, —$C_1$-$C_4$ alkylene-C(=O)O$R^{11}$, —$C_1$-$C_4$ alkylene-O$R^{10}$, or $C_1$-$C_4$ alkylene-N($R^b$)($R^{10}$);
$R^{10}$ is hydrogen, $C_1$-$C_4$alkyl, $C_1$-$C_4$fluoroalkyl, —C(=O)$R^{11}$, —C(=O)—O—$R^{11}$, —C(=O)N($R^{12}$)$R^{13}$, —S(=O)$_2R^{11}$, or —C(=O)$R^{11}$; or $R^{10}$ and $R^b$ are taken together with the N atom to which they are attached to form a $C_2$-$C_6$heterocycle;
or $R^3$ and $R^4$ taken together with the nitrogen to which they are attached form an optionally substituted $C_2$-$C_6$heterocycloalkyl;
$R^5$ and $R^6$ are each independently selected from hydrogen, halogen, —OH, and $C_1$-$C_4$alkyl, or when on the same carbon, $R^5$ and $R^6$ are taken together form an oxo;
$R^7$ is hydrogen, halogen, —CN, —OH, —NO$_2$, —N($R^{12}$)—$R^{13}$, —C(=O)—N($R^{12}$)—$R^{13}$, —N$R^{12}$C(=O)$R^{11}$, —C(=O)—O—$R^{11}$, —O—C(=O)—$R^{11}$, —S$R^{12}$, —S(=O)$R^{11}$, —S(=O)$_2R^{11}$, —N($R^{12}$)S(=O)$_2R^{11}$, —S(=O)$_2$—N($R^{12}$)—$R^{13}$, —C(=O)$R^{11}$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, optionally substituted 5- or 6-membered heteroaryl;

each $R^{11}$ is independently selected from the group consisting of optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl;

each of $R^{12}$ and $R^{13}$ is independently selected from the group consisting of hydrogen, optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl; or $R^{12}$ and $R^{13}$, when on the same nitrogen atom, are taken together with the nitrogen atom to which they are attached to form an optionally substituted $C_2$-$C_6$heterocycloalkyl; and m is 1, 2, 3 or 4; and provided that the compound is not 4-(4-(2-(azetidin-1-yl)phenyl)piperazin-1-yl)-2-cyclopropyl-N,N-dimethylquinazolin-6-amine, 4-(4-(2-(azetidin-1-yl)phenyl)piperazin-1-yl)-2-cyclopropyl-N-ethyl-N-methylquinazolin-6-amine, or 4-(4-(2-(azetidin-1-yl)phenyl)piperidin-1-yl)-2-cyclopropyl-N,N-dimethylquinazolin-6-amine.

In some embodiments ring A is monocyclic heteroaryl. In some embodiments ring A is pyridine, pyrimidine, pyrazine, pyridazine, or thiophene. In some embodiments ring A is pyridine. In some embodiments ring A is thiophene.

In some embodiments ring A is $C_3$-$C_6$cycloalkyl or phenyl. In some embodiments ring A phenyl.

In some embodiments ring A is $C_3$-$C_6$cycloalkyl. In some embodiment ring A is cyclopropyl, cyclobutyl, cyclopentyl, cyclohexyl, or cycloheptyl. In some embodiments ring A is cyclopentyl.

In some embodiments the compound of Formula (III), or a pharmaceutically acceptable salt, solvate, prodrug, or N-oxide thereof has the following structure:

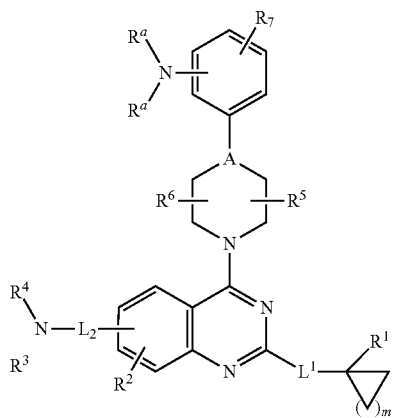

In some embodiments $L^1$ is absent; and $L^2$ is absent.

In some embodiments $R^2$ is hydrogen, halogen, —CN, —OH, —NO$_2$, optionally substituted $C_1$-$C_4$alkyl, optionally substituted $C_1$-$C_4$alkoxy, optionally substituted $C_1$-$C_4$haloalkyl. In some embodiments $R^2$ is hydrogen, halogen, or methyl.

In some embodiments Formula (III), or a pharmaceutically acceptable salt, solvate, prodrug, or N-oxide thereof has the following structure of Formula (IIIa):

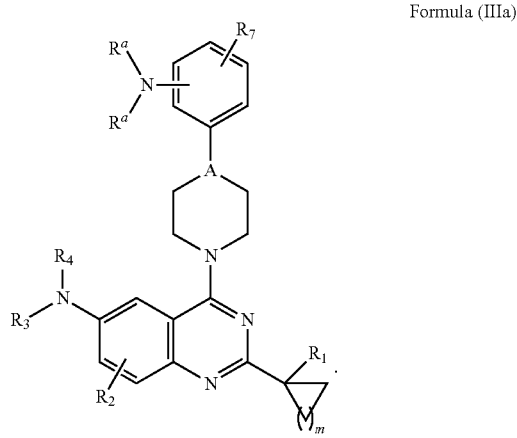

Formula (IIIa)

In some embodiments $R^3$ is hydrogen or $C_1$-$C_4$alkyl; and $R^4$ is $C_1$-$C_4$ alkyl, $C_1$-$C_4$ alkylene-$OR^{10}$, or $C_1$-$C_4$ alkylene-$N(R^b)(R^{10})$. In some embodiments $R^{10}$ and $R^b$ are taken together with the N atom to which they are attached to form a $C_2$-$C_6$heterocycle. In some embodiments $R^{10}$ and $R^b$ are taken together with the N atom to which they are attached to form a $C_2$-$C_6$heterocycle, where the $C_2$-$C_6$heterocycle is a 5 or 6 membered heterocycle. In some embodiments $R^{10}$ and $R^b$ are taken together with the N atom to which they are attached to form a $C_2$-$C_6$heterocycle, where the $C_2$-$C_6$heterocycle is pyrrolidinyl, piperidinyl, or morpholinyl.

In some embodiments $R^3$ and $R^4$ taken together with the nitrogen to which they are attached form an optionally substituted $C_2$-$C_5$heterocycloalkyl. In some embodiments $R^3$ and $R^4$ taken together with the nitrogen to which they are attached form an optionally substituted $C_2$-$C_5$heterocycloalkyl, wherein the optionally substituted $C_2$-$C_5$heterocycloalkyl is optionally substituted azetidenyl, optionally substituted pyrrolidinyl, or optionally substituted piperidinyl. In some embodiments the optionally substituted $C_2$-$C_5$heterocycloalkyl is optionally substituted pyrrolidinyl.

In some embodiments A is CH.

In some embodiments A is N.

In some embodiments $R^1$ is hydrogen, halogen, $C_1$-$C_4$alkyl, $C_1$-$C_4$haloalkyl, or —$N(R^a)_2$.

In some embodiments m is 1 or 2.

In some embodiments each $R^a$ is independently selected from a group consisting of hydrogen and $C_1$-$C_4$ alkyl; or 2 $R^a$ taken together with the nitrogen to which they are attached form an optionally substituted $C_2$-$C_4$heterocycloalkyl.

In some embodiments each $R^a$ is methyl. In some embodiments 2 $R^a$ taken together with the nitrogen to which they are attached form an azeridinyl or azetidinyl ring.

In some embodiments $R^7$ is hydrogen, halogen, —CN, —OH, $C_1$-$C_4$alkyl, $C_1$-$C_4$alkoxy, $C_1$-$C_4$haloalkyl, or $C_1$-$C_4$haloalkoxy.

In yet another aspect, provided herein is a compound of Formula (IV), or a pharmaceutically acceptable salt, solvate, prodrug, or N-oxide thereof:

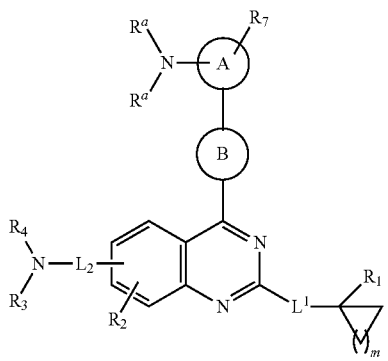

Formula (IV)

wherein, ring A is $C_3$-$C_6$cycloalkyl, $C_2$-$C_6$heterocycloalkyl, phenyl or monocyclic heteroaryl;

ring B is an optionally substituted bicyclic heterocycloalkyl or an optionally substituted tricyclic heterocycloalkyl;

$L^1$ is absent, $C_1$-$C_4$alkylene, $C_1$-$C_4$alkenylene, $C_1$-$C_4$alkynylene, or $N(R^b)$—;

$R^b$ is hydrogen, $C_1$-$C_4$alkyl or $C_1$-$C_4$haloalkyl, —C(=O)$R^{11}$, —C(=O)—O—$R^{11}$, —S(=O)$_2R^{11}$, or —C(=O)$R^{11}$;

$L^2$ is absent or an optionally substituted $C_1$-$C_4$alkylene;

$R^1$ is hydrogen, halogen, $C_1$-$C_4$alkyl, $C_1$-$C_4$alkoxy, $C_1$-$C_4$haloalkyl, $C_1$-$C_4$haloalkoxy, or —N($R^a$)$_2$;

each $R^a$ is independently selected from the group consisting of hydrogen and $C_1$-$C_4$ alkyl, —C(=O)$R^{11}$, —C(=O)—O—$R^{11}$, —S(=O)$_2R^{11}$, —C(=O)$R^{11}$, or 2 $R^a$ taken together with the nitrogen to which they are attached form an optionally substituted $C_2$-$C_6$heterocycloalkyl;

$R^2$ is hydrogen, halogen, —CN, —OH, —NO$_2$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, and optionally substituted 5- or 6-membered heteroaryl;

$R^3$ is hydrogen, $C_1$-$C_4$alkyl or $C_1$-$C_4$haloalkyl;

$R^4$ is hydrogen, optionally substituted $C_1$-$C_4$ alkyl, —$C_1$-$C_4$ alkylene-C(=O)O$R^{11}$, —$C_1$-$C_4$ alkylene-O$R^{10}$, or —$C_1$-$C_4$ alkylene-N($R^b$)($R^{10}$);

$R^{10}$ is hydrogen, $C_1$-$C_4$alkyl, $C_1$-$C_4$fluoroalkyl, —C(=O)$R^{11}$, —C(=O)—O—$R^{11}$, —C(=O)N($R^{12}$)$R^{13}$, —S(=O)$_2R^{11}$, or —C(=O)$R^{11}$; or $R^{10}$ and $R^b$ are taken together with the N atom to which they are attached to form a $C_2$-$C_6$heterocycle;

or $R^3$ and $R^4$ taken together with the nitrogen to which they are attached form an optionally substituted $C_2$-$C_6$heterocycloalkyl;

$R^7$ is hydrogen, halogen, —CN, —OH, —NO$_2$, —N($R^{12}$)—$R^{13}$, —C(=O)—N($R^{12}$)—$R^{13}$, —N$R^{12}$C(=O)$R^{11}$, —C(=O)—O—$R^{11}$, —O—C(=O)—$R^{11}$, —S$R^{12}$, —S(=O)$R^{11}$, —S(=O)$_2R^{11}$, —N($R^{12}$)S(=O)$_2R^{11}$, —S(=O)$_2$—N($R^{12}$)—$R^{13}$, —C(=O)$R^{11}$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, optionally substituted 5- or 6-membered heteroaryl;

each $R^{11}$ is independently selected from the group consisting of optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl;

each of $R^{12}$ and $R^{13}$ is independently selected from the group consisting of hydrogen, optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl; or $R^{12}$ and $R^{13}$, when on the same nitrogen atom, are taken together with the nitrogen atom to which they are attached to form an optionally substituted $C_2$-$C_6$heterocycloalkyl; and m is 1, 2, 3 or 4.

In some embodiments ring A is monocyclic heteroaryl. In some embodiments ring A is pyridine, pyrimidine, pyrazine, pyridazine, or thiophene. In some embodiments ring A is pyridine. In some embodiments ring A is thiophene.

In some ring A is $C_3$-$C_6$cycloalkyl or phenyl.

In some embodiment ring A is cyclopropyl, cyclobutyl, cyclopentyl, cyclohexyl, or cycloheptyl. In some embodiments ring A is cyclopentyl.

In some embodiments the compound of Formula (IV), or a pharmaceutically acceptable salt, solvate, prodrug, or N-oxide thereof has the following structure:

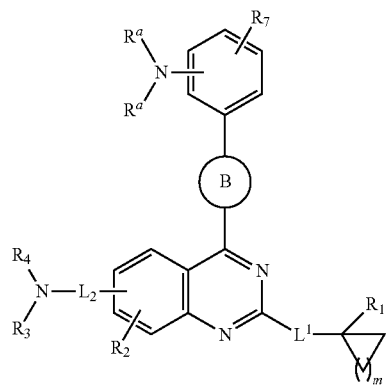

In some embodiments $L^1$ is absent; and $L^2$ is absent.

In some embodiments $R^2$ is hydrogen, halogen, —CN, —OH, —NO$_2$, optionally substituted $C_1$-$C_4$alkyl, optionally substituted $C_1$-$C_4$alkoxy, optionally substituted $C_1$-$C_4$haloalkyl. In some embodiments $R^2$ is hydrogen, halogen, or methyl.

In some embodiments the compound of Formula (IV), or a pharmaceutically acceptable salt, solvate, prodrug, or N-oxide thereof has the following structure of Formula (IVa):

Formula (IVa)

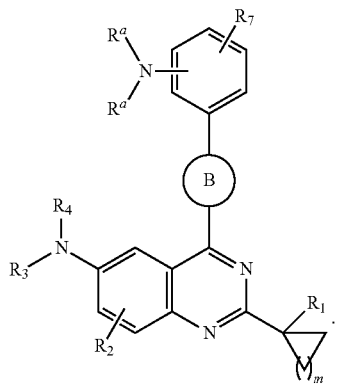

In some embodiments R³ is hydrogen or $C_1$-$C_4$alkyl; and R⁴ is $C_1$-$C_4$ alkyl, $C_1$-$C_4$ alkylene-OR¹⁰, or $C_1$-$C_4$ alkylene-N(R$^b$)(R¹⁰). In some embodiments R¹⁰ and R$^b$ are taken together with the N atom to which they are attached to form a $C_2$-$C_6$heterocycle. In some embodiments the $C_2$-$C_6$heterocycle is pyrrolidinyl, piperidinyl, or morpholinyl.

In some embodiments R³ and R⁴ taken together with the nitrogen to which they are attached form an optionally substituted $C_2$-$C_5$heterocycloalkyl;

In some embodiments the optionally substituted $C_2$-$C_5$heterocycloalkyl is optionally substituted azetidenyl, optionally substituted pyrrolidinyl, or optionally substituted piperidinyl. In some embodiments the optionally substituted $C_2$-$C_5$heterocycloalkyl is optionally substituted pyrrolidinyl.

In some embodiments R¹ is hydrogen, halogen, $C_1$-$C_4$alkyl, $C_1$-$C_4$haloalkyl, or —N(R$^a$)₂.

In some embodiments m is 1 or 2.

In some embodiments each R$^a$ is independently selected from a group consisting of hydrogen and $C_1$-$C_4$ alkyl; or 2 R$^a$ taken together with the nitrogen to which they are attached form an optionally substituted $C_2$-$C_4$heterocycloalkyl.

In some embodiments each R$^a$ is methyl. In some embodiments 2 R$^a$ taken together with the nitrogen to which they are attached form an azeridinyl or azetidinyl ring.

In some embodiments R⁷ is hydrogen, halogen, —CN, —OH, $C_1$-$C_4$alkyl, $C_1$-$C_4$alkoxy, $C_1$-$C_4$haloalkyl, or $C_1$-$C_4$haloalkoxy. In some embodiments R⁷ is hydrogen or halogen. In some embodiments R⁷ is hydrogen.

In some embodiments ring B is an N-containing optionally substituted bicyclic heterocycloalkyl or an N-containing optionally substituted tricyclic heterocycloalkyl. In some embodiments ring B is an N-containing optionally substituted bicyclic heterocycloalkyl or an N-containing optionally substituted tricyclic heterocycloalkyl, wherein the N-containing optionally substituted bicyclic heterocycloalkyl or an N-containing optionally substituted tricyclic heterocycloalkyl is octahydropyrrolo[3,4-c]pyrrolyl, decahydro-2,6-naphthyridinyl, decahydro-2,7-naphthyridinyl, octahydro-1H-pyrrolo[3,4-c]pyridinyl, or 2,6-diazaspiro[3.3]heptanyl.

In some embodiments ring B is

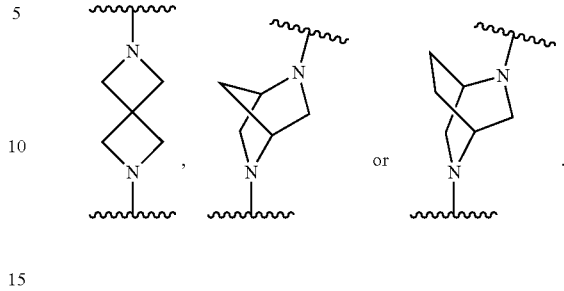

In another aspect, provided herein is a compound of Formula (V), or a pharmaceutically acceptable salt, solvate, prodrug, or N-oxide thereof:

Formula (V)

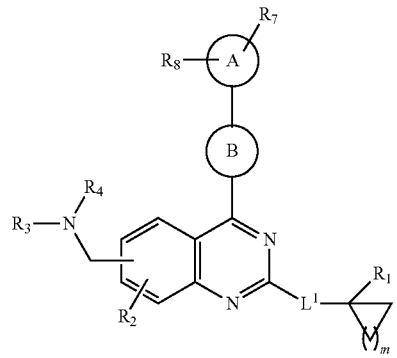

wherein:
ring A is $C_3$-$C_6$cycloalkyl, $C_2$-$C_6$heterocycloalkyl, phenyl or monocyclic heteroaryl;
ring B is an optionally substituted hetereocycloalkyl, wherein if ring B is substituted then it is substituted with R⁵ and R⁶;
L¹ is absent, $C_1$-$C_4$alkylene, $C_1$-$C_4$alkenylene, $C_1$-$C_4$alkynylene, or N(R$^b$)—;
R$^b$ is hydrogen, $C_1$-$C_4$alkyl or $C_1$-$C_4$haloalkyl, —C(=O)R¹¹, —C(=O)—O—R¹¹, —S(=O)₂R¹¹, or —C(=O)R¹¹;
R¹ is hydrogen, halogen, $C_1$-$C_4$alkyl, $C_1$-$C_4$alkoxy, $C_1$-$C_4$haloalkyl, $C_1$-$C_4$haloalkoxy, or —N(R$^a$)₂;
each R$^a$ is independently selected from the group consisting of hydrogen and $C_1$-$C_4$ alkyl, —C(=O)R¹¹, —C(=O)—O—R¹¹, —S(=O)₂R¹¹, —C(=O)R¹¹, or 2 R$^a$ taken together with the nitrogen to which they are attached form an optionally substituted $C_2$-$C_6$heterocycloalkyl;
R² is hydrogen, halogen, —CN, —OH, —NO₂, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted C$_2$-C$_6$heterocycloalkyl, optionally substituted phenyl, and optionally substituted 5- or 6-membered heteroaryl;

R$^3$ is hydrogen, C$_1$-C$_4$alkyl or C$_1$-C$_4$haloalkyl;

R$^4$ is hydrogen, optionally substituted C$_1$-C$_4$ alkyl, —C$_1$-C$_4$ alkylene-C(=O)OR$^{11}$, —C$_1$-C$_4$ alkylene-OR$^{10}$, or —C$_1$-C$_4$ alkylene-N(R$^b$)(R$^{10}$);

R$^{10}$ is hydrogen, C$_1$-C$_4$alkyl, C$_1$-C$_4$fluoroalkyl, —C(=O)R$^{11}$, —C(=O)—O—R$^{11}$, —C(=O)N(R$^{12}$)R$^{13}$, —S(=O)$_2$R$^{11}$, or —C(=O)R$^{11}$; or R$^{10}$ and R$^b$ are taken together with the N atom to which they are attached to form a C$_2$-C$_6$heterocycle;

or R$^3$ and R$^4$ taken together with the nitrogen to which they are attached form an optionally substituted C$_2$-C$_6$heterocycloalkyl;

R$^5$ and R$^6$ are each independently selected from hydrogen, halogen, —OH, and C$_1$-C$_4$alkyl, or when on the same carbon, R$^5$ and R$^6$ are taken together form an oxo;

R$^7$ is hydrogen, halogen, —CN, —OH, —NO$_2$, —N(R$^{12}$)—R$^{13}$, —C(=O)—N(R$^{12}$)—R$^{13}$, —NR$^{12}$C(=O)R$^{11}$, —C(=O)—O—R$^{11}$, —O—C(=O)—R$^{11}$, —SR$^{12}$, —S(=O)R$^{11}$, —S(=O)$_2$R$^{11}$, —N(R$^{12}$)S(=O)$_2$R$^{11}$, —S(=O)$_2$—N(R$^{12}$)—R$^{13}$, —C(=O)R$^{11}$, optionally substituted C$_1$-C$_4$alkyl, optionally substituted C$_1$-C$_4$alkoxy, optionally substituted C$_1$-C$_4$haloalkyl, optionally substituted C$_1$-C$_4$haloalkoxy, optionally substituted C$_3$-C$_6$cycloalkyl, optionally substituted C$_2$-C$_6$heterocycloalkyl, optionally substituted phenyl, optionally substituted 5- or 6-membered heteroaryl;

R$^8$ is hydrogen, —OH, C$_1$-C$_4$alkyl, C$_1$-C$_4$fluoroalkyl, C$_1$-C$_4$alkoxy, C$_1$-C$_4$fluoroalkoxy, or —N(R$^a$)$_2$;

each R$^{11}$ is independently selected from the group consisting of optionally substituted C$_1$-C$_4$alkyl, optionally substituted C$_1$-C$_4$fluoroalkyl, optionally substituted C$_3$-C$_6$cycloalkyl, optionally substituted C$_2$-C$_6$heterocycloalkyl, optionally substituted phenyl, and optionally substituted 5- or 6-membered heteroaryl;

each of R$^{12}$ and R$^{13}$ is independently selected from the group consisting of hydrogen, optionally substituted C$_1$-C$_4$alkyl, optionally substituted C$_1$-C$_4$fluoroalkyl, optionally substituted C$_3$-C$_6$cycloalkyl, optionally substituted C$_2$-C$_6$heterocycloalkyl, optionally substituted phenyl, and optionally substituted 5- or 6-membered heteroaryl; or R$^{12}$ and R$^{13}$, when on the same nitrogen atom, are taken together with the nitrogen atom to which they are attached to form an optionally substituted C$_2$-C$_6$heterocycloalkyl; and m is 1, 2, 3 or 4.

In some embodiments ring A is C$_3$-C$_6$cycloalkyl, or phenyl. In some embodiments ring A is phenyl. In some embodiments ring A is C$_3$-C$_6$cycloalkyl. In some embodiment ring A is cyclopropyl, cyclobutyl, cyclopentyl, cyclohexyl, or cycloheptyl. In some embodiments ring A is cyclopentyl.

In some embodiments ring A is monocyclic heteroaryl. In some embodiments ring A is pyridine, pyrimidine, pyrazine, pyridazine, or thiophene. In some embodiments ring A is pyridine. In some embodiments ring A is thiophene.

In some embodiments the compound of Formula (V), or a pharmaceutically acceptable salt, solvate, prodrug, or N-oxide thereof has the following structure:

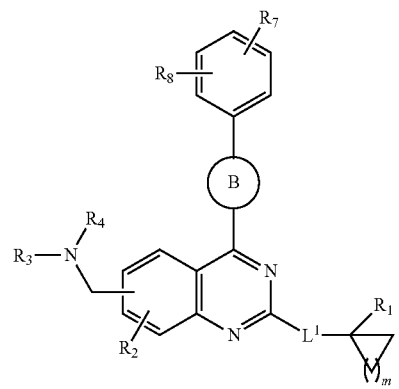

In some embodiments L$^1$ is absent.

In some embodiments R$^2$ is hydrogen, halogen, —CN, —OH, —NO$_2$, optionally substituted C$_1$-C$_4$alkyl, optionally substituted C$_1$-C$_4$alkoxy, optionally substituted C$_1$-C$_4$haloalkyl. In some embodiments R$^2$ is hydrogen, halogen, or methyl.

In some embodiments the compound of Formula (V), or a pharmaceutically acceptable salt, solvate, prodrug, or N-oxide thereof has the following structure of Formula (Va):

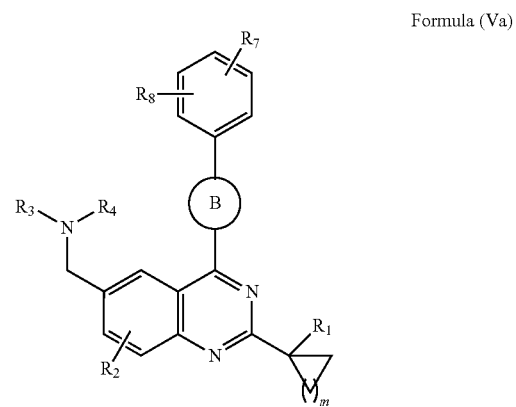

Formula (Va)

In some embodiments R$^3$ is hydrogen or C$_1$-C$_4$alkyl; and R$^4$ is optionally substituted C$_1$-C$_4$ alkyl, —C$_1$-C$_4$ alkylene-OR$^{10}$, or —C$_1$-C$_4$ alkylene-N(R$^b$)(R$^{10}$). In some embodiments R$^{10}$ and R$^b$ are taken together with the N atom to which they are attached to form a C$_2$-C$_6$heterocycle. In some embodiments the C$_2$-C$_6$heterocycle is pyrrolidinyl, piperidinyl, or morpholinyl.

In some embodiments R$^3$ and R$^4$ taken together with the nitrogen to which they are attached form an optionally substituted C$_2$-C$_5$heterocycloalkyl;

In some embodiments the optionally substituted C$_2$-C$_5$heterocycloalkyl is optionally substituted azetidenyl, optionally substituted pyrrolidinyl, or optionally substituted piperidinyl. In some embodiments the optionally substituted C$_2$-C$_5$heterocycloalkyl is optionally substituted pyrrolidinyl.

In some embodiments ring B is an N-containing optionally substituted monocyclic heterocycloalkyl.

In some embodiments ring B is

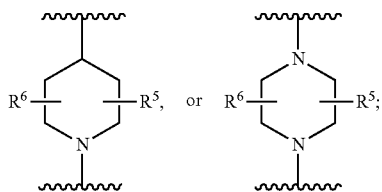

and

R⁵ and R⁶ are each independently selected from hydrogen, halogen, —OH, and C₁-C₄alkyl, or when on the same carbon, R⁵ and R⁶ are taken together form an oxo. In some embodiments R⁵ and R⁶ are each hydrogen.

In some embodiments ring B is an N-containing optionally substituted bicyclic heterocycloalkyl or an N-containing optionally substituted tricyclic heterocycloalkyl. In some embodiments ring B is an N-containing optionally substituted bicyclic heterocycloalkyl or an N-containing optionally substituted tricyclic heterocycloalkyl, wherein the N-containing optionally substituted bicyclic heterocycloalkyl or an N-containing optionally substituted tricyclic heterocycloalkyl is octahydropyrrolo[3,4-c]pyrrolyl, decahydro-2,6-naphthyridinyl, decahydro-2,7-naphthyridinyl, octahydro-1H-pyrrolo[3,4-c]pyridinyl, or 2,6-diazaspiro[3.3]heptanyl.

In some embodiments ring B is

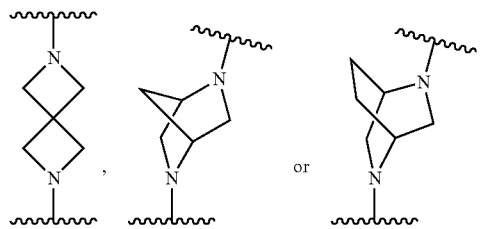

In some embodiments R¹ is hydrogen, halogen, C₁-C₄alkyl, C₁-C₄haloalkyl, or —N(Rᵃ)₂.

In some embodiments m is 1 or 2.

In some embodiments R⁸ is C₁-C₄alkoxy, or —N(Rᵃ)₂. In some embodiments the C₁-C₄alkoxy is methoxy. In some embodiments the —N(Rᵃ)₂ is dimethylamino. In some embodiments the —N(Rᵃ)₂ is azetidenyl.

In some embodiments R⁷ is hydrogen, halogen, —CN, —OH, C₁-C₄alkyl, C₁-C₄alkoxy, C₁-C₄haloalkyl, or C₁-C₄haloalkoxy. In some embodiments R⁷ is hydrogen or halogen. In some embodiments R⁷ is hydrogen.

In yet another aspect, provided herein is a compound of Formula (VI), or a pharmaceutically acceptable salt, solvate, prodrug, or N-oxide thereof:

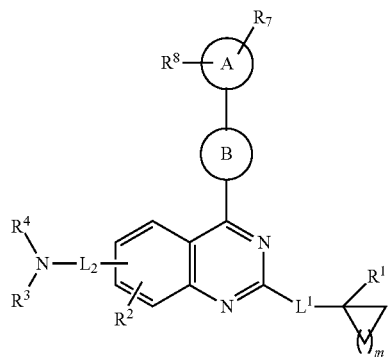

Formula (VI)

wherein, ring A is C₃-C₆cycloalkyl, C₂-C₆heterocycloalkyl, or monocyclic heteroaryl;

ring B is an optionally substituted hetereocycloalkyl, wherein if ring B is substituted then it is substituted with R⁵ and R⁶;

R¹ is hydrogen, halogen, C₁-C₄alkyl, C₁-C₄alkoxy, C₁-C₄haloalkyl, C₁-C₄haloalkoxy, or —N(Rᵃ)₂;

each Rᵃ is independently selected from the group consisting of hydrogen and C₁-C₄ alkyl, —C(=O)R¹¹, —C(=O)—O—R¹¹, —S(=O)₂R¹¹, —C(=O)R¹¹, or 2 Rᵃ taken together with the nitrogen to which they are attached form an optionally substituted C₂-C₆heterocycloalkyl;

L¹ is absent, C₁-C₄alkylene, C₁-C₄alkenylene, C₁-C₄alkynylene, or —N(Rᵇ)—;

Rᵇ is hydrogen, C₁-C₄alkyl or C₁-C₄haloalkyl, —C(=O)R¹¹, —C(=O)—O—R¹¹, —S(=O)₂R¹¹, or —C(=O)R¹¹;

R² is hydrogen, halogen, —CN, —OH, —NO₂, optionally substituted C₁-C₄alkyl, optionally substituted C₁-C₄alkoxy, optionally substituted C₁-C₄haloalkyl, optionally substituted C₁-C₄haloalkoxy, optionally substituted C₃-C₆cycloalkyl, optionally substituted C₂-C₆heterocycloalkyl, optionally substituted phenyl, and optionally substituted 5- or 6-membered heteroaryl;

L² is absent or an optionally substituted C₁-C₄alkylene;

R³ is hydrogen, C₁-C₄alkyl or C₁-C₄haloalkyl;

R⁴ is hydrogen, optionally substituted C₁-C₄ alkyl, —C₁-C₄ alkylene-C(=O)OR¹¹, —C₁-C₄ alkylene-OR¹⁰, or —C₁-C₄ alkylene-N(Rᵇ)(R¹⁰);

R¹⁰ is hydrogen, C₁-C₄alkyl, C₁-C₄fluoroalkyl, —C(=O)R¹¹, —C(=O)—O—R¹¹, —C(=O)N(R¹²)R¹³, —S(=O)₂R¹¹, or —C(=O)R¹¹; or R¹⁰ and Rᵇ are taken together with the N atom to which they are attached to form a C₂-C₆heterocycle;

or R³ and R⁴ taken together with the nitrogen to which they are attached form an optionally substituted C₂-C₆heterocycloalkyl;

R⁵ and R⁶ are each independently selected from hydrogen, halogen, —OH, and C₁-C₄alkyl, or when on the same carbon, R⁵ and R⁶ are taken together form an oxo;

R⁷ is hydrogen, halogen, —CN, —OH, —NO₂, —N(R¹²)—R¹³, —C(=O)—N(R¹²)—R¹³, —NR¹²C(=O)R¹¹, —C(=O)—O—R¹¹, —O—C(=O)—R¹¹, —$SR^{12}$, —$S(=O)R^{11}$, —$S(=O)_2R^{11}$, —$N(R^{12})S(=O)_2R^{11}$, —$S(=O)_2$—$N(R^{12})$—$R^{13}$, —$C(=O)R^{11}$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, optionally substituted 5- or 6-membered heteroaryl;

$R^8$ is hydrogen, —OH, $C_1$-$C_4$alkyl, $C_1$-$C_4$fluoroalkyl, $C_1$-$C_4$alkoxy, $C_1$-$C_4$fluoroalkoxy, or —$N(R^a)_2$;

X is —O— or —$N(R^b)$—;

$R^{10}$ is hydrogen, $C_1$-$C_4$alkyl, $C_1$-$C_4$fluoroalkyl, —$C(=O)R^{11}$, —$C(=O)$—O—$R^{11}$, —$C(=O)N(R^{12})R^{13}$, —$S(=O)_2R^{11}$, or —$C(=O)R^{11}$;

each $R^H$ is independently selected from the group consisting of optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl;

each of $R^{12}$ and $R^{13}$ is independently selected from the group consisting of hydrogen, optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl; or $R^{12}$ and $R^{13}$, when on the same nitrogen atom, are taken together with the nitrogen atom to which they are attached to form an optionally substituted $C_2$-$C_6$heterocycloalkyl;

n is 1, 2 or 3; and m is 1, 2, 3 or 4.

In some embodiments ring A is $C_3$-$C_6$cycloalkyl. In some embodiment ring A is cyclopropyl, cyclobutyl, cyclopentyl, cyclohexyl, or cycloheptyl. In some embodiments ring A is cyclopentyl.

In some embodiments ring A is monocyclic heteroaryl. In some embodiments ring A is monocyclic 5 membered or 6 membered heteroaryl. In some embodiments ring A is monocyclic 5 membered heteroaryl. In some embodiments ring A is monocyclic 6 membered heteroaryl.

In some embodiments ring A is pyridine, pyrimidine, pyrazine, pyridazine, or thiophene. In some embodiments ring A is pyridine. In some embodiments ring A is thiophene.

In some embodiments $L^1$ is absent; and $L^2$ is absent or —$CH_2$—.

In some embodiments $R^2$ is hydrogen, halogen, —CN, —OH, —$NO_2$, optionally substituted $C_1$-$C_4$alkyl, optionally substituted $C_1$-$C_4$alkoxy, optionally substituted $C_1$-$C_4$haloalkyl. In some embodiments $R^2$ is hydrogen, halogen, or methyl.

In some embodiments $R^3$ is hydrogen or $C_1$-$C_4$alkyl; and $R^4$ is $C_1$-$C_4$ alkyl, —$C_1$-$C_4$ alkylene-$OR^{10}$, or —$C_1$-$C_4$ alkylene-$N(R^b)(R^{10})$. In some embodiments $R^{10}$ and $R^b$ are taken together with the N atom to which they are attached to form a $C_2$-$C_6$heterocycle. In some embodiments the $C_2$-$C_6$heterocycle is pyrrolidinyl, piperidinyl, or morpholinyl.

In some embodiments $R^3$ and $R^4$ taken together with the nitrogen to which they are attached form an optionally substituted $C_2$-$C_5$heterocycloalkyl.

In some embodiments the optionally substituted $C_2$-$C_5$heterocycloalkyl is optionally substituted azetidenyl, optionally substituted pyrrolidinyl, or optionally substituted piperidinyl. In some embodiments the optionally substituted $C_2$-$C_5$heterocycloalkyl is optionally substituted pyrrolidinyl.

In some embodiments $R^1$ is hydrogen, halogen, $C_1$-$C_4$alkyl, $C_1$-$C_4$haloalkyl, or —$N(R^a)_2$. In some embodiment $R^1$ is hydrogen. In some embodiments $R^1$ is methyl. $R^1$ is F. $R^1$ is $CF_3$.

In some embodiments m is 1 or 2.

In some embodiments $R^7$ is hydrogen, halogen, —CN, —OH, $C_1$-$C_4$alkyl, $C_1$-$C_4$alkoxy, $C_1$-$C_4$haloalkyl, or $C_1$-$C_4$haloalkoxy. In some embodiments $R^7$ is hydrogen or halogen. $R^7$ is hydrogen.

In some embodiments ring B is an N-containing optionally substituted monocyclic heterocycloalkyl.

In some embodiments ring B is

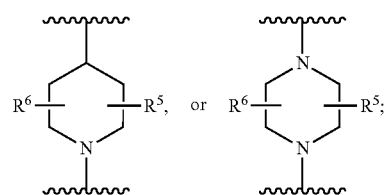

and $R^5$ and $R^6$ are each independently selected from hydrogen, halogen, —OH, and $C_1$-$C_4$alkyl, or when on the same carbon, $R^5$ and $R^6$ are taken together form an oxo. In some embodiments $R^5$ and $R^6$ are each hydrogen.

In some embodiments ring B is an N-containing optionally substituted bicyclic heterocycloalkyl or an N-containing optionally substituted tricyclic heterocycloalkyl.

In some embodiments the N-containing optionally substituted bicyclic heterocycloalkyl is octahydropyrrolo[3,4-c]pyrrolyl, decahydro-2,6-naphthyridinyl, decahydro-2,7-naphthyridinyl, octahydro-1H-pyrrolo[3,4-c]pyridinyl, or 2,6-diazaspiro[3.3]heptanyl.

In some embodiments ring B is

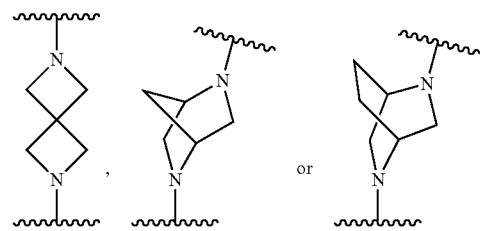

In another aspect, provided herein is a compound of Formula (VII), or a pharmaceutically acceptable salt, solvate, prodrug, or N-oxide thereof:

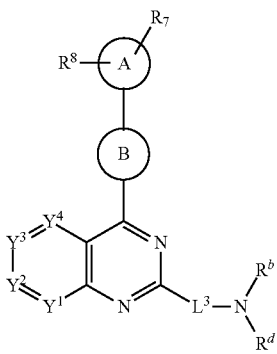

Formula (VII)

wherein:
ring A is $C_3$-$C_6$cycloalkyl, $C_2$-$C_6$heterocycloalkyl, phenyl or monocyclic heteroaryl;
ring B is an optionally substituted hetereocycloalkyl; wherein if ring B is substituted then it is substituted with $R^5$ and $R^6$;
$L^3$ is absent or an optionally substituted $C_1$-$C_4$alkylene;
$R^b$ is hydrogen, optionally substituted $C_1$-$C_4$alkyl, optionally substituted $C_1$-$C_4$haloalkyl, —C(=O)$R^{11}$, —C(=O)—O—$R^{11}$, —S(=O)$_2R^{11}$, or —C(=O)$R^{11}$;
$R^d$ is hydrogen, optionally substituted $C_1$-$C_4$alkyl, optionally substituted $C_1$-$C_4$haloalkyl, or optionally substituted $C_1$-$C_6$heterocycloalkyl, wherein if $R^d$ is substituted then it is substituted with $R^1$;
$R^1$ is hydrogen, halogen, $C_1$-$C_4$alkyl, $C_1$-$C_4$alkoxy, $C_1$-$C_4$haloalkyl, $C_1$-$C_4$haloalkoxy, or —N($R^a$)$_2$;
each $R^a$ is independently selected from the group consisting of hydrogen and $C_1$-$C_4$ alkyl, —C(=O)$R^{11}$, —C(=O)—O—$R^{11}$, —S(=O)$_2R^{11}$, —C(=O)$R^{11}$, or 2 $R^a$ taken together with the nitrogen to which they are attached form an optionally substituted $C_2$-$C_6$heterocycloalkyl;
or $R^b$ and $R^d$ taken together with the nitrogen to which they are attached form an optionally substituted $C_2$-$C_6$heterocycloalkyl;
each $Y^1$, $Y^2$, $Y^3$, and $Y^4$ is independently selected from N and $CR^2$, provided that at least 1 of $Y^1$, $Y^2$, $Y^3$, and $Y^4$ is $CR^2$.
$R^2$ is hydrogen, halogen, —CN, —OH, —NO$_2$, —N($R^3$)—$R^4$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, and optionally substituted 5- or 6-membered heteroaryl;
$R^3$ is hydrogen, $C_1$-$C_4$alkyl or $C_1$-$C_4$haloalkyl;
$R^4$ is hydrogen, optionally substituted $C_1$-$C_4$ alkyl, —$C_1$-$C_4$ alkylene-C(=O)O$R^{11}$, —$C_1$-$C_4$ alkylene-O$R^{10}$, or —$C_1$-$C_4$ alkylene-N($R^b$)($R^{10}$);
$R^{10}$ is hydrogen, $C_1$-$C_4$alkyl, $C_1$-$C_4$fluoroalkyl, —C(=O)$R^{11}$, —C(=O)—O—$R^{11}$, —C(=O)N($R^{12}$)$R^{13}$, —S(=O)$_2R^{11}$, or —C(=O)$R^{11}$; or $R^b$ and $R^{10}$ are taken together with the nitrogen to which they are attached form an optionally substituted $C_2$-$C_6$heterocycloalkyl;
or $R^3$ and $R^4$ taken together with the nitrogen to which they are attached form an optionally substituted $C_2$-$C_6$heterocycloalkyl;

$R^5$ and $R^6$ are each independently selected from hydrogen, halogen, —OH, and $C_1$-$C_4$alkyl, or when on the same carbon, $R^5$ and $R^6$ are taken together form an oxo;
$R^7$ is hydrogen, halogen, —CN, —OH, —NO$_2$, —N($R^{12}$)—$R^{13}$, —C(=O)—N($R^{12}$)—$R^{13}$, —N$R^{12}$C(=O)$R^{11}$, —C(=O)—O—$R^{11}$, —O—C(=O)—$R^{11}$, —S$R^{12}$, —S(=O)$R^{11}$, —S(=O)$_2R^{11}$, —N($R^{12}$)S(=O)$_2R^{11}$, —S(=O)$_2$—N($R^{12}$)—$R^{13}$, —C(=O)$R^{11}$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, optionally substituted 5- or 6-membered heteroaryl;
$R^8$ is hydrogen, —OH, $C_1$-$C_4$alkyl, $C_1$-$C_4$fluoroalkyl, $C_1$-$C_4$alkoxy, $C_1$-$C_4$fluoroalkoxy, or —N($R^a$)$_2$;
each $R^{11}$ is independently selected from the group consisting of optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl;
each of $R^{12}$ and $R^{13}$ is independently selected from the group consisting of hydrogen, optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl; or $R^{12}$ and $R^{13}$, when on the same nitrogen atom, are taken together with the nitrogen atom to which they are attached to form an optionally substituted $C_2$-$C_6$heterocycloalkyl.

In some embodiments ring A is $C_3$-$C_6$cycloalkyl or phenyl.

In some embodiment ring A is cyclopropyl, cyclobutyl, cyclopentyl, cyclohexyl, or cycloheptyl. In some embodiments ring A is cyclopentyl.

In some embodiments ring A is monocyclic heteroaryl. In some embodiments ring A is pyridine, pyrimidine, pyrazine, pyridazine, or thiophene. In some embodiments ring A is pyridine. In some embodiments ring A is thiophene.

In some embodiments the compound of Formula (VII), or a pharmaceutically acceptable salt, solvate, prodrug, or N-oxide thereof has the following structure of Formula (VIIa):

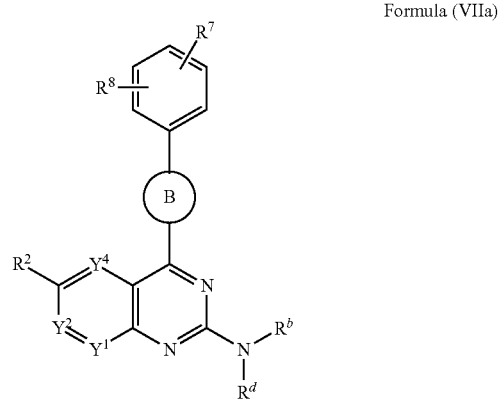

Formula (VIIa)

In some embodiments $Y^1$ is N. In some embodiments $Y^2$ is N. In some embodiments $Y^4$ is N.

In some embodiments $R^2$ is —N($R^3$)—$R^4$; and $Y^2$ is CH.

In some embodiments $Y^2$ is $CR^2$; and each $R^2$ is independently selected from a group consisting of hydrogen and optionally substituted $C_1$-$C_4$alkoxy. In some embodiments the optionally substituted $C_1$-$C_4$alkoxy is methoxy.

In some embodiments ring B is an N-containing optionally substituted monocyclic heterocycloalkyl.

In some embodiments ring B is

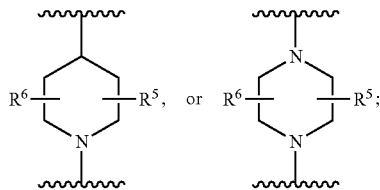

and
$R^5$ and $R^6$ are each independently selected from hydrogen, halogen, —OH, and $C_1$-$C_4$alkyl, or when on the same carbon, $R^5$ and $R^6$ are taken together form an oxo. In some embodiments $R^5$ and $R^6$ are each hydrogen.

In some embodiments ring B is an N-containing optionally substituted bicyclic heterocycloalkyl or an N-containing optionally substituted tricyclic heterocycloalkyl. In some embodiments ring B is an N-containing optionally substituted bicyclic heterocycloalkyl or an N-containing optionally substituted tricyclic heterocycloalkyl, wherein the N-containing optionally substituted bicyclic heterocycloalkyl or an N-containing optionally substituted tricyclic heterocycloalkyl is octahydropyrrolo[3,4-c]pyrrolyl, decahydro-2,6-naphthyridinyl, decahydro-2,7-naphthyridinyl, octahydro-1H-pyrrolo[3,4-c]pyridinyl, or 2,6-diazaspiro[3.3]heptanyl.

In some embodiments ring B is

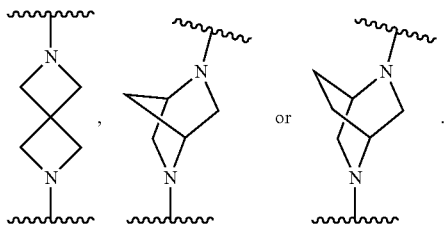

In some embodiments $R^b$ is hydrogen or optionally substituted $C_1$-$C_4$alkyl; and $R^d$ is optionally substituted $C_1$-$C_4$alkyl or optionally substituted $C_1$-$C_6$heterocycloalkyl; or $R^b$ and $R^d$ taken together with the nitrogen to which they are attached form an optionally substituted $C_2$-$C_5$heterocycloalkyl. In some embodiments the optionally substituted $C_2$-$C_5$heterocycle is optionally substituted pyrrolidinyl, piperidinyl, or morpholinyl.

In some embodiments $R^8$ is $C_1$-$C_4$alkoxy, or —N($R^a$)$_2$; and $R^7$ is hydrogen, halogen, —CN, —OH, $C_1$-$C_4$alkyl, $C_1$-$C_4$alkoxy, $C_1$-$C_4$haloalkyl, or $C_1$-$C_4$haloalkoxy. In some embodiments $R^8$ is methoxy or —N($R^a$)$_2$. In some embodiments —N($R^a$)$_2$ is dimethylamino, aziridinyl, or azetidinyl. In some embodiments —N($R^a$)$_2$ is dimethylamino. In some embodiments —N($R^a$)$_2$ is azetidinyl.

In yet another aspect, provided herein is a compound of Formula (VIII), or a pharmaceutically acceptable salt, solvate, prodrug, or N-oxide thereof:

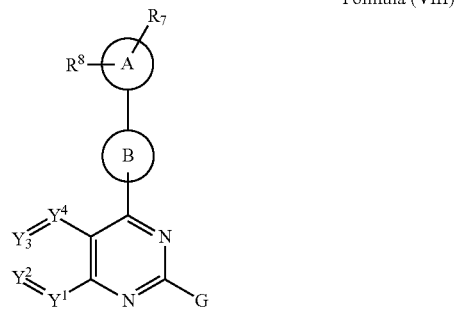

Formula (VIII)

wherein:
ring A is $C_3$-$C_6$cycloalkyl, $C_2$-$C_6$heterocycloalkyl, phenyl or monocyclic heteroaryl;
ring B is an optionally substituted hetereocycloalkyl;
each $Y^1$, $Y^2$, $Y^3$, and $Y^4$ is independently selected from N and $CR^2$, provided that at least 1 of $Y^1$, $Y^2$, $Y^d$, and $Y^4$ is N;
G is optionally substituted $C_1$-$C_4$alkyl, optionally substituted $C_1$-$C_4$haloalkyl, -$L^1$-$R^d$, or -$L^3$-N($R^b$)—$R^d$;
$L^1$ is absent, $C_1$-$C_4$alkylene, $C_1$-$C_4$alkenylene, $C_1$-$C_4$alkynylene, or —N($R^b$)—;
$L^3$ is absent or an optionally substituted $C_1$-$C_4$alkylene;
$R^b$ is hydrogen, optionally substituted $C_1$-$C_4$alkyl, optionally substituted $C_1$-$C_4$haloalkyl, —C(=O)R$^{11}$, —C(=O)—O—R$^{11}$, —S(=O)$_2$R$^{11}$, or —C(=O)R$^{11}$;
$R^d$ is hydrogen, optionally substituted $C_1$-$C_4$alkyl, optionally substituted $C_1$-$C_4$haloalkyl, or optionally substituted $C_1$-$C_6$heterocycloalkyl, wherein if $R^d$ is substituted then it is substituted with $R^1$;
$R^1$ is hydrogen, halogen, $C_1$-$C_4$alkyl, $C_1$-$C_4$alkoxy, $C_1$-$C_4$haloalkyl, $C_1$-$C_4$haloalkoxy, or —N($R^a$)$_2$;
each $R^a$ is independently selected from the group consisting of hydrogen and $C_1$-$C_4$ alkyl, —C(=O)R$^{11}$, —C(=O)—O—R$^{11}$, —S(=O)$_2$R$^{11}$, —C(=O)R$^{11}$, or 2 $R^a$ taken together with the nitrogen to which they are attached form an optionally substituted $C_2$-$C_6$heterocycloalkyl;
or $R^b$ and $R^d$ taken together with the nitrogen to which they are attached form an optionally substituted $C_2$-$C_6$heterocycloalkyl;
$R^2$ is hydrogen, halogen, —CN, —OH, —NO$_2$, —N($R^3$)—$R^4$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, and optionally substituted 5- or 6-membered heteroaryl;
$R^3$ is hydrogen, $C_1$-$C_4$alkyl or $C_1$-$C_4$haloalkyl;
$R^4$ is hydrogen, optionally substituted $C_1$-$C_4$ alkyl, —$C_1$-$C_4$ alkylene-C(=O)OR$^{11}$, —$C_1$-$C_4$ alkylene-OR$^{10}$, or —$C_1$-$C_4$ alkylene-N($R^b$)($R^{10}$);

$R^{10}$ is hydrogen, $C_1$-$C_4$alkyl, $C_1$-$C_4$fluoroalkyl, —C(=O)$R^{11}$, —C(=O)—O—$R^{11}$, —C(=O)N($R^{12}$)$R^{13}$, —S(=O)$_2R^{11}$, or —C(=O)$R^{11}$; or $R^b$ and $R^{10}$ are taken together with the nitrogen to which they are attached form an optionally substituted $C_2$-$C_6$heterocycloalkyl;

or $R^3$ and $R^4$ taken together with the nitrogen to which they are attached form an optionally substituted $C_2$-$C_6$heterocycloalkyl;

$R^7$ is hydrogen, halogen, —CN, —OH, —NO$_2$, —N($R^{12}$)—$R^{13}$, —C(=O)—N($R^{12}$)—$R^{13}$, —N$R^{12}$C(=O)$R^{11}$, —C(=O)—O—$R^{11}$, —O—C(=O)—$R^{11}$, —S$R^{12}$, —S(=O)$R^{11}$, —S(=O)$_2R^{11}$, —N($R^{12}$)S(=O)$_2R^{11}$, —S(=O)$_2$—N($R^{12}$)—$R^{13}$, —C(=O)$R^{11}$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, optionally substituted 5- or 6-membered heteroaryl;

$R^8$ is hydrogen, —OH, $C_1$-$C_4$alkyl, $C_1$-$C_4$fluoroalkyl, $C_1$-$C_4$alkoxy, $C_1$-$C_4$fluoroalkoxy, or —N($R^a$)$_2$;

each $R^a$ is independently selected from the group consisting of hydrogen and $C_1$-$C_4$ alkyl, —C(=O)$R^{11}$, —C(=O)—O—$R^{11}$, —S(=O)$_2R^{11}$, —C(=O)$R^{11}$, or 2 $R^a$ taken together with the nitrogen to which they are attached form an optionally substituted $C_2$-$C_6$heterocycloalkyl;

each is independently selected from the group consisting of optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl;

each of $R^{12}$ and $R^{13}$ is independently selected from the group consisting of hydrogen, optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl; or $R^{12}$ and $R^{13}$, when on the same nitrogen atom, are taken together with the nitrogen atom to which they are attached to form an optionally substituted $C_2$-$C_6$heterocycloalkyl;

provided that the compound is not 2-cyclopropyl-6-methoxy-4-(4-(2-methoxyphenyl)piperazin-1-yl)pyrido[3,4-d]pyrimidine or 2-cyclopropyl-4-(4-(2-methoxyphenyl)piperazin-1-yl)pyrido[2,3-d]pyrimidine.

In some embodiments ring A is $C_3$-$C_6$cycloalkyl or phenyl.

In some embodiment ring A is cyclopropyl, cyclobutyl, cyclopentyl, cyclohexyl, or cycloheptyl. In some embodiments ring A is cyclopentyl.

In some embodiments the compound of Formula (VIII), or a pharmaceutically acceptable salt, solvate, prodrug, or N-oxide thereof has the following structure:

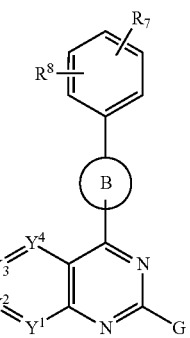

In some embodiments ring A is monocyclic heteroaryl.

In some embodiments ring A is pyridine, pyrimidine, pyrazine, pyridazine, or thiophene. In some embodiments ring A is pyridine. In some embodiments ring A is thiophene.

In some embodiments $Y^1$ is N. In some embodiments $Y^2$ is N. In some embodiments $Y^3$ is N. In some embodiments $Y^4$ is N.

In some embodiments the compound of Formula (VIII), or a pharmaceutically acceptable salt, solvate, prodrug, or N-oxide thereof has the following structure of Formula (VIIIa):

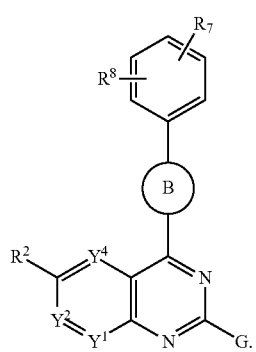

Formula (VIIIa)

In some embodiments $Y^2$ is N; $R^2$ is —N($R^3$)—$R^4$; $R^3$ is hydrogen or $C_1$-$C_4$alkyl; $R^4$ is hydrogen, optionally substituted $C_1$-$C_4$ alkyl, —$C_1$-$C_4$ alkylene-O$R^{10}$, or —$C_1$-$C_4$ alkylene-N($R^b$)(e), and $_RE)_{is}$ hydrogen, $C_1$-$C_4$alkyl, $C_1$-$C_4$fluoroalkyl, —C(=O)$R^{11}$, —C(=O)—O—$R^{11}$, —C(=O)N($R^{12}$)$R^{13}$, —S(=O)$_2R^{11}$, or —C(=O)$R^{11}$; or $R^b$ and $R^{10}$ are taken together with the nitrogen to which they are attached form an optionally substituted $C_2$-$C_6$heterocycloalkyl. In some embodiments $R^b$ and $R^{10}$ are taken together with the nitrogen to which they are attached form an optionally substituted $C_2$-$C_6$heterocycloalkyl, wherein the optionally substituted $C_2$-$C_6$heterocycloalkyl is optionally substituted pyrrolidinyl, piperidinyl, or morpholinyl.

In some embodiments $Y^2$ is N; $R^2$ is —N($R^3$)—$R^4$; and $R^3$ and $R^4$ taken together with the nitrogen to which they are attached form an optionally substituted $C_2$-$C_6$heterocycloalkyl.

In some embodiments the optionally substituted $C_2$-$C_6$heterocycloalkyl is optionally substituted azetidenyl, optionally substituted pyrrolidinyl, or optionally substituted piperidinyl. In some embodiments the optionally substituted $C_2$-$C_6$heterocycloalkyl is optionally substituted pyrrolidinyl.

In some embodiments $Y^2$ is $CR^2$; and each $R^2$ is independently selected from the group consisting of hydrogen and optionally substituted $C_1$-$C_4$alkoxy. In some embodiments the optionally substituted $C_1$-$C_4$alkoxy is methoxy.

In some embodiments ring B is an N-containing optionally substituted monocyclic heterocycloalkyl.

In some embodiments ring B is

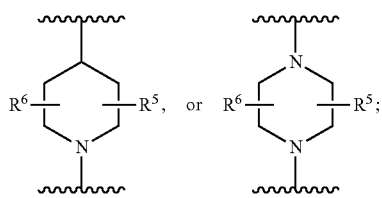

and $R^5$ and $R^6$ are each independently selected from hydrogen, halogen, —OH, and $C_1$-$C_4$alkyl, or when on the same carbon, $R^5$ and $R^6$ are taken together form an oxo.

In some embodiments $R^5$ and $R^6$ are each hydrogen.

In some embodiments ring B is an N-containing optionally substituted bicyclic heterocycloalkyl or an N-containing optionally substituted tricyclic heterocycloalkyl. In some embodiments ring B is an N-containing optionally substituted bicyclic heterocycloalkyl or an N-containing optionally substituted tricyclic heterocycloalkyl, wherein the N-containing optionally substituted bicyclic heterocycloalkyl or an N-containing optionally substituted tricyclic heterocycloalkyl is octahydropyrrolo[3,4-c]pyrrolyl, decahydro-2,6-naphthyridinyl, decahydro-2,7-naphthyridinyl, octahydro-1H-pyrrolo[3,4-c]pyridinyl, or 2,6-diazaspiro[3.3]heptanyl.

In some embodiments ring B is

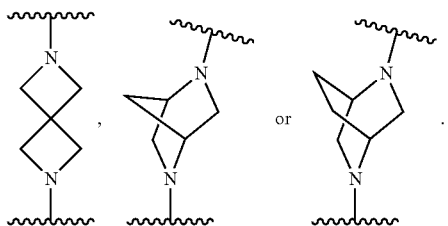

In some embodiments, G is -$L^1$-$R^d$; $L^1$ is absent; and $R^d$ is an optionally substituted $C_3$-$C_6$cycloalkyl.

In some embodiments $R^d$ is

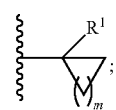

$R^1$ is hydrogen, halogen, $C_1$-$C_4$alkyl or $C_1$-$C_4$haloalkyl; and m is 1 or 2.

In some embodiments, $R^1$ is hydrogen, halogen, $C_1$-$C_4$alkyl, or $C_1$-$C_4$haloalkyl. In some embodiments, $R^1$ is hydrogen, F, $C_1$-$C_4$alkyl, or $C_1$-$C_4$fluoroalkyl.

In some embodiments $R^1$ is F or $C_1$-$C_4$fluoroalkyl. In some embodiments $R^1$ is F or $CF_3$.

In some embodiments $R^d$ is cyclopropyl, cyclobutyl, or cyclopentyl. In some embodiments, $R^d$ is cyclopropyl. In some embodiments $R^1$ is F, methyl, or $CF_3$. In some embodiment $R^1$ is F.

In some embodiments $R^8$ is $C_1$-$C_4$alkoxy, or —$N(R^a)_2$; and $R^7$ is hydrogen, halogen, —CN, —OH, $C_1$-$C_4$alkyl, $C_1$-$C_4$alkoxy, $C_1$-$C_4$haloalkyl, or $C_1$-$C_4$haloalkoxy. In some embodiment $R^8$ is methoxy or —$N(R^a)_2$. In some embodiments —$N(R^a)_2$ is dimethylamino, azeridinyl, or azetidinyl. In some embodiments —$N(R^a)_2$ is azetidinyl. In some embodiments $R^7$ is hydrogen or halogen. In some embodiments $R^7$ is hydrogen.

Non-limiting examples of compounds of Formula (I), (II), (III), (IV), (V), (VI), (VII) or (VIII), include:

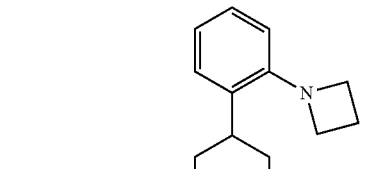

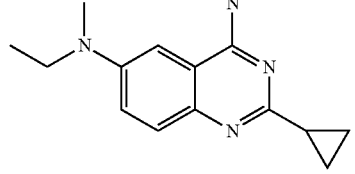

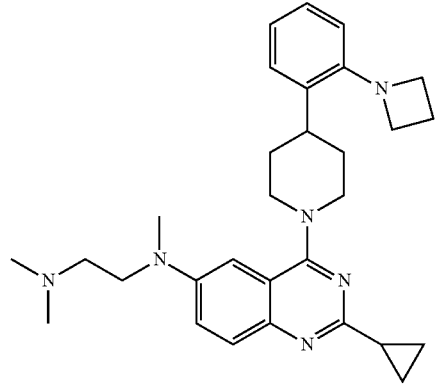

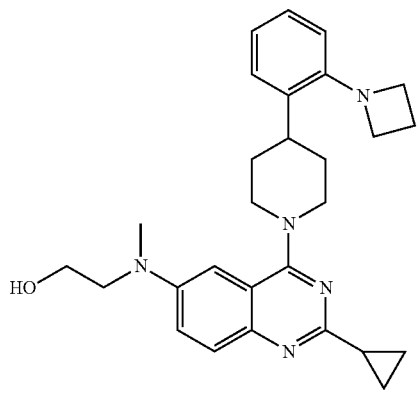

49
-continued
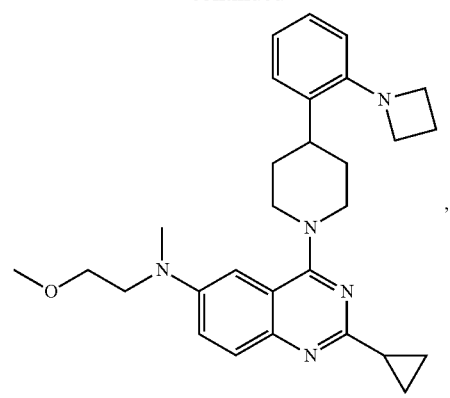
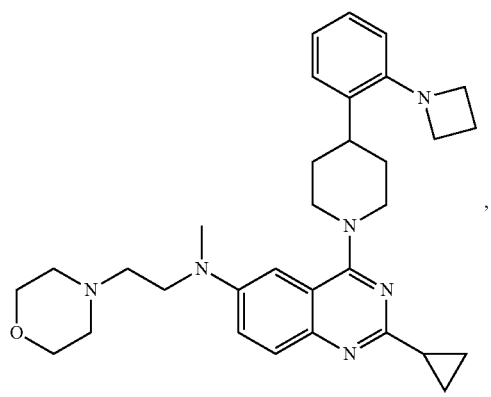
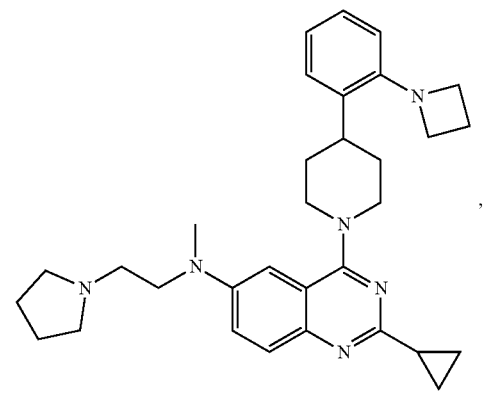
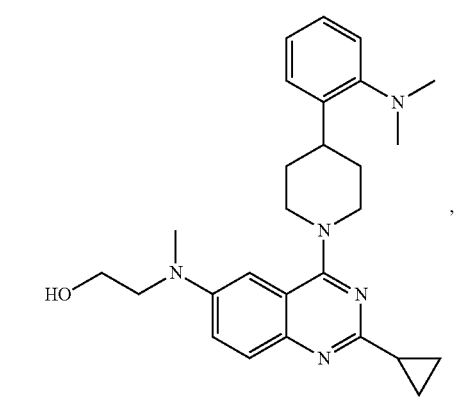
50
-continued
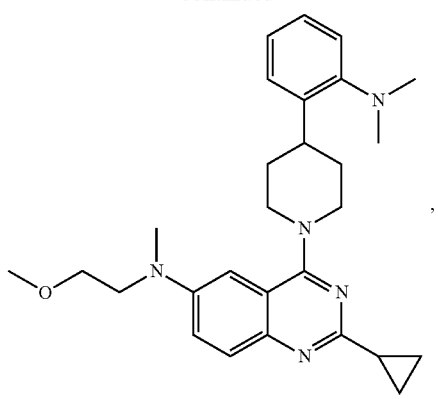
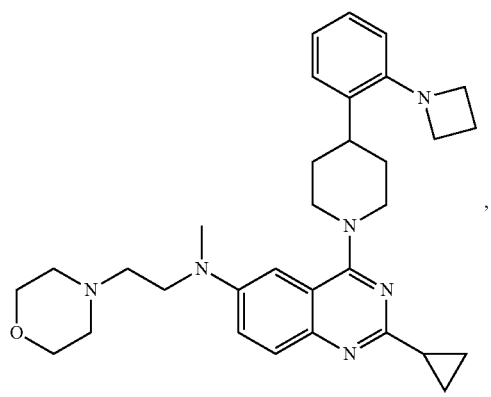

51
-continued
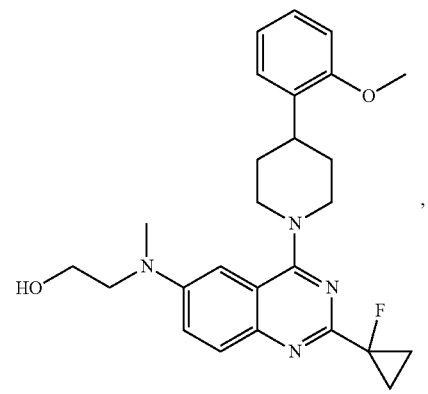
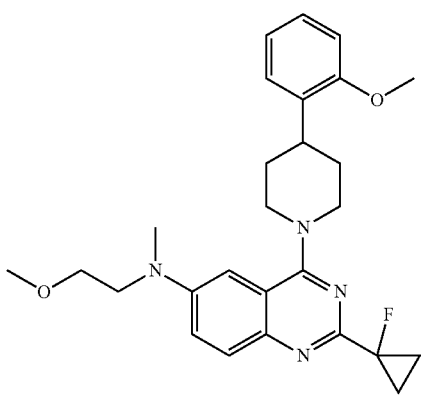
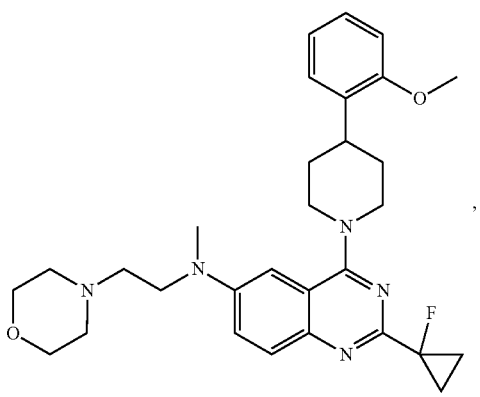
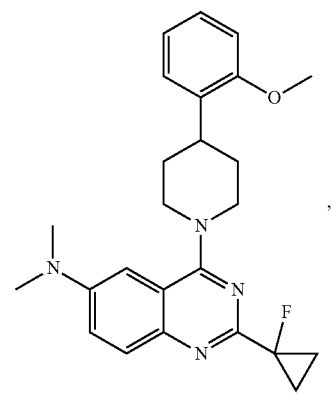
52
-continued
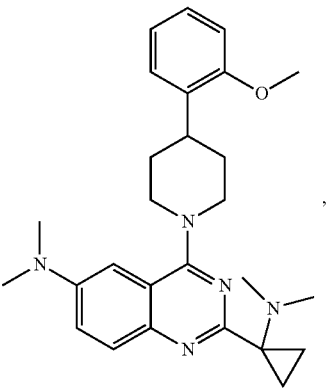
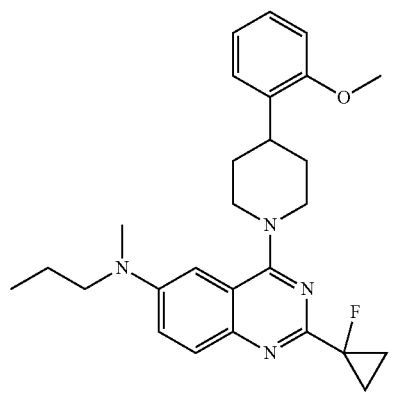
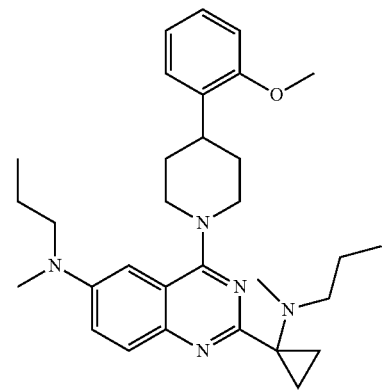
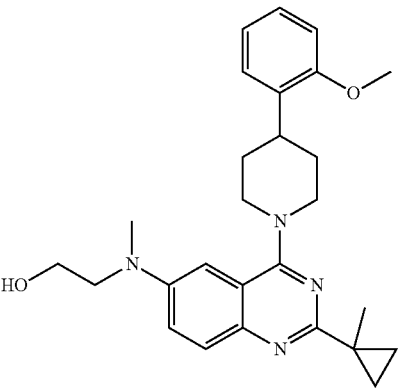

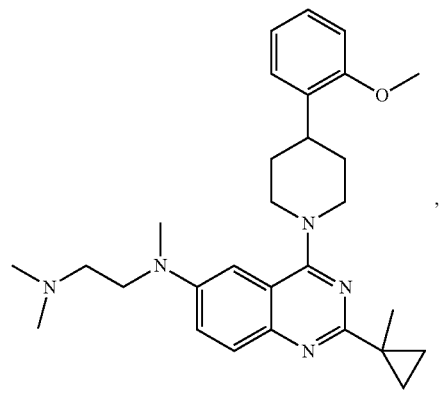,
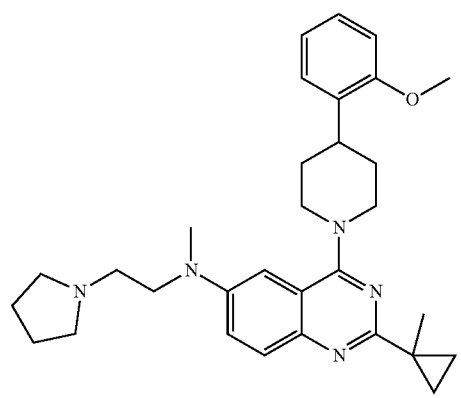,
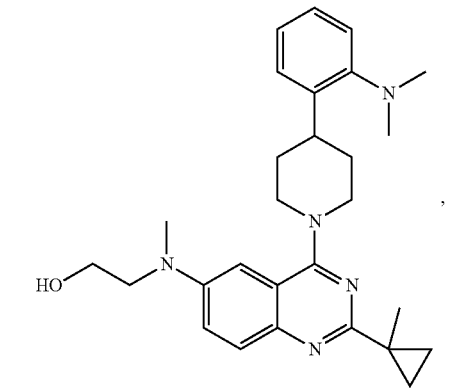,
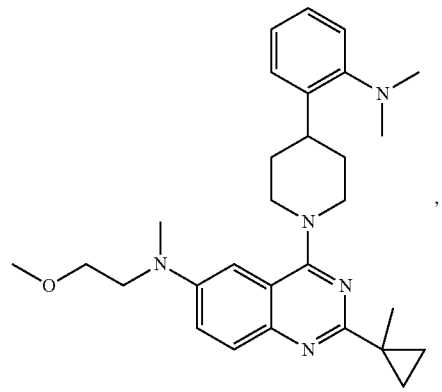,
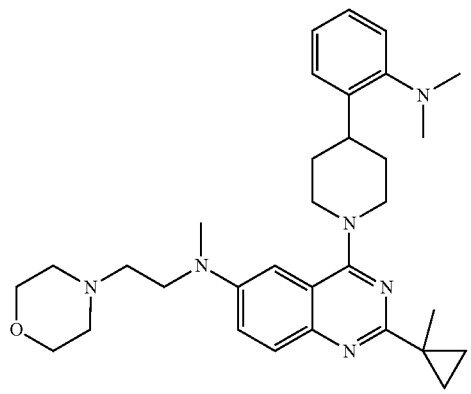,
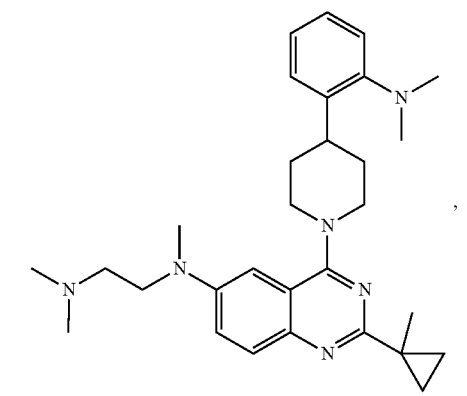,
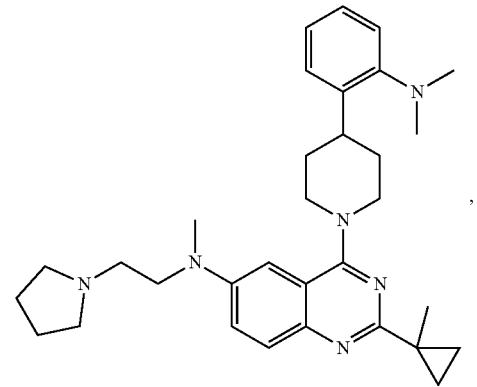,
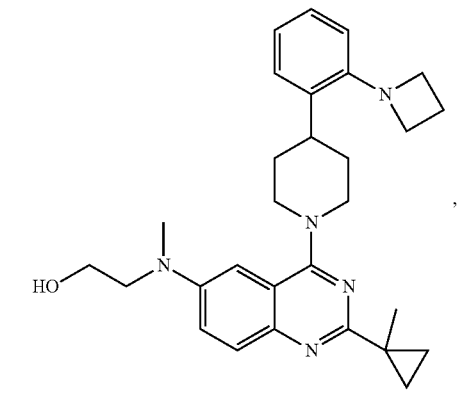, 55
-continued
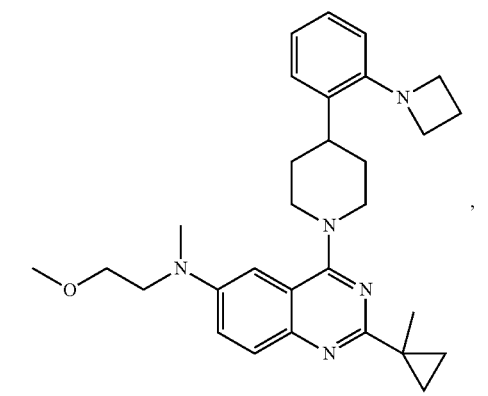
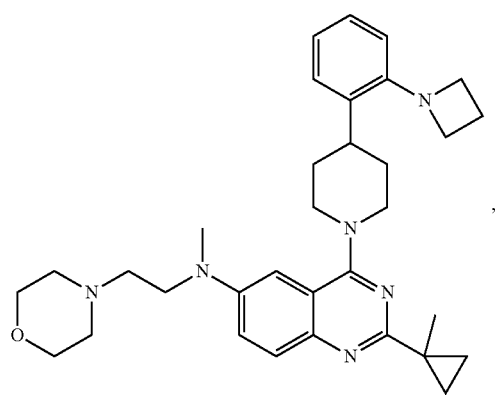
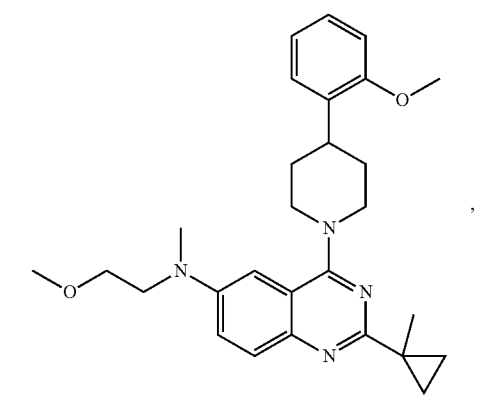
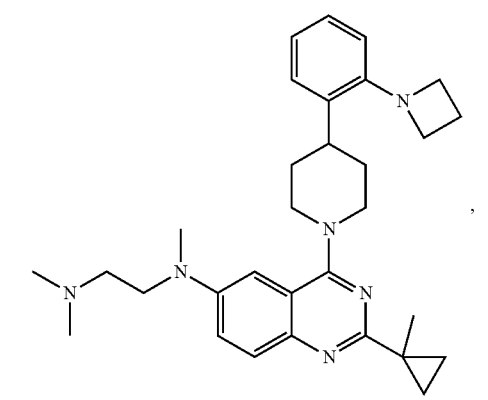
56
-continued
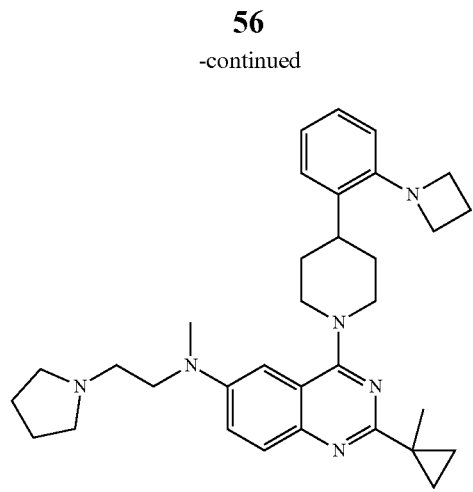
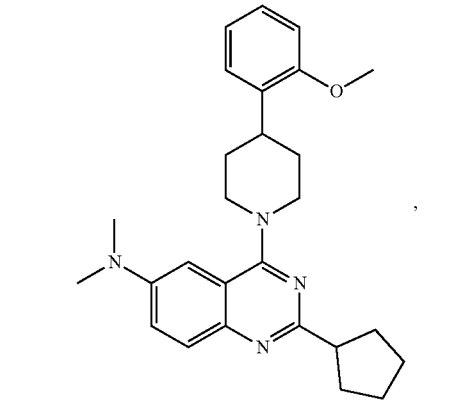
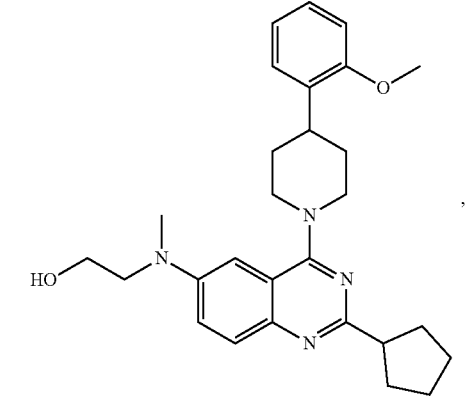
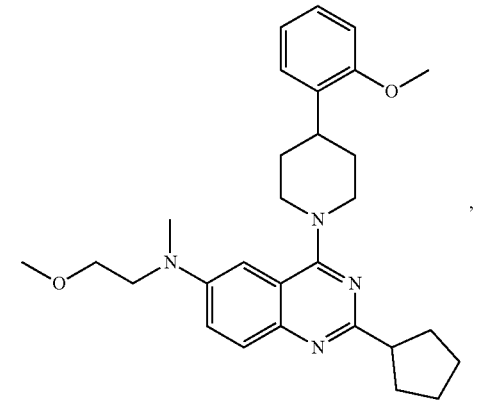

57
-continued
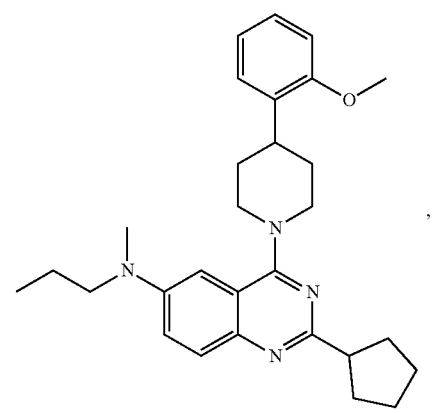
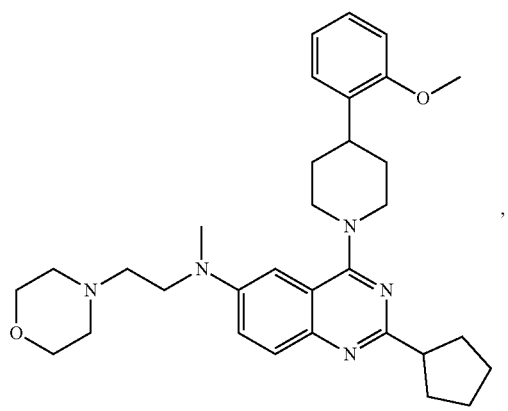
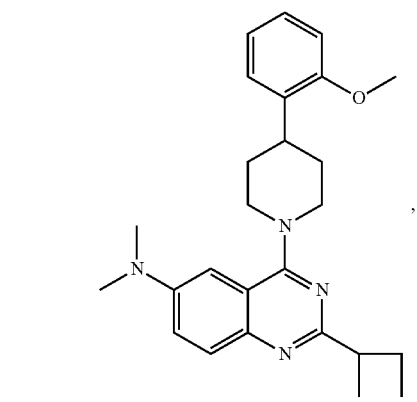
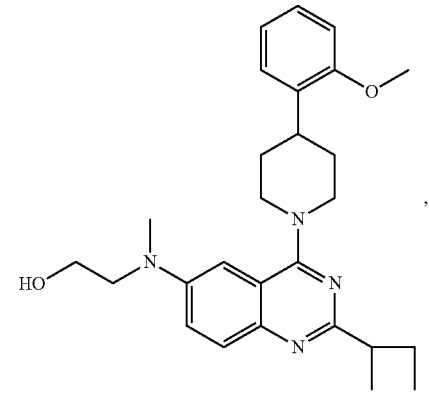
58
-continued
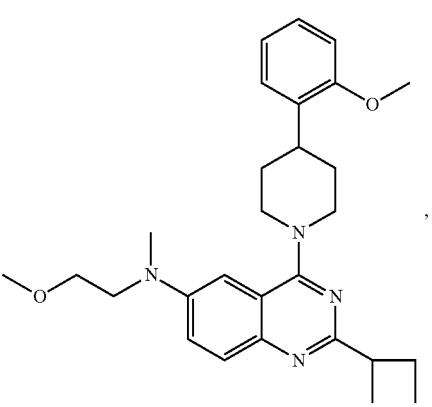
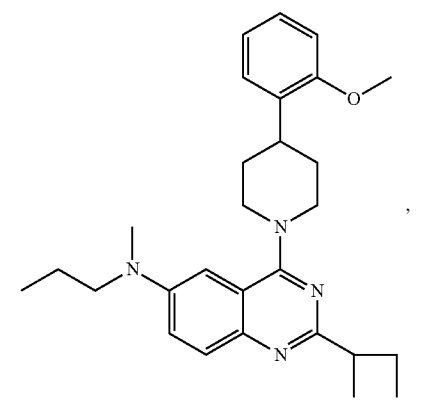
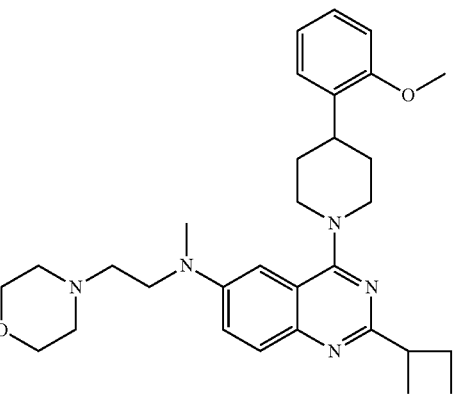
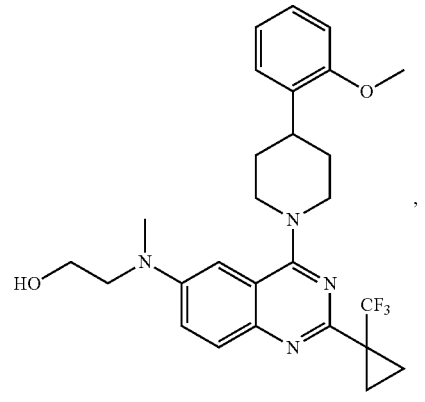

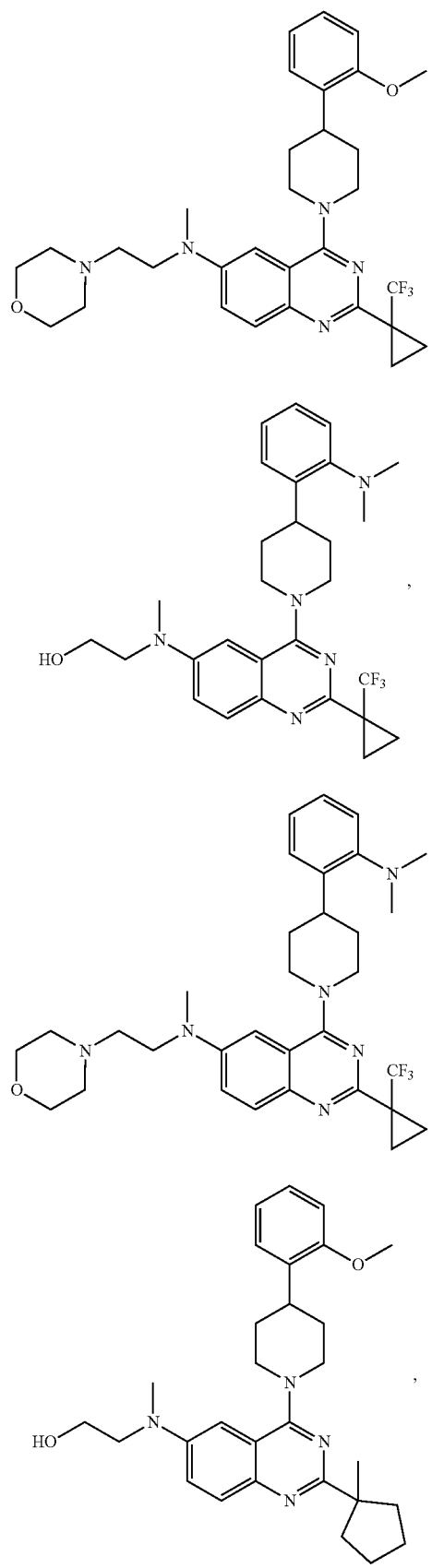

61
-continued
62
-continued
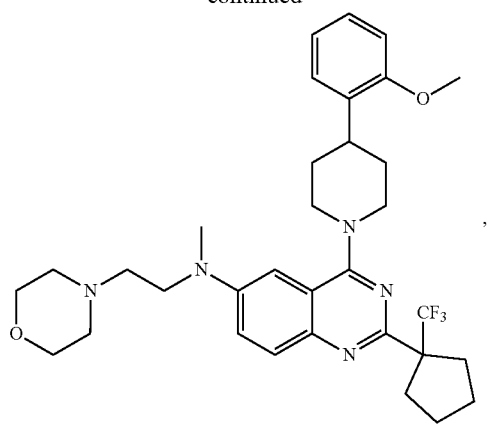
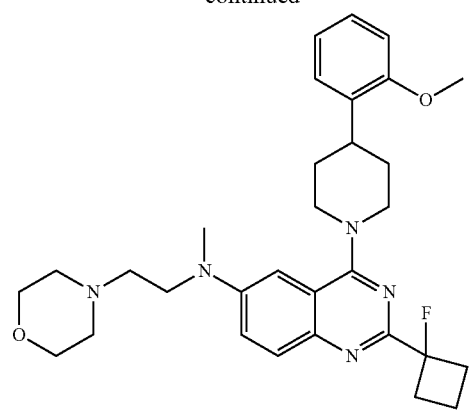

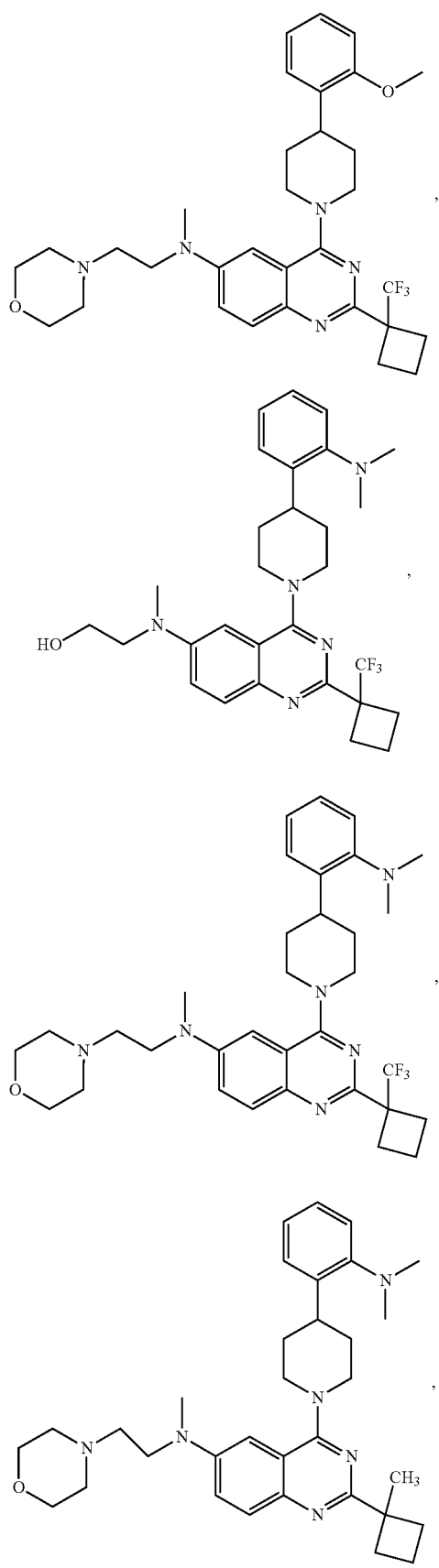
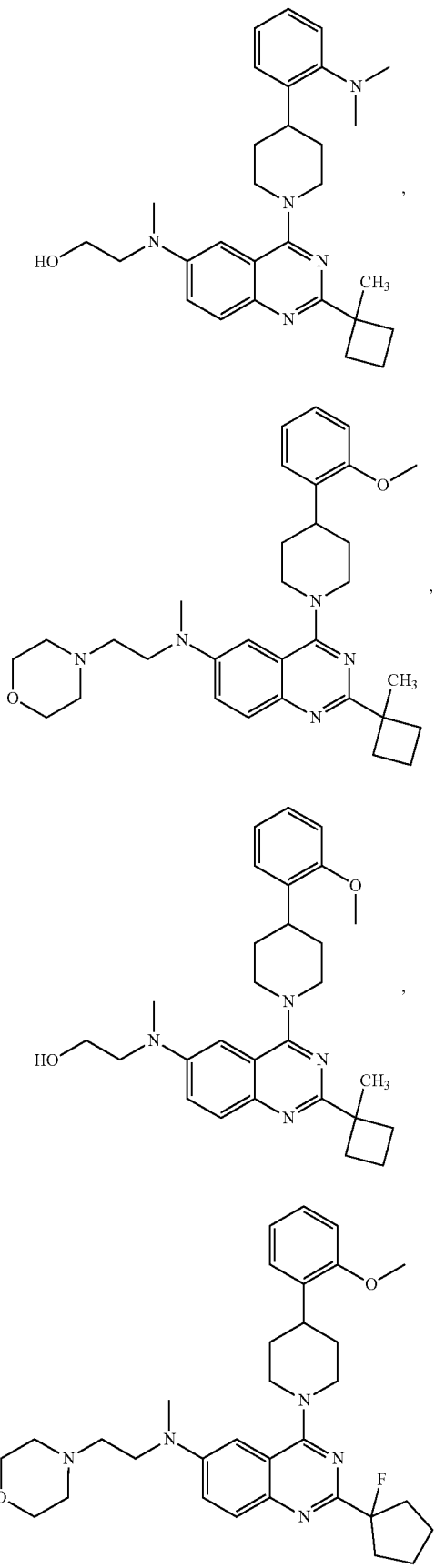

65
-continued
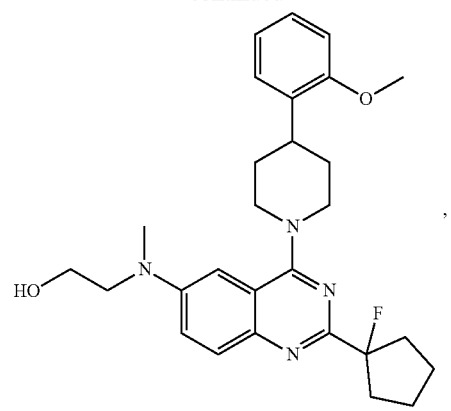
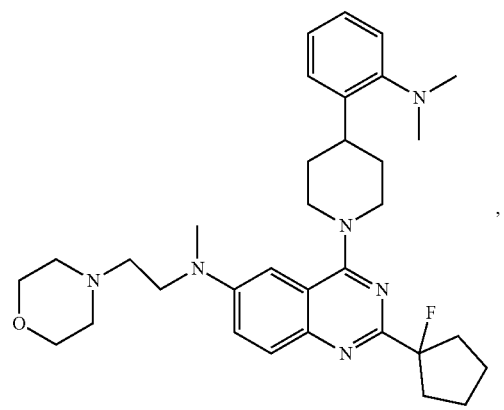
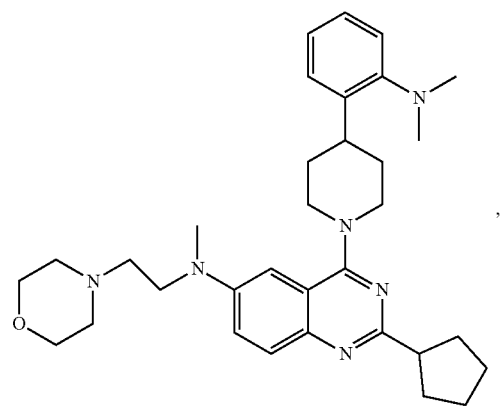
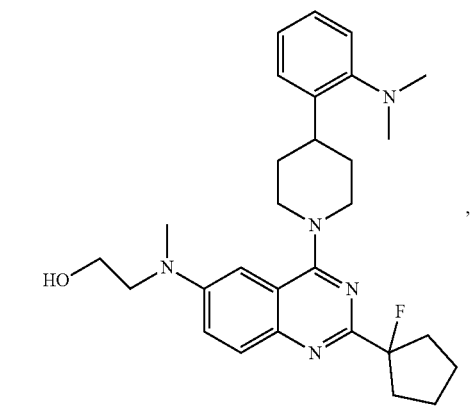
66
-continued
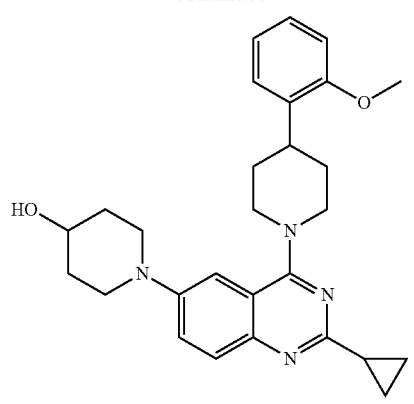
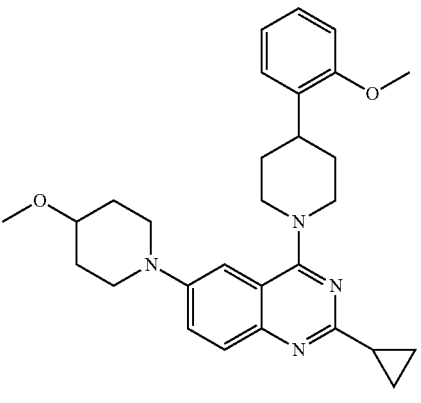
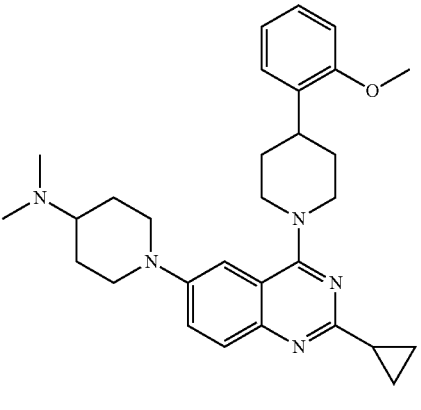
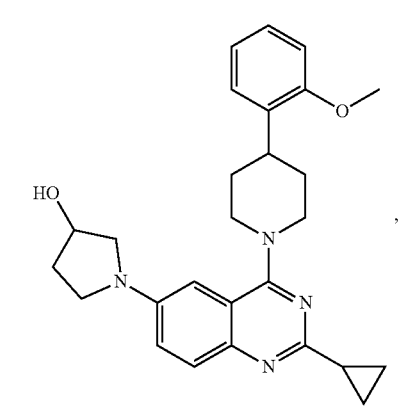

67
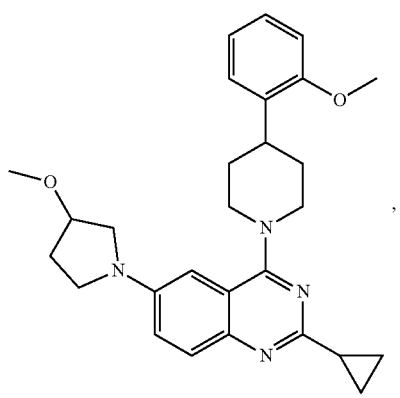
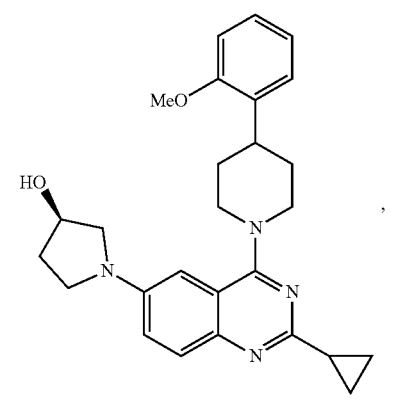
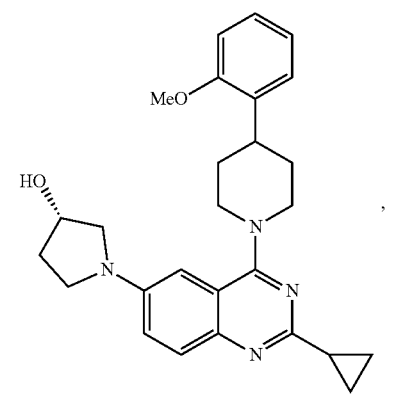
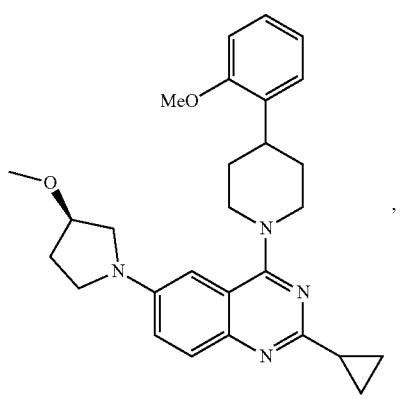
68
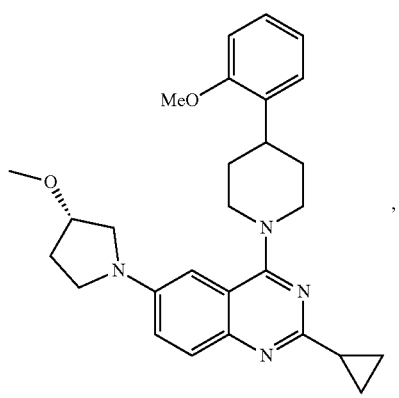
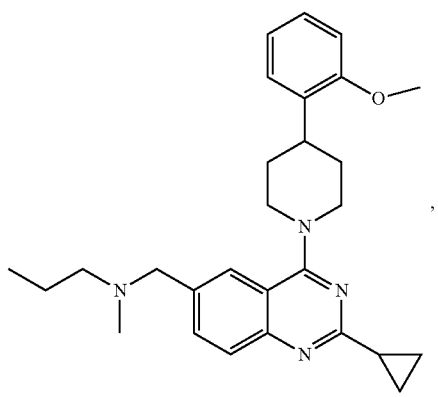
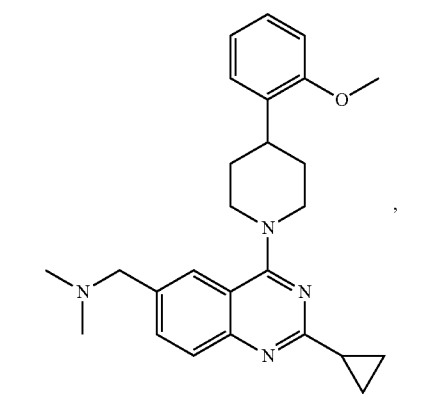
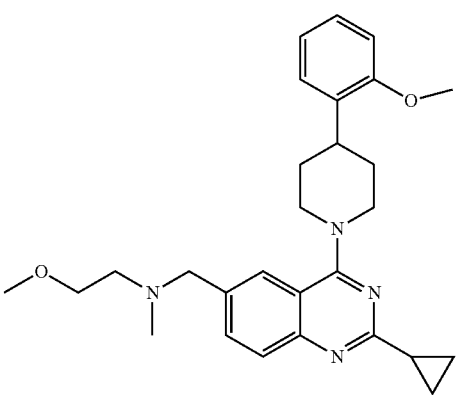

69
-continued
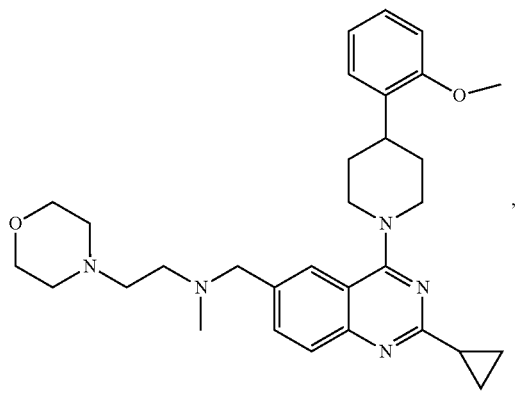
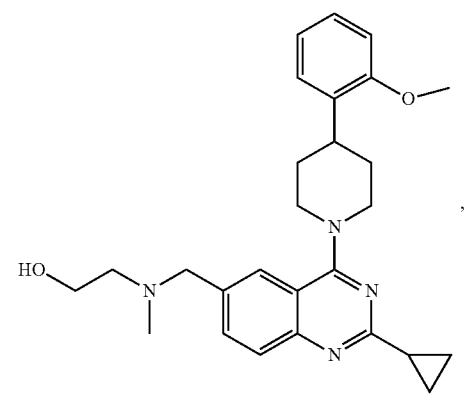
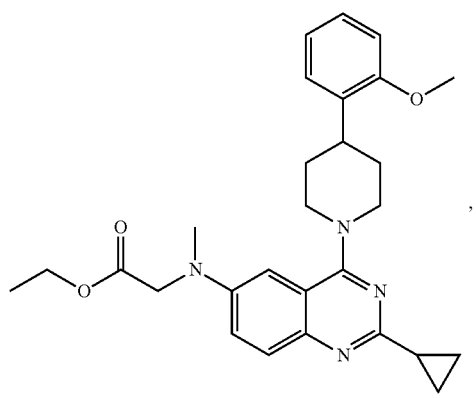
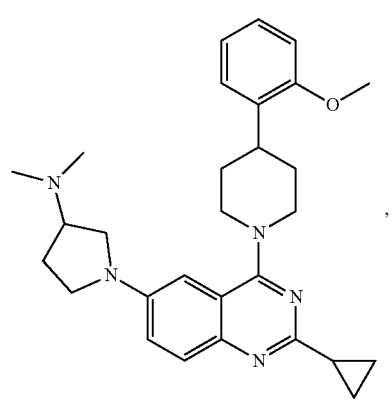
70
-continued
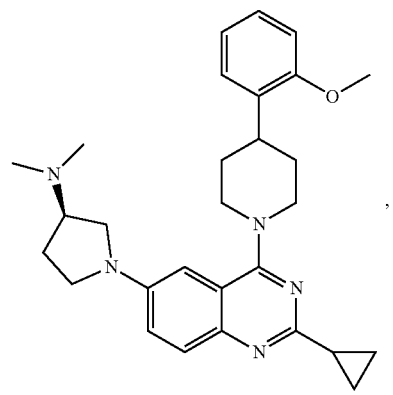
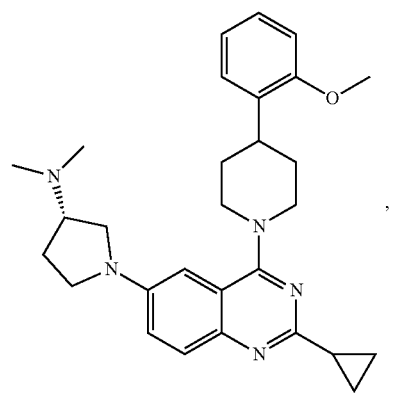
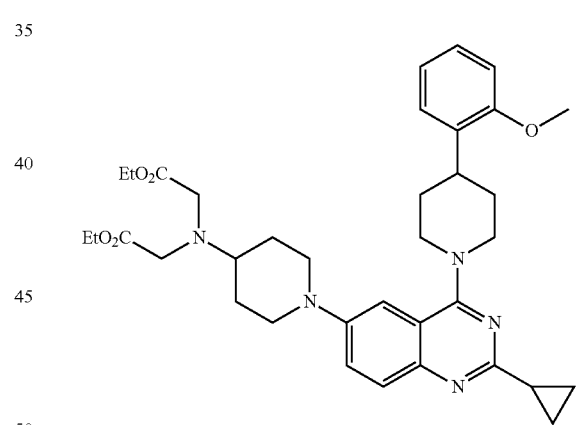
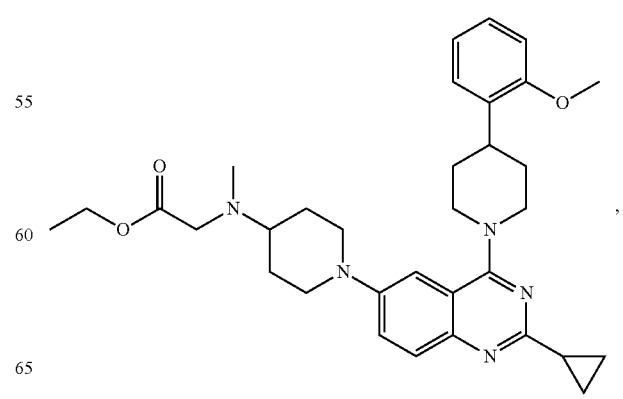

71
-continued
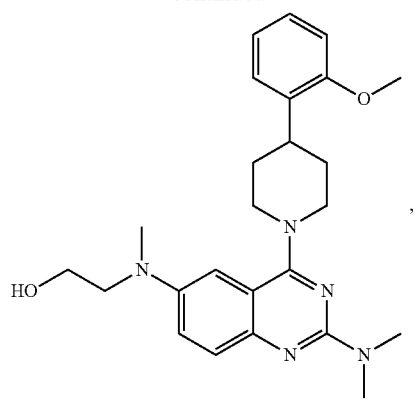
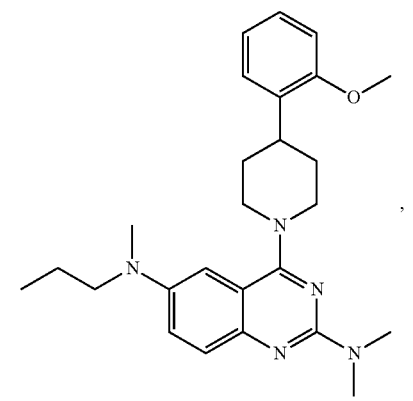
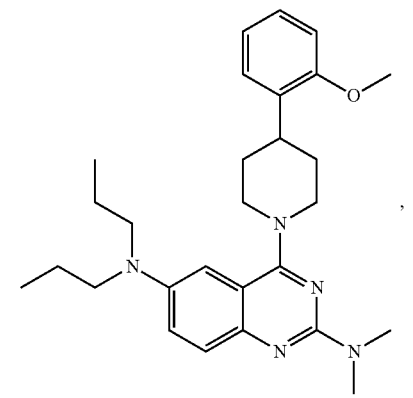
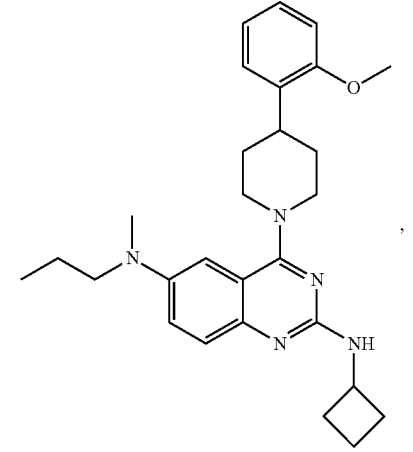
72
-continued
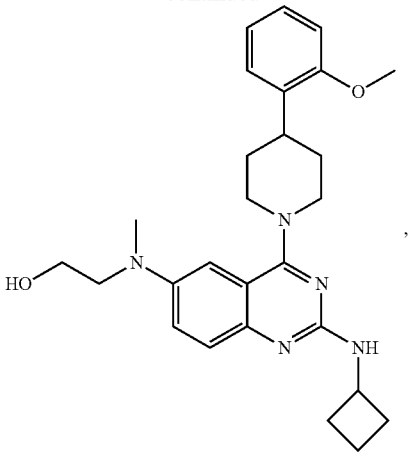
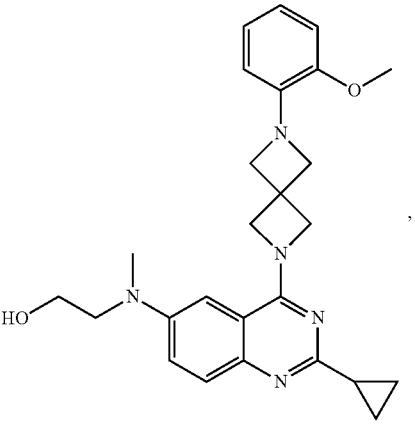
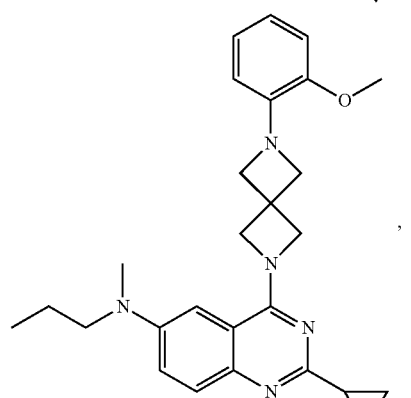
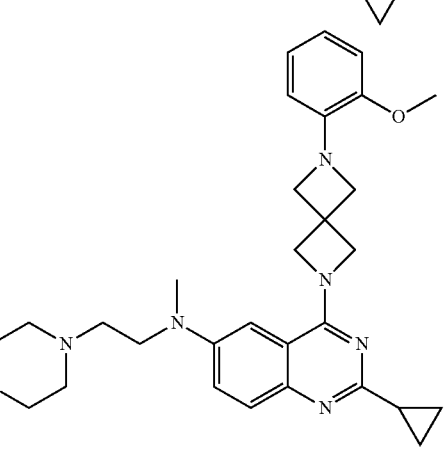

73
-continued
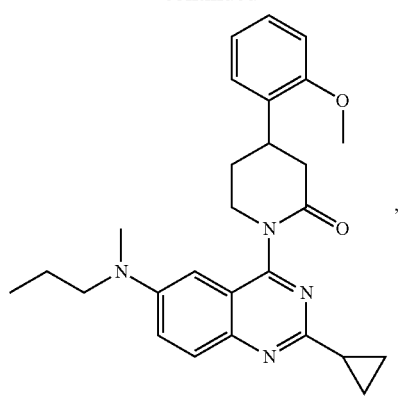
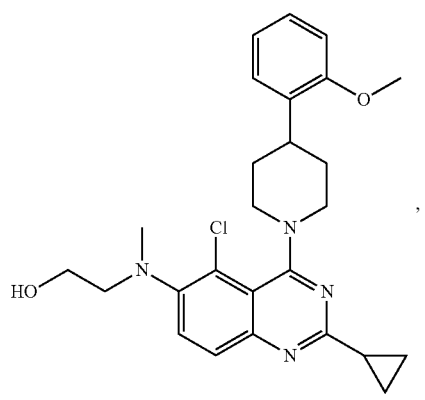
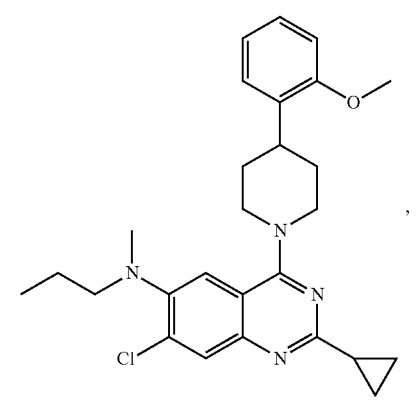
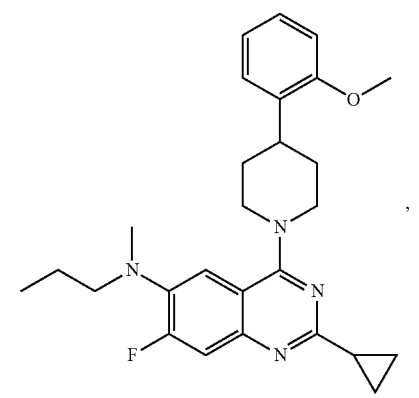
74
-continued
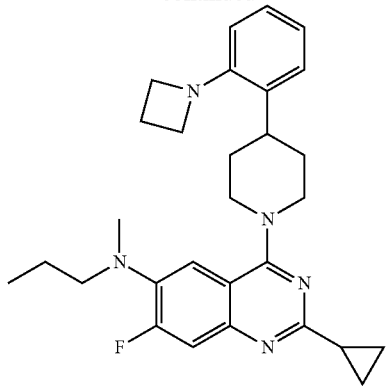
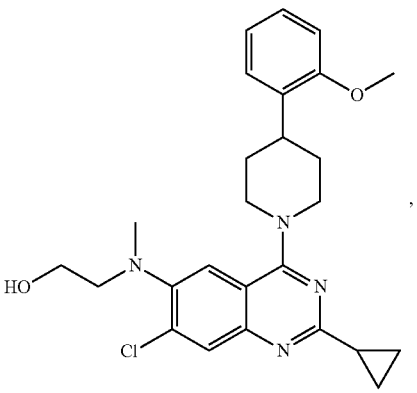
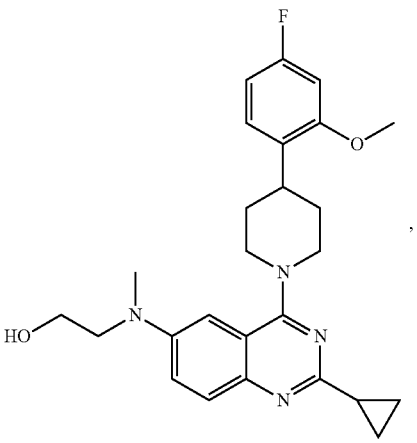
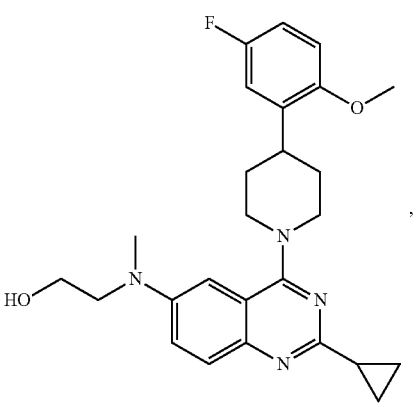

75
-continued
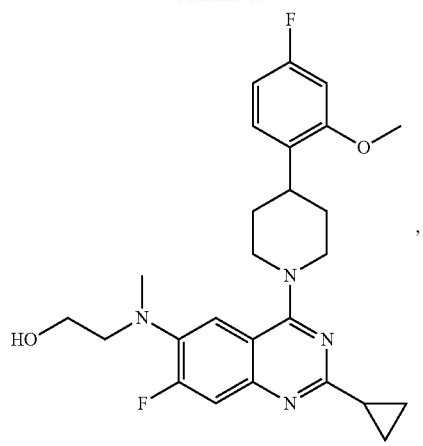
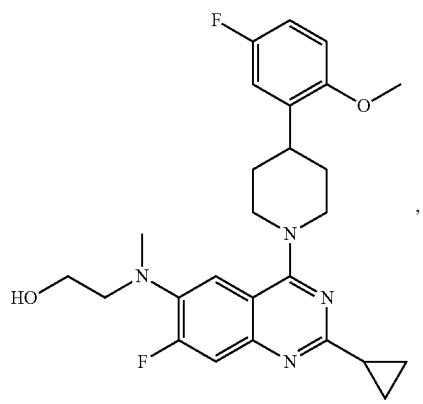
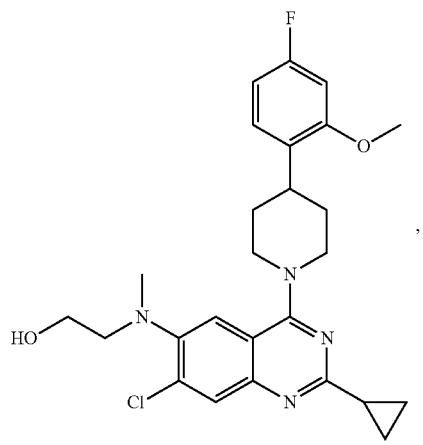
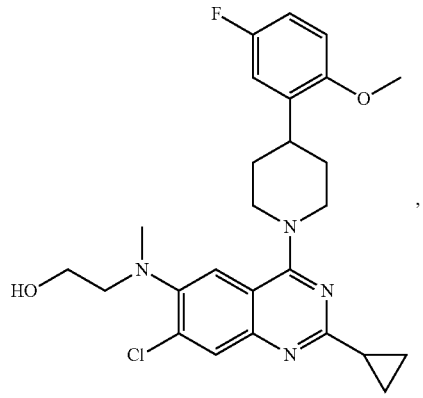
76
-continued
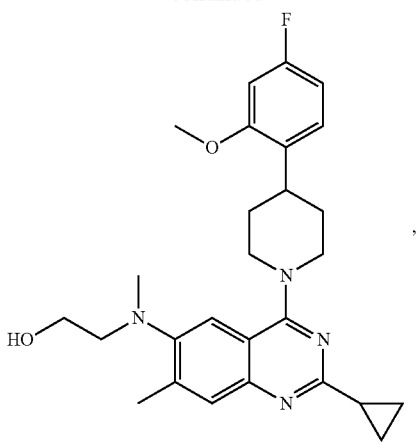
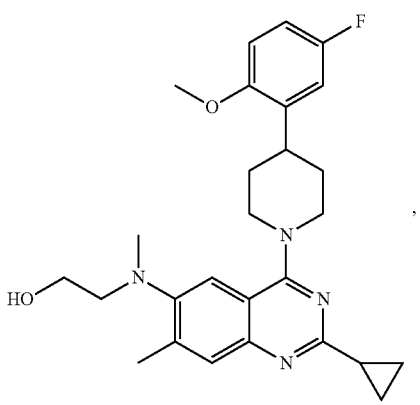
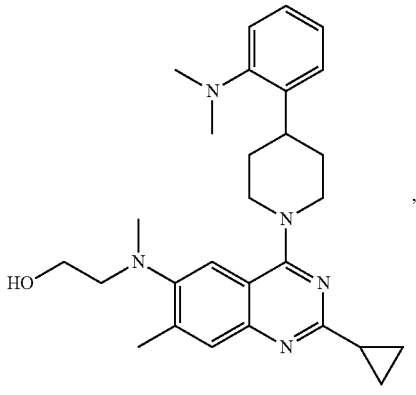
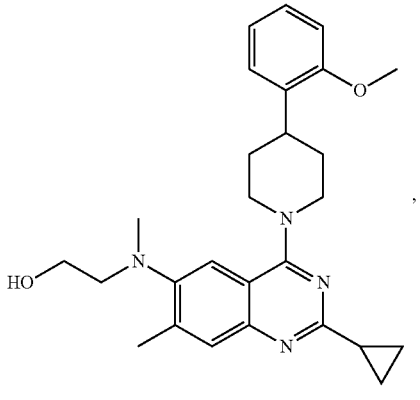

77
-continued
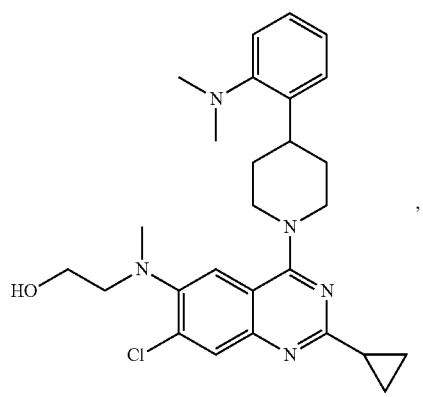
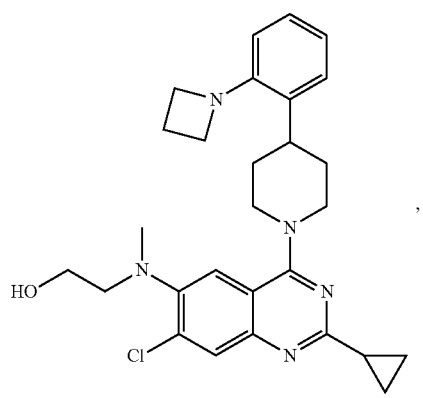
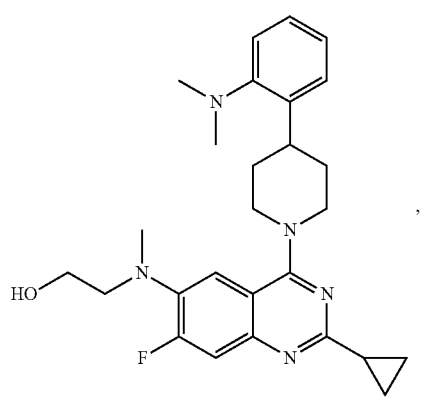
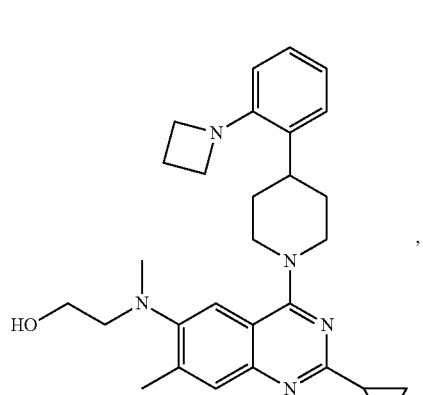
78
-continued
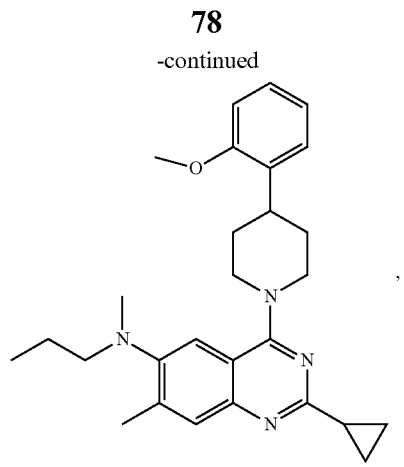
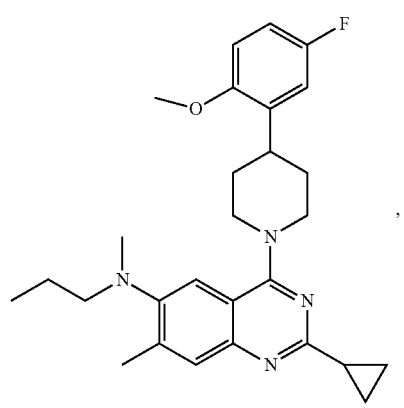
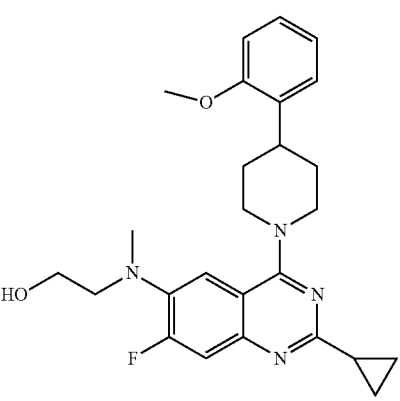
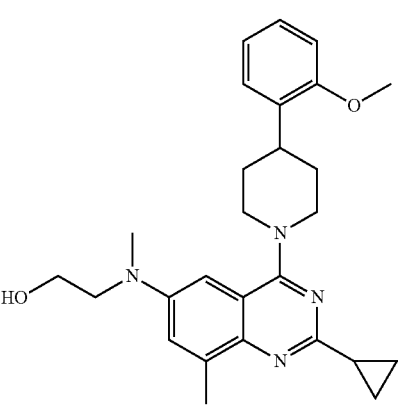

79
-continued
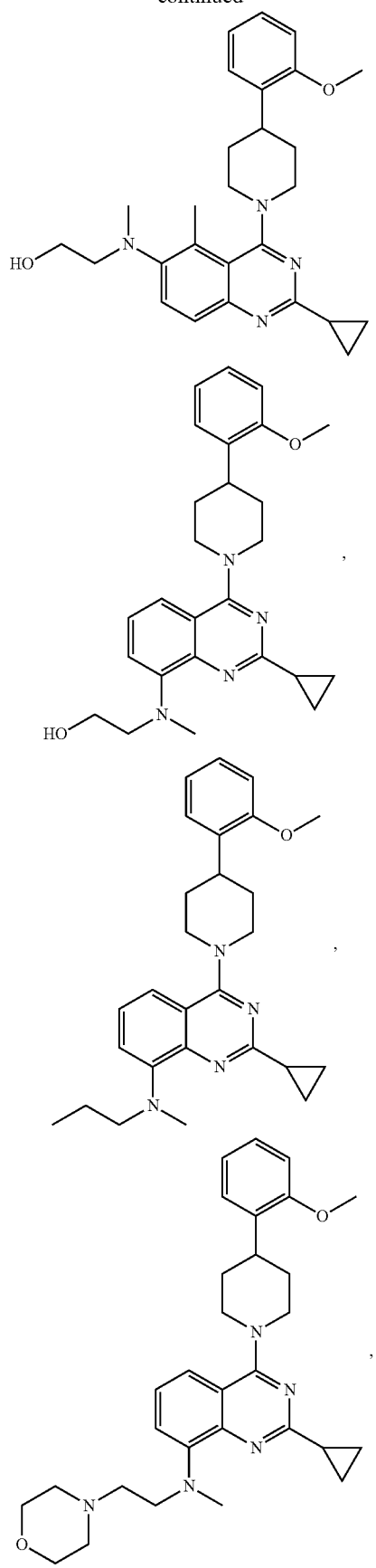
80
-continued
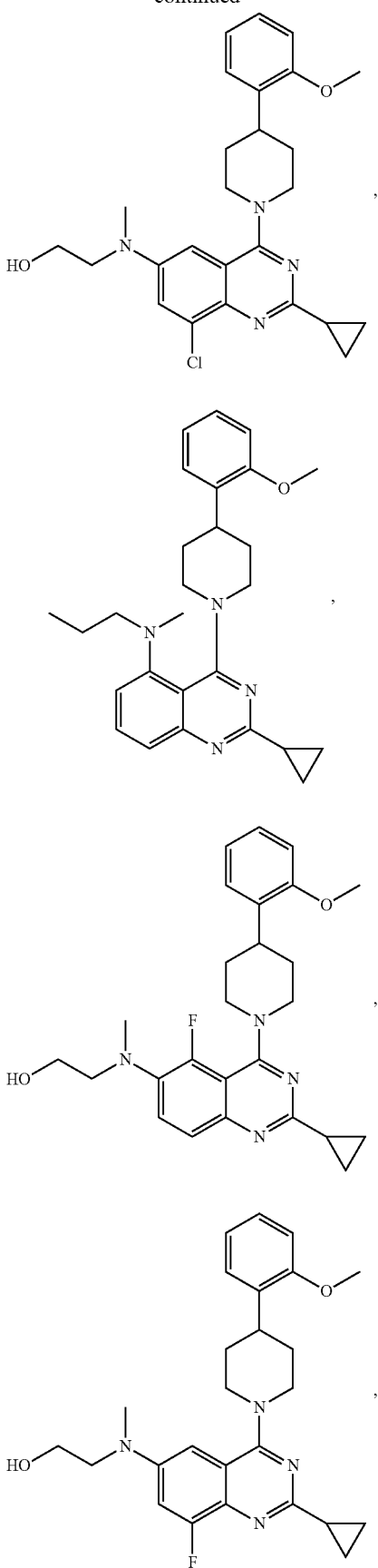

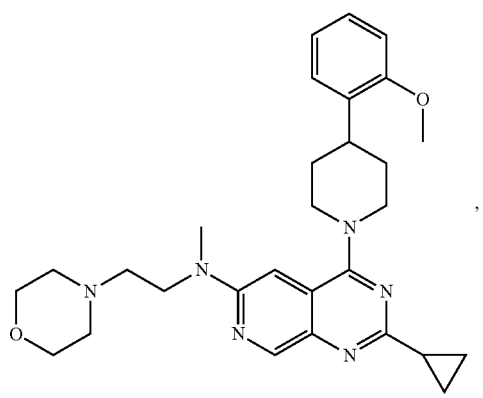
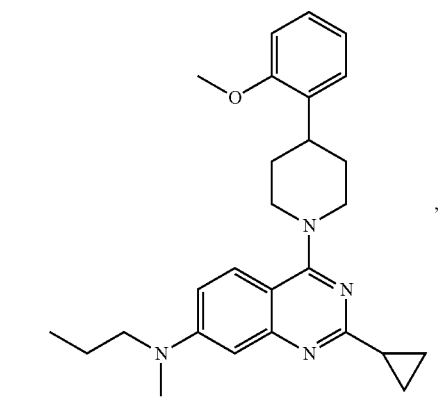
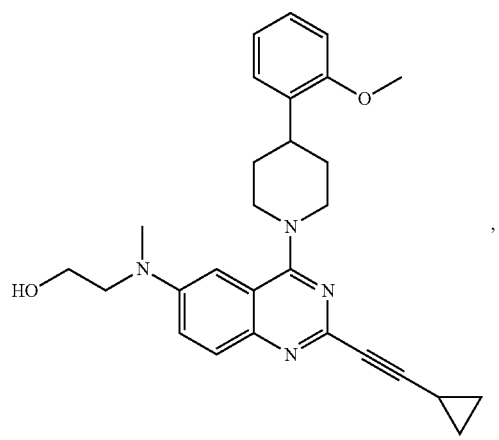
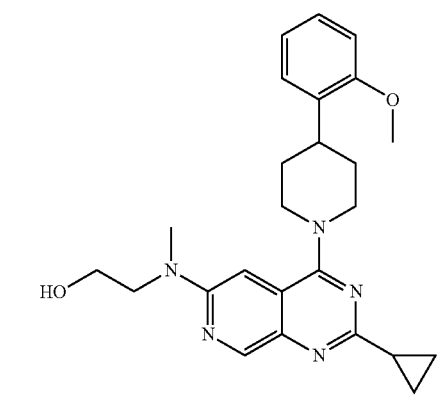
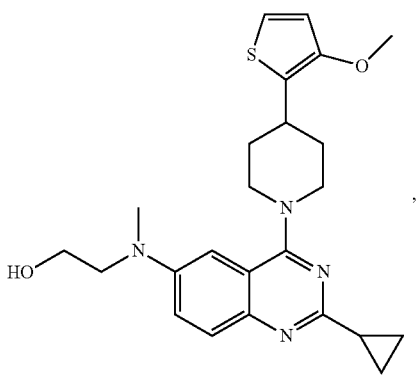
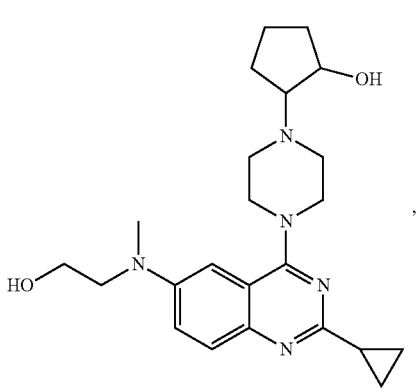
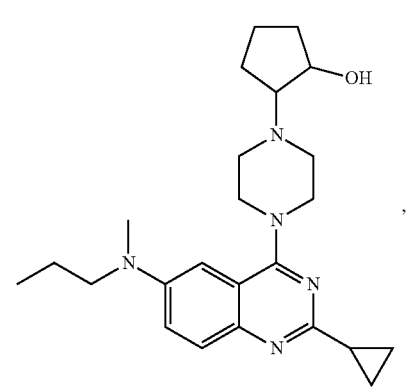
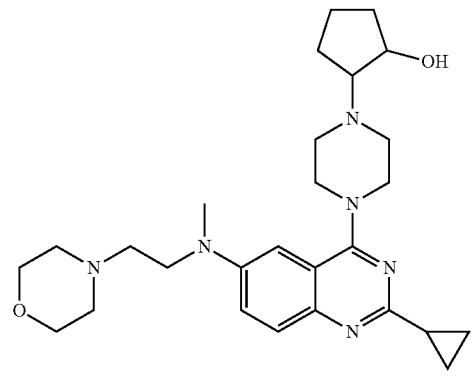

-continued
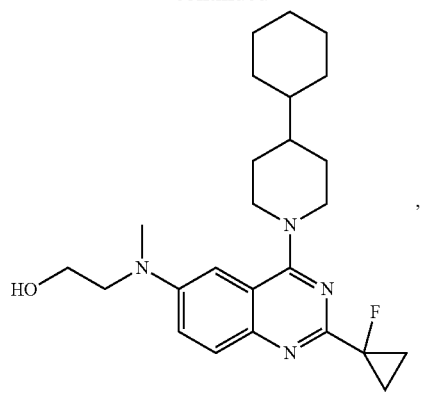
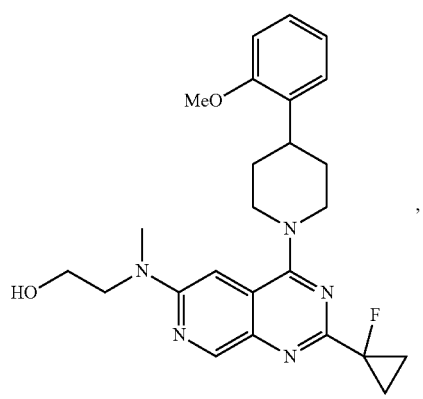
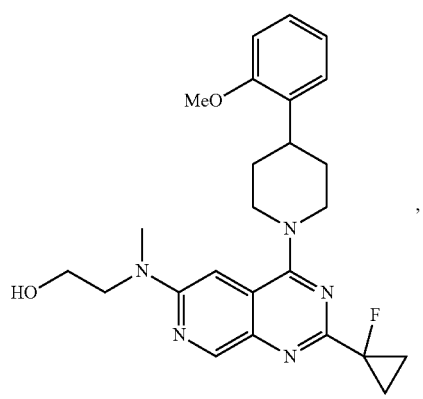
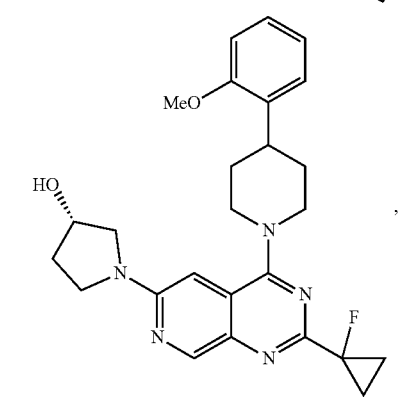
-continued
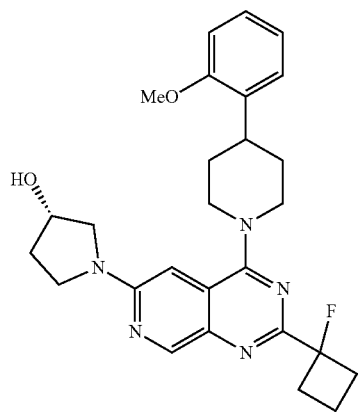
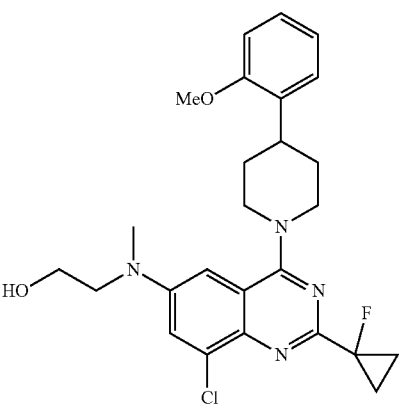
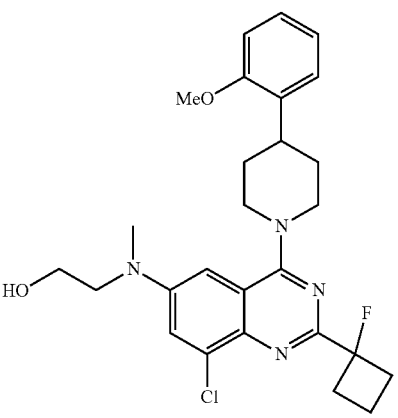
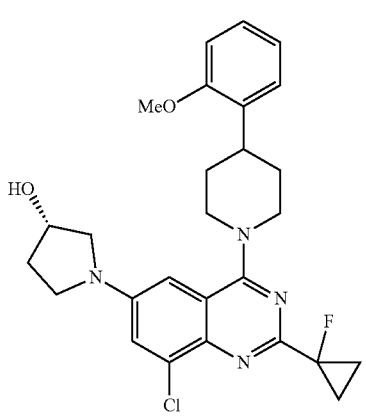

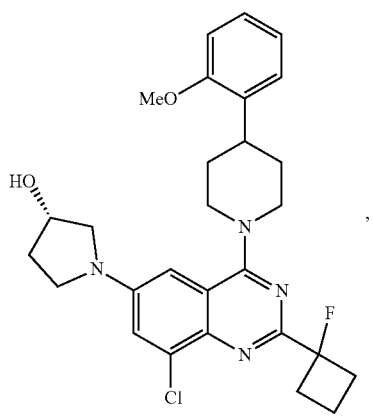
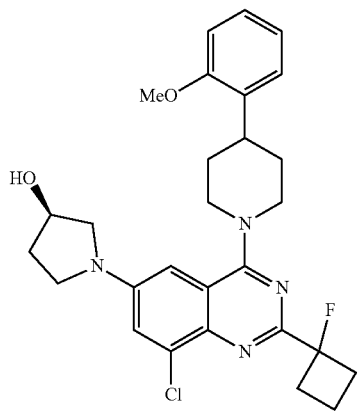

-continued

-continued
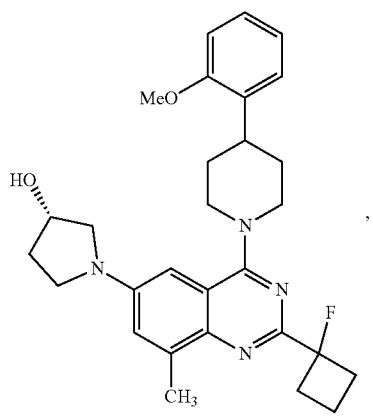
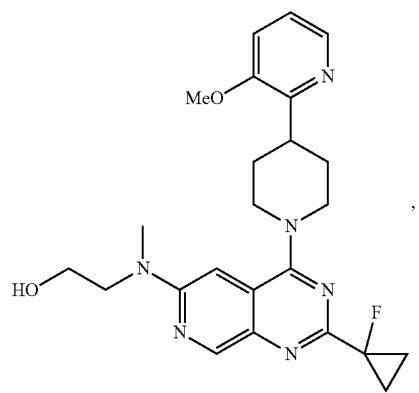
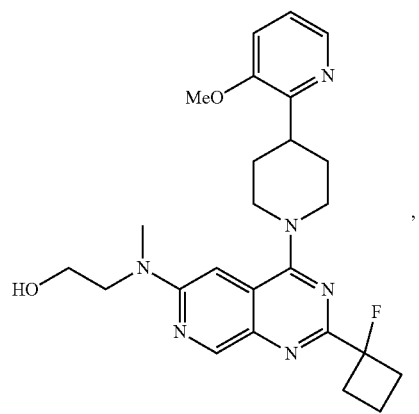
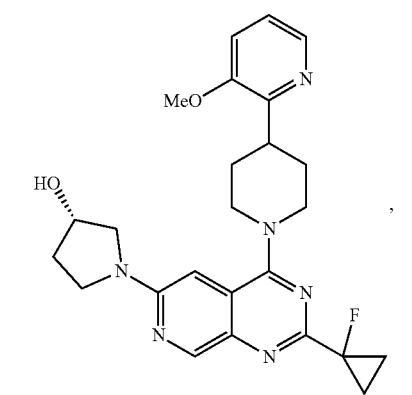
-continued
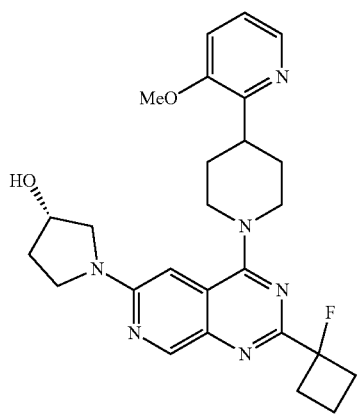
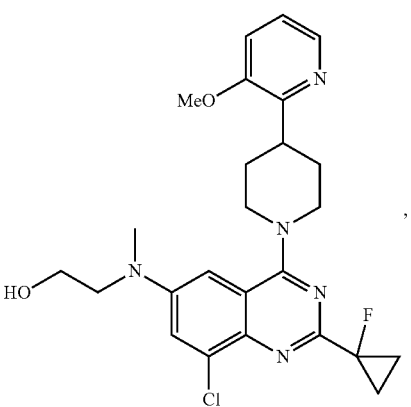
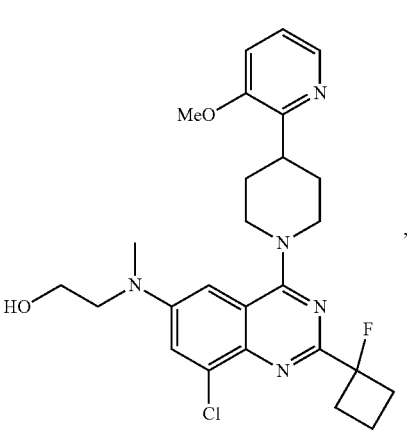
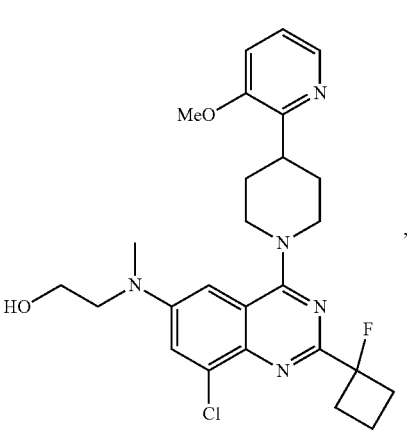

91
-continued
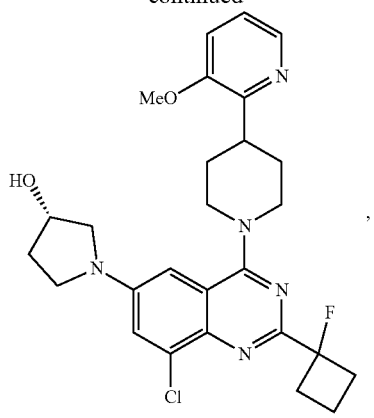
,
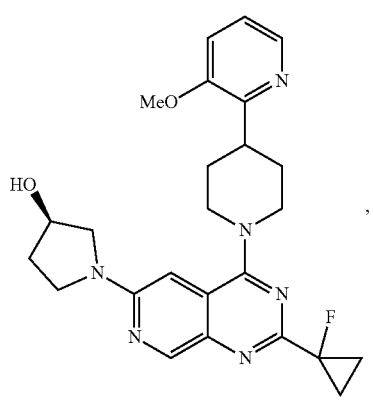
,
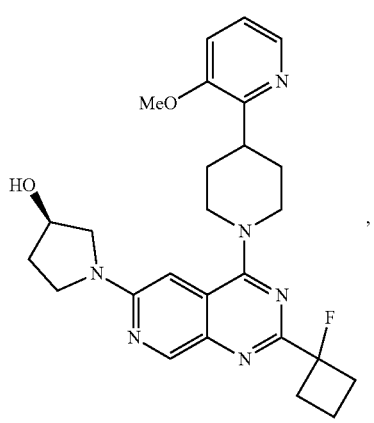
,
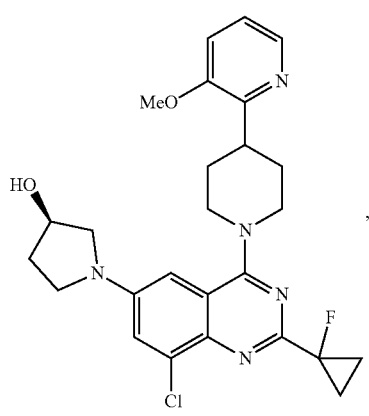
,
92
-continued
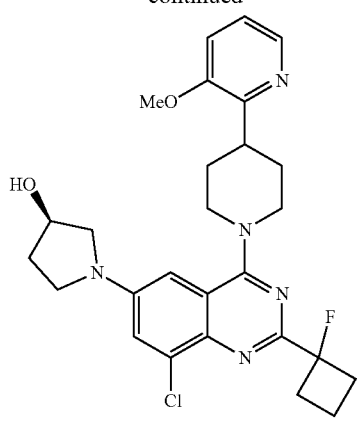
,
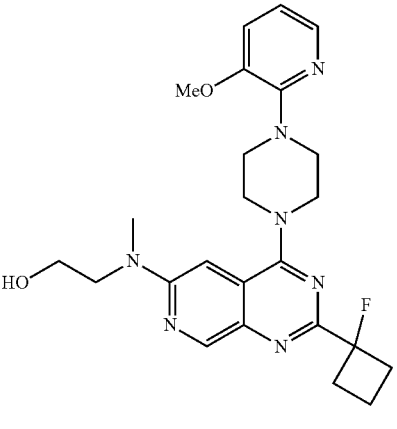
,
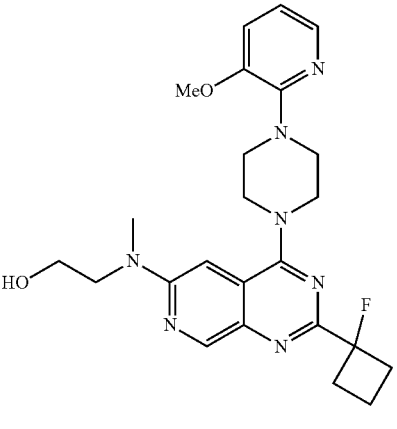
,
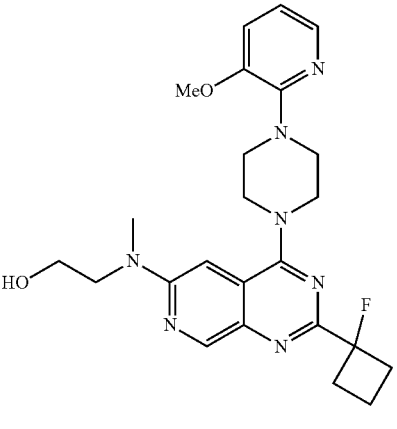
,

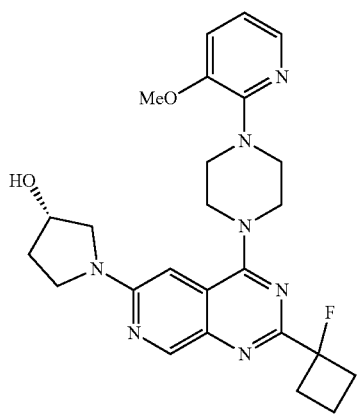
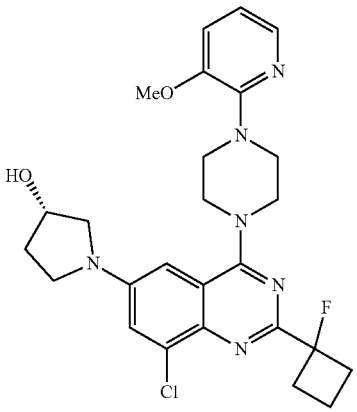

95
-continued
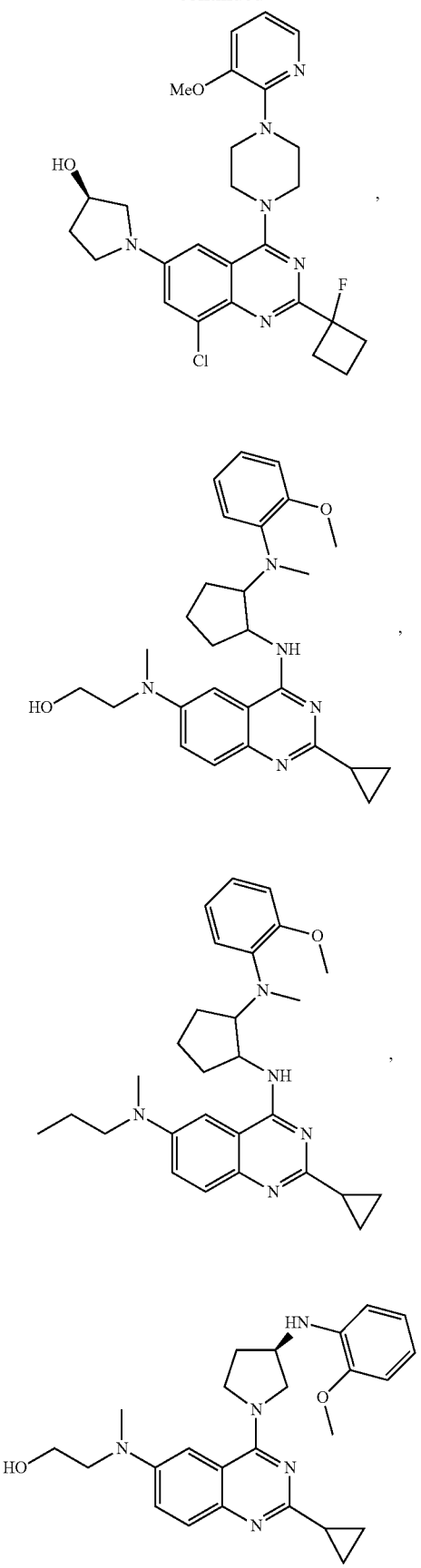
96
-continued
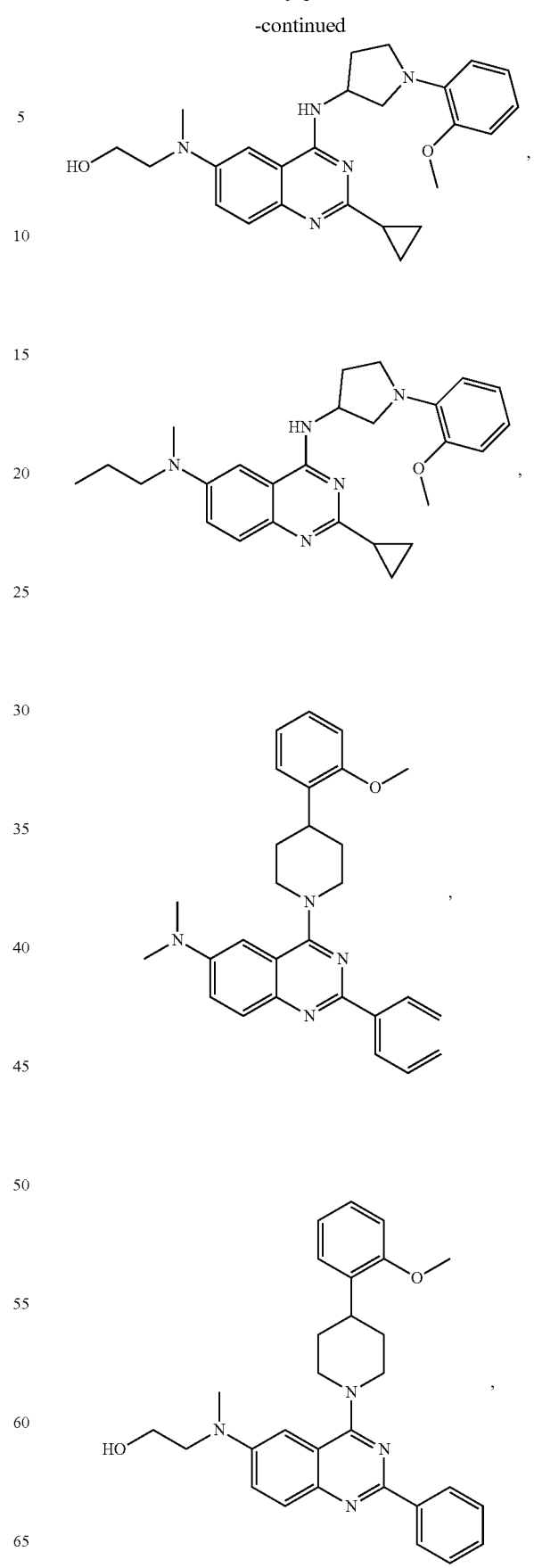

-continued
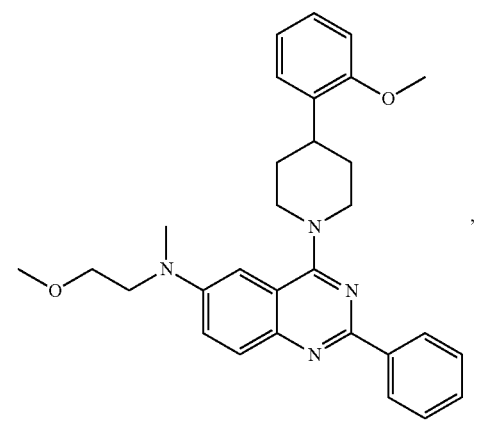
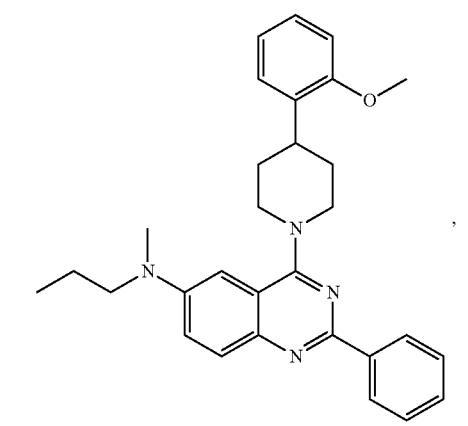
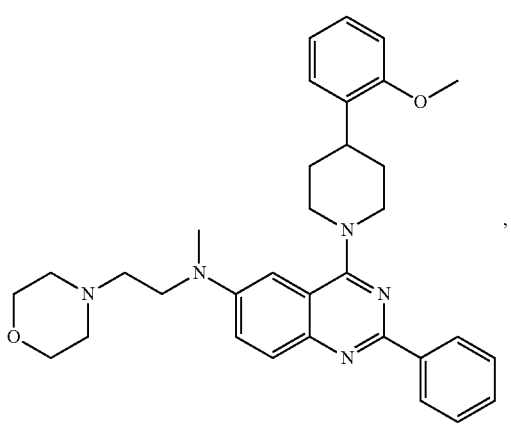
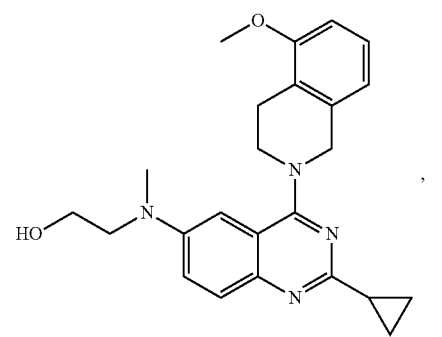
-continued
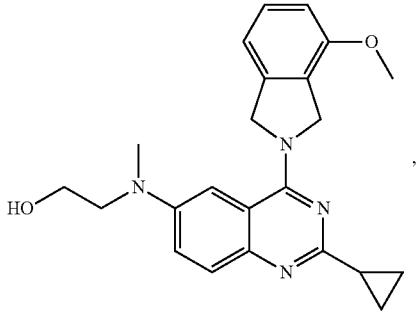
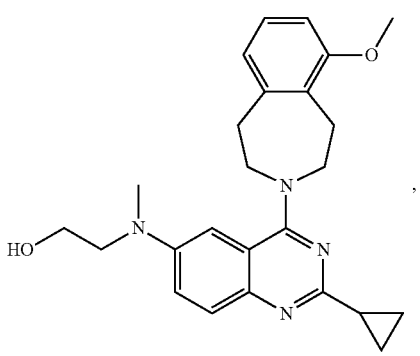
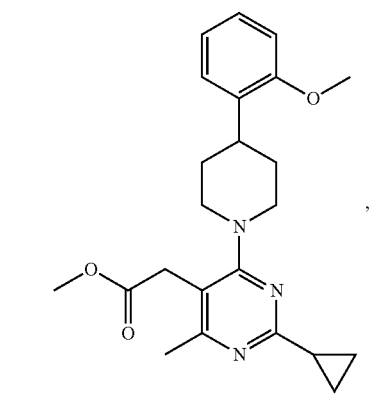
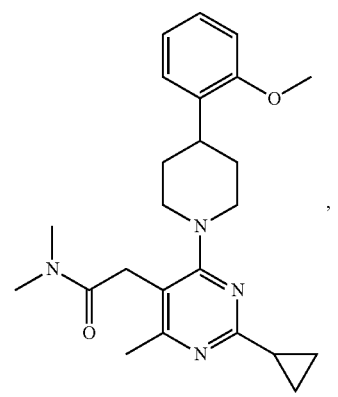

99
-continued
100
-continued
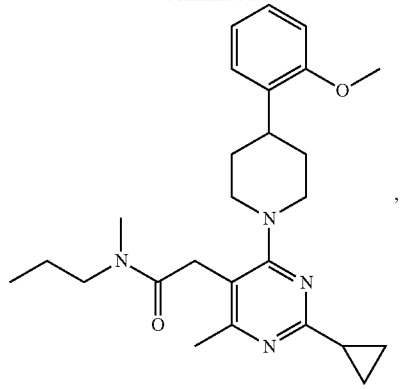
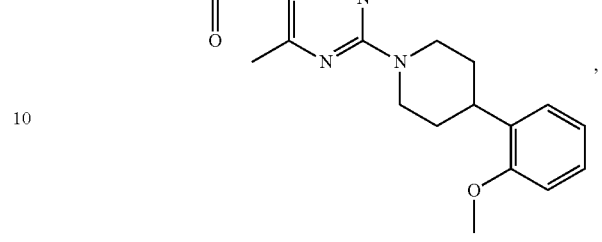
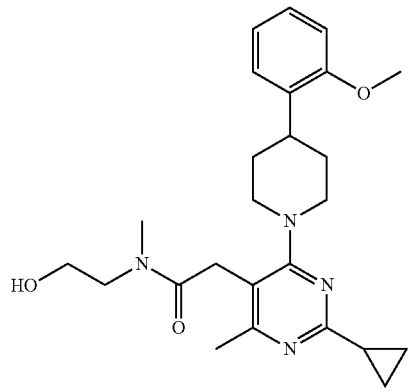
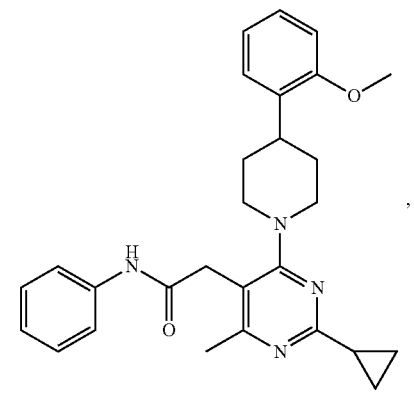
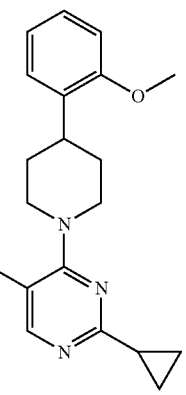
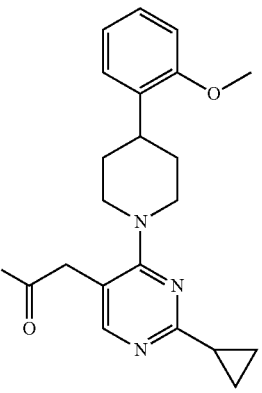

| 101 -continued | 102 -continued |
|---|---|
| 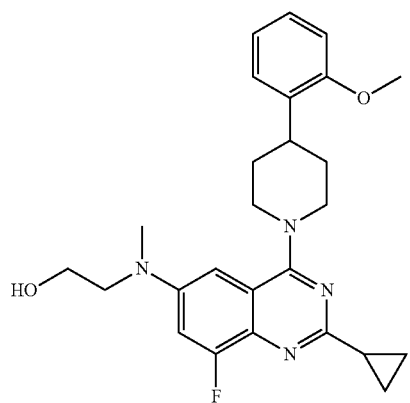 | 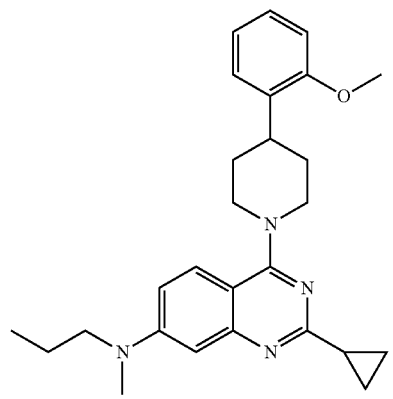 |
| 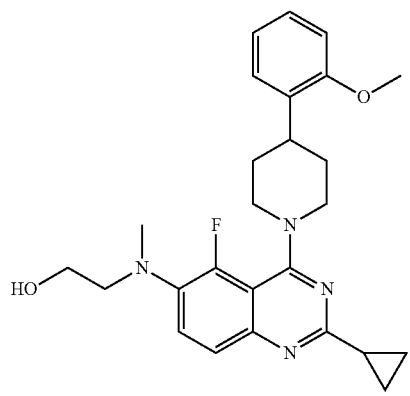 | 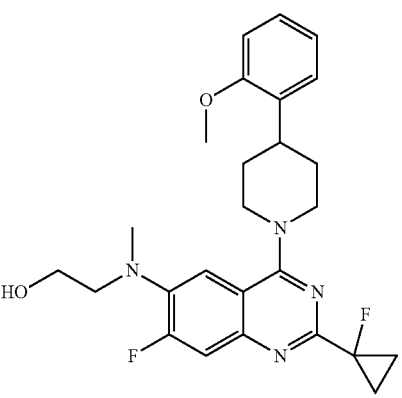 |
| 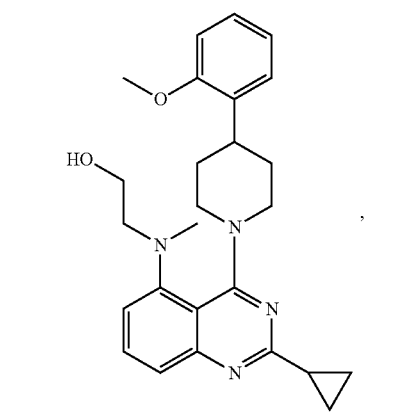 | 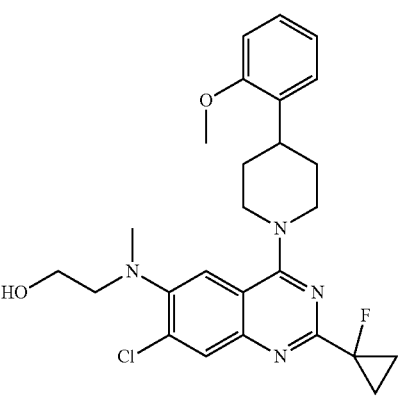 |
| 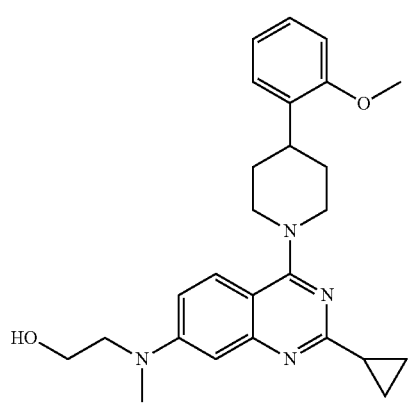 | 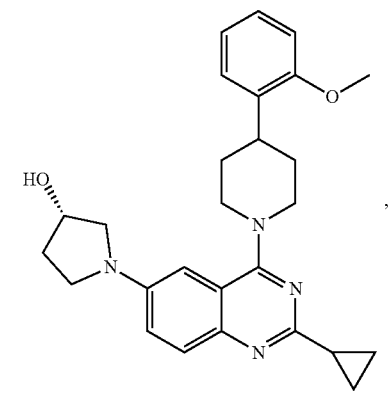 |

103
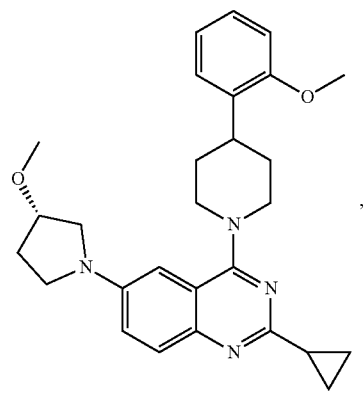
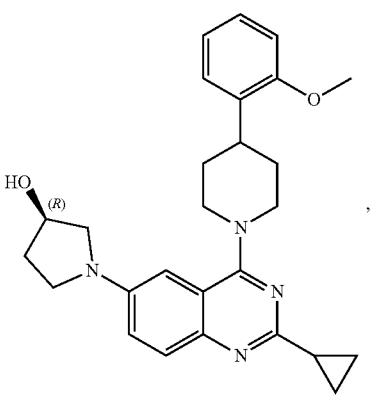
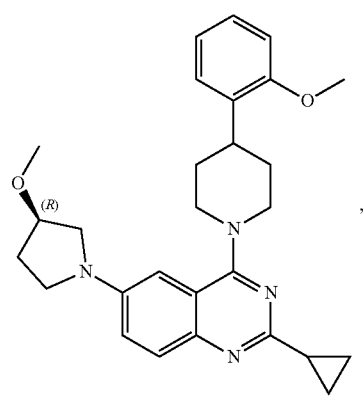
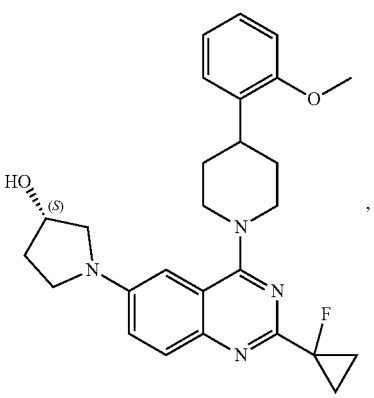
104
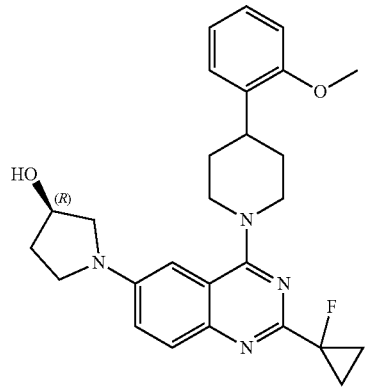
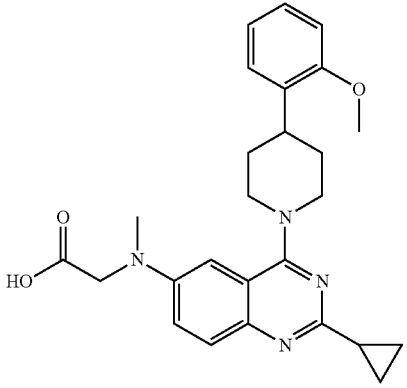
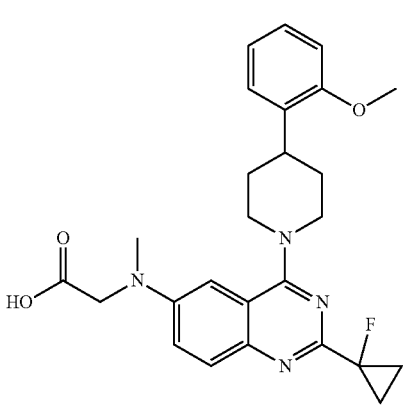
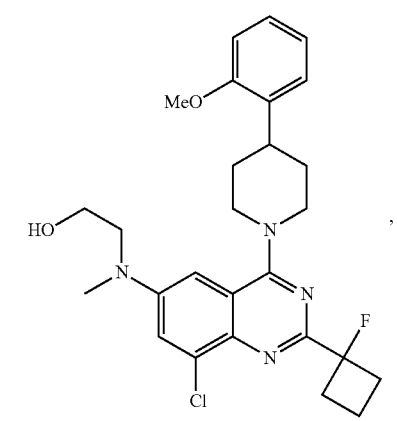

105
-continued
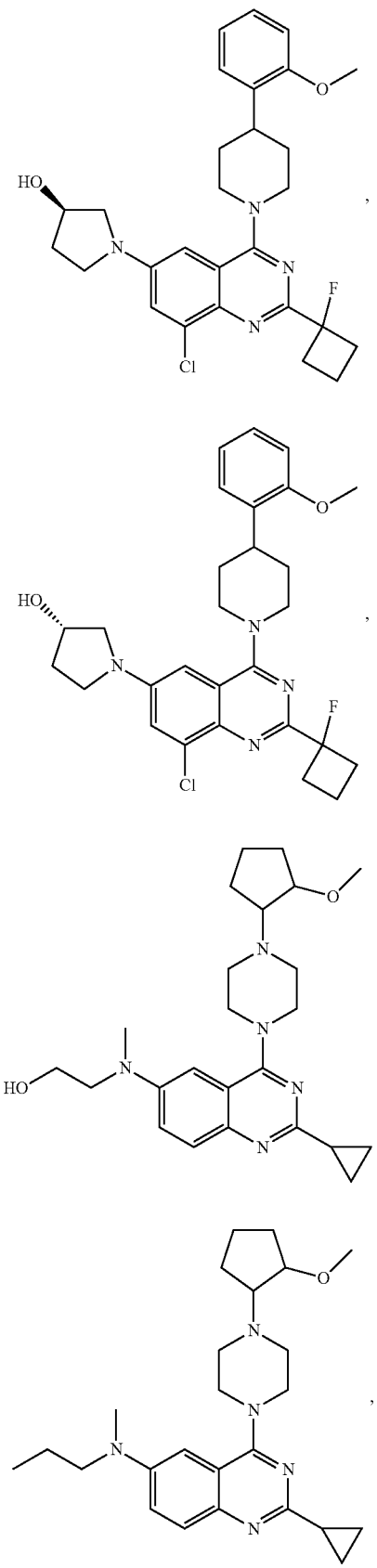
106
-continued
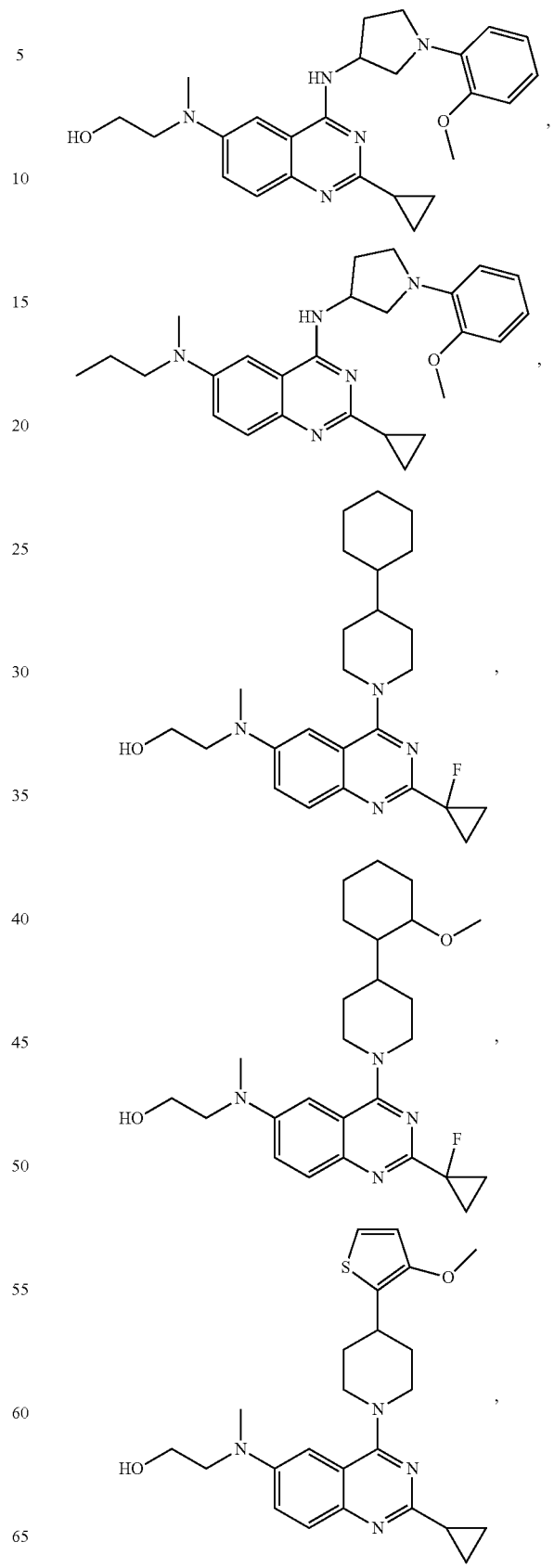

107
-continued
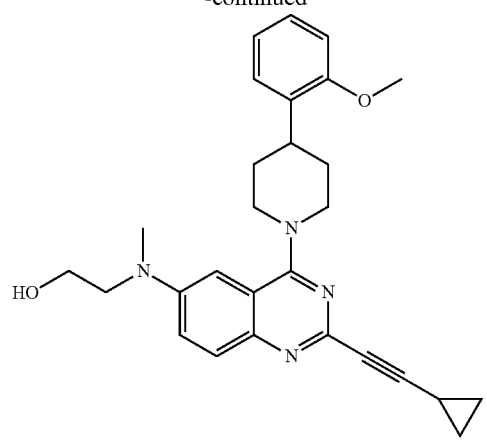
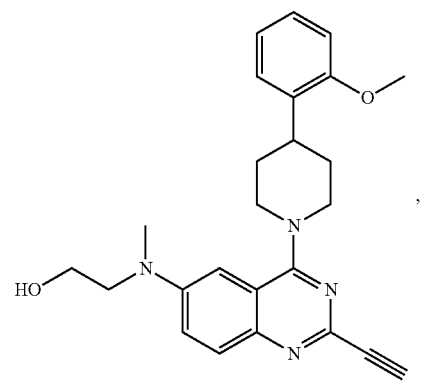
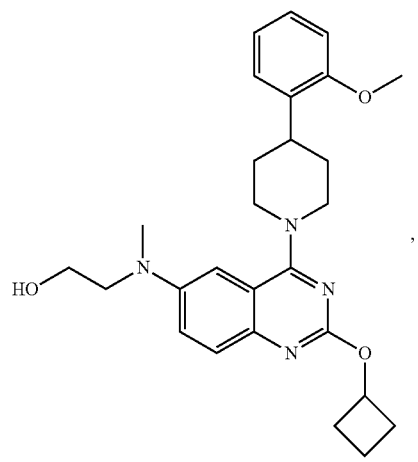
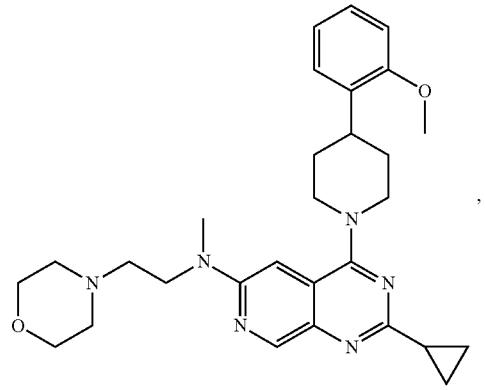
108
-continued
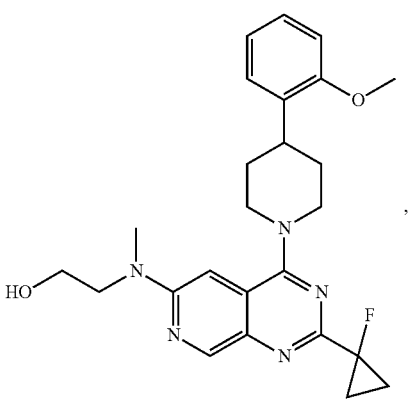
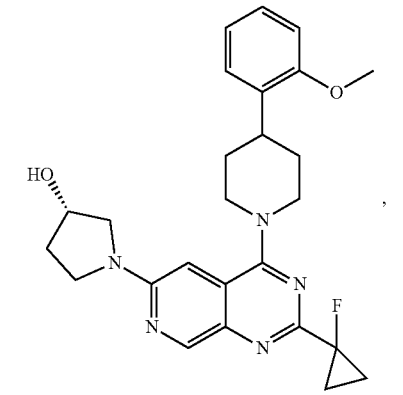
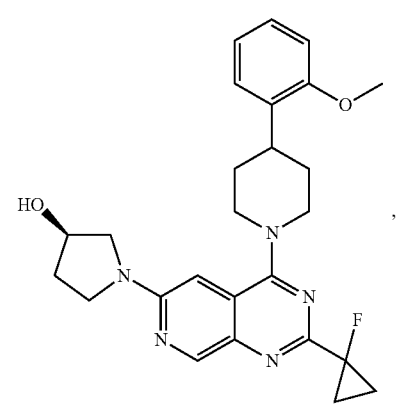
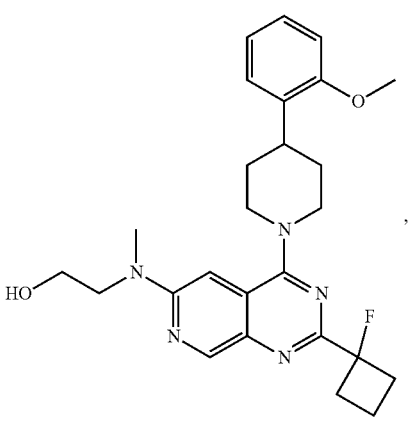

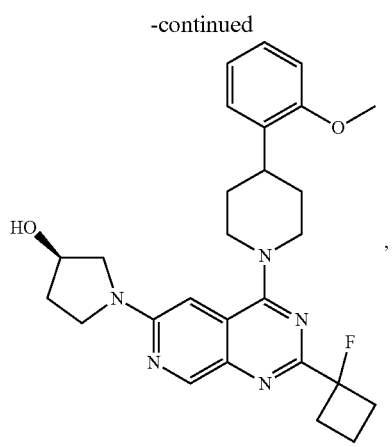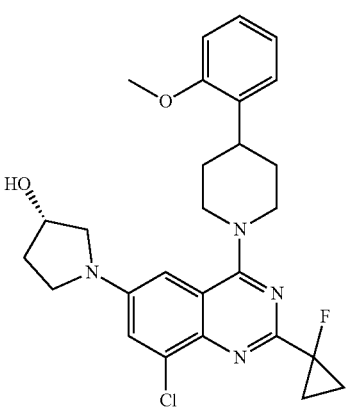

111
-continued
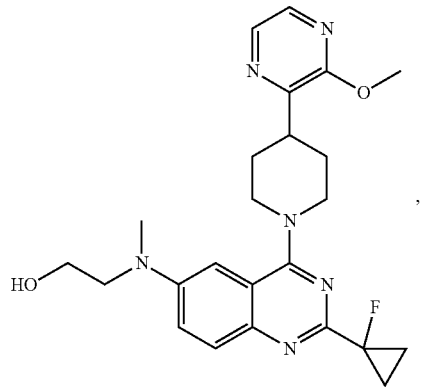
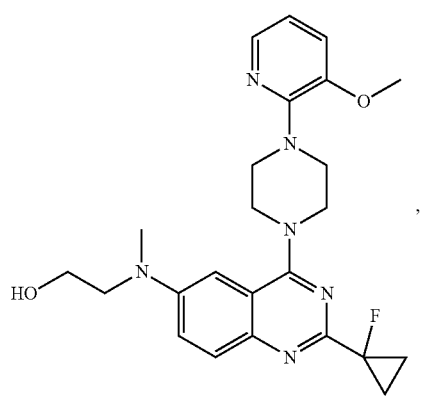
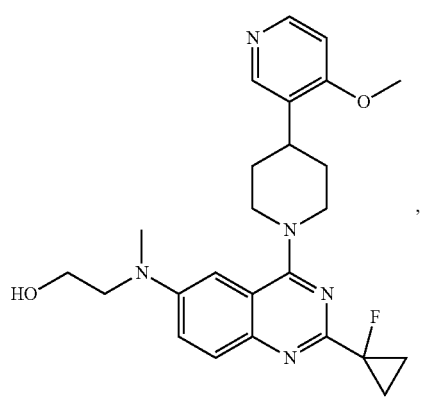
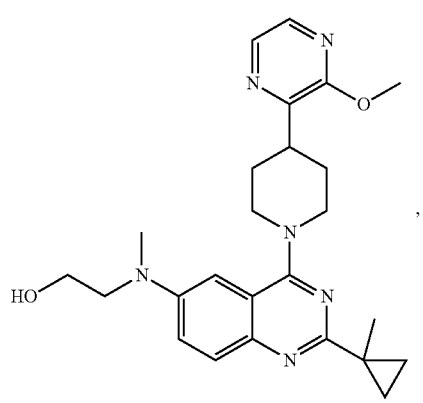
112
-continued
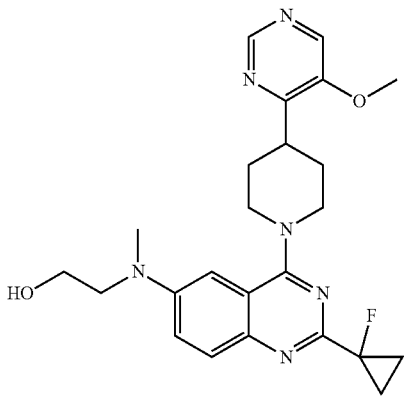
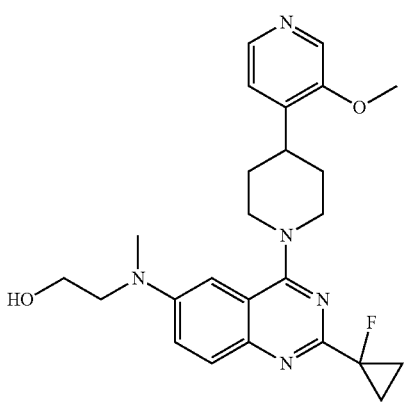
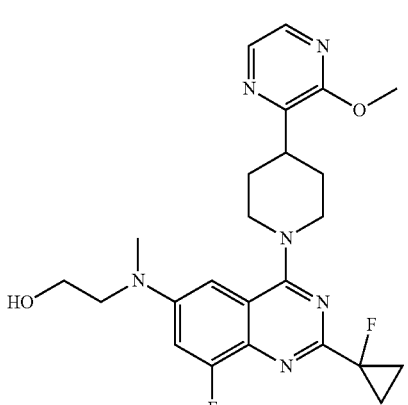
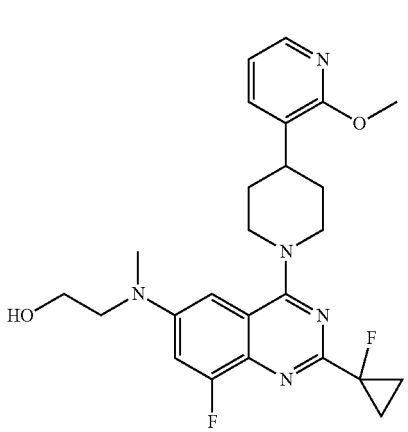

113
-continued
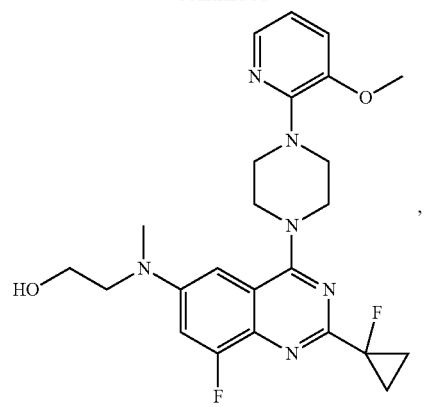
,
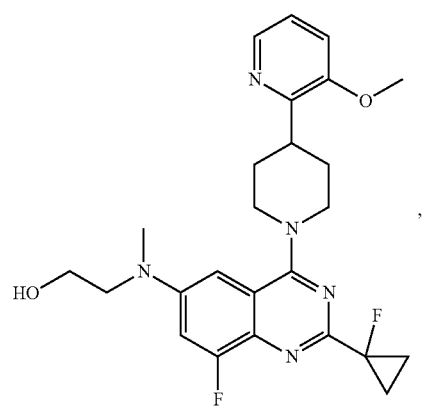
,
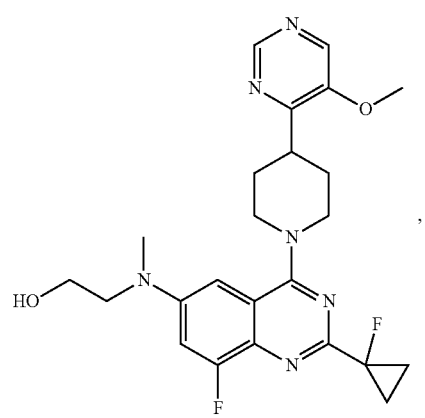
,
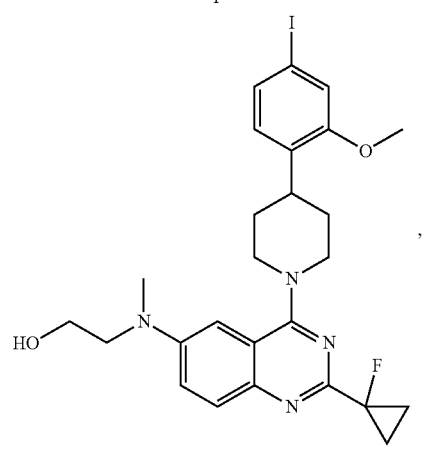
,
114
-continued
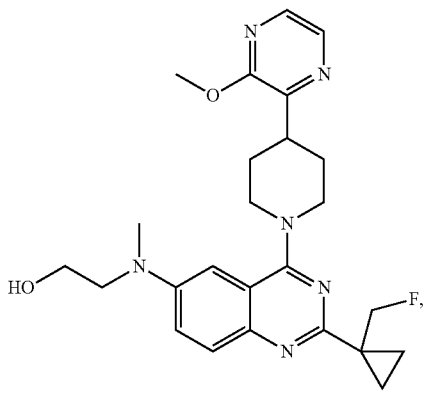
,
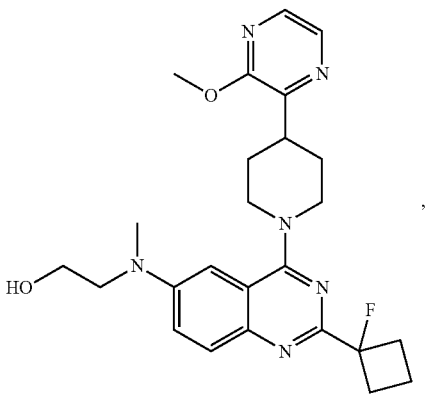
,
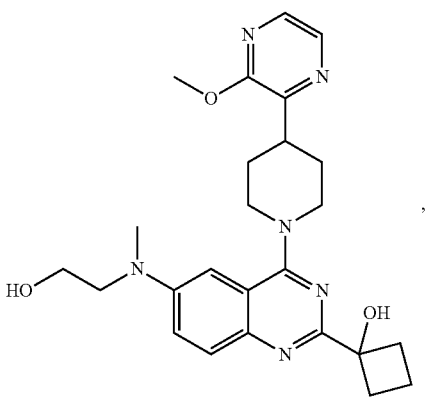
,
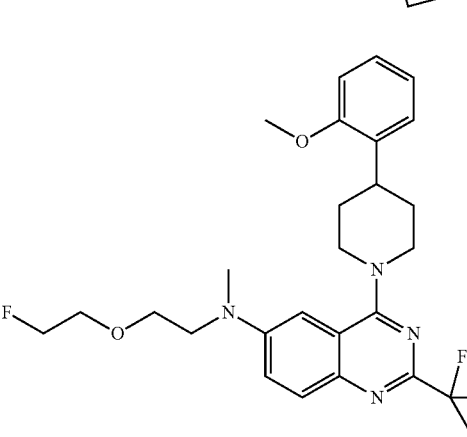
,

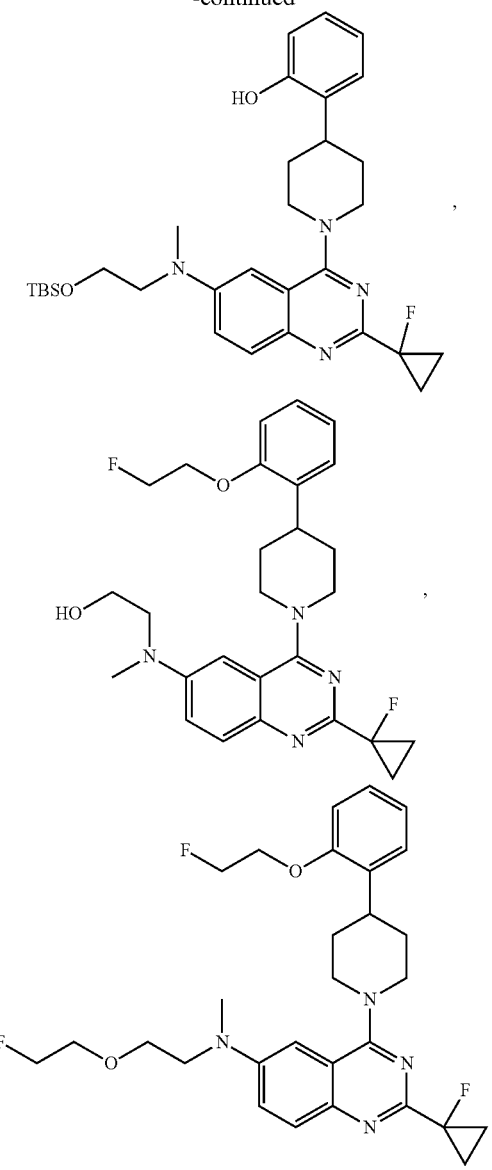

or pharmaceutically acceptable salt, solvate, prodrug, or N-oxide thereof of any one of the preceding compounds.

Further Forms of Compounds

In one aspect, the compound of Formula (I), (II), (III), (IV), (V), (VI), (VII) or (VIII), possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In one aspect, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design prodrugs of the compound is possible. (see, for example, Nogrady (1985) Medicinal Chemistry A Biochemical Approach, Oxford University Press, New York, pages 388-392; Silverman (1992), The Organic Chemistry of Drug Design and Drug Action, Academic Press, Inc., San Diego, pages 352-401, Rooseboom et al., Pharmacological Reviews, 56:53-102, 2004; Aesop Cho, "Recent Advances in Oral Prodrug Discovery", Annual Reports in Medicinal Chemistry, Vol. 41, 395-407, 2006; T. Higuchi and V. Stella, Pro-drugs as Novel Delivery Systems, Vol. 14 of the A.C.S. Symposium Series).

In some cases, some of the herein-described compounds may be a prodrug for another derivative or active compound.

In some embodiments, sites on the aromatic ring portion of compounds described herein are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^2$H, $^3$H, $^{13}$C, $^{14}$C, $^{15}$N, $^{18}$O, $^{17}$O, $^{35}$S, $^{18}$F, $^{36}$Cl. In one aspect, isotopically-labeled compounds described herein, for example those into which radioactive isotopes such as $^3$H and $^{14}$C are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable" as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formula (I), (II), (III), (IV), (V), (VI), (VII) or (VIII) with acids. Pharmaceutically acceptable salts are also obtained by reacting a compound of Formula (I), (II), (III), (IV), (V), (VI), (VII) or (VIII) with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms, particularly solvates. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FisherScientific (Fisher Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

In some embodiments, compounds described herein are prepared as shown in Scheme A.

Scheme A

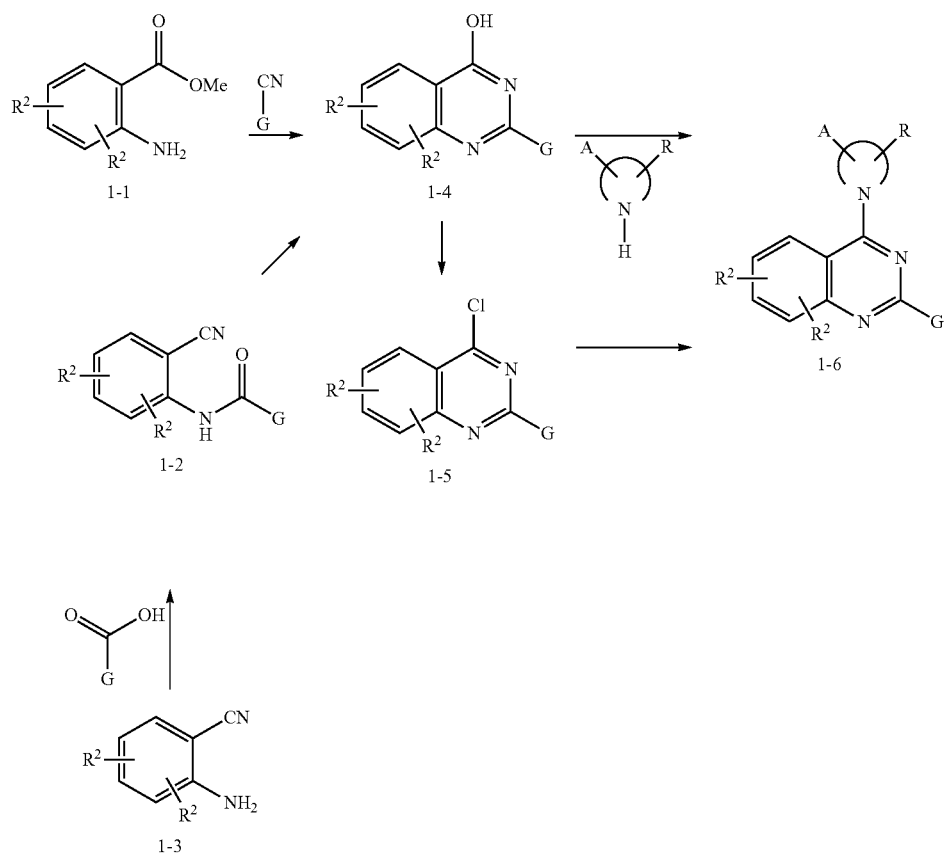

In some embodiments, the synthesis of quinazoline-derived compounds 1-6 described herein is accomplished starting from suitably substituted methyl anthranilates 1-1 as shown in Scheme A. Acid catalyzed (i.e. HCl) condensation of substituted methyl anthranilates (1-1) with substituted carbonitrile affords 4-hydroxyquinazoline intermediates (1-4). Chlorination (i.e. $POCl_3$) of the 4-hydroxyquinazoline intermediates followed by amination of the resulting 4-chloroquinazoline intermediates (1-5) with various substituted aryl piperidines, piperazines or pyrrolidines affords quinazoline analogs 1-6. In some embodiments, the 4-hydroxyquinazoline intermediates (1-4) are directly reacted with various substituted aryl piperidines, piperazines or pyrrolidines using a coupling reagent (i.e. BOP) and a base (i.e. DBU) to afford quinazoline analogs 1-6. In some embodiments, the synthesis of the 4-hydroxyquinazoline intermediates (1-4) is accomplished in two steps by 1) amide condensation of a substituted anthranilonitrile (1-3) and a substituted carboxylic acid using an amide coupling reagent (i.e HATU) to afford N-(2-cyanophenyl)amide derivatives 1-2 and 2) cyclization under basic (i.e. NaOH) and oxidative (i.e. $H_2O_2$) conditions to afford 4-hydroxyquinazoline intermediates (1-4).

In some embodiments, compounds described herein are prepared as shown in Scheme B.

Scheme B:

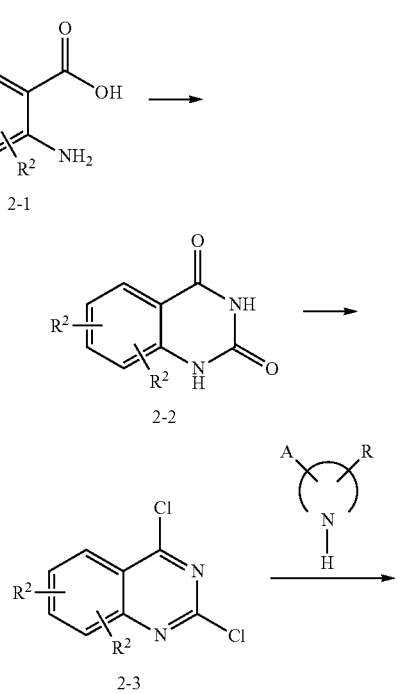

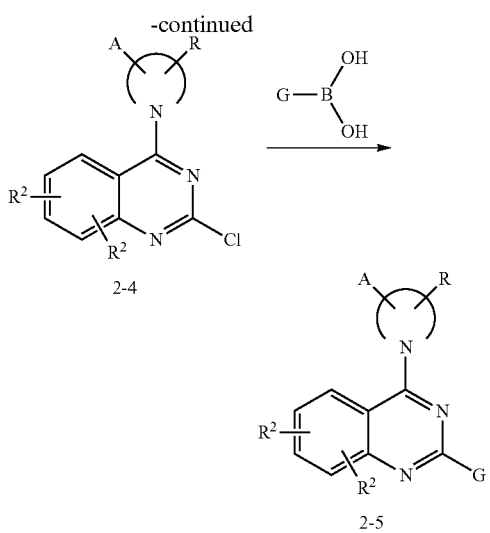

In some embodiments, suitably substituted anthranilic acids 2-1 are used to prepare quinazoline compounds 2-5 as shown in Scheme B. In some embodiments, cyclization of anthranilic acid 2-1 with a cyanate salt (i.e. KOCN) affords quinazoline-(1H,3H)-dione compound 2-2. In some embodiments, quinazoline-(1H,3H)-dione compound 2-2 is chlorinated to yield 2,4-dichloroquinazoline compound 2-3. In some embodiments, the chlorinating agent is $POCl_3$. In some embodiments, dichloroquinazoline compound 2-3 are selectively aminated at the 4-position using an optionally substituted aryl piperidine, aryl piperazines or aryl pyrrolidines to yield compounds of structure 2-4. In some embodiments, a palladium calalyzed Suzuki type reaction with compounds of structure 2-4 and a suitably substituted boronic acid afforded the quinazoline analogs 2-5.

In some embodiments, compounds described herein are prepared as shown in Scheme C.

Scheme C:

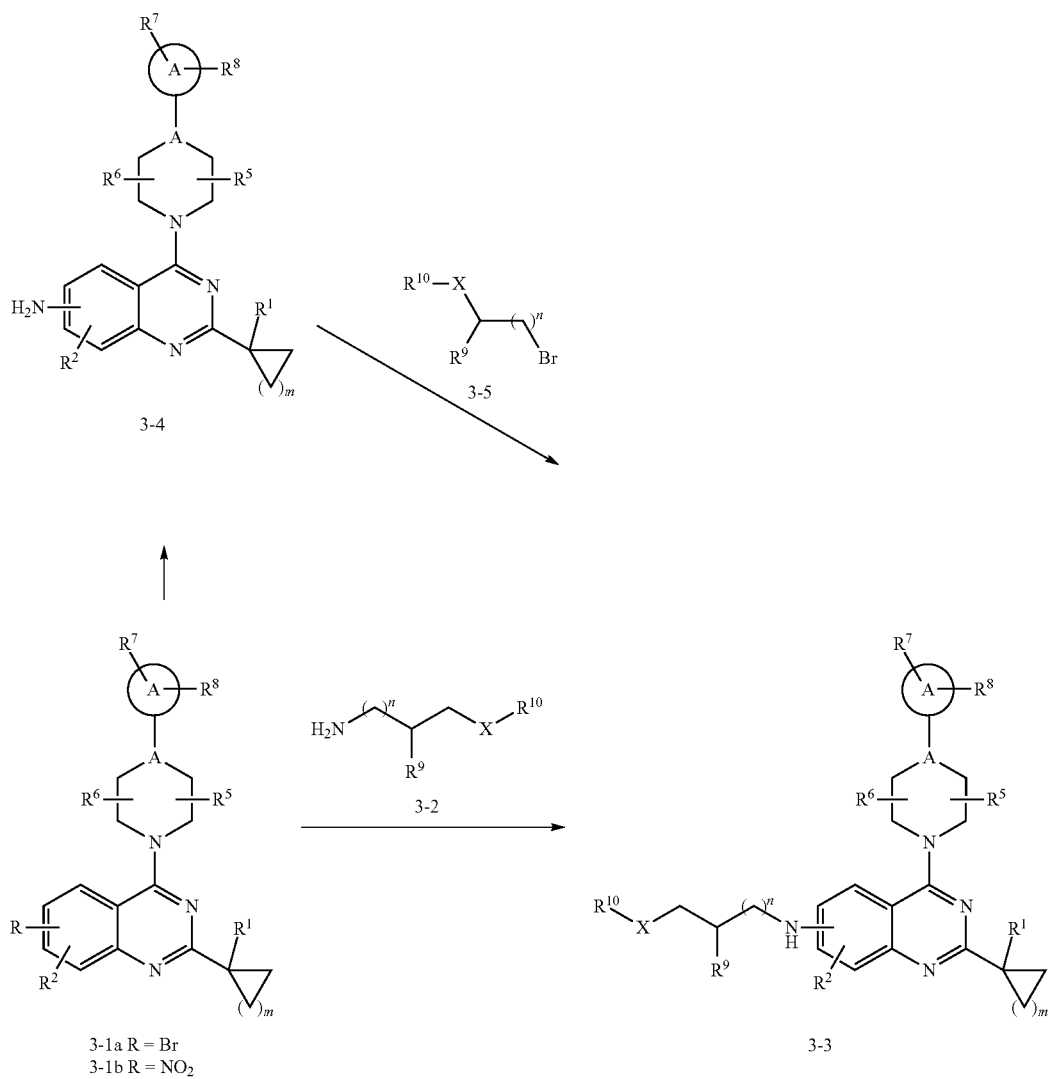

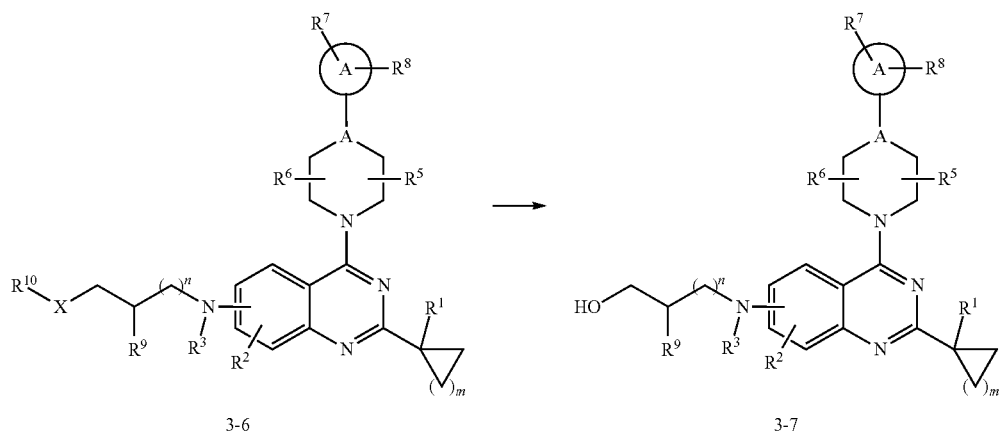

3-6 → 3-7

In some embodiment, suitably substituted bromo-quinazolin-4-ol 3-1a (synthesized from procedures described in either Scheme A or Scheme B) were reacted with a suitably substituted aniline 3-2 using Buchwald type reaction conditions to afford quinazoline derivatives 3-3. In some alternative embodiments, a suitably substituted nitro-quinazolin-4-ol 3-1b (synthesized from procedures described in either Scheme A or Scheme B) were hydrogenated to the aniline derivatives 3-4. In some embodiment these anilines were further reacted with an alkyl halide (3-5) to afford quinazoline derivatives 3-3. In some embodiments, the quinazoline derivatives 3-3 are further functionalized by reacting a suitably substituted aldehyde using reductive amidation conditions to provide derivatives 3-6. In some embodiments, when X is O and $R^{10}$ is a silyl protecting group, quinazoline derivatives 3-6 can be deprotected in the presence of a fluoride source to provide compounds 3-7.

In some embodiments, compounds described herein are prepared as shown in Scheme D.

Scheme D:

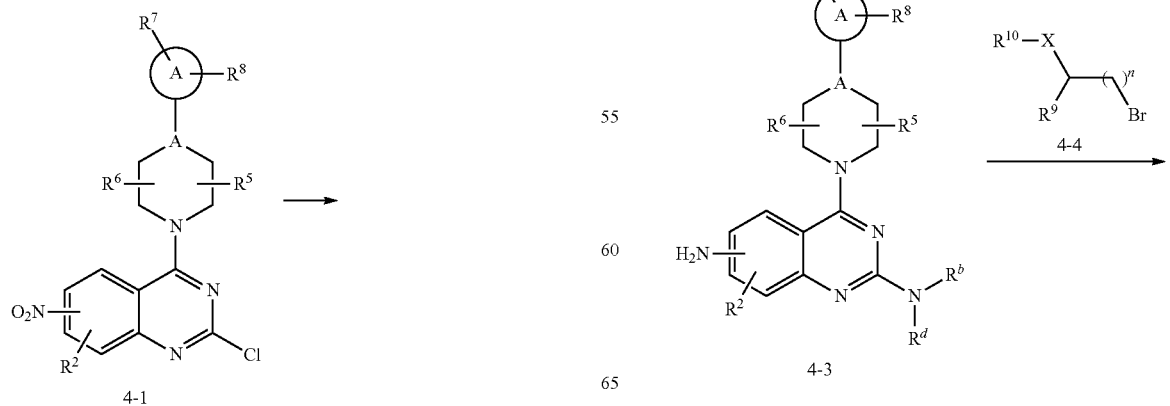

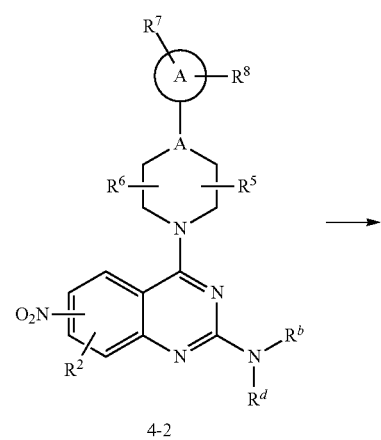

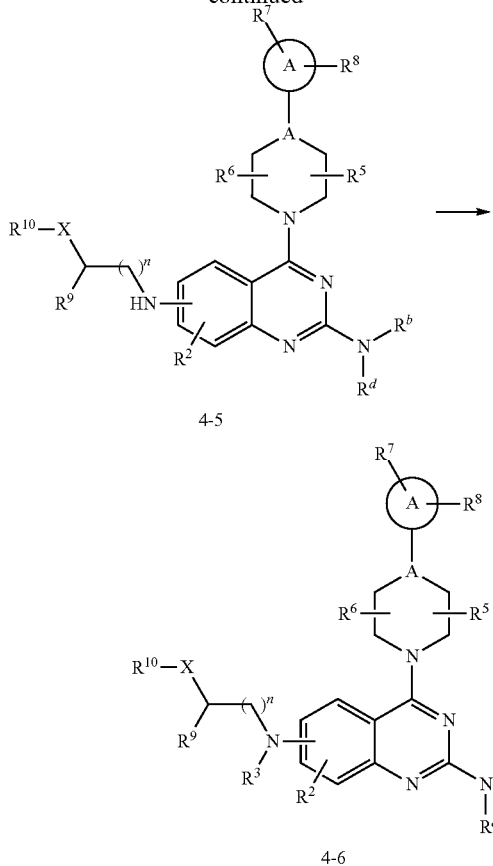

4-5

4-6

In some embodiment, the 2-chloro on the nitro substituted quinazoline ring of compounds 4-1 is displaced by a suitable amine to provide compounds 4-2. In some embodiment the nitro group is reduced to an amino to yield compounds 4-3. In some embodiments, quinazoline 4-3 can be further reacted with an appropriate alkyl halide (4-4) to provide substituted quinazolines 4-5 which can be, in some embodiments further functionalized using an appropriate aldehyde under reductive amination conditions to provide compounds 4-6.

It will be understood that the reactions shown above are illustrative.

In one aspect, compounds are synthesized as described in the Examples section.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —$NH_2$ radical.

"Cyano" refers to the —CN radical.

"Hydroxy" or "hydroxyl" refers to the —OH radical.

"Nitro" refers to the —$NO_2$ radical.

"Oxo" refers to the =O substituent.

"Thioxo" refers to the =S substituent.

"Alkyl" refers to a straight or branched hydrocarbon chain radical, having from one to thirty carbon atoms, and which is attached to the rest of the molecule by a single bond. Alkyls comprising any number of carbon atoms from 1 to 10 are included. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarily. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, and the like. Unless stated otherwise specifically in the specification, an alkyl group may be optionally substituted as described below. "Alkylene" or "alkylene chain" refers to a straight or branched divalent hydrocarbon chain linking the rest of the molecule to a radical group.

"Alkoxy" refers to a radical of the formula —OR where R is an alkyl radical as defined. Unless stated otherwise specifically in the specification, an alkoxy group may be optionally substituted as described below.

"Heteroalkylene" refers to an alkyl radical as described above where one or more carbon atoms of the alkyl is replaced with a O, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —$OCH_2CH_2OMe$, $OCH_2CH_2OCH_2CH_2NH_2$, or $OCH_2CH_2OCH_2CH_2OCH_2CH_2N(Me)_2$.

Representative heteroalkylene groups include, but are not limited to —$OCH_2CH_2O$—, $OCH_2CH_2OCH_2CH_2O$—, or $OCH_2CH_2OCH_2CH_2OCH_2CH_2O$—.

"Alkylamino" refers to a radical of the formula —NHR or —NRR where each R is, independently, an alkyl radical as defined above. Unless stated otherwise specifically in the specification, an alkylamino group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of benzene, indane, indene, and naphthalene. Unless stated otherwise specifically in the specification, the term "aryl" or the prefix "ar-" (such as in "aralkyl") is meant to include aryl radicals that are optionally substituted.

"Carboxy" refers to CO₂H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

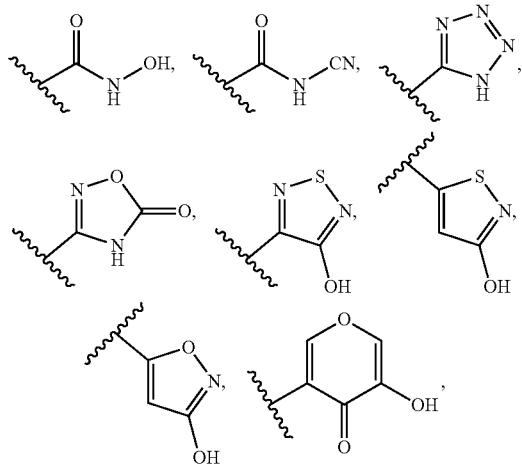

and the like.

"Cycloalkyl" refers to a stable, non-aromatic, monocyclic or polycyclic carbocyclic ring, which may include fused or bridged ring systems, which is saturated or unsaturated, and attached to the rest of the molecule by a single bond. Representative cycloalkyls include, but are not limited to, cycloaklyls having from three to fifteen carbon atoms, from three to ten carbon atoms, from three to eight carbon atoms, from three to six carbon atoms, from three to five carbon atoms, or three to four carbon atoms. Monocyclic cyclcoalkyl radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and 7,7-dimethyl-bicyclo[2.2.1]heptanyl. Unless otherwise stated specifically in the specification, a cycloalkyl group may be optionally substituted. Illustrative examples of cycloalkyl groups include, but are not limited to, the following moieties:

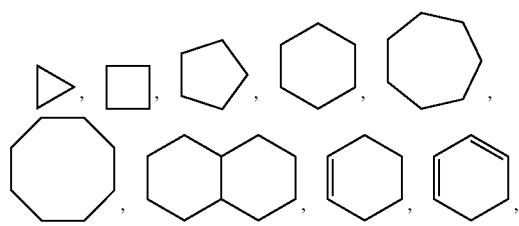

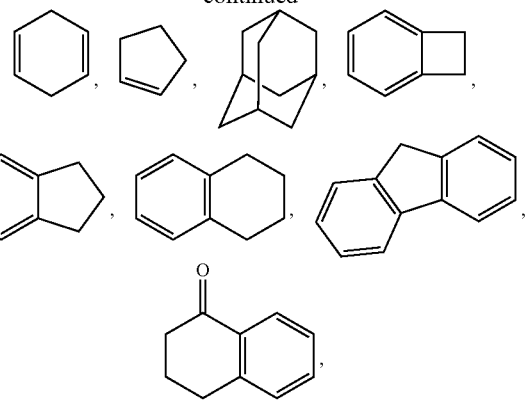

and the like.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Perhalo" or "perfluoro" refers to a moiety in which each hydrogen atom has been replaced by a halo atom or fluorine atom, respectively.

"Heterocyclyl" or "heterocyclic ring" or "hetercycloalkyl" refers to a stable 3- to 14-membered non-aromatic ring radical comprising 2 to 13 carbon atoms and from one to 6 heteroatoms selected from the group consisting of nitrogen, oxygen, and sulfur. Unless stated otherwise specifically in the specification, the heterocyclyl radical may be a monocyclic, or bicyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. Unless stated otherwise specifically in the specification, a heterocyclyl group may be optionally substituted. Illustrative examples of heterocycloalkyl groups, also referred to as non-aromatic heterocycles, include:

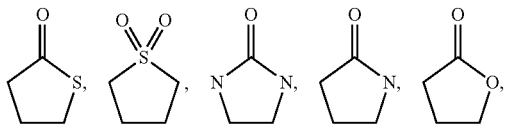

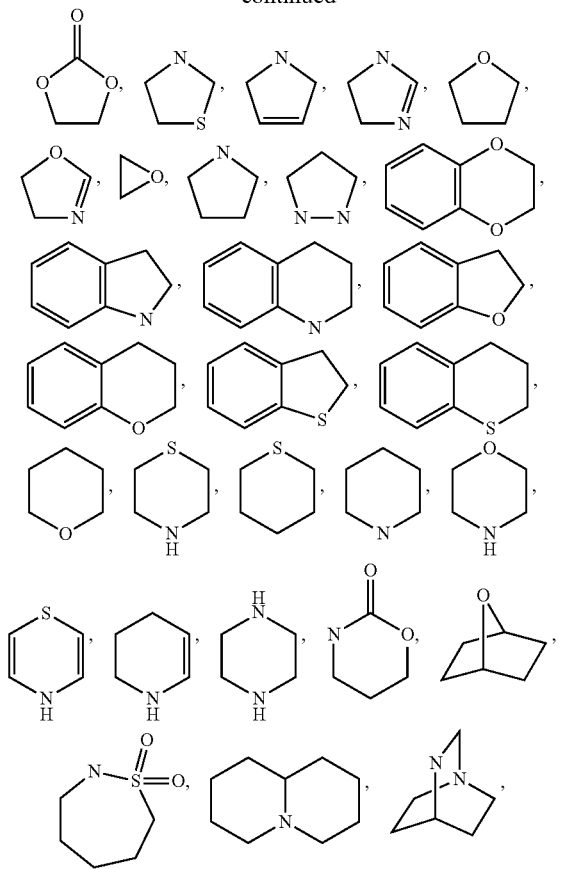

and the like. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups may be further functionalized wherein at least one hydrogen atom is replaced by a bond to a non-hydrogen atom substituent. Unless stated specifically in the specification, a substituted group may include one or more substituents selected from: oxo, —CO$_2$H, nitrile, nitro, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heteroaryl, dialkylamines, arylamines, alkylarylamines, diarylamines, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with —C(=O)R$_g$, —C(=O)OR$_g$, —CH$_2$SO$_2$R$_g$, —CH$_2$SO$_2$NR$_g$R$_h$, —SH, —SR$_g$ or —SSR$_g$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, heterocyclylalkyl, heteroaryl, and/or heteroarylalkyl. In addition, each of the foregoing substituents may also be optionally substituted with one or more of the above substituents. In some embodiments, optional substituents are independently selected from hydrogen, halogen, —CN, —OH, —NO$_2$, —N(R$^{12}$)—R$^{13}$, —C(=C)—N(R$^{12}$)—R$^{13}$, —NR$^{12}$C(=O)R$^{11}$, —C(=O)—O—R$^{11}$, —C—O(=O)—R$^{11}$, —SR$^{12}$, —S(=O)R$^{11}$, —S(=O)$_2$R$^{11}$, —N(R$^{12}$)S(=O)$_2$R$^{11}$, —S(=O)$_2$—N(R$^{12}$)—R$^{13}$, —C(=O)R$^{11}$, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl; each of R$^{12}$ and R$^{13}$ is independently selected from the group consisting of hydrogen, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl; or R$^{12}$ and R$^{13}$, when on the same nitrogen atom, are taken together with the nitrogen atom to which they are attached to form an optionally substituted heterocycloalkyl; R$^{15}$ is selected from the group consisting of optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl. In some embodiments, optional substituents are independently selected from hydrogen, halogen, —CN, —OH, —NO$_2$, —N(R$^{12}$)—R$^{13}$, —C(=C)—N(R$^{12}$)—R$^{13}$, —NR$^{12}$C(=O)R$^{11}$, —C(=O)—O—R$^{11}$, —C—O(=O)—R$^{11}$, —SR$^{12}$, —S(=O)R$^{11}$, —S(=O)$_2$R$^{11}$, —N(R$^{12}$)S(=O)$_2$R$^{11}$, —S(=O)$_2$—N(R$^{12}$)—R$^{13}$, —C(=O)R$^{11}$, alkyl, cycloalkyl, heterocycloalkyl, alkoxy, haloalkyl, haloalkoxy, phenyl, and 5- or 6-membered heteroaryl; each of R$^{12}$ and R$^{13}$ is independently selected from the group consisting of hydrogen, alkyl, cycloalkyl, heterocycloalkyl, alkoxy, haloalkyl, haloalkoxy, phenyl, and 5- or 6-membered heteroaryl; or R$^{12}$ and R$^{13}$, when on the same nitrogen atom, are taken together with the nitrogen atom to which they are attached to form an optionally substituted heterocycloalkyl; R$^{15}$ is selected from the group consisting of alkyl, cycloalkyl, heterocycloalkyl, alkoxy, haloalkyl, haloalkoxy, phenyl, and 5- or 6-membered heteroaryl.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), (II), (III), (IV), (V), (VI), (VII) or (VIII) and a co-agent, are both administered to a patient simultaneously in the form of a single entity or dosage. The term "non-fixed combination" means that the active ingredients, e.g. a compound of Formula (I), (II), (III), (IV), (V), (VI), (VII) or (VIII) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "subject" or "patient" encompasses mammals. Examples of mammals include, but are not limited to, humans. In one embodiment, the mammal is a human.

The terms "treat," "treating" or "treatment," as used herein, include alleviating, abating or ameliorating at least one symptom of a disease disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

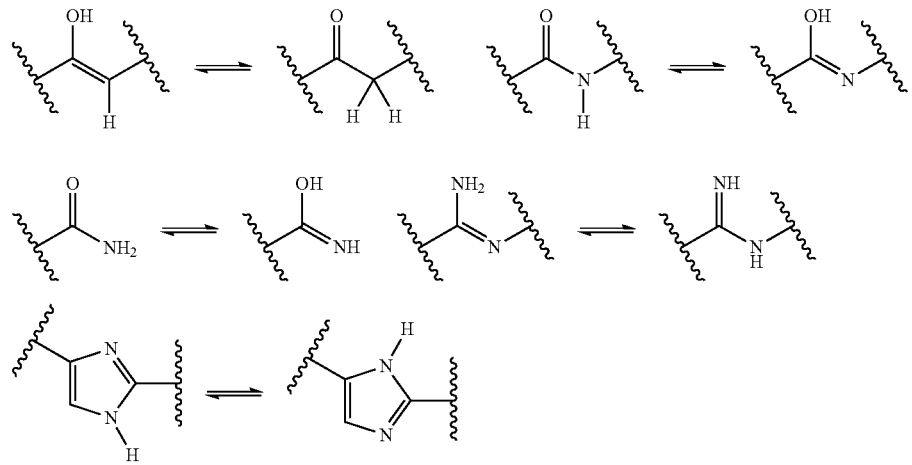

-continued

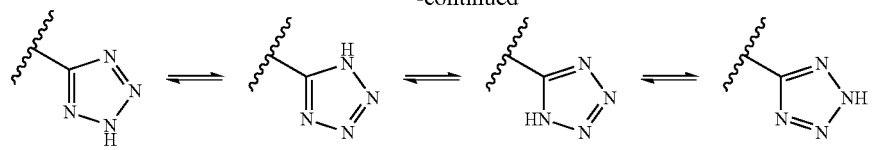

Administration and Pharmaceutical Composition

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula (I), (II), (III), (IV), (V), (VI), (VII) or (VIII) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

Pharmaceutical formulations described herein are administerable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds of Formula (I), (II), (III), (IV), (V), (VI), (VII) or (VIII) are administered orally.

In some embodiments, the compounds of Formula (I), (II), (III), (IV), (V), (VI), (VII) or (VIII) are administered topically. In such embodiments, the compound of Formula (I), (II), (III), (IV), (V), (VI), (VII) or (VIII) is formulated into a variety of topically administrable compositions, such as solutions, suspensions, lotions, gels, pastes, shampoos, scrubs, rubs, smears, medicated sticks, medicated bandages, balms, creams or ointments. In one aspect, the compounds of Formula (I), (II), (III), (IV), (V), (VI), (VII) or (VIII) are administered topically to the skin.

In another aspect, the compounds of Formula (I), (II), (III), (IV), (V), (VI), (VII) or (VIII) are administered by inhalation.

In another aspect, the compounds of Formula (I), (II), (III), (IV), (V), (VI), (VII) or (VIII) are formulated for intranasal administration. Such formulations include nasal sprays, nasal mists, and the like.

In another aspect, the compounds of Formula (I), (II), (III), (IV), (V), (VI), (VII) or (VIII) are formulated as eye drops.

In any of the aforementioned aspects are further embodiments in which the effective amount of the compound of Formula (I), (II), (III), (IV), (V), (VI), (VII) or (VIII) is: (a) systemically administered to the mammal; and/or (b) administered orally to the mammal; and/or (c) intravenously administered to the mammal; and/or (d) administered by inhalation to the mammal; and/or (e) administered by nasal administration to the mammal; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain embodiments, a compound as described herein is administered in a local rather than systemic manner.

In some embodiments, the compound described herein is administered topically. In some embodiments, the compound described herein is administered systemically.

In some embodiments, the pharmaceutical formulation is in the form of a tablet. In other embodiments, pharmaceutical formulations of the compounds of Formula (I), (II), (III), (IV), (V), (VI), (VII) or (VIII) are in the form of a capsule.

In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a compound of Formula (I), (II), (III), (IV), (V), (VI), (VII) or (VIII) is formulated for use as an aerosol, a mist or a powder.

For buccal or sublingual administration, the compositions may take the form of tablets, lozenges, or gels formulated in a conventional manner.

In some embodiments, compounds of Formula (I), (II), (III), (IV), (V), (VI), (VII) or (VIII) are prepared as transdermal dosage forms.

In one aspect, a compound of Formula (I), (II), (III), (IV), (V), (VI), (VII) or (VIII) is formulated into a pharmaceutical composition suitable for intramuscular, subcutaneous, or intravenous injection.

In some embodiments, the compounds described herein may be administered topically and can be formulated into a variety of topically administrable compositions, such as solutions, suspensions, lotions, gels, pastes, medicated sticks, balms, creams or ointments.

In some embodiments, the compounds of Formula (I), (II), (III), (IV), (V), (VI), (VII) or (VIII) are formulated in rectal compositions such as enemas, rectal gels, rectal foams, rectal aerosols, suppositories, jelly suppositories, or retention enemas.

Methods of Dosing and Treatment Regimens

In one embodiment, the compounds of Formula (I), (II), (III), (IV), (V), (VI), (VII) or (VIII) are used in the preparation of medicaments for the treatment of diseases or conditions described herein. In addition, a method for treating any of the diseases or conditions described herein in a subject in need of such treatment, involves administration of pharmaceutical compositions that include at least one compound of Formula (I), (II), (III), (IV), (V), (VI), (VII) or (VIII) or a pharmaceutically acceptable salt, active metabolite, prodrug, or solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition.

In certain embodiments, the dose of drug being administered may be temporarily reduced or temporarily suspended for a certain length of time (i.e., a "drug holiday").

Doses employed for adult human treatment are typically in the range of 0.01 mg-5000 mg per day or from about 1 mg to about 1000 mg per day. In one embodiment, the desired dose is conveniently presented in a single dose or in divided doses.

Combination Treatments

In certain instances, it is appropriate to administer at least one compound of Formula (I), (II), (III), (IV), (V), (VI), (VII) or (VIII) in combination with another therapeutic agent.

In one specific embodiment, a compound of Formula (I), (II), (III), (IV), (V), (VI), (VII) or (VIII) is co-administered with a second therapeutic agent, wherein the compound of Formula (I), (II), (III), (IV), (V), (VI), (VII) or (VIII) and the second therapeutic agent modulate different aspects of the disease, disorder or condition being treated, thereby providing a greater overall benefit than administration of either therapeutic agent alone.

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

In some embodiments, compounds of Formula (I), (II), (III), (IV), (V), (VI), (VII) or (VIII) are administered to a mammal in combination with an anti-inflammatory agent. In some embodiments, compounds of Formula (I), (II), (III), (IV), (V), (VI), (VII) or (VIII) are administered in combination with an anti-psychotic agent. In some embodiments, compounds of Formula (I), (II), (III), (IV), (V), (VI), (VII) or (VIII) are administered to a mammal in combination with a neuroleptic. In some embodiments, compounds of Formula (I), (II), (III), (IV), (V), (VI), (VII) or (VIII) are administered to a mammal in combination with an atypical antipsychotic. In some embodiments, compounds of Formula (I), (II), (III), (IV), (V), (VI), (VII) or (VIII) are administered in combination with a dopamine agonist. In some embodiments, compounds of Formula (I), (II), (III), (IV), (V), (VI), (VII) or (VIII) are administered in combination with an anticholinergic. In some embodiments, compounds of Formula (I), (II), (III), (IV), (V), (VI), (VII) or (VIII) are administered in combination with a COMT inhibitor. In some embodiments, compounds of Formula (I), (II), (III), (IV), (V), (VI), (VII) or (VIII) are administered to a mammal in combination with an analgesic. In some embodiments, compounds of Formula (I), (II), (III), (IV), (V), (VI), (VII) or (VIII) are administered to a mammal in combination with an antidepressant.

In some embodiments, compounds of Formula (I), (II), (III), (IV), (V), (VI), (VII) or (VIII) are administered to a mammal in combination with an NSAID, COX-2 inhibitor, opiate, morphinomimetic, or combinations thereof.

In some embodiments, compounds of Formula (I), (II), (III), (IV), (V), (VI), (VII) or (VIII) are administered in combination with an anti-schizophrenia drug. In some embodiments, compounds of Formula (I), (II), (III), (IV), (V), (VI), (VII) or (VIII) are administered to a mammal in combination with thorazine, haloperidol, fluphenazine, tiotixene, trifluoperazine, perphenazine, thioridazine, clozapine, aripiprazole, ziprasidone, paliperidone, lurasidone, risperidone, asenapine, quetiapine, olanzapine, dihydrexidine, roxindole or combinations thereof.

In some embodiments, compounds of Formula (I), (II), (III), (IV), (V), (VI), (VII) or (VIII) are administered in combination with an anti-Parkinson's drug. In some embodiments, compounds of Formula (I), (II), (III), (IV), (V), (VI), (VII) or (VIII) are administered in combination with L-DOPA, carbidopa, carbidopa/L-DOPA, ropinirole, pramipexole, rotigotine, amantadine, trihexyphenidyl, benzatropine, selegiline, rasagiline, tolcapone, entacapone, apomorphine, bromocriptine, dihydrexidine, dinapsoline, lisuride, pergolide, piribedil, roxindole, sumanirole, or combinations thereof.

In some embodiments, compounds of Formula (I), (II), (III), (IV), (V), (VI), (VII) or (VIII) are administered to a mammal in combination with other therapeutics used in the treatment of drug abuse.

In some embodiments, compounds of Formula (I), (II), (III), (IV), (V), (VI), (VII) or (VIII) are administered to a mammal in combination with a stroke treatment. In some embodiments, compounds of Formula (I), (II), (III), (IV), (V), (VI), (VII) or (VIII) are administered to a mammal in combination with a thrombolytic. In some embodiments, compounds of Formula (I), (II), (III), (IV), (V), (VI), (VII) or (VIII) are administered to a mammal in combination with tissue plasminogen activator (tPA), or a recombinant tissue plasminogen activator. In some embodiments, compounds of Formula (I), (II), (III), (IV), (V), (VI), (VII) or (VIII) are administered to a mammal in combination with alteplase, reteplase, tenecteplase, or combinations thereof.

In some embodiments, compounds of Formula (I), (II), (III), (IV), (V), (VI), (VII) or (VIII) are administered to a mammal in combination with a treatment for neuropathic pain. In some embodiments, compounds of Formula (I), (II), (III), (IV), (V), (VI), (VII) or (VIII) are administered to a mammal in combination with duloxetine, venlafaxine, and milnacipran, amitriptyline, nortriptyline, desipramine, bupropion, pregabalin, gabapentin, carbamazepine, oxcarbazepine, lamotrigine, methadone, ketobemidone, lidocaine, gallium maltolate, capsaicin, botulinum toxin type A, ketamine, dextromethorphan, memantine, alpha lipoic acid, benfotiamine, and combinations thereof.

EXAMPLES

The following examples are intended to illustrate but not limit the disclosed embodiments. All reactions involving air and moisture-sensitive reagents and solvents were performed under a nitrogen atmosphere using standard chemical techniques. Anhydrous solvents were purchased and freshly used from Sigma-Aldrich or EMD Biosciences. All organic reagents were used as purchased. Analytical thin-layer chromatography was performed on Partisil K6F silica gel 60 Å, 250 µm. Microwave-assisted reactions were performed using a CEM Discover system. $^1$H and $^{13}$C chemical shifts are reported in δ values in ppm in the corresponding solvent. All solvents used for chromatography on the synthetic materials were Fisher Scientific HPLC grade, and the water was Millipore Milli-Q PP filtered. LCMS analysis of synthetic materials was completed on a Waters Autopurification system, which consists of a 2767 sample manager, a 2545 binary gradient module, a system fluidics organizer, a 2489 UV/vis detector, and a 3100 mass detector, all controlled with MassLynx software. A Sunfire Analytical C18 5 nm column (4.6×50 mm) and stepwise gradient {10% [(MeCN+0.1% TFA) in (water+0.1% TFA)] to 98% [(MeCN+0.1% TFA) in (water+0.1% TFA)] for 9 min.} was used for analytical LCMS of final compounds. The final compounds were purified by silica gel flash chromatography with ethyl acetate/hexanes as the eluant. All NMR spectra for the synthetic materials were recorded on a Bruker Avance II 400 or DRX-500 MHz instrument. The MestReNova 7 program was used to process and interpret NMR spectra. High Resolution Mass Spectrometry (HRMS) spectra were carried out on an Agilent 6224A Accurate-Mass Time-of-Flight (TOF) LC/MS system with electron spray ionization (ESI).

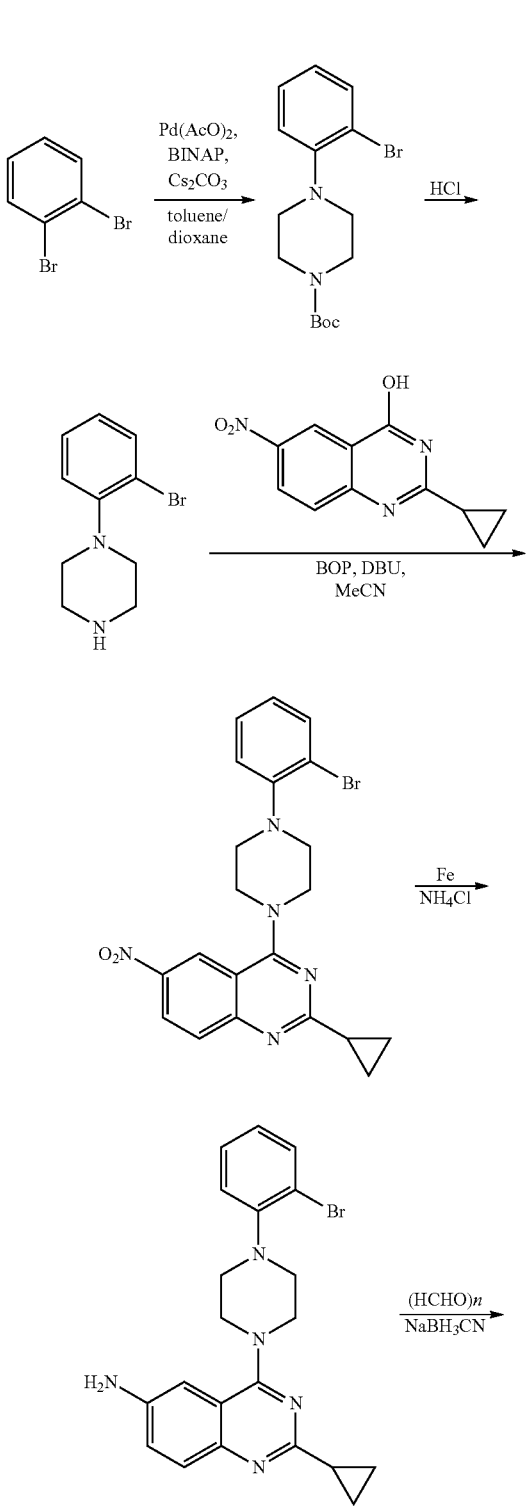

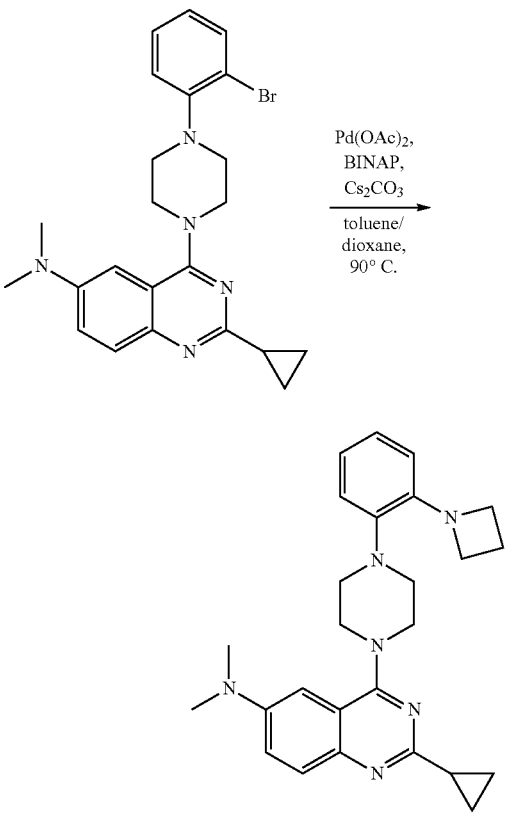

Example 1: Preparation of {4-[4-(2-azetidin-1-yl-phenyl)-piperazin-1-yl]-2-cyclopropyl-quinazolin-6-yl}-dimethyl-amine

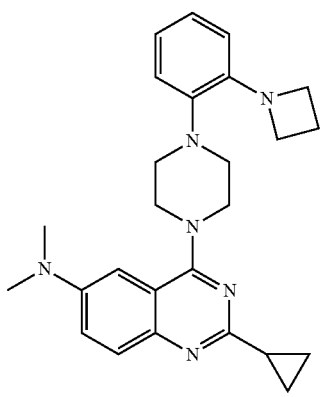

A mixture of 1,2-dibromobenzene (2.36 g, 10 mmol), piperazine-1-carboxylic acid tert-butyl ester (1.86 g, 10 mmol), Pd(OAc)₂ (224.5 mg, 1.0 mmol), BINAP (1.2 g, 2.0 mmol), Cs₂CO₃ (6.5 g, 20 mmol) and toluene/1,4-dioxaen (15 mL/15 mL) was heated to 90° C. overnight. The reaction mixture was filtered and the filtrate was concentrated to dryness. The residue was purified by silica gel column chromatography (PE/EtOAc=1/50) to afford tert-butyl 4-(2-bromophenyl)piperazine-1-carboxylate (1.8 g, yield: 53%) as a colorless oil.

A mixture of tert-butyl 4-(2-bromophenyl)piperazine-1-carboxylate (1.5 g, 4.4 mmol) and HCl/EtOAc (2M, 20 mL) was stirred for 1 hour at room temperature. The reaction mixture was filtered and the solid was dried to afford 1-(2-bromophenyl)piperazine (1.0 g, yield: 85%) as a white solid. A mixture of 2-cyclopropyl-6-nitro-quinazolin-4-ol (700 mg, 3.0 mmol), 1-(2-bromophenyl)piperazine (924 mg, 3.33 mmol), BOP (2.0 g, 4.54 mmol) and DBU (921 mg, 6.06 mmol) in MeCN (20 mL) was stirred at room temperature overnight. The reaction mixture was filtered and the filtrate was concentrated to dryness in vacuum. The residue was purified by silica gel column chromatography (PE/EtOAc=1/50) to afford 4-(4-(2-bromophenyl)piperazin-1-yl)-2-cyclopropyl-6-nitroquinazoline (550 mg, yield: 40%) as a yellow semi-solid.

A mixture of 4-(4-(2-bromophenyl)piperazin-1-yl)-2-cyclopropyl-6-nitroquinazoline (550 mg, 1.21 mmol), active iron powder (340 mg, 6.05 mmol), saturated aqueous NH₄Cl solution (10 mL) in MeOH (20 mL) was heated to 85° C. for 2 hours. After cooled to room temperature, the mixture was filtered through celite. The filtrate was concentrated to remove most of the organic solvent. The aqueous phase was extracted with DCM (10 mL×2). The combined organic layers were dried over Na₂SO₄ and concentrated to give crude product. The crude product was purified by silica gel column chromatography (MeOH/DCM=1/20) to afford 4-(4-(2-bromophenyl)piperazin-1-yl)-2-cyclopropylquinazolin-6-amine (350 mg, yield: 68%) as a yellow semi-solid.

A solution of 4-(4-(2-bromophenyl)piperazin-1-yl)-2-cyclopropylquinazolin-6-amine (300 mg, 0.71 mmol), NaBH₃CN (447.3 mg, 7.1 mmol), HCHO (40% in H₂O, 0.5 mL) in MeOH (5 mL) was stirred at room temperature overnight. 15 mL of water was added and the mixture was extracted with EtOAc (15 mL×3). The organic layer was washed with water (15 mL) and brine (15 mL) and dried over Na₂SO₄. The solution was concentrated to give a residue, which was purified by prep-TLC to afford 4-(4-(2-bromophenyl)piperazin-1-yl)-2-cyclopropyl-N,N-dimethylquinazolin-6-amine (250 mg, yield: 78%) as a yellow semi-solid.

A mixture of 4-(4-(2-bromophenyl)piperazin-1-yl)-2-cyclopropyl-N,N-dimethylquinazolin-6-amine (150 mg, 0.33 mmol), azetidine (38 mg, 0.66 mmol), Pd(OAc)₂ (7.4 mg, 0.033 mmol), BINAP (41 mg, 0.066 mmol), Cs₂CO₃ (324 mg, 0.99 mmol) and toluene/1,4-dioxane (5 mL/5 mL) was heated to 90° C. overnight. The reaction mixture was filtered and the filtrate was concentrated to dryness. The residue was purified by silica gel column chromatography (PE/EtOAc=3/7) then by prep-HPLC to afford {4-[4-(2-azetidin-1-yl-phenyl)-piperazin-1-yl]-2-cyclopropyl-quinazolin-6-yl}-dimethyl-amine (33 mg, yield: 21%) as a yellow solid. $^1$H NMR (400 MHz, DMSO-d$_6$): δ=7.59 (d, J=12.4 Hz, 1H), 7.46-7.43 (m, 1H), 7.02-6.91 (m, 2H), 6.81-6.73 (m, 2H), 6.48-6.46 (m, 1H), 3.89-3.84 (m, 4H), 3.74-3.67 (m, 4H), 3.07-3.00 (m, 10H), 2.21-2.07 (m, 3H), 1.02-0.99 (m, 2H), 0.94-0.89 (m, 2H). MS: m/z 429.3 (M+H⁺).

Example 2: Preparation of {4-[4-(2-azetidin-1-yl-phenyl)-piperazin-1-yl]-2-cyclopropyl-quinazolin-6-yl}-ethyl-methyl-amine

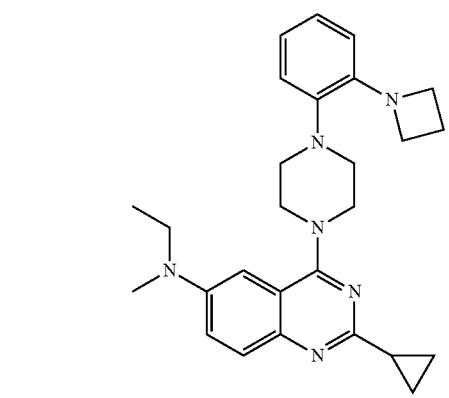

The title compound was prepared as described for {4-[4-(2-azetidin-1-yl-phenyl)-piperazin-1-yl]-2-cyclopropyl-quinazolin-6-yl}-dimethyl-amine except that formaldehyde was substituted for acetaldehyde. $^1$H NMR (400 MHz, CDCl$_3$): δ=7.74 (d, J=7.6 Hz, 1H), 7.32 (d, J=10.4 Hz, 1H), 7.05-7.00 (m, 2H), 6.83-6.79 (m, 2H), 6.53 (d, J=8.4 Hz, 1H), 3.97-3.93 (m, 4H), 3.78-3.70 (m, 4H), 3.50-3.44 (m, 2H), 3.15 (m, 4H), 2.98 (s, 3H), 2.26-2.19 (m, 3H), 1.17-1.14 (m, 5H), 0.98-0.96 (m, 2H). MS: m/z 443.3 (M+H$^+$).

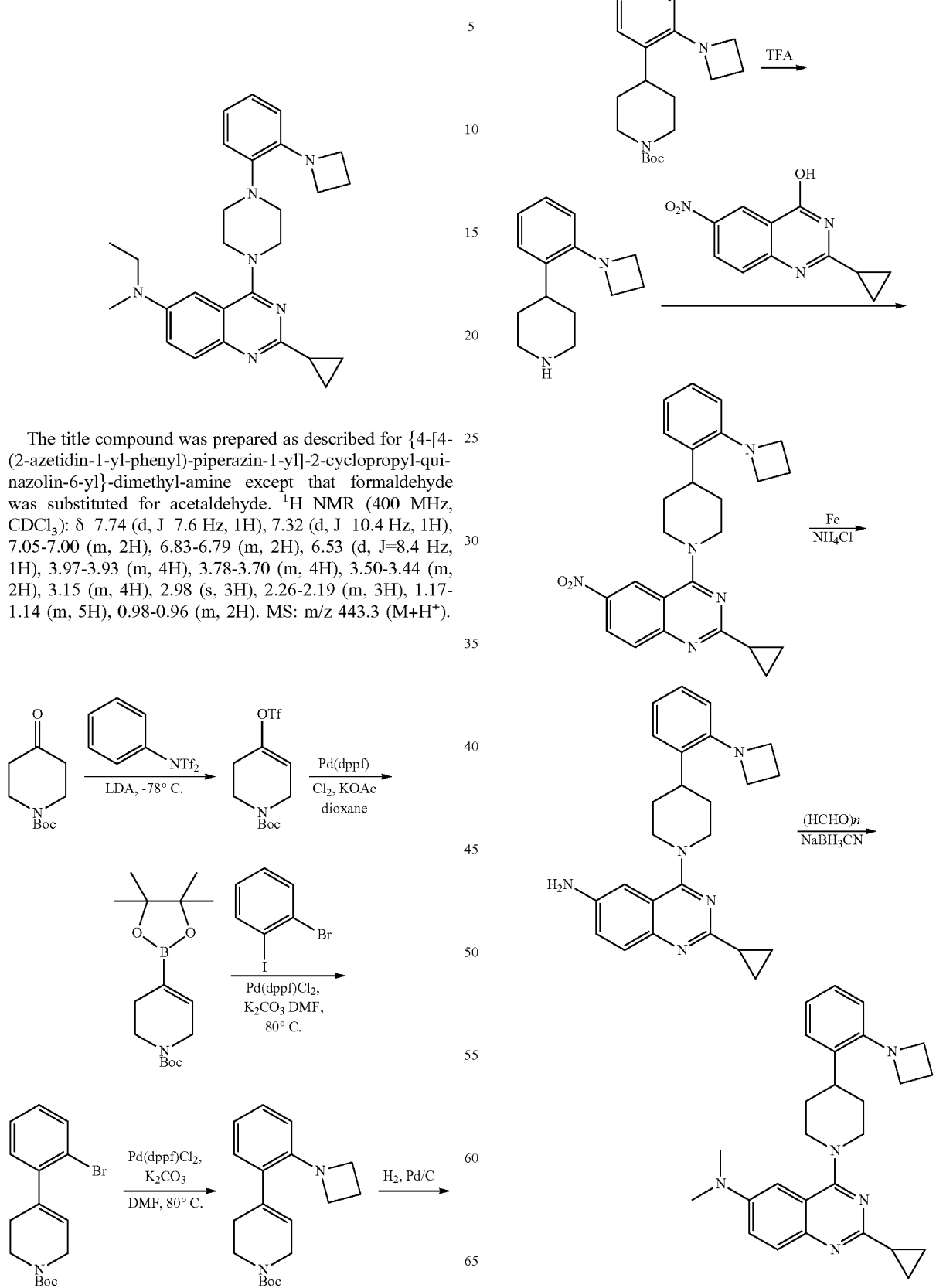

Example 3: Preparation of 4-[4-(2-azetidin-1-yl-phenyl)-piperidin-1-yl]-2-cyclopropyl-quinazolin-6-yl}-dimethyl-amine

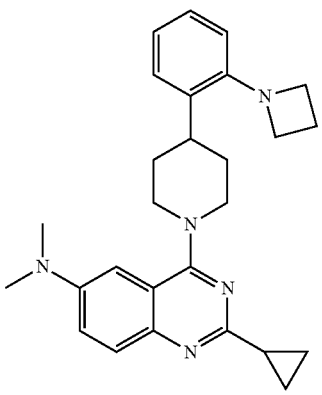

LDA (2M, 65 mL) was added to a solution of 4-oxo-piperidine-1-carboxylic acid tert-butyl ester (20 g, 100 mmol) in 300 mL of dry THF at −78° C. and the mixture was stirred for 30 min. A solution of N,N-bis-(trifluoromethanesulfonyl)aniline in dry THF (100 mL) was added slowly at −78° C. and the mixture was allowed to warm to room temperature and stirred overnight. The reaction was quenched with sat. NH$_4$Cl solution (50 mL) and water (400 mL). The mixture was extracted with EtOAc (200 mL). The organic layer was washed with water (50 mL) and brine (50 mL), and dried over Na$_2$SO$_4$. The solution was concentrated to dryness and the residue was purified by silica gel column chromatography (PE/EA=50/1) to give compound 4-trifluoromethanesulfonyloxy-3,6-dihydro-2H-pyridine-1-carboxylic acid tert-butyl ester (24.5 g, yield: 74%) as a yellow oil. $^1$H NMR (300 MHz, CDCl$_3$): δ=5.76 (s, 1H), 4.04 (d, J=1.8 Hz, 2H), 3.62 (t, J=5.6 Hz, 2H), 2.43 (s, 2H), 1.47 (s, 9H).

A mixture of compound 4-trifluoromethanesulfonyloxy-3,6-dihydro-2H-pyridine-1-carboxylic acid tert-butyl ester (24.5 g, 74 mmol), bis(pinacolato)diboron (21.6 g, 85 mmol), KOAc (25.4 g, 259 mmol), Pd(dppf)Cl$_2$ (1.6 g, 2.22 mmol), dppf (1.23 g, 2.22 mmol) and 250 mL of 1,4-dioxane was stirred at 80° C. overnight. The reaction mixture was poured into water (500 mL) and extracted with EtOAc (200 mL). The organic layer was washed with water (100 mL) and brine (100 mL), dried over Na$_2$SO$_4$, concentrated and purified by silica gel column (PE/EA=20/1) to give compound 4-(4,4,5,5-tetramethyl-[1,3,2]dioxaborolan-2-yl)-3,6-dihydro-2H-pyridine-1-carboxylic acid tert-butyl ester (28 g, quantitative) as a white solid. $^1$H NMR (300 MHz, CDCl$_3$): δ=6.45 (s, 1H), 3.94 (d, J=2.7 Hz, 2H), 3.62 (t, J=5.6 Hz, 2H), 2.22 (s, 2H), 1.45 (s, 9H), 1.25 (s, 12H).

A mixture of compound 4-(4,4,5,5-tetramethyl-[1,3,2]dioxaborolan-2-yl)-3,6-dihydro-2H-pyridine-1-carboxylic acid tert-butyl ester (16.1 g, 52 mmol), 1-bromo-2-iodo-benzene (9.8 g, 35 mmol), K$_2$CO$_3$ (19.3 g, 140 mmol), Pd(dppf)Cl$_2$ (1.25 g, 1.75 mmol), 225 mL of 1,4-dioxane and 75 mL of water was stirred at 70° C. overnight. The reaction mixture was poured into water (500 mL) and extracted with EtOAc (300 mL). The organic layer was washed with water and brine, dried over Na$_2$SO$_4$, concentrated and purified by silica gel column (PE/EA=60/1) to give compound 4-(2-bromo-phenyl)-3,6-dihydro-2H-pyridine-1-carboxylic acid tert-butyl ester (8 g, yield: 67%) as a white solid. $^1$H NMR (300 MHz, CDCl$_3$): δ=7.55 (d, J=7.8 Hz, 1H), 7.29-7.24 (m, 1H), 7.1-7.09 (m, 2H), 5.62 (s, 1H), 4.04 (d, J=2.1 Hz, 2H), 3.64 (t, J=5.6 Hz, 2H), 2.42 (s, 2H), 1.50 (s, 9H).

A mixture of compound 4-(2-bromo-phenyl)-3,6-dihydro-2H-pyridine-1-carboxylic acid tert-butyl ester (7.1 g, 20.11 mmol), azetidine (1.4 g, 24.1 mmol), Pd(AcO)$_2$ (451 mg, 2.01 mmol), BINAP (2.5 g, 4.02 mmol), Cs$_2$CO$_3$ (13.07 g, 40.22 mmol) and toluene/1,4-dioxane (40 mL/40 mL) was stirred at 90° C. Filtration and concentration resulted in a brown residue which was purified by silica gel column (PE/EA=60/1) to give compound 4-(2-azetidin-1-yl-phenyl)-3,6-dihydro-2H-pyridine-1-carboxylic acid tert-butyl ester (5.0 g, 79%) as a yellow oil. $^1$H NMR (300 MHz, CDCl$_3$): δ=7.16-7.12 (m, 1H), 6.96 (dd, J=7.8, 7.5 Hz, 1H), 6.76 (t, J=7.4 Hz, 1H), 6.48 (d, J=8.1 Hz, 1H), 5.62 (m, 1H), 4.01 (d, J=2.1 Hz, 2H), 3.78 (t, J=7.2 Hz, 4H), 3.61 (t, J=5.6 Hz, 2H), 2.40 (s, 2H), 2.26-2.16 (m, 2H), 1.49 (s, 9H).

A mixture of to give compound 4-(2-azetidin-1-yl-phenyl)-3,6-dihydro-2H-pyridine-1-carboxylic acid tert-butyl ester (5.0 g, 15.9 mmol), wet 10% Pd/C (1 g) and MeOH (200 mL) was stirred at 40° C. under 50 psi of H$_2$ overnight. The reaction mixture was filtered and concentrated to give compound 4-(2-azetidin-1-yl-phenyl)-piperidine-1-carboxylic acid tert-butyl ester (5.0 g, quantitive) as a colorless oil.

A mixture of compound 4-(2-azetidin-1-yl-phenyl)-piperidine-1-carboxylic acid tert-butyl ester (5.0 g, 15.9 mmol) was dissolved in DCM (80 mL), CF$_3$CO$_2$H (80 mL) was added and stirred at room temperature for 2 hours. The reaction solution was concentrated and the residue was treated with saturated NaHCO$_3$ solution (100 mL) and extracted with EtOAc (100 mL×5). The organic layer was combined and washed with brine, dried over Na$_2$SO$_4$ and concentrated to give compound 4-(2-azetidin-1-yl-phenyl)-piperidine (2.5 g, yield: 74%) as a white solid.

The title compound was prepared as described for {4-[4-(2-azetidin-1-yl-phenyl)-piperazin-1-yl]-2-cyclopropyl-quinazolin-6-yl}-dimethyl-amine for the last 3 steps. $^1$HNMR (300 MHz, CDCl$_3$): δ=7.78-7.76 (m, 1H), 7.35 (dd, J=9.3 Hz, 1H), 7.24-7.15 (m, 2H), 6.93-6.87 (m, 2H), 6.64-6.61 (m, 1H), 4.41-4.37 (m, 2H), 3.96 (t, J=7.1 Hz, 4H), 3.81-3.04 (m, 8H), 2.35-2.23 (m, 3H), 2.04-1.91 (m, 5H), 1.18-1.15 (m, 2H), 1.00-0.97 (m, 2H). MS: m/z 428.2 (M+H$^+$).

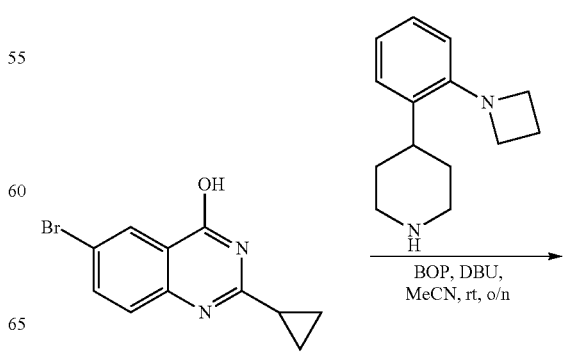

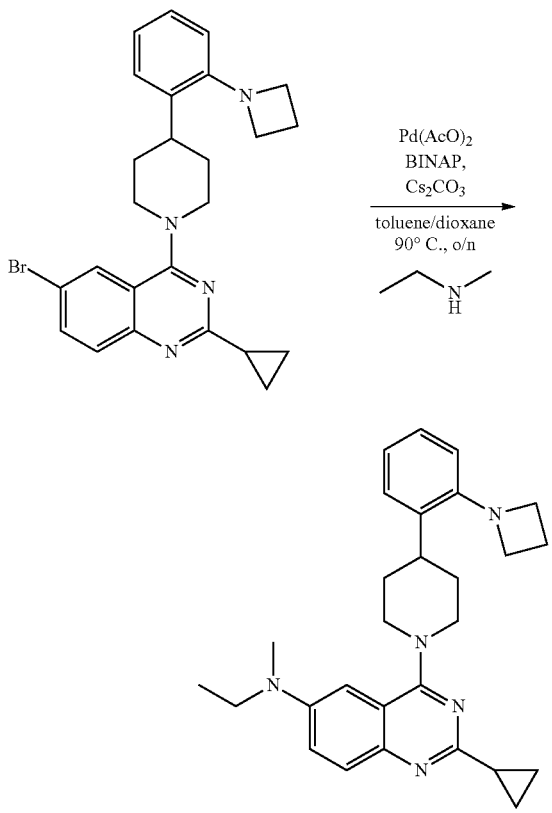

Example 4: Preparation of {4-[4-(2-azetidin-1-yl-phenyl)-piperidin-1-yl]-2-cyclopropyl-quinazolin-6-yl}-ethyl-methyl-amine To a solution of 6-bromo-2-cyclopropylquinazolin-4-ol (530 mg, 2.0 mmol) in ACN (50 mL) were added 4-(2-(azetidin-1-yl)phenyl)piperidine (475 mg, 2.2 mmol), BOP (1.33 g, 3 mmol) and DBU (912 mg, 6.0 mmol). The mixture was stirred at room temperature overnight. The resulting solid was collected by filtration to give the desired compound. The filtrate was poured into water (50 mL) and extracted with EtOAc (20 mL). The organic layer was washed with water and brine and dried over anhydrous $Na_2SO_4$. The solvent was removed and the residue was purified by silica gel column chromatography (PE/EA, 10/1-5/1) to give 4-(4-(2-(azetidin-1-yl)phenyl)piperidin-1-yl)-6-bromo-2-cyclopropylquinazoline (590 mg, yield: 64%) as a white solid. $^1$HNMR (300 MHz, $CDCl_3$): δ=7.96 (d, J=2.1 Hz, 1H), 7.74-7.64 (m, 2H), 7.20-7.13 (m, 2H), 6.89 (t, J=7.5 Hz, 1H), 6.61 (d, J=8.1 Hz, 1H), 4.39 (d, J=12.9 Hz, 2H), 3.96 (t, J=7.2, 4H), 3.32-3.02 (m, 3H), 2.34-2.29 (m, 2H), 2.21-2.15 (m, 1H), 2.03-1.86 (m, 4H), 1.20-1.15 (m, 2H), 1.03-0.97 (m, 2H). MS: m/z 462.9 (M+H$^+$).

A mixture of 4-(4-(2-(azetidin-1-yl)phenyl)piperidin-1-yl)-6-bromo-2-cyclopropylquinazoline (100 mg, 0.22 mmol), N-methylethanamine (26 mg, 0.44 mmol), Pd(OAc)$_2$ (5 mg, 0.022 mmol), BINAP (27.4 mg, 0.044 mmol), $Cs_2CO_3$ (143 mg, 0.44 mmol) and toluene/1,4-dioxaen (5 mL/5 mL) was heated to 90° C. overnight. The reaction mixture was filtered and the filtrate was concentrated to dryness. The residue was purified by prep-TLC (pure EtOAc) then by prep-HPLC to afford {4-[4-(2-azetidin-1-yl-phenyl)-piperidin-1-yl]-2-cyclopropyl-quinazolin-6-yl}-ethyl-methyl-amine (24 mg, yield: 21%) as a yellow solid. $^1$H NMR (300 MHz, $CDCl_3$): δ=7.77-7.74 (m, 1H), 7.33-7.13 (m, 3H), 6.92-6.83 (m, 2H), 6.10 (d, J=8.4 Hz, 1H), 4.40-4.36 (m, 2H), 3.94 (t, J=6.9 Hz, 4H), 3.51-3.45 (m, 2H), 3.12-2.98 (m, 6H), 2.33-2.22 (m, 3H), 2.04-1.89 (m, 4H), 1.30-1.10 (m, 5H), 0.98-0.96 (m, 2H). MS: m/z 442.3 (M+H$^+$).

Example 5: Preparation of N-{4-[4-(2-azetidin-1-yl-phenyl)-piperidin-1-yl]-2-cyclopropyl-quinazolin-6-yl}-N,N',N'-trimethyl-ethane-1,2-diamine

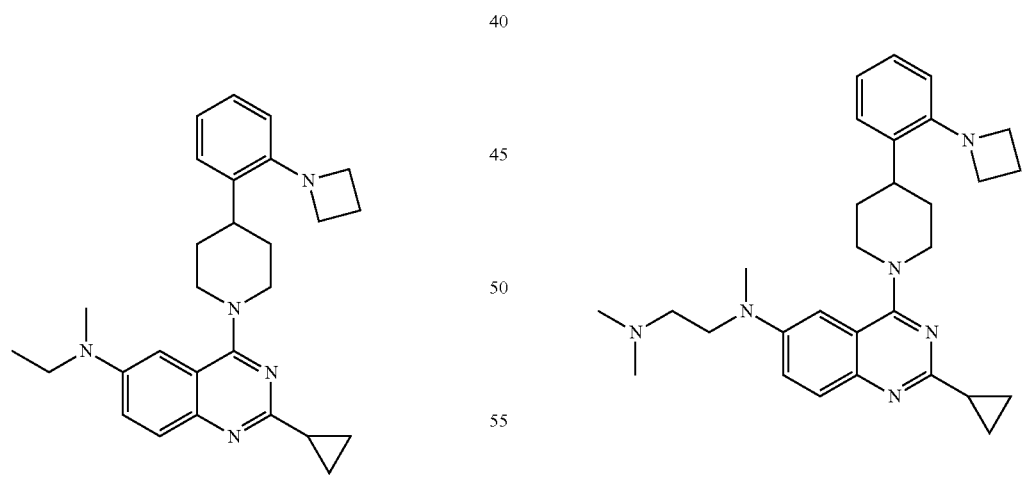

The title compound was prepared as described for {4-[4-(2-azetidin-1-yl-phenyl)-piperidin-1-yl]-2-cyclopropyl-quinazolin-6-yl}-ethyl-methyl-amine. $^1$H NMR (400 MHz, DMSO-d$_6$): δ=7.57 (d, J=9.2 Hz, 1H), 7.39 (dd, J=9.2, 2.8 Hz, 1H), 7.15 (d, J=6.8 Hz, 1H), 7.07 (t, J=8.0 Hz, 1H), 6.80-6.77 (m, 2H), 6.52 (d, J=8.0 Hz, 1H), 4.23 (d, J=12.4 Hz, 2H), 3.87 (t, J=6.8 Hz, 4H), 3.51 (t, J=7.2 Hz, 2H), 3.09-2.94 (m, 6H), 2.41-2.38 (m, 2H), 2.25-2.17 (m, 8H), 2.06-2.02 (m, 1H), 1.90-1.79 (m, 4H), 1.01- 0.97 (m, 2H), 0.91-0.87 (m, 2H). MS: m/z 485.3 (M+H$^+$).

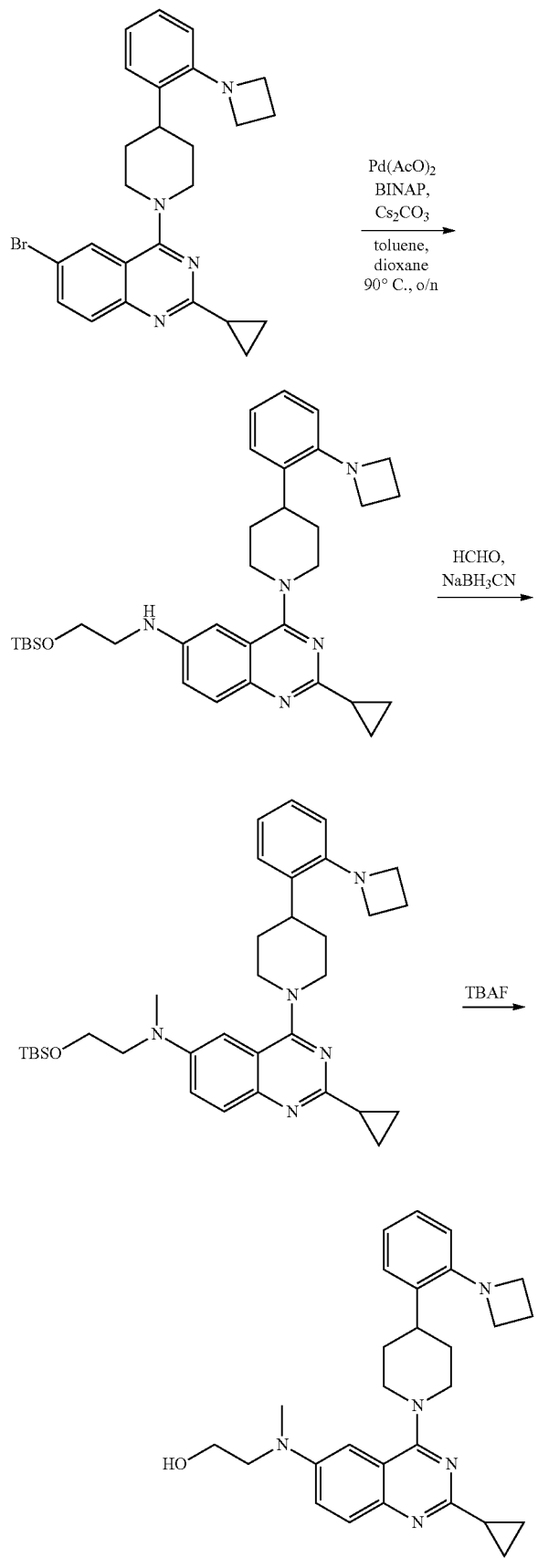

Example 6: Preparation of 2-({4-[4-(2-azetidin-1-yl-phenyl)-piperidin-1-yl]-2-cyclopropyl-quinazolin-6-yl}-methyl-amino)-ethanol A mixture of 4-[4-(2-azetidin-1-yl-phenyl)-piperidin-1-yl]-6-bromo-2-cyclopropyl-quinazoline (150 mg, 0.32 mmol), 2-(tert-Butyl-dimethyl-silanyloxy)-ethylamine (112 mg, 0.64 mmol), Pd(OAc)$_2$ (7.2 mg, 0.032 mmol), BINAP (46 mg, 0.064 mmol), Cs$_2$CO$_3$ (209 mg, 0.64 mmol) and toluene/1,4-dioxaen (5 mL/5 mL) was heated to 90° C. overnight. The reaction mixture was filtered and the filtrate was concentrated to afford crude {4-[4-(2-azetidin-1-yl-phenyl)-piperidin-1-yl]-2-cyclopropyl-quinazolin-6-yl}-[2-(tert-butyl-dimethyl-silanyloxy)-ethyl]-amine (crude 350 mg, yield: quantitative) as a yellow gel.

To the solution of crude {4-[4-(2-azetidin-1-yl-phenyl)-piperidin-1-yl]-2-cyclopropyl-quinazolin-6-yl}-[2-(tert-butyl-dimethyl-silanyloxy)-ethyl]-amine (crude 350 mg, 0.32 mmol) in MeOH (20 mL) was added HCHO (38% in H$_2$O, 0.52 mL), followed by NaBH(AcO)$_3$ (678 mg, 3.2 mmol) and NaBH$_3$CN (202 mg, 3.2 mmol). The solution was stirred at RT overnight. The resulting solution was poured into sat. NaHCO$_3$ solution (30 mL) and the aqueous phase was extracted with EtOAc (20 mL). The organic layer was washed with water and brine, dried over Na$_2$SO$_4$, concentrated to give crude {4-[4-(2-azetidin-1-yl-phenyl)-piperidin-1-yl]-2-cyclopropyl-quinazolin-6-yl}-[2-(tert-butyl-dimethyl-silanyloxy)-ethyl]-methyl-amine (used for next step directly without purification) as a yellow gel.

To the solution of crude {4-[4-(2-azetidin-1-yl-phenyl)-piperidin-1-yl]-2-cyclopropyl-quinazolin-6-yl}-[2-(tert-butyl-dimethyl-silanyloxy)-ethyl]-methyl-amine (crude, 0.32 mmol) in THF (10 mL) was added TBAF (1 M in THF, 1 mL). The solution was stirred at RT overnight. The resulting solution was concentrated, purified by prep-TLC (DCM/MeOH=10/1) then further purified by prep-HPLC to give 2-({4-[4-(2-azetidin-1-yl-phenyl)-piperidin-1-yl]-2-cyclopropyl-quinazolin-6-yl}-methyl-amino)-ethanol (30 mg, yield: 20% over 3 steps) as a yellow gel. $^1$H NMR (300 MHz, CDCl$_3$): δ=7.70 (d, J=9.0 Hz, 1H), 7.35 (dd, J=9.0, 2.7 Hz, 1H), 7.24-7.14 (m, 2H), 6.96-6.90 (m, 2H), 6.62 (d, J=8.4, 1H), 4.37-4.31 (m, 2H), 3.97-3.86 (m, 6H), 3.58-3.54 (m, 2H), 3.13-3.01 (m, 6H), 2.35-2.30 (m, 2H), 2.20-2.18 (m, 1H), 2.00-1.89 (m, 4H), 1.17-1.14 (m, 2H), 1.00-0.95 (m, 2H). MS: m/z 458.3 (M+H$^+$).

Example 7: Preparation of {4-[4-(2-azetidin-1-yl-phenyl)-piperidin-1-yl]-2-cyclopropyl-quinazolin-6-yl}-(2-methoxy-ethyl)-methyl-amine

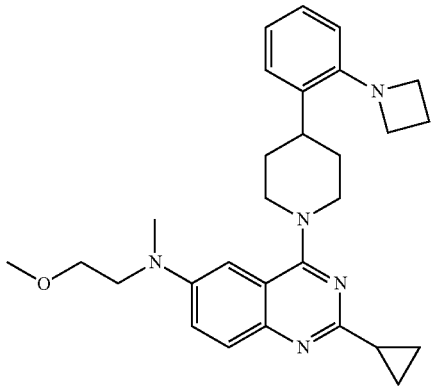 [SMILES: COCCN(C)c1ccc2nc(C3CC3)nc(N3CCC(c4ccccc4N4CCC4)CC3)c2c1]

The title compound was prepared as described for 2-({4-[4-(2-azetidin-1-yl-phenyl)-piperidin-1-yl]-2-cyclopropyl-quinazolin-6-yl}-methyl-amino)-ethanol. $^1$H NMR (400 MHz, CDCl$_3$): δ=7.72 (d, J=9.2 Hz, 1H), 7.33 (d, J=8.4 Hz, 1H), 7.22 (d, J=7.6 Hz, 1H), 7.15 (t, J=7.2 Hz, 1H), 6.89-6.87 (m, 2H), 6.61 (d, J=7.6 Hz, 1H), 4.34 (d, J=12.8 Hz, 2H), 3.94 (t, J=6.8 Hz, 4H), 3.59 (s, 4H), 3.35 (s, 3H), 3.09-3.00 (m, 6H), 2.32-2.29 (m, 2H), 2.20-2.18 (m, 1H), 1.98-1.90 (m, 4H), 1.17-1.14 (m, 2H), 0.96-0.94 (m, 2H). MS: m/z 472.3 (M+H$^+$).

Example 8: Preparation of {4-[4-(2-azetidin-1-yl-phenyl)-piperidin-1-yl]-2-cyclopropyl-quinazolin-6-yl}-methyl-(2-morpholin-4-yl-ethyl)-amine

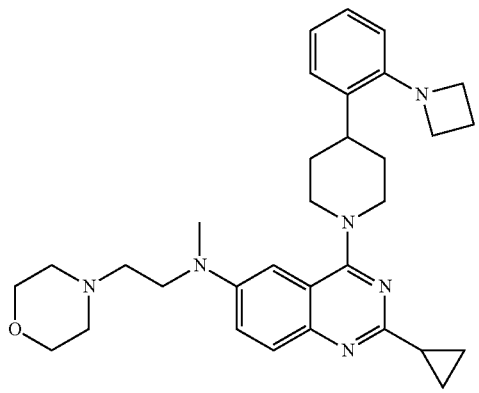 [SMILES: CN(CCN1CCOCC1)c1ccc2nc(C3CC3)nc(N3CCC(c4ccccc4N4CCC4)CC3)c2c1]

The title compound was prepared as described for 2-({4-[4-(2-Azetidin-1-yl-phenyl)-piperidin-1-yl]-2-cyclopropyl-quinazolin-6-yl}-methyl-amino)-ethanol. $^1$H NMR (400 MHz, CDCl$_3$): δ=7.72 (d, J=9.6 Hz, 1H), 7.31 (dd, J=9.2, 2.8 Hz, 1H), 7.21 (d, J=6.8 Hz, 1H), 7.15 (t, J=7.6 Hz, 1H), 6.90-6.85 (m, 2H), 6.61 (d, J=8.0 Hz, 1H), 4.33 (d, J=12.8 Hz, 2H), 3.94 (t, J=7.2 Hz, 4H), 3.69 (t, J=4.4 Hz, 4H), 3.56 (t, J=7.2 Hz, 2H), 3.09-3.00 (m, 6H), 2.58-2.50 (m, 6H), 2.34-2.27 (m, 2H), 2.20-2.16 (m, 1H), 2.02-1.90 (m, 4H), 1.16-1.13 (m, 2H), 0.98-0.93 (m, 2H). MS: m/z 527.3 (M+H$^+$).

Example 9: Preparation of {4-[4-(2-azetidin-1-yl-phenyl)-piperidin-1-yl]-2-cyclopropyl-quinazolin-6-yl}-methyl-(2-pyrrolidin-1-yl-ethyl)-amine

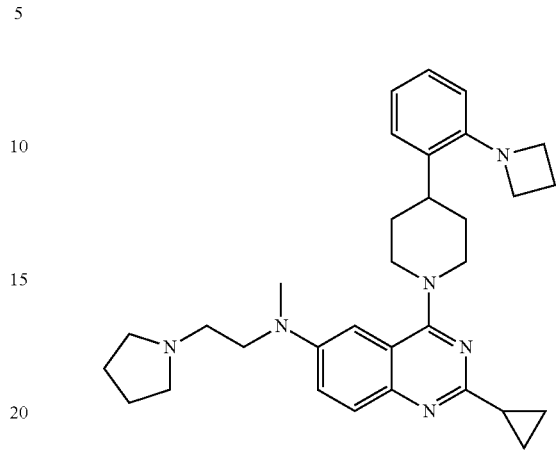

The title compound was prepared as described in 2-({4-[4-(2-azetidin-1-yl-phenyl)-piperidin-1-yl]-2-cyclopropyl-quinazolin-6-yl}-methyl-amino)-ethanol. $^1$H NMR (400 MHz, DMSO-d$_6$): δ=7.57 (d, J=9.6 Hz, 1H), 7.38 (dd, J=9.2, 2.4 Hz, 1H), 7.14 (d, J=7.6 Hz, 1H), 7.07 (t, J=7.2 Hz, 1H), 6.80-6.76 (m, 2H), 6.52 (d, J=8.0 Hz, 1H), 4.22 (d, J=12.4 Hz, 2H), 3.86 (t, J=7.6 Hz, 4H), 3.53 (t, J=7.6 Hz, 2H), 3.08-2.92 (m, 6H), 2.61-2.50 (m, 6H), 2.25-2.18 (m, 2H), 2.06-2.02 (m, 1H), 1.91-1.79 (m, 4H), 1.65 (s, 4H), 1.01-0.98 (m, 2H), 0.91-0.87 (m, 2H). MS: m/z 511.3 (M+H$^+$).

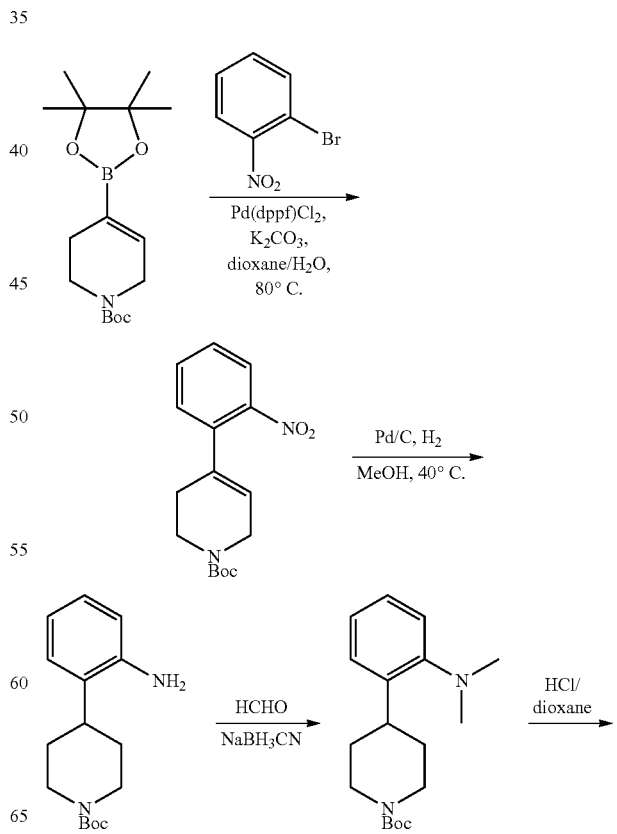

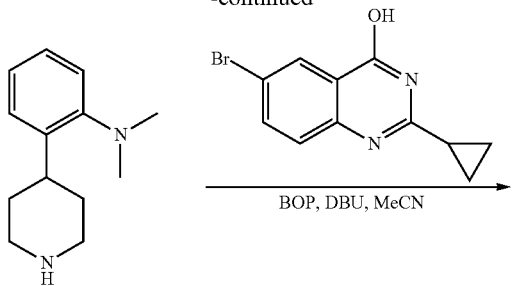

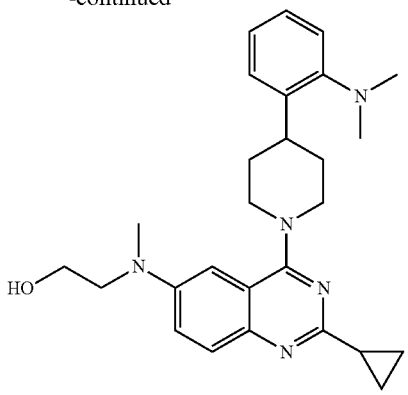

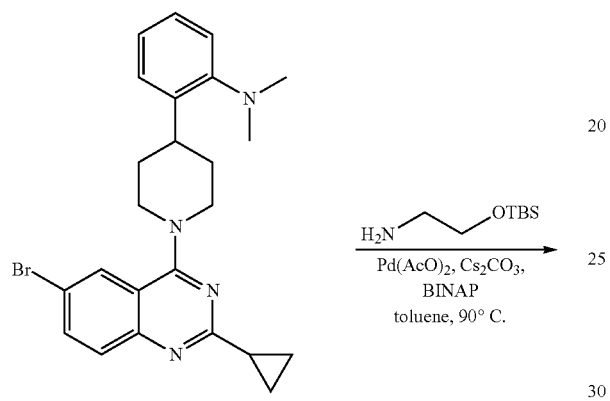

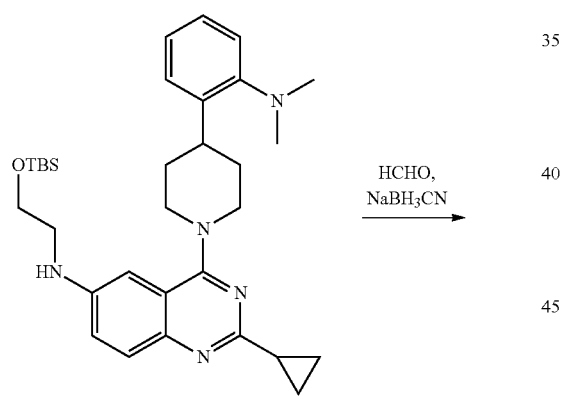

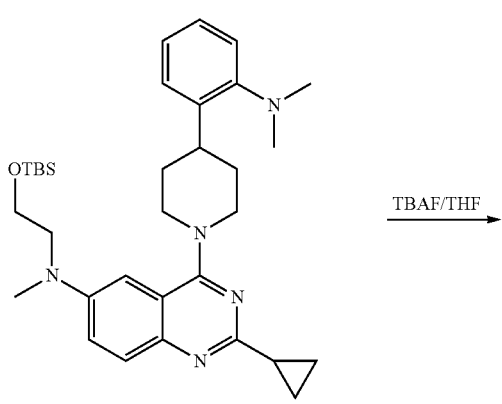

Example 10: Preparation of 2-({2-cyclopropyl-4-[4-(2-dimethylamino-phenyl)-piperidin-1-yl]-quinazolin-6-yl}-methyl-amino)-ethanol A mixture of tert-butyl 4-(4,4,5,5-tetramethyl-1,3,2-dioxaborolan-2-yl)-5,6-dihydropyridine-1(2H)-carboxylate (10.1 g, 32.7 mmol), 1-bromo-2-nitro-benzene (4.4 g, 21.8 mmol), $K_2CO_3$ (12.0 g, 87.2 mmol), Pd(dppf)$Cl_2$ (0.78 g, 1.09 mmol), 90 mL of 1,4-dioxane and 30 mL of water was stirred at 80° C. overnight. The reaction mixture was poured into water (200 mL) and extracted with EtOAc (200 mL). The organic layer was washed with water and brine, dried over $Na_2SO_4$, concentrated and purified by silica gel column (PE/EA=60/1) to give tert-butyl 4-(2-nitrophenyl)-5,6-dihydropyridine-1(2H)-carboxylate (4.5 g, yield: 68%) as a yellow oil. MS: m/z 204.9 (M+H$^+$).

A mixture of tert-butyl 4-(2-nitrophenyl)-5,6-dihydropyridine-1(2H)-carboxylate (3.1 g, 15.2 mmol), wet 10% Pd/C (0.6 g) and MeOH (35 mL) was stirred at 40° C. under 50 psi of $H_2$ overnight. The reaction mixture was filtered to give a solution of tert-butyl 4-(2-aminophenyl)piperidine-1-carboxylate used for next step directly. MS: m/z 177.0 (M+H$^+$).

To the solution of tert-butyl 4-(2-aminophenyl)piperidine-1-carboxylate in MeOH (70 mL) was added HCHO (38% in $H_2O$, 7 mL), followed by NaBH(AcO)$_3$ (6.4 g, 30.2 mmol) and NaBH$_3$CN (4.8 g, 76 mmol). The solution was stirred at RT overnight. The resulting solution was poured into sat. NaHCO$_3$ solution (100 mL) and the aqueous phase was extracted with EtOAc (100 mL). The organic layer was washed with water and brine, dried over $Na_2SO_4$, concentrated and purified by silica gel column (PE/EA=15/1) to give tert-butyl 4-(2-(dimethylamino)phenyl)piperidine-1-carboxylate (1.5 g, yield: 33% over 2 steps) as a white solid. MS: m/z 305.0 (M+H$^+$).

To a solution tert-butyl 4-(2-(dimethylamino)phenyl)piperidine-1-carboxylate (1.5 g, 4.93 mmol) in EA (15 mL) was added HCl/dioxane (5M, 15 mL) and the mixture was stirred at room temperature for 2 hours. The reaction solution was concentrated to give HCl salt of N,N-dimethyl-2-(piperidin-4-yl) aniline (1.2 g, yield: 88%) as a white solid. MS: m/z 204.8 (M+H$^+$).

A mixture of N,N-dimethyl-2-(piperidin-4-yl)aniline (600 mg, 2.16 mmol), 6-bromo-2-cyclopropylquinazolin-4-ol (530 mg, 2.0 mmol), BOP (1.33 g, 3.0 mmol) and DBU (1.2 g, 8 mmol) in MeCN (50 mL) was stirred at room temperature overnight. The reaction mixture was filtered and the cake was dried to afford 2-(1-(6-bromo-2-cyclopropylquinazolin-4-yl) piperidin-4-yl)-N,N-dimethylaniline (730 mg, yield: 81%) as a white solid. $^1$HNMR (300 MHz, CDCl$_3$): δ=7.98 (d, J=1.8 Hz, 1H), 7.74-7.64 (m, 2H), 7.28-7.07 (m, 4H), 4.42-4.37 (m, 2H), 3.53-3.48 (m, 1H), 3.27-3.18 (m, 2H), 2.70 (s, 6H), 2.21-2.15 (m, 1H), 1.92-1.86 (m, 4H), 1.21-1.16 (m, 2H), 1.03-0.97 (m, 2H).

The title compound was prepared as described for 2-({4-[4-(2-azetidin-1-yl-phenyl)-piperidin-1-yl]-2-cyclopropyl-quinazolin-6-yl}-methyl-amino)-ethanol for the last three steps. $^1$H NMR (300 MHz, CDCl$_3$): δ=7.83 (d, J=6.0 Hz, 1H), 7.40 (d, J=2.7 Hz, 1H), 7.30-7.11 (m, 4H), 6.98 (d, J=3.0 Hz, 1H), 4.46 (d, J=12.9 Hz, 2H), 3.88 (t, J=5.7 Hz, 2H), 3.59-3.49 (m, 3H), 3.23-3.15 (m, 2H), 3.06 (s, 3H), 2.71 (s, 6H), 2.32-2.28 (m, 1H), 1.95-1.77 (m, 4H), 1.27-1.17 (m, 2H), 1.05-1.00 (m, 2H). MS: m/z 446.3 (M+H$^+$).

Example 11: Preparation of {2-cyclopropyl-4-[4-(2-dimethylamino-phenyl)-piperidin-1-yl]-quinazolin-6-yl}-(2-methoxy-ethyl)-methyl-amine

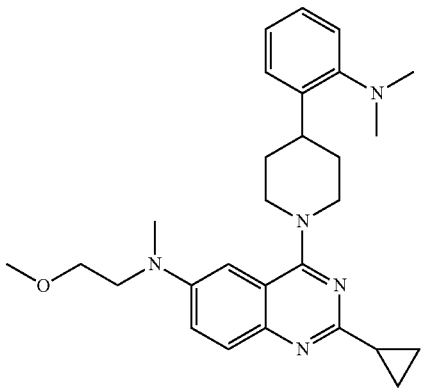 [SMILES: COCCN(C)c1ccc2nc(C3CC3)nc(N3CCC(c4ccccc4N(C)C)CC3)c2c1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (300 MHz, CDCl$_3$): δ=8.31-8.28 (m, 1H), 7.35 (dd, J=9.3, 2.4 Hz, 1H), 7.25-7.18 (m, 3H), 7.13-7.08 (m, 1H), 6.90 (d, J=2.7 Hz, 1H), 4.82-4.78 (m, 2H), 3.63-3.58 (m, 5H), 3.40-3.31 (m, 5H), 3.05 (s, 3H), 2.79-2.78 (m, 1H), 2.69 (s, 6H), 2.02-1.83 (m, 4H), 1.25-1.18 (m, 4H). MS: m/z 460.3 (M+H$^+$).

Example 12: Preparation of {2-Cyclopropyl-4-[4-(2-dimethylamino-phenyl)-piperidin-1-yl]-quinazolin-6-yl}-methyl-(2-morpholin-4-yl-ethyl)-amine

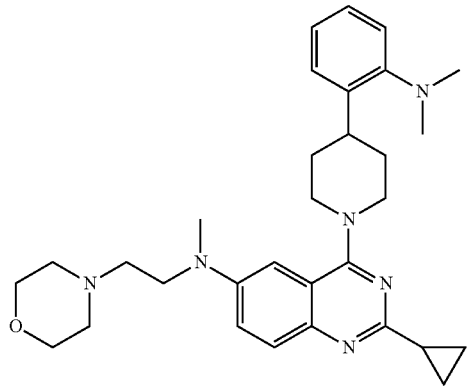 [SMILES: CN(C)c1ccccc1C1CCN(c2nc(C3CC3)nc3ccc(N(C)CCN4CCOCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (300 MHz, CDCl$_3$): δ=8.32-8.30 (m, 1H), 7.37-7.10 (m, 5H), 6.80 (d, J=2.4 Hz, 1H), 4.80-4.75 (m, 2H), 3.70-3.55 (m, 7H), 3.36-3.31 (m, 2H), 3.05 (s, 3H), 2.77-2.70 (m, 7H), 2.58-2.48 (m, 6H), 2.02-1.85 (m, 4H), 1.28-1.18 (m, 4H). MS: m/z 515.4 (M+H$^+$).

Example 13: Preparation of {2-cyclopropyl-4-[4-(2-dimethylamino-phenyl)-piperidin-1-yl]-quinazolin-6-yl}-methyl-(2-pyrrolidin-1-yl-ethyl)-amine

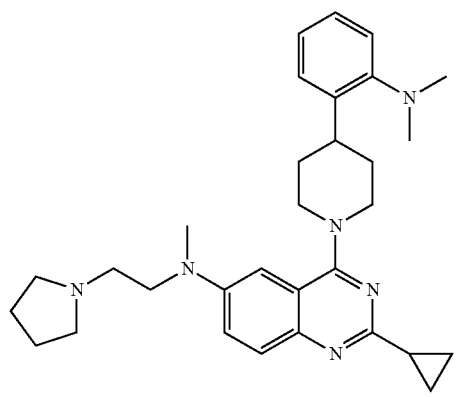 [SMILES: CN(C)c1ccccc1C1CCN(c2nc(C3CC3)nc3ccc(N(C)CCN4CCCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=8.01-7.98 (m, 1H), 7.32 (dd, J=9.2, 2.4 Hz, 1H), 7.24-7.16 (m, 3H), 7.11-7.07 (m, 1H), 6.94 (s, 1H), 4.55-4.51 (m, 2H), 3.86-3.84 (m, 2H), 3.58-3.52 (m, 1H), 3.33-3.27 (m, 2H), 3.08 (s, 3H), 3.01-2.90 (m, 4H), 2.74 (s, 6H), 2.45-2.42 (m, 1H), 2.02-1.82 (m, 10H), 1.26-1.17 (m, 2H), 1.08-1.06 (m, 2H). MS: m/z 499.3 (M+H$^+$).

Example 14: Preparation of N-{2-cyclopropyl-4-[4-(2-dimethylamino-phenyl)-piperidin-1-yl]-quinazolin-6-yl}-N,N',N'-trimethyl-ethane-1,2-diamine

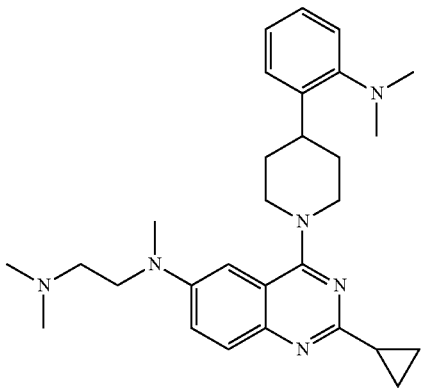 [SMILES: CN(C)CCN(C)c1ccc2nc(C3CC3)nc(N3CCC(c4ccccc4N(C)C)CC3)c2c1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.93 (m, 1H), 7.31 (dd, J=10.0, 3.2 Hz, 1H), 7.26-7.16 (m, 3H), 7.10 (t, J=7.6 Hz, 1H), 6.86 (d, J=2.4 Hz, 1H), 4.50-4.47 (m, 2H), 3.58-3.52 (m, 3H), 3.24-3.18 (m, 2H), 3.04 (s, 3H), 2.70 (s, 6H), 2.55-2.51 (m, 2H), 2.32 (s, 6H), 1.93-1.88 (m, 4H), 1.18-1.17 (m, 2H), 1.04-1.01 (m, 2H). MS: m/z 473.3 (M+H+).

Example 15: Preparation of 2-({2-(1-Fluoro-cyclopropyl)-4-[4-(2-methoxy-phenyl)-piperidin-1-yl]-quinazolin-6-yl}-methyl-amino)-ethanol

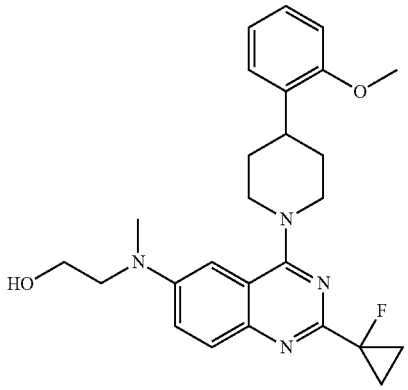

The title compound was prepared as described in example 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.89 (d, J=9.2 Hz, 1H), 7.40 (dd, J=9.2 Hz, 1H), 7.26-7.20 (m, 2H), 6.98-6.94 (m, 2H), 6.89 (d, J=8.4 Hz, 1H), 4.35 (d, J=12.8 Hz, 2H), 3.89-3.85 (m, 5H), 3.57 (t, J=5.6 Hz, 2H), 3.31-3.25 (m, 1H), 3.17-3.06 (m, 5H), 1.98-1.84 (m, 4H), 1.61-1.47 (m, 4H). MS: m/z 451.2 (M+H⁺).

Example 16: Preparation of {2-(1-fluoro-cyclopropyl)-4-[4-(2-methoxy-phenyl)-piperidin-1-yl]-quinazolin-6-yl}-(2-methoxy-ethyl)-methyl-amine

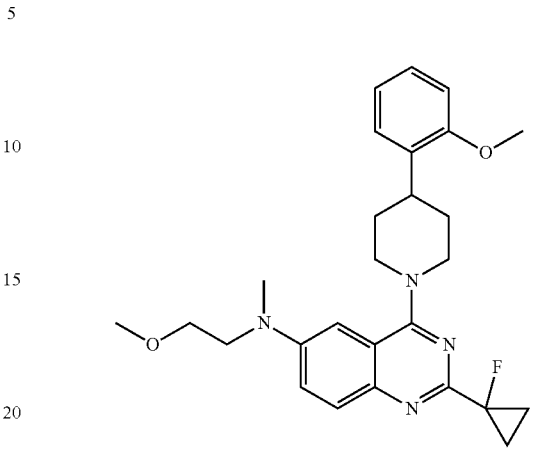

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.87 (d, J=9.2 Hz, 1H), 7.36 (dd, J=9.2 Hz, 1H), 7.26-7.20 (m, 2H), 6.98-6.88 (m, 3H), 4.35 (d, J=12.8 Hz, 2H), 3.85 (s, 3H), 3.60 (s, 4H), 3.36 (s, 3H), 3.30-3.25 (m, 1H), 3.15-3.07 (m, 5H), 1.97-1.84 (m, 4H), 1.53-1.44 (m, 4H). MS: m/z 465.2 (M+H⁺).

Example 17: Preparation of {2-(1-fluoro-cyclopropyl)-4-[4-(2-methoxy-phenyl)-piperidin-1-yl]-quinazolin-6-yl}-methyl-(2-morpholin-4-yl-ethyl)-amine

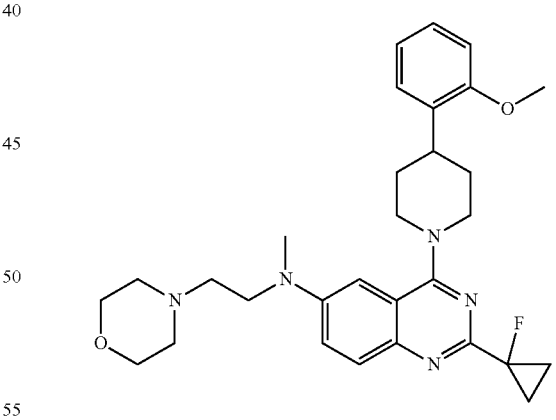

The title compound was prepared as described for 2-({2-cyclopropyl-4-[4-(2-dimethylamino-phenyl)-piperidin-1-yl]-quinazolin-6-yl}-methyl-amino)-ethanol ¹H NMR (400 MHz, CDCl₃): δ=7.87 (d, J=9.2 Hz, 1H), 7.34 (dd, J=9.2 Hz, 1H), 7.26-7.20 (m, 2H), 6.96 (t, J=7.6 Hz, 1H), 6.90-6.86 (m, 2H), 4.33 (d, J=13.2 Hz, 2H), 3.85 (s, 3H), 3.69 (t, J=4.4 Hz, 1H), 3.58 (s, J=7.2 Hz, 3H), 3.31-3.25 (m, 1H), 3.15-3.05 (m, 5H), 2.59-2.51 (m, 6H), 1.97-1.85 (m, 4H), 1.53-1.46 (m, 4H). MS: m/z 520.3 (M+H⁺).

Example 18: Preparation of {2-(1-fluoro-cyclopropyl)-4-[4-(2-methoxy-phenyl)-piperidin-1-yl]-quinazolin-6-yl}-dimethyl-amine

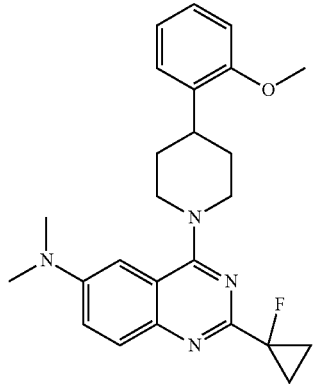 [SMILES: COc1ccccc1C1CCN(c2nc(C3(F)CC3)nc3ccc(N(C)C)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.90 (dd, J=10.0 Hz, 1H), 7.40 (dd, J=9.2 Hz, 1H), 7.26-7.20 (m, 2H), 6.96 (t, J=7.6 Hz, 1H), 6.90-6.88 (m, 2H), 4.36 (d, J=12.8 Hz, 2H), 3.85 (s, 3H), 3.57 (t, J=5.6 Hz, 2H), 3.32-3.24 (m, 1H), 3.16-3.08 (m, 2H), 3.05 (s, 6H), 1.98-1.84 (m, 4H), 1.63-1.44 (m, 4H). MS: m/z 421.2 (M+H⁺).

Example 19: Preparation of {2-(1-dimethylamino-cyclopropyl)-4-[4-(2-methoxy-phenyl)-piperidin-1-yl]-quinazolin-6-yl}-dimethyl-amine

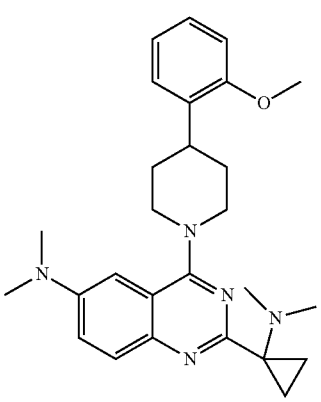

The title compound was prepared as a byproduct of {2-(1-fluoro-cyclopropyl)-4-[4-(2-methoxy-phenyl)-piperidin-1-yl]-quinazolin-6-yl}-dimethyl-amine. ¹H NMR (400 MHz, CD₃OD): δ=7.96-7.92 (m, 3H), 7.19 (d, J=7.2 Hz, 1H), 7.09 (t, J=7.8 Hz, 1H), 6.86-6.76 (m, 3H), 6.47 (s, 1H), 5.02-5.94 (m, 2H), 4.36 (s, 2H), 3.75 (s, 3H), 3.71-3.65 (m, 2H), 3.53-3.44 (m, 1H), 3.20-3.18 (m, 8H), 2.87 (s, 6H), 2.05-2.03 (m, 4H). MS: m/z 446.3 (M+H⁺).

Example 20: Preparation of {2-(1-fluoro-cyclopropyl)-4-[4-(2-methoxy-phenyl)-piperidin-1-yl]-quinazolin-6-yl}-methyl-propyl-amine

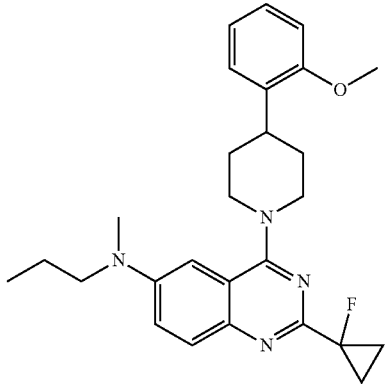 [SMILES: CCCN(C)c1ccc2nc(C3(F)CC3)nc(N3CCC(c4ccccc4OC)CC3)c2c1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.89 (d, J=8.4 Hz, 1H), 7.32 (dd, J=9.6 Hz, 1H), 7.26-7.20 (m, 2H), 6.96 (t, J=7.4 Hz, 1H), 6.89 (d, J=8.4 Hz, 1H), 6.83 (d, J=3.2 Hz, 1H), 4.35 (d, J=12.8 Hz, 2H), 3.85 (s, 3H), 3.37 (t, J=7.4 Hz, 2H), 3.29-3.25 (m, 1H), 3.15-3.09 (m, 2H), 3.03 (s, 3H), 1.98-1.88 (m, 4H), 1.67-1.60 (m, 2H), 1.55-1.47 (m, 4H), 0.95 (t, J=7.4 Hz, 3H). MS: m/z 421.2 (M+H⁺).

Example 21: Preparation of {4-[4-(2-methoxy-phenyl)-piperidin-1-yl]-2-[1-(methyl-propyl-amino)-cyclopropyl]-quinazolin-6-yl}-methyl-propyl-amine

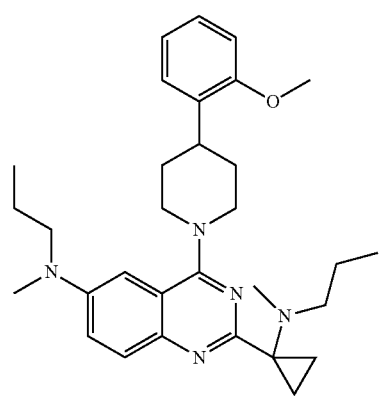 [SMILES: CCCN(C)c1ccc2nc(C3(N(C)CCC)CC3)nc(N3CCC(c4ccccc4OC)CC3)c2c1]

The title compound was prepared as a byproduct of {2-(1-fluoro-cyclopropyl)-4-[4-(2-methoxy-phenyl)-piperidin-1-yl]-quinazolin-6-yl}-methyl-propyl-amine. ¹H NMR (400 MHz, CD₃OD): δ=8.06-7.97 (m, 3H), 7.30-7.28 (m, 1H), 7.20 (t, J=7.8 Hz, 1H), 6.98-6.84 (m, 3H), 6.58-6.55 (m, 1H), 5.11-5.08 (m, 2H), 4.75 (d, J=13.2 Hz, 1H), 4.22 (d, J=10.8 Hz, 1H), 3.86 (s, 3H), 3.81-3.72 (m, 2H), 3.60-3.51 (m, 3H), 3.34-3.16 (m, 7H), 2.90 (s, 3H), 2.13 (s, 4H), 1.92-1.86 (m, 2H), 1.70-1.64 (m, 2H), 1.01-0.96 (m, 6H). MS: m/z 502.3 (M+H⁺).

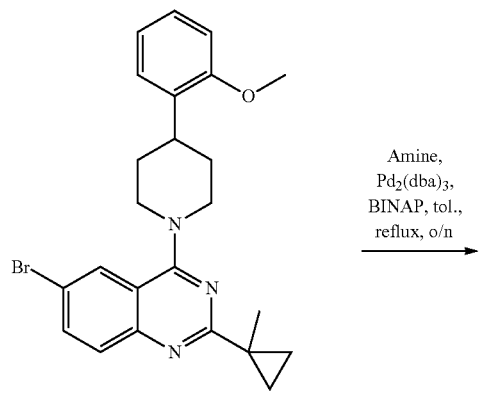

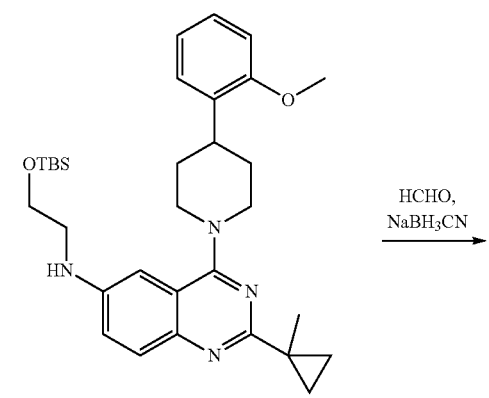

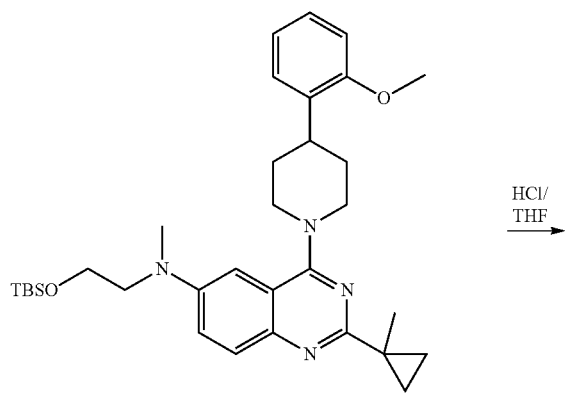

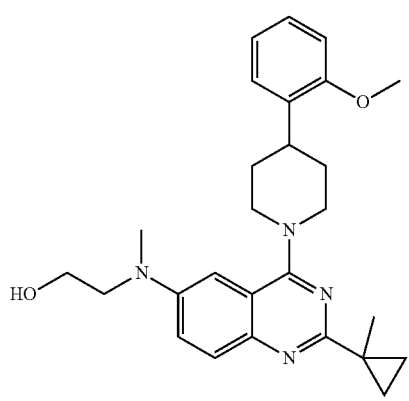 [SMILES: COc1ccccc1C1CCN(c2nc(C3(C)CC3)nc3ccc(N(C)CCO)cc23)CC1]

Example 22: Preparation of 2-{[4-[4-(2-methoxy-phenyl)-piperidin-1-yl]-2-(1-methyl-cyclopropyl)-quinazolin-6-yl]-methyl-amino}-ethanol

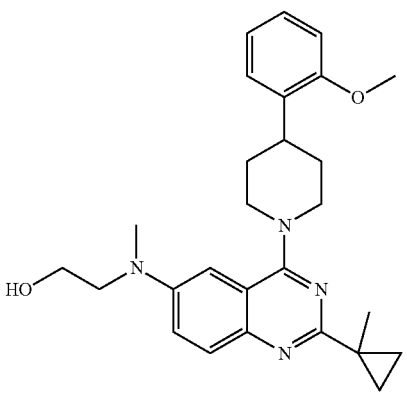

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (300 MHz, CDCl$_3$): δ=7.79-7.75 (m, 1H), 7.35-7.21 (m, 3H), 7.00-6.89 (m, 3H), 4.34 (d, J=13.2 Hz, 2H), 3.87-3.85 (m, 5H), 3.56-3.53 (m, 2H), 3.30-3.09 (m, 3H), 3.05 (s, 3H), 2.00-1.84 (m, 4H), 1.64 (s, 3H), 1.43-1.40 (m, 2H), 0.82-0.81 (m, 2H). MS: m/z 447.3 (M+H$^+$).

Example 23: Preparation of N-[4-[4-(2-methoxy-phenyl)-piperidin-1-yl]-2-(1-methyl-cyclopropyl)-quinazolin-6-yl]-N,N',N'-trimethyl-ethane-1,2-diamine

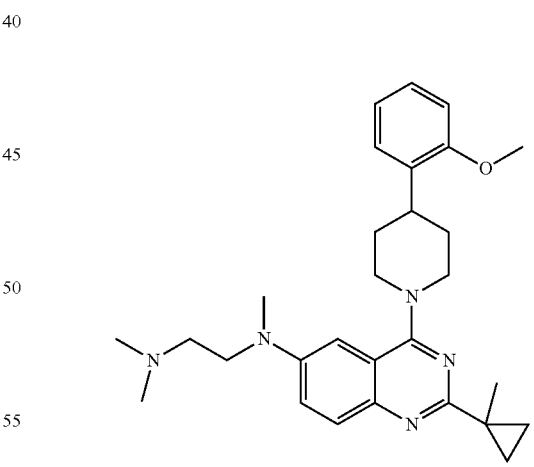

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.90 (brs, 1H), 7.27 (d, J=2.8 Hz, 1H), 7.19-7.13 (m, 2H), 6.91-6.79 (m, 3H), 4.37 (d, J=12.8 Hz, 2H), 3.79 (s, 3H), 3.59 (brs, 2H), 3.24-3.10 (m, 3H), 2.99 (s, 3H), 2.63-2.60 (m, 2H), 2.36 (d, J=15.6 Hz, 6H), 1.95-1.80 (m, 4H), 1.60 (s, 3H), 1.42-1.38 (m, 2H), 0.82-0.79 (m, 2H). MS: m/z 474.3 (M+H$^+$).

Example 24: Preparation of [4-[4-(2-methoxy-phenyl)-piperidin-1-yl]-2-(1-methyl-cyclopropyl)-quinazolin-6-yl]-methyl-(2-pyrrolidin-1-yl-ethyl)-amine

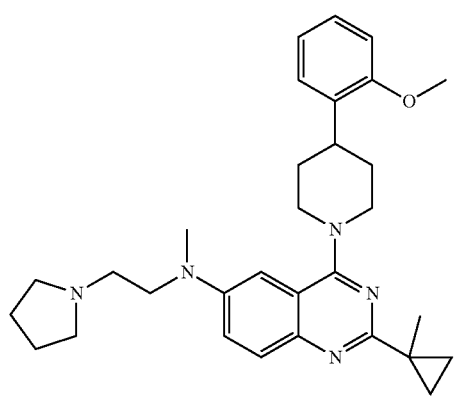 [SMILES: COc1ccccc1C1CCN(c2nc(C3(C)CC3)nc3ccc(N(C)CCN4CCCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=8.45 (brs, 1H), 7.37 (d, J=5.2 Hz, 1H), 7.36 (s, 1H), 7.27-7.17 (m, 1H), 7.02-6.88 (m, 3H), 4.62 (d, J=13.6 Hz, 2H), 4.03 (brs, 2H), 3.85 (s, 3H), 3.42-3.17 (m, 9H), 3.12 (s, 3H), 2.12 (brs, 4H), 2.07-2.03 (m, 2H), 1.87-1.54 (m, 2H), 1.60 (s, 3H), 1.42-1.38 (m, 2H), 0.82-0.79 (m, 2H). MS: m/z 500.3 (M+H$^+$).

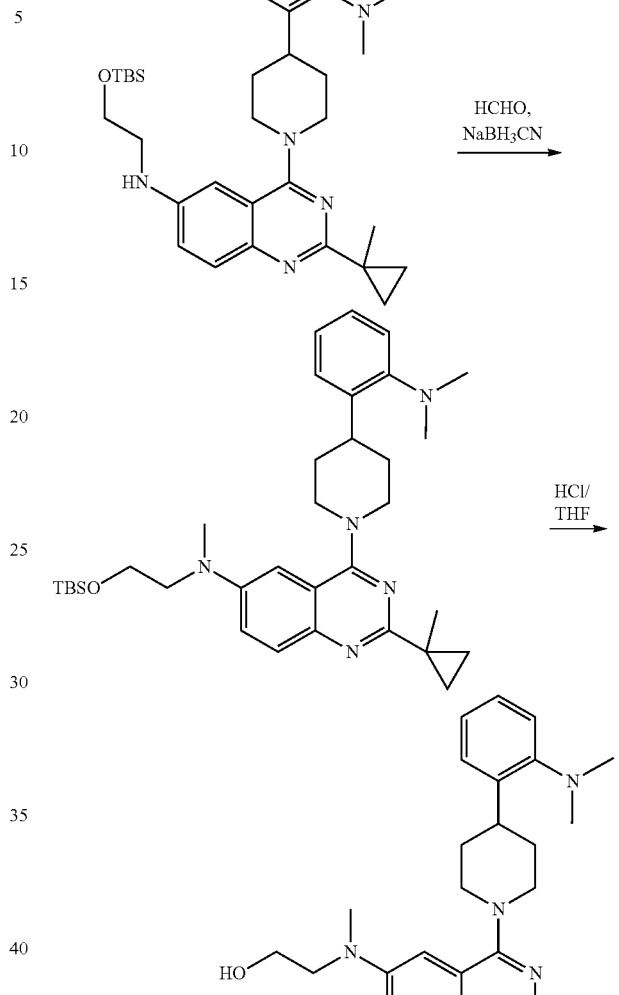

Example 25: Preparation of 2-{[4-[4-(2-dimethyl-amino-phenyl)-piperidin-1-yl]-2-(1-methyl-cyclopropyl)-quinazolin-6-yl]-methyl-amino}-ethanol

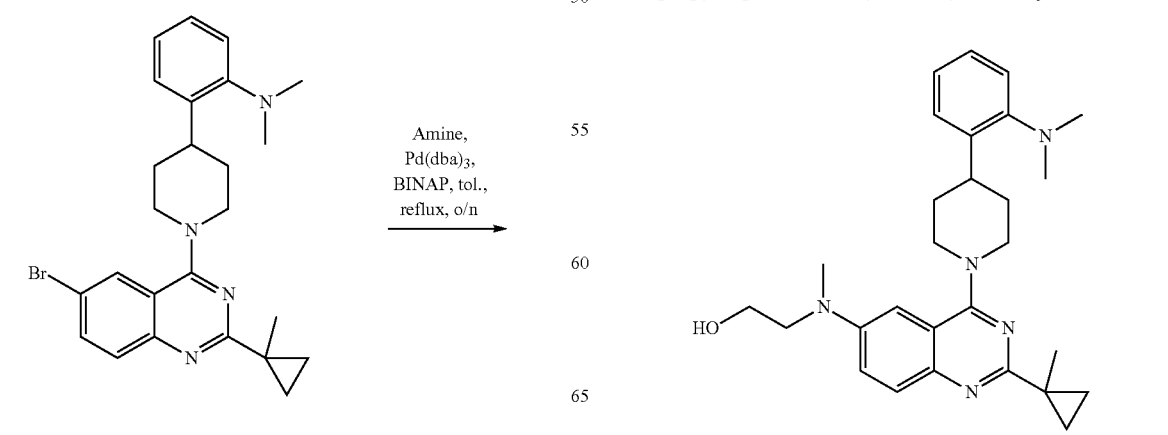

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (300 MHz, CDCl₃): δ=7.92-7.82 (m, 1H), 7.38-7.11 (m, 5H), 7.00 (s, 1H), 4.39 (d, J=13.2 Hz, 2H), 3.89-3.86 (m, 2H), 3.56-3.49 (m, 2H), 3.20-3.12 (m, 2H), 3.06 (s, 3H), 2.71 (s, 6H), 2.11-1.65 (m, 4H), 1.63 (s, 3H), 1.44-1.40 (m, 2H), 0.82-0.81 (m, 2H). MS: m/z 460.3 (M+H⁺).

Example 26: Preparation of [4-[4-(2-dimethyl-amino-phenyl)-piperidin-1-yl]-2-(1-methyl-cyclopropyl)-quinazolin-6-yl]-(2-methoxy-ethyl)-methyl-amine

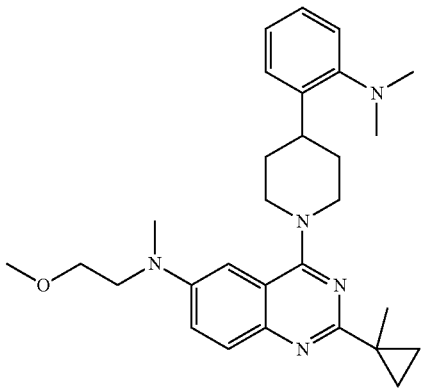

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (300 MHz, CDCl₃): δ=7.77 (d, J=9.3 Hz, 1H), 7.36-7.12 (m, 6H), 6.94 (s, 1H), 4.35 (d, J=12.3 Hz, 2H), 3.61 (s, 4H), 3.50-3.48 (m, 1H), 3.37 (s, 3H), 3.18-3.08 (m, 5H), 3.05 (s, 6H), 2.00-1.84 (m, 4H), 1.64 (s, 3H), 1.43-1.40 (m, 2H), 0.82-0.81 (m, 2H). MS: m/z 474.3 (M+H⁺).

Example 27: Preparation of [4-[4-(2-dimethyl-amino-1-vinyl-propenyl)-piperidin-1-yl]-2-(1-methyl-cyclopropyl)-quinazolin-6-yl]-methyl-(2-morpholin-4-yl-ethyl)-amine

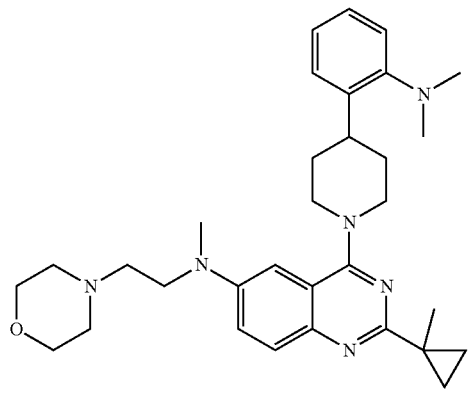 [SMILES: CN(C)c1ccccc1C1CCN(c2nc(C3(C)CC3)nc3ccc(N(C)CCN4CCOCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (300 MHz, CDCl₃): δ=7.77 (d, J=9.3 Hz, 1H), 7.34-7.11 (m, 6H), 6.90 (brs, 1H), 4.33 (d, J=12.9 Hz, 2H), 3.73-3.70 (m, 4H), 3.61-3.50 (m, 3H), 3.18-3.09 (m, 2H), 3.06 (s, 3H), 2.72 (s, 6H), 2.61-2.52 (m, 6H), 2.30-2.24 (m, 1H), 1.99-1.92 (m, 4H), 1.64 (s, 3H), 1.45-1.41 (m, 2H), 0.83-0.79 (m, 2H). MS: m/z 529.4 (M+H⁺).

Example 28: Preparation of N-[4-[4-(2-dimethyl-amino-phenyl)-piperidin-1-yl]-2-(1-methyl-cyclopropyl)-quinazolin-6-yl]-N,N',N'-trimethyl-ethane-1,2-diamine

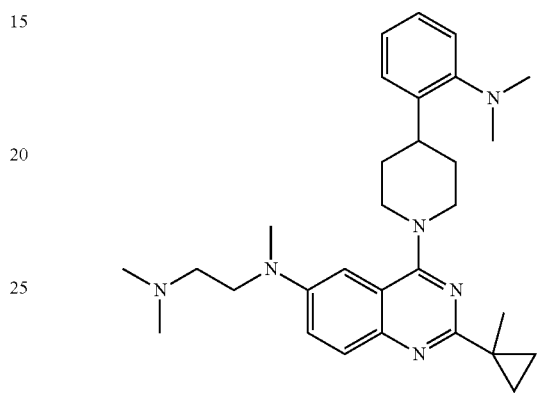

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (300 MHz, CDCl₃): δ=7.79 (brs, 1H), 7.34-7.25 (m, 2H), 7.24-6.95 (m, 3H), 6.82 (s, 1H), 4.28 (d, J=11.6 Hz, 2H), 3.53-3.39 (m, 3H), 3.10-3.04 (m, 2H), 2.97 (s, 3H), 2.62 (d, J=12.8 Hz, 6H), 2.50 (brs, 2H), 2.25 (d, J=19.6 Hz, 6H), 1.92-1.83 (m, 4H), 1.51 (s, 3H), 1.37-1.33 (m, 2H), 0.77-0.73 (m, 2H). MS: m/z 487.3 (M+H⁺).

Example 29: Preparation of [4-[4-(2-dimethyl-amino-phenyl)-piperidin-1-yl]-2-(1-methyl-cyclopropyl)-quinazolin-6-yl]-methyl-(2-pyrrolidin-1-yl-ethyl)-amine

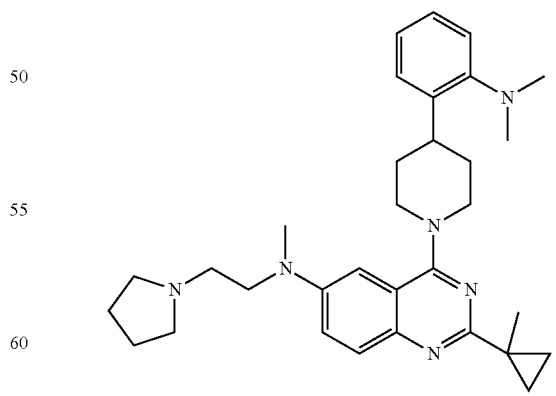

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (300 MHz, CDCl₃): δ=7.67 (d, J=9.6 Hz, 1H), 7.27-7.01 (m, 5H), 6.83 (s, 1H), 4.23 (d, J=12.4 Hz, 2H), 3.53-3.47 (m, 3H), 3.07-2.95 (m, 5H), 2.70-2.50 (m, 12H), 2.00-1.72 (m, 8H), 1.55 (s, 3H), 1.35-1.31 (m, 2H), 0.73-0.69 (m, 2H). MS: m/z 513.3 (M+H$^+$).

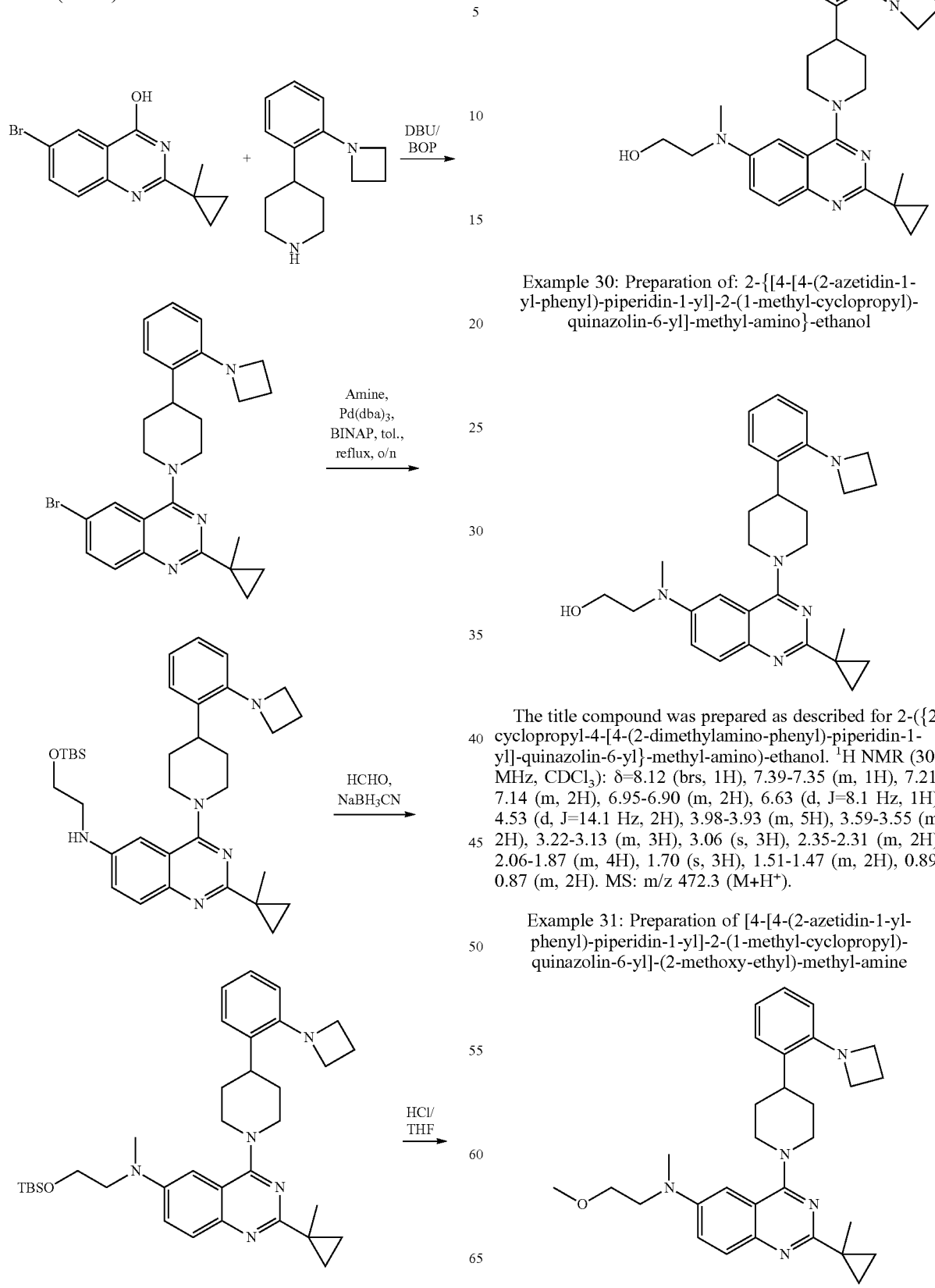

Example 30: Preparation of: 2-{[4-[4-(2-azetidin-1-yl-phenyl)-piperidin-1-yl]-2-(1-methyl-cyclopropyl)-quinazolin-6-yl]-methyl-amino}-ethanol

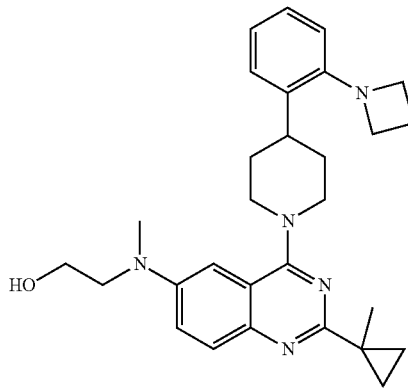

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (300 MHz, CDCl$_3$): δ=8.12 (brs, 1H), 7.39-7.35 (m, 1H), 7.21-7.14 (m, 2H), 6.95-6.90 (m, 2H), 6.63 (d, J=8.1 Hz, 1H), 4.53 (d, J=14.1 Hz, 2H), 3.98-3.93 (m, 5H), 3.59-3.55 (m, 2H), 3.22-3.13 (m, 3H), 3.06 (s, 3H), 2.35-2.31 (m, 2H), 2.06-1.87 (m, 4H), 1.70 (s, 3H), 1.51-1.47 (m, 2H), 0.89-0.87 (m, 2H). MS: m/z 472.3 (M+H$^+$).

Example 31: Preparation of [4-[4-(2-azetidin-1-yl-phenyl)-piperidin-1-yl]-2-(1-methyl-cyclopropyl)-quinazolin-6-yl]-(2-methoxy-ethyl)-methyl-amine

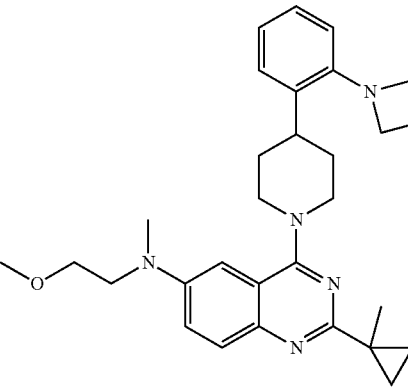

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (300 MHz, CDCl₃): δ=7.77 (d, J=9.0 Hz, 1H), 7.36-7.15 (m, 3H), 7.94-6.91 (m, 2H), 6.62 (d, J=8.1 Hz, 1H), 4.34 (d, J=12.9 Hz, 2H), 3.99-3.94 (m, 4H), 3.61 (s, 4H), 3.38 (s, 3H), 3.11-3.02 (m, 6H), 2.35-2.31 (m, 2H), 2.00-1.93 (m, 4H), 1.65 (s, 3H), 1.43-1.42 (m, 2H), 0.82-0.81 (m, 2H). MS: m/z 486.3 (M+H⁺).

Example 32: Preparation of [4-[4-(2-azetidin-1-yl-phenyl)-piperidin-1-yl]-2-(1-methyl-cyclopropyl)-quinazolin-6-yl]-methyl-(2-morpholin-4-yl-ethyl)-amine

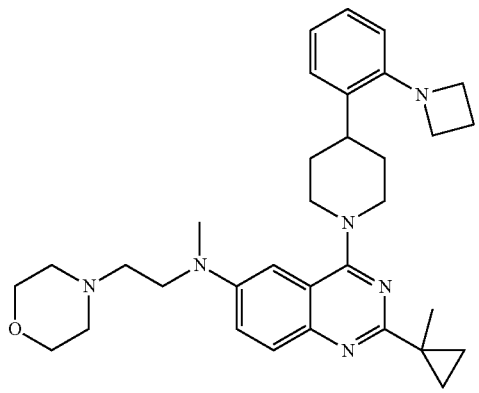 [SMILES: CN(CCN1CCOCC1)c1ccc2nc(C3(C)CC3)nc(N3CCC(c4ccccc4N4CCC4)CC3)c2c1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (300 MHz, CDCl₃): δ=7.77 (d, J=8.7 Hz, 1H), 7.34-7.14 (m, 3H), 6.93-6.88 (m, 3H), 6.62 (d, J=8.1 Hz, 1H), 4.35-4.28 (m, 2H), 3.98-3.93 (m, 4H), 3.73-3.70 (m, 4H), 3.60-3.56 (m, 4H), 3.11-2.98 (m, 6H), 2.60-2.52 (m, 6H), 2.37-2.28 (m, 2H), 2.03-1.88 (m, 4H), 1.64 (s, 3H), 1.45-1.39 (m, 2H), 0.81-0.80 (m, 2H). MS: m/z 541.4 (M+H⁺).

Example 33: Preparation of N-(2-methoxyethyl)-4-(4-(2-methoxyphenyl)piperidin-1-yl)-N-methyl-2-(1-methylcyclopropyl)quinazolin-6-amine

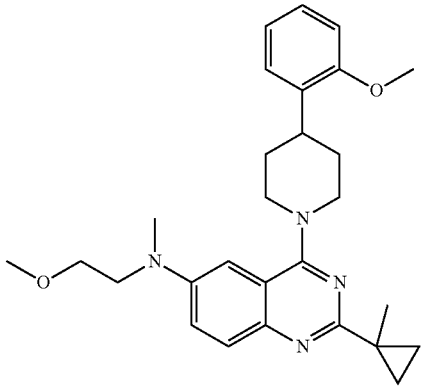 [SMILES: COCCN(C)c1ccc2nc(C3(C)CC3)nc(N3CCC(c4ccccc4OC)CC3)c2c1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (300 MHz, CDCl₃): δ=7.91 (brs, 1H), 7.36-7.20 (m, 3H), 7.01-6.88 (m, 3H), 4.41 (d, J=12.3 Hz, 2H), 3.87 (s, 3H), 3.61-3.58 (m, 4H), 3.37 (s, 3H), 3.35-3.32 (m, 1H), 3.18-3.10 (m, 2H), 3.06 (s, 3H), 2.00-1.84 (m, 4H), 1.64 (s, 3H), 1.43-1.40 (m, 2H), 0.82-0.81 (m, 2H). MS: m/z 461.0 (M+H⁺).

Example 34: Preparation of 4-(4-(2-methoxyphenyl)piperidin-1-yl)-N-methyl-2-(1-methylcyclopropyl)-N-(2-morpholinoethyl)quinazolin-6-amine

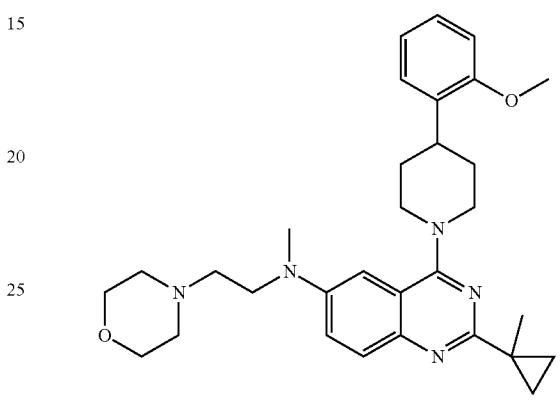

The title compound was prepared as described for 2-({2-cyclopropyl-4-[4-(2-dimethylamino-phenyl)-piperidin-1-yl]-quinazolin-6-yl}-methyl-amino)-ethanol ¹H NMR (300 MHz, CDCl₃): δ=7.75 (d, J=9.0 Hz, 1H), 7.33-7.21 (m, 3H), 7.00-6.90 (m, 3H), 4.33 (d, J=13.8 Hz, 2H), 3.87 (s, 3H), 3.72-3.69 (m, 4H), 3.60-3.55 (m, 2H), 3.13-3.08 (m, 3H), 3.05 (s, 3H), 2.60-2.50 (m, 6H), 1.97-1.89 (m, 4H), 1.65 (s, 3H), 1.42 (s, 2H), 0.82-0.79 (m, 2H), MS: m/z 516.0 (MAT).

Example 35: Preparation of N-[4-[4-(2-azetidin-1-yl-phenyl)-piperidin-1-yl]-2-(1-methyl-cyclopropyl)-quinazolin-6-yl]-N,N',N'-trimethyl-ethane-1,2-diamine

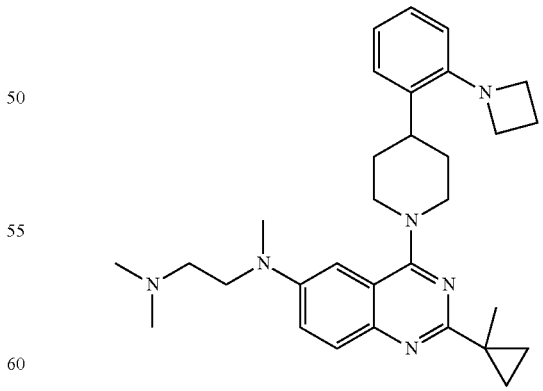

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.77 (bs, 1H), 7.4-7.27 (m, 1H), 7.21-7.13 (m, 2H), 6.90-6.87 (m, 2H), 6.61 (d, J=8 Hz, 1H), 4.35-4.31

(m, 2H), 3.96-3.92 (m, 4H), 3.61-3.56 (m, 2H), 3.11-2.90 (m, 3H), 3.00 (s, 3H), 2.59-2.56 (m, 1H), 2.35-2.28 (m, 7H), 2.00-1.90 (m, 4H), 1.66-1.63 (m, 2H), 1.45-1.39 (m, 2H), 0.81-0.80 (m, 2H). MS: m/z 499.3 (M+H⁺).

Example 36: Preparation of [4-[4-(2-azetidin-1-yl-phenyl)-piperidin-1-yl]-2-(1-methyl-cyclopropyl)-quinazolin-6-yl]-methyl-(2-pyrrolidin-1-yl-ethyl)-amine

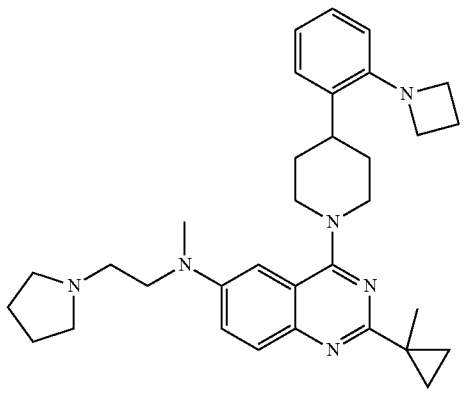 [SMILES: CN(CCN1CCCC1)c1ccc2nc(C3(C)CC3)nc(N3CCC(c4ccccc4N4CCC4)CC3)c2c1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (300 MHz, CDCl₃): δ=7.87 (d, J=8.7 Hz, 1H), 7.36-7.27 (m, 1H), 7.21-7.14 (m, 2H), 6.92-6.87 (m, 2H), 6.63 (d, J=8.1 Hz, 1H), 4.39-4.33 (m, 2H), 3.98-3.86 (m, 6H), 3.17-2.93 (m, 12H), 2.36-2.34 (m, 2H), 2.07-1.64 (m, 8H), 1.61 (s, 3H), 1.45-1.43 (m, 2H), 0.83-0.81 (m, 2H).

Example 37: Preparation of {2-cyclopentyl-4-[4-(2-methoxy-phenyl)-piperidin-1-yl]-quinazolin-6-yl}-dimethyl-amine

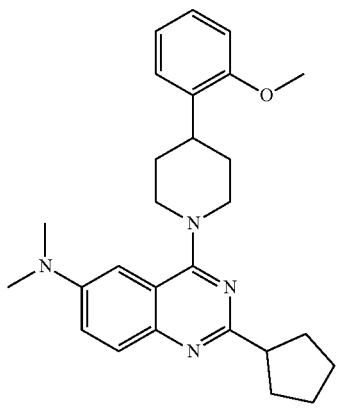 [SMILES: COc1ccccc1C1CCN(c2nc(C3CCCC3)nc3ccc(N(C)C)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.90 (brs, 1H), 7.30-7.28 (m, 1H), 7.24-7.21 (m, 1H), 6.99-6.95 (m, 1H), 6.91-6.87 (m, 2H), 6.43-6.52 (m, 2H), 3.86 (s, 3H), 3.46-3.28 (m, 4H), 3.04 (s, 6H), 2.12-1.70 (m, 12H). MS: m/z 431.2 (M+H⁺).

Example 38: Preparation of 2-({2-cyclopentyl-4-[4-(2-methoxy-phenyl)-piperidin-1-yl]-quinazolin-6-yl}-methyl-amino)-ethanol

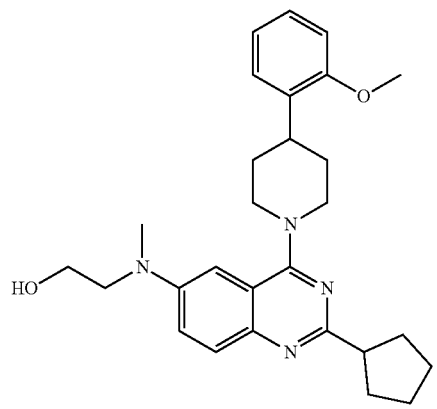

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.76 (d, J=8.8 Hz, 1H), 7.37-7.34 (m, 1H), 7.25-7.20 (m, 2H), 6.98-6.89 (m, 3H), 4.44-4.39 (m, 2H), 3.89-3.86 (m, 2H), 3.85 (s, 3H), 3.57-3.54 (m, 2H), 3.33-3.27 (m, 2H), 3.21-3.14 (m, 2H), 3.05 (s, 3H), 2.12-1.73 (m, 10H), 1.70-1.63 (m, 2H). MS: m/z 461.2 (M+H⁺)

Example 39: Preparation of {2-cyclopentyl-4-[4-(2-methoxy-phenyl)-piperidin-1-yl]-quinazolin-6-yl}-(2-methoxy-ethyl)-methyl-amine

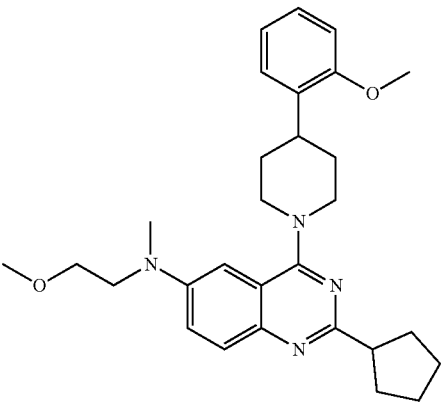 [SMILES: COCCN(C)c1ccc2nc(C3CCCC3)nc(N3CCC(c4ccccc4OC)CC3)c2c1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.85 (brs, 1H), 7.38-7.36 (m, 1H), 7.25-7.23 (m, 1H), 7.19-7.17 (m, 1H), 4.93-4.90 (brs, 2H), 3.87 (s, 3H), 3.80-3.70 (m, 1H), 3.59-3.36 (m, 3H), 3.33 (s, 3H), 3.06 (s, 3H), 2.21-2.07 (m, 4H), 1.97-1.60 (m, 11H). MS: m/z 475.3 (M+H⁺).

Example 40: Preparation of 2-cyclopentyl-4-[4-(2-methoxy-phenyl)-piperidin-1-yl]-quinazolin-6-yl}-methyl-propyl-amine

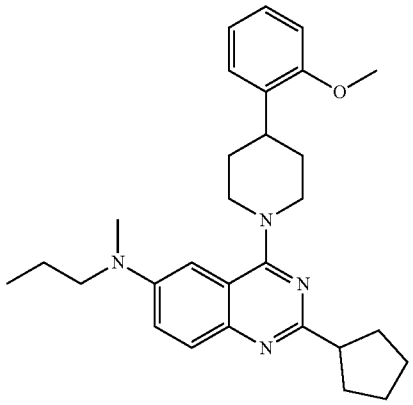 [SMILES: CCCN(C)c1ccc2nc(C3CCCC3)nc(N3CCC(c4ccccc4OC)CC3)c2c1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.78-7.74 (m, 1H), 7.31-7.29 (m, 1H), 7.28-7.20 (m, 2H), 6.99-6.85 (m, 3H), 4.41 (d, J=12.4 Hz, 2H), 3.84 (s, 3H), 3.38-3.28 (m, 4H), 3.27-3.12 (m, 2H), 3.02 (s, 3H), 2.10-1.70 (m, 10H), 1.69-1.61 (m, 4H), 0.95 (t, d, J=7.2 Hz, 3H). MS: m/z 459.3 (M+H$^+$).

Example 41: Preparation of 2-cyclopentyl-4-[4-(2-methoxy-phenyl)-piperidin-1-yl]-quinazolin-6-yl}-methyl-(2-morpholin-4-yl-ethyl)-amine

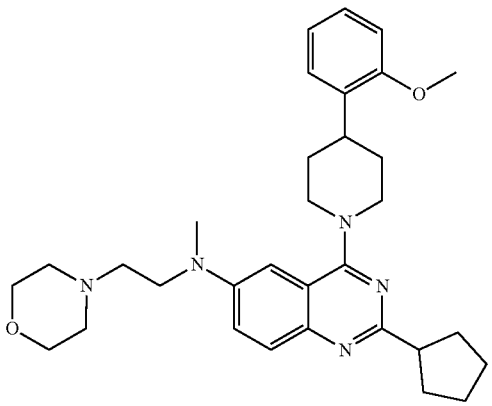 [SMILES: COc1ccccc1C1CCN(c2nc(C3CCCC3)nc3ccc(N(C)CCN4CCOCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.83-7.75 (m, 1H), 7.33-7.30 (m, 1H), 7.25-7.21 (m, 2H), 6.99-6.95 (m, 1H), 6.91-6.88 (m, 2H), 4.45-4.35 (m, 2H), 3.86 (s, 3H), 3.70-3.68 (m, 4H), 3.59-3.55 (m, 2H), 333-3.30 (m, 2H), 3.21-3.15 (m, 2H), 3.04 (s, 3H), 2.58-2.54 (m, 2H), 2.50 (bs, 4H), 2.15-1.71 (m, 10H), 1.68-1.50 (m, 2H). MS: m/z 530.3 (M+H$^+$).

Example 42: Preparation of {2-cyclobutyl-4-[4-(2-methoxy-phenyl)-piperidin-1-yl]-quinazolin-6-yl}-dimethyl-amine

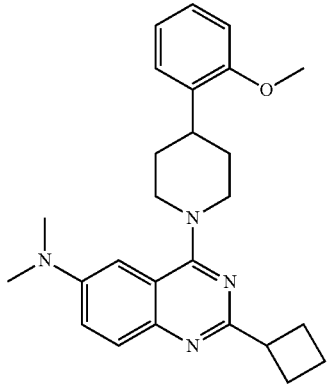 [SMILES: COc1ccccc1C1CCN(c2nc(C3CCC3)nc3ccc(N(C)C)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (300 MHz, CDCl$_3$): δ=7.69 (d, J=9.2 Hz, 1H), 7.28-7.13 (m, 3H), 6.92-6.82 (m, 3H), 4.39 (d, J=12.8 Hz, 2H), 3.79 (s, 3H), 3.70-3.66 (m, 1H), 3.25-3.09 (m, 3H), 2.96 (s, 6H), 2.48-2.43 (m, 2H), 2.31-2.27 (m, 2H), 1.99-1.88 (m, 6H). MS: m/z 417.2 (M+H$^+$).

Example 43: Preparation of 2-({2-cyclobutyl-4-[4-(2-methoxy-phenyl)-piperidin-1-yl]-quinazolin-6-yl}-methyl-amino)-ethanol

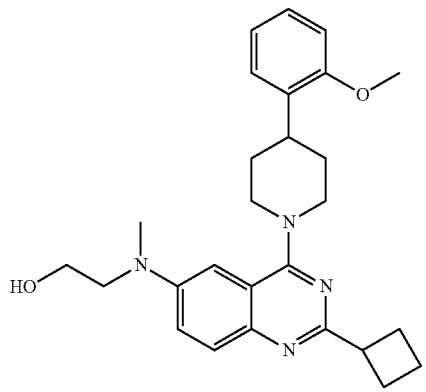 [SMILES: COc1ccccc1C1CCN(c2nc(C3CCC3)nc3ccc(N(C)CCO)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.67 (d, J=9.2 Hz, 1H), 7.26-7.20 (m, 3H), 6.99-6.89 (m, 3H), 4.44 (d, J=12.4 Hz, 2H), 3.86-3.73 (m, 6H), 3.54-3.53 (m, 2H), 3.31-3.16 (m, 3H), 3.04 (s, 3H), 2.54-2.49 (m, 2H), 2.35-2.33 (m, 2H), 2.06-1.93 (m, 6H). MS: m/z 447.2 (M+H$^+$).

Example 44: Preparation of 2-cyclobutyl-4-[4-(2-methoxy-phenyl)-piperidin-1-yl]-quinazolin-6-yl}-(2-methoxy-ethyl)-methyl-amine

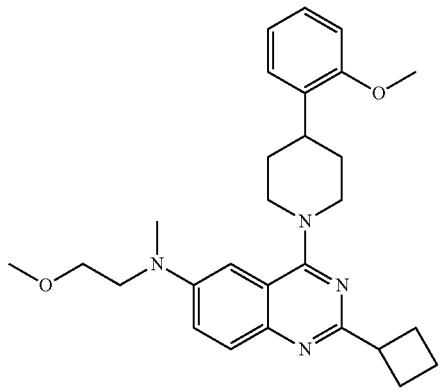 [SMILES: COCCN(C)c1ccc2nc(C3CCC3)nc(N3CCC(c4ccccc4OC)CC3)c2c1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.71 (d, J=9.2 Hz, 1H), 7.28-7.27 (m, 1H), 7.26-7.13 (m, 2H), 6.91-6.82 (m, 3H), 4.41 (d, J=12.8 Hz, 2H), 3.79 (m, 3H), 3.76-3.68 (m, 1H), 3.67-3.54 (m, 1H), 3.52 (s, 3H), 3.28-3.25 (m, 4H), 3.16-3.10 (m, 2H), 2.99 (s, 3H), 2.48-2.42 (m, 2H), 2.31-2.27 (m, 2H), 1.99-1.87 (m, 6H). MS: m/z 461.3 (M+H$^+$).

Example 45: Preparation of {2-cyclobutyl-4-[4-(2-methoxy-phenyl)-piperidin-1-yl]-quinazolin-6-yl}-methyl-propyl-amine

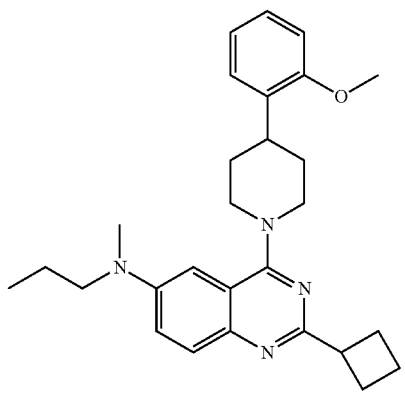 [SMILES: CCCN(C)c1ccc2nc(C3CCC3)nc(N3CCC(c4ccccc4OC)CC3)c2c1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.75 (d, J=9.2 Hz, 1H), 7.31-7.21 (m, 3H), 7.00-6.86 (m, 3H), 4.45 (d, J=13.6 Hz, 2H), 3.86 (s, 3H), 3.85-3.74 (m, 1H), 3.38-3.30 (m, 3H), 3.21-3.16 (m, 2H), 3.02 (s, 3H), 2.55-2.50 (m, 2H), 2.36-2.34 (m, 2H), 2.06-1.96 (m, 6H), 1.67-1.61 (m, 2H), 0.95 (t, 3H). MS: m/z 445.3 (M+H$^+$).

Example 46: Preparation of {2-cyclobutyl-4-[4-(2-methoxy-phenyl)-piperidin-1-yl]-quinazolin-6-yl}-methyl-(2-morpholin-4-yl-ethyl)-amine

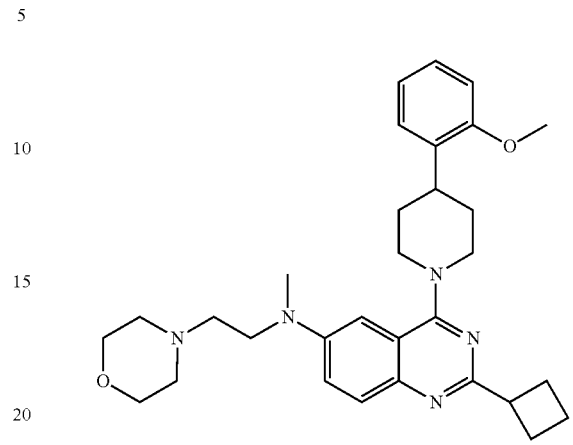

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.76 (d, J=8.8 Hz, 1H), 7.28-7.27 (m, 1H), 7.26-7.13 (m, 2H), 6.91-6.83 (m, 2H), 6.76 (s, 1H), 4.71 (d, J=11.6 Hz, 2H), 3.94-3.92 (m, 1H), 3.80 (s, 3H), 3.77-3.62 (m, 4H), 3.61-3.48 (m, 2H), 3.31-3.25 (m, 3H), 2.98 (s, 3H), 2.50-2.30 (m, 10H), 2.05-1.86 (m, 6H). MS: m/z 516.3 (M+H$^+$).

Example 47: Preparation of 2-{[4-[4-(2-methoxy-phenyl)-piperidin-1-yl]-2-(1-trifluoromethyl-cyclo-propyl)-quinazolin-6-yl]-methyl-amino}-ethanol

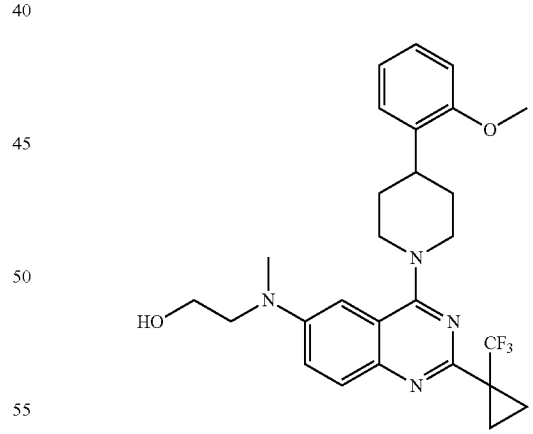

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.81 (d, J=8.0 Hz, 1H), 7.39-7.36 (m, 1H), 7.24-7.20 (m, 2H), 6.98-6.88 (m, 3H), 4.43 (d, J=12.0 Hz, 2H), 3.87 (s, 3H), 3.86-3.85 (m, 2H), 3.57-3.55 (m, 2H), 3.31-3.16 (m, 3H), 3.06 (s, 3H), 1.99-1.85 (m, 4H), 1.67-1.63 (m, 2H), 1.46-1.43 (m, 2H). MS: m/z 501.2 (M+H$^+$).

Example 48: Preparation of [4-(2-methoxy-phenyl)-piperidin-1-yl]-2-(1-trifluoromethyl-cyclopropyl)-quinazolin-6-yl]-methyl-(2-morpholin-4-yl-ethyl)-amine

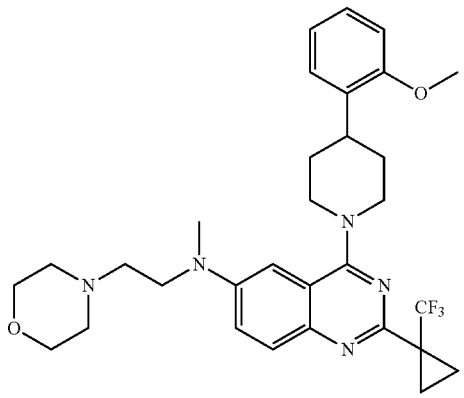 [SMILES: COc1ccccc1C1CCN(c2nc(C3(C(F)(F)F)CC3)nc3ccc(N(C)CCN4CCOCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (300 MHz, CDCl$_3$): δ=7.80 (d, J=8.8 Hz, 1H), 7.40-7.10 (m, 3H), 6.95-6.88 (m, 3H), 4.42 (d, J=13.8 Hz, 2H), 3.87 (s, 3H), 3.73-3.57 (m, 6H), 3.61-3.48 (m, 2H), 3.32-3.14 (m, 3H), 3.06 (s, 3H), 2.62-2.49 (m, 6H), 2.01-1.69 (m, 4H), 092-0.85 (m, 2H). MS: m/z 570.3 (M+H$^+$).

Example 49: Preparation of 2-{[4-[4-(2-dimethyl-amino-phenyl)-piperidin-1-yl]-2-(1-trifluoromethyl-cyclopropyl)-quinazolin-6-yl]-methyl-amino}-ethanol

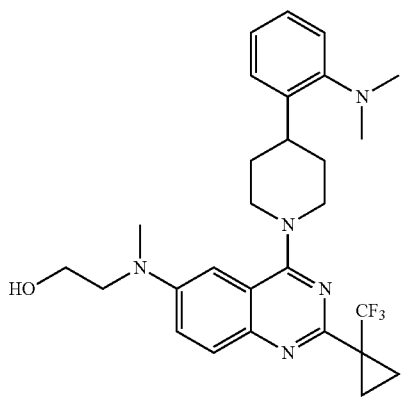

The title compound was prepared as described in example 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.77 (d, J=8.8 Hz, 1H), 7.39-7.39 (m, 1H), 7.29-7.26 (m, 1H), 7.21-7.09 (m, 3H), 6.97 (s, 1H), 4.42 (d, J=13.2 Hz, 2H), 3.88-3.85 (m, 2H), 3.58-3.50 (m, 3H), 3.22-3.17 (m, 2H), 3.06 (s, 3H), 2.70 (s, 6H), 1.96-1.81 (m, 4H), 1.63 (bs, 2H), 1.45-1.43 (bs, 2H). MS: m/z 514.2 (M+H$^+$).

Example 50: Preparation of [4-[4-(2-dimethyl-amino-phenyl)-piperidin-1-yl]-2-(1-trifluoromethyl-cyclopropyl)-quinazolin-6-yl]-methyl-(2-morpholin-4-yl-ethyl)-amine The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.74 (d, J=8.0 Hz, 1H), 7.33-7.08 (m, 5H), 6.87 (s, 1H), 4.39 (d, J=12.8 Hz, 2H), 3.70 (brs, 4H), 3.58-3.50 (m, 3H), 3.20-3.14 (m, 2H), 3.05 (s, 3H), 2.70 (s, 6H), 2.59-2.51 (m, 6H), 1.94-1.91 (m, 4H), 1.61-1.59 (m, 2H), 1.44-1.42 (m, 2H). MS: m/z 583.3 (M+H$^+$).

Example 51: Preparation of 2-{[4-[4-(2-methoxy-phenyl)-piperidin-1-yl]-2-(1-methyl-cyclopentyl)-quinazolin-6-yl]-methyl-amino}-ethanol The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.40 (d, J=8.8 Hz, 1H), 7.25-7.20 (m, 3H), 7.00-6.89 (m, 3H), 4.42 (d, J=13.8 Hz, 2H), 3.88-3.86 (m, 5H), 3.57-3.55 (m, 2H), 3.20-3.10 (m, 3H), 3.05 (s, 3H), 3.06 (s, 3H), 2.42-2.40 (m, 2H), 2.01-1.91 (m, 4H), 1.75-1.65 (m, 5H), 1.54-1.48 (m, 2H), 1.33-1.22 (m, 4H). MS: m/z 475.3 (M+H$^+$).

Example 52: Preparation of 4-[4-(2-methoxy-phenyl)-piperidin-1-yl]-2-(1-methyl-cyclopentyl)-quinazolin-6-yl]-methyl-(2-morpholin-4-yl-ethyl)-amine

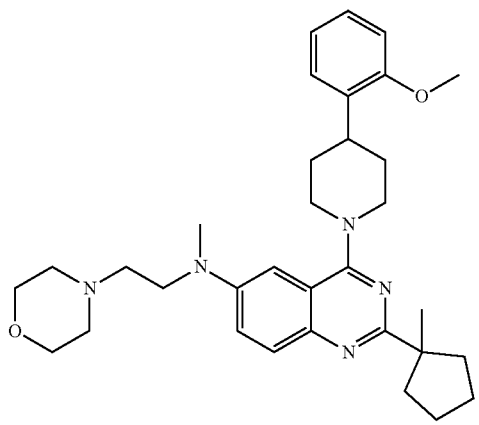 [SMILES: COc1ccccc1C1CCN(c2nc(C3(C)CCCC3)nc3ccc(N(C)CCN4CCOCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.34 (d, J=8.8 Hz, 1H), 7.25-7.15 (m, 3H), 6.98-6.90 (m, 2H), 6.83-6.82 (m, 1H) 3.86 (s, 3H), 3.70-3.68 (m, 4H), 3.59-3.57 (m, 2H), 3.56-3.28 (m, 3H), 3.05 (s, 3H), 2.57-2.40 (m, 8H), 2.07-1.71 (m, 12H), 1.60-1.58 (m, 3H). MS: m/z 544.3 (M+H$^+$).

Example 53: Preparation of {[4-[4-(2-Dimethyl-amino-phenyl)-piperidin-1-yl]-2-(1-methyl-cyclo-pentyl)-quinazolin-6-yl]-methyl-amino}-ethanol

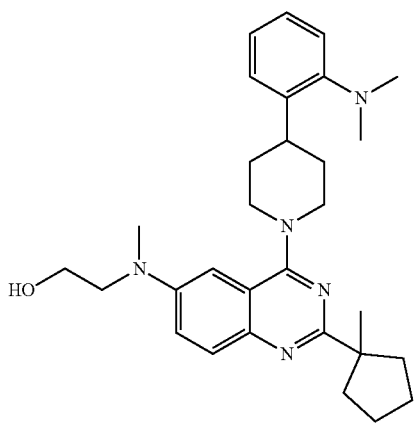 [SMILES: CN(C)c1ccccc1C1CCN(c2nc(C3(C)CCCC3)nc3ccc(N(C)CCO)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (300 MHz, CDCl$_3$): δ=8.30 (m, 1H), 7.38-7.35 (m, 1H), 7.19-7.14 (m, 3H), 7.04-7.03 (m, 1H), 6.87 (bs, 1H), 4.84 (d, J=13.8 Hz, 2H), 3.80 (bs, 2H), 3.58-3.50 (m, 3H), 3.38-3.36 (m, 2H), 3.00 (s, 3H), 2.63 (s, 6H), 2.32-2.26 (m, 2H), 1.97-1.52 (m, 10H), 1.37 (s, 3H). MS: m/z 488.3 (M+H$^+$).

Example 54: Preparation of [4-[4-(2-dimethyl-amino-phenyl)-piperidin-1-yl]-2-(1-methyl-cyclo-pentyl)-quinazolin-6-yl]-methyl-(2-morpholin-4-yl-ethyl)-amine

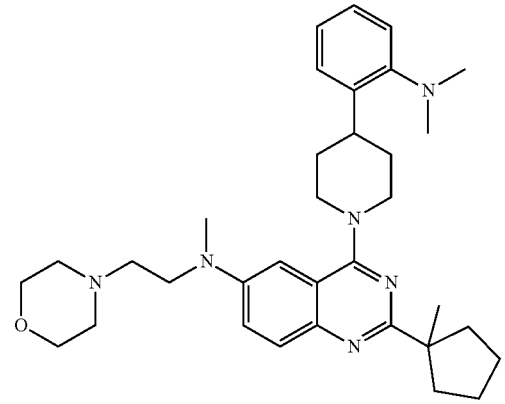 [SMILES: CN(C)c1ccccc1C1CCN(c2nc(C3(C)CCCC3)nc3ccc(N(C)CCN4CCOCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.45-7.35 (m, 2H), 7.23-7.18 (m, 4H), 6.88 (bs, 1H), 5.00 (d, J=13.8 Hz, 2H), 3.79-3.69 (m, 10H), 3.07 (s, 3H), 2.71-2.64 (m, 9H), 2.40-2.30 (m, 3H), 2.04-1.70 (m, 11H), 1.60 (s, 3H). MS: m/z 557.4 (M+H$^+$).

Example 55: Preparation of 2-{[4-[4-(2-methoxy-phenyl)-piperidin-1-yl]-2-(1-trifluoromethyl-cyclo-pentyl)-quinazolin-6-yl]-methyl-amino}-ethanol

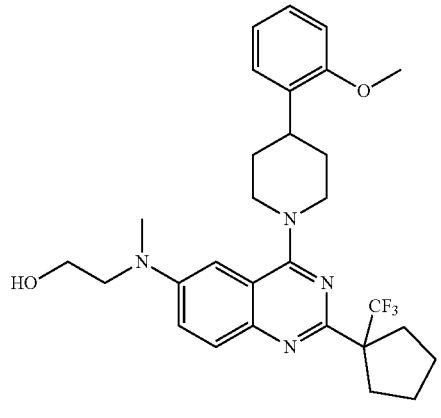 [SMILES: COc1ccccc1C1CCN(c2nc(C3(C(F)(F)F)CCCC3)nc3ccc(N(C)CCO)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.85 (d, J=9.2 Hz, 1H), 7.41-7.38 (m, 1H), 7.23-7.20 (m, 2H), 6.98-6.88 (m, 3H) 4.43 (d, J=12.8 Hz, 2H), 3.88-3.87 (m, 2H), 3.85 (s, 3H), 3.59-3.56 (m, 2H), 3.21-3.15 (m, 3H), 3H), 3.07 (s, 3H), 2.86-2.83 (m, 2H), 2.24-2.20 (m, 2H), 1.96-1.90 (m, 4H), 1.77-1.75 (m, 2H), 1.66-1.63 (m, 4H). MS: m/z 529.3 (M+H$^+$).

Example 56: Preparation of [4-[4-(2-methoxy-phenyl)-piperidin-1-yl]-2-(1-trifluoromethyl-cyclopentyl)-quinazolin-6-yl]-methyl-(2-morpholin-4-yl-ethyl)-amine

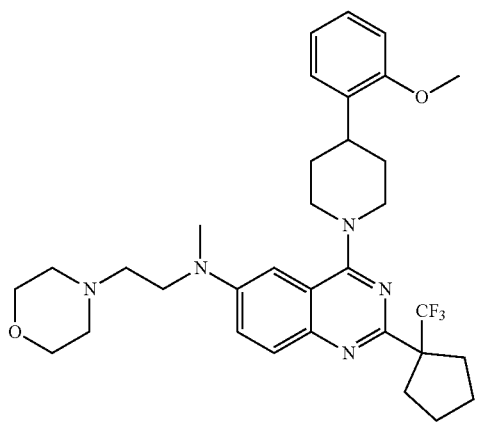 [SMILES: COc1ccccc1C1CCN(c2nc(C3(C(F)(F)F)CCCC3)nc3ccc(N(C)CCN4CCOCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.82 (d, J=8.8 Hz, 1H), 7.35-7.32 (m, 1H), 7.23-7.20 (m, 2H), 6.98-6.88 (m, 3H) 4.40 (d, J=12.8 Hz, 2H), 3.85 (s, 3H), 3.71-3.60 (m, 6H), 3.30-3.15 (m, 3H), 3.06 (s, 3H), 2.89-2.83 (m, 2H), 2.58-2.52 (m, 5H), 2.24-2.17 (m, 2H), 1.97-1.91 (m, 4H), 1.77-1.75 (m, 2H), 1.66-1.62 (m, 4H). MS: m/z 598.3 (M+H⁺).

Example 57: Preparation of 2-{[4-[4-(2-dimethyl-amino-phenyl)-piperidin-1-yl]-2-(1-trifluoromethyl-cyclopentyl)-quinazolin-6-yl]-methyl-amino}-ethanol

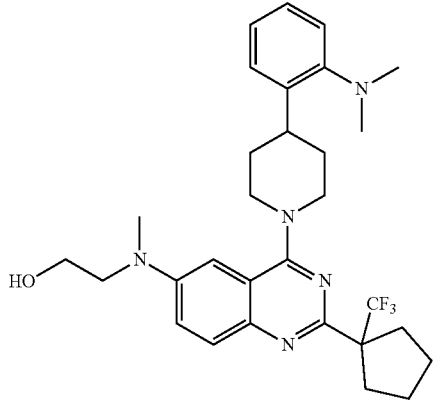

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=8.2 (bs, 1H), 7.46 (d, J=9.2 Hz, 1H), 7.29-7.26 (m, 1H), 7.26-7.13 (m, 4H), 6.97 (s, 1H) 4.58 (d, J=12.8 Hz, 2H), 3.88-3.86 (m, 2H), 3.61-3.59 (m, 3H), 3.34-3.32 (m, 2H), 3.13-3.11 (m, 2H), 3.06 (s, 3H), 2.91-2.84 (m, 2H), 2.75 (s, 6H), 2.31-2.24 (m, 2H), 1.94-1.92 (m, 2H), 1.79-1.78 (m, 2H), 1.69-1.66 (m, 2H). MS: m/z 542.3 (M+H⁺).

Example 58: Preparation of [4-[4-(2-dimethyl-amino-phenyl)-piperidin-1-yl]-2-(1-trifluoromethyl-cyclopentyl)-quinazolin-6-yl]-methyl-(2-morpholin-4-yl-ethyl)-amine

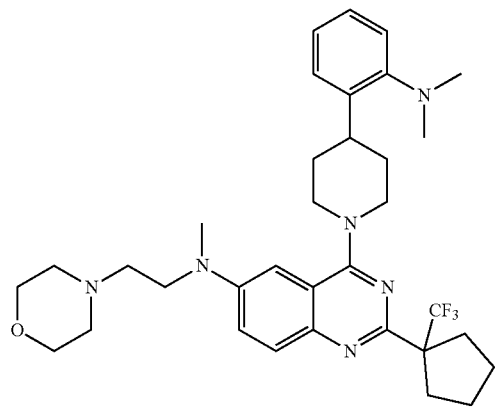 [SMILES: CN(C)c1ccccc1C1CCN(c2nc(C3(C(F)(F)F)CCCC3)nc3ccc(N(C)CCN4CCOCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.76 (d, J=9.2 Hz, 1H), 7.29-7.26 (m, 1H), 7.25-7.02 (m, 4H), 6.83 (s, 1H) 4.33 (d, J=12.8 Hz, 2H), 3.65 (bs, 4H), 3.55-3.45 (m, 3H), 3.16-3.10 (m, 2H), 3.00 (s, 3H), 2.82-2.76 (m, 2H), 2.63 (s, 6H), 2.53-2.47 (m, 6H), 2.18-2.11 (m, 2H), 1.91-1.80 (m, 4H), 1.70-1.68 (m, 2H), 1.59-1.56 (m, 2H). MS: m/z 611.3 (M+H⁺).

Example 59: Preparation of 2-({2-(1-fluoro-cyclobutyl)-4-[4-(2-methoxy-phenyl)-piperidin-1-yl]-quinazolin-6-yl}-methyl-amino)-ethanol

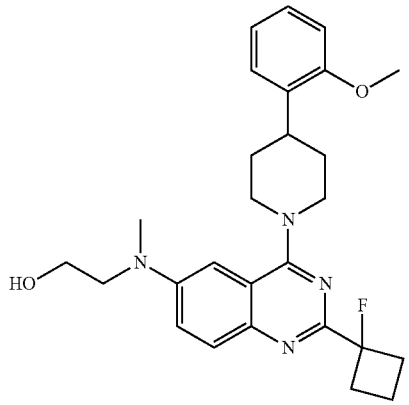 [SMILES: COc1ccccc1C1CCN(c2nc(C3(F)CCC3)nc3ccc(N(C)CCO)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (300 MHz, CDCl₃): δ=7.78 (d, J=9.6 Hz, 1H), 7.32-7.29 (m, 1H), 7.19-7.14 (m, 3H), 6.91-6.82 (m, 3H), 4.39 (d, J=13.2 Hz, 2H), 3.82-3.80 (m, 2H), 3.79 (s, 3H), 3.52-3.49 (m, 2H), 3.24-3.12 (m, 3H), 3.00 (s, 3H), 2.81-2.76 (m, 2H), 2.60-2.54 (m, 2H), 1.97-1.83 (m, 6H). MS: m/z 465.2 (M+H⁺).

Example 60: Preparation of {2-(1-fluoro-cyclobutyl)-4-[4-(2-methoxy-phenyl)-piperidin-1-yl]-quinazolin-6-yl}-methyl-(2-morpholin-4-yl-ethyl)-amine

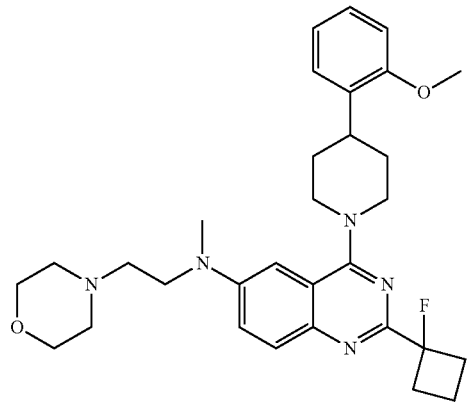 [SMILES: COc1ccccc1C1CCN(c2nc(C3(F)CCC3)nc3ccc(N(C)CCN4CCOCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (300 MHz, CDCl₃): δ=7.89 (d, J=9.3 Hz, 1H), 7.38-7.20 (m, 3H), 7.01-6.91 (m, 3H), 4.46 (d, J=12.6 Hz, 2H), 3.88 (s, 3H), 3.72-3.70 (m, 4H), 3.63-3.58 (m, 2H), 3.34-3.18 (m, 3H), 3.08 (s, 3H), 2.91-2.87 (m, 2H), 2.73-2.52 (m, 8H), 2.01-1.94 (m, 6H). MS: m/z 534.3 (M+H⁺).

Example 61: 2-{[4-[4-(2-dimethylamino-phenyl)-piperidin-1-yl]-2-(1-fluoro-cyclobutyl)-quinazolin-6-yl]-methyl-amino}-ethanol

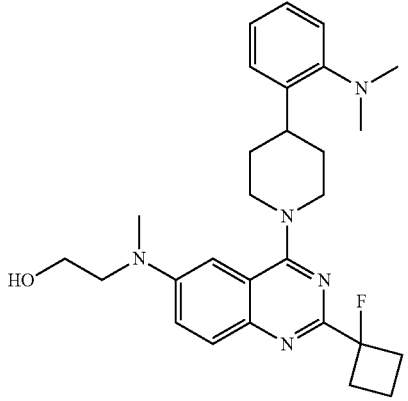 [SMILES: CN(C)c1ccccc1C1CCN(c2nc(C3(F)CCC3)nc3ccc(N(C)CCO)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.83 (d, J=8.8 Hz, 1H), 7.37-7.10 (m, 5H), 6.98 (s, 1H), 4.46 (d, J=12.4 Hz, 2H), 3.87 (brs, 2H), 3.59-3.53 (m, 3H), 325-3.10 (m, 2H), 3.07 (s, 3H), 2.87-2.86 (m, 2H), 2.70 (s, 6H), 2.64-2.62 (m, 2H), 2.01-1.94 (m, 6H). MS: m/z 478.3 (M+H⁺).

Example 62: Preparation of [4-[4-(2-dimethylamino-phenyl)-piperidin-1-yl]-2-(1-fluoro-cyclobutyl)-quinazolin-6-yl]-methyl-(2-morpholin-4-yl-ethyl)-amine

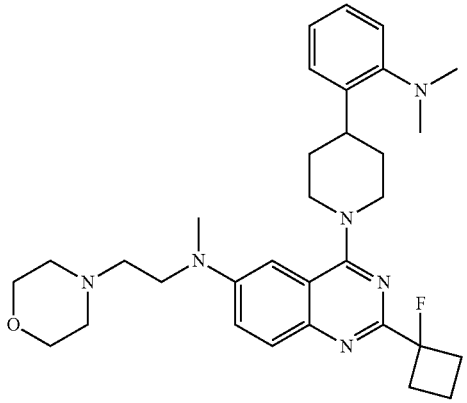 [SMILES: CN(C)c1ccccc1C1CCN(c2nc(C3(F)CCC3)nc3ccc(N(C)CCN4CCOCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.90 (d, J=9.2 Hz, 1H), 7.37-7.09 (m, 5H), 6.91 (s, 1H), 4.46 (d, J=12.6 Hz, 2H), 3.76-3.52 (m, 7H), 3.26-3.20 (m, 2H), 3.08 (s, 3H), 2.91-2.83 (m, 2H), 2.71 (s, 6H), 2.68-2.54 (m, 7H), 2.00-1.94 (m, 7H). MS: m/z 547.4 (M+H⁺).

Example 63: Preparation of 2-{[4-[4-(2-methoxy-phenyl)-piperidin-1-yl]-2-(1-trifluoromethyl-cyclobutyl)-quinazolin-6-yl]-methyl-amino}-ethanol

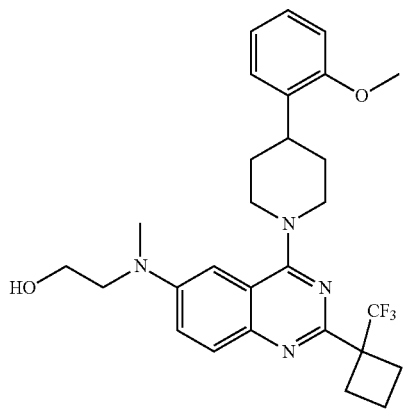 [SMILES: COc1ccccc1C1CCN(c2nc(C3(C(F)(F)F)CCC3)nc3ccc(N(C)CCO)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.86 (d, J=6.8 Hz, 1H), 7.43-7.40 (m, 1H), 7.26-7.20 (m, 2H), 7.00-6.88 (m, 3H) 4.45 (d, J=13.2 Hz, 2H), 3.3.88-3.87 (m, 2H), 3.85 (s, 3H), 3.60-3.57 (m, 2H), 3.33-3.18 (m, 3H), 3.08 (s, 3H), 2.94-2.87 (m, 2H), 2.76-2.69 (m, 2H), 2.12-2.05 (m, 1H), 1.96-1.73 (m, 5H). MS: m/z 515.2 (M+H⁺).

Example 64: Preparation of [4-[4-(2-methoxy-phenyl)-piperidin-1-yl]-2-(1-trifluoromethyl-cyclobutyl)-quinazolin-6-yl]-methyl-(2-morpholin-4-yl-ethyl)-amine

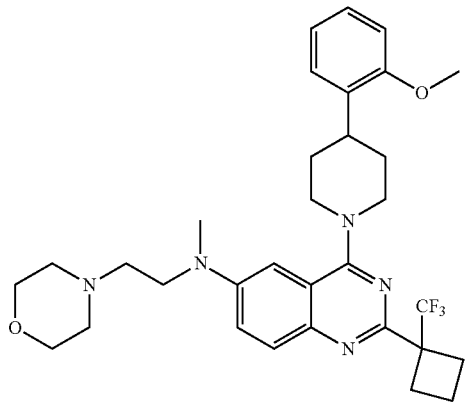 [SMILES: COc1ccccc1C1CCN(c2nc(C3(C(F)(F)F)CCC3)nc3ccc(N(C)CCN4CCOCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.83 (d, J=9.2 Hz, 1H), 7.36-7.33 (m, 1H), 7.26-7.20 (m, 2H), 6.98-6.88 (m, 3H) 4.41 (d, J=12.8 Hz, 2H), 3.85 (s, 3H), 3.71-3.70 (m, 4H), 3.61-3.58 (m, 2H), 3.31-3.15 (m, 3H), 3.07 (s, 3H), 2.93-2.86 (m, 2H), 2.76-2.71 (m, 2H), 2.68-2.52 (m, 6H), 2.10-2.07 (m, 1H), 1.97-1.91 (m, 5H). MS: m/z 584.3 (M+H$^+$).

Example 65: Preparation of 2-{[4-[4-(2-Dimethyl-amino-phenyl)-piperidin-1-yl]-2-(1-trifluoromethyl-cyclobutyl)-quinazolin-6-yl]-methyl-amino}-ethanol

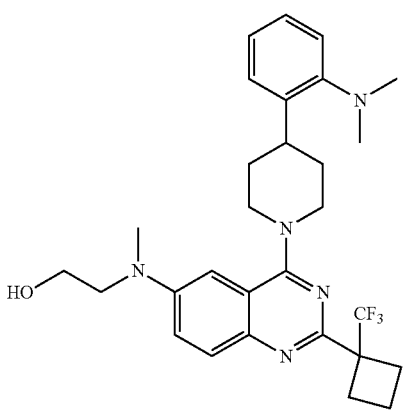 [SMILES: CN(C)c1ccccc1C1CCN(c2nc(C3(C(F)(F)F)CCC3)nc3ccc(N(C)CCO)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (300 MHz, CDCl$_3$): δ=7.84 (d, J=9.6 Hz, 1H), 7.51-7.00 (m, 6H) 4.42 (d, J=12.8 Hz, 2H), 3.92-3.87 (m, 2H), 3.64-3.52 (m, 3H), 3.28-3.24 (m, 2H), 3.20 (s, 3H), 2.94-2.85 (m, 2H), 2.80-2.73 (m, 2H), 2.72 (s, 6H), 2.25-1.80 (m, 6H). MS: m/z 528.3 (M+H$^+$).

Example 66: Preparation of [4-[4-(2-dimethyl-amino-phenyl)-piperidin-1-yl]-2-(1-trifluoromethyl-cyclobutyl)-quinazolin-6-yl]-methyl-(2-morpholin-4-yl-ethyl)-amine

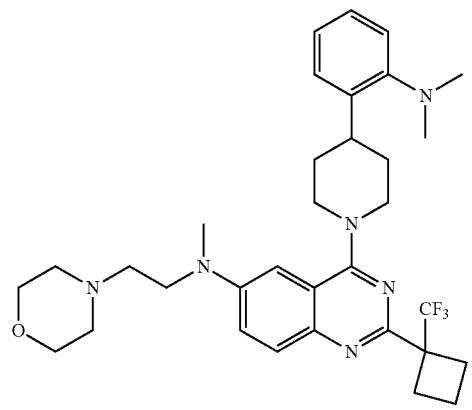 [SMILES: CN(C)c1ccccc1C1CCN(c2nc(C3(C(F)(F)F)CCC3)nc3ccc(N(C)CCN4CCOCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.84 (d, J=9.6 Hz, 1H), 7.37-7.34 (m, 1H), 7.27-7.07 (m, 4H), 6.91 (s, 1H) 4.41 (d, J=12.8 Hz, 2H), 3.72-3.62 (m, 4H), 3.60-3.50 (m, 3H), 3.22-3.17 (m, 2H), 3.07 (s, 3H), 2.94-2.87 (m, 2H), 2.76-2.73 (m, 2H), 2.72 (s, 6H), 270-2.49 (m, 6H), 2.10-1.86 (m, 6H). MS: m/z 597.3 (M+H$^+$).

Example 67: Preparation of [4-[4-(2-dimethyl-amino-phenyl)-piperidin-1-yl]-2-(1-methyl-cyclobutyl)-quinazolin-6-yl]-methyl-(2-morpholin-4-yl-ethyl)-amine

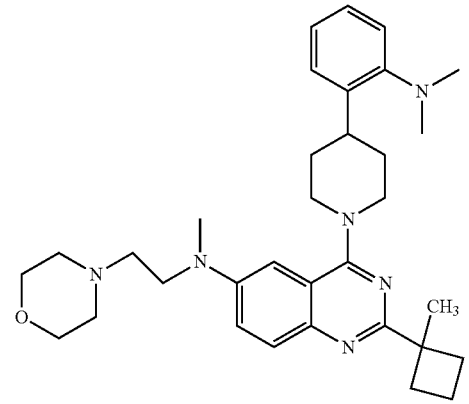 [SMILES: CN(C)c1ccccc1C1CCN(c2nc(C3(C)CCC3)nc3ccc(N(C)CCN4CCOCC4)cc23)CC1]

The title compound was prepared as described for 2-({2-cyclopropyl-4-[4-(2-dimethylamino-phenyl) piperidin-1-yl]-quinazolin-6-yl}-methyl-amino)-ethanol. $^1$H NMR (400 MHz, DMSO-d$_6$): δ=7.64 (d, J=8.8 Hz, 1H), 7.44-7.41 (m, 1H), 7.29-7.28 (m, 1H), 7.18-7.17 (m, 2H), 7.07-7.03 (m, 1H), 6.84 (s, 1H), 4.30 (d, J=12.8 Hz, 2H), 3.60-3.43 (m, 7H), 3.33-3.02 (m, 5H), 2.68-2.61 (m, 9H), 2.50-2.42 (m, 4H), 2.01-1.78 (m, 8H), 1.54 (s, 3H). MS: m/z 543.4 (M+H$^+$).

Example 68: Preparation of 2-{[4-[4-(2-dimethyl-amino-phenyl)-piperidin-1-yl]-2-(1-methyl-cyclobutyl)-quinazolin-6-yl]-methyl-amino}-ethanol

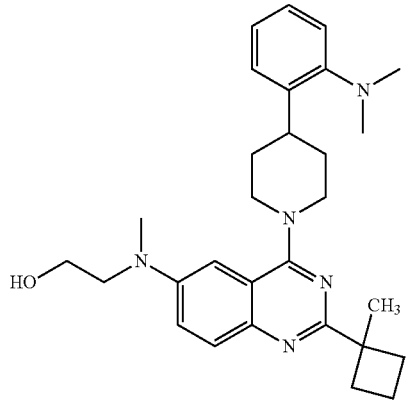 [SMILES: CN(C)c1ccccc1C1CCN(c2nc(C3(C)CCC3)nc3ccc(N(C)CCO)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.64 (d, J=8.8 Hz, 1H), 7.44-7.41 (m, 1H), 7.24-7.14 (m, 2H), 7.00-6.93 (m, 2H), 6.81 (s, 1H), 3.88-3.84 (m, 2H), 3.64-3.49 (m, 3H), 3.39-3.34 (m, 2H), 3.07 (s, 3H), 2.80-2.73 (m, 2H), 2.68-2.64 (m, 6H), 2.21- 1.50 (m, 10H), 1.25 (s, 3H), 0.90-0.81 (m, 2H). MS: m/z 474.3 (M+H+).

Example 69: Preparation of [4-[4-(2-methoxy-phenyl)-piperidin-1-yl]-2-(1-methyl-cyclobutyl)-quinazolin-6-yl]-methyl-(2-morpholin-4-yl-ethyl)-amine

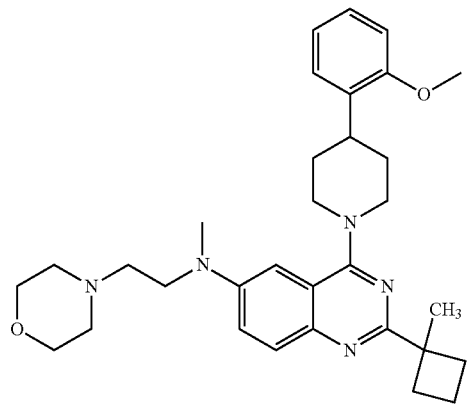 [SMILES: COc1ccccc1C1CCN(c2nc(C3(C)CCC3)nc3ccc(N(C)CCN4CCOCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, DMSO-d$_6$): δ=7.64 (d, J=8.8 Hz, 1H), 7.44-7.41 (m, 1H), 7.24-7.14 (m, 2H), 7.00-6.93 (m, 2H), 6.81 (s, 1H), 4.30 (d, J=11.6 Hz, 2H), 3.81 (s, 3H), 3.59-3.51 (m, 6H), 3.30-3.07 (m, 3H), 3.02 (s, 3H), 2.67-2.60 (m, 2H), 1.95-1.81 (m, 6H), 1.53 (s, 3H). MS: m/z 530.3 (M+H+).

Example 70: Preparation of 2-{[4-[4-(2-Methoxy-phenyl)-piperidin-1-yl]-2-(1-methyl-cyclobutyl)-quinazolin-6-yl]-methyl-amino}-ethanol

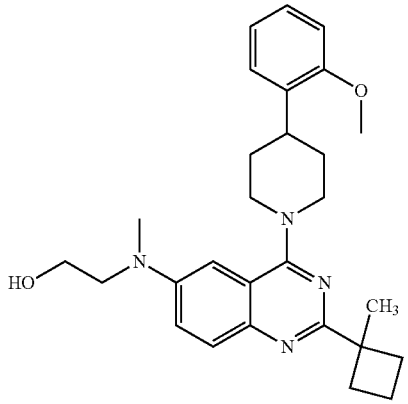 [SMILES: COc1ccccc1C1CCN(c2nc(C3(C)CCC3)nc3ccc(N(C)CCO)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, DMSO-d$_6$): δ=7.63 (d, J=8.8 Hz, 1H), 7.45-7.41 (m, 1H), 7.25-7.18 (m, 2H), 7.00-6.91 (m, 2H), 6.82 (s, 1H), 4.74-4.72 (m, 1H), 4.32 (d, J=11.6 Hz, 2H), 3.81 (s, 3H), 3.60-3.58 (m, 2H), 3.51-3.48 (m, 2H), 3.12-3.09 (m, 3H), 3.03 (s, 3H), 2.67-2.61 (m, 4H), 2.01-1.80 (m, 6H), 1.54 (s, 3H). MS: m/z 461.3 (M+H$^+$).

Example 71: Preparation of {2-(1fluoro-cyclopentyl)-4-[4-(2-methoxy-phenyl)-piperidin-1-yl]-quinazolin-6-yl}-methyl-(2-morpholin-4-yl-ethyl)-amine

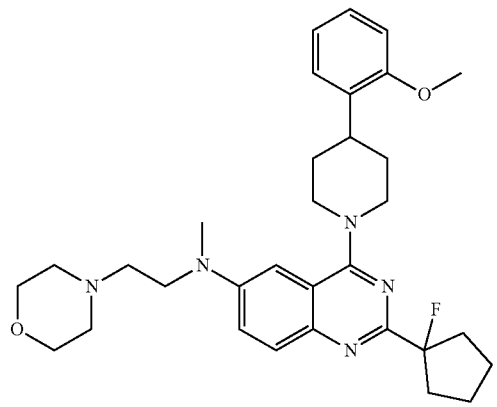 [SMILES: COc1ccccc1C1CCN(c2nc(C3(F)CCCC3)nc3ccc(N(C)CCN4CCOCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.91 (d, J=8.8 Hz, 1H), 7.35-7.32 (m, 1H), 7.26-7.20 (m, 2H), 6.96-6.89 (m, 3H) 4.49 (d, J=12.8 Hz, 2H), 3.85 (s, 3H), 3.71-3.60 (m, 6H), 3.30-3.15 (m, 3H), 3.06 (s, 3H), 2.61-2.57 (m, 2H), 2.49-2.40 (m, 4H), 2.38-2.02 (m, 4H), 2.01-1.89 (m, 8H). MS: m/z 548.3 (M+H+).

Example 72: Preparation of 2-({2-(1-fluoro-cyclopentyl)-4-[4-(2-methoxy-phenyl)-piperidin-1-yl]-quinazolin-6-yl}-methyl-amino)-ethanol

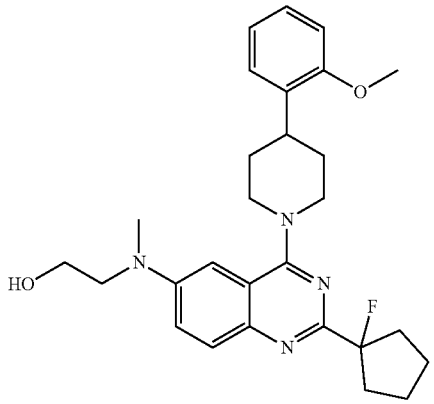 [SMILES: COc1ccccc1C1CCN(c2nc(C3(F)CCCC3)nc3ccc(N(C)CCO)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.94 (d, J=8.8 Hz, 1H), 7.35-7.29 (m, 1H), 7.26-7.21 (m, 2H), 6.99-6.89 (m, 3H) 4.47 (d, J=12.8 Hz, 2H), 3.89-3.85 (m, 5H), 3.60-3.57 (m, 2H), 3.32-3.18 (m, 3H), 3.06 (s, 3H), 2.61-2.57 (m, 2H), 2.49-2.40 (m, 4H), 2.38-2.02 (m, 4H), 2.01-1.89 (m, 8H). MS: m/z 479.3 (M+H+).

Example 73: Preparation of [4-[4-(2-dimethylamino-phenyl)-piperidin-1-yl]-2-(1-fluoro-cyclopentyl)-quinazolin-6-yl]-methyl-(2-morpholin-4-yl-ethyl)-amine

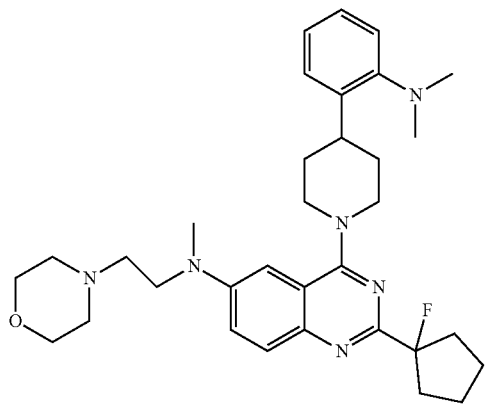 [SMILES: CN(C)c1ccccc1C1CCN(c2nc(C3(F)CCCC3)nc3ccc(N(C)CCN4CCOCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.91 (d, J=12.8 Hz, 1H), 7.33-7.08 (m, 5H), 6.90 (s, 1H), 4.41 (d, J=12.8 Hz, 2H), 3.72-3.60 (m, 4H), 3.58-3.50 (m, 3H), 3.22-3.15 (m, 2H), 3.07 (s, 3H), 2.68 (s, 6H), 2.61-2.57 (m, 2H), 2.52-2.25 (m, 8H), 2.01-1.87 (m, 8H). MS: m/z 561.4 (M+H+).

Example 74: Preparation of {2-cyclopentyl-4-[4-(2-dimethylamino-phenyl)-piperidin-1-yl]-quinazolin-6-yl}-methyl-(2-morpholin-4-yl-ethyl)-amine

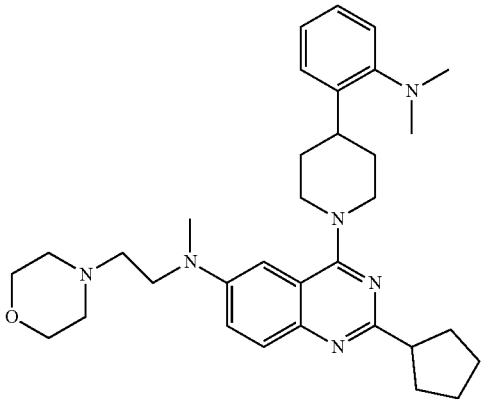 [SMILES: CN(C)c1ccccc1C1CCN(c2nc(C3CCCC3)nc3ccc(N(C)CCN4CCOCC4)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.81 (brs, 1H), 7.33-7.32 (m, 2H), 7.26-7.21 (m, 2H), 7.12-7.09 (m, 1H), 6.92 (s, 1H) 4.40-4.37 (m, 2H), 3.70-3.68 (m, 4H), 3.60-3.57 (m, 3H), 3.20-3.14 (m, 2H), 3.06 (s, 3H), 2.95-2.91 (m, 2H), 2.70 (s, 6H), 2.60-2.56 (m, 2H), 2.52-2.51 (m, 5H), 2.10-1.92 (m, 6H), 1.57 (m, 4H). MS: m/z 541.3 (M+H$^+$).

Example 75: Preparation of 2-{[4-[4-(2-dimethylamino-phenyl)-piperidin-1-yl]-2-(1-fluoro-cyclopentyl)-quinazolin-6-yl]-methyl-amino}-ethanol The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.96 (d, J=9.2 Hz, 1H), 7.44-7.40 (m, 1H), 7.28 (s, 1H), 7.21-7.19 (m, 2H), 7.12 (s, 1H), 7.10 (s, 1H), 4.33 (d, J=12.8 Hz, 2H), 3.90-3.87 (m, 2H), 3.61-3.49 (m, 3H), 3.30-3.20 (m, 2H), 3.08 (s, 3H), 2.78 (s, 6H), 2.53-2.20 (m, 4H), 2.02-1.88 (m, 8H). MS: m/z 492.3 (M+H+).

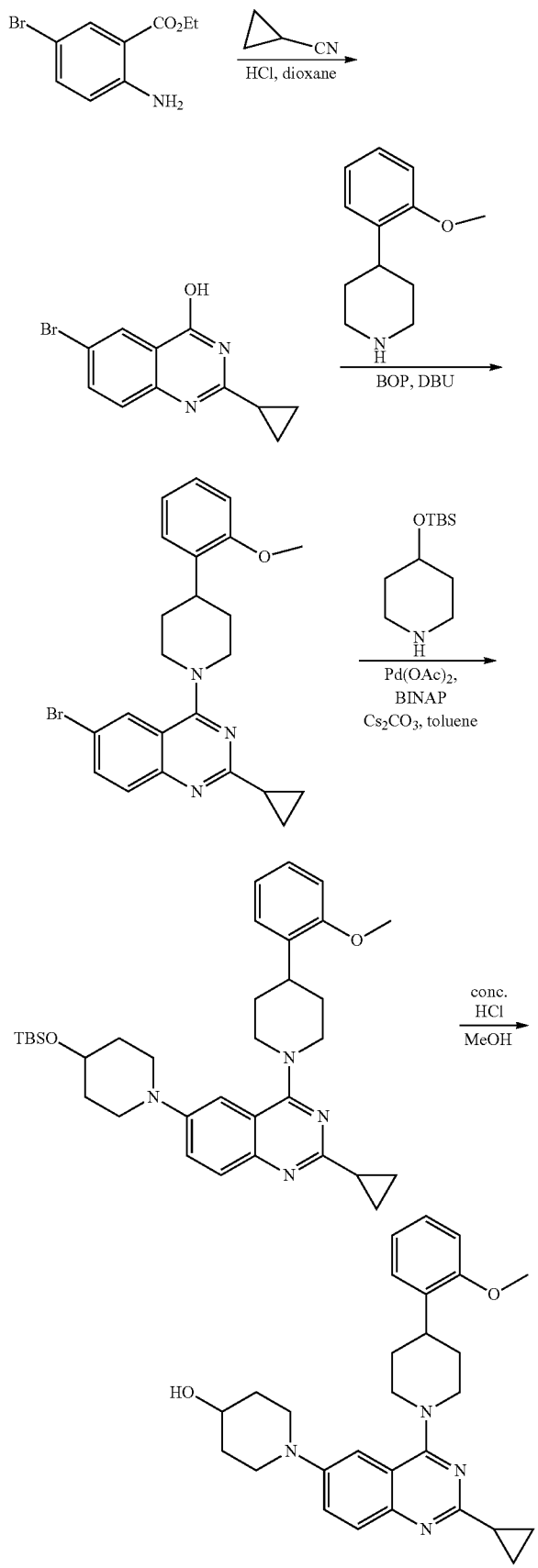

Example 76: Preparation of 1-{2-cyclopropyl-4-[4-(2-methoxy-phenyl)-piperidin-1-yl]-quinazolin-6-yl}-piperidin-4-ol

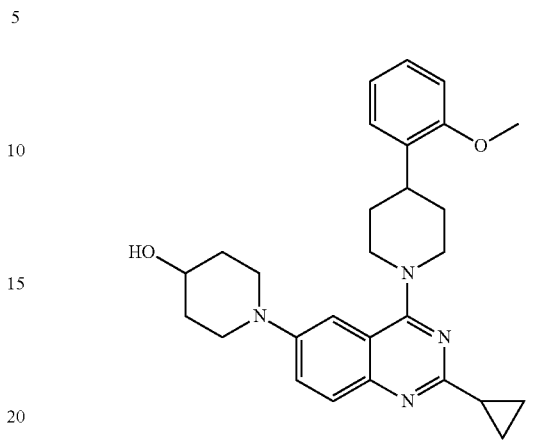

The mixture of 2-amino-5-bromo-benzoic acid ethyl ester (3.0 g, 13.16 mmol) and cyclopropanecarbonitrile (2.6 g, 39.47 mmol) in 6 M HCl/dioxane (60 mL) was stirred at reflux overnight. The solid was filtered, dried in vacuum to give 6-bromo-2-cyclopropyl-quinazolin-4-ol (3.3 g, yield: 95%) as crude product. MS: m/z 249.1 (M+H$^+$).

A mixture of 6-bromo-2-cyclopropyl-quinazolin-4-ol (3.3 g, 13.16 mmol), 4-(2-methoxy-phenyl)-piperidine hydrochloride (3.3 g, 14.48 mmol), DBU (8.0 g, 52.64 mmol), and BOP (8.7 g, 19.47 mmol) in ACN (30 mL) was stirred at 25° C. overnight. The mixture was partitioned between water (60 mL) and EtOAc (60 mL). The aqueous phase was extracted with EtOAc (40 mL×2). The extracts were dried over Na$_2$SO$_4$, and concentrated to dryness. The residue was purified by silica gel column chromatography (PE/EA=10/1) to afford 6-bromo-2-cyclopropyl-4-[4-(2-methoxy-phenyl)-piperidin-1-yl]-quinazoline (4.2 g, yield: 73%) as a white solid. $^1$H NMR (400 HMz, CDCl$_3$): δ=7.97 (s, 1H), 7.72-7.64 (m, 2H), 7.23-7.20 (m, 1H), 6.98-6.88 (m, 2H), 4.40-4.36 (m, 2H), 3.86 (s, 3H), 3.30-3.19 (m, 3H), 2.20-2.16 (m, 1H), 1.98-1.77 (m, 4H), 1.20-1.16 (m, 2H), 1.03-0.98 (m, 2H).

To a mixture of 6-bromo-2-cyclopropyl-4-[4-(2-methoxy-phenyl)-piperidin-1-yl]-quinazoline (100 mg, 0.237 mmol), 4-(tert-butyl-dimethyl-silanyloxy)-piperidine (102 mg, 0.474 mmol) and Cs$_2$CO$_3$ (154 mg, 0.474 mmol) in anhydrous toluene (20 mL) was added BINAP (30 mg, 0.048 mmol) and Pd(OAc)$_2$ (5.0 mg, 0.024 mmol). The mixture was refluxed under N$_2$ overnight. The mixture was concentrated under reduced pressure and the residue was partitioned between water (60 mL) and EtOAc (30 mL). The aqueous phase was extracted with EtOAc (15 mL×2). The extracts were dried over Na$_2$SO$_4$ and concentrated to dryness. The residue was purified by Pre-TLC (PE/EA=5/1) to give 6-[4-(tert-butyl-dimethyl-silanyloxy)-piperidin-1-yl]-2-cyclopropyl-4-[4-(2-methoxy-phenyl)-piperidin-1-yl]-quinazoline (100 mg, yield: 74%) as a pale yellow solid. MS: m/z 572.0 (M+H$^+$).

To a solution of 6-[4-(tert-butyl-dimethyl-silanyloxy)-piperidin-1-yl]-2-cyclopropyl-4-[4-(2-methoxy-phenyl)-piperidin-1-yl]-quinazoline (100 mg, 0.180 mmol) in MeOH (1 mL) was added conc.HCl (one drop), the reaction mixture was stirred at room temperature overnight. The mixture was concentrated under reduced pressure. The residue was partitioned between water (30 mL) and EtOAc (30 mL). The aqueous phase was extracted with EtOAc (20 mL×2). The extracts were dried over Na$_2$SO$_4$ and concentrated to dryness. The residue was purified by Pre-TLC (DCM/MeOH=10/1) to give 1-{2-cyclopropyl-4-[4-(2-methoxy-phenyl)-piperidin-1-yl]-quinazolin-6-yl}-piperidin-4-ol (40 mg, yield: 48%) as a yellow solid. $^1$H NMR (400 HMz, CDCl$_3$): δ=7.73-7.71 (m, 1H), 7.48-7.45 (m, 1H), 7.26-7.21 (m, 2H), 7.11 (d, J=2.1 Hz, 1H), 6.99-6.97 (m, 1H), 6.90 (d, J=8.0 Hz, 1H), 4.36-4.33 (m, 2H), 3.91-3.89 (m, 1H), 3.86 (s, 3H), 3.54-3.52 (m, 2H), 3.33-3.17 (m, 3H), 3.00-2.97 (m, 2H), 2.30-2.27 (m, 1H), 2.07-1.72 (m, 9H), 1.18-1.16 (m, 2H), 1.02-1.00 (m, 2H). MS: m/z 459.3 (M+H$^+$).

Example 77: Preparation of {2-cyclopropyl-4-[4-(2-methoxy-phenyl)-piperidin-1-yl]-6-(4-methoxy-piperidin-1-yl)-quinazoline

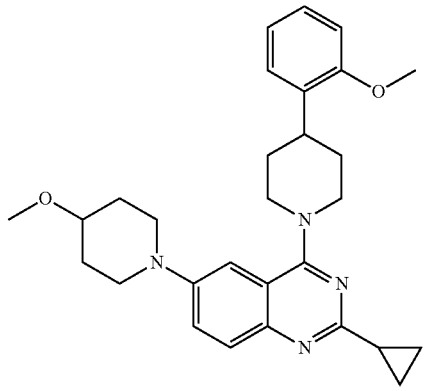 [SMILES: COc1ccccc1C1CCN(c2nc(C3CC3)nc3ccc(N4CCC(OC)CC4)cc23)CC1]

The title compound was prepared as described for 1-{2-cyclopropyl-4-[4-(2-methoxy-phenyl)-piperidin-1-yl]-quinazolin-6-yl}-piperidin-4-ol. $^1$HNMR (400 HMz, CDCl$_3$): δ=7.84-7.79 (m, 1H), 7.48-7.45 (m, 1H), 7.24-7.21 (m, 2H), 7.10 (d, J=2.4 Hz, 1H), 6.99-6.96 (m, 1H), 6.90 (d, J=8.8 Hz, 1H), 4.43-4.38 (m, 2H), 3.86 (s, 3H), 3.55-3.50 (m, 2H), 3.42-3.38 (m, 4H), 3.30-3.26 (m, 1H), 3.15 (t, J=12.4 Hz, 2H), 3.04-2.96 (m, 2H), 2.10-2.23 (m, 1H), 2.06-1.74 (m, 8H), 1.17-1.15 (m, 2H), 0.98-0.97 (m, 2H). MS: m/z 474.3 (M+H$^+$).

Example 78: (1-{2-cyclopropyl-4-[4-(2-methoxy-phenyl)-piperidin-1-yl]-quinazolin-6-yl}-piperidin-4-yl)-dimethyl-amine

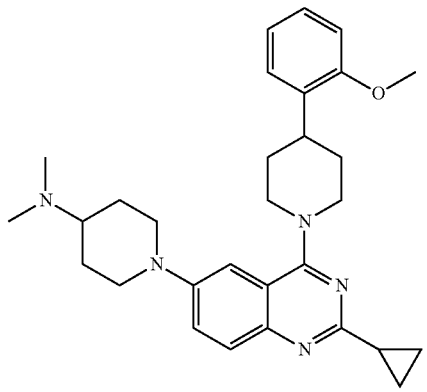 [SMILES: COc1ccccc1C1CCN(c2nc(C3CC3)nc3ccc(N4CCC(N(C)C)CC4)cc23)CC1]

The title compound was prepared as described for 1-{2-cyclopropyl-4-[4-(2-methoxy-phenyl)-piperidin-1-yl]-quinazolin-6-yl}-piperidin-4-ol. $^1$H NMR (400 HMz, CDCl$_3$): δ=7.75-7.74 (m, 1H), 7.45 (dd, J=8.0, 0.8 Hz, 1H), 7.23-7.21 (m, 2H), 7.11 (s, 1H), 6.99-6.96 (m, 1H), 6.90 (d, J=8.4 Hz, 1H), 4.37-4.34 (m, 2H), 3.86 (s, 3H), 3.79-3.76 (m, 2H), 3.31-3.16 (m, 3H), 2.81-2.75 (m, 2H), 2.43 (s, 6H), 2.22-2.20 (m, 1H), 2.08-1.70 (m, 9H), 1.25-1.16 (m, 2H), 0.99-0.97 (m, 2H). MS: m/z 486.3 (M+H$^+$).

Example 79: Preparation of 1-{2-cyclopropyl-4-[4-(2-methoxy-phenyl)-piperidin-1-yl]-quinazolin-6-yl}-pyrrolidin-3-ol

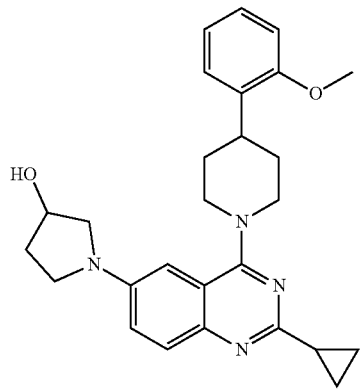 [SMILES: COc1ccccc1C1CCN(c2nc(C3CC3)nc3ccc(N4CCC(O)C4)cc23)CC1]

The title compound was prepared as described for 1-{2-cyclopropyl-4-[4-(2-methoxy-phenyl)-piperidin-1-yl]-quinazolin-6-yl}-piperidin-4-ol. $^1$H NMR (400 HMz, CDCl$_3$): δ=7.84-7.83 (m, 1H), 7.26-7.21 (m, 2H), 7.06 (dd, J=9.6, 2.0 Hz, 1H), 6.97 (t, J=7.6 Hz, 1H), 6.90 (dd, J=8.4, 3.2 Hz, 1H), 6.65 (s, 1H), 4.68-4.66 (m, 1H), 4.48-4.4.46 (m, 2H), 3.86 (s, 3H), 3.60-3.55 (m, 2H), 3.43-3.28 (m, 3H), 3.19-3.13 (m, 2H), 2.34-2.32 (m, 1H), 2.24-1.81 (m, 8H), 1.02-1.01 (m, 2H), 1.01-0.99 (m, 2H). MS: m/z 445.3 (M+H$^+$).

Example 80: Preparation of 2-cyclopropyl-4-[4-(2-methoxy-phenyl)-piperidin-1-yl]-6-(3-methoxy-pyrrolidin-1-yl)-quinazoline

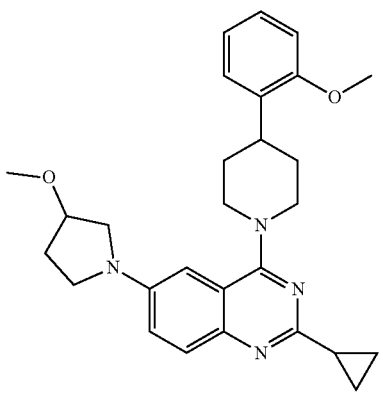 [SMILES: COc1ccccc1C1CCN(c2nc(C3CC3)nc3ccc(N4CCC(OC)C4)cc23)CC1]

The title compound was prepared as described for 1-{2-cyclopropyl-4-[4-(2-methoxy-phenyl)-piperidin-1-yl]-quinazolin-6-yl}-piperidin-4-ol. $^1$H NMR (400 HMz, CDCl$_3$):

δ=7.68-7.66 (m, 1H), 7.19-7.13 (m, 2H), 7.07 (dd, J=8.8, 2.1 Hz, 1H), 6.90 (t, J=7.6 Hz, 1H), 6.82 (d, J=8.8 Hz, 1H), 6.62 (s, 1H), 4.32-4.29 (m, 2H), 4.08-4.06 (m, 1H), 3.79 (s, 3H), 3.51-3.37 (m, 3H), 3.36 (s, 3H), 3.22-3.19 (m, 1H), 3.08-3.01 (m, 2H), 2.13-2.06 (m, 2H), 1.92-1.77 (m, 6H), 1.10-1.06 (m, 2H), 0.91-0.87 (m, 2H). MS: m/z 459.2 (M+H$^+$).

Example 81: Preparation of (R)-1-{2-cyclopropyl-4-[4-(2-methoxy-phenyl)-piperidin-1-yl]-quinazolin-6-yl}-pyrrolidin-3-ol, HCl salt

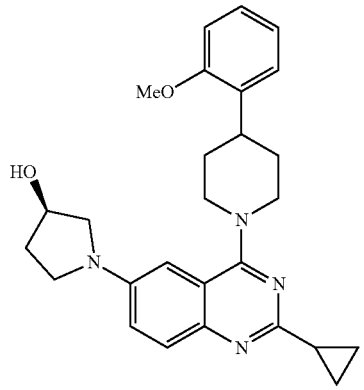 [SMILES: COc1ccccc1C1CCN(c2nc(C3CC3)nc3ccc(N4CC[C@@H](O)C4)cc23)CC1]

The title compound was prepared as described for 1-{2-cyclopropyl-4-[4-(2-methoxy-phenyl)-piperidin-1-yl]-quinazolin-6-yl}-piperidin-4-ol. $^1$H NMR (400 HMz, CD$_3$OD): δ=7.62 (d, J=8.8 Hz, 1H), 7.42-7.39 (m, 1H), 7.21 (d, J=7.6 Hz, 2H), 7.00-6.90 (m, 3H), 5.03-5.00 (m, 2H), 4.62-4.60 (m, 1H), 3.88 (s, 3H), 3.52-3.37 (m, 6H), 3.60-3.51 (m, 6H), 2.26-2.23 (m, 1H), 2.18-2.09 (m, 4H) 1.97- 1.91 (m, 2H), 1.37-1.29 (m, 4H). MS: m/z 445.2 (M+H$^+$).

Example 82: Preparation of (S)-1-(2-cyclopropyl-4-(4-(2-methoxyphenyl)piperidin-1-yl) quinazolin-6-yl)pyrrolidin-3-ol

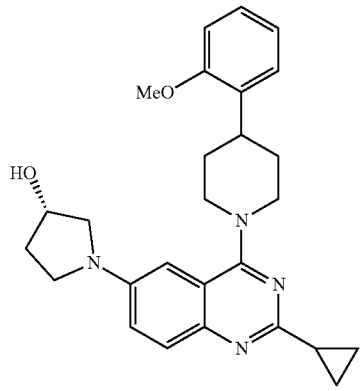 [SMILES: COc1ccccc1C1CCN(c2nc(C3CC3)nc3ccc(N4CC[C@H](O)C4)cc23)CC1]

The title compound was prepared as described for 2-({2-cyclopropyl-4-[3-(2-methoxy-phenylamino)-pyrrolidin-1-yl]-quinazolin-6-yl}-methyl-amino)-ethanol. $^1$H NMR (400 HMz, CD$_3$OD): δ=7.49 (dd, J=9.2, 1.8 Hz, 1H), 7.29-7.24 (m, 1H), 7.13-7.07 (m, 2H), 6.88-6.74 (m, 3H), 4.88 (d, J=12.4 Hz, 2H), 4.50-4.48 (m, 1H), 3.74 (s, 3H), 3.53-3.34 (m, 6H), 2.14-1.94 (m, 5H), 1.82-1.77 (m, 2H), 1.26-1.15 (m, 2H). MS: m/z 445.2 (M+H$^+$).

Example 83: Preparation of (R)-2-cyclopropyl-4-(4-(2-methoxyphenyl)piperidin-1-yl)-6-(3-methoxypyrrolidin-1-yl)quinazoline, HCl salt

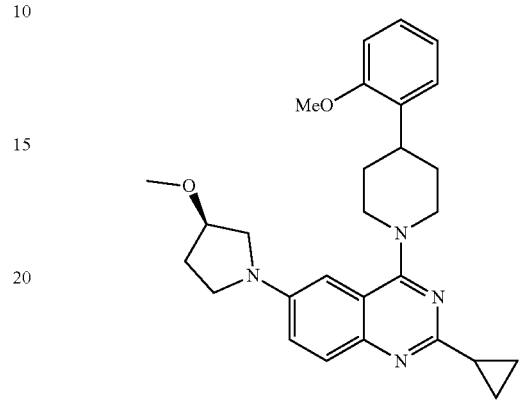

The title compound was prepared as described for 2-({2-cyclopropyl-4-[3-(2-methoxy-phenylamino)-pyrrolidin-1-yl]-quinazolin-6-yl}-methyl-amino)-ethanol. $^1$HNMR (400 HMz, CD$_3$OD): δ=7.52 (d, J=8.8 Hz, 1H), 7.18-7.05 (m, 3H), 6.86-6.78 (m, 2H), 6.65 (d, J=2.4 Hz, 1H), 4.36 (d, J=14.0 Hz, 2H), 4.09-4.06 (m, 1H), 3.84 (s, 3H), 3.50-3.35 (m, 1H), 3.40-3.20 (m, 7H), 3.11-3.00 (m, 2H), 2.12-1.96 (m, 3H), 1.85-1.78 (m, 4H), 1.07 (m, 2H), 0.92-0.85 (m, 2H). MS: m/z 459.2 (M+H$^+$)

Example 84: Preparation of (S)-2-cyclopropyl-4-(4-(2-methoxyphenyl)piperidin-1-yl)-6-(3-methoxypyrrolidin-1-yl)quinazoline

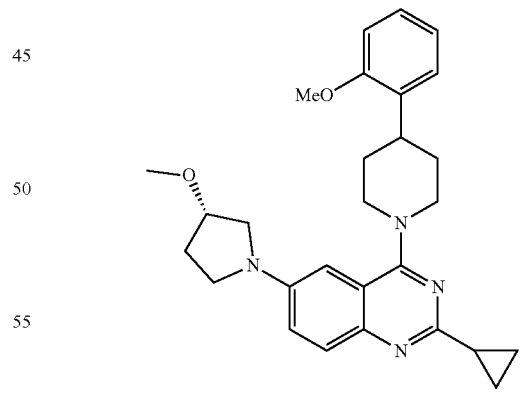

The title compound was prepared as described for 2-({2-cyclopropyl-4-[3-(2-methoxy-phenylamino)-pyrrolidin-1-yl]-quinazolin-6-yl}-methyl-amino)-ethanol. $^1$H NMR (400 HMz, CD$_3$OD): δ=7.49 (d, J=9.2 Hz, 1H), 7.26 (dd, J=9.2, 2.4 Hz, 1H), 7.12-7.08 (m, 2H), 6.88-6.74 (m, 3H), 4.89-4.83 (m, 2H), 4.10-4.07 (m, 1H), 3.75 (s, 3H), 3.50-3.32 (m, 7H), 3.28 (s, 3H), 2.20-1.93 (m, 5H), 1.85-1.78 (m, 2H), 1.24-1.12 (m, 4H). MS: m/z 459.2 (M+H$^+$)

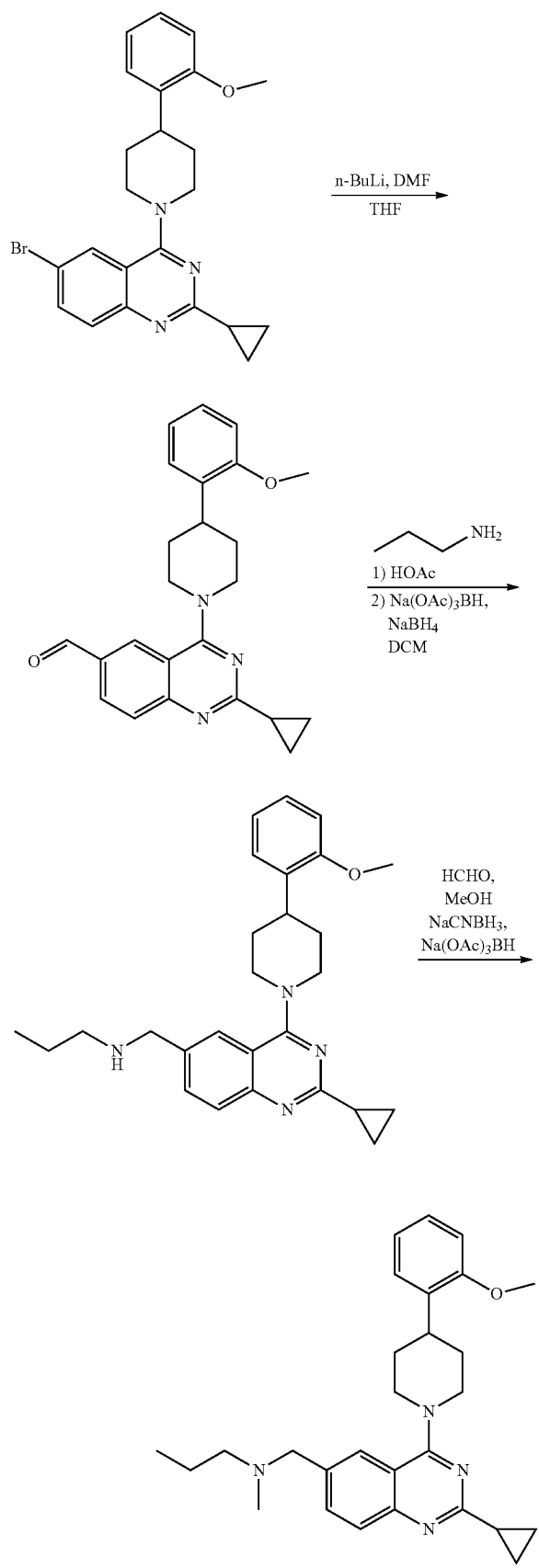

Example 85: Preparation of {2-cyclopropyl-4-[4-(2-methoxy-phenyl)-piperidin-1-yl]-quinazolin-6-ylm-ethyl}-methyl-propyl-amine To a mixture of 6-bromo-2-cyclopropyl-4-[4-(2-methoxy-phenyl)-piperidin-1-yl]-quinazoline (1.09 g, 2.5 mmol) in THF (25 mL) at −78° C. was added n-BuLi (1 mL, 2.5 mmol). The resulting mixture was stirred at −78° C. for 2 hours. Then DMF (0.4 mL, 5.0 mmol) was added into the mixture. The reaction mixture was allowed to warm to room temperature and stirred for another 2 hours. The mixture was partitioned between NH$_4$Cl (aq. 50 mL) and EtOAc (50 mL). The aqueous phase was extracted with EtOAc (50 mL×2). The extracts were washed with water (100 mL×2), brine (100 mL), and dried over Na$_2$SO$_4$. The solution was concentrated to dryness and the residue was purified by silica gel column chromatography (PE/EA=10/1) to afford 2-cyclopropyl-4-[4-(2-methoxy-phenyl)-piperidin-1-yl]-quinazoline-6-carbaldehyde (600 mg, yield: 73%) as a pale yellow solid. $^1$H NMR (400 HMz, CDCl$_3$): δ=9.96 (s, 1H), 9.26 (d, J=1.2 Hz, 1H), 8.03 (dd, J=8.8, 1.6 Hz, 1H), 7.76 (d, J=8.8 Hz, 1H), 7.17-7.13 (m, 2H), 6.89 (t, J=7.2 Hz, 1H), 6.83 (d, J=8.0 Hz, 1H), 4.51-4.48 (m, 2H), 3.79 (s, 3H), 3.29-3.23 (m, 2H), 2.15-2.10 (m, 1H), 1.97-1.80 (m, 5H), 1.16-1.13 (m, 2H), 1.00-0.97 (m, 2H). MS: m/z 388.3 (M+H$^+$).

To a mixture of 2-cyclopropyl-4-[4-(2-methoxy-phenyl)-piperidin-1-yl]-quinazoline-6-carbaldehyde (80 mg, 0.21 mmol) in DCM (8 mL) was added propylamine (29 mg, 0.42 mmol) and HOAc (one drop). The mixture was stirred at 30° C. overnight. Then Na(OAc)$_3$BH (219 mg, 1.04 mmol) and NaBH$_4$ (39 mg, 1.04 mmol) were added and the resulting mixture was stirred at 30° C. overnight again. The mixture was partitioned between water (30 mL) and DCM (30 mL). The aqueous phase was extracted with DCM (30 mL×2). The extracts were washed with water (50 mL×2), dried over Na$_2$SO$_4$. The solution was concentrated to dryness give {2-cyclopropyl-4-[4-(2-methoxy-phenyl)-piperidin-1-yl]-quinazolin-6-ylmethyl}-propyl-amine (89 mg, yield: 98%) as a colorless oil. MS: m/z 431.3 (M+H$^+$).

To a mixture of {2-cyclopropyl-4-[4-(2-methoxy-phenyl)-piperidin-1-yl]-quinazolin-6-ylmethyl}-propyl-amine (89 mg, 0.21 mmol) in MeOH (5 mL), was added HCHO (3 mL) and HOAc (one drop). The resulting mixture was stirred for 1 hour at room temperature. Then Na(OAc)$_3$BH (87 mg, 0.41 mmol) and NaBCNH$_3$ (64 mg, 1.03 mmol) were added and the resulting mixture was stirred at room temperature overnight again. The mixture was partitioned between water (30 mL) and EtOAc (30 mL). The aqueous phase was extracted with EtOAc (30 mL×2). The extracts were washed with water (50 mL×2), and brine (50 mL) and dried over Na$_2$SO$_4$. The solution was concentrated and purified by Prep-TLC (DCM/MeOH=10/1), lyophilized with 2N HCl to afford {2-cyclopropyl-4-[4-(2-methoxyphenyl)-piperidin-1-yl]-quinazolin-6-ylmethyl}-methyl-propyl-amine (40 mg, yield: 43%) as a white solid. ¹H NMR (400 HMz, CD₃OD): δ=8.26 (s, 1H), 7.99 (d, J=8.4 Hz, 1H), 7.70 (d, J=7.6 Hz, 1H), 7.13-7.09 (m, 2H), 6.87 (d, J=7.6 Hz, 1H), 6.81 (t, J=7.6 Hz, 1H), 4.57 (d, J=12.8 Hz, 1H), 4.36 (d, J=12.8 Hz, 1H), 3.75 (s, 3H), 3.44-3.38 (m, 2H), 6.89 (t, J=14.8 Hz, 1H), 6.83 (d, J=8.0 Hz, 1H), 5.15-4.78 (m, 2H), 4.55 (d, J=13.2 Hz, 1H), 4.38 (d, J=13.2 Hz, 1H), 3.75 (s, 3H), 3.73-3.22 (m, 3H), 3.13-3.08 (m, 1H), 3.04-3.01 (m, 1H), 2.72 (s, 3H), 2.12-2.10 (m, 1H), 2.02-1.99 (m, 2H), 1.85-1.73 (m, 4H), 1.33-1.27 (m, 4H), 0.92 (t, J=7.2 Hz, 3H). MS: m/z 445.3 (M+H⁺).

Example 86: Preparation of {2-cyclopropyl-4-[4-(2-methoxy-phenyl)-piperidin-1-yl]-quinazolin-6-ylmethyl}-dimethyl-amine

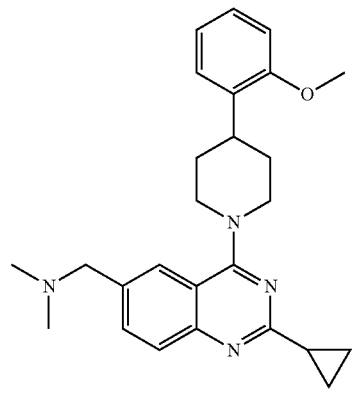 [SMILES: COc1ccccc1C1CCN(c2nc(C3CC3)nc3ccc(CN(C)C)cc23)CC1]

The title compound was prepared as described for {2-cyclopropyl-4-[4-(2-methoxy-phenyl)-piperidin-1-yl]-quinazolin-6-ylmethyl}-methyl-propyl-amine. ¹H NMR (400 HMz, CD₃OD): δ=8.28 (s, 1H), 7.99 (dd, J=8.4, 1.2 Hz, 1H), 7.71 (d, J=8.8 Hz, 1H), 7.13-7.08 (m, 2H), 6.88-6.79 (m, 2H), 4.59 (s, 2H), 3.76 (s, 3H), 3.41-3.40 (m, 1H), 3.22-3.20 (m, 4H), 2.80 (s, 6H), 2.13-2.10 (m, 1H), 2.02-2.00 (m, 2H), 1.87-1.83 (m, 2H), 1.32-1.26 (m, 4H). MS: m/z 417.2 (M+H⁺).

Example 87: Preparation of {2-cyclopropyl-4-[4-(2-methoxy-phenyl)-piperidin-1-yl]-quinazolin-6-ylmethyl}-(2-methoxy-ethyl)-methyl-amine

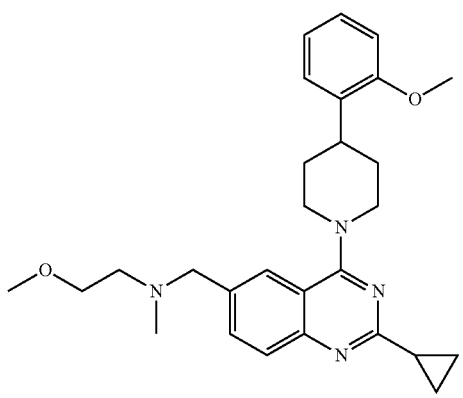 [SMILES: COCCN(C)Cc1ccc2nc(C3CC3)nc(N3CCC(c4ccccc4OC)CC3)c2c1]

The title compound was prepared as described for {2-cyclopropyl-4-[4-(2-methoxy-phenyl)-piperidin-1-yl]-quinazolin-6-ylmethyl}-methyl-propyl-amine. ¹H NMR (400 HMz, CD₃OD): δ=8.25 (s, 1H), 8.01-7.80 (m, 1H), 7.71 (d, J=8.8 Hz, 1H), 7.12-7.08 (m, 2H), 6.87 (d, J=8.0 Hz, 1H), 6.81 (t, J=7.6 Hz, 1H), 4.57 (d, J=13.2 Hz, 1H), 4.43 (d, J=13.2 Hz, 1H), 3.75 (s, 3H), 3.68 (t, J=6.8 Hz, 2H), 3.42-3.38 (m, 3H), 3.35 (s, 3H), 3.34-3.21 (m, 3H), 2.81 (s, 3H), 2.12-2.11 (m, 1H), 2.03-1.99 (m, 2H), 1.85-1.83 (m, 2H), 1.33-1.26 (m, 4H). MS: m/z 461.3 (M+H⁺).

Example 88: Preparation of {2-cyclopropyl-4-[4-(2-methoxy-phenyl)-piperidin-1-yl]-quinazolin-6-ylmethyl}-methyl-(2-morpholin-4-yl-ethyl)-amine

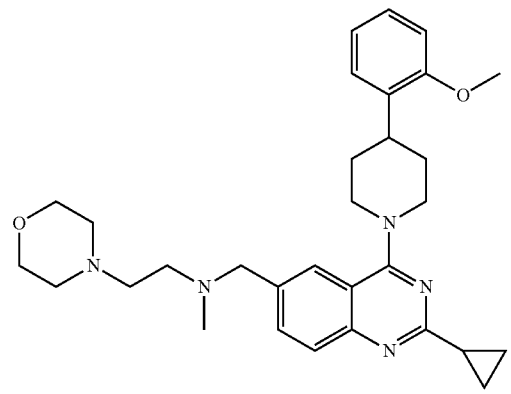 [SMILES: COc1ccccc1C1CCN(c2nc(C3CC3)nc3ccc(CN(C)CCN4CCOCC4)cc23)CC1]

The title compound was prepared as described for {2-cyclopropyl-4-[4-(2-methoxy-phenyl)-piperidin-1-yl]-quinazolin-6-ylmethyl}-methyl-propyl-amine. ¹H NMR (400 HMz, CD₃OD): δ=8.43 (s, 1H), 8.09 (d, J=8.8 Hz, 1H), 7.69 (d, J=8.4 Hz, 1H), 7.16-7.09 (m, 2H), 6.86 (d, J=8.0 Hz, 1H), 6.81 (t, J=7.6 Hz, 1H), 3.94-3.89 (m, 6H), 3.81 (s, 3H), 3.80-3.40 (m, 7H), 3.22-3.20 (m, 5H), 2.80 (s, 3H), 2.12-2.11 (m, 1H), 2.03-2.00 (m, 2H), 1.89-1.88 (m, 2H), 1.33-1.26 (m, 4H). MS: m/z 516.3 (M+H⁺).

Example 89: Preparation of 2-({2-cyclopropyl-4-[4-(2-methoxy-phenyl)-piperidin-1-yl]-quinazolin-6-ylmethyl}-methyl-amino)-ethanol

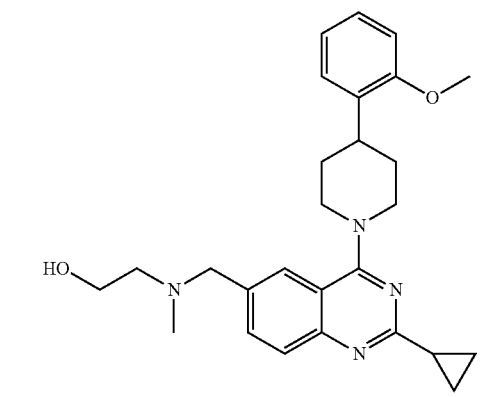 [SMILES: COc1ccccc1C1CCN(c2nc(C3CC3)nc3ccc(CN(C)CCO)cc23)CC1]

The title compound was prepared as described for {2-cyclopropyl-4-[4-(2-methoxy-phenyl)-piperidin-1-yl]-quinazolin-6-ylmethyl}-methyl-propyl-amine. $^1$H NMR (400 HMz, CD$_3$OD): δ=8.37 (s, 1H), 8.12 (d, J=8.4 Hz, 1H), 7.82 (d, J=8.8 Hz, 1H), 7.25-7.21 (m, 2H), 7.00 (d, J=6.8 Hz, 1H), 6.93 (t, J=6.8 Hz, 1H), 5.09-5.01 (m, 2H), 4.72-4.71 (m, 1H), 4.58-4.54 (m, 1H), 3.95 (t, J=4.8 Hz, 2H), 3.87 (s, 3H), 3.56-3.50 (m, 5H), 2.96 (s, 3H), 2.23-2.21 (m, 1H), 2.15-2.12 (m, 2H), 1.97-1.94 (m, 2H), 1.45-1.37 (m, 4H). MS: m/z 447.3 (M+H$^+$).

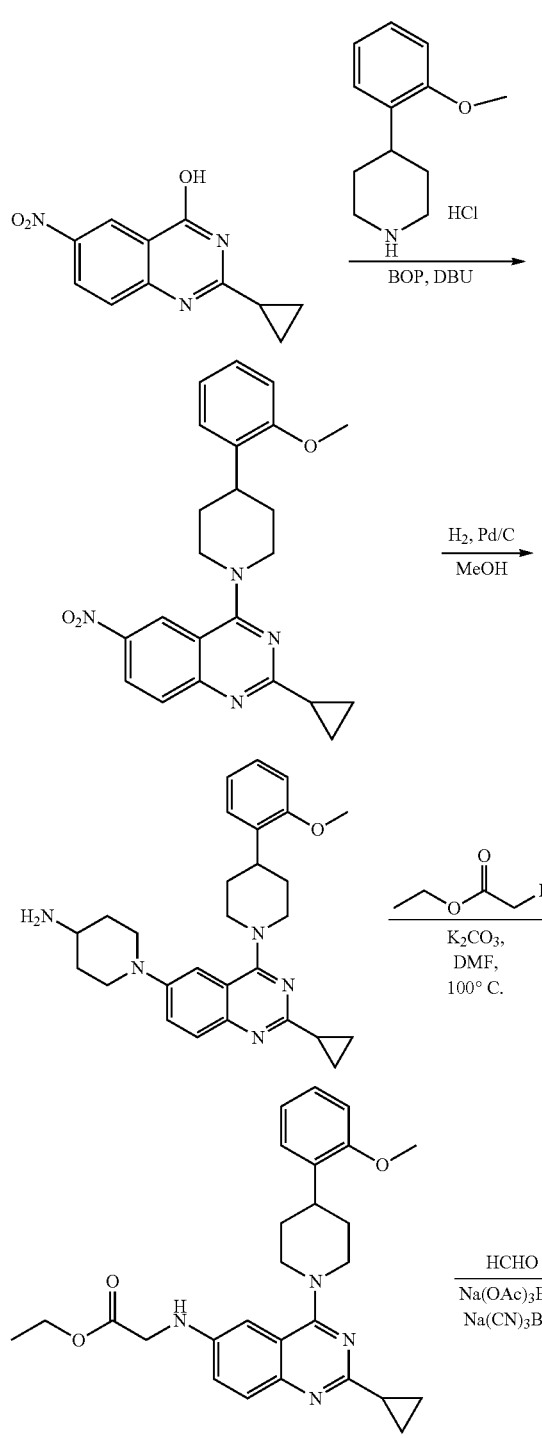

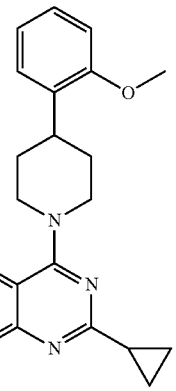

Example 90: Preparation of ({2-cyclopropyl-4-[4-(2-methoxy-phenyl)-piperidin-1-yl]-quinazolin-6-yl}-methyl-amino)-acetic acid ethyl ester

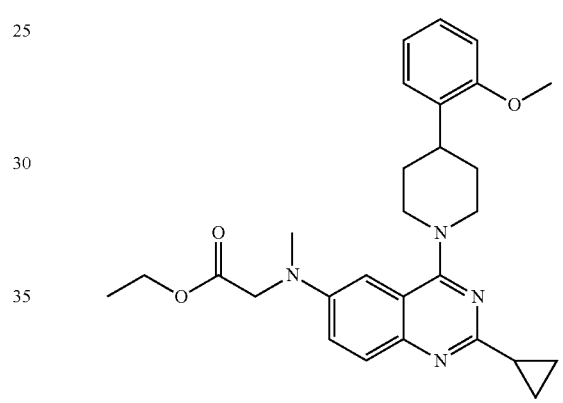

A mixture of 2-cyclopropyl-6-nitro-quinazolin-4-ol (500 mg, 2.32 mmol), 4-(2-methoxy-phenyl)-piperidine hydrochloride (581 mg, 2.55 mmol), DBU (1.41 g, 9.260 mmol), and BOP (1.54 g, 3.47 mmol) in ACN (5 mL) was stirred at 25° C. overnight. The mixture was partitioned between water (30 mL) and EtOAc (30 mL), extracted with EtOAc (20 mL×2), dried over Na$_2$SO$_4$, The solution was concentrated to dryness and the residue was purified silica gel column chromatography (PE/EA=10/1) to afford 2-cyclopropyl-4-[4-(2-methoxy-phenyl)-piperidin-1-yl]-6-nitroquinazoline (520 mg, yield: 56%) as a yellow solid. MS: m/z 405.3 (M+H$^+$).

To a mixture of 2-cyclopropyl-4-[4-(2-methoxy-phenyl)-piperidin-1-yl]-6-nitro-quinazoline (260 mg, 0.642 mmol) in MeOH (10 mL), was added Pd/C (10% wet, 80 mg) under N$_2$. The suspension was degassed under reduced pressure and purged with N$_2$ atmosphere several times. The resulting mixture was stirred overnight at room temperature. The solvent was concentrated after filtration, dried in vacuo to give 2-cyclopropyl-4-[4-(2-methoxy-phenyl)-piperidin-1-yl]-quinazolin-6-ylamine (240 mg, yield: 100%) as a yellow solid.

To a solution of 2-cyclopropyl-4-[4-(2-methoxy-phenyl)-piperidin-1-yl]-quinazolin-6-ylamine (160 mg, 0.42 mmol) in DMF (10 mL), was added bromo-acetic acid ethyl ester (142 mg, 0.85 mmol) and K$_2$CO$_3$ (235 mg, 1.70 mmol). The reaction mixture was stirred at 100° C. for overnight. The mixture was partitioned between water (50 mL) and EtOAc (50 mL), extracted with EtOAc (50 mL×2), the organic layer was dried over Na$_2$SO$_4$, The solution was concentrated to dryness and the residue was purified silica gel column chromatography (PE/EA=10/1) (DCMMeOH=20/1) to give {2-cyclopropyl-4-[4-(2-methoxy-phenyl)-piperidin-1-yl]-quinazolin-6-ylamino}-acetic acid ethyl ester (170 mg, yield: 87%) as a yellow solid. MS: m/z 461.3 (M+H$^+$).

To a mixture of {2-cyclopropyl-4-[4-(2-methoxy-phenyl)-piperidin-1-yl]-quinazolin-6-ylamino}-acetic acid ethyl ester (170 mg, 0.36 mmol) in MeOH (10 mL), was added HCHO (5 mL) and HOAc (one drop), The resulting mixture was stirred for 1 hour at room temperature. Then Na(OAc)$_3$BH (391 mg, 1.85 mmol) and NaBCNH$_3$ (114 mg, 1.85 mmol). The resulting mixture was stirred for overnight room temperature. The solvent was removed under reduced pressure and the residue was partitioned between water (30 mL) and EtOAc (30 mL), extracted with EtOAc (30 mL×2), washed the organic layers with water (50 mL×2) and brine (50 mL×1), dried over Na$_2$SO$_4$, The solution was concentrated to dryness and the residue was purified by Prep-HPLC, lyophilized with 2N HCl to afford ({2-cyclopropyl-4-[4-(2-methoxy-phenyl)-piperidin-1-yl]-quinazolin-6-yl}-methyl-amino)-acetic acid ethyl ester (25.8 mg, yield: 15%) as a yellow solid. $^1$H NMR (300 HMz, CD$_3$OD): δ=7.62 (d, J=9.3 Hz, 2H), 7.54 (dd, J=9.0, 2.4 Hz, 2H), 7.02-6.93 (m, 3H), 4.97-4.91 (m, 2H), 4.34 (s, 2H), 4.15 (q, J=6.9 Hz, 2H), 3.87 (s, 3H), 3.52-3.47 (m, 3H), 3.20 (s, 3H), 2.15-2.07 (m, 3H), 1.93-1.88 (m, 2H), 1.36-1.29 (m, 4H), 1.20 (t, J=7.2 Hz, 3H). MS: m/z 475.3 (M+H$^+$).

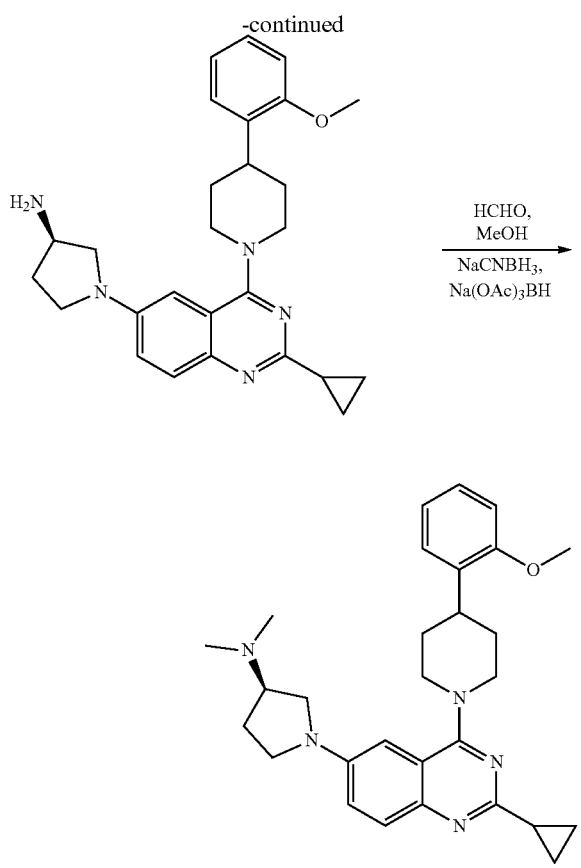

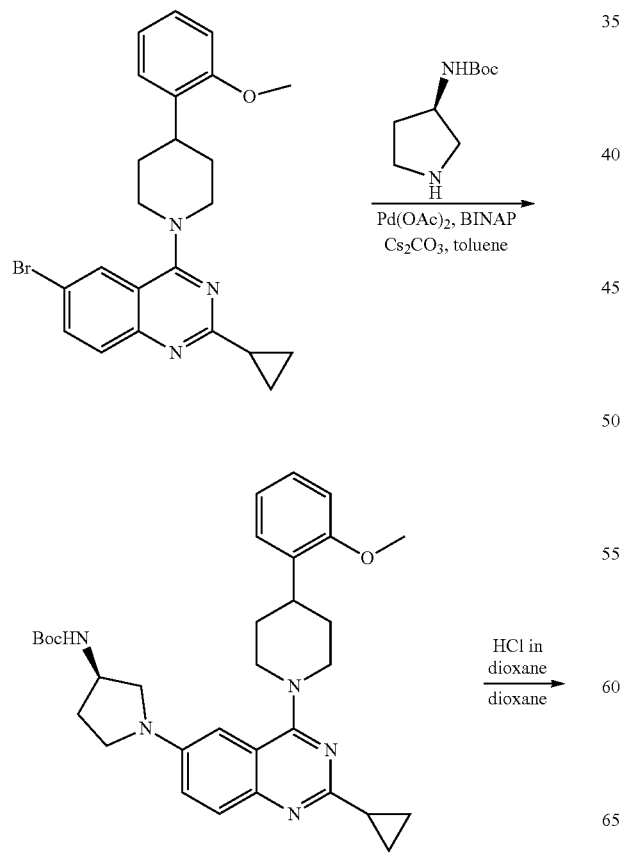

Example 91: Preparation of (1-{2-cyclopropyl-4-[4-(2-methoxy-phenyl)-piperidin-1-yl]-quinazolin-6-yl}-pyrrolidin-3-yl)-dimethyl-amine The 1$^{st}$ two steps are similar to (1-{2-cyclopropyl-4-[4-(2-methoxy-phenyl)-piperidin-1-yl]-quinazolin-6-yl}-piperidin-4-yl)-ethoxycarbonylmethyl-amino]-acetic acid ethyl ester.

To a mixture of 1-{2-Cyclopropyl-4-[4-(2-methoxy-phenyl)-piperidin-1-yl]-quinazolin-6-yl}-pyrrolidin-3-ylamine (62 mg, 0.112 mmol) in MeOH (5 mL), was added HCHO (3 mL) and HOAc (one drop). The resulting mixture was stirred for 1 hour at room temperature. Then Na BH(OAc)₃ (119 mg, 0.560 mmol) and NaBCNH₃ (35 mg, 0.560 mmol) were added. The resulting mixture was stirred at room temperature overnight. The solvent was removed under reduced pressure and the residue was purified by Prep-HPLC and lyophilized with 2N HCl to afford (1-{2-cyclopropyl-4-[4-(2-methoxy-phenyl)-piperidin-1-yl]-quinazolin-6-yl}-pyrrolidin-3-yl)-dimethyl-amine (3.7 mg, yield: 7%) as a white solid. ¹H NMR (300 HMz, CD₃OD): δ=7.67 (d, J=9.0 Hz, 1H), 7.48 (d, J=9.0 Hz, 1H), 7.24-7.19 (m, 2H), 7.00-6.92 (m, 3H), 5.03-4.98 (m, 2H), 4.15-4.12 (m, 1H), 3.93-3.89 (m, 1H), 3.86 (s, 3H), 3.77-3.73 (m, 2H), 3.56-3.48 (m, 4H), 3.20 (s, 3H), 3.01 (s, 3H), 2.68-2.64 (m, 1H), 2.44-2.37 (m, 1H), 2.18-2.07 (m, 3H), 1.92-1.87 (m, 2H), 1.37-1.31 (m, 4H). MS: m/z 472.3 (M+H⁺).

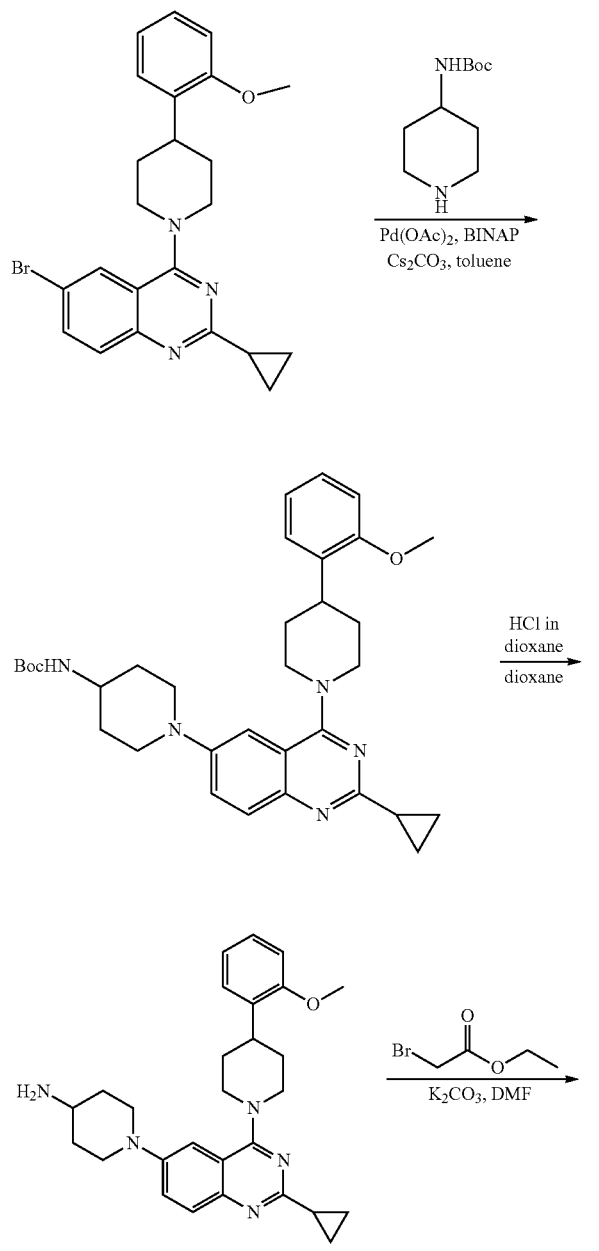

Example 92: Preparation of (1-{2-cyclopropyl-4-[4-(2-methoxy-phenyl)-piperidin-1-yl]-quinazolin-6-yl}-piperidin-4-yl)-ethoxycarbonylmethyl-amino]-acetic acid ethyl ester

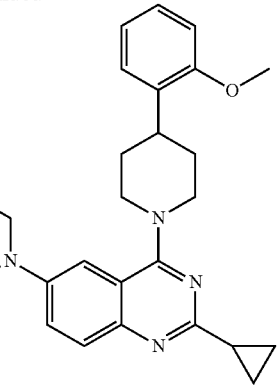

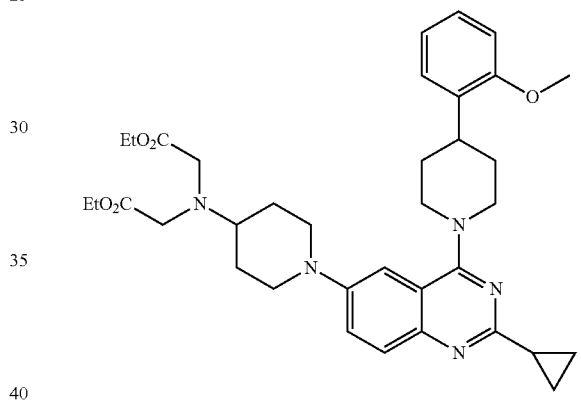

To a mixture of 6-bromo-2-cyclopropyl-4-[4-(2-methoxy-phenyl)-piperidin-1-yl]-quinazoline (1.12 g, 2.557 mmol), piperidin-4-yl-carbamic acid tert-butyl ester (1.02 g, 5.114 mmol) and Cs₂CO₃ (1.67 g, 5.114 mmol) in anhydrous toluene (100 mL), was added BINAP (318 mg, 0.511 mmol) and Pd(OAc)₂ (57 mg, 0.256 mmol). The mixture was refluxed under N₂ at 110° C. overnight. The mixture was concentrated under reduced pressure. The residue was partitioned between water (100 mL) and EtOAc (100 mL). The aqueous phase was extracted with EtOAc (100 mL×2) and the extracts were dried over Na₂SO₄. The solution was concentrated and the residue was purified silica gel column chromatography (PE/EA=30/1) to give (1-{2-cyclopropyl-4-[4-(2-methoxy-phenyl)-piperidin-1-yl]-quinazolin-6-yl}-piperidin-4-yl)-carbamic acid tert-butyl ester (3.3 g, yield: 27%) as a yellow solid. MS: m/z 558.3 (M+H⁺).

To a solution of (1-{2-cyclopropyl-4-[4-(2-methoxy-phenyl)-piperidin-1-yl]-quinazolin-6-yl}-piperidin-4-yl)-carbamic acid tert-butyl ester (380 mg, 0.681 mmol) in dioxane (2 mL) was added HCl in dioxane (4M, 0.68 mL). The reaction mixture was stirred at room temperature overnight. The mixture was concentrated under reduced pressure and the solid was dried in vacuum to give 1-{2-cyclopropyl-4-[4-(2-methoxy-phenyl)-piperidin-1-yl]-quinazolin-6-yl}-piperidin-4-ylamine (380 mg, yield: 100%) as a yellow solid. MS: m/z 458.3 (M+H⁺).

To a mixture of 1-{2-cyclopropyl-4-[4-(2-methoxy-phenyl)-piperidin-1-yl]-quinazolin-6-yl}-piperidin-4-ylamine (20 mg, 0.044 mmol) in DMF (2 mL), was added bromoacetic acid ethyl ester (29 mg, 0.176 mmol) and $K_2CO_3$ (24 mg, 0.176 mmol). The resulting mixture was stirred at 100° C. overnight. The resulting mixture was stirred at room temperature overnight. The mixture was purified by Prep-HPLC and lyophilized to afford (1-{2-cyclopropyl-4-[4-(2-methoxy-phenyl)-piperidin-1-yl]-quinazolin-6-yl}-piperidin-4-yl)-ethoxycarbonylmethyl-amino]-acetic acid ethyl ester (3.6 mg, yield: 13%) as a white solid. $^1$H NMR (300 HMz, $CD_3OD$): δ=7.81 (dd, J=9.3, 2.1 Hz, 1H), 7.66 (d, J=9.3 Hz, 1H), 7.39-7.37 (m, 1H), 7.24-7.19 (m, 2H), 7.00-6.92 (m, 2H), 4.99-4.97 (m, 2H), 4.38-4.31 (m, 6H), 4.05-4.00 (m, 2H), 3.86 (s, 3H), 3.64-3.37 (m, 6H), 3.02-2.95 (m, 2H), 2.23-1.92 (m, 9H), 1.39-1.30 (m, 10H). MS: m/z 630.3 (M+H$^+$).

Example 93: [(1-{2-cyclopropyl-4-[4-(2-methoxy-phenyl)-piperidin-1-yl]-quinazolin-6-yl}-piperidin-4-yl)-methyl-amino]-acetic acid ethyl ester The title compound was prepared as described for (1-{2-cyclopropyl-4-[4-(2-methoxy-phenyl)-piperidin-1-yl]-quinazolin-6-yl}-piperidin-4-yl)-ethoxycarbonylmethyl-amino]-acetic acid ethyl ester. $^1$H NMR (300 HMz, $CD_3OD$): δ=7.98-7.95 (m, 1H), 7.75-7.72 (m, 2H), 7.24-7.19 (m, 2H), 6.99-6.92 (m, 2H), 5.00-4.93 (m, 2H), 4.36 (q, J=7.2 Hz, 2H), 4.04-4.00 (m, 2H), 3.87 (s, 3H), 3.77-3.50 (m, 5H), 3.27-3.23 (m, 2H), 3.02 (s, 3H), 2.34-2.13 (m, 9H), 1.39-1.31 (m, 8H). MS: m/z 558.3 (M+H$^+$).

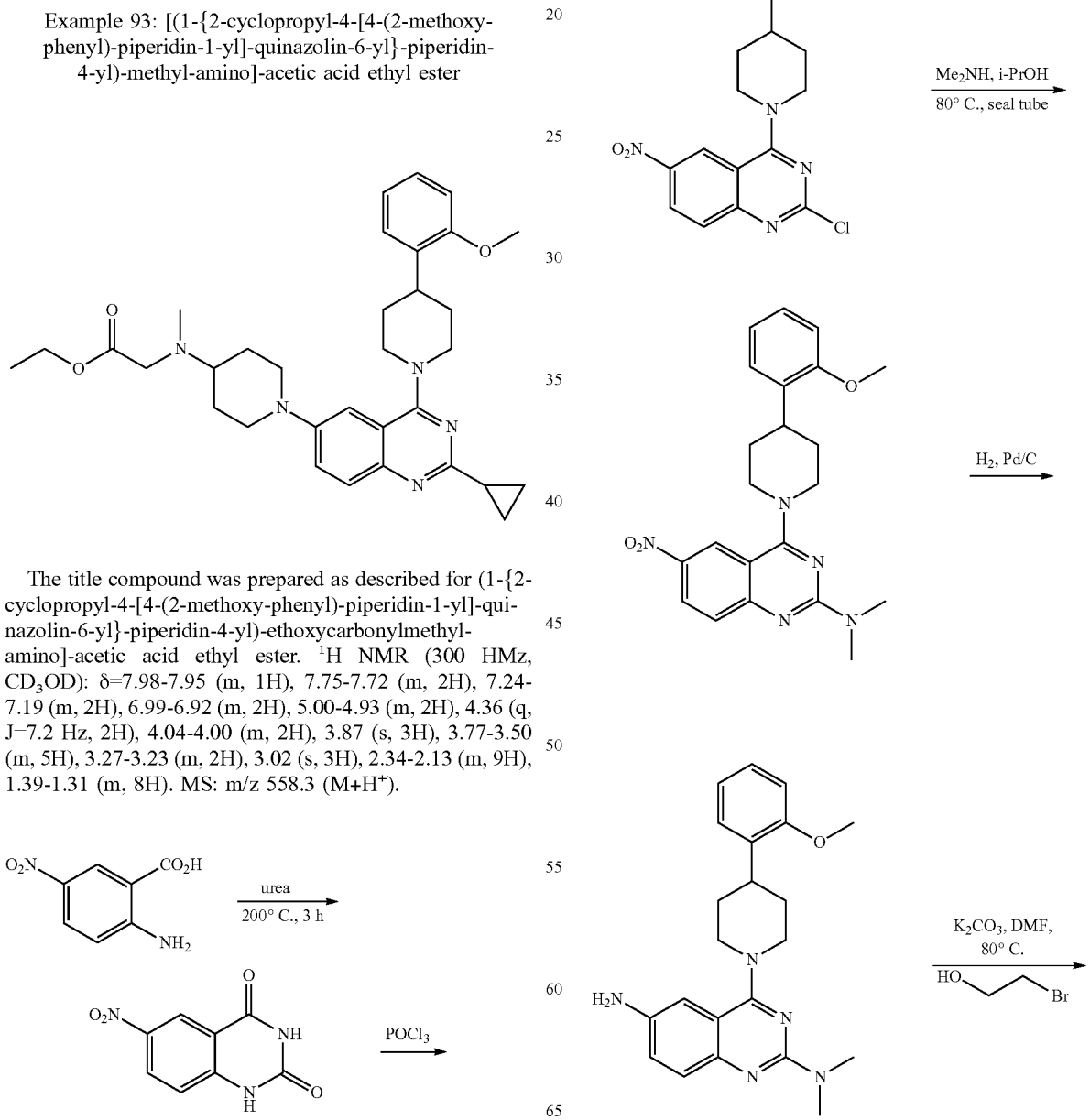

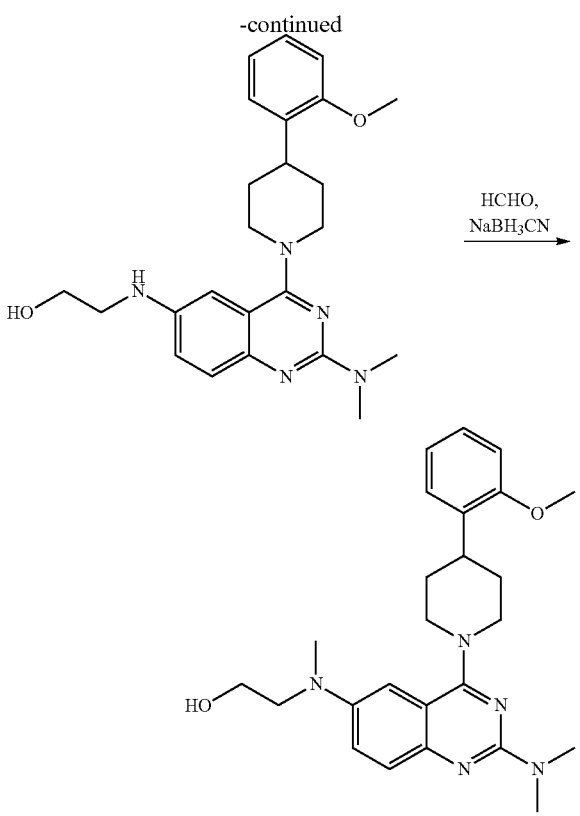

Example 94: Preparation of 2-{2-Dimethylamino-4-[4-(2-methoxy-phenyl)-piperidin-1-yl]-quinazolin-6-ylamino}-ethanol

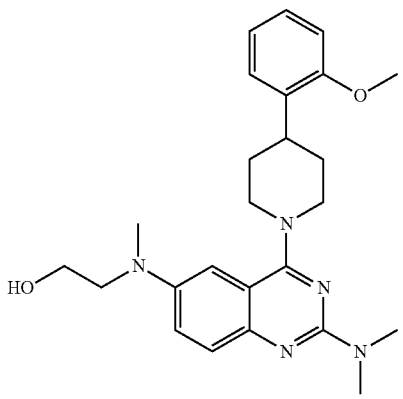 [SMILES: COc1ccccc1C1CCN(c2nc(N(C)C)nc3ccc(N(C)CCO)cc23)CC1]

A mixture of 2-amino-5-nitrobenzoic acid (20 g, 109.8 mmol) and urea (33 g, 549.1 mmol) was heated at 200° C. for 2 hours. The resulting mixture was washed with water, and the resulting solid was filtered and dried to give 6-nitroquinazoline-2,4(1H,3H)-dione (26 g, quantitative) as a yellow solid.

To a solution of 6-nitroquinazoline-2,4(1H,3H)-dione (34 g, 164.14 mmol) in POCl$_3$ (150 mL) was added dimethylphenyl-amine (60 g, 492.42 mmol). The mixture was stirred at 110° C. for 5 hours. The mixture was concentrated in vacuum and the remaining residue was neutralized by aq. NaHCO$_3$. The aqueous phase was extracted with EtOAc (80 mL×3). The organic phase was concentrated to dryness and the residue was purified by silica gel column chromatography (DCM:PE=2:1) to give 2,4-dichloro-6-nitroquinazoline (5 g, yield: 13%) as a yellow solid.

To a solution of 2,4-dichloro-6-nitroquinazoline (3 g, 12.29 mmol) in EtOAc (50 mL) was added 4-(2-methoxyphenyl)piperidine (2.4 g, 12.29 mmol) and DIEA (3.2 g, 24.59 mmol). The mixture was stirred at r.t. overnight. The reactant was diluted with PE and the mixture was stirred for 15 min. The resulting solid was filtered to give 2-chloro-4-(4-(2-methoxyphenyl)piperidin-1-yl)-6-nitroquinazoline (4.5 g, yield: 92%) as a yellow solid. $^1$H NMR (400 MHz, DMSO-d6): δ=8.83 (d, J=2.0 Hz, 1H), 8.50 (d, J=9.2, 2.4 Hz, 1H), 7.83 (d, J=9.6 Hz, 1H), 7.28-7.17 (m, 2H), 6.99 (d, J=7.6 Hz, 1H), 6.92 (d, J=7.2 Hz, 1H), 4.67 (d, J=13.2 Hz, 2H), 3.82 (s, 3H), 3.53 (t, J=12.0 Hz, 2H), 3.40-3.34 (m, 1H), 1.94-1.83 (m, 4H).

To a solution of 2-chloro-4-(4-(2-methoxyphenyl)piperidin-1-yl)-6-nitroquinazoline (500 mg, 1.25 mmol) in i-PrOH (5 mL) was added dimethyl-amine HCl salt (511 mg, 6.27 mmol) and TEA (1 g, 10 mmol). The mixture was stirred at 80° C. for 3 hours. The mixture was concentrated to dryness in vacuum and diluted with water (10 mL). The aqueous phase was extracted with CHCl$_3$ (20 mL×3). The organic phase was concentrated to afford 4-(4-(2-methoxyphenyl)piperidin-1-yl)-N,N-dimethyl-6-nitroquinazolin-2-amine (500 mg, yield: 98%) as a yellow solid.

To a solution of 4-(4-(2-methoxyphenyl)piperidin-1-yl)-N,N-dimethyl-6-nitroquinazolin-2-amine (1 g, 2.45 mmol) in MeOH (20 mL) was added 10% Pd/C (200 mg). The suspension was was stirred at rt under H$_2$ atmosphere overnight. The suspension was filtered and the organic phase was concentrated in vacuum to give 4-(4-(2-methoxyphenyl)piperidin-1-yl)-N,N-dimethylquinazoline-2,6-diamine (900 mg, yield: 97%) as a yellow solid. $^1$H NMR (400 MHz, DMSO-d6): δ=7.76 (d, J=8.8 Hz, 1H), 7.24-7.18 (m, 2H), 7.13 (dd, J=8.8, 2.0 Hz, 1H), 7.05 (d, J=2.0 Hz, 1H), 6.99 (d, J=8.0 Hz, 1H), 6.92 (t, J=7.6 Hz, 1H), 5.55 (brs, 2H), 4.67 (d, J=12.8 Hz, 2H), 3.80 (s, 3H), 3.42-3.32 (m, 3H), 3.23 (s, 6H), 1.94-1.78 (m, 4H).

To a solution of 4-(4-(2-methoxyphenyl)piperidin-1-yl)-N,N-dimethylquinazoline-2,6-diamine (300 mg, 0.79 mmol) in DMF (5 mL) was added 2-bromo-ethanol (119 mg, 0.95 mmol) and K$_2$CO$_3$ (329 mg, 2.38 mmol). And the mixture was stirred at 80° C. overnight. The reactant was diluted with water (10 mL) and the mixture was extracted with EtOAc (15 mL×3). The organic phase was dried over Na$_2$SO$_4$ and concentrated to give 2-((2-(dimethylamino)-4-(4-(2-methoxyphenyl)piperidin-1-yl) quinazolin-6-yl) amino)ethanol (300 mg, crude) as a yellow oil.

To a solution of 2-((2-(dimethylamino)-4-(4-(2-methoxyphenyl)piperidin-1-yl)quinazolin-6-yl)amino)ethanol (150 mg, 0.36 mmol) in MeOH (5 mL) was added paraformaldehyde (108 mg, 3.6 mmol) and NaCNBH$_3$ (113 mg, 1.8 mmol). And the mixture was stirred at r.t. overnight. The resulting mixture was concentrated in vacuum and the residue was purified by Prep-HPLC to give 2-{2-Dimethylamino-4-[4-(2-methoxy-phenyl)-piperidin-1-yl]-quinazolin-6-ylamino}-ethanol (11 mg, yield: 7%) as a yellow solid. $^1$H NMR (300 MHz, DMSO-d$_6$): δ=7.32-7.20 (m, 4H), 7.00-6.93 (m, 2H), 6.77 (s, 1H), 4.59 (t, J=6.8 Hz, 1H), 4.28-4.23 (m, 2H), 3.81 (s, 3H), 3.58-3.32 (m, 5H), 3.13-3.07 (m, 8H), 2.95 (s, 3H), 1.88-1.85 (m, 4H). LC-MS: 436.2 (M+H$^+$).

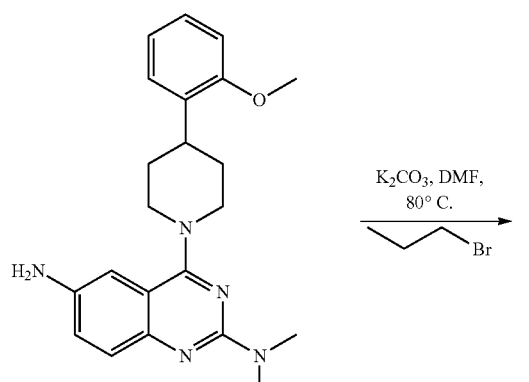
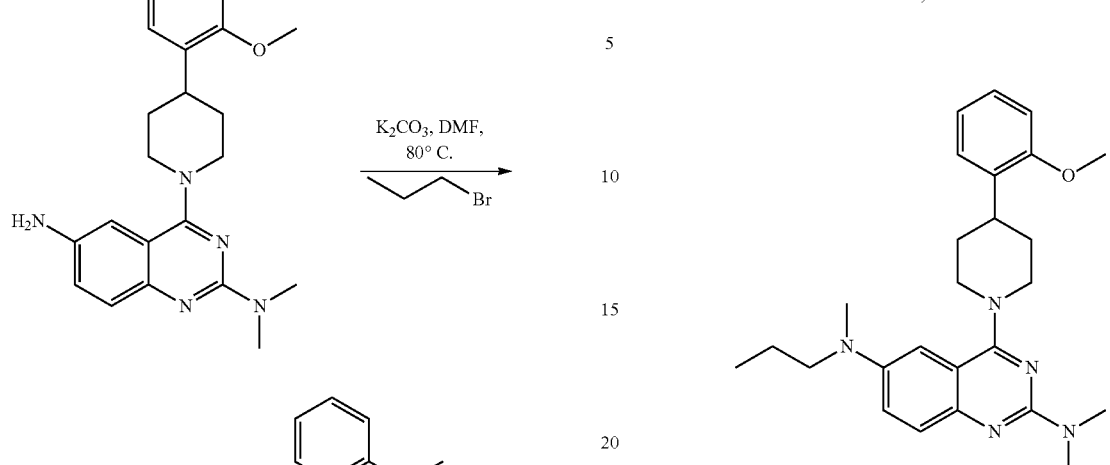
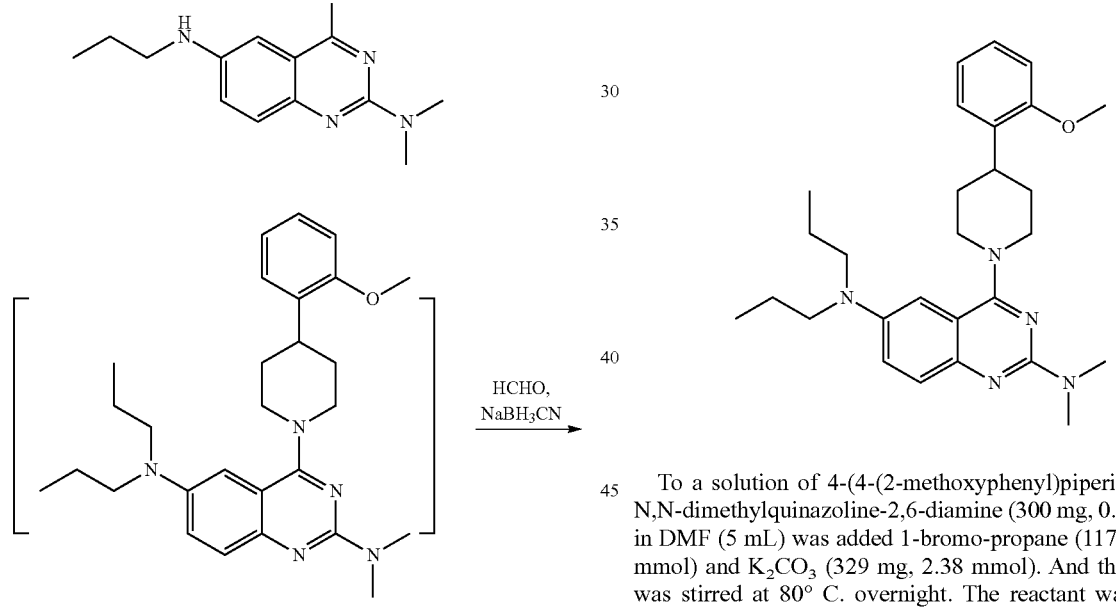

Example 95: Preparation of 4-(4-(2-methoxyphenyl)piperidin-1-yl)-N2,N2,N6-trimethyl-N6-propylquinazoline-2,6-diamine and Example 96: Preparation of 4-(4-(2-methoxyphenyl)piperidin-1-yl)-N2,N2-dimethyl-N6,N6-dipropylquinazoline-2,6-diamine To a solution of 4-(4-(2-methoxyphenyl)piperidin-1-yl)-N,N-dimethylquinazoline-2,6-diamine (300 mg, 0.79 mmol) in DMF (5 mL) was added 1-bromo-propane (117 mg, 0.95 mmol) and K₂CO₃ (329 mg, 2.38 mmol). And the mixture was stirred at 80° C. overnight. The reactant was diluted with water (10 mL) and the mixture was extracted with EtOAc (15 mL×3). The organic phase was dried over Na₂SO₄ and concentrated to dryness. The residue was purified by prep-HPLC to afford byproduct 4-(4-(2-methoxyphenyl)piperidin-1-yl)-N2,N2-dimethyl-N6,N6-dipropylquinazoline-2,6-diamine (20 mg) as a yellow solid and intermediate 4-(4-(2-methoxyphenyl)piperidin-1-yl)-N2,N2-dimethyl-N6-propylquinazoline-2,6-diamine (50 mg, yield: 15%) as a yellow oil.

Byproduct: ¹H NMR (400 MHz, CD₃OD): δ=7.80-7.91 (m, 3H), 7.26-7.21 (m, 2H), 7.00-6.92 (m, 2H), 4.84 (d, J=13.2 Hz, 2H), 3.88 (s, 3H), 3.63-3.39 (m, 7H), 3.39 (s, 6H), 2.12-1.97 (m, 4H), 1.71-1.56 (m, 4H), 0.99 (t, J=6.8 Hz, 6H). LC-MS: 462.3 (M+H⁺).

To a solution of 4-(4-(2-methoxyphenyl)piperidin-1-yl)-N2,N2-dimethyl-N6-propylquinazoline-2,6-diamine (150 mg, 0.36 mmol) in MeOH (5 mL) was added paraformaldehyde (128 mg, 3.6 mmol), NaCNBH₃ (113 mg, 1.8 mmol).

The mixture was stirred at r.t. overnight. The resulting mixture was concentrated to dryness in vacuum and the residue was purified by prep-HPLC to afford 4-(4-(2-methoxyphenyl)piperidin-1-yl)-N2,N2,N6-trimethyl-N6-propylquinazoline-2,6-diamine (15 mg, yield: 10%) as a yellow solid. $^1$H NMR (400 MHz, CD$_3$OD): δ=7.46 (d, J=9.2 Hz, 1H), 7.30-7.17 (m, 3H), 6.96-6.87 (m, 3H), 4.34 (d, J=12.8 Hz, 2H), 3.85 (s, 3H), 3.34-3.24 (m, 3H), 3.21 (s, 6H), 3.13-3.06 (m, 2H), 2.96 (s, 3H), 1.96-1.91 (m, 4H), 1.65-1.60 (m, 2H), 0.95 (t, J=7.2 Hz, 3H). LC-MS: 434.3 (M+H$^+$).

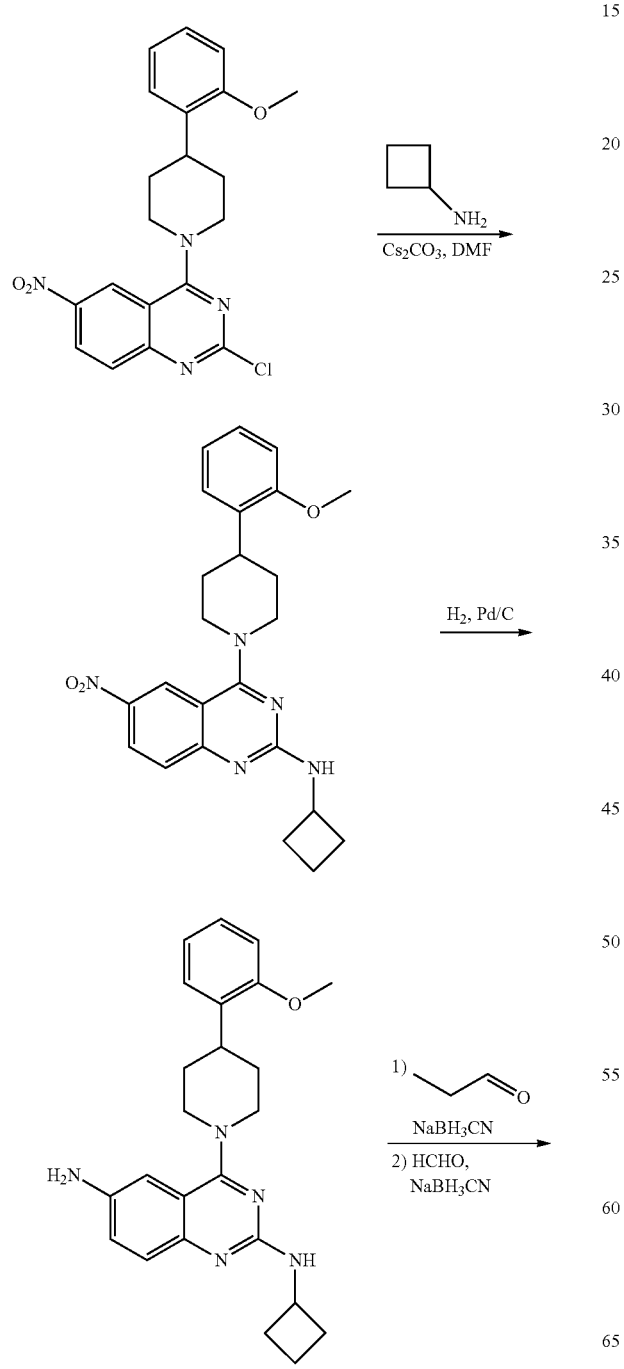

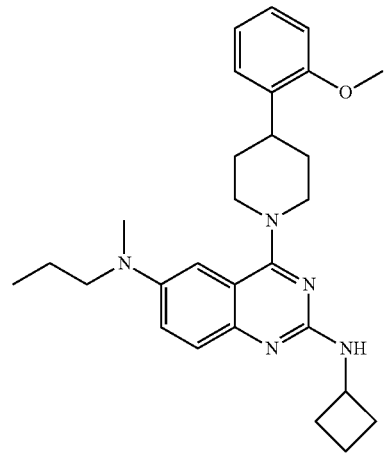 [SMILES: CCCN(C)c1ccc2nc(NC3CCC3)nc(N3CCC(c4ccccc4OC)CC3)c2c1]

Example 97: Preparation of N2-Cyclobutyl-4-[4-(2-methoxy-phenyl)-piperidin-1-yl]-N6-methyl-N6-propyl-quinazoline-2,6-diamine The title compound was prepared as described for 4-(4-(2-methoxyphenyl)piperidin-1-yl)-N2,N2,N6-trimethyl-N6-propylquinazoline-2,6-diamine. $^1$H NMR (300 MHz, DMSO-d$_6$): δ=8.32-8.30 (m, 1H), 7.45-6.89 (m, 5H), 6.82 (s, 1H), 4.72-4.62 (m, 2H), 4.53-4.43 (m, 1H), 3.81 (s, 3H), 3.46-3.26 (m, 5H), 2.94 (s, 3H), 2.37-2.26 (m, 2H), 2.10-1.48 (m, 10H), 1.65-1.60 (m, 2H), 0.92 (t, J=7.2 Hz, 3H). LC-MS: 460.3 (M+H$^+$).

Example 98: Preparation of 2-((2-(cyclobutylamino)-4-(4-(2-methoxyphenyl)piperidin-1-yl)quinazolin-6-yl)(methyl)amino)ethanol

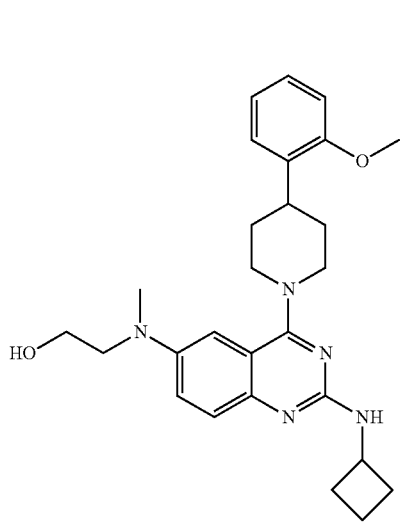 [SMILES: COc1ccccc1C1CCN(c2nc(NC3CCC3)nc3ccc(N(C)CCO)cc23)CC1]

The title compound was prepared as described for 4-(4-(2-methoxyphenyl)piperidin-1-yl)-N2,N2,N6-trimethyl-N6-propylquinazoline-2,6-diamine. $^1$H NMR (400 MHz, DMSO-d6): δ=7.28-7.20 (m, 4H), 7.01-6.93 (m, 2H), 6.78 (s, 1H), 6.63-6.61 (m, 1H), 4.68 (s, 1H), 4.46-4.43 (m, 1H), 4.23-4.18 (m, 2H), 3.83 (s, 3H), 3.59-3.50 (m, 2H), 3.23-3.18 (m, 1H), 3.05-3.00 (m, 2H), 2.96 (s, 3H), 2.54-2.23 (m, 2H), 2.00-1.87 (m, 6H), 1.65-1.62 (m, 2H). LC-MS: 462.3 (M+H$^+$).

Example 99: Preparation of 2-({2-cyclopropyl-4-[6-(2-methoxy-phenyl)-2,6-diaza-spiro[3.3]hept-2-yl]-quinazolin-6-yl}-methyl-amino)-ethanol

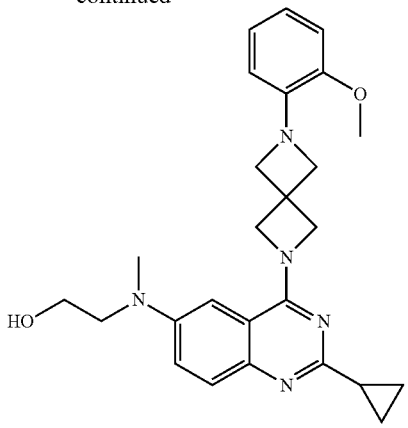

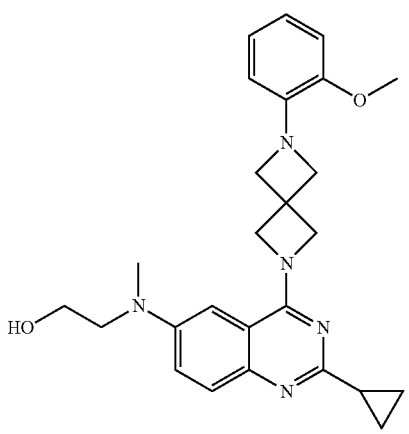 [SMILES: COc1ccccc1N1CC2(C1)CN(c1nc(C3CC3)nc3ccc(N(C)CCO)cc13)C2]

To a solution of 2,6-diaza-spiro[3.3]heptane-2-carboxylic acid tert-butyl ester (1 g, 5.1 mmol) in toluene (20 mL) was added 2-methoxy-phenylamine (807 mg, 6.56 mmol), Pd$_2$(dba)$_3$ (200 mg), x-phos (300 mg) and Cs$_2$CO$_3$ (3.29 g, 10.2 mmol). It was then refluxed overnight. Resultant was purified by flash column (EA in PE: 0 to 50%) to afford 6-(2-methoxy-phenyl)-2,6-diaza-spiro[3.3]heptane-2-carboxylic acid tert-butyl ester (1.2 g, yield: 78%) as a white solid.

To as solution of 6-(2-methoxy-phenyl)-2,6-diaza-spiro[3.3]heptane-2-carboxylic acid tert-butyl ester (200 mg, 0.66 mmol) in DCM (5 mL) was added TFA (5 mL), it was then stirred overnight. Resultant was concentrated in vacuum to afford crude 2-(2-methoxy-phenyl)-2,6-diaza-spiro[3.3]heptanes without further purification.

The last step is similar to example 2-[(2-cyclopropyl-4-{2-[(2-methoxy-phenyl)-methyl-amino]-cyclopentylamino}-quinazolin-6-yl)-methyl-amino]-ethanol. $^1$HNMR (400 MHz, CD$_3$OD): δ=7.55 (d, J=9.3 Hz, 1H), 7.38 (d, J=8.8, 2.4 Hz, 1H), 6.94 (s, 1H), 6.85 (d, J=5.4 Hz, 3H), 6.55-6.53 (m, 1H), 4.61 (brs, 4H), 4.04 (brs, 4H), 3.81-3.75 (m, 5H), 3.54-3.51 (m, 2H), 3.06 (s, 3H), 2.04 (m, 1H), 1.13 (s, 2H), 0.94-0.92 (m, 2H). MS: m/z 446.2 (M+H$^+$).

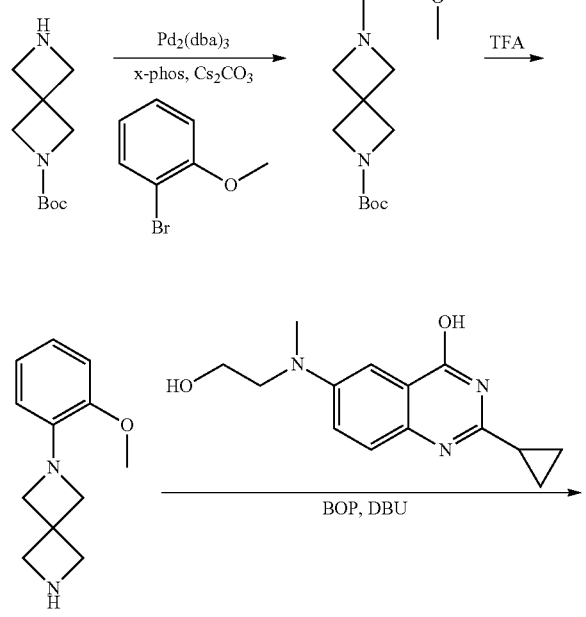

Example 100: Preparation of {2-cyclopropyl-4-[6-(2-methoxy-phenyl)-2,6-diaza-spiro[3.3]hept-2-yl]-quinazolin-6-yl}-methyl-propyl-amine

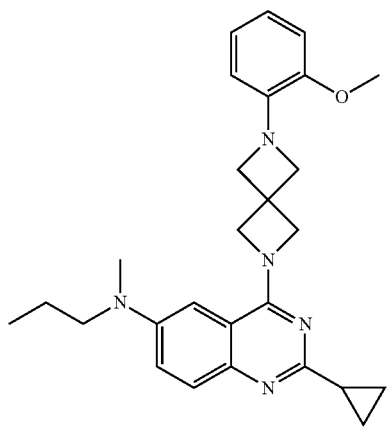 [SMILES: CCCN(C)c1ccc2nc(C3CC3)nc(N3CC4(CN(c5ccccc5OC)C4)C3)c2c1]

The title compound was prepared as described for 2-({2-cyclopropyl-4-[6-(2-methoxy-phenyl)-2,6-diaza-spiro[3.3]hept-2-yl]-quinazolin-6-yl}-methyl-amino)-ethanol.
$^1$HNMR (400 MHz, CDCl$_3$): δ=7.64 (d, J=9.2 Hz, 1H), 7.27-7.24 (m, 1H), 6.91-6.78 (m, 4H), 6.49 (d, J=7.6 Hz, 1H), 4.60 (s, 4H), 4.11 (s, 4H), 3.81 (s, 3H), 3.32 (t, J=5.4 Hz, 2H), 2.98 (s, 3H), 2.13-2.09 (m, 1H), 1.65-1.60 (m, 2H), 1.12-1.10 (m, 2H), 0.96-0.89 (m, 5H). MS: m/z 444.2 (M+H$^+$).

Example 101: Preparation of {2-cyclopropyl-4-[6-(2-methoxy-phenyl)-2,6-diaza-spiro[3.3]hept-2-yl]-quinazolin-6-yl}-methyl-(2-morpholin-4-yl-ethyl)-amine

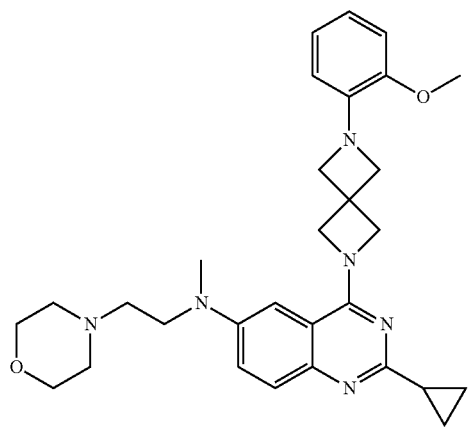 [SMILES: COc1ccccc1N1CC2(C1)CN(c1nc(C3CC3)nc3ccc(N(C)CCN4CCOCC4)cc13)C2]

The title compound was prepared as described for 2-({2-cyclopropyl-4-[6-(2-methoxy-phenyl)-2,6-diaza-spiro[3.3]hept-2-yl]-quinazolin-6-yl}-methyl-amino)-ethanol.
$^1$HNMR (400 MHz, CD$_3$OD): δ=7.57 (d, J=9.2 Hz, 1H), 7.37 (dd, J=9.2, 2.4 Hz, 1H), 6.88-6.81 (m, 4H), 6.51 (dd, J=7.6, 2.4 Hz, 1H), 4.60 (s, 4H), 4.02 (s, 4H), 3.79 (s, 3H), 3.68 (t, J=4.8 Hz, 4H), 3.55 (t, J=7.2 Hz, 2H), 3.02 (s, 3H), 2.56-2.50 (m, 6H), 2.05-2.03 (m, 1H), 1.15-1.12 (m, 2H), 0.96-0.93 (m, 2H). MS: m/z 515.3 (M+H$^+$)

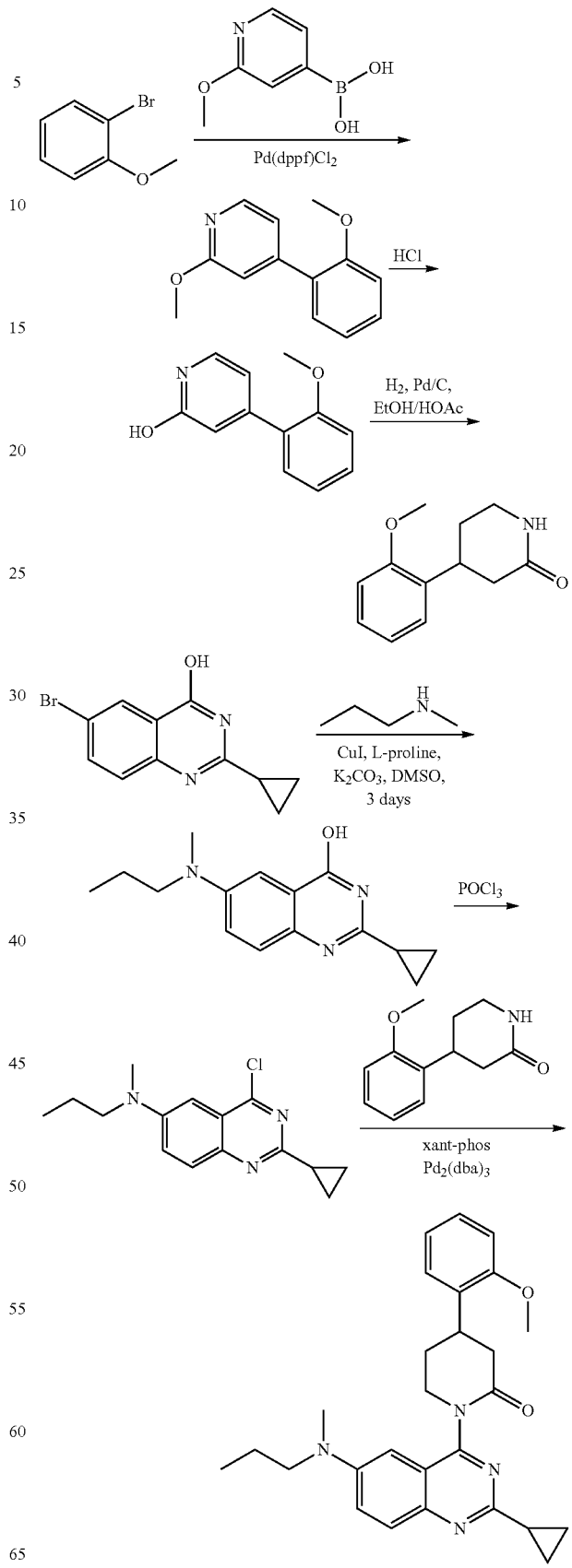

Example 102: Preparation of 1-[2-cyclopropyl-6-(methyl-propyl-amino)-quinazolin-4-yl]-4-(2-methoxy-phenyl)-piperidin-2-one

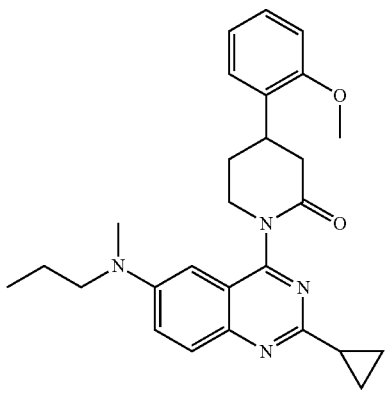 [SMILES: CCCN(C)c1ccc2nc(C3CC3)nc(N3CCC(c4ccccc4OC)CC3=O)c2c1]

To a mixture of 1-bromo-2-methoxy-benzene (5.1 g, 27.2 mmol), 2-bethoxypyridne-4-boronic acid (5.0 g, 32.7 mmol), H₂O (30 mL) and K₂CO₃ (7.5 g, 54 mmol) in dioxane (90 mL) was added Pd(dppf)Cl₂ (222 mg, 0.27 mmol). The mixture was stirred at 100° C. under N₂ for overnight, cooled to room temperature and evaporated under reduced pressure to dryness. The residue was diluted with EA (100 mL×2) and washed with water, dried over anhydrous Na₂SO₄, filtered. The filtrate was evaporated in vacuum to residue, which was purified by silica gel chromatography (from PE to PE/EA=10/1) to give (5.3 g, yield: 91%) of 2-methoxy-4-(2-methoxy-phenyl)-pyridine as yellow oil. MS: m/z 216.2 (M+H⁺).

To a stirred solution of 2-methoxy-4-(2-methoxy-phenyl)-pyridine (2.2 g, 10.2 mmol) in dioxane (40 mL) was added HCl (14 mL). The mixture was then heated to reflux overnight. The reaction was cooled to room temperature and was concentrated. The residue was washed with water and DCM. and the solid was evaporated in vacuum to dryness to afford (1.4 g yield: 67%) of 4-(2-methoxy-phenyl)-pyridin-2-ol as a white solid. MS: m/z 202.2 (M+H⁺).

A suspension of 4-(2-methoxy-phenyl)-pyridin-2-ol (1.0 g, 5.0 mmol), CH₃COOH (5 ml) and Pd/C (600 mg) in ethanol (20 mL) was degassed with H₂ for 3 times, and the resulting mixture was stirred under H₂ (4 MPa) for 16 hours. TLC showed the reaction was completed. Then the reaction was filtered, he residue was washed with ethanol (10 ml). and the solid was evaporated in vacuum to dryness to afford (800 mg, yield: 52%) of 4-(2-methoxy-phenyl)-piperidin-2-one as a white solid.

To a solution of 6-bromo-2-cyclopropyl-quinazolin-4-ol (2 g, 7.6 mmol) in DMSO (20 mL) were added methyl-propyl-amine (693 mg, 11.4 mmol), CuI (500 mg), proline (500 mg) and K₂CO₃ (6.4 g, 16.7 mmol). The mixture was stirred at 90° C. overnight under the protection of N₂. The resultant was purified by pre-HPLC to give (1.4 g, yield: 75%) of 2-cyclopropyl-6-(methyl-propyl-amino)-quinazolin-4-ol.

To a stirred solution of 2-cyclopropyl-6-(methyl-propyl-amino)-quinazolin-4-ol (100 mg, 0.39 mmol) in POCl₃ (10 mL). The mixture was then heated to reflux 2 h. The reaction was cooled to room temperature and was concentrated. and added into ice water (50 mL) dropwise. The aqueous mixture was neutralized with sat.NaHCO₃ to pH=8 and extracted with EA (20 mL×2). The combined organic layers were washed with brine (10 mL), dried over anhydrous Na₂SO₄ and filtered. The filtrate was evaporated in vacuum to residue, which was purified by silica gel chromatography (from PE to PE/EA=5/1) to give (100 mg, yield: 93%) of (4-Chloro-2-cyclopropyl-quinazolin-6-yl)-methyl-propyl-amine as yellow solid. MS: m/z 276.1 (M+H⁺).

To a suspension of (4-chloro-2-cyclopropyl-quinazolin-6-yl)-methyl-propyl-amine (100 mg, 0.36 mmol) in anhydrous THF (20 mL) was added 4-(2-methoxy-phenyl)-piperidin-2-one (88 mg, 0.43 mmol), xant-phos (6 mg, 0.01 mmol), Cs₂CO₃ (236 mg, 0.72 mmol) and Pd₂(dba)₃ (5.0 mg, 0.024 mmol). The mixture was refluxed under N₂ for o/n. The mixture was concentrated under reduced pressure, the residue was partitioned between water (60 mL) and EA (30 mL), extracted with EA (15 mL×2), dried over Na₂SO₄, concentrated, purified Pre-TLC (PE/EA=5/1) to give 100 mg of 1-[2-cyclopropyl-6-(methyl-propyl-amino)-quinazolin-4-yl]-4-(2-methoxy-phenyl)-piperidin-2-one as a pale yellow-solid. ¹H NMR (400 MHz, CD₃OD): δ=7.67 (d, J=9.6 Hz, 1H), 7.52 (dd, J=9.2, 2.4 Hz, 1H), 7.19-7.14 (m, 2H), 6.92-6.85 (m, 2H), 6.50 (d, J=2.4 Hz, 1H), 3.66-3.62 (m, 2H), 3.34 (t, J=7.6 Hz, 2H), 2.96 (s, 3H), 2.80-2.61 (m, 2H), 2.25-2.13 (m, 3H), 1.59-1.53 (m, 2H), 1.05-0.96 (m, 4H), 0.94-0.92 (m, 3H). MS: m/z 445.2 (M+H⁺).

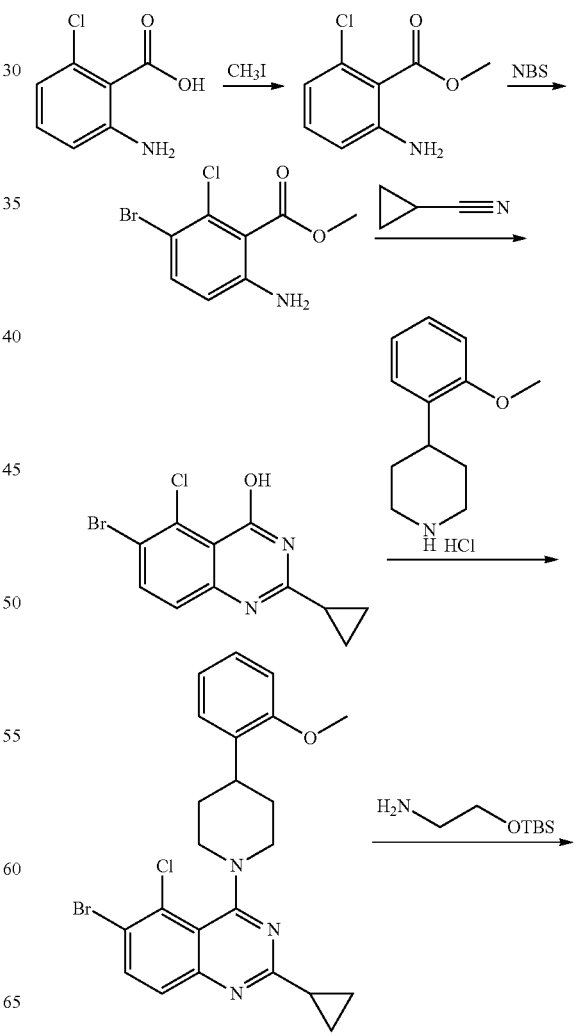

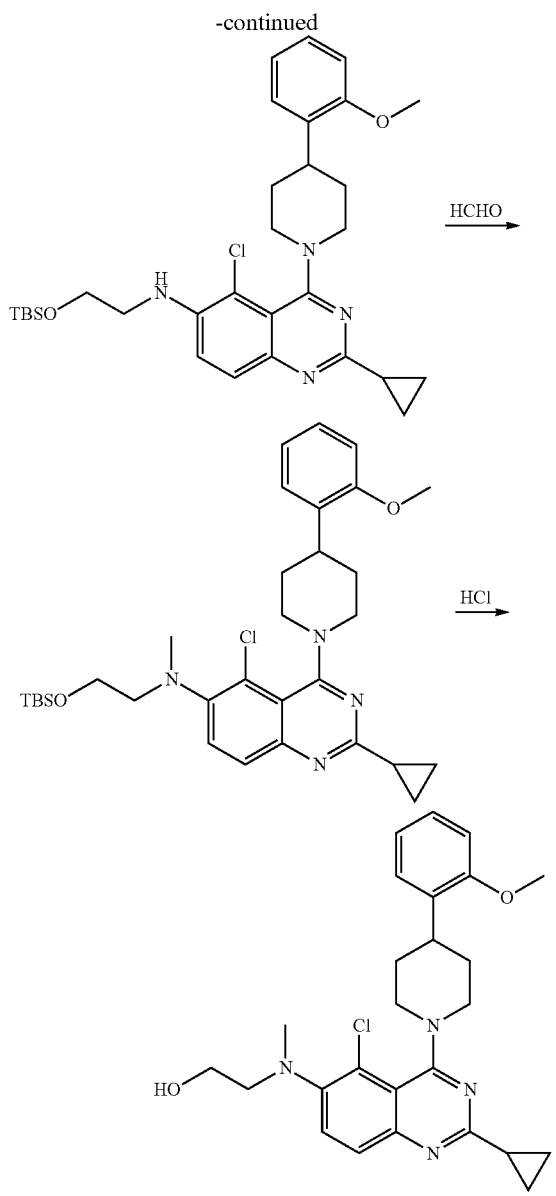

Example 103: Preparation of 2-({5-chloro-2-cyclopropyl-4-[4-(2-methoxy-phenyl)-piperidin-1-yl]-quinazolin-6-yl}-methyl-amino)-ethanol

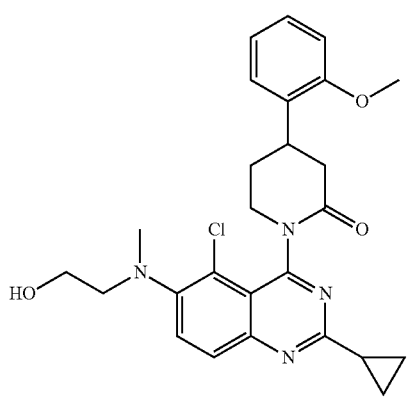 [SMILES: COc1ccccc1C1CCN(c2nc(C3CC3)nc3ccc(N(C)CCO)c(Cl)c23)C(=O)C1]

To a mixture of 2-amino-6-chloro-benzoic acid (2.0 g, 11.6 mmol) and K$_2$CO$_3$ (2.4 g, 17.4 mmol) in DMF (30 mL) was added dropwise Iodomethane (0.94 mL, 15.1 mmol) and the reaction mixture was stirred at rt for 18 h. The reaction mixture was quenched with water (200 mL), the aqueous layer was extracted with Et$_2$O (3×100 mL), dried over Na$_2$SO$_4$. The mixture was filtered and the solvent removed by evaporation under reduced pressure to give an orange residue, which was purified by column (PE/EA=50/1-40/1-20/1) to give 2-amino-6-chloro-benzoic acid methyl ester (1.7 g, yield: 82%) as an orange oil. $^1$H NMR (400 MHz, CDCl$_3$): δ=7.07 (t, J=8.0 Hz, 1H), 6.74 (d, J=7.6 Hz, 1H), 6.57 (d, J=8.8 Hz, 1H), 4.87 (brs, 2H), 3.92 (s, 3H).

To a solution of 2-amino-6-chloro-benzoic acid methyl ester (1.7 g, 9.1 mmol) in DMF (10 mL) at −10° C., NBS (1.6 g, 9.1 mmol) in DMF (6 mL) was added dropwise over 10 min. After the addition was complete, the reaction mixture was stirred at −10° C. for 1 h. The reaction was quenched with aqueous sodium bisulfate (50 mL), the aqueous layer was extracted with EA (2×100 mL), the organic layers were washed with brine (100 mL×2), dried over Na$_2$SO$_4$, concentrated and purified by column (PE/EA=50/1-40/1) to afford 6-amino-3-bromo-2-chloro-benzoic acid methyl ester (2 g, yield: 82%) as an orange solid. 1H NMR (400 MHz, CDCl$_3$): δ=7.39 (d, J=8.8 Hz, 1H), 6.50 (d, J=8.8 Hz, 1H), 4.68 (brs, 2H), 3.94 (s, 3H).

The mixture of 6-amino-3-bromo-2-chloro-benzoic acid methyl ester (1.0 g, 3.8 mmol) and cyclopropanecarbonitrile (1.3 g, 18.8 mmol) in HCl/dioxane (10 mL) was stirred at reflux overnight. The solid was filtered, dried to give 6-bromo-5-chloro-2-cyclopropyl-quinazolin-4-ol (1.0 g, yield: 91%) as white solid. $^1$H NMR (400 HMz, DMSO-d$_6$): δ=8.04 (d, J=9.2 Hz, 1H), 7.46 (d, J=9.2 Hz, 1H), 2.05-2.03 (m, 1H), 1.19-1.11 (m, 4H).

A mixture of 6-bromo-5-chloro-2-cyclopropyl-quinazolin-4-ol (200 mg, 0.67 mmol), 4-(2-methoxy-phenyl)-piperidine hydrochloride (167 mg, 0.74 mmol), DBU (509 mg, 3.35 mmol), and BOP (444 mg, 1.0 mmol) in ACN (20 mL) was stirred at 25° C. for 16 h. The solid appeared, then filtered, the solid was washed with ACN, dried to give (153 mg, yield: 48%) 6-bromo-5-chloro-2-cyclopropyl-4-[4-(2-methoxy-phenyl)-piperidin-1-yl]-quinazoline as a white solid.

To a solution of 6-bromo-5-chloro-2-cyclopropyl-4-[4-(2-methoxy-phenyl)-piperidin-1-yl]-quinazoline (153 mg, 0.32 mmol) in anhydrous toluene (10 mL) was added BINAP (60 mg, 0.096 mmol), Pd(OAc)$_2$ (11 mg, 0.048 mmol) and Cs$_2$CO$_3$ (209 mg, 0.64 mmol), purged with N$_2$ for 15 min, 2-(tert-butyl-dimethyl-silanyloxy)-ethylamine (114 mg, 0.64 mmol) was added. The mixture was refluxed under N$_2$ for 16 h. The mixture was cooled to rt, filtered, the filtraction was concentrated to give [2-(tert-butyl-dimethyl-silanyloxy)-ethyl]-{5-chloro-2-cyclopropyl-4-[4-(2-methoxy-phenyl)-piperidin-1-yl]-quinazolin-6-yl}-amine as a crude product, which was used to next step without further purification.

To a solution of [2-(tert-butyl-dimethyl-silanyloxy)-ethyl]-{5-chloro-2-cyclopropyl-4-[4-(2-methoxy-phenyl)-piperidin-1-yl]-quinazolin-6-yl}-amine (crude, 0.32 mmol) in MeOH (20 mL) was added HCHO (0.5 mL, 40% in $H_2O$, 6.4 mmol), $NaBH(ACO)_3$ (678 mg, 3.2 mmol) and $NaBH_3CN$ (202 mg, 3.2 mmol). Then the reaction mixture was stirred at rt overnight. $NaHCO_3$ solution was added, then extracted with EA (50 mL×3), the organic layer was washed with brine, dried over $Na_2SO_4$, concentrated, the residue was used to next step without further purification To a solution of [2-(tert-butyl-dimethyl-silanyloxy)-ethyl]-{5-chloro-2-cyclopropyl-4-[4-(2-methoxy-phenyl)-piperidin-1-yl]-quinazolin-6-yl}-methyl-amine (crude, 0.32 mmol) in MeOH (30 mL) was added con. HCl (0.3 mL), the reaction mixture was stirred at rt overnight. $NH_3H_2O$ was added to adjust pH to 7-8, the mixture was concentrated, purified by prep-TLC (DCM/MeOH=20/1), further purified by prep-HPLC to give (23.3 mg, yield: 61%) 2-({5-chloro-2-cyclopropyl-4-[4-(2-methoxy-phenyl)-piperidin-1-yl]-quinazolin-6-yl}-methyl-amino)-ethanol as a yellow solid. $^1$H NMR (400 MHz, $CDCl_3$): δ=7.71-7.56 (m, 2H), 7.31-7.15 (m, 2H), 7.02-6.99 (m, 1H), 6.90-6.84 (m, 1H), 4.30 (d, J=10.4 Hz, 1H), 4.08 (d, J=10.0 Hz, 1H), 3.84 (d, J=8.0 Hz, 3H), 3.68-3.67 (m, 2H), 3.48-3.41 (m, 1H), 3.32-3.11 (m, 3H), 2.88-2.72 (m, 5H), 2.18-1.96 (m, 3H), 1.77-1.59 (m, 1H), 1.18-1.15 (m, 2H), 1.03-0.99 (m, 2H). MS: m/z 467 (M+H$^+$)

Example 104: Preparation of {7-chloro-2-cyclopropyl-4-[4-(2-methoxy-phenyl)-piperidin-1-yl]-quinazolin-6-yl}-methyl-propyl-amine

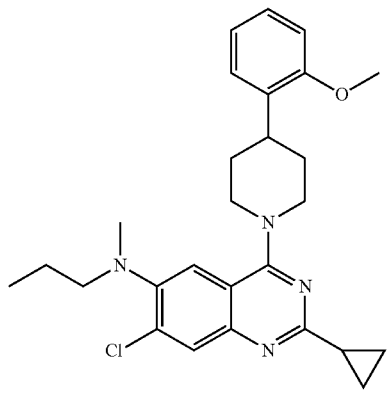

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, $CDCl_3$): δ=7.75 (s, 1H), 7.19-7.15 (m, 3H), 6.90-6.87 (m, 1H), 6.83 (d, J=8.4 Hz, 1H), 4.27 (d, J=13.2 Hz, 2H), 3.79 (s, 3H), 3.25-3.11 (m, 3H), 2.96-2.92 (m, 2H), 2.75 (s, 3H), 2.11-2.05 (m, 1H), 1.89-1.83 (m, 4H), 1.56-1.55 (m, 2H), 1.09-1.08 (m, 2H), 0.92-0.89 (m, 2H), 0.85 (t, J=7.6 Hz, 3H). MS: m/z 465.2 (M+H$^+$)

Example 105: Preparation of {2-cyclopropyl-7-fluoro-4-[4-(2-methoxy-phenyl)-piperidin-1-yl]-quinazolin-6-yl}-methyl-propyl-amine

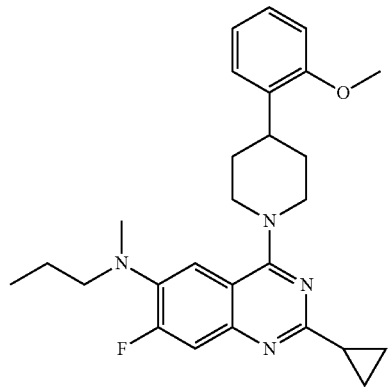 [SMILES: CCCN(C)c1cc2c(N3CCC(c4ccccc4OC)CC3)nc(C3CC3)nc2cc1F]

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, $CDCl_3$): δ=7.39 (d, J=13.2 Hz, 1H), 7.24-7.21 (m, 2H), 7.13 (d, J=9.6 Hz, 1H), 6.97 (t, J=7.4 Hz, 1H), 6.90 (d, J=8.4 Hz, 1H), 4.32 (d, J=12.8 Hz, 2H), 3.86 (s, 3H), 3.30-3.25 (m, 1H), 3.18-3.12 (m, 4H), 2.89 (s, 3H), 2.18-2.15 (m, 1H), 1.98-1.87 (m, 4H), 1.64-1.59 (m, 3H), 1.16-1.14 (m, 2H), 0.99-0.97 (m, 2H), 0.93 (t, J=7.2 Hz, 3H). MS: m/z 449.2 (M+H$^+$)

Example 106: Preparation of {4-[4-(2-azetidin-1-yl-phenyl)-piperidin-1-yl]-2-cyclopropyl-7-fluoro-quinazolin-6-yl}-methyl-propyl-amine

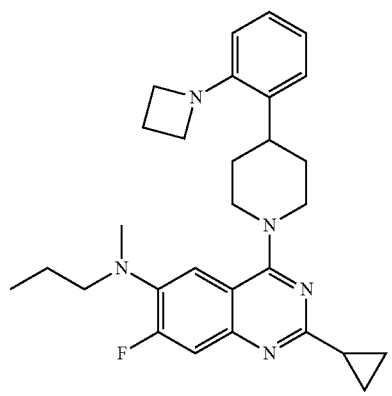 [SMILES: CCCN(C)c1cc2c(N3CCC(c4ccccc4N4CCC4)CC3)nc(C3CC3)nc2cc1F]

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, $CDCl_3$): δ=7.39 (d, J=14.0 Hz, 1H), 7.22-7.11 (m, 3H), 6.90 (t, J=7.4 Hz, 1H), 6.61 (d, J=7.6 Hz, 1H), 4.31 (d, J=12.8 Hz, 2H), 3.94 (t, J=7.2 Hz, 4H), 3.17-2.98 (m, 5H), 2.89 (s, 3H), 2.33-2.30 (m, 2H), 2.18-2.15 (m, 1H), 2.03-1.89 (m, 4H), 1.64-1.59 (m, 3H), 1.16-1.14 (m, 2H), 0.99-0.97 (m, 2H), 0.93 (t, J=7.2 Hz, 3H). MS: m/z 474.3 (M+H$^+$)

Example 107: Preparation of 2-({7-chloro-2-cyclopropyl-4-[4-(2-methoxy-phenyl)-piperidin-1-yl]-quinazolin-6-yl}-methyl-amino)-ethanol

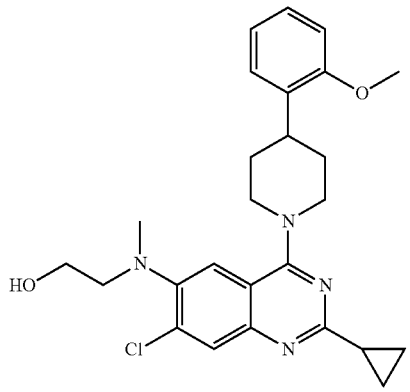 [SMILES: COc1ccccc1C1CCN(c2nc(C3CC3)nc3cc(Cl)c(N(C)CCO)cc23)CC1]

The title compound was prepared as described in example 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, CDCl$_3$): δ=8.32 (brs, 1H), 7.46 (s, 1H), 7.25-7.17 (m, 2H), 6.99-6.97 (m, 1H), 6.91 (d, J=8.0 Hz, 1H), 4.70 (brs, 2H), 3.86 (s, 3H), 3.83-3.80 (m, 2H), 3.41-3.36 (m, 3H), 3.29-3.27 (m, 2H), 2.88 (s, 3H), 2.75 (brs, 1H), 2.10-2.07 (m, 2H), 1.91-1.83 (m, 2H), 1.25-1.20 (m, 5H). MS: m/z 467.2 (M+H$^+$)

Example 108: Preparation of 2-({2-cyclopropyl-4-[4-(4-fluoro-2-methoxy-phenyl)-piperidin-1-yl]-quinazolin-6-yl}-methyl-amino)-ethanol

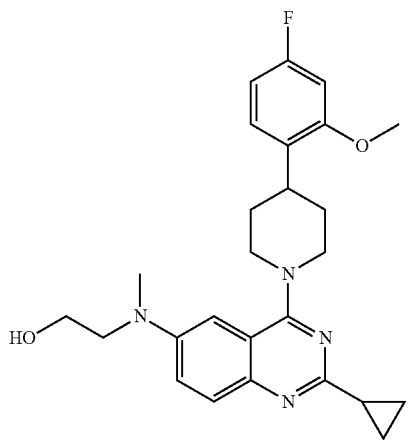 [SMILES: COc1cc(F)ccc1C1CCN(c2nc(C3CC3)nc3ccc(N(C)CCO)cc23)CC1]

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, CDCl$_3$): δ=7.70 (d, J=8.8 Hz, 1H), 7.36-7.34 (m, 1H), 7.15 (d, J=7.6 Hz, 1H), 6.95 (s, 1H), 6.67-6.60 (m, 2H), 4.33 (d, J=13.2 Hz, 2H), 3.88-3.84 (m, 5H), 3.56-3.53 (m, 2H), 3.21-3.09 (m, 3H), 3.04 (s, 3H), 2.17 (brs, 1H), 21.94-1.83 (m, 4H), 1.17-1.14 (m, 2H), 0.97-0.94 (m, 2H). MS: m/z 451.2 (M+H$^+$)

Example 109: Preparation of 2-({2-cyclopropyl-4-[4-(5-fluoro-2-methoxy-phenyl)-piperidin-1-yl]-quinazolin-6-yl}-methyl-amino)-ethanol

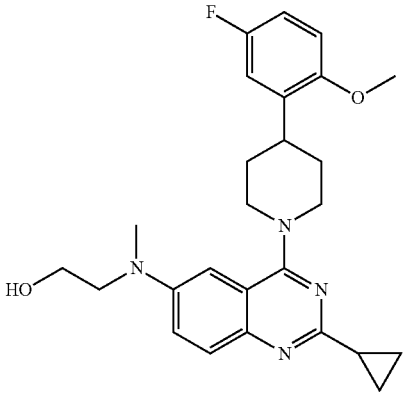 [SMILES: COc1ccc(F)cc1C1CCN(c2nc(C3CC3)nc3ccc(N(C)CCO)cc23)CC1]

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, CDCl$_3$): δ=7.76 (brs, 1H), 7.38-7.35 (m, 1H), 6.96-6.81 (m, 4H), 4.35 (d, J=8.4 Hz, 2H), 3.87 (t, J=5.6 Hz, 2H), 3.83 (s, 3H), 3.55 (t, J=5.2 Hz, 2H), 3.28-3.13 (m, 3H), 3.05 (s, 3H), 2.22-2.21 (m, 1H), 1.98-1.82 (m, 5H), 1.16-0.97 (m, 4H). MS: m/z 451.3 (M+H$^+$)

Example 110: Preparation of 2-({2-cyclopropyl-7-fluoro-4-[4-(4-fluoro-2-methoxy-phenyl)-piperidin-1-yl]-quinazolin-6-yl}-methyl-amino)-ethanol

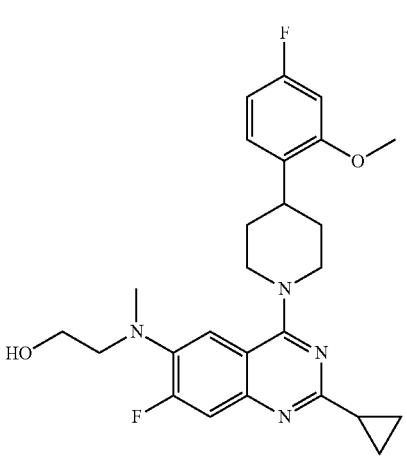

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, CDCl$_3$): δ=7.98 (d, J=12.8 Hz, 1H), 7.25-7.23 (m, 1H), 7.11-7.07 (m, 1H), 6.67-6.61 (m, 2H), 4.79-4.75 (m, 2H), 3.88-3.84 (m, 5H), 3.43-3.32 (m, 5H), 3.00 (s, 3H), 2.72-2.70 (m, 1H), 2.08-2.04 (m, 2H), 1.83-1.80 (m, 2H), 1.38-1.18 (m, 5H). MS: m/z 469.3 (M+H$^+$)

Example 111: Preparation of 2-({2-cyclopropyl-7-fluoro-4-[4-(5-fluoro-2-methoxy-phenyl)-piperidin-1-yl]-quinazolin-6-yl}-methyl-amino)-ethanol

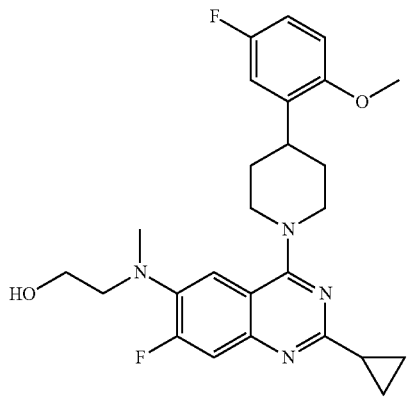 [SMILES: COc1ccc(F)cc1C1CCN(c2nc(C3CC3)nc3cc(F)c(N(C)CCO)cc23)CC1]

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (300 HMz, CDCl$_3$): δ=7.46 (d, J=12.6 Hz, 1H), 7.30 (s, 1H), 6.93-6.83 (m, 3H), 4.32 (d, J=11.1 Hz, 2H), 3.87-3.85 (m, 5H), 3.34-3.13 (m, 5H), 2.95 (s, 3H), 2.21-2.19 (m, 1H), 1.89-1.77 (m, 4H), 1.19-1.16 (m, 2H), 1.03-1.00 (m, 2H). MS: m/z 469.3 (M+H$^+$)

Example 112: Preparation of 2-({7-chloro-2-cyclopropyl-4-[4-(4-fluoro-2-methoxy-phenyl)-piperidin-1-yl]-quinazolin-6-yl}-methyl-amino)-ethanol

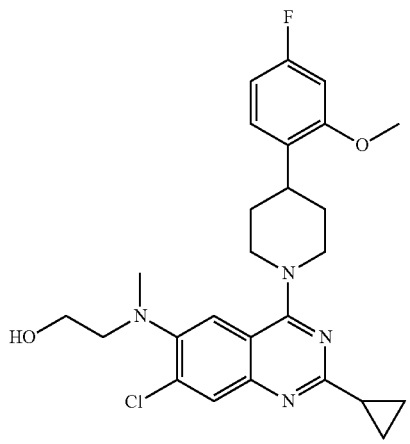

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, CDCl$_3$): δ=7.85 (s, 1H), 7.46 (s, 1H), 7.15-7.11 (t, J=7.8 Hz, 1H), 6.67-6.61 (m, 2H), 4.34 (d, J=12.8 Hz, 2H), 3.84 (s, 3H), 3.79-3.76 (m, 2H), 3.25-3.16 (m, 5H), 2.83 (s, 3H), 2.51-2.49 (m, 1H), 2.17 (brs, 1H), 1.96-1.82 (m, 4H), 1.18-1.16 (m, 2H), 1.02-0.99 (m, 2H). MS: m/z 485.2 (M+H$^+$)

Example 113: Preparation of 2-({7-chloro-2-cyclopropyl-4-[4-(5-fluoro-2-methoxy-phenyl)-piperidin-1-yl]-quinazolin-6-yl}-methyl-amino)-ethanol

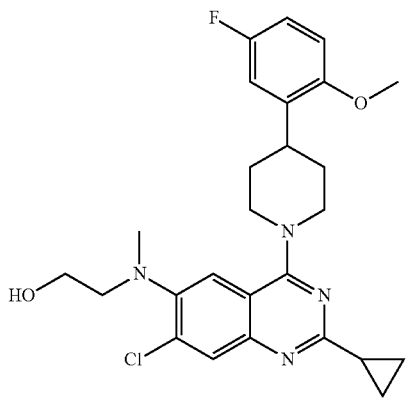 [SMILES: COc1ccc(F)cc1C1CCN(c2nc(C3CC3)nc3cc(Cl)c(N(C)CCO)cc23)CC1]

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, CDCl$_3$): δ=7.77 (s, 1H), 7.39 (s, 1H), 6.88-6.82 (m, 2H), 6.75-6.73 (m, 1H), 4.25 (d, J=13.2 Hz, 2H), 3.76 (s, 3H), 3.73-3.70 (m, 2H), 3.19-3.08 (m, 5H), 2.77 (s, 3H), 2.60 (brs, 1H), 2.12-2.06 (m, 1H), 1.91-1.88 (m, 2H), 1.77-1.73 (m, 2H), 1.10-1.08 (m, 2H), 0.94-0.91 (m, 2H). MS: m/z 485.2 (M+H$^+$)

Example 114: Preparation of 2-({2-cyclopropyl-4-[4-(4-fluoro-2-methoxy-phenyl)-piperidin-1-yl]-7-methyl-quinazolin-6-yl}-methyl-amino)-ethanol

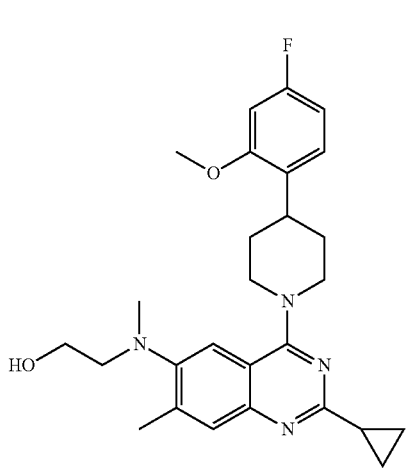 [SMILES: COc1cc(F)ccc1C1CCN(c2nc(C3CC3)nc3cc(C)c(N(C)CCO)cc23)CC1]

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, CDCl$_3$): δ=7.63 (s, 1H), 7.42 (s, 1H), 7.16-7.13 (m, 1H), 6.67-6.60 (m, 2H), 4.35 (d, J=13.2 Hz, 2H), 3.84 (s, 3H), 3.77-3.74 (m, 2H), 3.21-3.15 (m, 5H), 2.73 (s, 3H), 2.47 (s, 3H), 2.18-2.15 (m, 1H), 1.95-1.83 (m, 4H), 1.17-1.15 (m, 2H), 0.99-0.97 (m, 2H). MS: m/z 429.3 (M+H$^+$)

Example 115: Preparation of 2-({2-cyclopropyl-4-[4-(5-fluoro-2-methoxy-phenyl)-piperidin-1-yl]-7-methyl-quinazolin-6-yl}-methyl-amino)-ethanol

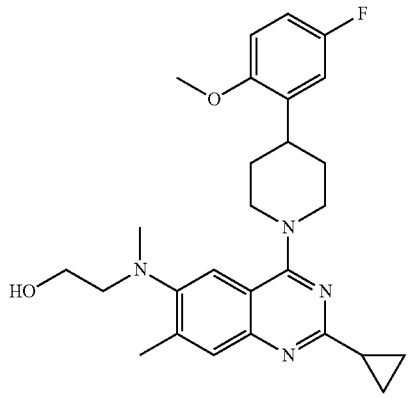 [SMILES: COc1ccc(F)cc1C1CCN(c2nc(C3CC3)nc3cc(C)c(N(C)CCO)cc23)CC1]

The title compound was prepared as described in example 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, CDCl$_3$): δ=7.62 (s, 1H), 7.42 (s, 1H), 6.96-6.93 (m, 1H), 6.89-6.86 (m, 1H), 6.82-6.79 (m, 1H), 4.33 (d, J=13.2 Hz, 2H), 3.83 (s, 3H), 3.78-3.75 (m, 2H), 3.25-3.13 (m, 5H), 2.73 (s, 3H), 2.47 (s, 3H), 2.19-2.16 (m, 1H), 1.97-1.81 (m, 4H), 1.17-1.14 (m, 2H), 0.99-0.96 (m, 2H). MS: m/z 465.3 (M+H$^+$)

Example 116: Preparation of 2-({2-cyclopropyl-4-[4-(2-dimethylamino-phenyl)-piperidin-1-yl]-7-methyl-quinazolin-6-yl}-methyl-amino)-ethanol

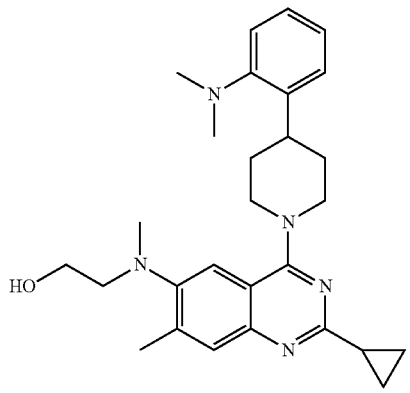 [SMILES: Cc1cc2nc(C3CC3)nc(N3CCC(c4ccccc4N(C)C)CC3)c2cc1N(C)CCO]

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, CDCl$_3$): δ=7.71 (s, 1H), 7.43 (s, 1H), 7.28-7.09 (m, 4H), 4.43 (d, J=13.2 Hz, 2H), 3.78-3.75 (m, 2H), 3.52-3.51 (m, 1H), 3.26-3.15 (m, 4H), 2.74 (s, 3H), 2.70 (s, 6H), 2.47 (s, 3H), 2.27 (brs, 1H), 1.93-1.91 (m, 4H), 1.19-1.17 (m, 2H), 1.03-1.01 (m, 2H). MS: m/z 460.3 (M+H$^+$)

Example 117: Preparation of 2-({2-cyclopropyl-4-[4-(2-methoxy-phenyl)-piperidin-1-yl]-7-methyl-quinazolin-6-yl}-methyl-amino)-ethanol

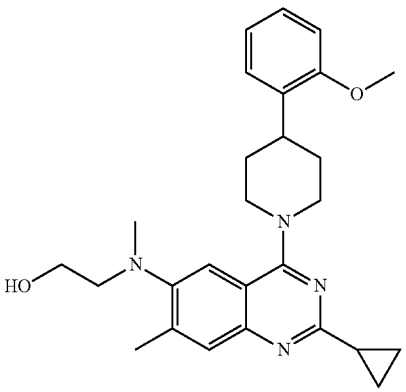 [SMILES: COc1ccccc1C1CCN(c2nc(C3CC3)nc3cc(C)c(N(C)CCO)cc23)CC1]

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, CDCl$_3$): δ=7.62 (s, 1H), 7.43 (s, 1H), 7.24-7.21 (m, 2H), 6.99-6.95 (m, 1H), 6.90 (d, J=8.0 Hz, 1H), 4.35 (d, J=13.2 Hz, 2H), 3.86 (s, 3H), 3.77-3.74 (m, 2H), 3.31-3.26 (m, 1H), 3.21-3.15 (m, 4H), 2.73 (s, 3H), 2.47 (s, 3H), 2.37-2.36 (m, 1H), 2.18-2.15 (m, 1H), 1.98-1.87 (m, 4H), 1.18-1.15 (m, 2H), 0.99-0.96 (m, 2H). MS: m/z 447.3 (M+H$^+$)

Example 118: Preparation of 2-({7-chloro-2-cyclopropyl-4-[4-(2-dimethylamino-phenyl)-piperidin-1-yl]-quinazolin-6-yl}-methyl-amino)-ethanol

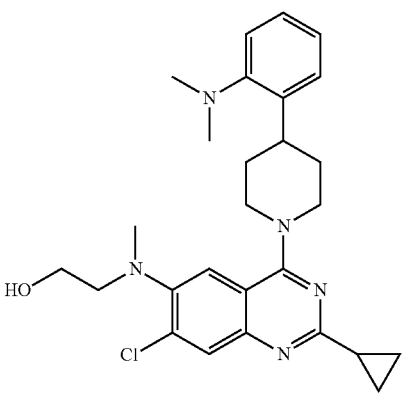 [SMILES: CN(C)c1ccccc1C1CCN(c2nc(C3CC3)nc3cc(Cl)c(N(C)CCO)cc23)CC1]

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, CDCl$_3$): δ=7.86 (s, 1H), 7.49 (s, 1H), 7.28 (m, 1H), 7.21-7.17 (m, 2H), 7.13-7.11 (m, 1H), 4.36 (d, J=13.2 Hz, 2H), 3.80-3.77 (m, 2H), 3.53-3.49 (m, 1H), 3.26-3.20 (m, 4H), 2.84 (s, 3H), 2.70 (s, 6H), 2.20-2.16 (m, 1H), 1.92-1.88 (m, 4H), 1.18-1.16 (m, 2H), 1.02-0.99 (m, 2H). MS: m/z 480.2 (M+H$^+$)

Example 119: Preparation of 2-({4-[4-(2-azetidin-1-yl-phenyl)-piperidin-1-yl]-7-chloro-2-cyclopropyl-quinazolin-6-yl}-methyl-amino)-ethanol

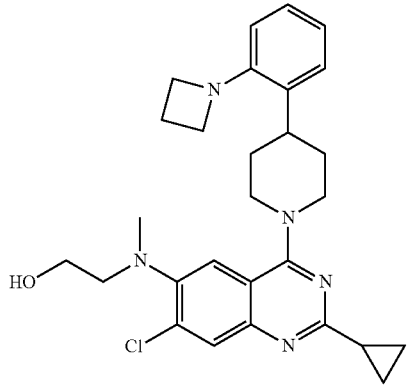 [SMILES: CN(CCO)c1cc2c(N3CCC(c4ccccc4N4CCC4)CC3)nc(C3CC3)nc2cc1Cl]

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, CDCl$_3$): δ=7.84 (s, 1H), 7.49 (s, 1H), 7.26-7.14 (m, 2H), 6.91-6.89 (m, 1H), 6.61 (d, J=7.6 Hz, 1H), 4.34 (d, J=13.2 Hz, 2H), 3.96-3.92 (m, 4H), 3.79-3.77 (m, 2H), 3.24-3.12 (m, 4H), 3.04-3.02 (m, 1H), 2.84 (s, 3H), 2.71-2.69 (m, 1H), 2.33-2.30 (m, 2H), 2.17 (brs, 1H), 2.04-1.88 (m, 4H), 1.18-1.15 (m, 2H), 0.99-0.96 (m, 2H). MS: m/z 492.3 (M+H$^+$)

Example 120: Preparation of 2-({2-cyclopropyl-4-[4-(2-dimethylamino-phenyl)-piperidin-1-yl]-7-fluoro-quinazolin-6-yl}-methyl-amino)-ethanol

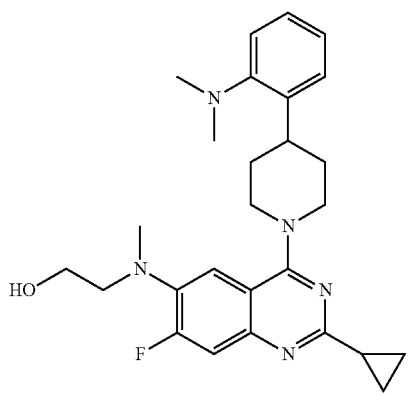 [SMILES: CN(C)c1ccccc1C1CCN(c2nc(C3CC3)nc3cc(F)c(N(C)CCO)cc23)CC1]

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, CDCl$_3$): δ=7.40 (d, J=13.6 Hz, 1H), 7.29-7.27 (m, 2H), 7.21-7.17 (m, 2H), 7.12-7.09 (m, 1H), 4.33 (d, J=13.2 Hz, 2H), 3.84 (m, 2H), 3.52-3.48 (m, 1H), 3.33 (m, 2H), 3.22-3.15 (m, 2H), 2.93 (s, 3H), 2.70 (s, 6H), 2.17-2.15 (m, 1H), 1.98-1.91 (m, 4H), 1.18-1.15 (m, 2H), 0.99-0.96 (m, 2H). MS: m/z 464.3 (M+H$^+$)

Example 121: Preparation of 2-({4-[4-(2-azetidin-1-yl-phenyl)-piperidin-1-yl]-2-cyclopropyl-7-methyl-quinazolin-6-yl}-methyl-amino)-ethanol

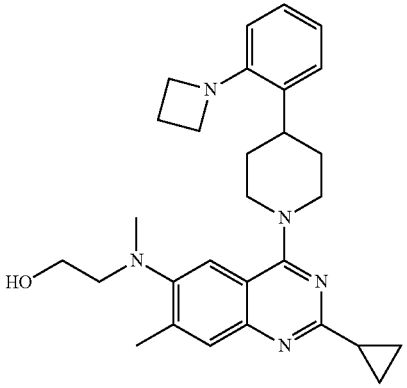 [SMILES: Cc1cc2nc(C3CC3)nc(N3CCC(c4ccccc4N4CCC4)CC3)c2cc1N(C)CCO]

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, CDCl$_3$): δ=7.63 (s, 1H), 7.42 (s, 1H), 7.22-7.14 (m, 2H), 6.91-6.89 (m, 1H), 6.62 (d, J=7.6 Hz, 1H), 4.34 (d, J=13.6 Hz, 2H), 3.96-3.93 (m, 4H), 3.77-3.75 (m, 2H), 3.18-3.09 (m, 5H), 2.74 (s, 3H), 2.48 (s, 3H), 2.35-2.20 (m, 3H), 2.02-1.89 (m, 4H), 1.17-1.15 (m, 2H), 0.99-0.97 (m, 2H). MS: m/z 472.3 (M+H$^+$)

Example 122: Preparation of {2-cyclopropyl-4-[4-(2-methoxy-phenyl)-piperidin-1-yl]-7-methyl-quinazolin-6-yl}-methyl-propyl-amine

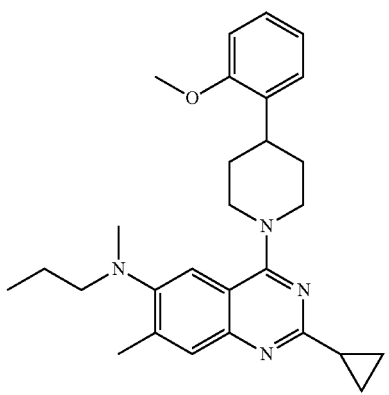 [SMILES: CCCN(C)c1cc2c(N3CCC(c4ccccc4OC)CC3)nc(C3CC3)nc2cc1C]

The title compound was prepared as described for 2-({5-chloro-2-cyclopropyl-4-[4-(2-methoxy-phenyl)-piperidin-1-yl]-quinazolin-6-yl}-methyl-amino)-ethanol. $^1$H NMR (400 MHz, CDCl$_3$): δ=7.60 (s, 1H), 7.32 (s, 1H), 7.26-7.20 (m, 2H), 6.99-6.95 (m, 1H), 6.90 (d, J=8.0 Hz, 1H), 4.35 (d, J=13.2 Hz, 2H), 3.86 (s, 3H), 3.29-3.12 (m, 3H), 2.89-2.86 (m, 2H), 2.72 (s, 3H), 2.44 (s, 3H), 2.17-2.16 (m, 1H), 1.98-1.88 (m, 5H), 1.61-1.56 (q, J=7.2 Hz, 2H), 1.18-1.15 (m, 2H), 0.98-0.93 (m, 5H). MS: m/z 445.3 (M+H$^+$)

Example 123: Preparation of {2-cyclopropyl-4-[4-(5-fluoro-2-methoxy-phenyl)-piperidin-1-yl]-7-methyl-quinazolin-6-yl}-methyl-propyl-amine

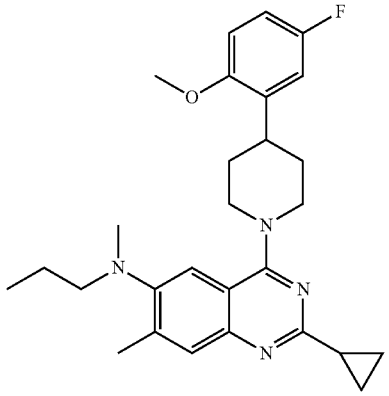 [SMILES: CCCN(C)c1cc2c(N3CCC(c4cc(F)ccc4OC)CC3)nc(C3CC3)nc2cc1C]

The title compound was prepared as described for 2-({5-chloro-2-cyclopropyl-4-[4-(2-methoxy-phenyl)-piperidin-1-yl]-quinazolin-6-yl}-methyl-amino)-ethanol. $^{1}$H NMR (400 MHz, CDCl$_3$): δ=7.61 (s, 1H), 7.31 (s, 1H), 6.97-6.94 (m, 1H), 6.91-6.87 (m, 1H), 6.82-6.81 (m, 1H), 4.34 (d, J=13.2 Hz, 2H), 3.83 (s, 3H), 3.29-3.22 (m, 1H), 3.17-3.11 (t, J=11.2 Hz, 2H), 2.90-2.86 (t, J=7.2 Hz, 2H), 2.72 (s, 3H), 2.44 (s, 3H), 2.21-2.16 (m, 1H), 1.97-1.82 (m, 4H), 1.62-1.56 (m, 2H), 1.16-1.14 (m, 2H), 0.98-0.89 (m, 5H). MS: m/z 463.3 (M+H$^+$)

Example 124: Preparation of 2-({2-cyclopropyl-7-fluoro-4-[4-(2-methoxy-phenyl)-piperidin-1-yl]-quinazolin-6-yl}-methyl-amino)-ethanol

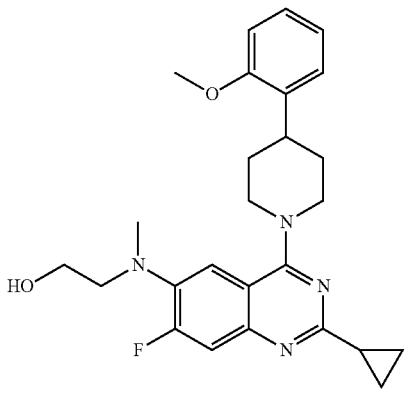 [SMILES: COc1ccccc1C1CCN(c2nc(C3CC3)nc3cc(F)c(N(C)CCO)cc23)CC1]

The title compound was prepared as described for 2-({5-chloro-2-cyclopropyl-4-[4-(2-methoxy-phenyl)-piperidin-1-yl]-quinazolin-6-yl}-methyl-amino)-ethanol. $^{1}$H NMR (400 MHz, CDCl$_3$): δ=7.40 (d, J=13.2 Hz, 1H), 7.30-7.20 (m, 3H), 6.98-6.95 (m, 1H), 6.91-6.89 (m, 1H), 4.32 (d, J=12.8 Hz, 2H), 3.86 (s, 3H), 3.83-3.82 (m, 2H), 3.33-3.28 (m, 3H), 3.20-3.14 (m, 2H), 2.92 (s, 3H), 2.18 (brs, 1H), 1.99-1.87 (m, 4H), 1.18-1.14 (m, 2H), 1.00-0.97 (m, 2H). MS: m/z 463.3 (M+H$^+$)

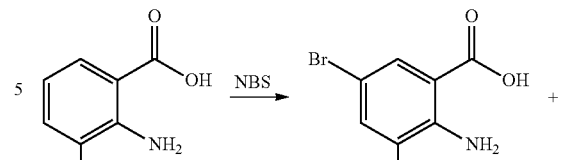
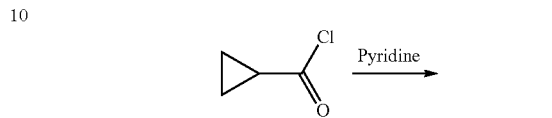
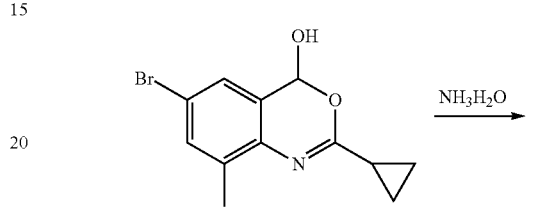
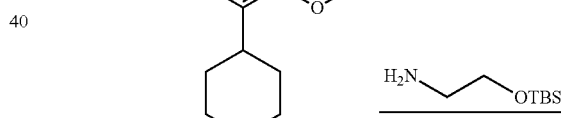
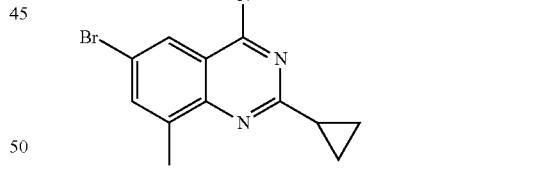

-continued

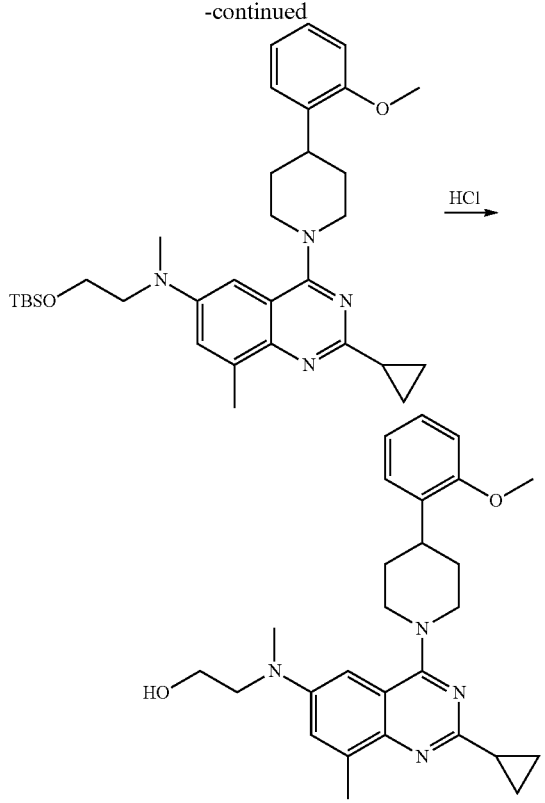

Example 125: Preparation of 2-({2-cyclopropyl-4-[4-(2-methoxy-phenyl)-piperidin-1-yl]-8-methyl-quinazolin-6-yl}-methyl-amino)-ethanol

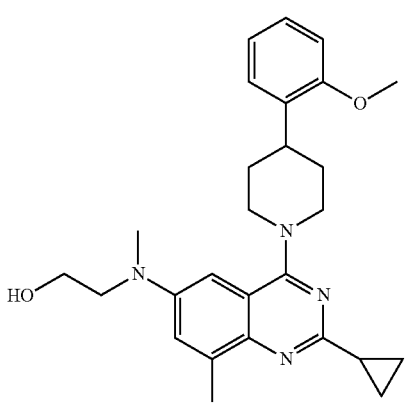 [SMILES: COc1ccccc1C1CCN(c2nc(C3CC3)nc3c(C)cc(N(C)CCO)cc23)CC1]

The procedures of most steps are similar to 2-({5-chloro-2-cyclopropyl-4-[4-(2-methoxy-phenyl)-piperidin-1-yl]-quinazolin-6-yl}-methyl-amino)-ethanol except step 2 and 3, which are identical to the first two steps of {2-cyclopropyl-4-[4-(2-methoxy-phenyl)-piperidin-1-yl]-quinazolin-5-yl}-methyl-propyl-amine. $^1$H NMR (300 HMz, CDCl3): δ=7.26-7.21 (m, 3H), 7.01-6.85 (m, 3H), 4.34 (d, J=10.8 Hz, 2H), 3.89-3.85 (m, 5H), 3.56-3.54 (m, 2H), 3.32-3.09 (m, 3H), 3.03 (s, 3H), 2.71 (s, 3H), 2.24-2.21 (m, 1H), 1.96-1.88 (m, 4H), 1.19-1.17 (m, 2H), 1.01-0.97 (m, 2H). MS: m/z 447.2 (M+H$^+$)

Example 126: Preparation of 2-({2-cyclopropyl-4-[4-(2-methoxy-phenyl)-piperidin-1-yl]-5-methyl-quinazolin-6-yl}-methyl-amino)-ethanol

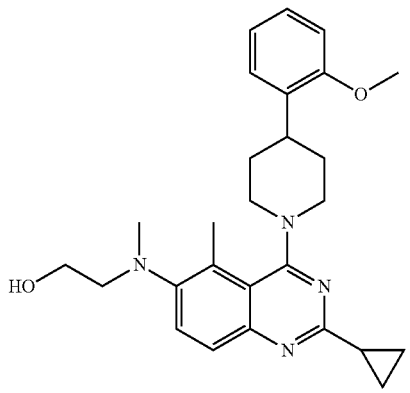 [SMILES: COc1ccccc1C1CCN(c2nc(C3CC3)nc3ccc(N(C)CCO)c(C)c23)CC1]

The title compound was prepared as described for 2-({2-cyclopropyl-4-[4-(2-methoxy-phenyl)-piperidin-1-yl]-8-methyl-quinazolin-6-yl}-methyl-amino)-ethanol. $^1$H NMR (400 MHz, CDCl$_3$): δ=7.63 (t, J=11.2 Hz, 1H), 7.52 (t, J=10.4 Hz, 1H), 7.28-7.14 (m, 2H), 7.00-6.83 (m, 2H), 4.25 (d, J=12.8 Hz, 1H), 3.95 (d, J=13.6 Hz, 1H), 3.83 (d, J=10.0 Hz, 3H), 3.71-3.68 (m, 2H), 3.38-3.33 (m, 1H), 3.18-3.15 (m, 2H), 2.84-2.78 (m, 3H), 2.74 (s, 3H), 2.60 (s, 1H), 2.18-2.16 (m, 1H), 2.02-1.99 (m, 2H), 1.71-1.53 (m, 5H), 1.19-1.15 (m, 2H), 0.98-0.97 (m, 2H). MS: m/z 447.2 (M+H$^+$)

Example 127: Preparation of 2-({2-cyclopropyl-4-[4-(2-methoxy-phenyl)-piperidin-1-yl]-quinazolin-8-yl}-methyl-amino)-ethanol

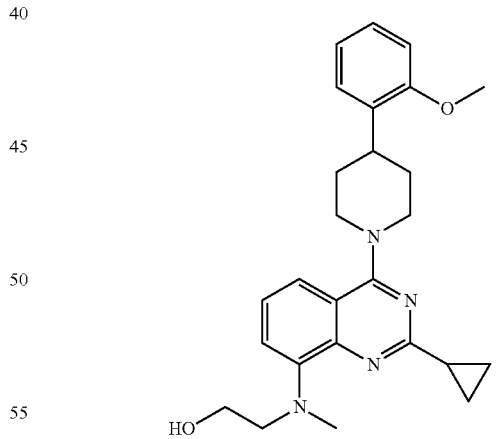

The title compound was prepared as described for 2-({2-cyclopropyl-4-[4-(2-methoxy-phenyl)-piperidin-1-yl]-8-methyl-quinazolin-6-yl}-methyl-amino)-ethanol. $^1$H NMR (400 MHz, CDCl$_3$): δ=8.29 (brs, 1H), 7.37 (d, J=7.6 Hz, 1H), 7.24-7.19 (m, 3H), 7.14 (d, J=7.6 Hz, 1H), 6.97-6.95 (m, 1H), 6.89 (d, J=7.6 Hz, 1H), 4.45 (d, J=13.2 Hz, 2H), 4.02-3.99 (m, 2H), 3.85 (s, 3H), 3.46-3.43 (m, 2H), 3.30-3.15 (m, 3H), 2.97 (s, 3H), 2.25-2.21 (m, 1H), 1.94-1.83 (m, 4H), 1.17-1.15 (m, 2H), 0.99-0.97 (m, 2H). MS: m/z 434.3 (M+H$^+$)

Example 128: Preparation of {2-cyclopropyl-4-[4-(2-methoxy-phenyl)-piperidin-1-yl]-quinazolin-8-yl}-methyl-propyl-amine

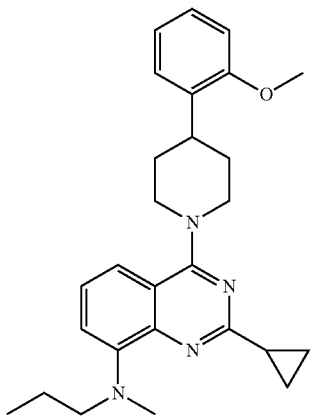 [SMILES: CCCN(C)c1cccc2c(N3CCC(c4ccccc4OC)CC3)nc(C3CC3)nc12]

The title compound was prepared as described for 2-({2-cyclopropyl-4-[4-(2-methoxy-phenyl)-piperidin-1-yl]-8-methyl-quinazolin-6-yl}-methyl-amino)-ethanol. $^1$H NMR (400 MHz, CDCl$_3$): δ=7.36 (d, J=8.0 Hz, 1H), 7.25-7.18 (m, 3H), 7.00-6.96 (m, 2H), 6.89 (d, J=8.4 Hz, 1H), 4.38 (d, J=12.8 Hz, 2H), 3.86 (s, 3H), 3.50-3.46 (m, 2H), 3.29-3.14 (m, 3H), 2.98 (s, 3H), 2.27-2.24 (m, 1H), 1.94-1.91 (m, 4H), 1.73-1.71 (m, 2H), 1.18-1.16 (m, 2H), 0.98-0.95 (m, 2H), 0.90 (t, J=7.6 Hz, 3H). MS: m/z 431.3 (M+H$^+$)

Example 129: Preparation of {2-cyclopropyl-4-[4-(2-methoxy-phenyl)-piperidin-1-yl]-quinazolin-8-yl}-methyl-(2-morpholin-4-yl-ethyl)-amine

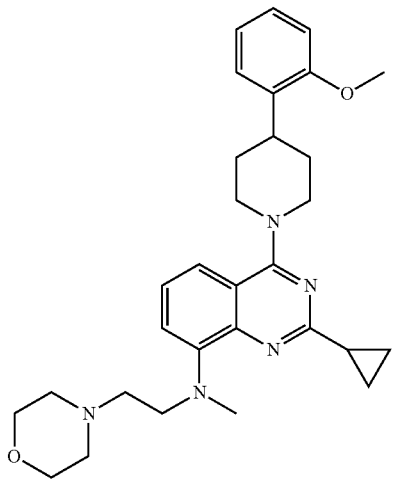 [SMILES: COc1ccccc1C1CCN(c2nc(C3CC3)nc3c(N(C)CCN4CCOCC4)cccc23)CC1]

The title compound was prepared as described for 2-({2-cyclopropyl-4-[4-(2-methoxy-phenyl)-piperidin-1-yl]-8-methyl-quinazolin-6-yl}-methyl-amino)-ethanol. $^1$H NMR (400 MHz, CDCl$_3$): δ=7.37 (d, J=8.0 Hz, 1H), 7.24-7.17 (m, 3H), 7.03-6.98 (m, 1H), 6.96-6.88 (m, 2H), 4.38 (d, J=12.8 Hz, 2H), 3.86 (s, 3H), 3.70-3.63 (m, 6H), 3.17-3.10 (m, 3H), 3.01 (s, 3H), 2.81-2.77 (m, 2H), 2.48 (brs, 4H), 2.25 (brs, 1H), 1.93-1.87 (m, 4H), 1.17-1.16 (m, 2H), 0.97-0.94 (m, 2H). MS: m/z 502.3 (M+H$^+$)

Example 130: Preparation of 2-({8-chloro-2-cyclopropyl-4-[4-(2-methoxy-phenyl)-piperidin-1-yl]-quinazolin-6-yl}-methyl-amino)-ethanol

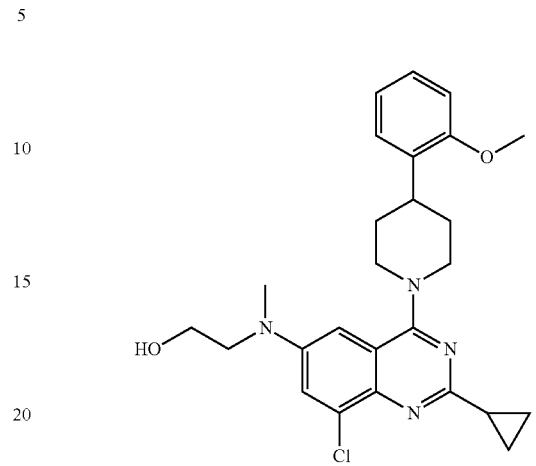

The title compound was prepared as described for 2-({2-cyclopropyl-4-[4-(2-methoxy-phenyl)-piperidin-1-yl]-8-methyl-quinazolin-6-yl}-methyl-amino)-ethanol. $^1$H NMR (400 MHz, CDCl$_3$): δ=7.46 (s, 1H), 7.24-7.20 (m, 2H), 6.98-6.88 (m, 3H), 6.90-6.84 (m, 1H), 4.32 (d, J=13.2 Hz, 2H), 3.88-3.85 (m, 5H), 3.55-3.52 (m, 2H), 3.34-3.14 (m, 3H), 3.04 (s, 3H), 2.28-2.32 (m, 1H), 1.94-1.87 (m, 5H), 1.18-1.16 (m, 2H), 0.99-0.97 (m, 2H). MS: m/z 467.3 (M+H$^+$)

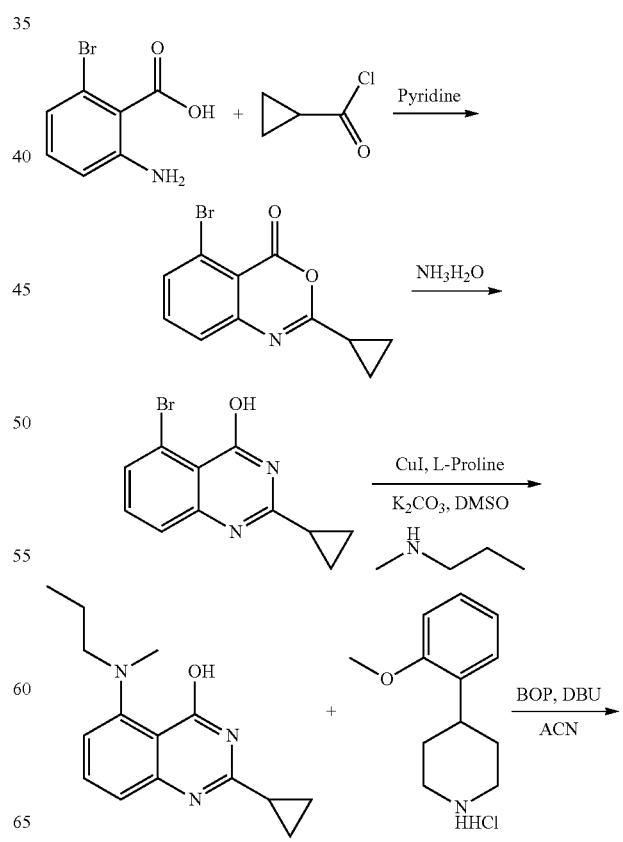

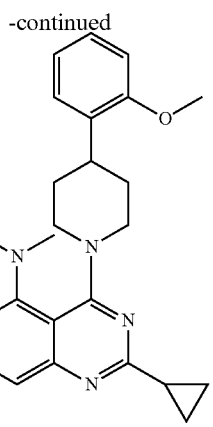

Example 131: Preparation of {2-cyclopropyl-4-[4-(2-methoxy-phenyl)-piperidin-1-yl]-quinazolin-5-yl}-methyl-propyl-amine

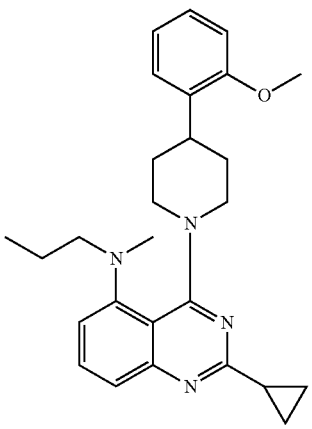 [SMILES: CCCN(C)c1cccc2nc(C3CC3)nc(N3CCC(c4ccccc4OC)CC3)c12]

To a solution of 2-amino-6-bromo-benzoic acid (2 g, 9.3 mmol) in pyridine (20 mL) was added cyclopropanecarbonyl chloride (1.25 mL, 13.9 mmol). The reaction mixture was stirred at 60° C. overnight. Cooled to 0° C., and poured into ice-water (100 mL), the resulting suspension was filtered and dried to give 5-bromo-2-cyclopropyl-benzo[d][1,3]oxazin-4-one (1.75 g, yield: 71%) as white solid. $^1$H NMR (300 HMz, CDCl$_3$): δ=7.68 (d, J=7.8 Hz, 1H), 7.53 (t, J=8.1 Hz, 1H), 7.44 (d, J=7.8 Hz, 1H), 1.95-1.90 (m, 1H), 1.31-1.27 (m, 2H), 1.16-1.11 (m, 2H).

A suspension of 5-bromo-2-cyclopropyl-benzo[d][1,3]oxazin-4-one (1 g, 3.79 mmol) in NH$_3$H$_2$O (50 mL, 28%) was heated at reflux overnight. Cooled to rt, filtered, the cake was washed with water, dried to give 5-bromo-2-cyclopropyl-quinazolin-4-ol (450 mg, 45% yield) as white solid. $^1$H NMR (300 HMz, CDCl$_3$): δ=7.64-7.62 (m, 1H), 7.56-7.53 (m, 1H), 7.50-7.47 (m, 1H), 1.84-1.82 (m, 1H), 1.32-1.28 (m, 2H), 1.17-1.13 (m, 2H).

To a suspension of 5-bromo-2-cyclopropyl-quinazolin-4-ol (100 mg, 0.38 mmol), L-proline (22 mg, 0.19 mmol), CuI (22 mg, 0.11 mmol) and K$_2$CO$_3$ (105 mg, 0.76 mmol) in DMSO (2 mL) was added methyl-propyl-amine (41 mg, 0.57 mmol) after purged with N$_2$ for 5 min. Then the mixture was heated to 90° C. and it was stirred at a sealed tube overnight. Cooled to rt, filtered, the filtration was purified by prep-HPLC to afford 2-cyclopropyl-5-(methyl-propyl-amino)-quinazolin-4-ol (23 mg, yield: 21%) as brown oil. MS: m/z 258.0 (M+H$^+$)

To a suspension of 2-cyclopropyl-5-(methyl-propyl-amino)-quinazolin-4-ol (23 mg, 0.09 mmol), 4-(2-methoxy-phenyl)-piperidine hydrochloride (23 mg, 0.1 mmol) and BOP (60 mg, 0.14 mmol) in ACN (10 mL) was added DBU (68 mg, 0.45 mmol), till the suspension was clear, then the mixture was stirred at rt overnight. The mixture was concentrated and purified by prep-TLC (DCM/MeOH=20/1) to afford {2-cyclopropyl-4-[4-(2-methoxy-phenyl)-piperidin-1-yl]-quinazolin-5-yl}-methyl-propyl-amine (46.9 mg, yield: 100%) as yellow solid. $^1$H NMR (400 MHz, CDCl$_3$): δ=7.64-7.43 (m, 2H), 7.22-7.20 (m, 1H), 7.08-6.88 (m, 4H), 5.28 (d, J=14.8 Hz, 1H), 3.84 (s, 3H), 3.76-3.74 (m, 1H), 3.71-3.59 (m, 1H), 3.55-3.22 (m, 3H), 3.00-2.95 (m, 3H), 2.77-2.75 (m, 1H), 2.54-2.51 (m, 1H), 2.08-2.03 (m, 1H), 1.81-1.78 (m, 3H), 1.68-1.64 (m, 2H), 1.31-1.22 (m, 3H), 1.06-1.04 (m, 2H), 0.69-0.67 (m, 2H). MS: m/z 432.3 (M+H$^+$)

Example 132: Preparation of 2-((2-cyclopropyl-5-fluoro-4-(4-(2-methoxyphenyl)piperidin-1-yl) quinazolin-6-yl)(methyl)amino)ethanol

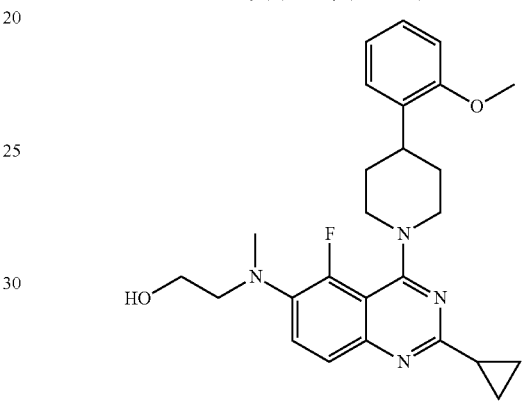

The title compound was prepared as described for 2-({2-cyclopropyl-4-[4-(2-methoxy-phenyl)-piperidin-1-yl]-8-methyl-quinazolin-6-yl}-methyl-amino)-ethanol. $^1$H NMR (400 MHz, CDCl$_3$): δ=7.56-7.48 (m, 2H), 7.23-7.17 (m, 2H), 6.95 (t, J=7.2 Hz, 1H), 6.88 (d, J=8.4 Hz, 1H), 4.20 (d, J=12.4 Hz, 2H), 3.85 (s, 3H), 3.74 (t, J=5.2 Hz, 2H), 3.25 (t, J=5.6 Hz, 2H), 3.10 (t, J=12.4 Hz, 2H), 2.88 (s, 3H), 2.16-2.13 (m, 1H), 1.95-1.82 (m, 4H), 1.19-1.14 (m, 2H), 1.00-0.95 (m, 2H). MS: m/z 451.2 (M+H$^+$)

Example 133: Preparation of 2-((2-cyclopropyl-8-fluoro-4-(4-(2-methoxyphenyl)piperidin-1-yl)quinazolin-6-yl)(methyl)amino)ethanol

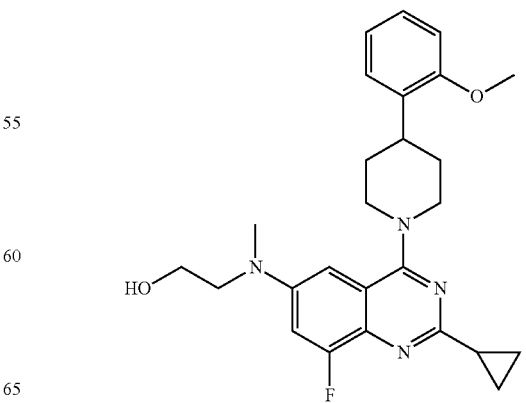

The title compound was prepared as described in example 2-({2-cyclopropyl-4-[4-(2-methoxy-phenyl)-piperidin-1-yl]-8-methyl-quinazolin-6-yl}-methyl-amino)-ethanol. ¹H NMR (400 MHz, CDCl₃): δ=7.25-7.08 (m, 2H), 7.05 (dd, J=13.2, 2.0 Hz, 1H), 6.97 (t, J=8.0 Hz, 1H), 6.88 (d, J=8.8 Hz, 1H), 6.71 (s, 1H), 4.35 (d, J=12.4 Hz, 2H), 3.90-3.85 (m, 5H), 3.53 (t, J=5.2 Hz, 2H), 3.29-3.25 (m, 1H), 3.13 (t, J=12.4 Hz, 2H), 2.78 (s, 3H), 2.26-2.23 (m, 1H), 1.95-1.82 (m, 5H), 1.19-1.14 (m, 2H), 1.00-0.95 (m, 2H). MS: m/z 451.2 (M+H⁺)

Example 134: Preparation of 2-cyclopropyl-4-(4-(2-methoxyphenyl)piperidin-1-yl)-N-methyl-N-(2-morpholinoethyl)pyrido[3,4-d]pyrimidin-6-amine

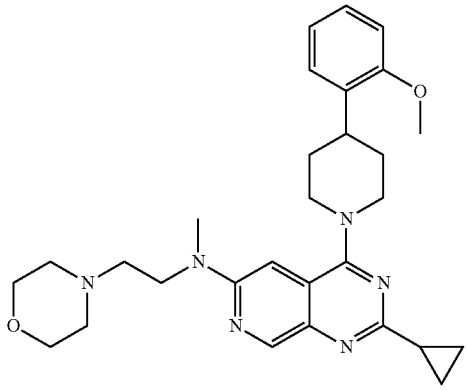

The title compound was prepared as described in example 2-({2-cyclopropyl-4-[4-(2-methoxy-phenyl)-piperidin-1-yl]-8-methyl-quinazolin-6-yl}-methyl-amino)-ethanol. ¹H NMR (400 MHz, CDCl₃): δ=8.90 (s, 1H), 7.20 (d, J=8.0 Hz, 2H), 6.98-6.88 (m, 2H), 6.50 (s, 1H), 4.43 (d, J=12.4 Hz, 2H), 3.86-3.80 (m, 5H), 3.71-3.65 (m, 4H), 3.31-3.28 (m, 1H), 3.19-3.12 (m, 2H), 3.09 (s, 3H), 2.62-2.51 (m, 6H), 2.20-2.18 (m, 1H), 2.00-1.84 (m, 4H), 1.15-1.12 (m, 2H), 1.00-0.87 (m, 2H). MS: m/z 503.3 (M+H⁺)

Example 135: Preparation of 2-cyclopropyl-4-(4-(2-methoxyphenyl)piperidin-1-yl)-N-methyl-N-propylquinazolin-7-amine

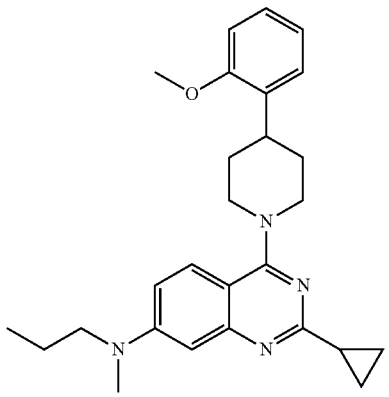 [SMILES: CCCN(C)c1ccc2c(N3CCC(c4ccccc4OC)CC3)nc(C3CC3)nc2c1]

The title compound was prepared as described in example 2-({2-cyclopropyl-4-[4-(2-methoxy-phenyl)-piperidin-1-yl]-8-methyl-quinazolin-6-yl}-methyl-amino)-ethanol. ¹H NMR (300 MHz, CDCl₃): δ=7.63 (d, J=9.3 Hz, 1H), 7.28-7.15 (m, 3H), 7.00-6.82 (m, 3H), 4.65 (d, J=12.4 Hz, 2H), 3.87 (s, 3H), 3.46-3.30 (m, 5H), 3.11 (s, 3H), 2.50-2.40 (m, 1H), 2.05-1.97 (m, 2H), 1.90-1.62 (m, 4H), 1.28-1.13 (m, 4H), 0.97 (t, J=7.5 Hz, 3H). MS: m/z 431.3 (M+H⁺)

Example 136: Preparation of 2-((2-(cyclopropylethynyl)-4-(4-(2-methoxyphenyl)piperidin-1-yl)quinazolin-6-yl)(methyl)amino)ethanol

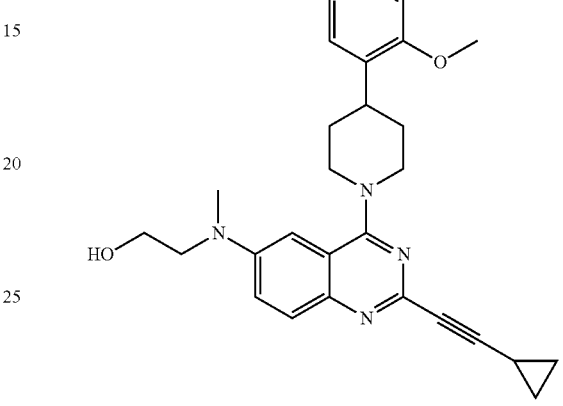

The title compound was prepared as described for 2-{2-Dimethylamino-4-[4-(2-methoxy-phenyl)-piperidin-1-yl]-quinazolin-6-ylamino}-ethanol. ¹H NMR (400 MHz, CDCl₃): δ=7.76 (d, J=8.8 Hz, 1H), 7.36 (dd, J=9.2, 2.8 Hz, 1H), 7.27-7.20 (m, 2H), 6.99-6.88 (m, 3H), 4.45-4.39 (m, 2H), 3.90-3.86 (m, 5H), 3.60-3.55 (m, 2H), 3.71-3.59 (m, 1H), 3.21-3.15 (m, 3H), 3.07 (s, 3H), 2.05-1.90 (m, 3H), 1.57-1.49 (m, 1H), 1.00-0.86 (m, 4H). MS: m/z 457.2 (M+H⁺)

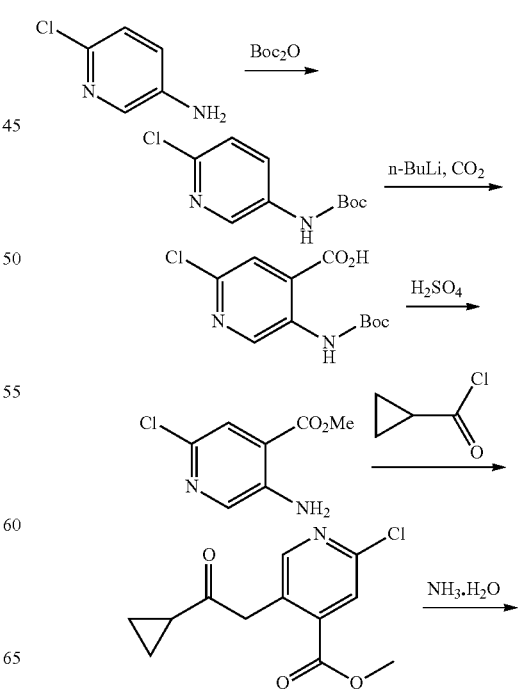

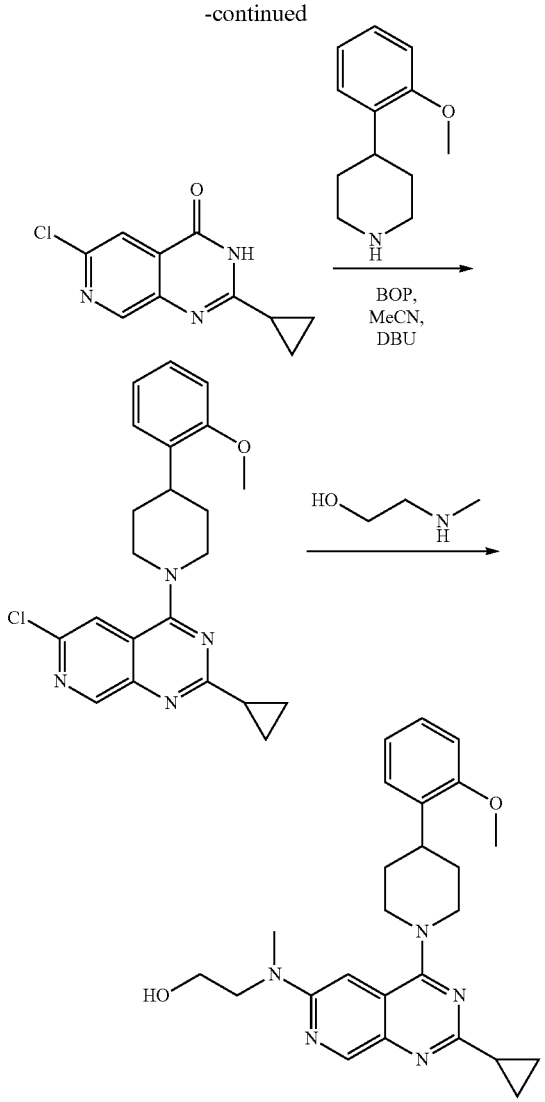

Example 137: Preparation of 2-({2-cyclopropyl-4-[4-(2-methoxy-phenyl)-piperidin-1-yl]-pyrido[3,4-d]pyrimidin-6-yl}-methyl-amino)-ethanol

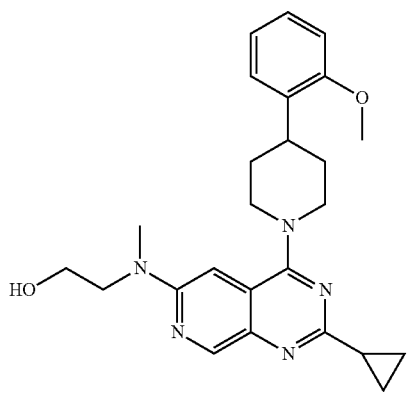

To a stirred solution of 6-chloro-pyridin-3-ylamine (10 g, 7.7 mmol) in DCM (150 mL) was added Boc₂O (18.5 g, 8.46 mmol) dropwised at 0° C. and DMAP (0.5 g, 4 mmol), Et₃N (16.3 g, 16.2 mmol) as follows. The mixture was allowed to warm to room temperature and stirred for 18 hours. The reactaction solution was concentrated under reduced pressure to dryness. The residue was purified by silica gel chromatography (from PE to PE/EA=20/1) to give (13.0 g, yield: 76%) of (6-chloro-pyridin-3-yl)-carbamic acid tert-butyl ester as yellow solid. NMR (300 MHz, CDCl₃): δ=8.21 (brs, 1H), 8.45 (s, 1H), 7.91 (d, J=6.3 Hz, 1H), 7.49 (d, J=8.4 Hz, 1H), 1.47-1.37 (m, 9H).

To a stirred solution of (6-chloro-pyridin-3-yl)-carbamic acid tert-butyl ester (5.6 g, 24.6 mmol) in THF (100 mL) was added n-BuLi (29 mL, 74.0 mmol) dropwise at −78° C. The mixture was stirred at this temperature for 1 hors. Then the vessel was charged with carbon dioxide to a pressure of 0.7 Mbar and stirred at −40° C. for 10 min. After warmed to room temperature, the mixture was poured into the ice water and the pH value was adjusted to pH=3. The aqueous phase was extracted with EA (100 mL×2). The combined organic layers were washed with brine (30 mL×2), dried over anhydrous Na₂SO₄ and filtered. The filtrate was evaporated in vacuum to give the product (crude, 8.0 g) of 5-tert-butoxycarbonylamino-2-chloro-isonicotinic acid as red oil.

To a stirred solution of 5-tert-butoxycarbonylamino-2-chloro-isonicotinic acid (crude, 8.0 g) in methanol (50 mL) was added H₂SO₄ (5.0 mL). The mixture was then heated to reflux overnight. The reaction was cooled to room temperature and was concentrated in vacuum. The residue was diluted with water. The aqueous mixture was neutralized with sat. NaHCO₃ to pH=8 and extracted with EA (100 mL×2). The combined organic layers were washed with brine (50 mL), dried over anhydrous Na₂SO₄ and filtered. The filtrate was evaporated in vacuum to residue, which was purified by silica gel chromatography (from PE to PE/EA=2/1) to give (1.1 g, two steps of yield: 24%) of 5-amino-2-chloro-isonicotinic acid methyl ester as yellow solid.

To a stirred solution of (5-amino-2-chloro-isonicotinic acid methyl ester (1.3 g, 7 mmol) in DCM (30 mL) was added Et₃N (1.4 g, 14 mmol) and cyclopropanecarbonyl chloride (1.1 g, 10.5 mmol) at 0° C. The mixture was stirred at room temperature overnight. The mixture was evaporated in vacuum. The residue was diluted with water (50 mL). The aqueous phase was extracted with EA (80 mL×2). The extracts were washed with water, dried over anhydrous Na₂SO₄ and filtered. The filtrate was evaporated in vacuum to residue, which was purified by silica gel chromatography (from PE to PE/EA=10/1) to give (1.0 g, yield: 56%) of 2-chloro-5-(cyclopropanecarbonyl-amino)-isonicotinic acid methyl ester as yellow solid. ¹H NMR (400 MHz, DMSO-d₆): δ=10.56 (brs, 1H), 8.79 (s, 1H), 7.23 (s, 1H), 3.82 (s, 3H), 1.87-1.80 (m, 3H), 0.94-0.83 (m, 4H).

A suspension of 2-chloro-5-(cyclopropanecarbonyl-amino)-isonicotinic acid methyl ester (1.0 g, 3.9 mmol) in NH₃.H₂O (10 mL) was heated to reflux for 3 days. The reaction was cooled to room temperature and was concentrated to dryness in vacuum. The residue (300 mg, yield: 20%) was washed with methanol and used directly in next step without further purification.

To a stirred solution of 6-chloro-2-cyclopropyl-3H-pyrido[3,4-d]pyrimidin-4-one (200 mg, 0.9 mmol) in acetonitrile (8 mL) was added DIEA (1.24 g, 10.9 mmol) and 4-(2-methoxy-phenyl)-piperidine (1.12 g, 4.9 mmol). The mixture was stirred at room temperature overnight. The mixture was evaporated in vacuum. The residue (180 mg, yield: 51%) was washed with methanol and used directly in next step without further purification.

To a stirred solution of 6-chloro-2-cyclopropyl-4-[4-(2-methoxy-phenyl)-piperidin-1-yl]-pyrido-[3,4-d]pyrimidine (60 mg, 0.15 mmol) in NMP (1 mL) was added DIEA (40 mg, 0.3 mmol) and 4-(2-methoxy-phenyl)-piperidine (68 mg, 0.9 mmol). The mixture was heated at 170° C. in a microwave for 5 hours. The residue was diluted with EA (200 mL) and washed with water, dried over anhydrous Na₂SO₄ and filtered. The filtrate was evaporated in vacuum to residue, which was purified by pre-HPLC (MeCN/H₂O from 5/100 to 95/100) to give (25.8 mg, yield: 40%) of 2-({2-cyclopropyl-4-[4-(2-methoxy-phenyl)-piperidin-1-yl]-pyrido-[3,4-d]pyrimidin-6-yl}-methyl-amino)-ethanol as yellow oil. ¹H NMR (400 MHz, CDCl₃): δ=8.88 (s, 1H), 7.28-7.25 (m, 2H), 7.01-6.94 (m, 1H), 6.62 (s, 1H), 4.49-4.46 (m, 2H), 3.95-3.89 (m, 7H), 3.38-3.32 (m, 1H), 3.25-3.16 (m, 5H), 2.22-2.18 (m, 1H), 2.05-1.87 (m, 4H), 1.20-1.17 (m, 2H), 1.03-0.99 (m, 2H). MS: m/z 434.2 (M+H⁺)

Example 138: Preparation of 2-((2-cyclopropyl-4-(4-(3-methoxythiophen-2-yl)piperidin-1-yl)quinazolin-6-yl)(methyl)amino)ethanol

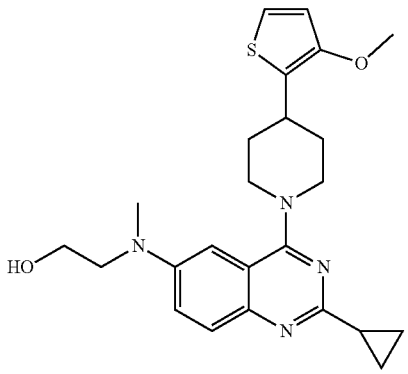 [SMILES: COc1ccsc1C1CCN(c2nc(C3CC3)nc3ccc(N(C)CCO)cc23)CC1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.57-7.52 (m, 1H), 7.33 (dd, J=8.8, 2.8 Hz, 1H), 7.04 (d, J=5.6 Hz, 1H), 6.92 (d, J=2.4 Hz, 1H), 6.85 (d, J=5.2 Hz, 1H), 4.34-4.30 (m, 2H), 3.88-3.83 (m, 5H), 3.56-3.53 (m, 2H), 3.25-3.23 (m, 1H), 3.11 (t, J=12.4 Hz, 2H), 3.04 (s, 3H), 2.09-2.00 (m, 3H), 1.93-1.85 (m, 2H), 1.17-1.13 (m, 2H), 0.99-0.95 (m, 2H). MS: m/z 439.2 (M+H⁺)

Example 139: Preparation of 2-((4-(4-cyclohexylpiperidin-1-yl)-2-(1-fluorocyclopropyl)quinazolin-6-yl)(methyl)amino)ethanol

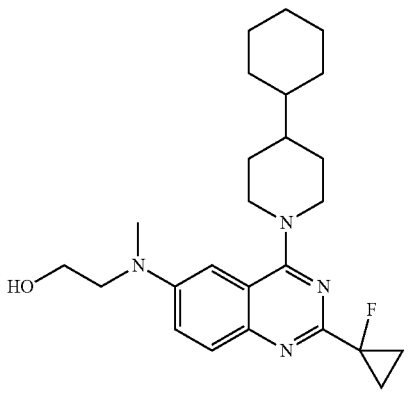 [SMILES: CN(CCO)c1ccc2nc(C3(F)CC3)nc(N3CCC(C4CCCCC4)CC3)c2c1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.89 (d, J=9.2 Hz, 1H), 7.38 (dd, J=9.2, 2.8 Hz, 1H), 6.93 (d, J=2.8 Hz, 1H), 4.24 (d, J=12.8 Hz, 2H), 3.88 (t, J=5.6 Hz, 2H), 3.57 (t, J=5.6 Hz, 2H), 3.07 (s, 3H), 2.93 (t, J=12.4 Hz, 2H), 1.83-0.98 (m, 21H). MS: m/z 427.3 (M+H⁺)

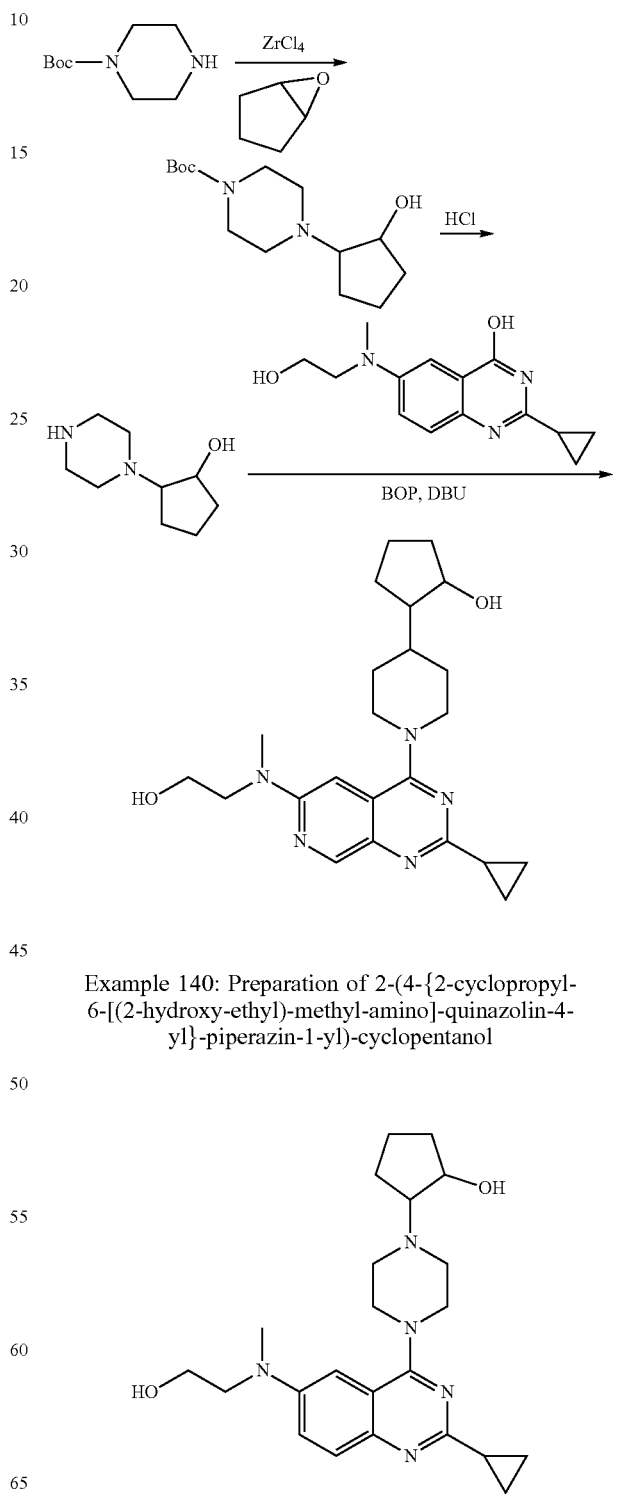

Example 140: Preparation of 2-(4-{2-cyclopropyl-6-[(2-hydroxy-ethyl)-methyl-amino]-quinazolin-4-yl}-piperazin-1-yl)-cyclopentanol The title compound was prepared as described for 2-[(2-cyclopropyl-4-{[(2-methoxy-phenyl)-methyl-amino]-cyclopentylamino}-quinazolin-6-yl)-methyl-amino]-ethanol.
¹HNMR (300 MHz, CD₃OD): δ=7.65 (d, J=9.3 Hz, 1H), 7.40 (dd, J=9.3, 2.7 Hz, 1H), 6.82 (d, J=2.7 Hz, 1H), 4.13-3.11 (m, 1H), 3.77-3.73 (m, 2H), 3.65-3.51 (m, 4H), 3.36-3.31 (m, 2H), 3.04 (s, 3H), 2.84-2.68 (m, 4H), 2.52-2.50 (m, 1H), 2.10-1.93 (m, 3H), 1.69-1.62 (s, 3H), 1.12-1.11 (m, 1H), 1.09-1.07 (m, 2H), 0.98-0.94 (m, 2H). MS: m/z 412.2 (M+H⁺)

Example 141: Preparation of 2-{4-[2-cyclopropyl-6-(methyl-propyl-amino)-quinazolin-4-yl]-piperazin-1-yl}-cyclopentanol

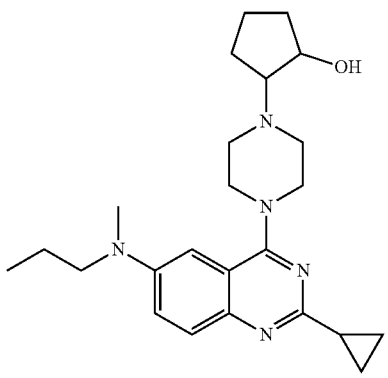 [SMILES: CCCN(C)c1ccc2nc(C3CC3)nc(N3CCN(C4CCCC4O)CC3)c2c1]

The title compound was prepared as described for 2-[(2-cyclopropyl-4-{2-(2-methoxy-phenyl)-methyl-amino]-cyclopentylamino}-quinazolin-6-yl)-methyl-amino]-ethanol.
¹HNMR (400 MHz, CD₃OD): δ=7.61 (d, J=9.2 Hz, 1H), 7.36 (dd, J=9.2, 2.4 Hz, 1H), 6.75 (d, J=2.8 Hz, 1H), 4.15-4.12 (m, 1H), 3.63 (brs, 4H), 3.36-3.32 (m, 2H), 2.99-2.64 (m, 4H), 2.54-2.51 (m, 1H), 2.12-2.08 (m, 1H), 1.99-1.93 (m, 2H), 1.73-1.43 (m, 5H), 1.12-1.10 (m, 1H), 0.97-0.95 (m, 2H), 0.95-0.93 (m, 5H). MS: m/z 410.2 (M+H⁺)

Example 142: Preparation of 2-(4-{2-cyclopropyl-6-[methyl-(2-morpholin-4-yl-ethyl)-amino]-quinazolin-4-yl}-piperazin-1-yl)-cyclopentanol

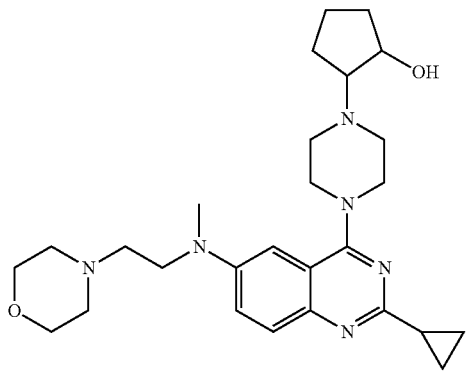 [SMILES: CN(CCN1CCOCC1)c1ccc2nc(C3CC3)nc(N3CCN(C4CCCC4O)CC3)c2c1]

The title compound was prepared as described for 2-[(2-cyclopropyl-4-{2-[(2-methoxy-phenyl)-methyl-amino]-cyclopentylamino}-quinazolin-6-yl)-methyl-amino]-ethanol.
¹HNMR (400 MHz, CD₃OD): δ=7.72 (d, J=9.2 Hz, 1H), 7.52 (dd, J=9.2, 2.4 Hz, 1H), 6.91 (d, J=2.8 Hz, 1H), 4.19-4.17 (m, 1H), 3.87 (brs, 4H), 3.73-3.65 (m, 6H), 3.10 (s, 3H), 3.00-2.85 (m, 4H), 2.67-2.56 (m, 7H), 2.13-1.97 (m, 3H), 1.75-1.53 (m, 4H), 1.20-1.07 (m, 4H). MS: m/z 481.2 (M+H⁺)

Example 143: Preparation of 4-[4-(2-methoxy-phenyl)-piperidin-1-yl]-2-phenyl-quinazolin-6-yl}-dimethyl-amine

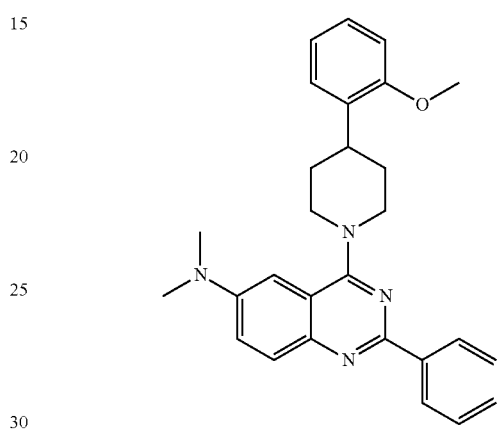

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=8.55 (d, J=6.4 Hz, 2H), 7.88 (d, J=9.2 Hz, 1H), 7.50-7.24 (m, 6H), 6.96-6.89 (m, 3H), 4.52 (d, J=12.0 Hz, 2H), 3.96 (s, 3H), 3.28-3.26 (m, 3H), 3.06 (s, 6H), 2.02 (bs, 4H). MS: m/z 439.2 (M+H⁺).

Example 144: Preparation of 2-({4-[4-(2-methoxyphenyl)-piperidin-1-yl]-2-phenyl-quinazolin-6-yl}-methyl-amino)-ethanol

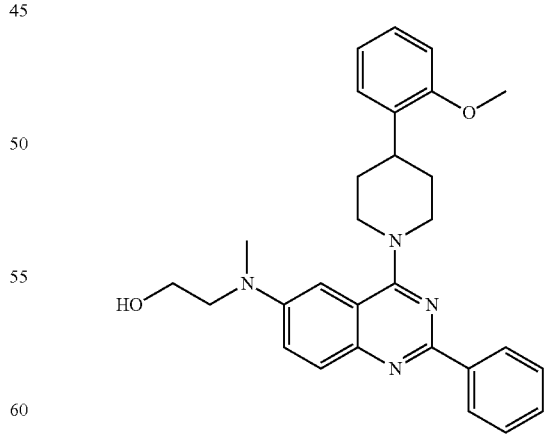

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=8.53 (d, J=7.2 Hz, 2H), 7.86 (d, J=8.8 Hz, 1H), 7.49-7.37 (m, 4H), 7.28-7.20 (m, 2H), 6.98-6.90 (m, 3H), 4.51 (d, J=12.4 Hz, 2H), 3.87 (brs, 5H), 3.58-3.56 (m, 2H), 3.34-3.23 (m, 3H), 3.04 (s, 3H), 2.03-1.98 (m, 4H). MS: m/z 469.2 (M+H⁺).

Example 145: Preparation of (2-methoxy-ethyl)-{4-[4-(2-methoxy-phenyl)-piperidin-1-yl]-2-phenyl-quinazolin-6-yl}-methyl-amine

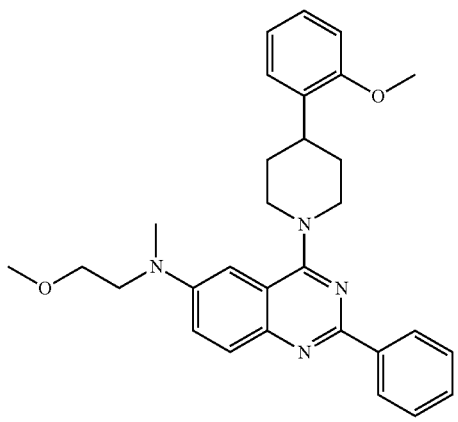 [SMILES: COCCN(C)c1ccc2nc(-c3ccccc3)nc(N3CCC(c4ccccc4OC)CC3)c2c1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=8.60 (d, J=6.6 Hz, 2H), 7.90 (d, J=8.4 Hz, 1H), 7.52-7.38 (m, 4H), 7.31-7.22 (m, 2H), 7.01-6.91 (m, 3H), 4.52 (d, J=12.9 Hz, 2H), 3.89 (s, 3H), 3.65 (s, 4H), 3.39-3.23 (m, 6H), 3.12 (s, 3H), 2.06-1.98 (m, 4H). MS: m/z 483.2 (M+H⁺).

Example 146: Preparation of {4-[4-(2-methoxy-phenyl)-piperidin-1-yl]-2-phenyl-quinazolin-6-yl}-methyl-propyl-amine

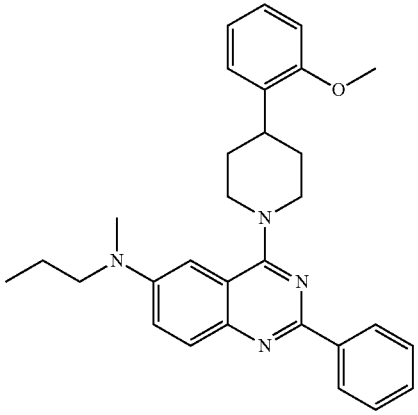 [SMILES: CCCN(C)c1ccc2nc(-c3ccccc3)nc(N3CCC(c4ccccc4OC)CC3)c2c1]

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=8.57 (d, J=6.4 Hz, 2H), 7.91 (d, J=6.8 Hz, 1H), 7.50-7.26 (m, 6H), 7.00-6.93 (m, 3H), 4.54 (d, J=11.2 Hz, 2H), 3.90 (s, 3H), 3.43-3.28 (m, 5H), 3.09 (s, 3H), 2.06 (brs, 4H), 1.71-1.70 (m, 2H), 1.00 (t, 3H). MS: m/z 467.2 (M+H⁺).

Example 147: Preparation of {4-[4-(2-methoxy-phenyl)-piperidin-1-yl]-2-phenyl-quinazolin-6-yl}-methyl-(2-morpholin-4-yl-ethyl)-amine

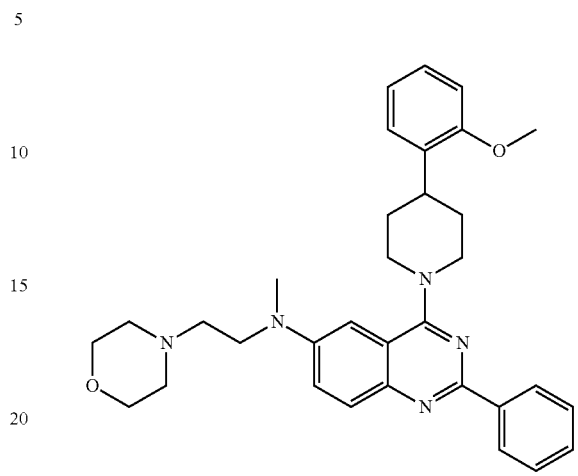

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (300 MHz, CDCl₃): δ=8.60 (d, J=6.6 Hz, 2H), 8.00 (d, J=9.2 Hz, 1H), 7.52-7.36 (m, 4H), 7.29-7.22 (m, 2H), 7.01-6.91 (m, 3H), 4.57 (d, J=12.6 Hz, 2H), 3.89 (s, 3H), 3.75-3.64 (m, 6H), 3.41-3.24 (m, 3H), 3.10 (s, 3H), 2.76-2.51 (m, 6H), 2.06-1.99 (m, 4H). MS: m/z 538.3 (M+H⁺).

Example 148: Preparation of {[2-cyclopropyl-4-(5-methoxy-3,4-dihydro-1H-isoquinolin-2-yl)-quinazolin-6-yl]-methyl-amino}-ethanol

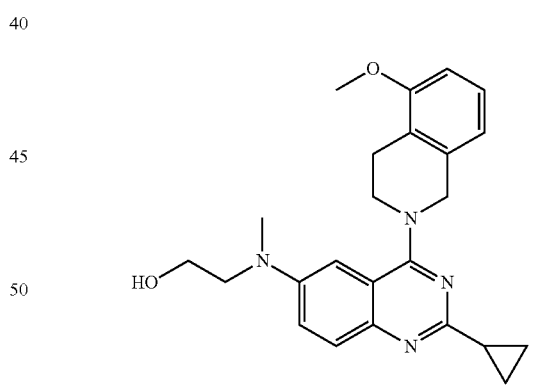

The title compound was prepared as described for 2-({2-cyclopropyl-4-[4-(2-dimethylamino-phenyl)-piperidin-1-yl]-quinazolin-6-yl}-methyl-amino)-ethanol. ¹H NMR (400 MHz, CDCl₃): δ=7.64 (d, J=8.8 Hz, 1H), 7.24-7.23 (m, 1H), 7.18-7.14 (m, 1H), 7.01 (s, 1H), 6.79 (d, J=7.6 Hz, 1H), 6.70 (d, J=8.0 Hz, 1H), 4.80 (brs, 2H), 3.91-3.88 (m, 4H), 3.83 (s, 3H), 3.57-3.54 (m, 2H), 3.09-3.07 (m, 2H), 3.05 (s, 3H), 2.21-2.17 (m, 1H), 1.17-1.16 (m, 2H), 0.98-0.95 (m, 2H). MS: m/z 405.2 (M+H⁺).

Example 149: Preparation of 2-{[2-cyclopropyl-4-(4-methoxy-1,3-dihydro-isoindol-2-yl)-quinazolin-6-yl]-methyl-amino}-ethanol

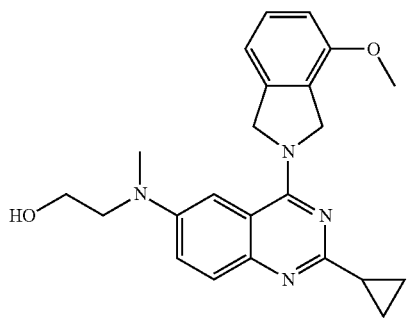 [SMILES: COc1cccc2c1CN(c1nc(C3CC3)nc3ccc(N(C)CCO)cc13)C2]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.82 (d, J=10.0 Hz, 1H), 7.42 (s, 1H), 7.33-7.29 (m, 2H), 7.01 (s, 1H), 6.92 (d, J=7.6 Hz, 1H), 6.79 (d, J=8.0 Hz, 1H), 5.22 (d, J=10.8 Hz, 2H), 3.95-3.89 (m, 2H), 3.87 (s, 3H), 3.59-3.57 (m, 2H), 3.09 (s, 3H), 2.42-2.38 (m, 1H), 1.25-1.22 (m, 2H), 1.06-1.04 (m, 2H). MS: m/z 391.2 (M+H$^+$).

Example 150: Preparation of 2-{[2-cyclopropyl-4-(6-methoxy-1,2,4,5-tetrahydro-benzo[d]azepin-3-yl)-quinazolin-6-yl]-methyl-amino}-ethanol

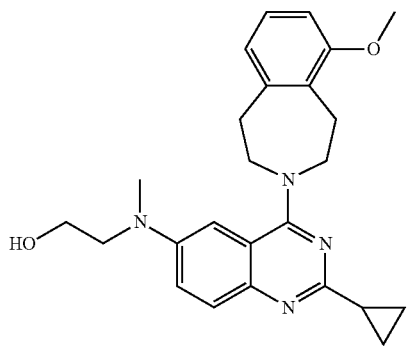 [SMILES: COc1cccc2c1CCN(c1nc(C3CC3)nc3ccc(N(C)CCO)cc13)CC2]

The title compound was prepared as described for 2-({2-cyclopropyl-4-[4-(2-dimethylamino-phenyl)-piperidin-1-yl]-quinazolin-6-yl}-methyl-amino)-ethanol. $^1$H NMR (300 MHz, CDCl$_3$): δ=$^1$H NMR (400 MHz, CDCl$_3$): δ=7.78 (d, J=9.0 Hz, 1H), 7.31-7.28 (m, 1H), 7.13-7.09 (m, 1H), 6.96 (s, 1H), 6.77 (d, J=8.0 Hz, 2H), 3.89-3.84 m, 6H), 3.82 (s, 3H), 3.57-3.54 (m, 2H), 3.27-3.24 (m, 2H), 3.16-3.13 (m, 2H), 3.06 (s, 3H), 2.20-2.18 (m, 1H), 1.16-1.12 (m, 2H), 0.98-0.95 (m, 2H). MS: m/z 419.2 (M+H$^+$).

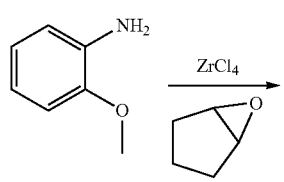

-continued

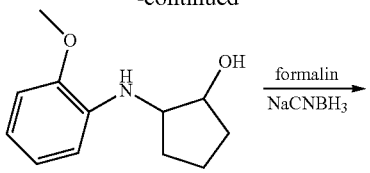

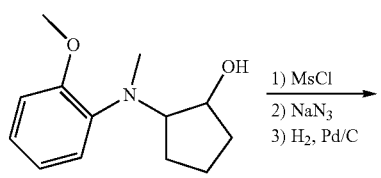

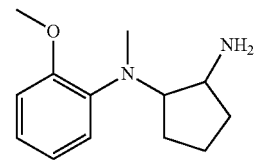

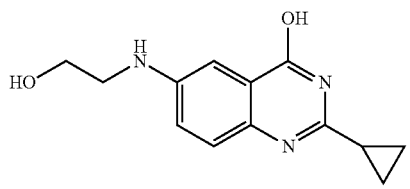

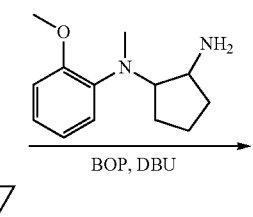

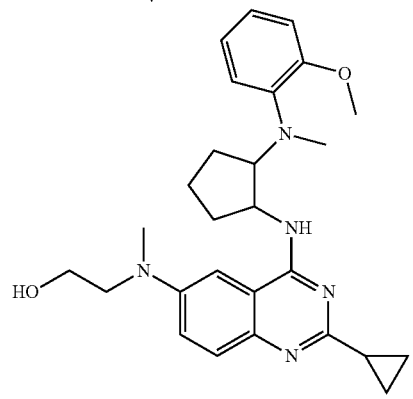

Example 151: Preparation of 2-[(2-cyclopropyl-4-{2-[(2-methoxy-phenyl)-methyl-amino]-cyclopentylamino}-quinazolin-6-yl)-methyl-amino]-ethanol

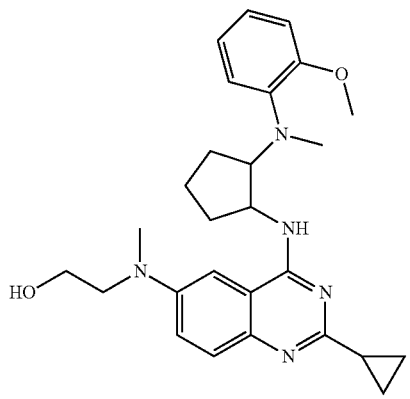 [SMILES: COc1ccccc1N(C)C1CCCC1Nc1nc(C2CC2)nc2ccc(N(C)CCO)cc12]

To a mixture of 6-oxa-bicyclo[3.1.0]hexane (2.0 g, 23.8 mmol) with 2-methoxy-phenylamine (2.34 g, 19.0 mmol) was added $ZrCl_4$ (500 mg), it was then stirred at r.t overnight. The resultant was diluted with EA (50 mL) and the resulting solid was filtered. The filtrate was concentrated in vacuum and the residue was purified by flash column (EA in PE: 0 to 30%) to afford 2-[(2-methoxy-phenyl)-methyl-amino]-cyclopentanol (2.2 g, yield: 53%) as a white solid.

The preparation of 2-((2-methoxyphenyl)(methyl)amino) cyclopentanol via reductive amination is similar to 2-cyclopropyl-6-[(2-hydroxy-ethyl)-methyl-amino]-quinazolin-4-ol.

To a solution of 2-[(2-methoxy-phenyl)-methyl-amino]-cyclopentanol (2.2 g, 9.95 mmol) in DCM was added methanesulfonyl chloride (1.24 g, 11 mmol) and the mixture was stirred at r.t. for 1 hour. The reaction was quenched with water (100 mL) and the mixture was extracted with EA (100 mL). The extracts were dried over $Na_2SO_4$. The organic layer was concentrated in vacuum and the crude for the next step without further purification.

The crude product was dissolved in DMF (40 mL) and then $NaN_3$ (715 mg, 11 mmol) was added. The reaction solution was heated to 90° C. and stirred overnight. The resultant was contracted directly to remove most of DMF. The remaining residue was then dissolved in MeOH (50 mL) and then Pd/C (500 mg) was added. It was degassed with $H_2$ for several times and stirred at r.t. under $H_2$ balloon pressure until LC/MS showed reaction was completed. The resultant was filttered to remove Pd/C and the filtrate was purified by flash column (EA im PE: 0 to 50%) to afford desired intermediate N-(2-methoxy-phenyl)-N-methyl-cyclopentane-1,2-diamine (1.1 g, yield: 50%) as a white solid.

To a solution of 6-bromo-2-cyclopropyl-quinazolin-4-ol (2 g, 7.6 mmol) in DMSO (20 mL) were added 2-aminoethanol (693 mg, 11.4 mmol), CuI (500 mg), proline (500 mg) and $Cs_2CO_3$ (6.4 g, 16.7 mmol). The mixture was stirred at 90° C. overnight under the protection of $N_2$. The resultant was purified by pre-HPLC to give 2-cyclopropyl-6-(2-hydroxy-ethylamino)-quinazolin-4-ol (1.4 g, yield: 75%) as a white solid.

To a solution of 2-cyclopropyl-6-(2-hydroxy-ethyl-amino)-quinazolin-4-ol (1.4 g, 5.7 mmol) in MeOH (20 mL) was added formalin (3 mL) and then $NaCNBH_3$ (28.5 mmol). The mixture was stirred at r.t. overnight. The resultant was concentrated to dryness and the residue was purified by flash column ($C_{18}$-silica ACN in water: 5% to 95%) to give 2-cyclopropyl-6-[(2-hydroxy-ethyl)-methyl-amino]-quinazolin-4-ol product (1.2 g, yield: 81%) as a white solid.

To a solution of N-(2-methoxy-phenyl)-N-methyl-cyclopentane-1,2-diamine (100 mg, 0.45 mmol) in ACN (20 mL) was added 2-cyclopropyl-6-[(2-hydroxy-ethyl)-methyl-amino]-quinazolin-4-ol (117 mg, 0.45 mmol), BOP (298 mg, 0.67 mmol) and DBU (0.5 mL). The mixture was stirred at room temperature overnight. The solvent was removed and the residue was dissolved in EA (50 mL). The mixture was washed with brine (30 mL×2). The organic layer was separated and dried over anhydrous $Na_2SO_4$ The solvent was removed and the residue was purified by pre-HPLC to give 2-[(2-cyclopropyl-4-{2-[(2-methoxy-phenyl)-methyl-amino]-cyclopentylamino}-quinazolin-6-yl)-methyl-amino]-ethanol (80 mg, yield: 38%) as a white solid. $^1$HNMR (400 MHz, $CD_3OD$): δ=7.38 (s, 2H), 6.86 (s, 1H), 6.77 (d, J=7.6 Hz, 1H), 6.63-6.59 (m, 2H), 6.47-6.43 (m, 1H), 4.87-4.81 (m, 1H), 4.10-4.08 (m, 1H), 3.66-3.64 (m, 5H), 3.51-3.48 (m, 2H), 2.99 (s, 3H), 2.65 (s, 3H), 2.04-1.99 (m, 2H), 1.92-1.88 (m, 1H), 1.98-1.78 (m, 2H), 1.67-1.63 (m, 1H), 1.29-1.14 (m, 4H). MS: m/z 462.2 (M+H$^+$).

Example 152: Preparation of 2-cyclopropyl-N4-{2-[(2-methoxy-phenyl)-methyl-amino]-cyclopentyl}-N6-methyl-N6-propyl-quinazoline-4,6-diamine

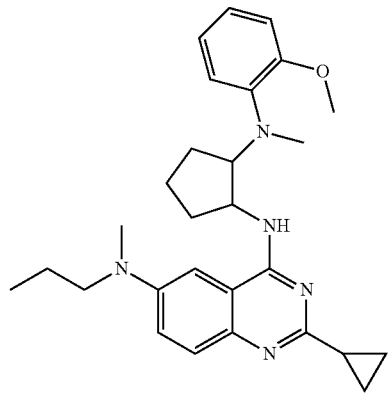 [SMILES: CCCN(C)c1ccc2nc(C3CC3)nc(NC3CCCC3N(C)c3ccccc3OC)c2c1]

The title compound was prepared as described for 2-[(2-cyclopropyl-4-{2-[(2-methoxy-phenyl)-methyl-amino]-cyclopentylamino}-quinazolin-6-yl)-methyl-amino]-ethanol.
$^1$H NMR (400 MHz, $CD_3OD$): δ=7.49 (d, J=9.2 Hz, 1H), 7.31 (dd, J=9.2, 2.4 Hz, 1H), 6.90 (d, J=7.6 Hz, 1H), 6.81 (d, J=4.0 Hz, 2H), 6.71 (d, J=2.4 Hz, 1H), 6.65-6.61 (m, 1H), 4.78-4.71 (m, 1H), 4.07-4.03 (m, 1H), 3.79 (s, 3H), 3.40-3.37 (m, 2H), 2.97 (s, 3H), 2.79 (s, 3H), 2.23-2.19 (m, 1H), 2.06-2.02 (m, 1H), 1.93-1.76 (m, 4H), 1.67-1.60 (m, 3H), 1.19-1.11 (m, 2H), 0.97-0.94 (m, 5H). MS: m/z 460.3 (M+H$^+$).

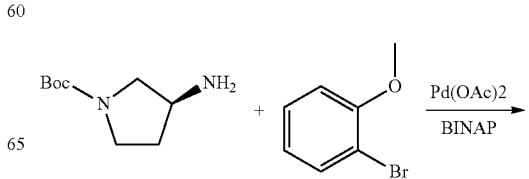

-continued

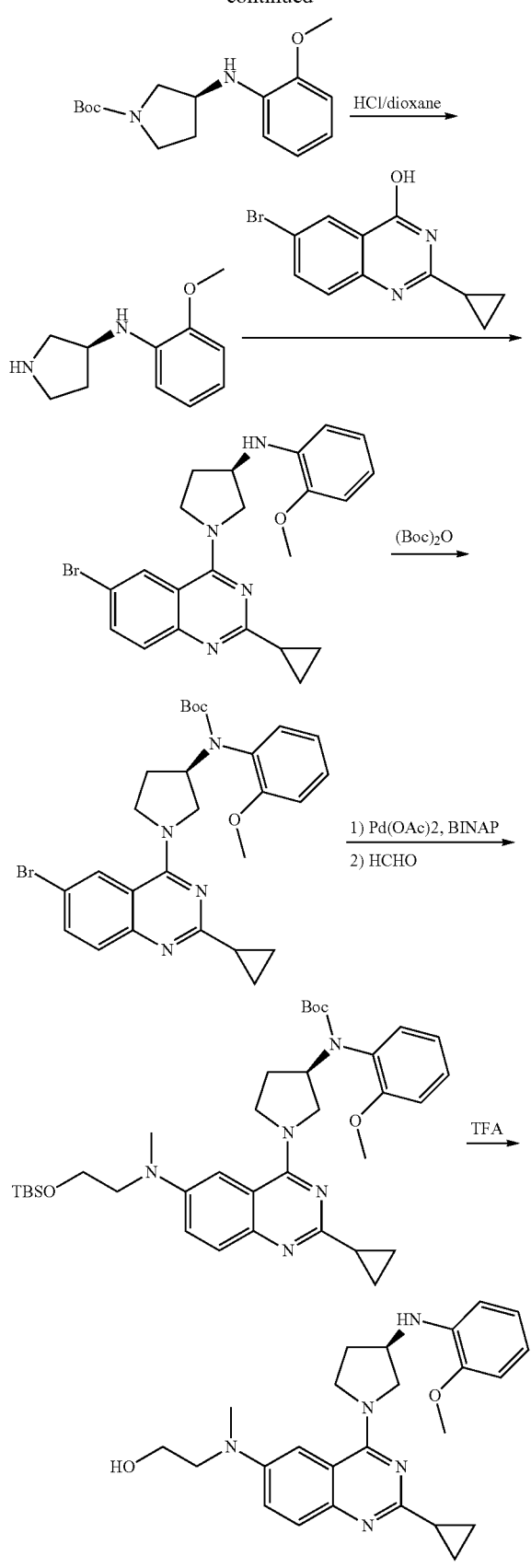

Example 153: Preparation of 2-({2-cyclopropyl-4-[3-(2-methoxy-phenylamino)-pyrrolidin-1-yl]-quinazolin-6-yl}-methyl-amino)-ethanol

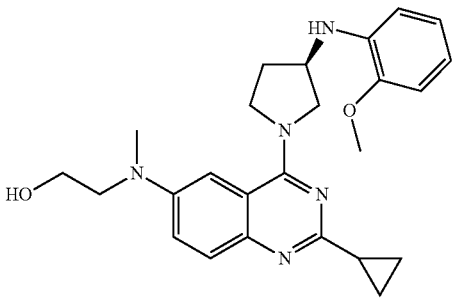 [SMILES: COc1ccccc1N[C@@H]1CCN(c2nc(C3CC3)nc3ccc(N(C)CCO)cc23)C1]

To a mixture of 3-amino-pyrrolidine-1-carboxylic acid tert-butyl ester (1.0 g, 5.37 mmol), 1-bromo-2-methoxy-benzene (1.2 g, 6.45 mmol) and Cs$_2$CO$_3$ (3.5 g, 10.8 mmol) in anhydrous toluene (50 mL) was added BINAP (673 mg, 1.1 mmol) and Pd(OAc)$_2$ (121 mg, 0.54 mmol). The mixture was refluxed under N$_2$ for 16 h. The mixture was cooled to rt, diluted with DCM (15 mL) and filtered, the filtraction was concentrated, purified by silica gel chromatography (from PE to PE/EA=50/1-20/1-5/1) to give (761 mg, yield: 48%) of 3-(2-methoxy-phenylamino)-pyrrolidine-1-carboxylic acid tert-butyl ester as yellow liquid. $^1$H NMR (400 MHz, CDCl$_3$): δ=6.89-6.86 (m, 1H), 6.79-6.77 (m, 1H), 6.71-6.69 (m, 1H), 6.62-6.60 (m, 1H), 4.29-4.28 (m, 1H), 4.04-4.01 (m, 1H), 3.84 (s, 3H), 3.76-3.67 (m, 1H), 3.54- 3.44 (m, 2H), 3.30-3.20 (m, 1H), 2.24-2.15 (m, 1H), 1.93-1.89 (m, 1H), 1.46 (s, 9H).

To a solution of 3-(2-methoxy-phenylamino)-pyrrolidine-1-carboxylic acid tert-butyl ester (761 mg, 2.6 mmol) in EA (10 mL) was added HCl/dioxane (10 mL), then the mixture was stirred at rt for 5 h. The mixture was concentrated to give (2-methoxy-phenyl)-pyrrolidin-3-yl-amine hydrochloride (700 mg, yield: 100%) as a green solid.

A suspension of [1-(6-bromo-2-cyclopropyl-quinazolin-4-yl)-pyrrolidin-3-yl]-(2-methoxy-phenyl)-amine (320 mg, 0.73 mmol) in (Boc)$_2$O (10 mL) was stirred at 90° C. overnight. The reaction mixture was concentrated and purified by silica gel chromatography (from PE to PE/EA=20/1-10/1-5/1) to give crude product, then further purified by prep-HPLC to afford (364 mg, yield: 92%) of [1-(6-bromo-2-cyclopropyl-quinazolin-4-yl)-pyrrolidin-3-yl]-(2-methoxy-phenyl) carbamic acid tert-butyl ester as white solid. $^1$HNMR (400 MHz, CDCl$_3$): δ=8.09-8.04 (m, 1H), 7.67-7.65 (m, 1H), 7.60-7.56 (m, 1H), 7.29-7.24 (m, 1H), 7.05-7.04 (m, 1H), 6.93-6.79 (m, 2H), 5.13-5.06 (m, 1H), 4.06-4.04 (m, 1H), 3.74- 3.58 (m, 5H), 2.25-2.23 (m, 1H), 1.61 (s, 4H), 1.31-1.29 (m, 9H), 1.11-1.05 (m, 2H), 0.96-0.91 (m, 2H).

To a solution of [1-(6-{[2-(tert-butyl-dimethyl-silanyloxy)-ethyl]-methyl-amino}-2-cyclopropyl-quinazolin-4-yl)-pyrrolidin-3-yl]-(2-methoxy-phenyl)-carbamic acid tert-butyl ester (50 mg, 0.08 mmol) in DCM (2 mL) was added TFA (2 mL), the reaction mixture was stirred at rt overnight. The reaction mixture was concentrated, purified by prep-HPLC (NH$_4$HCO$_3$) to afford (3.1 mg, yield: 30%) of 2-({2-cyclopropyl-4-[3-(2-methoxy-phenylamino)-pyrrolidin-1-yl]-quinazolin-6-yl}-methyl-amino)-ethanol as yellow solid. $^1$H NMR (400 MHz, CDCl$_3$): δ=7.88 (d, J=8.4 Hz, 1H), 7.31 (s, 1H), 7.25-7.23 (m, 1H), 6.90-6.88 (m, 1H), 6.81-6.74 (m, 2H), 6.66 (d, J=7.2 Hz, 1H), 4.33-4.20 (m, 5H), 3.95-3.90 (m, 1H), 3.84-3.82 (m, 5H), 3.52-3.49 (m, 2H), 3.01 (s, 3H), 2.37-2.02 (m, 4H), 1.19-0.88 (m, 4H). MS: m/z 434.2 (M+H$^+$)

Example 154: Preparation of 2-((2-cyclopropyl-4-((1-(2-methoxyphenyl)pyrrolidin-3-yl)amino)quinazolin-6-yl)(methyl)amino)ethanol

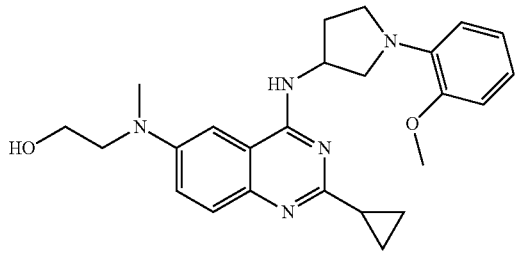 [SMILES: COc1ccccc1N1CCC(Nc2nc(C3CC3)nc3ccc(N(C)CCO)cc23)C1]

The title compound was prepared as described for 2-({2-cyclopropyl-4-[3-(2-methoxy-phenylamino)-pyrrolidin-1-yl]-quinazolin-6-yl}-methyl-amino)-ethanol. $^1$H NMR (400 MHz, CDCl$_3$): δ=7.58 (d, J=9.2 Hz, 1H), 7.18 (dd, J=9.2, 2.4 Hz, 1H), 6.92-6.78 (m, 5H), 6.31 (brs, 1H), 4.92-4.88 (m, 1H), 3.85-3.80 (m, 5H), 3.63-3.52 (m, 4H), 3.46-3.40 (m, 1H), 3.27-3.23 (m, 1H), 3.00 (s, 3H), 2.48- 2.42 (m, 1H), 2.19-2.08 (m, 2H), 1.27-1.23 (m, 2H), 0.98-0.93 (m, 2H). MS: m/z 434.2 (M+H$^+$)

Example 155: Preparation of 2-cyclopropyl-N4-(1-(2-methoxyphenyl)pyrrolidin-3-yl)-N6-methyl-N6-propylquinazoline-4,6-diamine

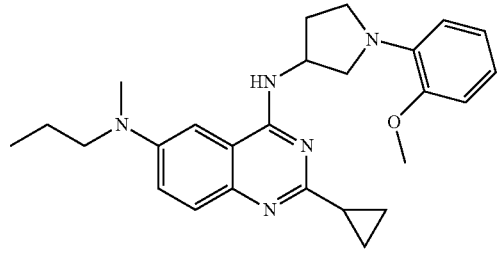 [SMILES: CCCN(C)c1ccc2nc(C3CC3)nc(NC3CCN(c4ccccc4OC)C3)c2c1]

The title compound was prepared as described for 2-({2-cyclopropyl-4-[3-(2-methoxy-phenylamino)-pyrrolidin-1-yl]-quinazolin-6-yl}-methyl-amino)-ethanol. $^1$H NMR (400 MHz, CDCl$_3$): δ=7.82-7.76 (m, 1H), 7.29-7.26 (m, 2H), 6.94-6.80 (m, 4H), 6.49 (brs, 1H), 4.94-4.90 (m, 1H), 3.87 (s, 3H), 3.63-3.58 (m, 2H), 3.50-3.47 (m, 1H), 3.36 (t, J=11.6 Hz, 2H), 3.27-3.23 (m, 1H), 3.01 (s, 3H), 2.50-2.42 (m, 1H), 2.08-2.05 (m, 1H), 1.67-1.58 (m, 3H), 1.27-1.23 (m, 2H), 0.98-0.95 (m, 2H), 0.93 (t, J=7.6 Hz, 3H). MS: m/z 432.2 (M+H$^+$).

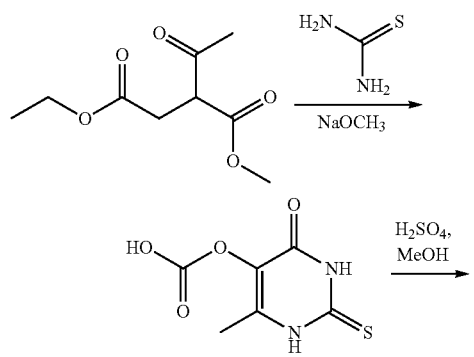

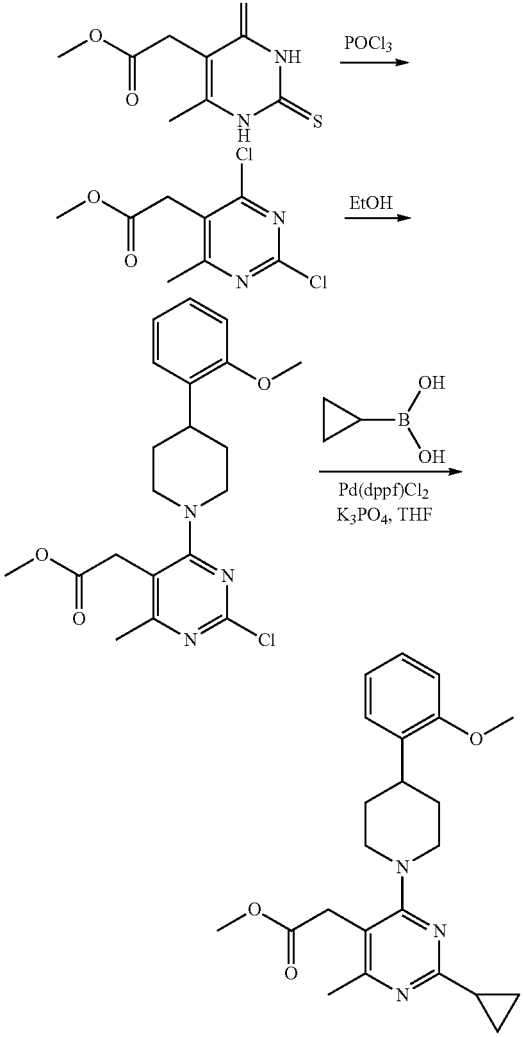

Example 156: Preparation of Methyl 2-(2-cyclopropyl-4-(4-(2-methoxyphenyl)piperidin-1-yl)-6-methylpyrimidin-5-yl)acetate

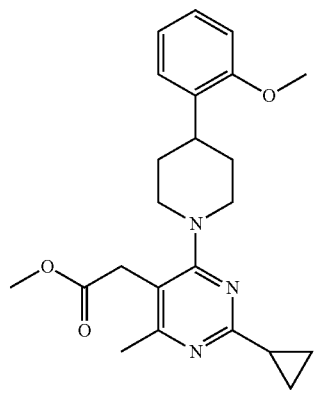 [SMILES: COC(=O)Cc1c(C)nc(C2CC2)nc1N1CCC(c2ccccc2OC)CC1]

Thiourea (7.1 g, 93.5 mmol) and 2-acetyl-succinic acid 4-ethyl ester 1-methyl ester (20.0 g, 92.6 mmol) were added at room temperature to a solution of sodium (4.3 g, 186.9 mmol) in methanol (300 mL) and the mixture is stirred under N$_2$ reflux for 18 h. After cooling, the precipitate was filtered off and added with stirring to a HCl (12 N) at 0° C. The white precipitate was filtered, washed with water and dried to give of title compound as a white power (7.0 g, yield: 37%). MS: m/z 200.7 (M+H$^+$).

To a stirred solution of (6-methyl-4-oxo-2-thioxo-1,2,3,4-tetrahydro-pyrimidin-5-yl)-acetic acid (7.0 g, 35.0 mmol) in methanol (150 mL) was added H$_2$SO$_4$ (7.0 mL). The mixture was then heated to reflux overnight. The reaction was cooled to room temperature and was concentrated. The residue was washed with water and EA. and the solid was evaporated in vacuum to dryness to afford (6.1 g, yield: 81.3%) of (6-methyl-4-oxo-2-thioxo-1,2,3,4-tetrahydro-pyrimidin-5-yl)-acetic acid methyl ester as a white solid.

To a stirred solution of (6-methyl-4-oxo-2-thioxo-1,2,3,4-tetrahydro-pyrimidin-5-yl)-acetic acid methyl ester (6.1 g, 28.5 mmol) in POCl$_3$(100 mL). The mixture was then heated to reflux for 2 days. The reaction was cooled to room temperature and was concentrated in vacuum. and added into ice water (150 mL) dropwise. The aqueous mixture was neutralized with sat. NaHCO$_3$ to pH=8 and extracted with EA (150 mL×2). The combined organic layers were washed with brine (30 mL×2), dried over anhydrous Na$_2$SO$_4$ and filtered. The filtrate was evaporated in vacuum to residue, which was purified by silica gel chromatography (from PE to PE/EA=5/1) to give (2.7 g, yield: 39.1%) of (2,4-dichloro-6-methyl-pyrimidin-5-yl)-acetic acid methyl ester as yellow solid. MS: m/z 235.1 (M+H$^+$).

To a stirred solution of (2,4-dichloro-6-methyl-pyrimidin-5-yl)-acetic acid methyl ester (1.15 g, 4.9 mmol) in ethanol (20 mL) was added DIEA (1.26 g, 9.8 mmol) and 4-(2-Methoxy-phenyl)-piperidine (1.0 g, 4.4 mmol). The mixture was stirred at room temperature for overnight. The mixture was evaporated in vacuum to residue, which was purified by silica gel chromatography (PE/EA from 10/1 to 5/1) to give 950 mg (yield: 50%) of {2-chloro-4-[4-(2-methoxy-phenyl)-piperidin-1-yl]-6-methyl-pyrimidin-5-yl}-acetic acid methyl ester (450 mg) MS Calculated 389.1, observed [M+H]=390.2. and {4-chloro-2-[4-(2-methoxy-phenyl)-piperidin-1-yl]-6-methyl-pyrimidin-5-yl}-acetic acid methyl ester (400 mg) as yellow solid. $^1$H NMR (400 MHz, CDCl$_3$): δ=7.31-7.28 (m, 1H), 7.24-7.19 (m, 1H), 6.97-6.91 (m, 2H), 4.95 (d, J=13.6 Hz, 1H), 3.90 (s, 3H), 3.77 (s, 3H), 3.72 (s, 2H), 3.33-3.21 (m, 1H), 3.00 (t, J=12.0 Hz, 2H), 2.40 (s, 3H), 1.93-1.90 (m, 2H), 1.91-1.63 (m, 2H). MS: m/z 390.5 (M+H$^+$)

To a mixture of {2-chloro-4-[4-(2-methoxy-phenyl)-piperidin-1-yl]-6-methyl-pyrimidin-5-yl}-acetic acid methyl ester (500 mg, 1.3 mmol), cyclopropane boronic acid (280 mg, 3.25 mmol) and K$_3$PO$_4$ (827 mg, 3.9 mmol) in THF (30 mL) was added Pd(dppf)Cl$_2$ (150 mg, 0.18 mmol). The mixture was stirred at 90° C. under N$_2$ for 18 h, cooled to room temperature and evaporated under reduced pressure to dryness. The residue was diluted with EA (200 mL) and washed with water, dried over anhydrous Na$_2$SO$_4$, filtered. The filtrate was evaporated in vacuum to residue, which was purified by silica gel chromatography (from PE to PE/EA=20/1) to give (210 mg, yield: 40%) of {2-cyclopropyl-4-[4-(2-methoxy-phenyl)-piperidin-1-yl]-6-methyl-pyrimidin-5-yl}-acetic acid methyl ester as yellow solid. $^1$H NMR (300 MHz, CDCl$_3$): δ=7.28-7.18 (m, 2H), 6.95 (t, J=7.6 Hz, 1H), 6.88 (d, J=8.0 Hz, 1H), 3.84 (s, 3H), 3.74 (s, 3H), 3.65-3.62 (m, 3H), 3.19-3.11 (m, 1H), 2.90 (t, J=9.0 Hz, 1H), 2.34 (s, 3H), 2.13-2.05 (m, 1H), 1.90-1.72 (m, 4H), 1.09-0.95 (m, 4H). MS: m/z 396.3 (M+H$^+$).

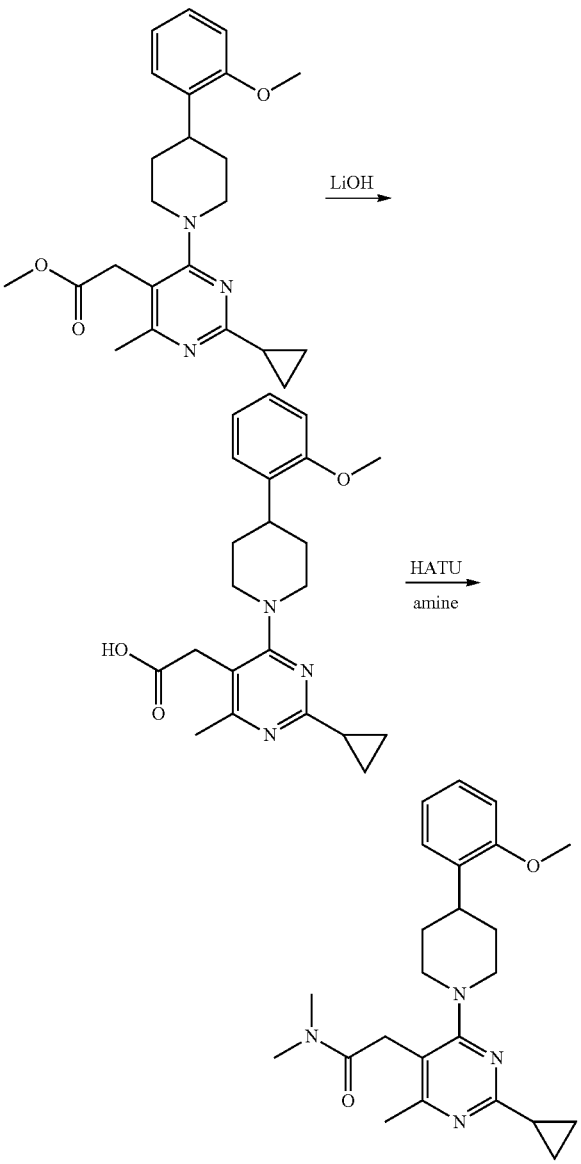

Example 157: Preparation of 2-{2-cyclopropyl-4-[4-(2-methoxy-phenyl)-piperidin-1-yl]-6-methyl-pyrimidin-5-yl}-N,N-dimethyl-acetamide

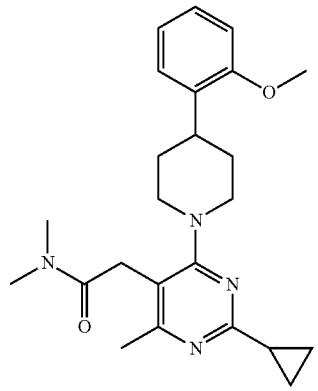 [SMILES: COc1ccccc1C1CCN(c2nc(C3CC3)nc(C)c2CC(=O)N(C)C)CC1]

A mixture of {2-cyclopropyl-4-[4-(2-methoxy-phenyl)-piperidin-1-yl]-6-methyl-pyrimidin-5-yl}-acetic acid methyl ester (1.0 g, 6.4 mmol) in THF (10 mL), and LiOH (0.61 g, 25.6 mmol) in water (2 mL) was added dropwise. The reaction mixture was stirred at room temperature overnight. The mixture was acidified with 1N HCl to pH=2. The suspension was filtered and the cake was washed with water (10 mL×2), then evaporated in vacuum to dryness to give (130 mg, yield: 48%) of {2-cyclopropyl-4-[4-(2-methoxy-phenyl)-piperidin-1-yl]-6-methyl-pyrimidin-5-yl}-acetic acid as yellow solid.

To a stirred solution of {2-cyclopropyl-4-[4-(2-methoxy-phenyl)-piperidin-1-yl]-6-methyl-pyrimidin-5-yl}-acetic acid (60 mg, 0.15 mmol) in DMF (2 mL) was added HATU (90 mg, 0.24 mmol) and dimethyl-amine (0.15 mL, 0.3 mmol). The mixture was stirred at room temperature overnight. The mixture was evaporated in vacuum to residue, which was purified by pre-HPLC (MeCN/H$_2$O from 5/100 to 95/100) to give (30 mg, yield: 47%) of 2-{2-cyclopropyl-4-[4-(2-methoxy-phenyl)-piperidin-1-yl]-6-methyl-pyrimidin-5-yl}-N,N-dimethyl-acetamide as a white solid. $^1$H NMR (400 MHz, CDCl$_3$): δ=7.26-7.21 (m, 2H), 6.98 (t, J=7.2 Hz, 1H), 6.91 (d, J=8.4 Hz, 1H), 3.87 (s, 3H), 3.71-3.60 (m, 4H), 3.24-3.11 (m, 4H), 3.22-2.95 (m, 5H), 2.53 (s, 3H), 2.14-2.09 (m, 1H), 1.92 (d, J=11.2 Hz, 2H), 1.80-1.76 (m, 2H), 1.13-0.95 (m, 4H). MS: m/z 409.3 (M+H$^+$)

Example 158: Preparation of 2-{2-cyclopropyl-4-[4-(2-methoxy-phenyl)-piperidin-1-yl]-6-methyl-pyrimidin-5-yl}-N-methyl-N-propyl-acetamide Example 159: Preparation of 2-{2-cyclopropyl-4-[4-(2-methoxy-phenyl)-piperidin-1-yl]-6-methyl-pyrimidin-5-yl}-N-(2-hydroxy-ethyl)-N-methyl-acetamide

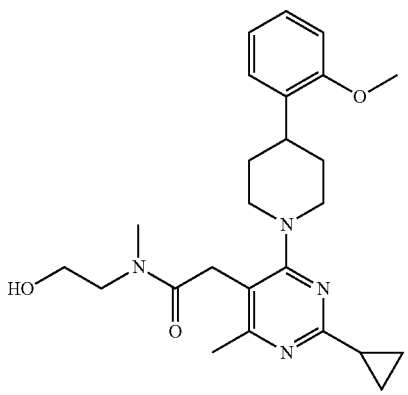

The title compound was prepared as described for 2-{2-cyclopropyl-4-[4-(2-methoxy-phenyl)-piperidin-1-yl]-6-methyl-pyrimidin-5-yl}-N,N-dimethyl-acetamide. $^1$H NMR (400 MHz, CDCl$_3$): δ=7.29-7.24 (m, 2H), 7.00-6.90 (m, 2H), 387-3.79 (m, 5H), 3.66-3.59 (m, 5H), 3.19 (s, 3H), 3.09-2.96 (m, 3H), 2.35 (s, 3H), 2.13-2.10 (m, 1H), 1.93-1.90 (m, 2H), 1.82-1.74 (m, 3H), 1.17-1.13 (m, 2H), 0.97-0.92 (m, 2H). MS: m/z 4329.3 (M+H$^+$)

Example 160: Preparation of 2-{2-cyclopropyl-4-[4-(2-methoxy-phenyl)-piperidin-1-yl]-6-methyl-pyrimidin-5-yl}-1-phenyl-ethanone

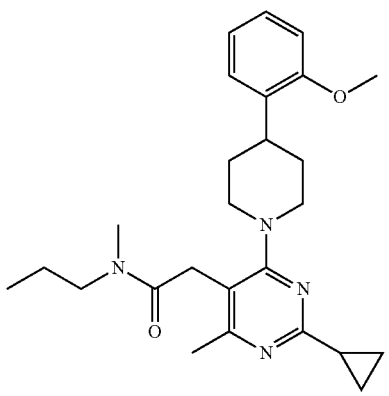 [SMILES: CCCN(C)C(=O)Cc1c(C)nc(C2CC2)nc1N1CCC(c2ccccc2OC)CC1]

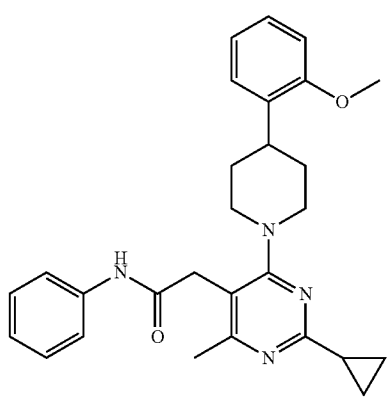 [SMILES: COc1ccccc1C1CCN(c2nc(C3CC3)nc(C)c2CC(=O)Nc2ccccc2)CC1]

The title compound was prepared as described for 2-{2-cyclopropyl-4-[4-(2-methoxy-phenyl)-piperidin-1-yl]-6-methyl-pyrimidin-5-yl}-N,N-dimethyl-acetamide. $^1$H NMR (400 MHz, CDCl$_3$): δ=7.25-7.22 (m, 2H), 6.98 (t, J=7.6 Hz, 1H), 6.91 (d, J=8.4 Hz, 1H), 3.87 (s, 3H), 3.67-3.62 (m, 4H), 3.44-3.32 (m, 2H), 3.18-3.11 (m, 3H), 3.02-2.95 (m, 3H), 2.35 (s, 3H), 2.13-2.09 (m, 1H), 1.92-1.55 (m, 6H), 1.12-1.10 (m, 2H), 0.98-0.88 (m, 4H). MS: m/z 437.3 (M+H$^+$)

The title compound was prepared as described for 2-{2-cyclopropyl-4-[4-(2-methoxy-phenyl)-piperidin-1-yl]-6-methyl-pyrimidin-5-yl}-N,N-dimethyl-acetamide. $^1$H NMR (400 MHz, CDCl$_3$): δ=8.04 (brs, 1H), 7.48 (d, J=8.0 Hz, 2H), 7.36-7.31 (m, 2H), 7.26-7.12 (m, 3H), 6.98 (t, J=7.6 Hz, 1H), 6.92 (d, J=8.4 Hz, 1H), 3.86 (s, 3H), 3.74-3.70 (m, 4H), 3.20-3.09 (m, 3H), 2.53 (s, 3H), 2.17-2.14 (m, 1H), 2.05-1.89 (m, 4H), 1.17-1.14 (m, 2H), 1.05-1.02 (m, 2H). MS: m/z 457.2 (M+H$^+$)

Example 161: Preparation of {4-cyclopropyl-2-[4-(2-methoxy-phenyl)-piperidin-1-yl]-6-methyl-pyrimidin-5-yl}-acetic acid methyl ester

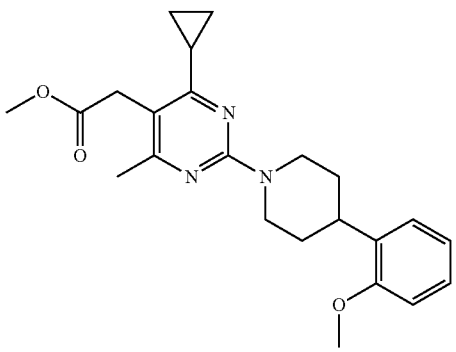 [SMILES: COC(=O)Cc1c(C)nc(N2CCC(c3ccccc3OC)CC2)nc1C1CC1]

The title compound was prepared as described for 2-{2-cyclopropyl-4-[4-(2-methoxy-phenyl)-piperidin-1-yl]-6-methyl-pyrimidin-5-yl}-N,N-dimethyl-acetamide. $^1$H NMR (400 MHz, CDCl$_3$): δ=7.25-7.19 (m, 2H), 6.96 (t, J=7.6 Hz, 1H), 6.92 (d, J=8.0 Hz, 1H), 4.94 (d, J=13.2 Hz, 2H), 3.89 (s, 3H), 3.74-3.62 (m, 5H), 3.26-3.20 (m, 1H), 2.94-2.88 (m, 2H), 2.41 (s, 3H), 2.03-1.99 (m, 1H), 1.91-1.88 (m, 2H), 1.71-1.61 (m, 2H), 1.17-1.13 (m, 2H), 0.97-0.92 (m, 2H). MS: m/z 396.2 (M+H$^+$)

Example 162: Preparation of 2-{4-cyclopropyl-2-[4-(2-methoxy-phenyl)-piperidin-1-yl]-6-methyl-pyrimidin-5-yl}-N-methyl-N-propyl-acetamide

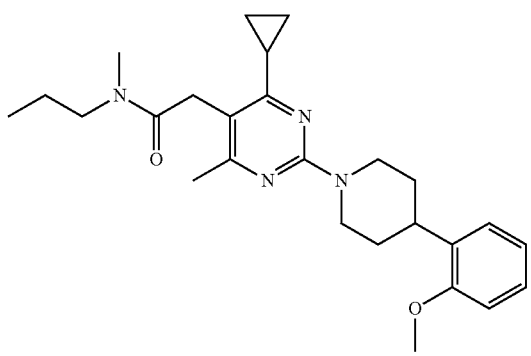 [SMILES: CCCN(C)C(=O)Cc1c(C)nc(N2CCC(c3ccccc3OC)CC2)nc1C1CC1]

The title compound was prepared as described in example 2-{2-cyclopropyl-4-[4-(2-methoxy-phenyl)-piperidin-1-yl]-6-methyl-pyrimidin-5-yl}-N,N-dimethyl-acetamide. $^1$H NMR (400 MHz, CDCl$_3$): δ=7.24-7.20 (m, 2H), 6.97 (t, J=7.6 Hz, 1H), 6.91 (d, J=8.0 Hz, 1H), 4.93 (d, J=13.2 Hz, 2H), 3.89 (s, 3H), 3.73 (d, J=10.0 Hz, 1H), 3.45-3.40 (m, 2H), 3.26-3.20 (m, 1H), 3.15-3.01 (m, 3H), 2.90 (t, J=12.0 Hz, 2H), 2.33 (s, 3H), 1.89-1.85 (m, 3H), 1.73-1.58 (m, 4H), 1.17-0.88 (m, 7H). MS: m/z 437.3 (M+H$^+$)

Example 163: Preparation of 2-{4-cyclopropyl-2-[4-(2-methoxy-phenyl)-piperidin-1-yl]-6-methyl-pyrimidin-5-yl}-N-(2-hydroxy-ethyl)-N-methyl-acetamide

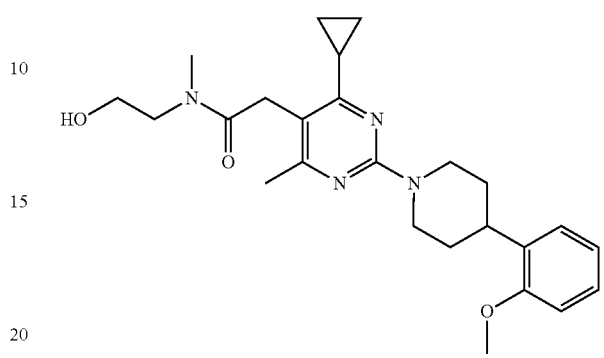

The title compound was prepared as described in example 2-{2-cyclopropyl-4-[4-(2-methoxy-phenyl)-piperidin-1-yl]-6-methyl-pyrimidin-5-yl}-N,N-dimethyl-acetamide. $^1$H NMR (400 MHz, CDCl$_3$): δ=7.24-7.19 (m, 2H), 6.96 (t, J=7.6 Hz, 1H), 6.91 (d, J=8.0 Hz, 1H), 4.93 (d, J=13.2 Hz, 2H), 3.89-3.77 (m, 7H), 3.66 (t, J=4.8 Hz, 2H), 3.25-3.22 (m, 4H), 2.90 (t, J=12.6 Hz, 2H), 2.34 (s, 3H), 1.90-1.63 (m, 5H), 1.17-1.15 (m, 2H), 0.94-0.89 (m, 2H). MS: m/z 439.3 (M+H$^+$)

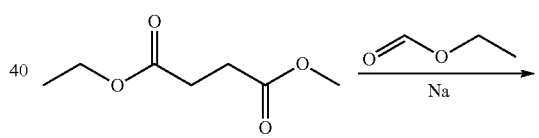

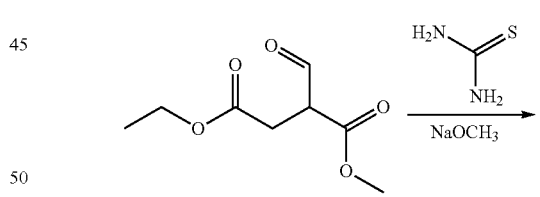

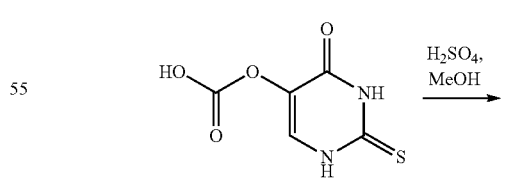

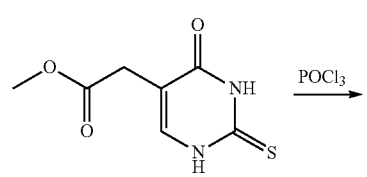

263
-continued

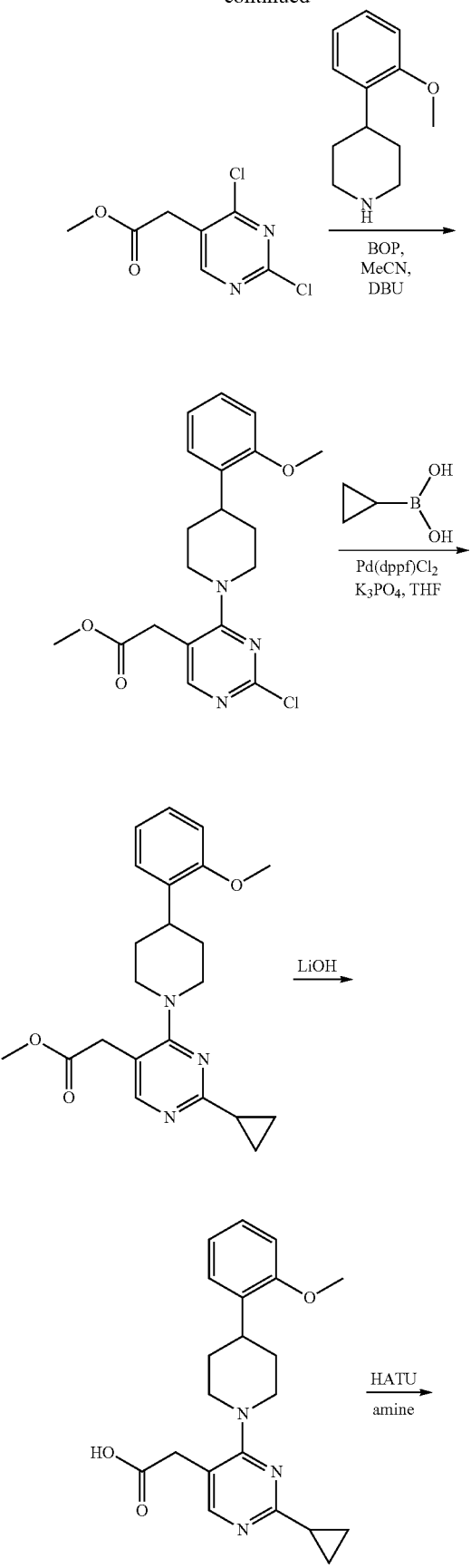

264
-continued

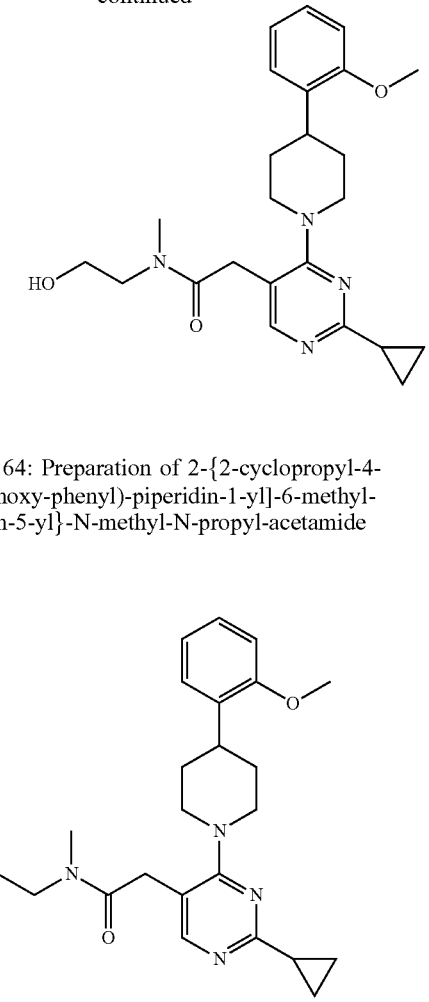

Example 164: Preparation of 2-{2-cyclopropyl-4-[4-(2-methoxy-phenyl)-piperidin-1-yl]-6-methyl-pyrimidin-5-yl}-N-methyl-N-propyl-acetamide To a stirred solution of sodium (7.0 g, 304 mmol) in diethyl ether (400 mL) was added Succinic acid ethyl ester methyl ester (50 g, 287 mmol) and formic acid ethyl ester (36.1 g, 488 mmol). The mixture was refluxed for 5 h. After the cooling to room temperature. Water was added to the mixture until the sodium sat was dissolved completely and aqueous layer was separated. The aqueous layer was neutralizied by 6 M HCl and extrate with diethyl ether. The extracts were washed with sat. $NaHCO_3$, dried over anhydrous $Na_2SO_4$ and filtered. The filtrate was evaporated in vacuum to residue, which was used directly next step without further purification.

Thiourea (19.7 g, 259 mmol) and 2-formyl-succinic acid 4-ethyl ester 1-methyl ester (56 g, 259 mmol) were added at room temperature to a solution of sodium (12 g, 518 mmol) in methanol (400 mL) and the mixture was stirred under $N_2$ reflux for 18 h. After cooling, the precipitate was filtered off and added with stirring to a HCl (12 N) at 0° C. The white precipitate was filtered, washed with water and dried to give of title compound (4-oxo-2-thioxo-1,2,3,4-tetrahydro-pyrimidin-5-yl)-acetic acid (25 g, yield: 35%) as a white power.

To a stirred solution of (4-oxo-2-thioxo-1,2,3,4-tetrahydro-pyrimidin-5-yl)-acetic acid (25 g, 134.4 mmol) in methanol (300 mL) was added $H_2SO_4$ (15 mL). The mixture was then heated to reflux overnight. The reaction was cooled to room temperature and was concentrated. The residue was washed with water and EA. and the solid was evaporated in vacuum to dryness to afford (13 g, yield: 52%) of (4-oxo-2-thioxo-1,2,3,4-tetrahydro-pyrimidin-5-yl)-acetic acid methyl ester as a white solid.

To a stirred solution of (4-oxo-2-thioxo-1,2,3,4-tetrahydro-pyrimidin-5-yl)-acetic acid methyl ester (13 g, 65 mmol) in POCl$_3$(100 mL). The mixture was then heated to reflux two days. The reaction was cooled to room temperature and was concentrated. and added into ice water (150 mL) dropwise. The aqueous mixture was neutralized with sat.NaHCO$_3$ to pH=8 and extracted with EA (200 mL×2). The combined organic layers were washed with brine (80 mL), dried over anhydrous Na$_2$SO$_4$ and filtered. The filtrate was evaporated in vacuum to residue, which was purified by silica gel chromatography (from PE to PE/EA=5/1) to give (7.9 g, yield: 55%) of (2,4-dichloro-6-methyl-pyrimidin-5-yl)-acetic acid methyl ester as yellow solid.

To a stirred solution of (2,4-dichloro-6-methyl-pyrimidin-5-yl)-acetic acid methyl ester (1.2 g, 5.5 mmol) in ethanol (20 mL) was added DIEA (1.24 g, 10.9 mmol) and 4-(2-methoxy-phenyl)-piperidine (1.12 g, 4.9 mmol). The mixture was stirred at room temperature for overnight. The mixture was evaporated in vacuum to residue, which was purified by silica gel chromatography (PE/EA from 10/1 to 5/1) to give (1.0 g, yield: 40%) of {2-chloro-4-[4-(2-methoxy-phenyl)-piperidin-1-yl]-6-methyl-pyrimidin-5-yl}-acetic acid methyl ester as yellow solid. MS Calculated 375.1, observed [M+H]=376.3.

To a mixture of {2-chloro-4-[4-(2-methoxy-phenyl)-piperidin-1-yl]-6-methyl-pyrimidin-5-yl}-acetic acid methyl ester (800 mg, 2.1 mmol), cyclopropane boronic acid (542 mg, 6.3 mmol) and K$_3$PO$_4$ (1.34 mg, 6.3 mmol) in THF (30 mL) was added Pd(dppf)Cl$_2$ (120 mg, 0.21 mmol). The mixture was stirred at 90° C. under N$_2$ for 18 h, cooled to room temperature and evaporated under reduced pressure to dryness. The residue was diluted with EA (200 mL) and washed with water, dried over anhydrous Na$_2$SO$_4$, filtered. The filtrate was evaporated in vacuum to residue, which was purified by silica gel chromatography (from PE to PE/EA=20/1) to give (180 mg, yield: 22.5%) of {2-cyclopropyl-4-[4-(2-methoxy-phenyl)-piperidin-1-yl]-6-methyl-pyrimidin-5-yl}-acetic acid methyl ester as yellow solid. $^1$H NMR (400 MHz, CDCl$_3$): δ=8.13 (s, 1H), 7.24-7.22 (m, 2H), 6.98 (t, J=7.6 Hz, 1H), 6.92 (d, J=7.6 Hz, 1H), 3.95-3.88 (m, 5H), 3.76 (s, 3H), 3.59 (s, 2H), 3.26-3.18 (m, 1H), 3.04 (t, J=12.0 Hz, 2H), 2.17-2.11 (m, 1H), 1.94-1.73 (m, 4H), 1.15-0.98 (m, 4H). MS: m/z 382.3 (M+H$^+$)

A mixture of {2-cyclopropyl-4-[4-(2-methoxy-phenyl)-piperidin-1-yl]-6-methyl-pyrimidin-5-yl}-acetic acid methyl ester (180 mg, 0.47 mmol) in THF (10 mL), and LiOH in water was added dropwise. The reaction mixture was stirred at room temperature for overnight. The aqueous mixture was acid with HCl to pH=2. The suspension was filtered and the cake was washed with water (10 mL×2), then evaporated in vacuum to dryness to give (90 mg, yield: 52%) of {2-cyclopropyl-4-[4-(2-methoxy-phenyl)-piperidin-1-yl]-6-methyl-pyrimidin-5-yl}-acetic acid as yellow solid.

To a stirred solution of {2-cyclopropyl-4-[4-(2-methoxy-phenyl)-piperidin-1-yl]-6-methyl-pyrimidin-5-yl}-acetic acid (60 mg, 0.15 mmol) in DMF (2 mL) was added HATU (90 mg, 0.24 mmol) and Dimethyl-amine (0.15 mL, 0.3 mmol). The mixture was stirred at room temperature for overnight. The mixture was evaporated in vacuum to residue, which was purified by pre-HPLC (MeCN/H$_2$O from 5/100 to 95/100) to give (30 mg, yield: 47%) of 2-{2-cyclopropyl-4-[4-(2-methoxy-phenyl)-piperidin-1-yl]-6-methyl-pyrimidin-5-yl}-N,N-dimethyl-acetamide as white solid. $^1$H NMR (400 MHz, CDCl$_3$): δ=8.08 (d, J=8.0 Hz, 1H), 7.24-7.21 (m, 2H), 6.98-6.90 (m, 2H), 3.87-3.74 (m, 8H), 3.61-3.45 (m, 3H), 3.32-3.16 (m, 1H), 3.14-2.96 (m, 5H), 2.14-2.11 (m, 1H), 1.91 (t, J=12.0 Hz, 2H), 1.78 (q, J=12.0 Hz, 2H), 1.12-0.97 (m, 4H). MS: m/z 425.2 (M+H$^+$).

Example 165: Preparation of 2-{2-cyclopropyl-4-[4-(2-methoxy-phenyl)-piperidin-1-yl]-pyrimidin-5-yl}-N-methyl-N-propyl-acetamide

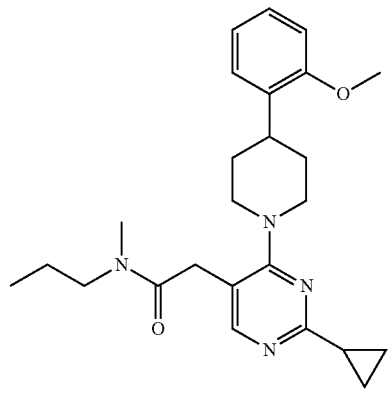 [SMILES: CCCN(C)C(=O)Cc1cnc(C2CC2)nc1N1CCC(c2ccccc2OC)CC1]

The title compound was prepared as described for 2-{2-cyclopropyl-4-[4-(2-methoxy-phenyl)-piperidin-1-yl]-6-methyl-pyrimidin-5-yl}-N,N-dimethyl-acetamide. $^1$H NMR (400 MHz, CDCl$_3$): δ=8.14 (s, 1H), 7.24-7.20 (m, 2H), 6.98 (t, J=8.0 Hz, 1H), 6.92 (d, J=8.0 Hz, 1H), 3.88-3.84 (m, 5H), 3.89 (t, J=7.6 Hz, 1H), 3.59 (d, J=8.4 Hz, 2H), 3.22-2.94 (m, 7H), 2.17-2.12 (m, 1H), 1.96-1.91 (m, 2H), 1.84-1.77 (m, 2H), 1.61-1.51 (m, 2H). MS: m/z 423.3 (M+H$^+$).

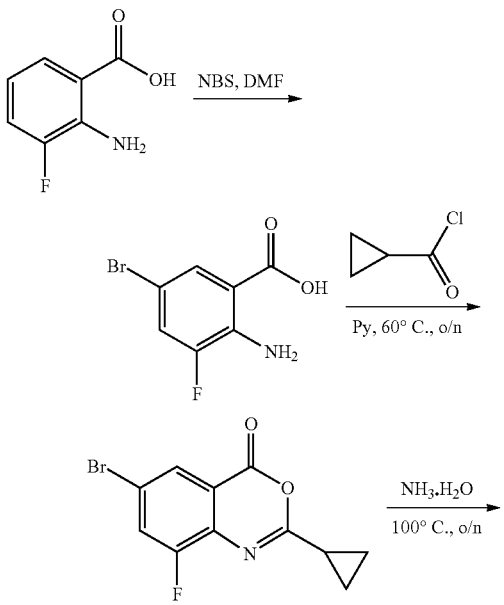

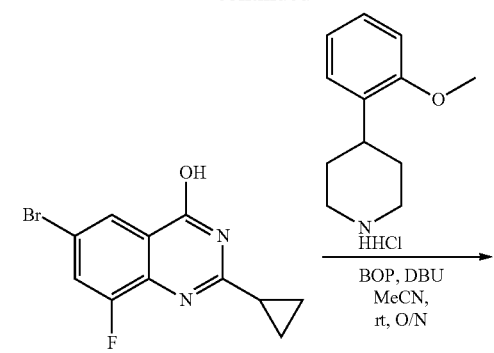
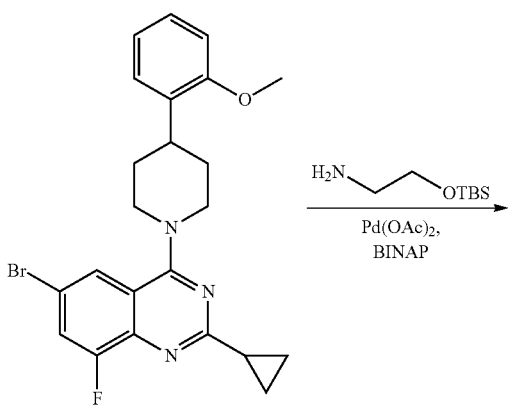
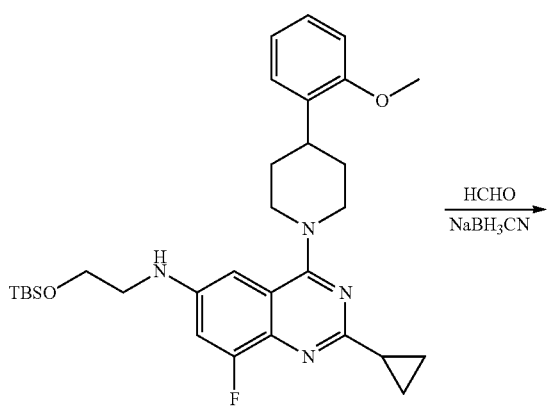
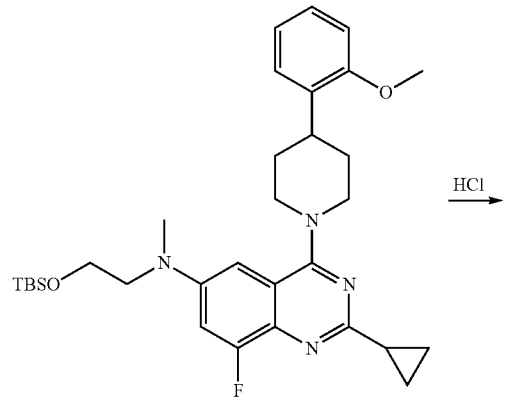

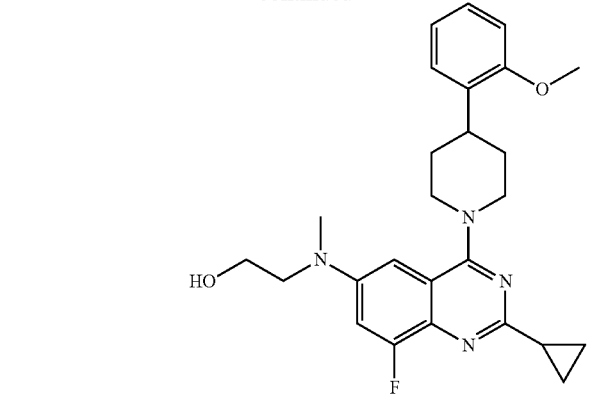

Example 166: Preparation of 2-({2-Cyclopropyl-8-fluoro-4-[4-(2-methoxy-phenyl)-piperidin-1-yl]-quinazolin-6-yl}-methyl-amino)-ethanol Step 1: To a solution of 2-amino-3-fluorobenzoic acid (1.0 g, 6.45 mmol) in DMF (10 mL) at −10° C., NBS (1.15 g, 6.45 mmol) in DMF (4 mL) was added dropwise over 10 min. After the addition was complete, the reaction mixture was stirred at −10° C. for 1 h. The reaction was quenched with aqueous sodium bisulfate (50 mL) and large amount of solid precipitated out. The resulting solid was collected by filtration and dried in vacuum to afford 2-amino-5-bromo-3-fluorobenzoic acid (1.2 g, yield: 80%) as a yellow solid.

Step 2: To a solution of 2-amino-5-bromo-benzoic acid (1.2 g, 5.17 mmol) in pyridine (12 mL) was added cyclopropanecarbonyl chloride (807 mg, 7.76 mmol). The reaction mixture was stirred at 60° C. overnight. After cooled to 0° C. at ice batch and poured into ice-water (100 mL), the resulting suspension was filtered and dried to give 6-bromo-2-cyclopropyl-8-fluoro-4H-benzo[d][1,3]oxazin-4-one (751 mg, yield: 51%) as a yellow solid. $^1$H NMR (400 MHz, DMSO-d6): δ=8.12 (dd, J=9.6, 2.0 Hz, 1H), 7.98 (s, 1H), 2.08-1.95 (m, 1H), 1.20-1.10 (m, 4H).

Step 3: A suspension of 6-bromo-2-cyclopropyl-8-fluoro-4H-benzo[d][1,3]oxazin-4-one (751 mg, 2.64 mmol) in NH$_3$.H$_2$O (40 mL, 28%) was heated at 100° C. in a sealed tube overnight. After cooled to room temperature, the resulting solid was filtered and the cake was washed with water, dried to give 6-bromo-2-cyclopropyl-8-fluoroquinazolin-4-ol (521 mg, yield: 69%) as a yellow solid. MS: m/z 282.8 (M+H$^+$).

Step 4: To a suspension of 6-bromo-2-cyclopropyl-8-fluoroquinazolin-4-ol (200 mg, 0.71 mmol), 4-(2-methoxyphenyl)-piperidine hydrochloride (177 mg, 0.78 mmol) and BOP (471 mg, 1.07 mmol) in ACN (20 mL) was added DBU (540 mg, 3.55 mmol). Then mixture was stirred at room temperature overnight. The resulting solid was collected by filtration and dried in vacuum to afford 6-bromo-2-cyclopropyl-8-fluoro-4-(4-(2-methoxyphenyl)piperidin-1-yl)quinazoline (179 mg, yield: 55%) as a white solid. MS: m/z 455.8 (M+H⁺).

Step 5: To a solution of 6-bromo-2-cyclopropyl-8-fluoro-4H-benzo[d][1,3]oxazin-4-one (179 mg, 0.39 mmol) in anhydrous toluene (10 mL) was added BINAP (73 mg, 0.117 mmol), Pd(OAc)₂ (13 mg, 0.059 mmol) and Cs₂CO₃ (254 mg, 0.78 mmol), purged with N₂ for 5 min, 2-(tert-butyl-dimethyl-silanyloxy)-ethylamine (138 mg, 0.79 mmol) was added. The mixture was stirred under N₂ overnight. After cooled to room temperature, the mixture was filtered. The filtrate was concentrated to give N-(2-((tert-butyldimethyl-silyl)oxy)ethyl)-2-cyclopropyl-8-fluoro-4-(4-(2-methoxyphenyl)piperidin-1-yl)-N-methylquinazolin-6-amine (375 mg crude) as a crude product, which was used to next step without further purification. MS: m/z 550.9 (M+H⁺).

Step 6: To a solution of N-(2-((tert-butyldimethylsilyl)oxy)ethyl)-2-cyclopropyl-8-fluoro-4-(4-(2-methoxyphenyl)piperidin-1-yl)-N-methylquinazolin-6-amine (crude, 375 mg, ~0.39 mmol) in MeOH (30 mL) was added HCHO (0.6 mL, 40% in H₂O, 7.8 mmol), NaBH(ACO)₃ (827 mg, 3.9 mmol) and NaBH₃CN (246 mg, 3.9 mmol). Then the reaction mixture was stirred at room temperature overnight. The reaction was quenched with saturated aqueous NaHCO₃ solution. The mixture was extracted with EA (30 mL×2). The organic layer was washed with brine, dried over Na₂SO₄. The solution was concentrated to dryness and the residue (381 mg crude) was used to next step without further purification. MS: m/z 564.9 (M+H⁺).

Step 7: To a solution of N-(2-((tert-butyldimethylsilyl)oxy)ethyl)-2-cyclopropyl-8-fluoro-4-(4-(2-methoxyphenyl)piperidin-1-yl)-N-methylquinazolin-6-amine (crude, 381 mg, ~0.39 mmol) in MeOH (20 mL) was added con. HCl (0.1 mL), the reaction mixture was stirred at room temperature overnight. NH₃.H₂O was added to adjust pH to 7-8. The mixture was concentrated and the residue was purified by prep-TLC (DCM/MeOH=20/1) to give 24(2-cyclopropyl-8-fluoro-4-(4-(2-methoxyphenyl)piperidin-1-yl)quinazolin-6-yl)(methyl)amino)ethanol (20 mg, 3-step yield: 11%) as a yellow solid. ¹H NMR (400 MHz, CDCl₃): δ=7.24-7.21 (m, 2H), 7.06 (dd, J=13.6, 2.4 Hz, 1H), 6.96 (t, J=8.0 Hz, 1H), 6.89 (d, J=8.8 Hz, 1H), 6.71 (s, 1H), 4.36 (d, J=13.2 Hz, 2H), 3.88-3.86 (m, 5H), 3.54-3.52 (m, 2H), 3.28-3.11 (m, 3H), 3.03 (s, 3H), 2.27-2.25 (m, 1H), 1.98-1.86 (m, 4H), 1.16-1.14 (m, 2H), 0.99-0.96 (m, 2H). MS: m/z 451.2 (M+H⁺).

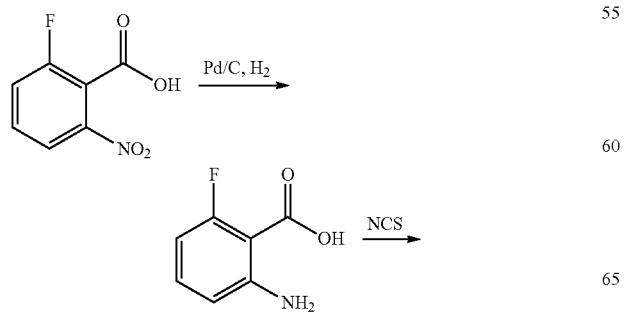

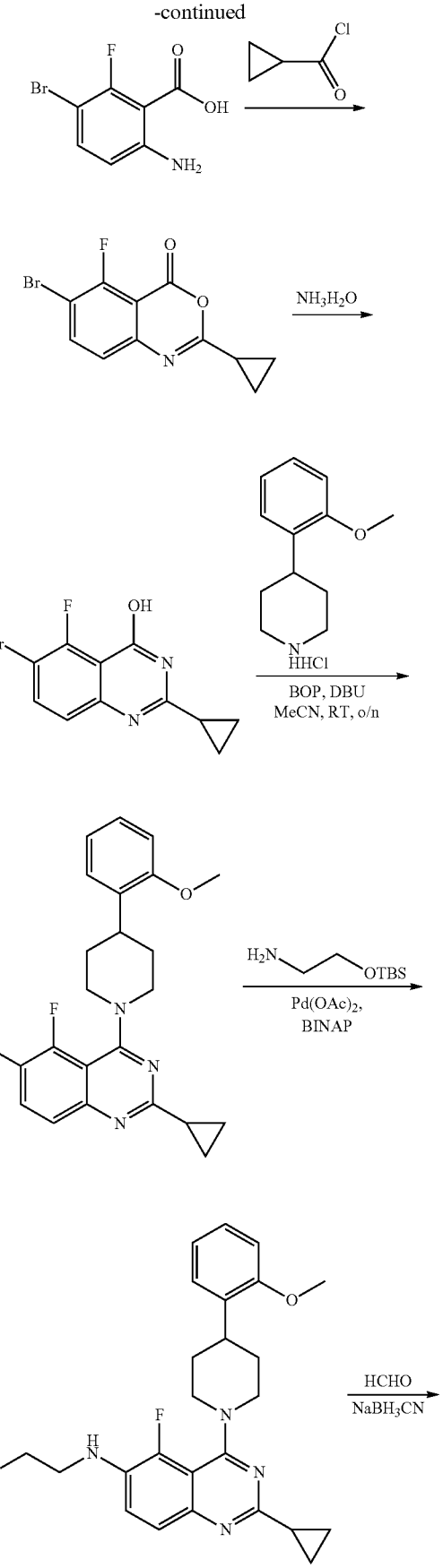

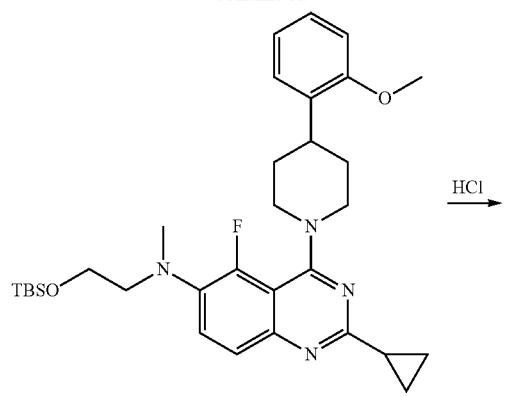
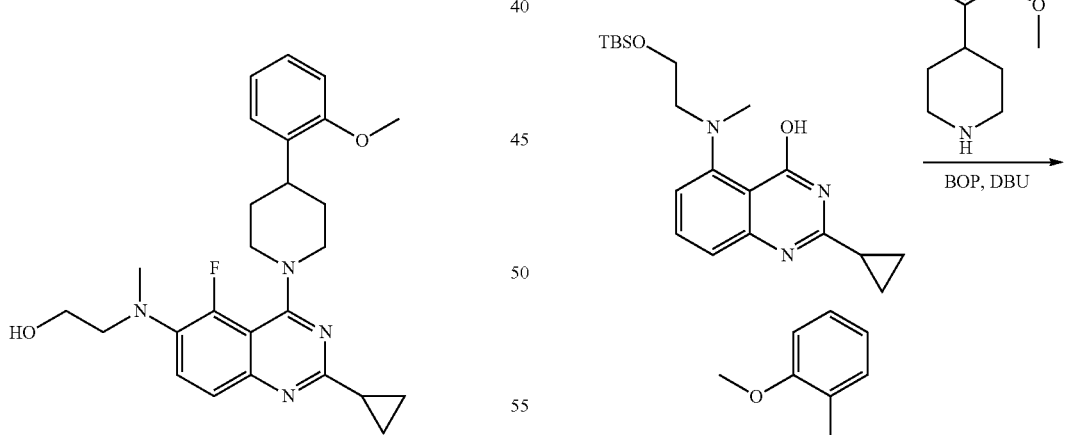
Example 167: Preparation of 2-({2-Cyclopropyl-5-fluoro-4-[4-(2-methoxy-phenyl)-piperidin-1-yl]-quinazolin-6-yl}-methyl-amino)-ethanol
The title compound was prepared as described in example 2-((2-cyclopropyl-8-fluoro-4-(4-(2-methoxyphenyl)piperidin-1-yl)quinazolin-6-yl)(methyl)amino)ethanol. ¹H NMR (400 MHz, CDCl₃): δ=7.56-7.48 (m, 2H), 7.23-7.17 (m, 2H), 6.95 (t, J=7.2 Hz, 1H), 6.88 (d, J=8.4 Hz, 1H), 4.20 (d, J=12.4 Hz, 2H), 3.85 (s, 3H), 3.74 (t, J=5.2 Hz, 2H), 3.25 (t, J=5.6 Hz, 2H), 3.10 (t, J=12.4 Hz, 2H), 2.88 (s, 3H), 2.16-2.13 (m, 1H), 1.95-1.82 (m, 4H), 1.19-1.14 (m, 2H), 1.00-0.95 (m, 2H). MS: m/z 451.2 (M+H⁺).
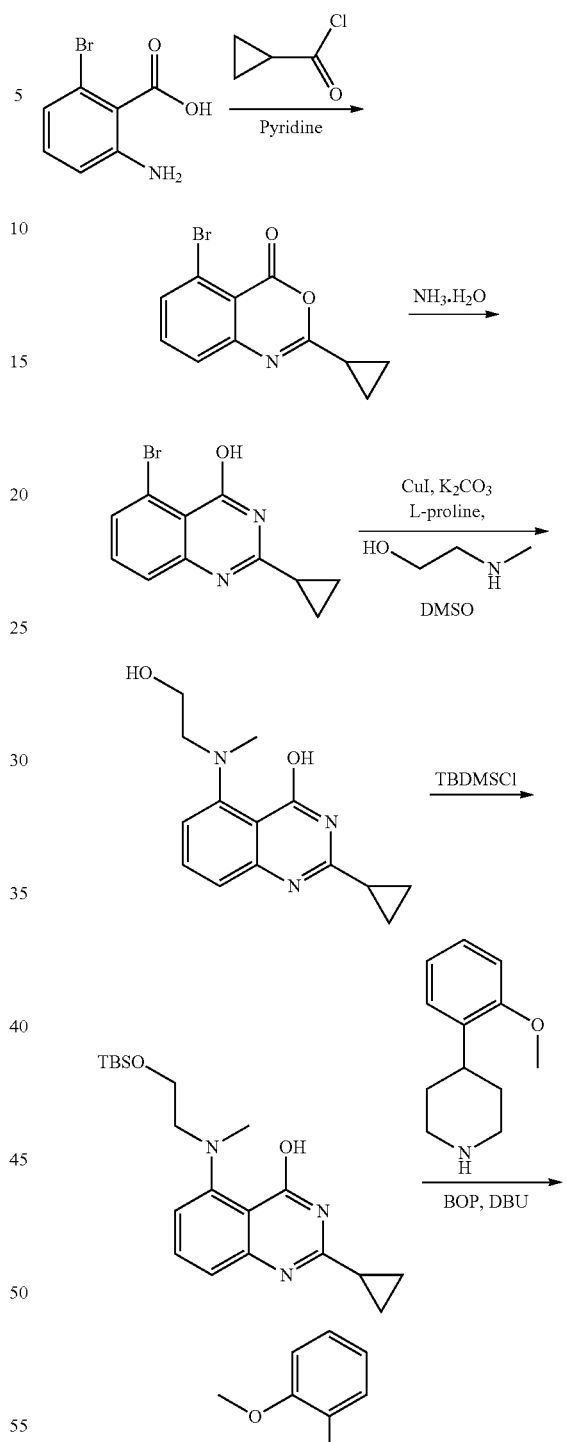

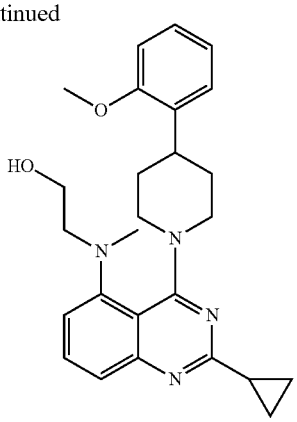

Example 168: Preparation of 2-({2-Cyclopropyl-4-[4-(2-methoxy-phenyl)-piperidin-1-yl]-quinazolin-5-yl}-methyl-amino)-ethanol

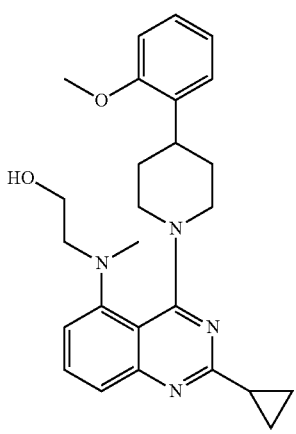 [SMILES: COc1ccccc1C1CCN(c2nc(C3CC3)nc3cccc(N(C)CCO)c23)CC1]

Step 1: To a solution of 2-amino-6-bromo-benzoic acid (2 g, 9.3 mmol) in pyridine (20 mL) was added cyclopropanecarbonyl chloride (1.25 mL, 13.9 mmol). The reaction mixture was stirred at 60° C. overnight. Cooled to 0° C., and poured into ice-water (100 mL), the resulting suspension was filtered and dried to give 5-bromo-2-cyclopropyl-benzo[d][1,3]oxazin-4-one (1.75 g, yield: 71%) as white solid. $^1$H NMR (300 MHz, CDCl$_3$): δ=7.68 (d, J=7.8 Hz, 1H), 7.53 (t, J=8.1 Hz, 1H), 7.44 (d, J=7.8 Hz, 1H), 1.95-1.90 (m, 1H), 1.31-1.27 (m, 2H), 1.16-1.11 (m, 2H).

Step 2: A suspension of 5-bromo-2-cyclopropyl-benzo[d][1,3]oxazin-4-one (1 g, 3.79 mmol) in NH$_3$H$_2$O (50 mL, 28%) was heated at reflux overnight. Cooled to rt, filtered, the cake was washed with water, dried to give 5-bromo-2-cyclopropyl-quinazolin-4-ol (450 mg, 45% yield) as white solid. $^1$H NMR (300 MHz, CDCl$_3$): δ=7.64-7.62 (m, 1H), 7.56-7.53 (m, 1H), 7.50-7.47 (m, 1H), 1.84-1.82 (m, 1H), 1.32-1.28 (m, 2H), 1.17-1.13 (m, 2H).

Step 3: To a suspension of 5-bromo-2-cyclopropyl-quinazolin-4-ol (215 mg, 0.81 mmol), L-proline (47 mg, 0.41 mmol), CuI (46 mg, 0.24 mmol) and K$_2$CO$_3$ (224 mg, 1.62 mmol) in DMSO (4 mL) was added 2-(methylamino)ethanol (91 mg, 1.22 mmol) after purged with N$_2$ for 5 min. Then the mixture was heated to 90° C. and it was stirred at a sealed tube overnight. After cooled to room temperature, the reactant was filtered. The filtrate was concentrated to dryness and the residue was purified by prep-HPLC (NH$_4$HCO$_3$ as additive) to afford 2-cyclopropyl-5-((2-hydroxyethyl)(methyl)amino)quinazolin-4-ol (50 mg, yield: 23%) as brown oil. $^1$H NMR (400 MHz, CDCl$_3$): δ=10.73 (brs, 1H), 7.55 (t, J=8.0 Hz, 1H), 7.19 (d, J=8.0 Hz, 1H), 7.01 (d, J=8.0 Hz, 1H), 4.40 (brs, 1H), 3.76-3.72 (m, 2H), 3.35-3.30 (m, 2H), 2.87 (s, 3H), 1.93-1.87 (m, 1H), 1.30-1.20 (m, 2H), 1.13-1.08 (m, 2H). MS: m/z 260.0 (M+H$^+$)

Step 4: To a solution of 2-cyclopropyl-5-((2-hydroxyethyl)(methyl)amino)quinazolin-4-ol (25 mg, 0.097 mmol) in DCM (5 mL) was added TBSCl (16 mg, 0.106 mmol) and TEA (19.6 mg, 0.194 mmol), and the mixture was stirred at room temperature for 2 h. But LC-MS showed no reaction. So the mixture was concentrated to dryness and the residue was dissolved in MeCN (5 mL), followed by the addition of K$_2$CO$_3$ (27 mg, 0.194 mmol, 2 eq.) and TBSCl (16 mg, 0.106 mmol, 1.1 eq). The mixture was stirred at 60° C. for 4 h. LC-MS showed the reaction was completed. The reaction was quenched by water (10 mL). The aqueous phase was extracted with DCM (20 mL×3). The extracts were washed with brine (20 mL×2) and dried over Na$_2$SO$_4$. The solution was concentrated to dryness and the residue (40.6 mg, yield: >100%) was used for next step without further purification. $^1$H NMR (400 MHz, CDCl$_3$): δ=10.55 (brs, 1H), 7.55-7.50 (m, 1H), 7.13-7.08 (m, 1H), 6.95-6.91 (m, 1H), 3.84 (t, J=6.0 Hz, 2H), 3.41 (t, J=6.0 Hz, 2H), 3.03 (s, 3H), 1.92-1.85 (m, 1H), 1.30-1.25 (m, 2H), 1.13-1.06 (m, 2H), 0.85 (s, 9H), 0.01 (s, 6H).

Step 5: To a suspension of 5-(2-((tert-butyldimethylsilyl)oxy)ethyl)(methyl)amino)-2-cyclopropylquinazolin-4-ol (40 mg, 0.11 mmol), 4-(2-methoxy-phenyl)-piperidine hydrochloride (26.7 mg, 0.12 mmol) and BOP (73 mg, 0.17 mmol) in ACN (10 mL) was added DBU (84 mg, 0.55 mmol). Then mixture was stirred at room temperature overnight. The reaction was quenched with water (10 mL) and the aqueous phase was extracted with EtOAc (20 mL×3). The extracts were dried over Na2SO4 and the solution was concentrated to dryness. The crude was submitted for next step without further purification. MS: m/z 547.0 (M+H$^+$).

Step 6: To a solution of N-(2-((tert-butyldimethylsilyl)oxy)ethyl)-2-cyclopropyl-4-(4-(2-methoxyphenyl)piperidin-1-yl)-N-methylquinazolin-5-amine (crude, 100 mg, ~0.11 mmol) in MeOH (10 mL) was added con. HCl (0.1 mL), the reaction mixture was stirred at room temperature overnight. NH$_3$.H$_2$O (0.1 mL) was added to adjust pH to 7~8. The mixture was concentrated and the residue was purified by prep-TLC (DCM/MeOH=20/1) to give 2-((2-cyclopropyl-8-fluoro-4-(4-(2-methoxyphenyl)piperidin-1-yl)quinazolin-6-yl)(methyl)amino)ethanol (14 mg, 3-step yield: 33%) as a yellow solid. $^1$H NMR (400 MHz, CDCl$_3$): δ=7.60 (d, J=8.0 Hz, 1H), 7.30-7.28 (m, 1H), 7.06-6.86 (m, 3H), 3.83 (s, 3H), 3.80-3.63 (m, 2H), 3.55-3.21 (m, 5H), 3.00-2.97 (m, 2H), 2.65 (d, J=9.6 Hz, 3H), 2.29-2.27 (m, 2H), 2.04-1.89 (m, 7H). MS: m/z 433.2 (M+H$^+$).

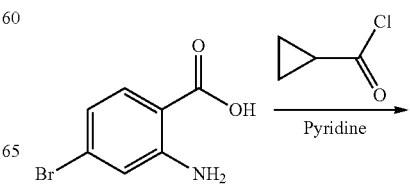

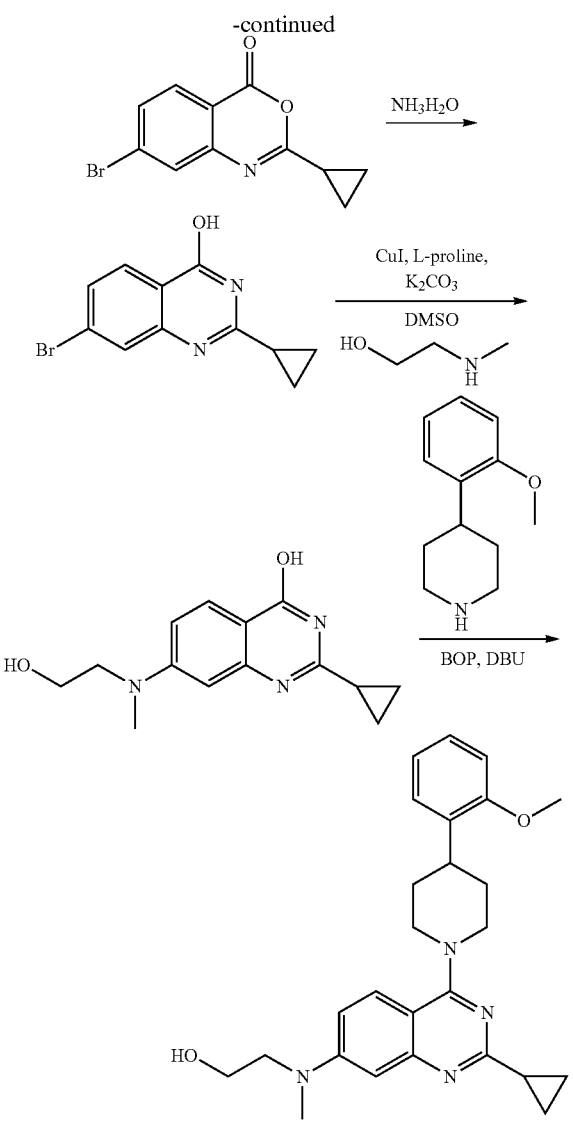

Example 169: Preparation of 2-({2-Cyclopropyl-4-[4-(2-methoxy-phenyl)-piperidin-1-yl]-quinazolin-7-yl}-methyl-amino)-ethanol The title compound was prepared as described in example 2-({2-cyclopropyl-4-[4-(2-methoxy-phenyl)-piperidin-1-yl]-quinazolin-5-yl}-methyl-amino)-ethanol. $^1$H NMR (400 MHz, CDCl$_3$): δ=7.67 (d, J=9.6 Hz, 1H), 7.22-7.19 (m, 2H), 6.97-6.88 (m, 4H), 4.37 (d, J=12.4 Hz, 2H), 3.88-3.85 (m, 5H), 3.63-3.62 (m, 2H), 3.29-3.23 (m, 1H), 3.18-3.11 (m, 5H), 2.13-2.12 (m, 1H), 1.90-1.82 (m, 5H), 1.16 (m, 2H), 0.95-0.93 (m, 2H). MS: m/z 433.2 (M+H$^+$).

Example 170: Preparation of {2-Cyclopropyl-4-[4-(2-methoxy-phenyl)-piperidin-1-yl]-quinazolin-7-yl}-methyl-propyl-amine

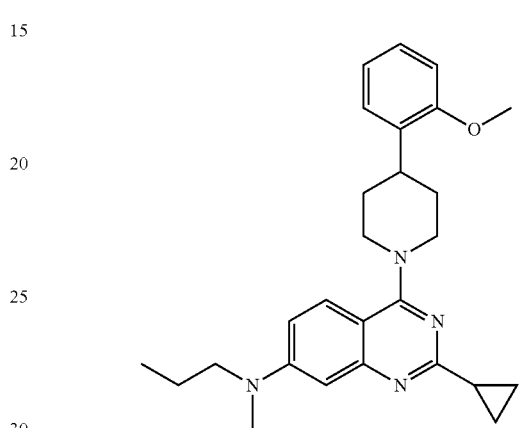

The title compound was prepared as described in example 2-({2-Cyclopropyl-4-[4-(2-methoxy-phenyl)-piperidin-1-yl]-quinazolin-5-yl}-methyl-amino)-ethanol. $^1$H NMR (300 MHz, CDCl$_3$): δ=7.63 (d, J=9.3 Hz, 1H), 7.28-7.15 (m, 3H), 6.97-6.89 (m, 2H), 6.83 (dd, J=9.0, 1.2 Hz, 1H), 4.67 (d, J=12.0 Hz, 2H), 3.87 (s, 3H), 3.47-3.31 (m, 5H), 3.11 (s, 3H), 2.50-2.40 (m, 1H), 2.05-1.98 (m, 2H), 1.92-1.62 (m, 4H), 1.27-1.13 (m, 4H), 0.97 (t, J=7.2 Hz, 3H). MS: m/z 431.3 (M+H$^+$).

Example 171: Preparation of (1-Fluoro-cyclopropyl)-{7-fluoro-6-[(2-hydroxy-ethyl)-methyl-amino]-4-[4-(2-methoxy-phenyl)-piperidin-1-yl]-quinazolin-2-yl}-methanone

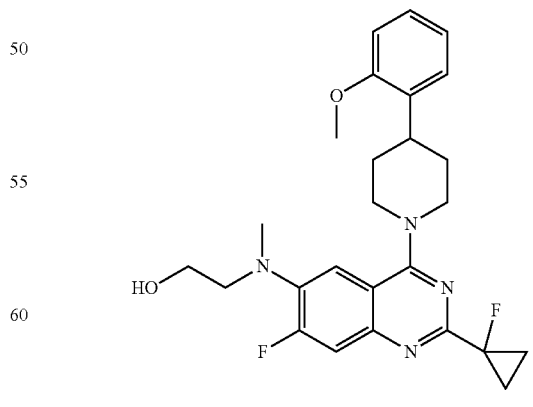

The title compound was prepared as described in example 2-((2-cyclopropyl-8-fluoro-4-(4-(2-methoxyphenyl)piperidin-1-yl)quinazolin-6-yl)(methyl)amino)ethanol. $^1$H NMR (400 MHz, CD₃OD): δ=7.50 (d, J=14.4 Hz, 1H), 7.34 (d, J=9.6 Hz, 1H), 7.23-7.18 (m, 2H), 6.98-6.93 (m, 2H), 4.46-4.43 (m, 2H), 3.86-3.79 (m, 6H), 3.45-3.42 (m, 2H), 3.27-3.21 (m, 2H), 3.06 (s, 3H), 1.96-1.93 (m, 4H), 1.55-1.48 (m, 4H). MS: m/z 469.2 (M+H⁺).

Example 172: Preparation of {7-Chloro-6-[(2-hydroxy-ethyl)-methyl-amino]-4-[4-(2-methoxy-phenyl)-piperidin-1-yl]-quinazolin-2-yl}-(1-fluoro-cyclopropyl)-methanone

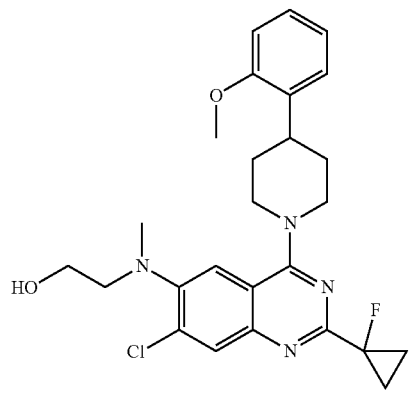 [SMILES: COc1ccccc1C1CCN(c2nc(C3(F)CC3)nc3cc(Cl)c(N(C)CCO)cc23)CC1]

The title compound was prepared as described in example 2-((2-cyclopropyl-8-fluoro-4-(4-(2-methoxyphenyl)piperidin-1-yl)quinazolin-6-yl)(methyl)amino)ethanol. ¹H NMR (400 MHz, CD₃OD): δ=7.97 (s, 1H), 7.75 (s, 1H), 7.25-7.21 (m, 2H), 7.00-6.91 (m, 2H), 4.96-4.93 (m, 2H), 3.87 (s, 3H), 3.83 (t, J=5.6 Hz, 2H), 3.64-3.51 (m, 3H), 3.40 (t, J=5.6 Hz, 2H), 3.04 (s, 3H), 2.14-2.11 (m, 2H), 1.98-1.74 (m, 6H). MS: m/z 485.2 (M+H⁺).

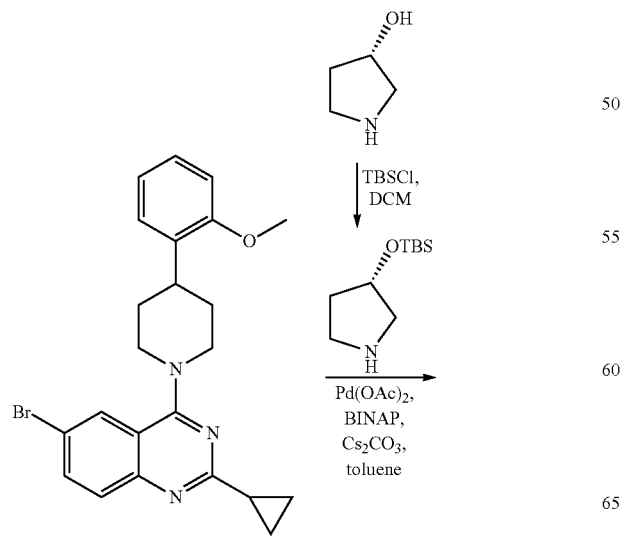

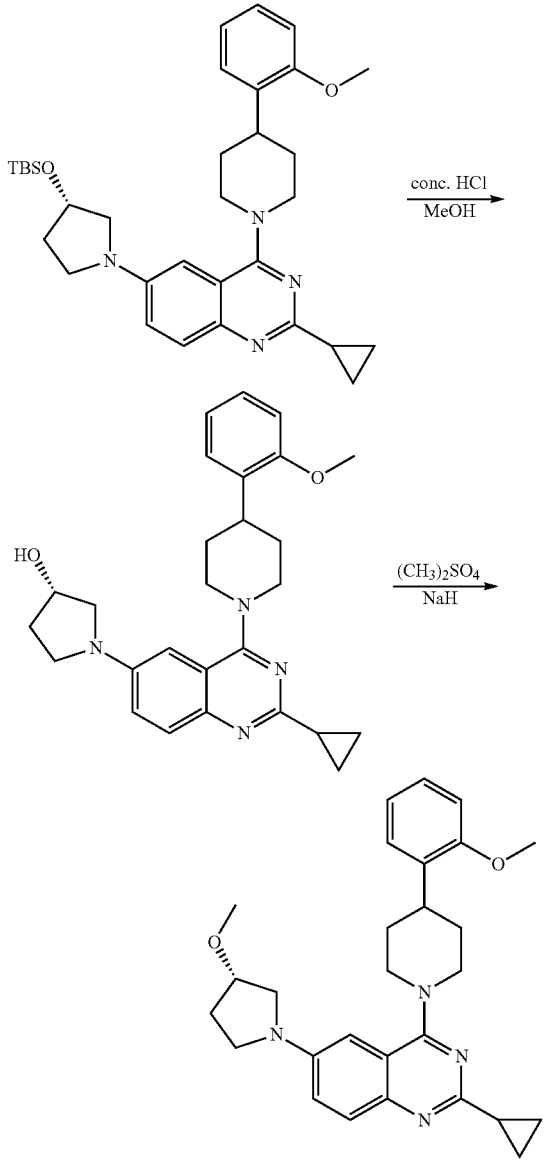

Example 173: Preparation of (S)-1-(2-cyclopropyl-4-(4-(2-methoxyphenyl)piperidin-1-yl)quinazolin-6-yl)pyrrolidin-3-ol and Example 174: Preparation of (S)-2-cyclopropyl-4-(4-(2-methoxyphenyl)piperidin-1-yl)-6-(3-methoxypyrrolidin-1-yl)quinazoline

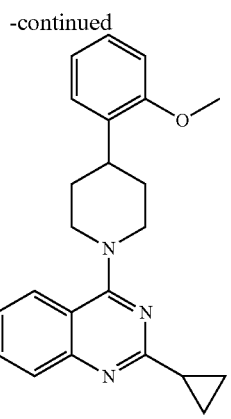

Step 1: To a mixture of (S)-pyrrolidin-3-ol (494 mg, 5.69 mmol) in DCM (15 mL) was added imidazole (772 mg, 11.37 mmol) and TBSCl (1.03 g, 6.81 mmol), cooled to 0° C. under $N_2$ atmosphere. The resulting mixture was stirred for overnight at room temperature. The mixture was partitioned between $NaHCO_3$ (sat. 50 mL) and DCM (50 mL). The aqueous phase was extracted with DCM (50 mL×2). The combined organic layer was washed with water (100 mL×2), dried over $Na_2SO_4$ and concentrated to give (S)-3-(tert-Butyl-dimethyl-silanyloxy)-pyrrolidine (576 mg, crude) as a yellow oil. $^1$H NMR (400 MHz, $CDCl_3$): 4.30-4.27 (m, 1H), 3.08-3.02 (m, 1H), 2.80-2.74 (m, 3H), 1.84-1.77 (m, 1H), 1.64-1.59 (m, 1H), 0.82 (s, 9H), 0.00 (s, 6H), Step 2: To a mixture of 6-bromo-2-cyclopropyl-4-[4-(2-methoxy-phenyl)-piperidin-1-yl]-quinazoline (438 mg, 1.00 mmol), (S)-3-(tert-Butyl-dimethyl-silanyloxy)-pyrrolidine (402 mg, 2.00 mmol) and $Cs_2CO_3$ (652 mg, 2.00 mmol) in anhydrous toluene (40 mL), BINAP (125 mg, 0.20 mmol) and Pd(OAc)$_2$ (5.0 mg, 0.024 mmol), and the mixture was stirred at at 90° C. overnight under $N_2$ atmosphere. The suspension was concentrated under reduced pressure. The residue was partitioned between water (80 mL) and EtOAc (80 mL). The aqueous phase was extracted with EtOAc (60 mL×2). The extracts were washed with water (100 mL×2) and brine (100 mL×1), then dried over $Na_2SO_4$. The solution was concentrated to dryness and the residue was purified by silica gel column chromatography (PE/EA=3/1) to give (S)-6-[3-(tert-butyl-dimethyl-silanyloxy)-pyrrolidin-1-yl]-2-cyclopropyl-4-[4-(2-methoxy-phenyl)-piperidin-1-yl]-quinazoline (470 mg, yield: 84%) as a yellow solid. MS: m/z 559.1 (M+H$^+$)

Step 3: To a solution of (S)-6-[3-(tert-butyl-dimethyl-silanyloxy)-pyrrolidin-1-yl]-2-cyclopropyl-4-[4-(2-methoxy-phenyl)-piperidin-1-yl]-quinazoline (470 mg, 0.84 mmol) in MeOH (20 mL) was added conc.HCl (four drops), and the reaction mixture was stirred at room temperature for overnight. The mixture was concentrated under reduced pressure. The residue was partitioned between $NaHCO_3$ (sat. 40 mL) and EtOAc (40 mL). The aqueous phase was extracted with EtOAc (40 mL×2). The combined organic layers were washed with water (100 mL×2) and brine (100 mL×1), and dried over $Na_2SO_4$. The solution was concentrated to dryness and the residue was purified by silica gel column chromatography (DCM/MeOH=30/1), lyophilized to afford (S)-1-{2-cyclopropyl-4-[4-(2-methoxy-phenyl)-piperidin-1-yl]-quinazolin-6-yl}-pyrrolidin-3-ol (370 mg, yield: 99%) as a white solid. $^1$H NMR (400 HMz, $CD_3OD$): δ=7.51 (dd, J=7.2, 1.2 Hz, 1H), 7.48 (dd, J=7.2, 2.4 Hz, 1H), 7.13-7.07 (m, 2H), 6.86 (d, J=8.0 Hz, 1H), 6.83-6.78 (m, 1H), 6.76 (d, J=2.4 Hz, 1H), 4.90-4.87 (m, 2H), 4.49-4.48 (m, 1H), 3.75 (s, 3H), 3.52-3.37 (m, 6H), 3.23-3.22 (m, 1H), 2.16-2.06 (m, 1H), 2.03-1.96 (m, 4H) 1.85- 1.75 (m, 2H), 1.26-1.15 (m, 4H). MS: m/z 445.2 (M+H$^+$)

Step 4: To a solution of (S)-1-{2-cyclopropyl-4-[4-(2-methoxy-phenyl)-piperidin-1-yl]-quinazolin-6-yl}-pyrrolidin-3-ol (150 mg, 0.34 mmol) in anhydrous THF (20 mL) was added NaH (60%, 54 mg, 1.35 mmol), and the mixture was stirred for 1 h at room temperature. Then $(CH_3)_2SO_4$ (42 mg, 0.34 mmol) was added into the mixture. The reaction mixture was stirred at room temperature for overnight. The mixture was concentrated under reduced pressure. The residue was partitioned between water (50 mL) and EtOAc (50 mL). The aqueous phase was extracted with EtOAc (50 mL×2). The organic layer was washed with water (80 mL×2) and brine (80 mL×1), dried over $Na_2SO_4$. The solution was concentrated to dryness and the residue was purified by Pre-TLC (DCM/MeOH=10/1) and lyophilized to give (S)-2-cyclopropyl-4-[4-(2-methoxy-phenyl)-piperidin-1-yl]-6-(3-methoxy-pyrrolidin-1-yl)-quinazoline (66 mg, yield: 42%) as a yellow solid. $^1$H NMR (400 HMz, $CD_3OD$): δ=7.49 (d, J=9.2 Hz, 1H), 7.26 (dd, J=9.2, 2.4 Hz, 1H), 7.12-7.07 (m, 2H), 6.86 (d, J=8.4 Hz, 1H), 6.81 (t, J=8.4 Hz, 1H), 6.76 (d, J=2.4 Hz, 1H), 4.88-4.85 (m, 2H), 4.10-4.09 (m, 1H), 3.75 (s, 3H), 3.51-3.31 (m, 7H), 3.28 (s, 3H), 2.16-1.95 (m, 5H), 1.81-1.77 (m, 2H), 1.24-1.15 (m, 4H). MS: m/z 459.2 (M+H$^+$).

Example 175: Preparation of (R)-1-{2-cyclopropyl-4-[4-(2-methoxy-phenyl)-piperidin-1-yl]-quinazolin-6-yl}-pyrrolidin-3-ol

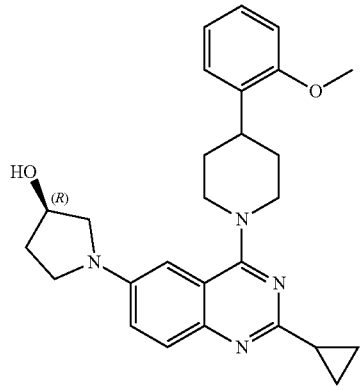

The title compound was prepared using general procedure for (S)-1-{2-cyclopropyl-4-[4-(2-methoxy-phenyl)-piperidin-1-yl]-quinazolin-6-yl}-pyrrolidin-3-ol. $^1$H NMR (400 HMz, $CD_3OD$): δ=7.62 (d, J=8.8 Hz, 1H), 7.42-7.39 (m, 1H), 7.24-7.20 (m, 2H), 7.00-6.90 (m, 3H), 5.03-5.00 (m, 2H), 4.62-4.60 (m, 1H), 3.88 (s, 3H), 3.52-3.37 (m, 6H), 3.60-3.51 (m, 6H), 2.26-2.23 (m, 1H), 2.18-2.09 (m, 4H) 1.97-1.91 (m, 2H), 1.37-1.29 (m, 4H). MS: m/z 445.2 (M+H$^+$).

Example 176: Preparation of (R)-2-cyclopropyl-4-[4-(2-methoxy-phenyl)-piperidin-1-yl]-6-(3-methoxy-pyrrolidin-1-yl)-quinazoline

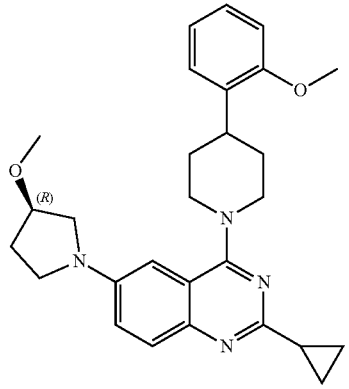

The title compound was prepared using general procedure for (S)-2-cyclopropyl-4-[4-(2-methoxy-phenyl)-piperidin-1-yl]-6-(3-methoxy-pyrrolidin-1-yl)-quinazoline. $^1$H NMR (400 HMz, CD$_3$OD): δ=7.52 (d, J=8.8 Hz, 1H), 7.18-7.06 (m, 3H), 6.86-6.80 (m, 2H), 6.65 (d, J=2.4 Hz, 1H), 4.38-4.34 (m, 2H), 4.09-4.08 (m, 1H), 3.75 (s, 3H), 3.50-3.46 (m, 1H), 3.37-3.29 (m, 4H), 3.28 (s, 3H), 3.11-3.04 (m, 2H), 2.12-1.97 (m, 3H), 1.84-1.79 (m, 2H), 1.06-1.03 (m, 2H), 0.90-0.86 (m, 4H). MS: m/z 459.2 (M+H$^+$).

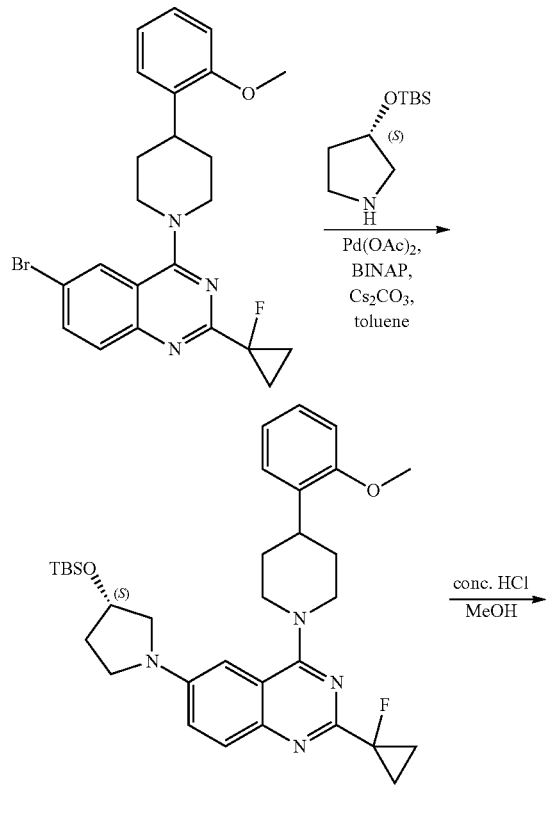

Example 177: Preparation of (S)-1-{2-(1-Fluoro-cyclopropyl)-4-[4-(2-methoxy-phenyl)-piperidin-1-yl]-quinazolin-6-yl}-pyrrolidin-3-ol

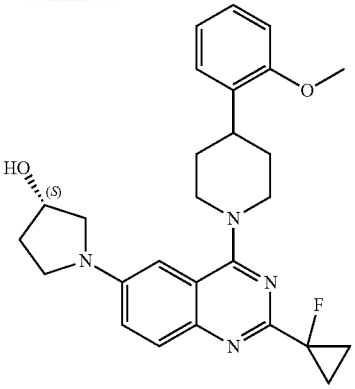

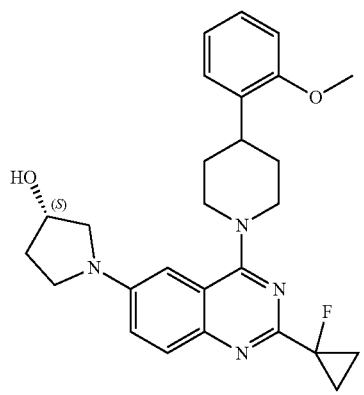

The title compound was prepared using general procedure for (S)-1-{2-cyclopropyl-4-[4-(2-methoxy-phenyl)-piperidin-1-yl]-quinazolin-6-yl}-pyrrolidin-3-ol. $^1$H NMR (400 HMz, CDCl$_3$): δ=7.91 (d, J=9.2 Hz, 1H), 7.26-7.16 (m, 3H), 6.99-6.95 (m, 1H), 6.89 (d, J=8.4 Hz, 1H), 6.71 (d, J=2.8 Hz, 1H), 4.68-4.66 (m, 1H), 4.38-4.35 (m, 2H), 3.86 (s, 3H), 3.63-3.60 (m, 2H), 3.47-3.45 (m, 1H), 3.38-3.36 (m, 1H), 3.29-3.27 (m, 1H), 3.15-3.09 (m, 2H), 2.26-2.21 (m, 1H) 2.15-2.13 (m, 1H), 1.98-1.87 (m, 4H), 0.89-0.83 (m, 4H). MS: m/z 463.2 (M+H$^+$)

Example 178: Preparation of (R)-1-{2-(1-Fluoro-cyclopropyl)-4-[4-(2-methoxy-phenyl)-piperidin-1-yl]-quinazolin-6-yl}-pyrrolidin-3-ol

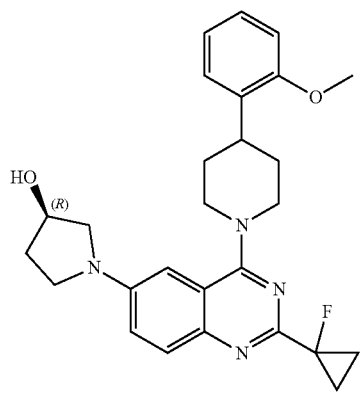

The title compound was prepared using general procedure for (S)-1-{2-cyclopropyl-4-[4-(2-methoxy-phenyl)-piperidin-1-yl]-quinazolin-6-yl}-pyrrolidin-3-ol. ¹H NMR (400 HMz, CDCl₃): δ=7.90 (d, J=9.2 Hz, 1H), 7.26-7.16 (m, 3H), 6.96 (t, J=7.6 Hz, 1H), 6.89 (d, J=8.4 Hz, 1H), 6.71 (d, J=2.8 Hz, 1H), 4.68-4.66 (m, 1H), 4.38-4.35 (m, 2H), 3.86 (s, 3H), 3.63-3.60 (m, 2H), 3.47-3.45 (m, 1H), 3.38-3.36 (m, 1H), 3.29-3.27 (m, 1H), 3.15-3.09 (m, 2H), 2.45-2.21 (m, 1H) 2.14-2.13 (m, 1H), 1.98-1.87 (m, 4H), 0.89-0.83 (m, 4H). MS: m/z 463.2 (M+H⁺)

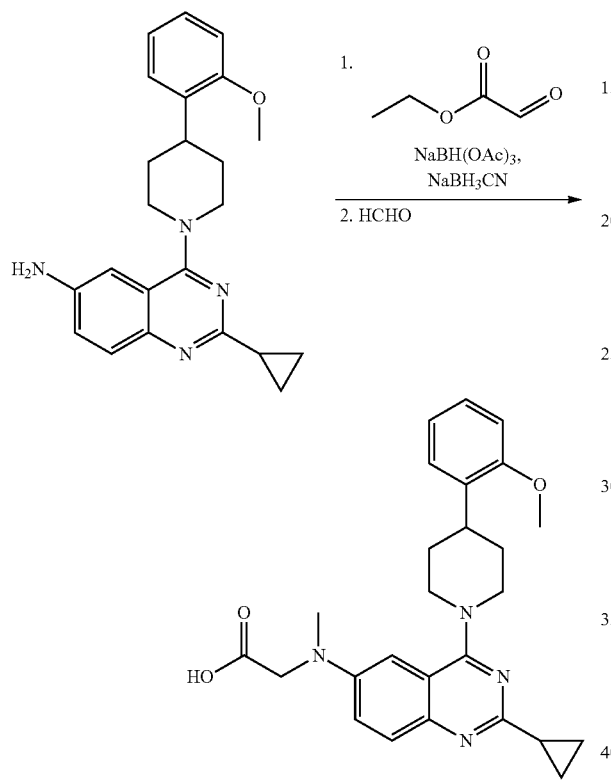

Example 179: Preparation of ({2-Cyclopropyl-4-[4-(2-methoxy-phenyl)-piperidin-1-yl]-quinazolin-6-yl}-methyl-amino)-acetic acid

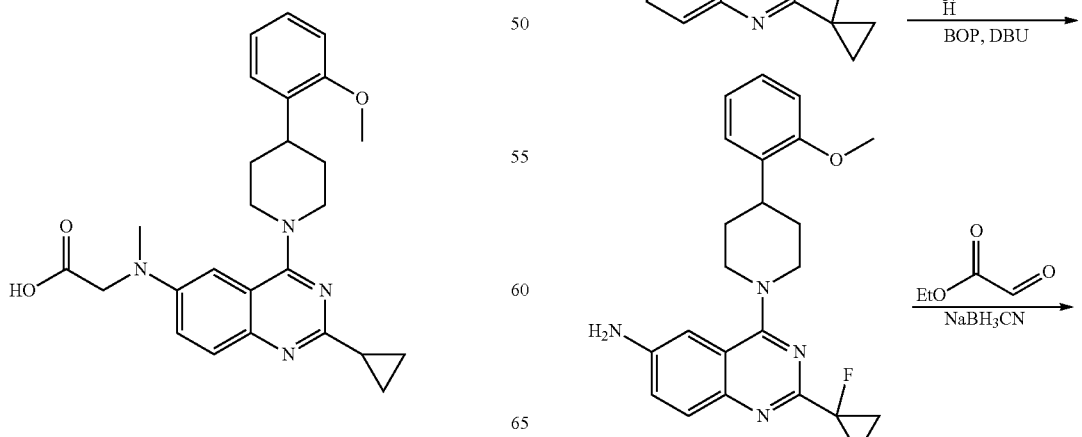

To a solution of 2-cyclopropyl-4-(4-(2-methoxyphenyl)piperidin-1-yl)quinazolin-6-amine (200 mg, 0.534 mmol) in MeOH (30 mL) was added ethyl 2-oxoacetate (470 mg, 5.34 mmol), followed by NaBH₃CN (1.13 g, 5.34 mmol) and NaBH(OAc)₃ (0.335 g, 5.34 mmol), and the resulting mixture was stirred at room temperature for overnight. Then to the reaction mixture was added HCHO (37-40%, 1.0 mL), and the reaction was stirred for overnight. The reaction mixture was concentrated to dryness in vacuum. The residue was diluted with ice-water (100 mL), and the mixture was extracted with EtOAc (100 mL×2). The combined organic layers were dried over Na₂SO₄, filtered and concentrated to give the crude product which was purified by Prep-HPLC to afford ({2-cyclopropyl-4-[4-(2-methoxy-phenyl)-piperidin-1-yl]-quinazolin-6-yl}-methyl-amino)-acetic acid (35 mg, yield: 21%) as a yellow solid. ¹H NMR (400 MHz, DMSO-d6): δ=8.02-8.00 (m, 1H), 7.27-7.20 (m, 1H), 7.15-7.09 (m, 2H), 6.96-6.82 (m, 3H), 4.85-4.82 (m, 2H), 4.16 (s, 2H), 3.85 (s, 3H), 3.43-3.35 (m, 3H), 3.10 (s, 3H), 2.72-2.69 (m, 1H), 2.08-2.04 (m, 2H), 1.84-1.77 (m, 2H), 1.30-1.15 (m, 4H). MS: m/z 447.2 (M+H⁺).

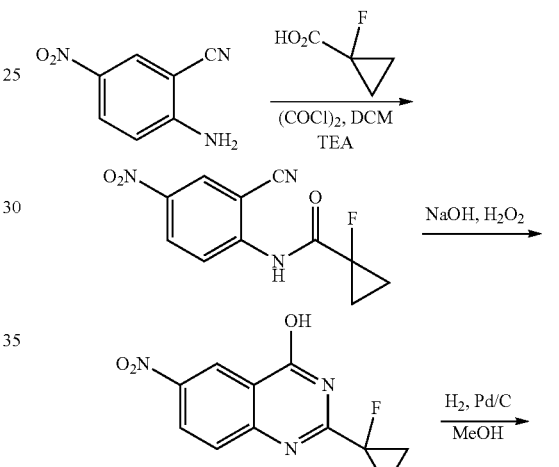

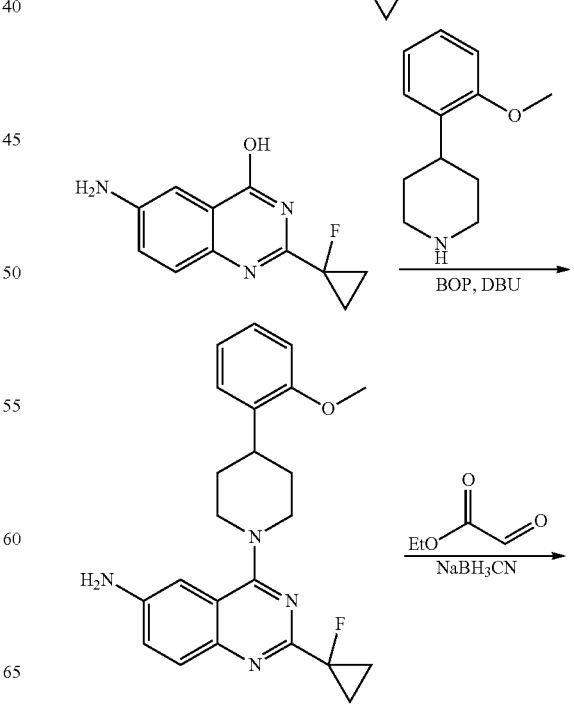

285
-continued
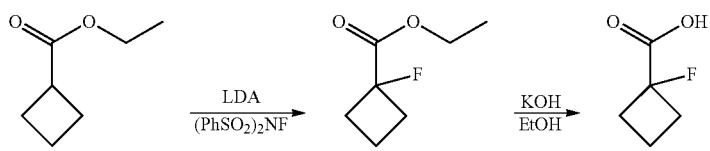
286
Example 180: Preparation of 2-((2-(1-fluorocyclopropyl)-4-(4-(2-methoxyphenyl)piperidin-1-yl)quinazolin-6-yl)(methyl)amino)acetic acid
The title compound was prepared using general procedure for ({2-cyclopropyl-4-[4-(2-methoxy-phenyl)-piperidin-1-yl]-quinazolin-6-yl}-methyl-amino)-acetic acid as a yellow solid. $^{1}$H NMR (400 MHz, DMSO-d6): δ=7.64-7.60 (m, 1H), 7.19-7.06 (m, 3H), 6.88-6.76 (m, 3H), 4.34-4.28 (m, 2H), 4.05-4.03 (m, 1H), 3.78-3.76 (m, 1H), 3.75 (s, 3H), 3.15-2.95 (m, 6H), 2.00-1.39 (m, 8H). MS: m/z 465.2 (M+H$^{+}$).
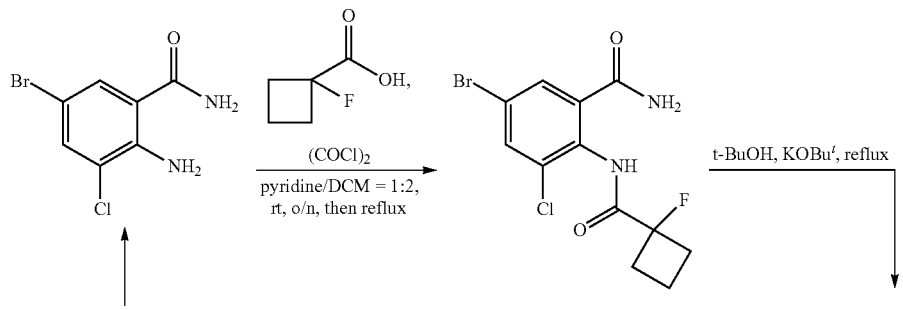
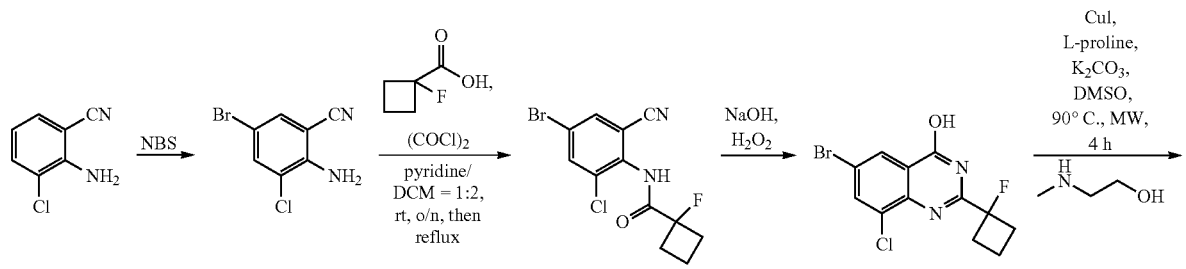

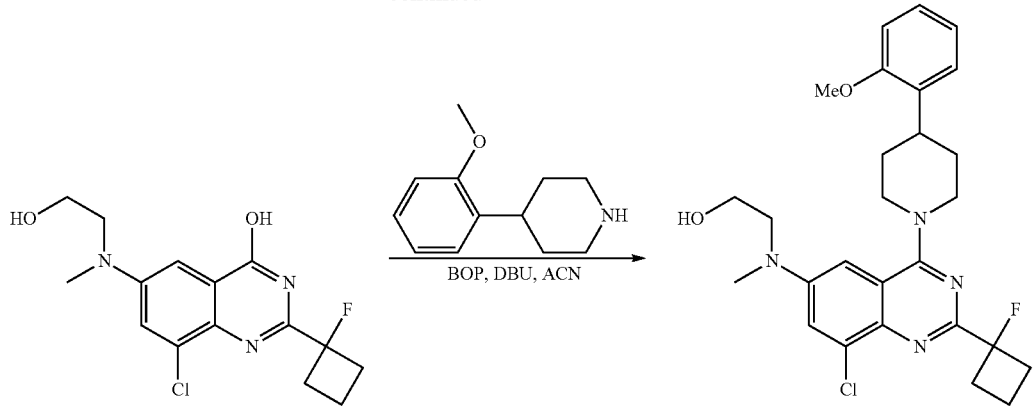

Example 181: Preparation of 2-((8-chloro-2-(1-fluorocyclobutyl)-4-(4-(2-methoxyphenyl)piperidin-1-yl)quinazolin-6-yl)(methyl)amino)ethanol

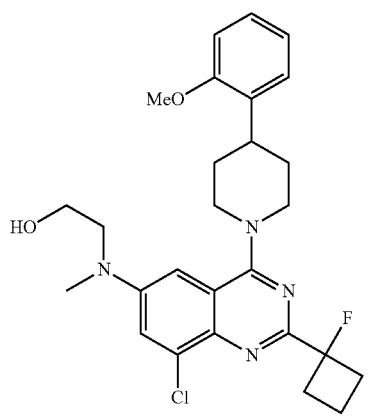 [SMILES: COc1ccccc1C1CCN(c2nc(C3(F)CCC3)nc3c(Cl)cc(N(C)CCO)cc23)CC1]

Step 1: To a solution of ethyl cyclobutanecarboxylate (38.4 g, 0.3 mol) and HMPA (80.5 g, 0.45 mol) in anhydrous THF (500 mL) was added LDA (2M, 225 mL) dropwise at −78° C. After addition, the mixture was stirred at this temperature for 25 min. N-fluoro-N-(phenylsulfonyl)benzenesulfonamide (113.4 g, 0.36 mol) was added thereto at −78° C. Then the solution was allowed to warm to room temperature and stirred overnight. The reaction solution was concentrated till one third of the volume was kept. The remaining solution was diluted with EtOAc (500 mL). The mixture was washed with 1N HCl (300 mL), sodium bicarbonate solution (300 mL), brine (300 mL×2) and dried over $Na_2SO_4$. The solvent was removed to give a crude product (107 g crude) as brown oil.

Step 2: To a solution of the crude ethyl 1-fluorocyclobutanecarboxylate (103 g crude) in EtOH (500 mL) was added aqueous KOH (100 mL water, 16.24 g, 0.29 mol). The mixture was stirred at room temperature for 6 h. The solution was concentrated to remove most of MeOH. The remaining solution was diluted with EtOAc (500 mL) and extracted with water (300 mL×2). The aqueous layer was acidified with HCl to pH=1-2 and then extracted with EtOAc (500 mL×2). The extracts were dried over $Na_2SO_4$ and concentrated to give crude 1-fluorocyclobutanecarboxylic acid (8.2 g) as brown oil. $^1$H NMR (400 MHz, $CDCl_3$): δ=2.53-2.48 (m, 2H), 2.35-2.20 (m, 2H), 2.10-1.92 (m, 2H).

Step 3: To a solution of 2-amino-3-chlorobenzonitrile (2 g, 13.1 mmol) in DMF (50 mL) was added NBS (2.4 g, 14.4 mmol), and the mixture was stirred at room temperature overnight. The reaction was quenced with water (100 mL). The mixture was extracted with EtOAc (100 mL×3). The extracts were concentrated to dryness and the residue was purified by combi flash (EtOAc/PE=0/1-3/7) to afford 2-amino-5-bromo-3-chlorobenzonitrile (1.8 g, yield: 58%) as a white solid.

Path 1 to 6-bromo-8-chloro-2-(1-fluorocyclobutyl)quinazolin-4-ol

Step 4, 5: To a solution of 1-fluorocyclobutanecarboxylic acid (300 mg crude) in anhydrous DCM (6 mL) was added oxalyl chloride (0.2 mL, 2.5 mmol) and 2 drops of DMF at 0° C., and the mixture was stirred at room temperature for 2 h. To another flash containing a solution of 2-amino-5-bromo-3-chlorobenzonitrile (520 mg, 2.25 mmol) in pyridine (3 mL) was added the above acyl chloride. The reaction mixture was stirred at reflux overnight. LCMS observed the desired mass value (330.7). The reaction was diluted with DCM (20 mL) and washed with 1N HCl (10 mL) and brine (20 mL). The organic layer was dried over $Na_2SO_4$ and concentrated to dryness. The residue was purified by prep-HPLC to afford N-(4-bromo-2-chloro-6-cyanophenyl)-1-fluorocyclobutanecarboxamide (43 mg, yield: 5.8%) as a yellow solid. $^1$H NMR (400 MHz, $CDCl_3$): δ=7.92 (brs, 1H), 7.78 (s, J=1.0 Hz), 7.68 (s, J=2.4 Hz), 2.78-2.68 (m, 2H), 2.54-2.38 (m, 2H), 2.00-1.54 (m, 2H). MS: m/z 330.7 (M+H$^+$).

To a solution of N-(4-bromo-2-chloro-6-cyanophenyl)-1-fluorocyclobutanecarboxamide (174 mg, 0.53 mmol) in EtOH (10 mL) was added $H_2O_2$ (1 mL) and NaOH (21 mg, 0.53 mmol), and the mixture was stirred at 90° C. for 2 h. LCMS showed the reaction was fine. The reaction was concentrated and the residue was washed with water (3 mL). The resulting solid was collected by filtration to afford 6-bromo-8-chloro-2-(1-fluorocyclobutyl)quinazolin-4-ol (136 mg, yield: 28%) as a white solid. MS: m/z 330.7 (M+H$^+$).

Path 2 to 6-bromo-8-chloro-2-(1-fluorocyclobutyl)quinazolin-4-ol

Step 4, 5, 6: To a solution of 2-amino-5-bromo-3-chlorobenzonitrile (2 g, 8.6 mmol) in the mixture solvent MeOH (2 mL), water (10 mL) and $H_2O_2$ (2 mL) was added NaOH (688 mg, 17.2 mmol), and the mixture was stirred at room temperature overnight. The resulting solid was collected by filtration to afford 2-amino-5-bromo-3-chlorobenzamide (2.3 g, >100% crude yield) as a white solid.

To a solution of 1-fluorocyclobutanecarboxylic acid (236 mg crude) in anhydrous DCM (4 mL) was added oxalyl chloride (254 mg, 2 mmol) and 2 drops of DMF at 0° C., and the mixture was stirred at room temperature for 2 h. To another flash containing a solution of 2-amino-5-bromo-3-chlorobenzamide (250 mg, 1 mmol) in pyridine (2 mL) was added the above acyl chloride. The reaction mixture was stirred at reflux overnight. LCMS observed the desired mass value (348.7). The reaction was diluted with DCM (20 mL) and washed with 1N HCl (10 mL) and brine (20 mL). The organic layer was dried over $Na_2SO_4$ and concentrated to dryness. The residue was purified by prep-TLC to afford 5-bromo-3-chloro-2-(1-fluorocyclobutanecarboxamido)benzamide (30 mg, yield: 8.6%) as a yellow solid. MS: m/z 348.7 (M+H$^+$). $^1$H NMR (400 MHz, CDCl$_3$): δ=8.50 (brs, 1H), 7.68 (d, J=2.0 Hz), 7.61 (d, J=2.4 Hz), 6.41 (brs, 1H), 6.02 (brs, 1H), 2.75-2.67 (m, 2H), 2.68-2.41 (m, 2H), 2.11-1.90 (m, 2H).

To a solution of 5-bromo-3-chloro-2-(1-fluorocyclobutanecarboxamido)benzamide (30 mg, 0.086 mmol) in t-BuOH (10 mL) was added t-BuOK (11.6 mg, 0.103 mmol), and the mixture was stirred at reflux for 1.5 h. LCMS showed the reaction was fine. The reaction was concentrated and the residue (40 mg crude) as a yellow solid was used for next step without further purification. MS: m/z 330.7 (M+H$^+$).

Step 7: To a suspension of 8-chloro-2-(1-fluorocyclobutyl)-6-((2-hydroxyethyl)(methyl)amino)quinazolin-4-ol (35 mg, 0.11 mmol), 4-(2-methoxy-phenyl)-piperidine hydrochloride (30 mg, 0.13 mmol) and BOP (75 mg, 0.17 mmol) in ACN (10 mL) was added DBU (50 mg, 0.33 mmol). Then mixture was stirred at room temperature overnight. The reactant was concentrated to dryness and the residue was purified by prep-HPLC to afford 2-((8-chloro-2-(1-fluorocyclobutyl)-4-(4-(2-methoxyphenyl)piperidin-1-yl)quinazolin-6-yl)(methyl)amino)ethanol (11 mg, yield: 20%) as a yellow solid. $^1$H NMR (400 MHz, CDCl$_3$): δ=7.89 (d, J=9.3 Hz, 1H), 7.24-7.20 (m, 2H), 6.98-6.89 (m, 3H), 4.43 (d, J=12.4 Hz, 2H), 3.88 (s, 3H), 3.72-3.70 (m, 4H), 3.63-3.58 (m, 2H), 3.34-3.18 (m, 3H), 3.08 (s, 3H), 2.90-2.88 (m, 2H), 2.67-2.62 (m, 2H), 2.01-1.96 (m, 6H). MS: m/z 499.2 (M+H$^+$).

Example 182: Preparation of 3-{8-Chloro-2-(1-fluoro-cyclobutyl)-4-[4-(2-methoxy-phenyl)-piperidin-1-yl]-quinazolin-6-yl}-cyclopentanol

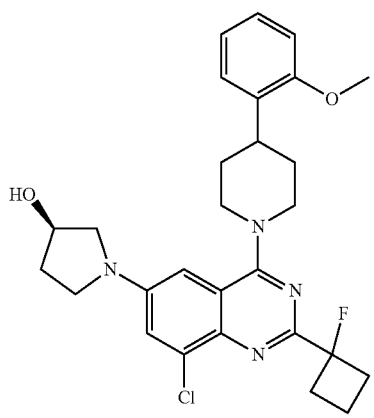 [SMILES: COc1ccccc1C1CCN(c2nc(C3(F)CCC3)nc3c(Cl)cc(N4CC[C@@H](O)C4)cc23)CC1]

The title compound was prepared using general procedure for 2-((8-chloro-2-(1-fluorocyclobutyl)-4-(4-(2-methoxyphenyl)piperidin-1-yl)quinazolin-6-yl)(methyl)amino)ethanol. $^1$H NMR (400 MHz, CDCl$_3$): δ=7.28-7.21 (m, 3H), 6.99-6.89 (m, 2H), 6.68 (s, 1H), 4.68 (brs, 1H), 4.43 (d, J=12.4 Hz, 2H), 3.88 (s, 3H), 3.62-3.56 (m, 2H), 3.46-3.18 (m, 5H), 3.94-2.70 (m, 2H), 2.67-2.62 (m, 2H), 2.24-2.13 (m, 2H), 2.02-1.78 (m, 7H). MS: m/z 511.2 (M+H$^+$).

Example 183: Preparation of 3-{8-Chloro-2-(1-fluoro-cyclobutyl)-4-[4-(2-methoxy-phenyl)-piperidin-1-yl]-quinazolin-6-yl}-cyclopentanol

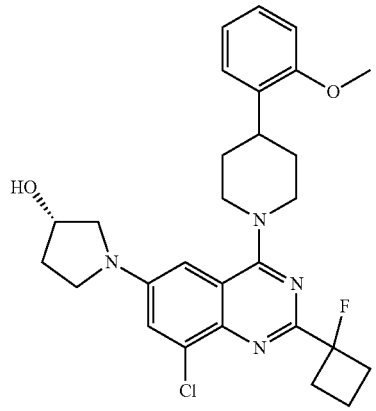 [SMILES: COc1ccccc1C1CCN(c2nc(C3(F)CCC3)nc3c(Cl)cc(N4CC[C@H](O)C4)cc23)CC1]

The title compound was prepared using general procedure for 2-((8-chloro-2-(1-fluorocyclobutyl)-4-(4-(2-methoxyphenyl)piperidin-1-yl)quinazolin-6-yl)(methyl)amino)ethanol. NMR (400 MHz, CDCl$_3$): δ=7.26-7.16 (m, 3H), 6.91-6.81 (m, 2H), 6.62 (s, 1H), 4.62 (brs, 1H), 4.40 (d, J=12.4 Hz, 2H), 3.79 (s, 3H), 3.56-3.50 (m, 2H), 3.40-3.18 (m, 5H), 2.87-2.82 (m, 2H), 2.63-2.56 (m, 2H), 2.15-2.05 (m, 2H), 1.93-1.79 (m, 7H). MS: m/z 511.2 (M+H$^+$).

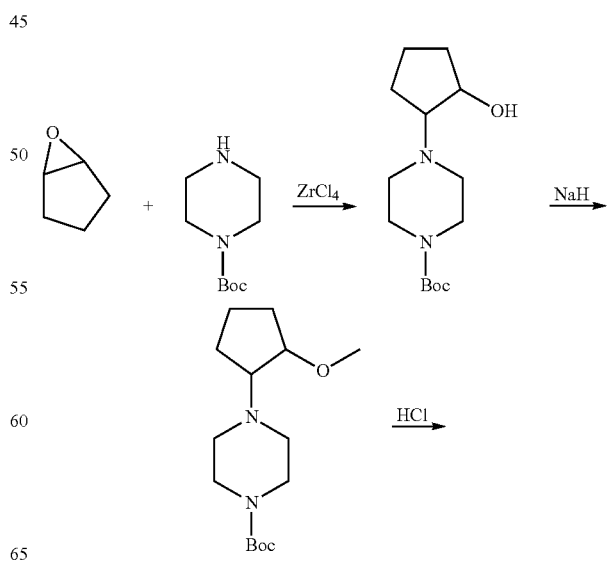

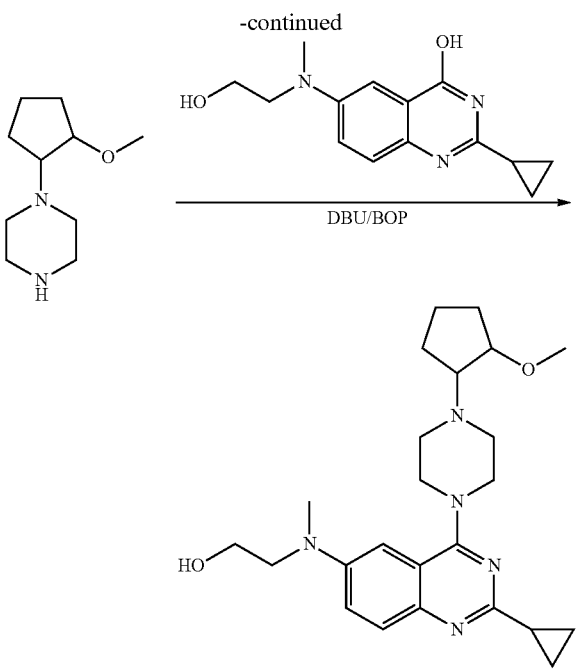

Example 184: Preparation of 2-({2-Cyclopropyl-4-[4-(2-methoxy-cyclopentyl)-piperazin-1-yl]-quinazolin-6-yl}-methyl-amino)-ethanol Step 1: To a mixture of 6-oxa-bicyclo[3.1.0]hexane (5 mL) and piperazine-1-carboxylic acid tert-butyl ester (2 g, 10.7 mmol) was added ZrCl₄ (246 mg, 1.07 mmol) and the reaction mixture was stirred at room temperature overnight. The reaction mixture was quenched with water (200 mL). The aqueous layer was extracted with EtOAc (100 mL×3). The extracts were dried over Na₂SO₄. The mixture was filtered and the solvent removed by evaporation under reduced pressure to give 2-amino-6-chloro-benzoic acid methyl ester (1.7 g, yield: 58%) as a colorless oil, which was used for next step without further purification.

Step 2: To a solution of tert-butyl 4-(2-hydroxycyclopentyl)piperazine-1-carboxylate (1.7 g, 6.29 mmol) in DMF (10 mL) at room temperature, was added NaH (310 mg, 7.6 mmol). After the addition was complete, the reaction mixture was stirred at room temperature for 0.5 h before CH₃I (981 mg, 6.29 mmol). The reaction was stirred at room temperature overnight and then quenched with water (150 mL). The aqueous layer was extracted with EtOAc (100 mL×2). The organic layers were washed with brine (100 mL×2) and dried over Na₂SO₄. The solution was concentrated and purified by silica gel column (PE/EA=50/1-10/1) to afford tert-butyl 4-(2-methoxycyclopentyl)piperazine-1-carboxylate (1.2 g, yield: 67%) as a colorless oil.

Step 3: To a solution of tert-butyl 4-(2-methoxycyclopentyl)piperazine-1-carboxylate (1.2 g, 4.2 mmol) in HCl/dioxane (10 mL) was stirred at room temperature overnight. The solid was filtered and dried to give 1-(2-methoxycyclopentyl)piperazine HCl salt (1.4 g, yield: >100%) as white solid.

Step 4: To a mixture of 2-cyclopropyl-6-((2-hydroxyethyl)(methyl)amino)quinazolin-4-ol (100 mg, 0.39 mmol) and 1-(2-methoxycyclopentyl)piperazine (128 mg, 0.58 mmol) in MeCN (20 mL) was added DBU (178 mg, 1.17 mmol) and BOP (165 mg, 0.57 mmol). Reaction mixture was stirred at room temperature overnight. Resultant was concentrated and purified by pre-HPLC to afford 2-((2-cyclopropyl-4-(4-(2-methoxycyclopentyl)piperazin-1-yl)quinazolin-6-yl)(methyl)amino)ethan-1-ol (35 mg, yield: 21%) as a yellow solid. ¹H NMR (400 MHz, DMSO-d6): δ=7.56 (d, J=9.2 Hz, 1H), 7.43 (dd, J=9.6, 2.8 Hz, 1H), 6.75 (d, J=1.6 Hz, 1H), 4.76-4.74 (m, 1H), 3.73-3.47 (m, 8H), 3.48-3.34 (m, 4H), 3.21 (s, 3H), 3.01 (s, 3H), 2.71-2.68 (m, 4H), 2.07-2.03 (m, 1H), 1.86-1.75 (m, 2H), 1.60-1.49 (m, 4H), 0.99-0.90 (m, 4H). MS: m/z 426.1 (M+H⁺).

Example 185: Preparation of 2-cyclopropyl-4-(4-(2-methoxycyclopentyl)piperazin-1-yl)-N-methyl-N-propylquinazolin-6-amine

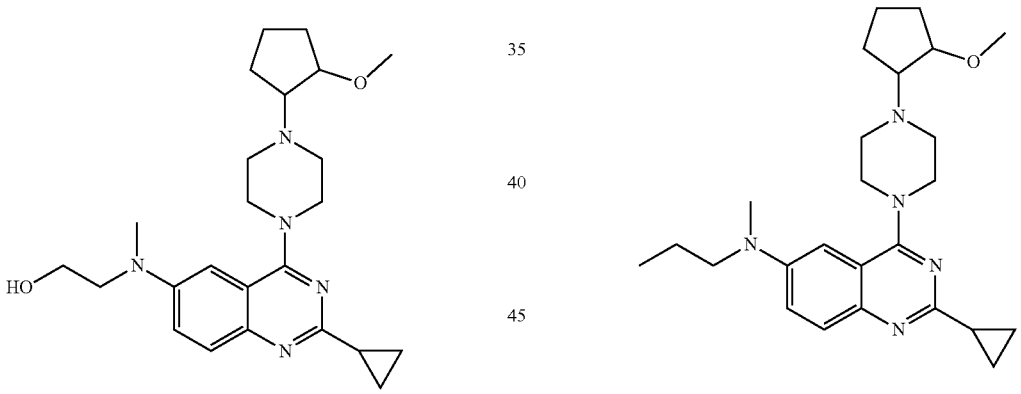

The title compound was prepared as described in example 2-{[8-fluoro-4-[4-(3-methoxy-pyrazin-2-yl)-piperidin-1-yl]-2-(1-methyl-cyclopropyl)-quinazolin-6-yl]-methyl-amino}-ethanol. ¹H NMR (400 MHz, DMSO-d6): δ=7.56 (d, J=9.3 Hz, 1H), 7.43 (dd, J=9.3, 2.7 Hz, 1H), 6.69 (d, J=2.4 Hz, 1H), 3.68-3.63 (m, 1H), 3.53-3.43 (m, 4H), 3.38-3.30 (m, 2H), 3.20 (s, 3H), 2.98 (s, 3H), 2.71-2.52 (m, 5H), 2.07-1.97 (m, 1H), 1.83-1.05 (m, 8H), 1.00-0.85 (m, 7H). MS: m/z 424.4 (M+H⁺).

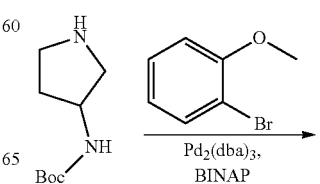

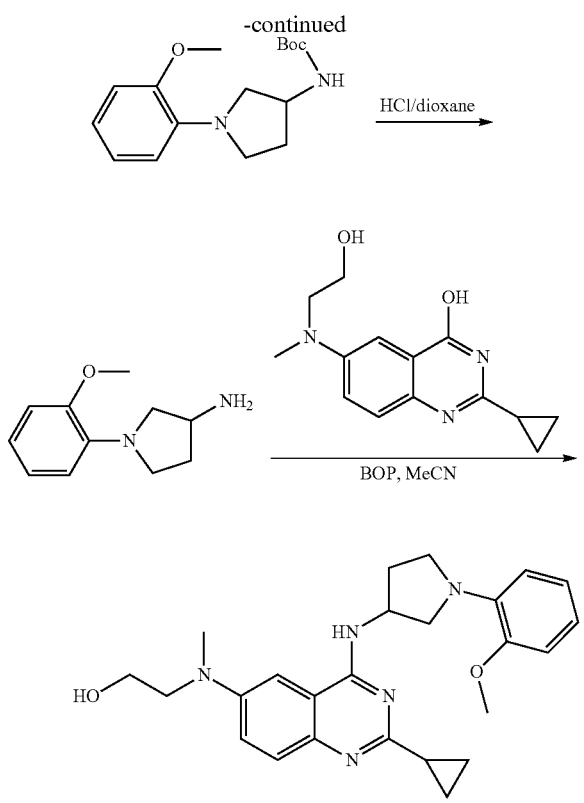

Example 186: Preparation of 2-({2-Cyclopropyl-4-[1-(2-methoxy-phenyl)-pyrrolidin-3-ylamino]-quinazolin-6-yl}-methyl-amino)-ethanol

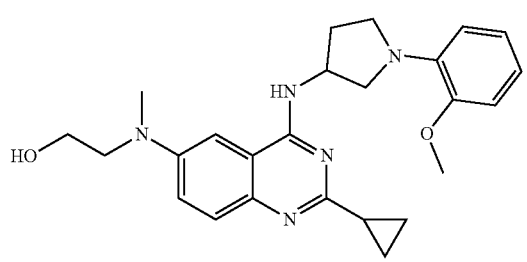 [SMILES: COc1ccccc1N1CCC(Nc2nc(C3CC3)nc3ccc(N(C)CCO)cc23)C1]

Step 1: To a solution of 2-bromo anisole (1.2 g, 6.45 mmol) in degassed toluene (20 mL) was added a suspension of $Pd_2(dba)_2$ (494 mg, 0.54 mmol), BINAP (1 g, 1.61 mmol) and tert-butyl pyrrolidin-3-ylcarbamate (1 g, 5.37 mmol), and the mixture was stirred at 100° C. for 16.5 h under argon. The reactant was portioned between water (30 mL) and EtOAc (20 mL). The organic layer was separated and the aqueous phase was extracted with EtOAc (20 mL×2). The combined organic layers were washed with brine (10 mL×2) and concentrated to dryness. The crude product was purified by Combi flash (PE/EtOAc=50/1-20/1) to give tert-butyl (1-(2-methoxyphenyl)pyrrolidin-3-yl)carbamate (1.43 g, yield: 91%) as yellow oil.

$^1$H NMR (400 MHz, CDCl$_3$): δ=6.91-6.84 (m, 4H), 6.73 (d, J=6.4 Hz, 1H), 4.85 (brs, 1H), 4.30 (brs, 1H), 3.83 (s, 3H), 3.55-3.44 (m, 2H), 3.25-3.15 (m, 2H), 2.31-2.23 (m, 1H), 1.85-1.79 (m, 1H), 1.45 (s, 9H).

Step 2: To a solution of tert-butyl (1-(2-methoxyphenyl) pyrrolidin-3-yl)carbamate (460 mg, 2.4 mmol) in EtOAc (10 mL) was added HCl/dioxane (10 mL), and the mixture was stirred at room temperature overnight. The resulting solid was filtered and the cake was dissolved in MeOH. The solution was concentrated in vacuum to give 1-(2-methoxyphenyl)pyrrolidin-3-amine (294 mg, yield: 70%) as HCl salt and brown oil. $^1$H NMR (400 MHz, DMSO-d6): δ=8.72 (brs, 3H), 7.38-7.36 (m, 1H), 7.22-7.13 (m, 1H), 7.00 (t, J=7.6 Hz, 1H), (brs, 1H), 3.98-3.96 (m, 1H), 3.88 (s, 3H), 3.81-3.48 (m, 4H), 2.45-2.40 (m, 1H), 2.21-2.16 (m, 1H).

Step 3: To a suspension of 2-cyclopropyl-6-((2-hydroxyethyl)(methyl)amino)quinazolin-4-ol (50 mg, 0.19 mmol), 1-(2-methoxyphenyl)pyrrolidin-3-amine hydrochloride (56 mg, 0.21 mmol) and BOP (126 mg, 0.29 mmol) in ACN (10 mL) was added DBU (144 mg, 0.95 mmol). Then mixture was stirred at room temperature for weekend. The reaction was quenched with water (10 mL) and the aqueous phase was extracted with EtOAc (20 mL×3). The extracts were dried over Na$_2$SO$_4$ and the solution was concentrated to dryness. The crude was purified by prep-TLC (DCM/MeOH=30/1) and prep-HPLC to afford 2-({2-Cyclopropyl-4-[1-(2-methoxy-phenyl)-pyrrolidin-3-ylamino]-quinazolin-6-yl}-methyl-amino)-ethanol (6.3 mg, yield: 7%) as yellow solid. $^1$H NMR (CDCl$_3$, 400 HMz): δ=7.58 (d, J=9.2 Hz, 1H), 7.20-7.17 (m, 1H), 6.92-6.87 (m, 3H), 6.82-6.79 (m, 2H), 6.32 (brs, 1H), 4.91 (d, J=6.8 Hz, 1H), 3.85-3.82 (m, 5H), 3.63-3.52 (m, 4H), 3.45-3.42 (m, 1H), 3.27-3.24 (m, 1H), 3.00 (s, 3H), 2.47-2.44 (m, 2H), 2.18-2.09 (m, 3H), 1.15 (m, 2H), 0.97-0.94 (m, 2H). MS: m/z 434.2 (M+H$^+$).

Example 187: Preparation of 2-Cyclopropyl-N4-[1-(2-methoxy-phenyl)-pyrrolidin-3-yl]-N6-methyl-N6-propyl-quinazoline-4,6-diamine

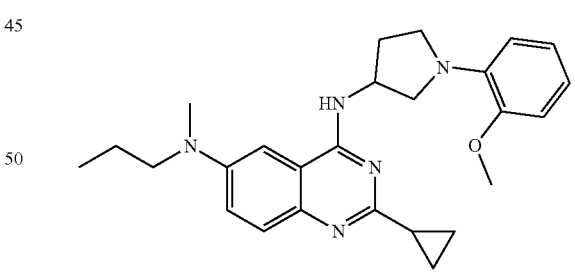

The title compound was prepared as described in example 2-({2-cyclopropyl-4-[1-(2-methoxy-phenyl)-pyrrolidin-3-ylamino]-quinazolin-6-yl}-methyl-amino)-ethanol. $^1$H NMR (400 HMz, CDCl$_3$): δ=7.81-7.78 (m, 1H), 7.29-7.26 (m, 1H), 6.94-6.89 (m, 3H), 6.84-6.82 (m, 1H), 6.49 (m, 1H), 4.93 (d, J=11.2 Hz, 1H), 3.87 (s, 3H), 3.61-3.56 (m, 2H), 3.49-3.48 (m, 1H), 3.36 (t, J=7.6 Hz, 2H), 3.27-3.24 (m, 1H), 3.01 (s, 3H), 2.50-2.47 (m, 1H), 2.08-2.04 (m, 1H), 1.67-1.59 (m, 3H), 1.26-1.16 (m, 2H), 1.05- 0.92 (m, 5H). MS: m/z 432.2 (M+H$^+$).

Example 188: Preparation of 2-{[4-(4-Cyclohexyl-piperidin-1-yl)-2-(1-fluoro-cyclopropyl)-quinazolin-6-yl]-methyl-amino}-ethanol

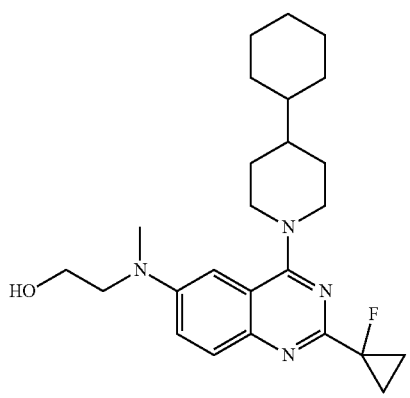 [SMILES: CN(CCO)c1ccc2nc(C3(F)CC3)nc(N3CCC(C4CCCCC4)CC3)c2c1]

The title compound was prepared as described in example 2-({2-cyclopropyl-4-[4-(2-dimethylamino-phenyl)-piperidin-1-yl]-quinazolin-6-yl}-methyl-amino)-ethanol. $^1$HNMR (400 MHz, CDCl$_3$): δ=7.89 (d, J=9.2 Hz, 1H), 7.40-7.37 (m, 1H), 6.92 (s, 1H), 4.25 (d, J=12.8 Hz, 2H), 3.88 (t, J=5.6 Hz, 2H), 3.57 (t, J=6.0 Hz, 2H), 3.07 (s, 3H), 2.96-2.90 (m, 2H), 1.82-1.75 (m, 7H), 1.51-1.39 (m, 6H), 1.25-1.16 (m, 5H), 0.99-0.96 (m, 2H). MS: m/z 427.3 (M+H$^+$).

Example 189: Preparation of 2-({2-(1-Fluoro-cyclopropyl)-4-[4-(2-methoxy-cyclohexyl)-piperidin-1-yl]-quinazolin-6-yl}-methyl-amino)-ethanol

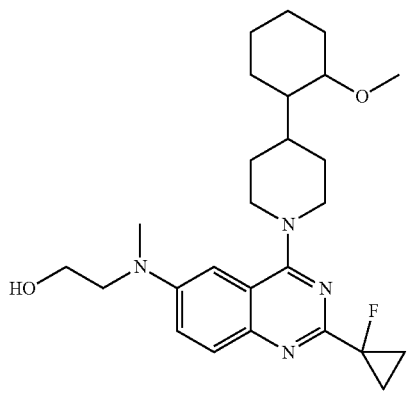 [SMILES: COC1CCCCC1C1CCN(c2nc(C3(F)CC3)nc3ccc(N(C)CCO)cc23)CC1]

The title compound was prepared as described in example 2-({2-cyclopropyl-4-[4-(2-dimethylamino-phenyl)-piperidin-1-yl]-quinazolin-6-yl}-methyl-amino)-ethanol. $^1$H NMR (400 MHz, CDCl$_3$): δ=7.89 (d, J=8.8 Hz, 1H), 7.41-7.37 (m, 1H), 6.93 (s, 1H), 4.25 (d, J=13.6 Hz, 2H), 3.88 (t, J=5.6 Hz, 2H), 3.57 (t, J=5.6 Hz, 2H), 3.52 (s, 1H), 3.30 (s, 3H), 3.07 (s, 3H), 3.02-2.93 (m, 2H), 2.12 (d, J=14.8 Hz, 1H), 1.92 (t, J=14.0 Hz, 2H), 1.76 (d, J=14.4 Hz, 2H), 1.49-1.42 (m, 6H), 1.34-1.24 (m, 5H), 1.19-1.14 (m, 2H). MS: m/z 457.3 (M+H$^+$).

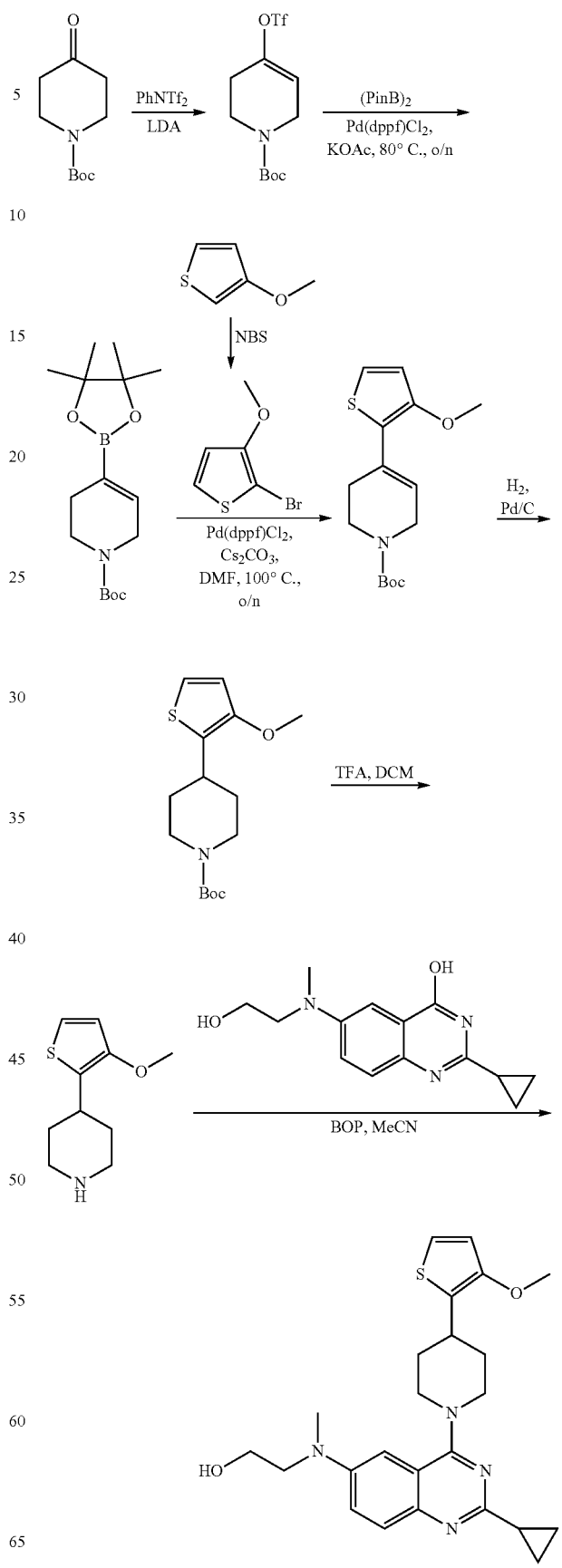

Example 190: Preparation of 2-({2-Cyclopropyl-4-[4-(3-methoxy-thiophen-2-yl)-piperidin-1-yl]-quinazolin-6-yl}-methyl-amino)-ethanol

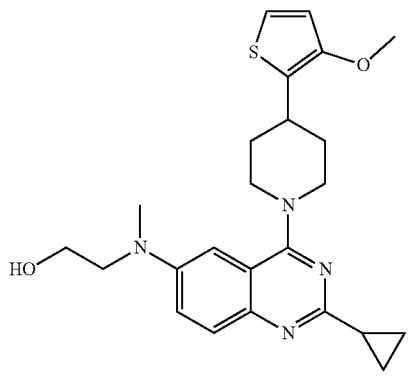 [SMILES: COc1ccsc1C1CCN(c2nc(C3CC3)nc3ccc(N(C)CCO)cc23)CC1]

Step 1: To a solution of tert-butyl 4-oxopiperidine-1-carboxylate (50 g, 251 mmol) in 600 mL of THF at −78° C. was dropwise added LiHMDS (1.0 M in THF, 325 mL, 325 mmol), then the mixture was stirred for 1 h at −78° C. before the addition of PhN(OTf)$_2$ (98.5 g, 276 mmol) at −78° C. The reaction was allowed to warm to room temperature and stirred overnight. The solution was quenched with water (100 mL) and the aqueous phase was extracted with EtOAc (200 mL×3). The extracts were washed with brine (500 mL) and dried over Na$_2$SO$_4$. The solution was evaporated in vacuum to give crude tert-butyl 4-(((trifluoromethyl)sulfonyl)oxy)-5,6-dihydropyridine-1(2H)-carboxylate (80.8 g, yield: 97%) as yellow oil, which was used for next step without further purification.

Step 2: To a solution of tert-butyl 4-(((trifluoromethyl)sulfonyl)oxy)-5,6-dihydropyridine-1(2H)-carboxylate (2.5 g, 7.55 mmol) in dioxane (10 mL) was added 4,4,5,5-tetramethyl-1,3,2-dioxaborolan-2-yl-4',4',5',5'-tetramethyl-1,3,2-dioxaborolane (2.9 g, 11.3 mmol), KOAc (1.5 g, 15.1 mmol) and Pd(dppf)Cl$_2$ under N$_2$. The mixture was stirred at 80° C. overnight. After cooled to room temperature, the reactant was concentrated to dryness and the residue was purified by silica gel column (PE/EA=20/1) to give tert-butyl 4-(4,4,5,5-tetramethyl-1,3,2-dioxaborolan-2-yl)-5,6-dihydropyridine-1(2H)-carboxylate (2 g, yield: 86%) as a white solid. $^1$H NMR (400 MHz, DMSO-d6): δ=6.38 (s, 1H), 3.86 (s, 2H), 3.36-3.28 (m, 2H), 2.09-2.05 (m, 2H), 1.44 (s, 9H), 1.11 (s, 12H).

Step 3: To a solution of 3-methoxythiophene (5.0 g, 43.8 mmol) in DCM (50 mL) was added NBS (7.8 g, 43.8 mmol) at 0° C. and the the mixture was stirred at this temperature for 0.5 h. The reaction was quenched with water (20 mL) and the mixture was extracted with DCM (30 mL×3). The extracts were dried over Na2SO4 and concentrated to give 2-bromo-3-methoxythiophene (8 g, yield: 95%) as a black oil. Note: this product goes bad easily in pure form at room temperature. But it is comparatively stable in solution. $^1$H NMR (400 MHz, DMSO-d6): δ=7.58 (d, J=6.0 Hz, 1H), 7.02 (d, J=6.0 Hz, 1H), 3.84 (s, 3H).

Step 4: To a solution of tert-butyl 4-(4,4,5,5-tetramethyl-1,3,2-dioxaborolan-2-yl)-5,6-dihydropyridine-1(2H)-carboxylate (500 mg, 2.6 mmol) in DMF (10 mL) was added 2-bromo-3-methoxythiophene (1.0 g, 3.9 mmol), Cs$_2$CO$_3$ (2.53 g, 7.8 mmol) and Pd(dppf)Cl$_2$.CH$_2$Cl$_2$(205 mg, 0.26 mmol). The mixture was stirred at 100° C. under N$_2$ overnight. The reactant was concentrated to dryness. The residue was combined with another batch (200 mg of 2-bromo-3-methoxythiophene) and the residue was purified by silica gel column (PE/EtOAc=20/1) to afford tert-butyl 4-(3-methoxy-thiophen-2-yl)-5,6-dihydropyridine-1(2H)-carboxylate (400 mg, yield: 13%) as a yellow oil. $^1$H NMR (400 MHz, DMSO-d6): δ=7.34 (d, J=5.6 Hz, 1H), 7.04 (d, J=5.6 Hz, 1H), 6.38 (s, 1H), 3.98-3.94 (m, 2H), 3.81 (s, 3H), 3.48 (t, J=5.2 Hz, 2H), 2.44-2.38 (m, 2H), 1.40 (s, 9H).

Step 5: To a solution of tert-butyl 4-(3-methoxythiophen-2-yl)-5,6-dihydropyridine-1(2H)-carboxylate (400 mg, 1.35 mmol) in MeOH (10 mL) was added 10% wet Pd/C (0.2 g), and the suspension was stirred at room temperature under balloon pressure overnight. The suspension was filtered and the filtrate was concentrated to give tert-butyl 4-(3-methoxy-thiophen-2-yl)piperidine-1-carboxylate (400 mg, yield: 99%) as a yellow oil. $^1$H NMR (400 MHz, CDCl$_3$): δ=7.01 (d, J=5.2 Hz, 1H), 6.81 (d, J=5.2 Hz, 1H), 4.20-4.15 (m, 2H), 3.85 (s, 3H), 3.10-3.01 (m, 1H), 2.82 (t, J=12.4 Hz, 2H), 1.88 (d, J=13.2 Hz, 2H), 1.62-1.50 (m, 2H), 1.46 (s, 9H).

Step 6: To a solution of tert-butyl 4-(3-methoxythiophen-2-yl)piperidine-1-carboxylate (300 mg, 1.01 mmol) in DCM (10 mL) was added TFA (2 mL), and the mixture was stirred at room temperature for 2 h. The reactant was concentrated to afford 4-(3-methoxythiophen-2-yl)piperidine as a dark oil. MS: m/z 198.2 (M+H$^+$).

Step 7: A mixture of compound 4-(3-methoxythiophen-2-yl)piperidine (125 mg, 0.424 mmol), 2-cyclopropyl-6-((2-hydroxyethyl)(methyl)amino)quinazolin-4-ol (100 mg, 0.386 mmol), BOP (256 mg, 0.580 mmol) and DBU (235 mg, 1.54 mmol) in acetonitrile (20 mL) was stirred room temperature overnight. LCMS showed the reaction was completed. Then the reaction mixture was poured into ice-water (100 mL), and the mixture was extracted with EtOAc (50 mL×3). The combined organic layers were washed with brine (100 mL), dried over Na$_2$SO$_4$, filtered and concentrated to give the crude product, which was purified by Prep-HPLC to afford 2-((2-cyclopropyl-4-(4-(3-methoxythiophen-2-yl)piperidin-1-yl)quinazolin-6-yl)(methyl)amino)ethanol (12 mg, yield: 7%) as a yellow solid. $^1$H NMR (400 MHz, CDCl$_3$): δ=7.77-7.70 (m, 1H), 7.34 (dd, J=9.2, 3.2 Hz, 1H), 7.04 (d, J=5.6 Hz, 1H), 6.92 (s, 1H), 6.85 (d, J=5.2 Hz, 1H), 4.33-4.30 (m, 2H), 3.88-3.85 (m, 5H), 3.56-3.53 (m, 2H), 3.26-3.24 (m, 3H), 3.04 (s, 3H), 1.92-1.86 (m, 5H), 1.17-1.13 (m, 2H), 0.99-0.97 (m, 2H). MS: m/z 439.2 (M+H$^+$).

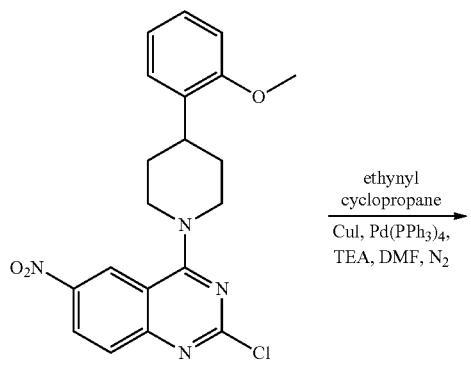

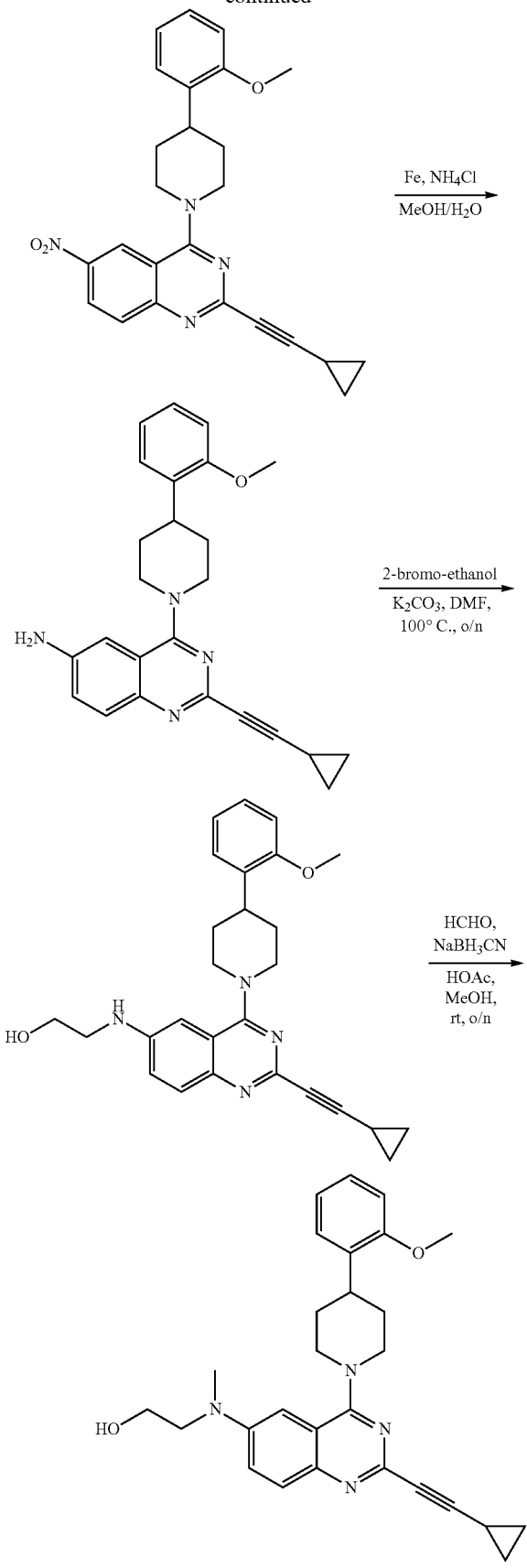

Example 191: Preparation of 2-({2-Cyclopropyl-ethynyl-4-[4-(2-methoxy-phenyl)-piperidin-1-yl]-quinazolin-6-yl}-methyl-amino)-ethanol

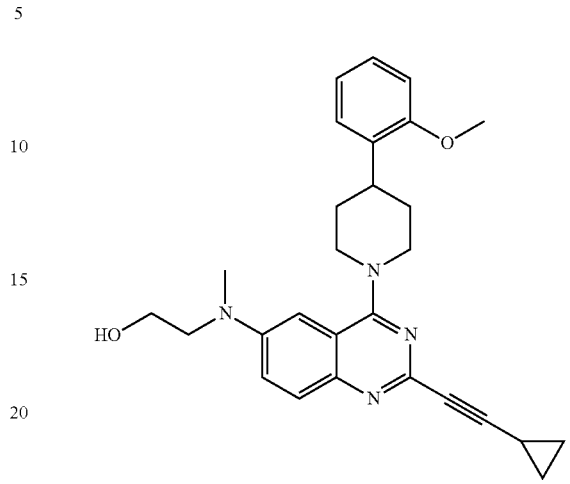

Step 1: A mixture of compound 2-chloro-4-(4-(2-methoxyphenyl)piperidin-1-yl)-6-nitroquinazoline (600 mg, 1.51 mmol), ethynyl-cyclopropane (573 mg, 7.54 mmol), CuI (60 mg, 030 mmol), TEA (457 mg, 4.52 mmol) and Pd(PPh$_3$)$_4$ (175 mg, 0.15 mmol) in DMF (20 mL) was charged with N$_2$ for 3 times, and the resulting mixture was heated to 100° C. overnight. LCMS showed the reaction was completed. The reaction mixture was concentrated to give the crude product which was purified by silica gel column chromatography (PE/EtOAc=1/1-5/1) to afford 2-(cyclopropylethynyl)-4-(4-(2-methoxyphenyl)piperidin-1-yl)-6-nitroquinazoline (500 mg, 77% yield) as a brown solid. MS: m/z 429.2 (M+H$^+$).

Step 2: A suspension of 2-(cyclopropylethynyl)-4-(4-(2-methoxyphenyl)piperidin-1-yl)-6-nitroquinazoline (500 mg, 1.17 mmol) and iron powder (327 mg, 5.84 mmol) in a mixture of MeOH (20 mL) and sat.NH$_4$Cl (2 mL) was heated to reflux for 30 min. LCMS showed the reaction was completed. The reaction suspension was concentrated to dryness. The residue was diluted with water (100 mL), and the mixture was extracted with EtOAc (100 mL×2). The extracts were washed brine (100 mL), dried over Na$_2$SO$_4$, filtered and concentrated to give the crude 2-(cyclopropylethynyl)-4-(4-(2-methoxyphenyl)piperidin-1-yl)quinazolin-6-amine (500 mg, yield: 95%) as a brown solid. MS: m/z 399.2 (M+H$^+$).

Step 3: A suspension of 2-(cyclopropylethynyl)-4-(4-(2-methoxyphenyl)piperidin-1-yl)quinazolin-6-amine (500 mg, 1.17 mmol), 2-bromo-ethanol (220 mg, 1.76 mmol) and K$_2$CO$_3$ (486 mg, 3.51 mmol) in DMF (10 mL) was heated to 100° C. for overnight. LCMS showed the reaction was completed. The reaction was diluted with water (100 mL), and the mixture was extracted with EtOAc (100 mL×2). The combined organic layers were washed with brine (100 mL×3), dried over Na$_2$SO$_4$, filtered and concentrated to give the crude 2-((2-(cyclopropylethynyl)-4-(4-(2-methoxyphenyl)piperidin-1-yl)quinazolin-6-yl)amino)ethanol (600 mg, about 60% purity, 40% yield) as a brown solid. MS: m/z 443.2 (M+H$^+$).

Step 4: To a solution of 2-((2-(cyclopropylethynyl)-4-(4-(2-methoxyphenyl)piperidin-1-yl)quinazolin-6-yl)amino) ethanol (crude 600 mg, 1.357 mmol) in MeOH (20 mL) was added HCHO (1.0 mL), followed by NaBH$_3$CN (0.85 g, 13.57 mmol) and HOAc (0.68 g, 13.57 mmol), and the resulting mixture was stirred at room temperature overnight. LCMS showed the reaction was completed. The reaction mixture was concentrated, and the residue was diluted with water (100 mL). The mixture was extracted with EtOAc (100 mL×2). The combined organic layers were dried over $Na_2SO_4$, filtered and concentrated to give the crude product which was purified by Prep-HPLC to afford 24(2-(cyclopropylethynyl)-4-(4-(2-methoxyphenyl)piperidin-1-yl)quinazolin-6-yl)(methyl)amino)ethanol (20 mg, yield: 5%) as a yellow solid. $^1$H NMR (400 MHz, DMSO-d6): δ=7.77 (d, J=8.8 Hz, 1H), 7.36 (dd, J=9.2 Hz, 2.8 Hz, 1H), 7.25-7.21 (m, 2H), 6.99-6.89 (m, 3H), 4.44-4.40 (m, 2H), 3.89-3.88 (m, 5H), 3.60-3.57 (m, 2H), 3.53-3.51 (m, 3H), 3.07 (s, 3H), 1.95-1.91 (m, 4H), 1.53-1.50 (m, 1H), 0.99-0.96 (m, 2H), 0.91-0.88 (m, 2H). MS: m/z 457.2 (M+H$^+$).

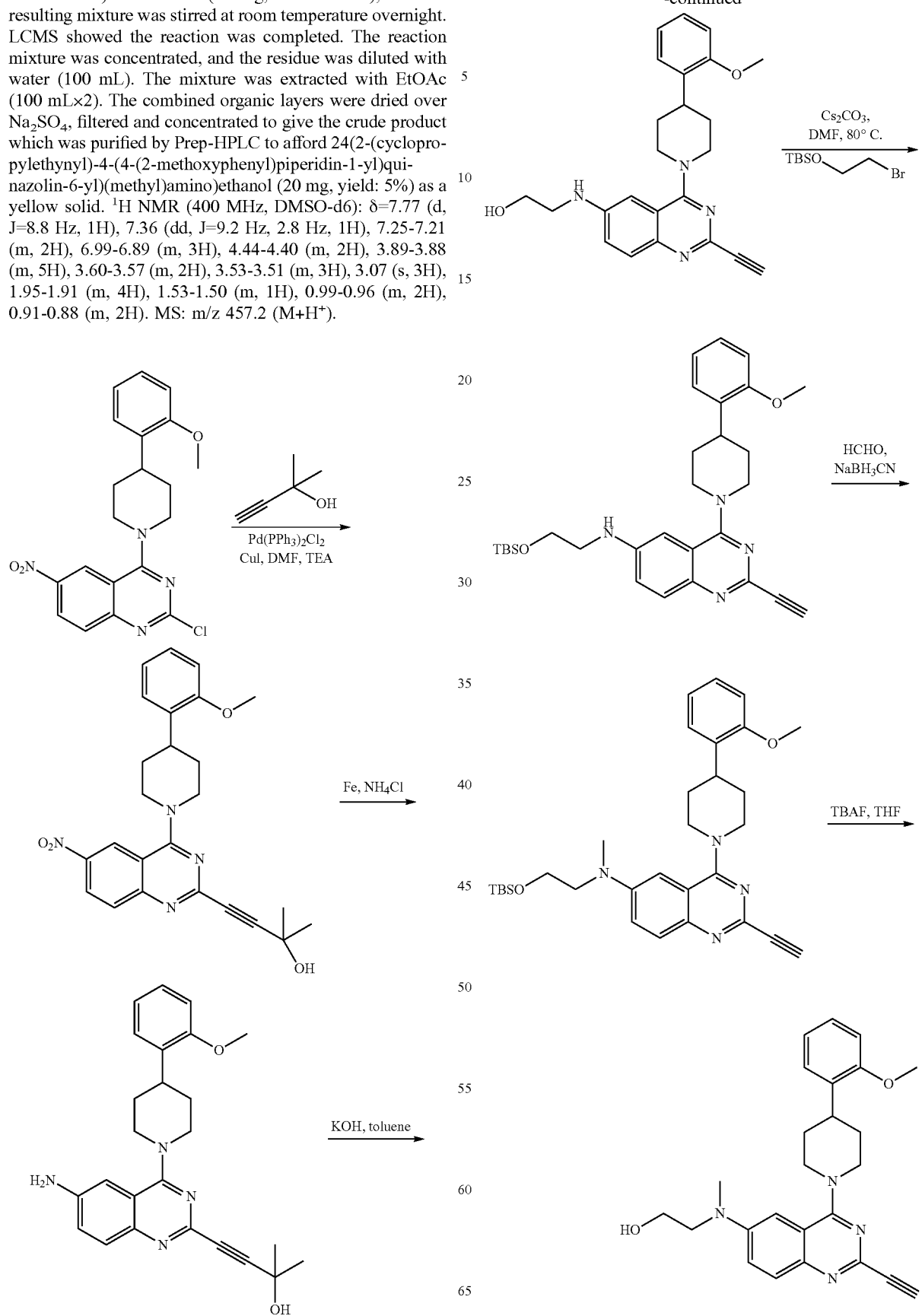

Example 192: Preparation of 2-({2-Ethynyl-4-[4-(2-methoxy-phenyl)-piperidin-1-yl]-quinazolin-6-yl}-methyl-amino)-ethanol

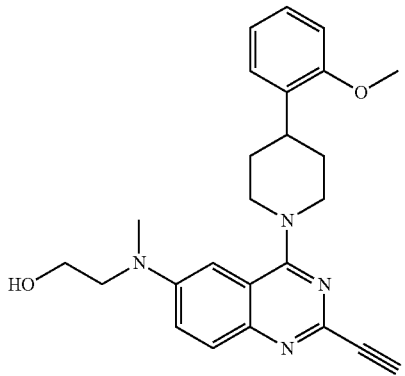 [SMILES: C#Cc1nc(N2CCC(c3ccccc3OC)CC2)c2cc(N(C)CCO)ccc2n1]

Step 1: A mixture of 2-chloro-4-(4-(2-methoxyphenyl)piperidin-1-yl)-6-nitroquinazoline (800 mg, 2.01 mmol), 2-methyl-but-3-yn-2-ol (845 mg, 10.05 mmol), CuI (76 mg, 0.04 mmol), TEA (610 mg, 6.03 mmol) and Pd(PPh$_3$)$_4$ (230 mg, 0.02 mmol) in DMF (20 mL) was charged with N$_2$ 3 times, and the resulting mixture was heated to 100° C. for overnight. LCMS showed the reaction was completed. The reaction mixture was concentrated to give the crude product which was purified by silica gel column chromatography (PE/EtOAc=1/1-5/1) to afford the desired 4-(4-(4-(2-methoxyphenyl)piperidin-1-yl)-6-nitroquinazolin-2-yl)-2-methylbut-3-yn-2-ol (520 mg, yield: 58%) as a brown solid.

Step 2: A suspension of 4-(4-(4-(2-methoxyphenyl)piperidin-1-yl)-6-nitroquinazolin-2-yl)-2-methylbut-3-yn-2-ol (520 mg, 1.16 mmol) and iron powder (326 mg, 5.83 mmol) in a mixture of MeOH (20 mL) and sat.NH$_4$Cl (2 mL) was heated to reflux for 30 min. LCMS showed the reaction was completed. The reaction suspension was concentrated, and the residue was diluted with water (100 mL). The mixture was extracted with EtOAc (100 mL×2). The combined organic layers were washed brine (100 mL), dried over Na$_2$SO$_4$, filtered and concentrated to give the crude 4-(6-amino-4-(4-(2-methoxyphenyl)piperidin-1-yl)quinazolin-2-yl)-2-methylbut-3-yn-2-ol (540 mg, yield: 80%) as a brown solid.

Step 3: To solution of 4-(6-amino-4-(4-(2-methoxyphenyl)piperidin-1-yl)quinazolin-2-yl)-2-methylbut-3-yn-2-ol (440 mg, 1.06 mmol) in toluene (50 mL) was added ground NaOH (850 mg, 21.20 mmol), and the resulting suspension was heated to 110° C. for 2 h. LCMS showed the reaction was completed. The reaction suspension was filtered and the filtrate was concentrated to give 2-((2-ethynyl-4-(4-(2-methoxyphenyl)piperidin-1-yl)quinazolin-6-yl)amino)ethanol (350 mg, yield: 78%) as a brown solid.

Step 4: A suspension of 2-((2-ethynyl-4-(4-(2-methoxyphenyl)piperidin-1-yl)quinazolin-6-yl)amino)ethanol (170 mg, 0.475 mmol), (2-bromo-ethoxy)-tert-butyl-dimethyl-silane (568 mg, 2.373 mmol) and Cs$_2$CO$_3$ (773 mg, 2.373 mmol) in DMF (10 mL) was heated to 150° C. for 2 h. LCMS showed the reaction was completed. The reaction suspension was diluted with ice-water (100 mL), and the mixture was extracted with EtOAc (50 mL×3). The combined organic layers were washed with brine (50 mL×3), dried over Na$_2$SO$_4$, filtered and concentrated to give the crude product which was purified by silica gel column chromatography (PE/EtOAc=3/1) to afford 2-((2-ethynyl-4-(4-(2-methoxyphenyl)piperidin-1-yl)quinazolin-6-yl)amino)ethanol (64 mg, yield: 19%) as a brown solid.

Step 5: To a solution of 2-((2-ethynyl-4-(4-(2-methoxyphenyl)piperidin-1-yl)quinazolin-6-yl)amino)ethanol (64 mg, 0.124 mmol) in MeOH (10 mL) was added HCHO (0.2 mL), followed by NaBH$_3$CN (39 mg, 0.62 mmol) and NaBH(OAc)$_3$ (131 mg, 0.62 mmol), and the resulting mixture was stirred at room temperature for overnight. The reaction mixture was concentrated, and the residue was diluted with water (50 mL). The mixture was extracted with EtOAc (30 mL×3). The combined organic layers were washed brine (100 mL), dried over Na$_2$SO$_4$, filtered and concentrated to give the desired product N-(2-((tert-butyldimethylsilyl)oxy)ethyl)-2-ethynyl-4-(4-(2-methoxyphenyl)piperidin-1-yl)-N-methylquinazolin-6-amine (crude 100 mg, yield: 90%) as a yellow solid.

Step 6: A mixture of N-(2-((tert-butyldimethylsilyl)oxy)ethyl)-2-ethynyl-4-(4-(2-methoxyphenyl)piperidin-1-yl)-N-methylquinazolin-6-amine (crude 100 mg, 0.194 mmol) and TBAF (253 mg, 0.968 mmol) in THF (10 mL) was stirred at room temperature for 2 h. LCMS showed the reaction was completed. The reaction mixture was diluted with sat.NH$_4$Cl (50 mL), and the mixture was extracted with EtOAc (30 mL×3). The combined organic layers were washed brine (100 mL), dried over Na$_2$SO$_4$, filtered and concentrated to give the crude product which was purified by Prep-TLC (PE/EtOAc=1/1) to afford 2-((2-ethynyl-4-(4-(2-methoxyphenyl)piperidin-1-yl)quinazolin-6-yl)(methyl)amino)ethanol (17 mg, 21% yield) as a yellow solid. NMR (400 MHz, DMSO-d6): δ=7.77 (d, J=9.6 Hz, 1H), 7.40 (dd, J=9.2 Hz, 2.8 Hz, 1H), 7.25-7.21 (m, 2H), 6.99-6.89 (m, 3H), 4.42-4.39 (m, 2H), 3.90-3.86 (m, 5H), 3.62-3.59 (m, 2H), 3.22-3.12 (m, 3H), 3.09 (s, 3H), 2.98 (s, 1H), 2.03-1.92 (m, 4H). MS: m/z 417.2 (M+H$^+$).

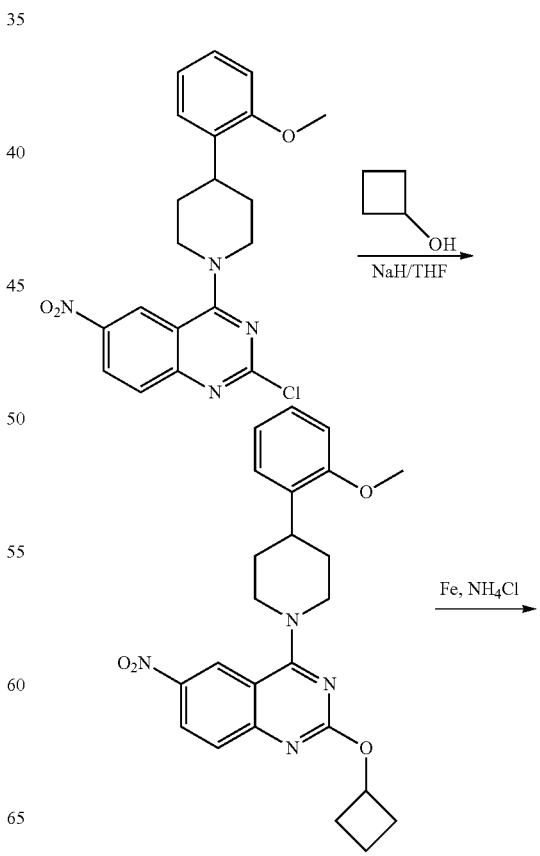

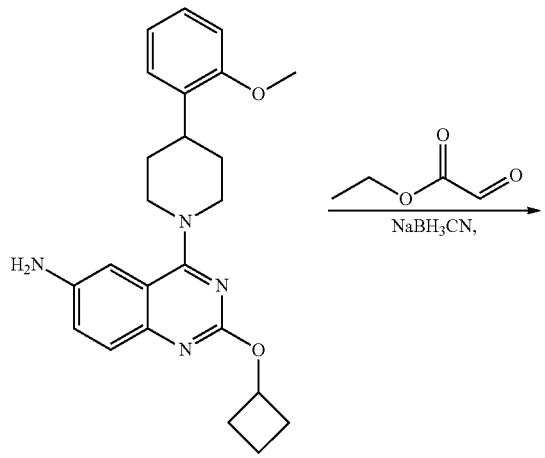

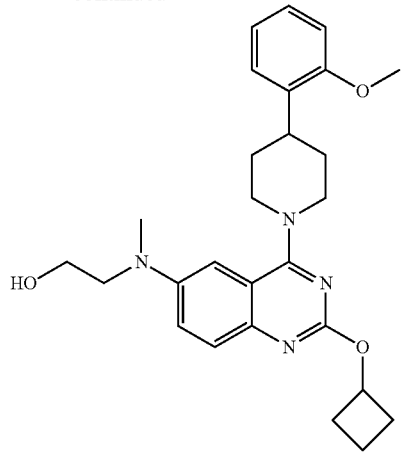 [SMILES: COc1ccccc1C1CCN(c2nc(OC3CCC3)nc3ccc(N(C)CCO)cc23)CC1]

Example 193: Preparation of 2-((2-cyclobutoxy-4-(4-(2-methoxyphenyl)piperidin-1-yl)quinazolin-6-yl)(methyl)amino)ethanol

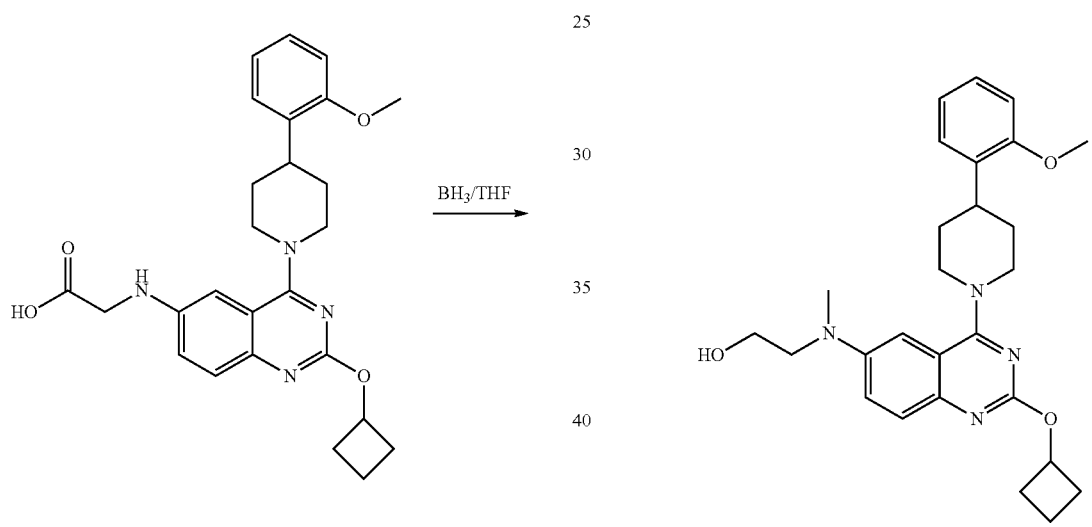

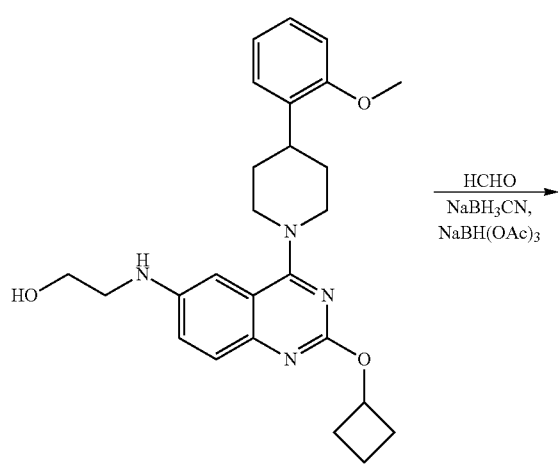

Step 1: To a suspension of NaH (60% in mineral oil, 110 mg, 2.76 mmol) in THF (20 mL) was added cyclobutanol (181 mg, 2.51 mmol), and the reaction was stirred at 0° C. for 30 min. Then to the mixture was added 2-chloro-4-(4-(2-methoxyphenyl)piperidin-1-yl)-6-nitroquinazoline (500 mg, 1.26 mmol), and the mixture was stirred at room temperature till 2-chloro-4-(4-(2-methoxyphenyl)piperidin-1-yl)-6-nitroquinazoline was consumed completely shown by TLC. The reaction was quenched with saturated $NH_4Cl$ (100 mL). The aqueous phase was extracted with EtOAc (50 mL×3). The combined organic layers were washed with brine (100 mL) and dried over $Na_2SO_4$. The solution was filtered and concentrated to give 2-cyclobutoxy-4-(4-(2-methoxyphenyl)piperidin-1-yl)-6-nitroquinazoline (540 mg crude, 80% LC purity, yield: 79%) as a brown solid.

Step 2: To a solution of 2-cyclobutoxy-4-(4-(2-methoxyphenyl)piperidin-1-yl)-6-nitroquinazoline (540 mg crude, 1.24 mmol) in MeOH (30 mL) was added iron (330 mg, 6.22 mmol) and saturated $NH_4Cl$ (5 mL), and the mixture was stirred at 80° C. till the reaction was completed shown by TLC. The reaction was concentrated and the residue was diluted with water (100 mL). The mixture was extracted with DCM (50 mL×3). The combined organic layers were washed with brine (100 mL) and dried over Na₂SO₄. The solution was filtered and concentrated to give 2-cyclobutoxy-4-(4-(2-methoxyphenyl)piperidin-1-yl)quinazolin-6-amine (530 mg crude) as a yellow solid.

Step 3: To a solution of 2-cyclobutoxy-4-(4-(2-methoxyphenyl)piperidin-1-yl)quinazolin-6-amine (530 mg crude, 1.31 mmol) in MeOH (30 mL) was added ethyl 2-oxoacetate (345 mg, 3.92 mmol), NaBH₃CN (266 mg, 3.92 mmol) and NaOAc (190 mg, 3.92 mmol), and the mixture was stirred at room temperature for 1 h. LCMS showed the reaction was completed. The reactant was concentrated and the residue was diluted with water (100 mL). The mixture was extracted with DCM (50 mL×3). The extracts were washed with brine (100 mL) and dried over Na₂SO₄. The solution was filtered and concentrated to give 2-((2-cyclobutoxy-4-(4-(2-methoxyphenyl)piperidin-1-yl)quinazolin-6-yl)amino)acetic acid (800 mg crude) as a yellow solid. MS: m/z 463.2 (M+H⁺).

Step 4: A mixture of 2-((2-cyclobutoxy-4-(4-(2-methoxyphenyl)piperidin-1-yl)quinazolin-6-yl)amino)acetic acid (800 mg crude, 1.72 mmol) and BH₃.Me₂S (8.5 mL, 17.3 mmol) in THF (20 mL) was heated to reflux overnight. The reaction was quenched with MeOH (10 mL), followed by 1N HCl (20 mL). The mixture was refluxed for 1 h. After cooled to room temperature, the reaction was extracted with EtOAc (50 mL×3). The extracts were washed with brine (100 mL) and dried over Na₂SO₄. The solution was filtered and concentrated to give 2-((2-cyclobutoxy-4-(4-(2-methoxyphenyl)piperidin-1-yl)quinazolin-6-yl)amino)ethanol (600 mg crude) as a yellow solid. MS: m/z 449.2 (M+H⁺).

Step 5: A mixture of 2-((2-cyclobutoxy-4-(4-(2-methoxyphenyl)piperidin-1-yl)quinazolin-6-yl)amino)ethanol (600 mg crude, 1.34 mmol), HCHO (1.0 mL), NaBH₃CN (0.84 g, 13.4 mmol) and NaBH(OAc)₃ (2.84 g, 13.4 mmol) in MeOH (50 mL) was stirred at room temperature till LCMS showed the reaction was completed. The reaction mixture was concentrated and the residue was diluted with ice water (100 mL). The mixture was extracted with DCM (50 mL×3). The extracts were washed with brine (100 mL) and dried over Na₂SO₄. The solution was filtered and concentrated to give 2-({2-Cyclobutoxy-4-[4-(2-methoxy-phenyl)-piperidin-1-yl]-quinazolin-6-yl}-methyl-amino)-ethanol (55 mg, five-step yield: 9.4%) as a yellow solid. ¹H NMR (400 MHz, CDCl3): δ=7.62 (d, J=9.2 Hz, 1H), 7.35 (dd, J=9.2 Hz, 1H), 7.24-7.20 (m, 3H), 7.02-6.87 (m, 3H), 5.30-5.23 (m, 1H), 4.52-4.47 (m, 2H), 3.87-3.82 (m, 5H), 3.53-3.48 (m, 2H), 3.30-3.25 (m, 3H), 3.01 (s, 3H), 2.51-2.46 (m, 2H), 2.31-2.25 (m, 2H), 1.99-1.92 (m, 6H). MS: m/z 423.2 (M+H⁺).

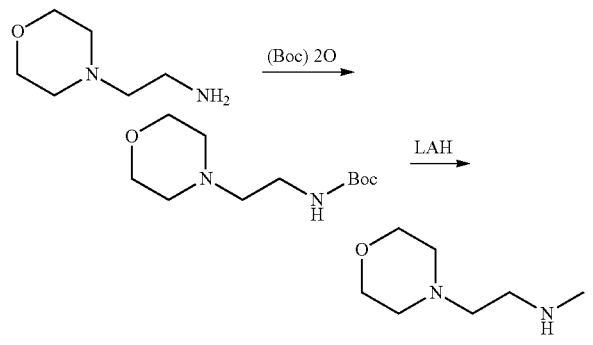

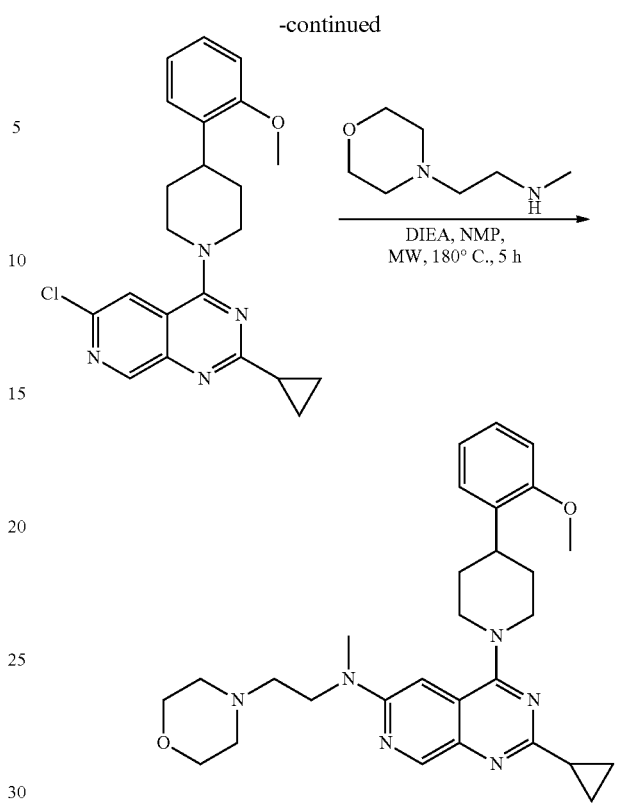

Example 194: Preparation of 2-cyclopropyl-4-(4-(2-methoxyphenyl)piperidin-1-yl)-N-methyl-N-(2-morpholinoethyl)pyrido[3,4-d]pyrimidin-6-amine

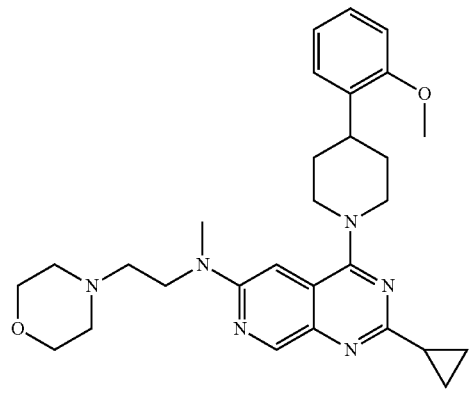 [SMILES: COc1ccccc1C1CCN(c2nc(C3CC3)nc3cnc(N(C)CCN4CCOCC4)cc23)CC1]

Step 1: A mixture of 2-morpholinoethanamine (1.00 g, 7.69 mmol), (Boc)₂O (1.66 g, 7.69 mmol) and TEA (0.93 g, 9.23 mmol) in DCM (50 mL) was stirred at room temperature for overnight. The reaction mixture was diluted with water (100 mL). The aqueous phase was extracted with DCM (100 mL×2), and the combined organic layers were washed with brine (100 mL), dried over Na₂SO₄, filtered and concentrated to give tert-butyl (2-morpholinoethyl)carbamate (1.60 g, yield: 90%) as yellow oil.

Step 2: To a solution of tert-butyl (2-morpholinoethyl) carbamate (1.0 g, 4.4 mmol) in THF (50 mL) was added LAH (0.5 g, 13 mmol), and the resulting suspension was heated to reflux for overnight. TLC showed the reaction was completed. The reaction suspension was cooled to 0° C., and then quenched with water (3.0 mL), followed by 5 N NaOH (2.0 mL). The resulting suspension was filtered and the filtrate was concentrated to give N-methyl-2-morpholinoethanamine (0.35 g, yield: 55%) as yellow oil.

Step 3: A mixture of 6-chloro-2-cyclopropyl-4-(4-(2-methoxyphenyl)piperidin-1-yl)pyrido[3,4-d]pyrimidine (50 mg, 0.127 mmol), N-methyl-2-morpholinoethanamine (37 mg, 0.254 mmol) and DIPEA (30 mg, 0.280 mmol) in NMP (5 mL) was heated to 180° C. in MW for 5 h. LCMS showed the reaction was completed. The reaction mixture was diluted with water (20 mL). The aqueous phase was extracted with EtOAc (50 mL×3). The combined organic layers were washed with brine (50 mL×3), dried over Na$_2$SO$_4$, filtered and concentrated to give the crude product, which was purified by Prep-HPLC to afford the desired 2-cyclopropyl-4-(4-(2-methoxyphenyl)piperidin-1-yl)-N-methyl-N-(2-morpholinoethyl)pyrido[3,4-d]pyrimidin-6-amine (15 mg, yield: 24%) as a yellow solid. $^1$H NMR (400 MHz, CDCl$_3$): δ=8.90 (s, 1H), 7.21 (d, J=8.0 Hz, 2H), 6.98-6.89 (m, 2H), 6.50 (s, 1H), 4.44-4.41 (m, 2H), 3.86-3.80 (m, 5H), 3.69-3.67 (m, 4H), 3.32-3.29 (m, 1H), 3.19-3.12 (m, 2H), 3.09 (s, 3H), 2.60- 2.52 (m, 6H), 1.99-1.96 (m, 4H), 1.15-1.12 (m, 2H), 0.99-0.95 (m, 2H). MS: m/z 503.3 (M+H$^+$).

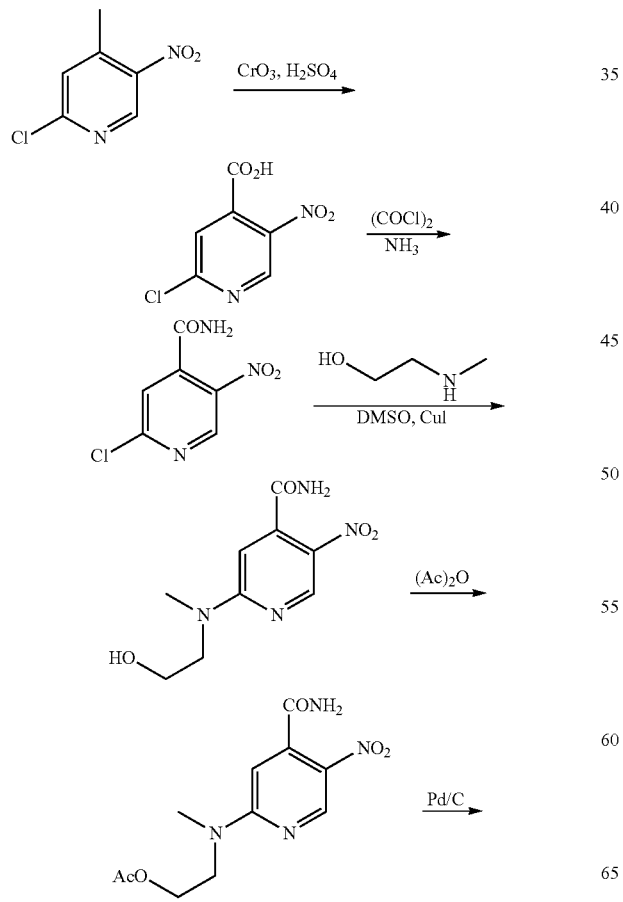

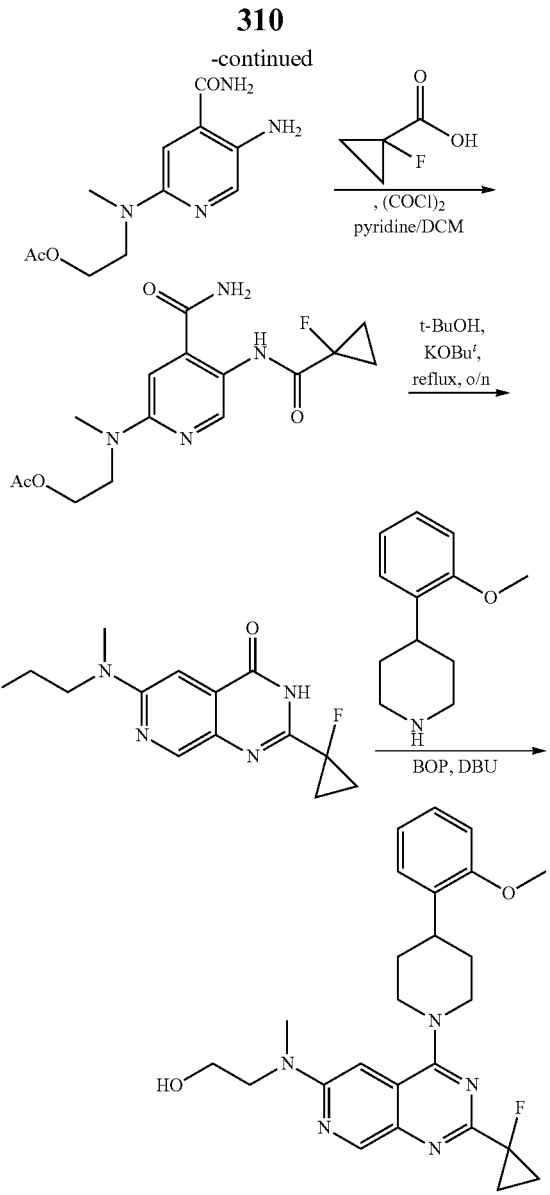

Example 195: Preparation of 2-({2-(1-Fluoro-cyclopropyl)-4-[4-(2-methoxy-phenyl)-piperidin-1-yl]-pyrido[3,4-d]pyrimidin-6-yl}-methyl-amino)-ethanol

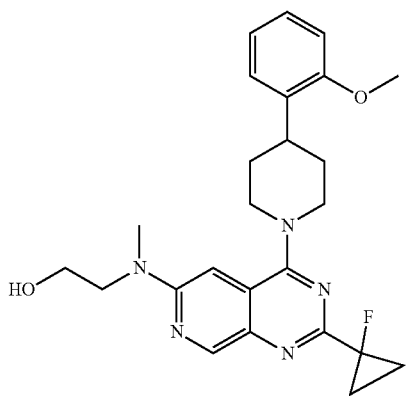 [SMILES: COc1ccccc1C1CCN(c2nc(C3(F)CC3)nc3cnc(N(C)CCO)cc23)CC1]

Step 1: To a solution of 2-chloro-4-methyl-5-nitro-pyridine (10.35 g, 60 mmol) in H₂S O₄ (100 mL), CrO₃ (19.8 g, 198 mmol) was added at 0° C. The mixture was stirred at 0° C. for 1 h and then was allowed to warm to room temperature and stirred overnight. The mixture was poured into ice water (500 mL). The resulting solid was filtered and dried to give 2-chloro-5-nitro-isonicotinic acid (8.89 g, yield: 73%) as a white solid. MS: m/z 200.9 (M−H⁺).

Step 2: To a solution of 2-chloro-5-nitro-isonicotinic acid (4.64 g, 23 mmol) in DCM (200 mL), 5 drops of DMF was added. Then (COCl)₂ (7.27 g, 57.3 mmol) was added dropwise at 0° C. The mixture was stirred at room temperature overnight. The solvent was removed and dry THF (200 mL) was added. NH₃ gas was bubbled into the solution for 0.5 h. The mixture was filtered and the filtrate was concentrated to give 2-chloro-5-nitro-isonicotinamide (4.61 g, 95%) as a white solid. ¹H NMR (400 MHz, DMSO-d6): δ=9.12 (s, 1H), 8.32 (brs, 1H), 8.07 (brs, 1H), 7.90 (s, 1H).

Step 3: To a solution of 2-chloro-5-nitro-isonicotinamide (1.0 g, 5.0 mmol) in 1,4-dioxane (40 mL), DIEPA (1.3 g, 10 mmol) and 2-methylamino-ethanol (1.13 g, 15 mmol) was added. The mixture was stirred at 90° C. overnight. The solvent was removed to give 2-[(2-hydroxy-ethyl)-methyl-amino]-5-nitro-isonicotinamide (2.3 g crude) as yellow oil. MS: m/z 238.9 (M−H⁺).

Step 4: To a solution of 2-[(2-hydroxy-ethyl)-methyl-amino]-5-nitro-isonicotinamide (2.3 g, crude) in pyridine (5 mL), Ac₂O (1.53 g, 15 mmol) was added. The mixture was stirred at 100° C. for 1 h. The solvent was removed and the residue was purified by silica gel column (DCM/MeOH=40/1) to give 2-((4-carbamoyl-5-nitropyridin-2-yl)(methyl)amino)ethyl acetate (0.99 g, two-step yield: 70%) as a yellow solid. MS: m/z 282.9 (M+H⁺).

Step 5: To a solution of 2-((4-carbamoyl-5-nitropyridin-2-yl)(methyl)amino)ethyl acetate (0.99 g, 3.5 mmol) in MeOH (30 mL), Pd/C (0.3 g) was added. The mixture was stirred at room temperature under H₂ balloon for 4 h. The mixture was filtered and the filtrate was concentrated to give 2-((5-amino-4-carbamoylpyridin-2-yl)(methyl)amino)ethyl acetate (0.81 g, yield: 92%) as brown oil. MS: m/z 253.0 (M+H⁺).

Step 6-8: These three steps are similar to 2-((8-chloro-2-(1-fluorocyclobutyl)-4-(4-(2-methoxyphenyl)piperidin-1-yl)quinazolin-6-yl)(methyl)amino)ethanol to afford 2-({2-(1-fluoro-cyclopropyl)-4-[4-(2-methoxy-phenyl)-piperidin-1-yl]-pyrido pyrimidin-6-yl}-methyl-amino)-ethanol (31 mg, three-step yield: 3.1%) as a yellow solid. ¹H NMR (300 MHz, CDCl₃): δ=9.00 (s, 1H), 7.25-7.20 (m, 2H), 6.97-6.92 (m, 2H), 6.61 (s, 1H), 4.45 (d, J=12.4 Hz, 2H), 3.90-3.83 (m, 7H), 3.20-3.14 (m, 3H), 3.12 (s, 3H), 2.02-1.63 (m, 4H), 1.58-1.49 (m, 4H). MS: m/z 452.2 (M+H⁺).

Example 196: Preparation of 1-{2-(1-Fluoro-cyclopropyl)-4-[4-(2-methoxy-phenyl)-piperidin-1-yl]-pyrido[3,4-d]pyrimidin-6-yl}-pyrrolidin-3-ol

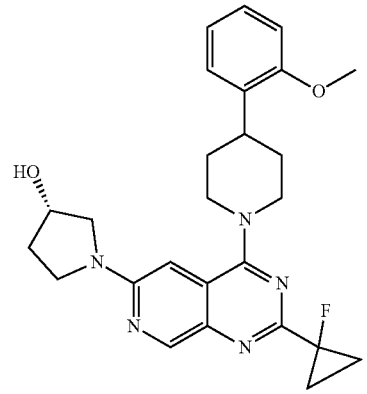 [SMILES: COc1ccccc1C1CCN(c2nc(C3(F)CC3)nc3cnc(N4CC[C@H](O)C4)cc23)CC1]

The title compound was prepared using general procedure for 2-({2-(1-fluoro-cyclopropyl)-4-[4-(2-methoxy-phenyl)-piperidin-1-yl]-pyrido[3,4-d]pyrimidin-6-yl}-methyl-amino)-ethanol. ¹HNMR (400 MHz, CDCl₃): δ=9.07 (s, 1H), 7.24-7.20 (m, 2H), 6.98-6.89 (m, 2H), 6.42 (s, 1H), 4.67 (brs, 1H), 4.45 (d, J=12.4 MHz, 2H), 3.86 (s 3H), 3.73-3.59 (m, 4H), 3.33-3.28 (m, 1H), 3.20-3.14 (m, 2H), 2.24.2.20 (m, 1H), 2.02-1.60 (m, 5H), 1.54-1.48 (m, 4H). MS: m/z 464.2 (M+H⁺).

Example 197: Preparation of 1-{2-(1-Fluoro-cyclopropyl)-4-[4-(2-methoxy-phenyl)-piperidin-1-yl]-pyrido[3,4-d]pyrimidin-6-yl}-pyrrolidin-3-ol

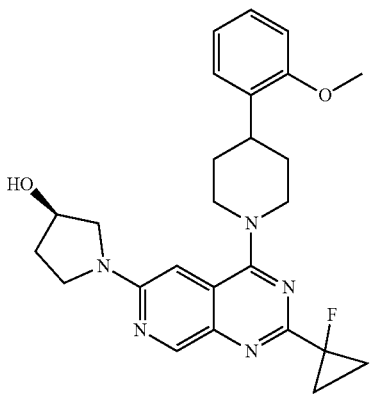 [SMILES: COc1ccccc1C1CCN(c2nc(C3(F)CC3)nc3cnc(N4CC[C@@H](O)C4)cc23)CC1]

The title compound was prepared using general procedure for 2-({2-(1-fluoro-cyclopropyl)-4-[4-(2-methoxy-phenyl)-piperidin-1-yl]-pyrido[3,4-d]pyrimidin-6-yl}-methyl-amino)-ethanol. ¹H NMR (400 MHz, CDCl₃): δ=9.07 (s, 1H), 7.26-7.21 (m, 2H), 6.96-6.89 (m, 2H), 6.42 (s, 1H), 4.69-4.65 (m, 1H), 4.45 (d, J=12.4 MHz, 2H), 3.86 (s 3H), 3.72-3.59 (m, 4H), 3.20-3.14 (m, 3H), 2.23-2.14 (m, 1H), 2.00-1.85 (m, 5H), 1.59-1.45 (m, 4H). MS: m/z 464.2 (M+H⁺).

Example 198: Preparation of 2-({2-(1-Fluoro-cyclobutyl)-4-[4-(2-methoxy-phenyl)-piperidin-1-yl]-pyrido[3,4-d]pyrimidin-6-yl}-methyl-amino)-ethanol

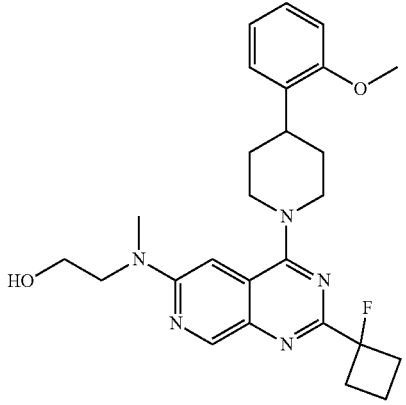 [SMILES: COc1ccccc1C1CCN(c2nc(C3(F)CCC3)nc3cnc(N(C)CCO)cc23)CC1]

The title compound was prepared using general procedure for 2-({2-(1-fluoro-cyclopropyl)-4-[4-(2-methoxy-phenyl)-piperidin-1-yl]-pyrido[3,4-d]pyrimidin-6-yl}-methyl-amino)-ethanol. $^1$H NMR (300 MHz, CDCl$_3$): δ=9.00 (s, 1H), 7.25-7.21 (m, 2H), 6.98-6.89 (m, 2H), 6.42 (s, 1H), 4.57 (d, J=12.4 MHz, 2H), 3.91-3.82 (m, 4H), 3.86 (s, 3H), 3.34-3.23 (m, 3H), 3.14 (s, 3H), 2.85-2.83 (m, 2H), 2.69-2.61 (m, 2H), 2.05-1.90 (m, 6H). MS: m/z 466.2 (M+H$^+$).

Example 199: Preparation of 1-{2-(1-Fluoro-cyclobutyl)-4-[4-(2-methoxy-phenyl)-piperidin-1-yl]-pyrido[3,4-d]pyrimidin-6-yl}-pyrrolidin-3-ol

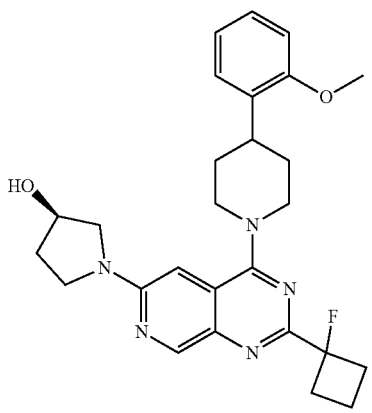 [SMILES: COc1ccccc1C1CCN(c2nc(C3(F)CCC3)nc3cnc(N4CC[C@@H](O)C4)cc23)CC1]

The title compound was prepared using general procedure for 2-({2-(1-fluoro-cyclopropyl)-4-[4-(2-methoxy-phenyl)-piperidin-1-yl]-pyrido[3,4-d]pyrimidin-6-yl}-methyl-amino)-ethanol. $^1$H NMR (300 MHz, CDCl$_3$): δ=9.07 (s, 1H), 7.25-7.20 (m, 2H), 6.96-6.89 (m, 2H), 6.44 (s, 1H), 4.70-4.66 (m, 1H), 4.57 (d, J=12.4 Hz, 2H), 3.86 (s, 3H), 3.71-3.61 (m, 4H), 3.35-3.20 (m, 3H), 2.88-2.64 (m, 4H), 2.24-2.20 (m, 4H), 2.05-1.91 (m, 4H). MS: m/z 478.2 (M+H$^+$).

Example 200: Preparation of 1-{2-(1-Fluoro-cyclobutyl)-4-[4-(2-methoxy-phenyl)-piperidin-1-yl]-pyrido[3,4-d]pyrimidin-6-yl}-pyrrolidin-3-ol

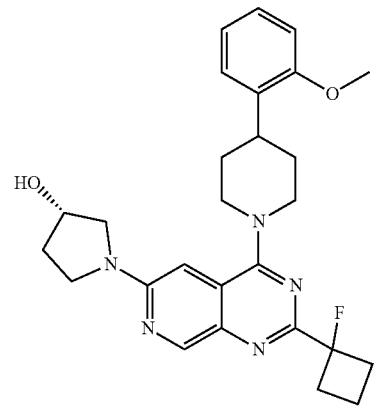 [SMILES: COc1ccccc1C1CCN(c2nc(C3(F)CCC3)nc3cnc(N4CC[C@H](O)C4)cc23)CC1]

The title compound was prepared using general procedure for 2-({2-(1-fluoro-cyclopropyl)-4-[4-(2-methoxy-phenyl)-piperidin-1-yl]-pyrido[3,4-d]pyrimidin-6-yl}-methyl-amino)-ethanol. $^1$H NMR (300 MHz, CDCl$_3$): δ=9.07 (s, 1H), 7.25-7.22 (m, 2H), 6.97-6.89 (m, 2H), 6.44 (s, 1H), 4.70-4.66 (m, 1H), 4.58 (d, J=12.4 Hz, 2H), 3.86 (s, 3H), 3.73-3.60 (m, 4H), 3.30-3.22 (m, 3H), 2.86-2.64 (m, 4H), 2.22-2.04 (m, 2H), 2.01-1.69 (m, 6H). MS: m/z 478.2 (M+H$^+$).

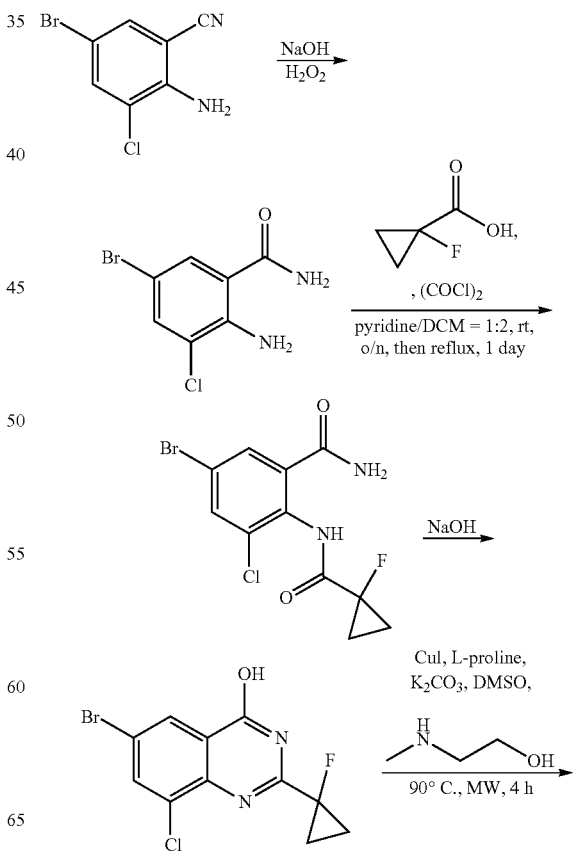

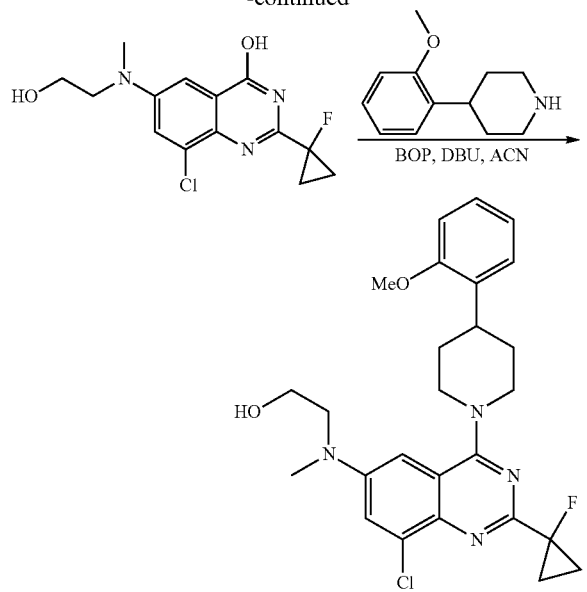

Example 201: Preparation of 2-({8-Chloro-2-(1-fluoro-cyclopropyl)-4-[4-(2-methoxy-phenyl)-piperidin-1-yl]-quinazolin-6-yl}-methyl-amino)-ethanol

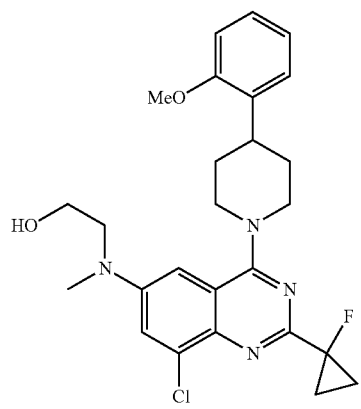

Step 1: To a solution of 2-amino-5-bromo-3-chloro-benzonitrile (3.50 g, 17.0 mmol) and NaOH (1.4 g, 34.0 mmol in MeOH/H$_2$O (1/5, 70 mL) was added H$_2$O$_2$ (18.5 mL, 170.0 mmol) at room temperature. The mixture was stirred at 90° C. overnight. After cooled to room temperature, the mixture was diluted with H$_2$O (50 mL) and filtered. The filter cake was dried to give 2-amino-5-bromo-3-chloro-benzamide (3.2 g, yield: 85%) as a white solid. NMR (400 MHz, DMSO-d$_6$): δ=8.03 (brs, 1H), 7.75 (d, J=2.0 Hz, 1H), 7.59 (d, J=2.0 Hz, 1H), 7.44 (brs, 1H), 6.84 (brs, 2H).

Step 2: To a mixture of 1-fluoro-cyclopropanecarboxylic acid (300 mg, 2.88 mmol) in DCM (5 mL) was added (COCl)$_2$ (439.0 mg, 3.46 mmol) and the mixture was stirred 38° C. for 2 h. Then, the mixture was added to the solution of 2-amino-5-bromo-3-chloro-benzamide (794.0 mg, 3.2 mmol) in pyridine (10 mL). The mixture was stirred at 80° C. overnight. Then, the mixture was concentrated and the residue was purified by flash column to give 5-bromo-3-chloro-2-[(1-fluoro-cyclopropanecarbonyl)-amino]-benzamide (450 mg, yield: 47%) as a white solid. MS: m/z 333.0 (M–H$^+$).

Step 3: The mixture of 5-bromo-3-chloro-2-[(1-fluoro-cyclopropanecarbonyl)-amino]-benzamide (450.0 mg, 1.4 mmol) and NaOH (190.0 mg, 2.7 mmol) in THF/H$_2$O (5:1, 10 mL) was refluxed for 12 h. Then, the mixture was concentrated and the residue was purified by flash column to give 6-bromo-8-chloro-2-(1-fluoro-cyclopropyl)-quinazolin-4-ol (330 mg, yield: 78%) as a white solid. $^1$H NMR (300 MHz, DMSO-d$_6$): δ=12.94 (s, 1H), 8.19 (d, J=2.4 Hz, 1H), 8.13 (d, J=2.1 Hz, 1H), 1.64-1.15 (m, 4H)

Step 4: The mixture of 6-bromo-8-chloro-2-(1-fluoro-cyclopropyl)-quinazolin-4-ol (110.0 mg, 0.35 mmol), 2-methylamino-ethanol (52.0 mg, 0.70 mmol), K$_2$CO$_3$ (120.0 mg, 0.87 mmol), L-proline (32 mg, 0.28 mmol) and CuI (26.0 mg, 0.14 mmol) in DMSO (2 mL) was heated to 90° C. by microwave for 5 h. The reaction mixture was filtered and the filtrate was purified by pre-HPLC to give 8-chloro-2-(1-fluoro-cyclopropyl)-6-[(2-hydroxy-ethyl)-methyl-amino]-quinazolin-4-ol (34.0 mg, yield: 31%) as a yellow solid. MS: m/z 309.9 (M–H$^+$).

Step 5: A mixture of 8-chloro-2-(1-fluoro-cyclopropyl)-6-[(2-hydroxy-ethyl)-methyl-amino]-quinazolin-4-ol (34.0 mg, 0.11 mmol), 4-(2-methoxy-phenyl)-piperidine (191.0 mg, 0.22 mmol), BOP (99.0 mg, 0.22 mmol) and DBU (68 mg, 0.44 mmol) in MeCN was stirred at room temperature overnight. The mixture was concentrated and the residue was purified by pre-HPLC to give 2-({8-chloro-2-(1-fluoro-cyclopropyl)-4-[4-(2-methoxy-phenyl)-piperidin-1-yl]-quinazolin-6-yl}-methyl-amino)-ethanol (4.2 mg, yield: 7.5%) as a yellow solid. $^1$H NMR (400 MHz, CDCl$_3$): δ=7.48 (d, J=2.4 Hz, 1H), 7.25-7.20 (m, 2H), 6.96 (t, J=7.6 Hz, 1H), 6.91-6.87 (m, 2H), 4.33 (d, J=12.8 Hz, 2H), 3.88-3.85 (m, 5H), 3.55 (t, J=2.4 Hz, 2H), 3.48 (m, 1H), 3.15 (t, J=11.6 Hz, 2H), 3.05 (s, 3H), 1.99-1.87 (m, 4H), 1.75-1.69 (m, 2H), 1.58-1.46 (m, 2H). MS: m/z 485.2 (M+H$^+$).

Example 202: Preparation of 1-{8-Chloro-2-(1-fluoro-cyclopropyl)-4-[4-(2-methoxy-phenyl)-piperidin-1-yl]-quinazolin-6-yl}-pyrrolidin-3-ol

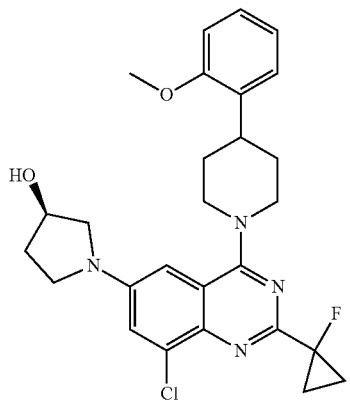 [SMILES: COc1ccccc1C1CCN(c2nc(C3(F)CC3)nc3c(Cl)cc(N4CC[C@@H](O)C4)cc23)CC1]

The title compound was prepared as described in example 2-({8-Chloro-2-(1-fluoro-cyclopropyl)-4-[4-(2-methoxy-phenyl)-piperidin-1-yl]-quinazolin-6-yl}-methyl-amino)-ethanol. $^1$H NMR (300 MHz, CDCl$_3$): δ=7.30-7.29 (m, 1H), 7.26-7.21 (m, 2H), 7.00-6.90 (m, 2H), 6.67-6.66 (d, J=2.7 Hz, 1H), 4.69-4.68 (m, 1H), 4.38-4.37 (d, J=12.8 Hz, 2H), 3.87 (s, 3H), 3.64-3.60 (m, 2H), 3.49-3.45 (m, 1H), 3.38-3.28 (m, 2H), 3.18-3.10 (m, 2H), 2.26-2.16 (m, 2H), 2.03-1.91 (m, 5H), 1.56-1.48 (m, 4H). MS: m/z 497.2 (M+H⁺).

Example 203: Preparation of 1-{8-Chloro-2-(1-fluoro-cyclopropyl)-4-[4-(2-methoxy-phenyl)-piperidin-1-yl]-quinazolin-6-yl}-pyrrolidin-3-ol

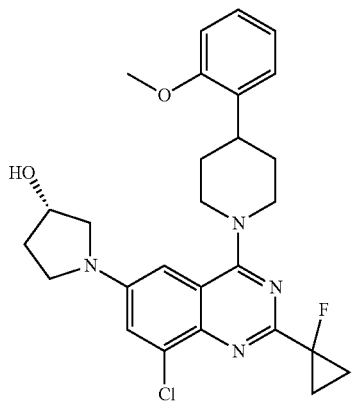 [SMILES: COc1ccccc1C1CCN(c2nc(C3(F)CC3)nc3c(Cl)cc(N4CC[C@H](O)C4)cc23)CC1]

The title compound was prepared as described in example 2-({8-Chloro-2-(1-fluoro-cyclopropyl)-4-[4-(2-methoxy-phenyl)-piperidin-1-yl]-quinazolin-6-yl}-methyl-amino)-ethanol. ¹H NMR (300 MHz, CDCl₃): δ=7.30-7.20 (m, 3H), 6.96 (t, J=7.6 Hz, 1H), 6.90 (d, J=3.6 Hz, 1H), 6.65 (d, J=2.4 Hz, 1H), 4.69-4.68 (m, 1H), 4.36-4.33 (d, J=12.8 Hz, 2H), 3.85 (s, 3H), 3.62-3.58 (m, 2H), 3.47-3.42 (m, 1H), 3.36-3.26 (m, 2H), 3.16-3.10 (m, 2H), 2.24-2.12 (m, 2H), 2.03-1.89 (m, 5H), 1.54-1.45 (m, 4H). MS: m/z 497.2 (M+H⁺).

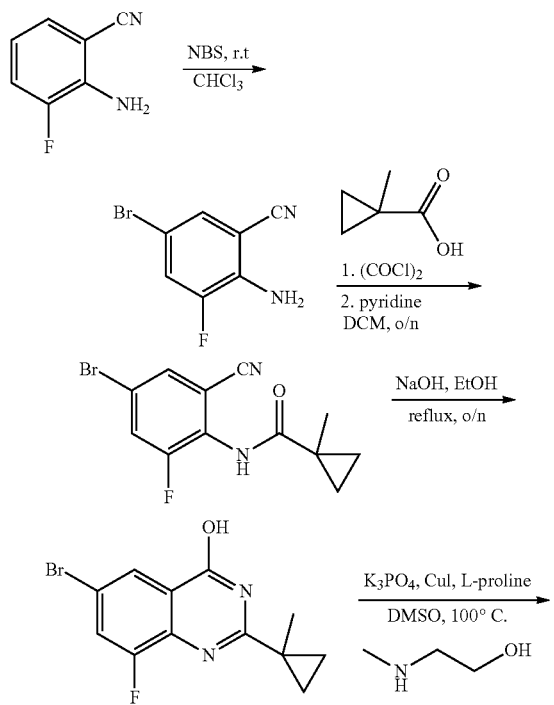

Example 204: Preparation of 2-{[8-Fluoro-4-[4-(3-methoxy-pyrazin-2-yl)-piperidin-1-yl]-2-(1-methyl-cyclopropyl)-quinazolin-6-yl]-methyl-amino}-ethanol

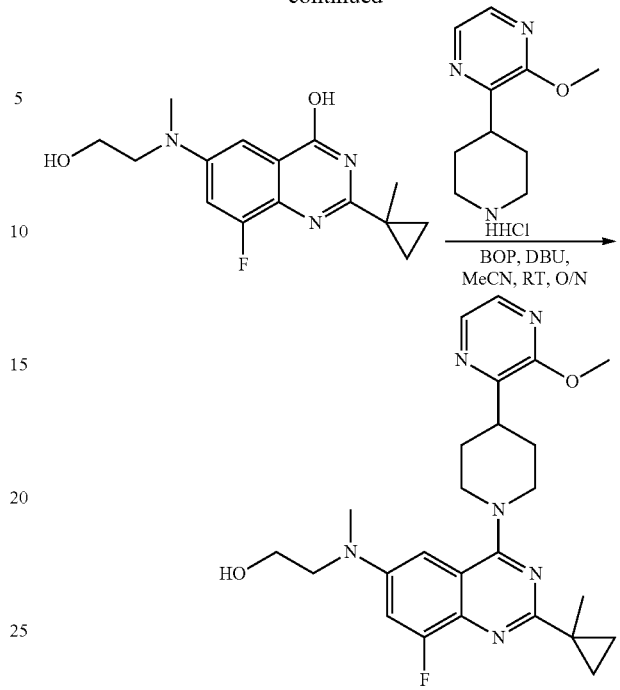

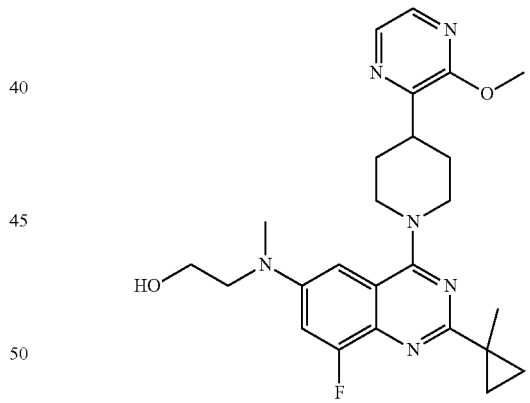

Step 1: A suspension of 2-amino-3-fluoro-benzonitrile (5.4 g, 40.0 mmol) and NBS (7.1 g, 40.0 mmol) in DCM (150 mL) was stirred at room temperature for overnight. TLC showed the reaction was completed. The reaction was quenched with Na₂SO₃ (aq, 50 mL), and the mixture was extracted with EtOAc (100 mL×3). The combined organic layers were washed with brine (150 mL), dried over Na₂SO₄, filtered and concentrated to give 2-amino-5-bromo-3-fluoro-benzonitrile (8.8 g, yield: 99.5%) as white solid. ¹H NMR (DMSO-d₆, 400 MHz): δ=7.60 (dd, J=12.4, 1.2 Hz, 1H), 7.53 (s, 1H), 6.44 (brs, 2H). MS: m/z 214.0 (M+H⁺).

Step 2: To a solution of 1-methyl-cyclopropanecarboxylic acid (200 mg, 2.00 mmol) in oxalyl chloride (0.2 mL) was added DMF (0.05 mL). The mixture was stirred at room temperature for 2 h. To a solution of 2-amino-5-bromo-3-fluoro-benzonitrile (513 mg, 2.40 mmol), pyridine (2.0 mL) in THF (10 mL) was added a solution of 1-methyl-cyclopropanecarbonyl chloride in THF (10 mL). The resulting mixture was stirred at room temperature for 2 h. The resultant was added to NaHCO₃ (50 mL) and the aqueous phase was extracted with EtOAc (40 mL×3). The organic layer was washed with brine (50 mL) and dried over Na₂SO₄. The solvent was removed in vacuum to afford 1-methyl-cyclopropanecarboxylic acid (4-bromo-2-cyano-6-fluoro-phenyl)-amide (500 mg, yield: 84%) as a yellow solid.

Step 3: To a solution of 1-methyl-cyclopropanecarboxylic acid (4-bromo-2-cyano-6-fluoro-phenyl)-amide (500 mg, 1.68 mmol) in ethanol (20 mL) was added H₂O₂ (3 mL) and NaOH (80 mg, 2.01 mmol). The mixture was stirred at 80° C. for 1 h. The solvent was removed in vacuum. Water (100 mL) was added. The mixture was extracted with DCM (30 mL×3). The organic layer was washed with brine (50 mL), dried over Na₂SO₄ and concentrated to give 6-bromo-8-fluoro-2-(1-methyl-cyclopropyl)-quinazolin-4-ol (298 mg, yield: 60%) as a white solid. $^1$H NMR (DMSO-d₆, 400 MHz): δ=12.06-11.99 (brs, 1H), 7.95-7.92 (m, 2H), 1.46 (s, 3H), 1.28-1.25 (m, 2H), 0.83-0.77 (m, 2H). MS: m/z 296.0 (M+H⁺)

Step 4: To a solution of 6-bromo-8-fluoro-2-(1-methyl-cyclopropyl)-quinazolin-4-ol (298 mg, 1.00 mmol) L-proline (115 mg, 1.00 mmol), CuI (96 mg, 0.50 mmol) and K₂CO₃ (553 mg, 4.00 mmol) in DMSO (5 mL) were added 2-methylamino-ethanol (226 mg, 3.00 mmol) under N₂. The reaction was stirred at 100° C. for overnight. LCMS showed the reaction was good. The reaction was quenched with water (10 mL), and the mixture was extracted with EtOAc (15 mL×3). The organic layer was washed with brine (15 mL), dried over Na₂SO₄, and evaporated in vacuum. The residue was purified by silica gel chromatography (EA/PE=1/5) to give 8-fluoro-6-[(2-hydroxy-ethyl)-methyl-amino]-2-(1-methyl-cyclopropyl)-quinazolin-4-ol (140 mg, yield: 48%) as yellow solid.

Step 5: To a suspension of 2-methoxy-3-piperidin-4-yl-pyrazine (121 mg, 0.53 mmol), BOP (314 mg, 0.73 mmol), 8-fluoro-6-[(2-hydroxy-ethyl)-methyl-amino]-2-(1-methyl-cyclopropyl)-quinazolin-4-ol in MeCN (10 mL) was added DBU (367 mg, 2.41 mmol), then the mixture was stirred at room temperature for overnight. TLC showed the reaction was completed. The reaction was quenched with water (20 mL), and the mixture was extracted with EtOAc (30 mL×3). The combined organic layers were washed with brine (50 mL), dried over Na₂SO₄. The solution was filtered and concentrated to dryness in vacuum. The residue was purified by Prep-HPLC to give 2-{[8-fluoro-4-[4-(3-methoxy-pyrazin-2-yl)-piperidin-1-yl]-2-(1-methyl-cyclopropyl)-quinazolin-6-yl]-methyl-amino}-ethanol (45 mg, yield: 20%) as a white solid. $^1$H NMR (400 MHz, DMSO-d₆): δ=8.07 (s, 1H), 7.97 (s, 1H), 7.06 (d, J=12.8 Hz, 1H), 6.73 (s, 1H), 4.29 (d, J=12.4 Hz, 2H), 4.00 (s, 3H), 3.86 (s, 2H), 3.52 (s, 2H), 3.32-3.29 (m, 1H), 3.14-3.03 (m, 5H), 2.13-1.99 (m, 4H), 1.71 (s, 3H), 1.44-1.38 (m, 2H), 0.83-0.77 (m, 2H). MS: m/z 466.9 (M+H⁺)

Example 205: Preparation of 2-{[4-[4-(3-Methoxy-pyrazin-2-yl)-piperidin-1-yl]-2-(1-methyl-cyclopropyl)-quinazolin-6-yl]-methyl-amino}-ethanol

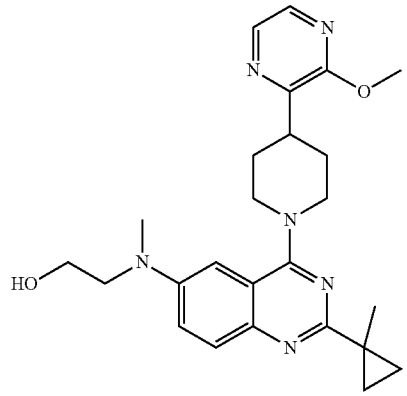 [SMILES: COc1nccnc1C1CCN(c2nc(C3(C)CC3)nc3ccc(N(C)CCO)cc23)CC1]

The title compound was prepared as described in example 2-{[8-fluoro-4-[4-(3-methoxy-pyrazin-2-yl)-piperidin-1-yl]-2-(1-methyl-cyclopropyl)-quinazolin-6-yl]-methyl-amino}-ethanol. $^1$H NMR (400 MHz, CDCl₃): δ=8.08 (d, J=2.8 Hz, 1H), 7.97 (d, J=2.8 Hz, 1H), 7.76 (d, J=8.4 Hz, 1H), 7.37-7.34 (m, 1H), 7.98 (d, J=2.8 Hz, 1H), 4.30 (d, J=12.8 Hz, 2H), 4.00 (s, 3H), 3.87-3.84 (m, 2H), 3.55-3.53 (m, 2H), 3.34-3.28 (m, 1H), 3.15-2.93 (m, 5H), 2.14-1.99 (m, 4H), 1.67 (s, 3H), 1.41-1.40 (m, 2H), 0.81-0.78 (m, 2H). MS: m/z 448.9 (M+H⁺).

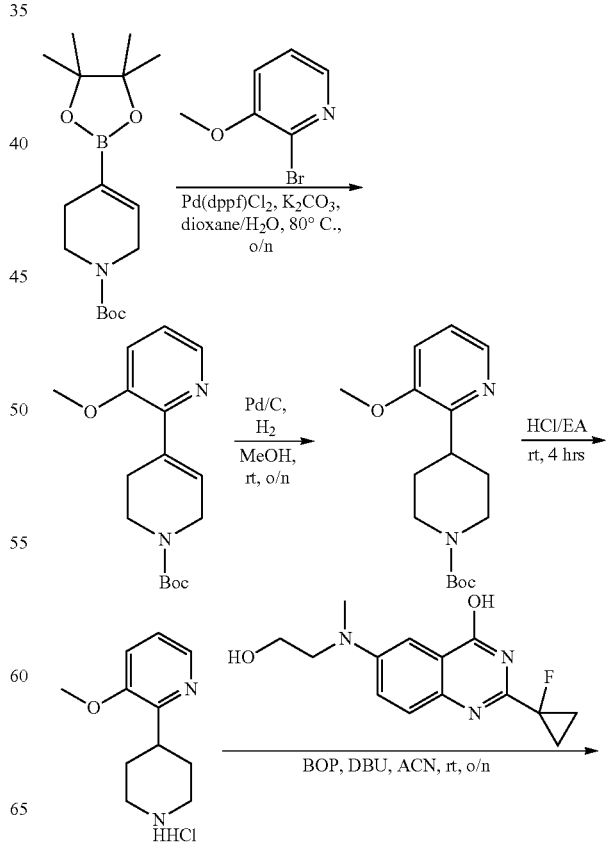

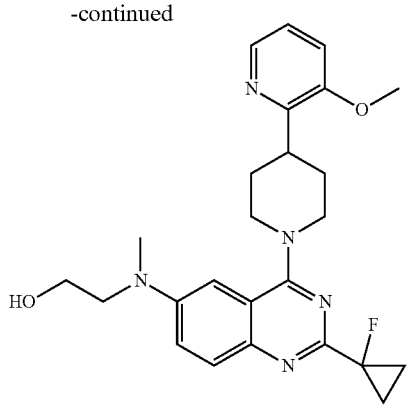

Example 206: Preparation of 2-{[2-(1-Fluoro-cyclopropyl)-4-(3-methoxy-3',4',5',6'-tetrahydro-2'H-[2,4']bipyridinyl-V-yl)-quinazolin-6-yl}-methyl-amino]-ethanol

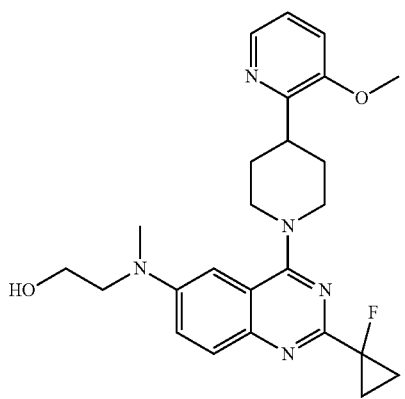

Step 1: To a solution of 4-(4,4,5,5-tetramethyl-[1,3,2]dioxaborolan-2-yl)-3,6-dihydro-2H-pyridine-1-carboxylic acid tert-butyl ester (1.45 g, 4.68 mmol) and 2-bromo-3-methoxy-pyridine (800 mg, 4.26 mmol) in dioxane/H$_2$O (30 mL+10 mL) were added Pd(dppf)Cl$_2$ (156 mg, 0.21 mmol) and K$_2$CO$_3$ (2.35 g, 17.0 mmol). The resulting mixture was stirred at 80° C. under N$_2$ atmosphere overnight. Then the reaction mixture was poured into H$_2$O (100 mL) and extracted with EtOAc (20 mL×3). The extracts were washed with brine (20 mL×3), dried over Na$_2$SO$_4$ and concentrated in vacuum to give a residue, which was purified by a silica gel column (DCM/MeOH=50/1) to afford 3-methoxy-3',6'-dihydro-2'H-[2,4']bipyridinyl-1'-carboxylic acid tert-butyl ester (1.12 g, yield: 91%) as a yellow oil. $^1$H NMR (400 MHz, CDCl$_3$): δ=8.18 (dd, J=4.4, 1.2 Hz, 1H), 7.22-7.11 (m, 2H), 6.58-6.30 (m, 1H), 4.18-4.08 (m, 2H), 3.84 (s, 3H), 3.67-3.57 (m, 2H), 2.70-2.60 (m, 2H), 1.49 (s, 9H).

Step 2: To a solution of 3-methoxy-3',6'-dihydro-2'H-[2,4']bipyridinyl-1'-carboxylic acid tert-butyl ester (1.12 g, 3.79 mmol) in MeOH (20 mL) was added wet Pd/C (110 mg, 10% wt). The resulting mixture was stirred at room temperature under H$_2$ atmosphere overnight. Then Pd/C was filtered off and the filtrate was concentrated in vacuum to afford 3-methoxy-3',4',5',6'-tetrahydro-2'H-[2,4']bipyridinyl-F-carboxylic acid tert-butyl ester (1.1 g, yield: 100%) as a colorless oil, which was used for next step without further purification.

Step 3: To a solution of 3-methoxy-3',4',5',6'-tetrahydro-2'H-[2,4']bipyridinyl-1'-carboxylic acid tert-butyl ester (1.1 g, 3.76 mmol) in EtOAc (20 mL) was added HCl/EtOAc (excess). The resulting mixture was stirred at room temperature for 4 hrs. The solid precipitated form the reaction mixture was collected by filtration. The cake was washed with EtOAc (60 mL), ether (60 mL) and air-dried to afford 3-methoxy-1',2',3',4',5',6'-hexahydro-[2,4']bipyridinyl (630 mg, yield: 73%) as a white solid. $^1$H NMR (400 MHz, DMSO-d6): δ=9.62-9.43 (m, 1H), 9.32-9.10 (m, 1H), 8.27 (d, J=4.4 Hz, 1H), 7.94 (d, J=8.0 Hz, 1H), 7.69 (t, J=5.6 Hz, 1H), 3.96 (s, 3H), 3.53 (t, J=11.2 Hz, 1H), 3.41-3.31 (m, 2H), 3.10-2.92 (m, 2H), 2.32-2.12 (m, 2H), 2.01-1.85 (m, 2H), 1.98-1.89 (m, 4H).

Step 4: To a mixture of 2-(1-fluoro-cyclopropyl)-6-[(2-hydroxy-ethyl)-methyl-amino]-quinazolin-4-ol (100 mg, 0.361 mmol) and 3-methoxy-1',2',3',4',5',6'-hexahydro-[2,4']bipyridinyl (91 mg, 0.397 mmol) in MeCN (20 mL) were added BOP (240 mg, 0.542 mmol) and DBU (220 mg, 1.44 mmol). The resulting mixture was stirred at room temperature overnight. Then MeCN was removed in vacuum to give a residue, which was purified by Prep-HPLC with NH$_4$OH as additive to afford 2-{[2-(1-Fluoro-cyclopropyl)-4-(3-methoxy-3',4',5',6'-tetrahydro-2'H-[2,4']bipyridinyl-1'-yl)-quinazolin-6-yl]-methyl-amino}-ethanol (20.7 mg, yield: 13%) as a yellow solid. $^1$H NMR (400 MHz, CDCl$_3$): δ=8.16 (t, J=2.8 Hz, 1H), 7.85 (d, J=9.2 Hz, 1H), 7.37 (dd, J=9.2 Hz, 2.8 Hz, 1H), 7.15 (d, J=2.8 Hz, 2H), 7.01 (d, J=2.8 Hz, 1H), 4.31 (d, J=13.2 Hz, 2H), 3.91-3.83 (m, 5H), 3.57 (t, J=5.6 Hz, 2H), 3.49-3.39 (m, 1H), 3.16-3.03 (m, 5H), 2.23-1.91 (m, 5H), 1.56-1.43 (m, 4H). MS: m/z 452.2 (M+H$^+$).

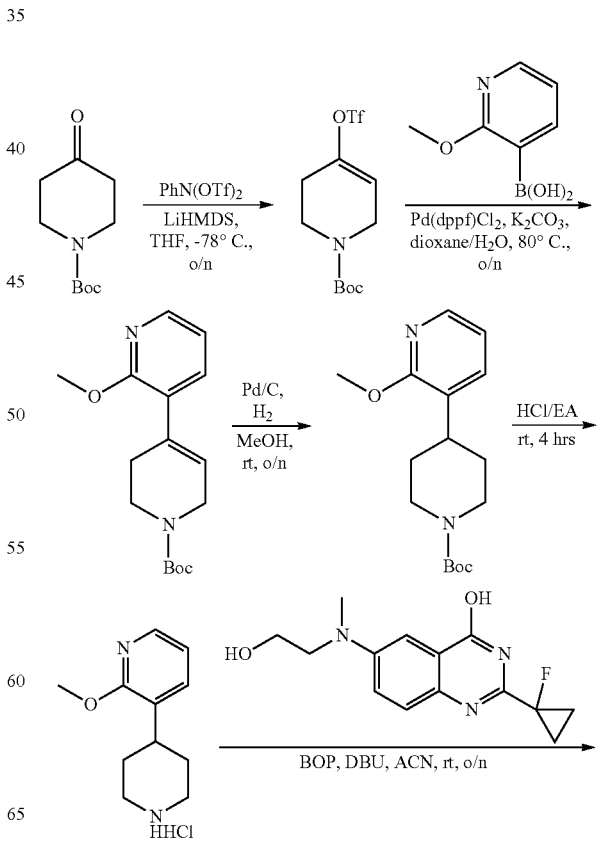

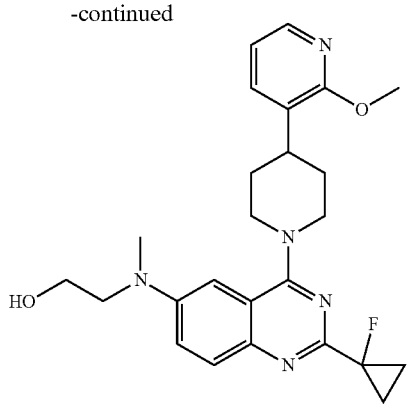

Example 207: Preparation of 2-{[2-(1-Fluoro-cyclopropyl)-4-(2-methoxy-3',4',5',6'-tetrahydro-2'H-[3,4'] bipyridinyl-V-yl)-quinazolin-6-yl]-methyl-amino}-ethanol

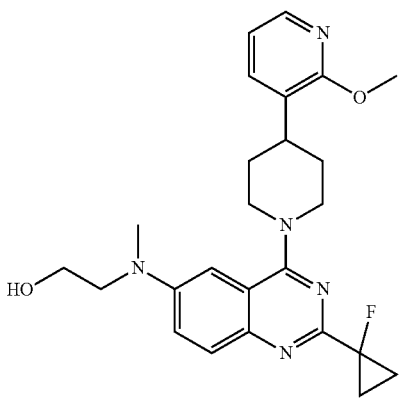 [SMILES: COc1ncccc1C1CCN(c2nc(C3(F)CC3)nc3ccc(N(C)CCO)cc23)CC1]

Step 1: To a solution of 4-oxo-piperidine-1-carboxylic acid tert-butyl ester (10.0 g, 50 mmol) in dry THF (100 mL) was added LiHMDS (65 mL, 65 mmol, 1 M in THF) dropwise at −78° C. under N₂ atmosphere. The resulting mixture was stirred at −78° C. for 1 hr. Then PhN(OTf)₂ was added into the reaction mixture, and the mixture was allowed to warm to room temperature and stirred overnight. The reaction mixture was quenched with H₂O (100 mL) and extracted with EtOAc (50 mL×2). The organic layers were washed with brine (50 mL×2), dried over Na₂SO₄ and concentrated in vacuum to give 4-trifluoromethanesulfonyloxy-3,6-dihydro-2H-pyridine-1-carboxylic acid tert-butyl ester (12.0 g, yield: 73%) as a yellow oil, which was used for next step without further purification.

Step 2: To a solution of 4-trifluoromethanesulfonyloxy-3,6-dihydro-2H-pyridine-1-carboxylic acid tert-butyl ester (2.0 g, 6.04 mmol) and 2-methoxypyridin-3-ylboronic acid (1.0 g, 6.6 mmol) in dioxane/H₂O (30 mL+20 mL) were added Pd(dppf)Cl₂ (220 mg, 0.3 mmol) and K₂CO₃ (3.33 g, 24 mmol). The resulting mixture was stirred at 80° C. under N₂ atmosphere overnight. Then the reaction mixture was poured into H₂O (100 mL) and extracted with EtOAc (20 mL×3). The extracts were washed with brine (20 mL×3), dried over Na₂SO₄ and concentrated in vacuum to give a residue, which was purified by a silica gel column (DCM/MeOH=50/1) to afford 2-methoxy-3',6'-dihydro-2'H-[3,4'] bipyridinyl-F-carboxylic acid tert-butyl ester (1.36 g, yield: 78%) as a yellow oil. MS: m/z 291.0 (M+H⁺).

Step 3: To a solution of 2-methoxy-3',6'-dihydro-2'H-[3,4']bipyridinyl-1'-carboxylic acid tert-butyl ester (1.36 g, 4.68 mmol) in MeOH (30 mL) was added wet Pd/C (140 mg, 10% wt). The resulting mixture was stirred at room temperature under H₂ atmosphere overnight. Then Pd/C was filtered off and the filtrate was concentrated in vacuum to afford 2-methoxy-3',4',5',6'-tetrahydro-2'H-[3,4']bipyridinyl-1'-carboxylic acid tert-butyl ester (1.30 g, yield: 95%) as a colorless oil.

Step 4: To a solution of 2-methoxy-3',4',5',6'-tetrahydro-2'H-[3,4']bipyridinyl-1'-carboxylic acid tert-butyl ester (1.30 g, 4.45 mmol) in EtOAc (20 mL) was added HCl/EtOAc (excess). The resulting mixture was stirred at room temperature for 4 hrs. The solid precipitated form the reaction mixture was collected by filtration. The cake was washed with EtOAc (60 mL), ether (60 mL) and air-dried to afford 2-methoxy-1',2',3',4',5',6'-hexahydro-[3,4']bipyridinyl (950 mg, yield: 93%) as a white solid. ¹H NMR (400 MHz, DMSO-d6): δ=9.28 (brs, 2H), 8.06 (dd, J=4.8, 1.2 Hz, 1H), 7.53 (d, J=6.8 Hz, 1H), 7.01 (dd, J=7.2, 5.2 Hz, 1H), 3.90 (s, 3H), 3.35-3.29 (m, 2H), 3.11-2.90 (m, 3H), 1.98-1.82 (m, 4H).

Step 5: To a mixture of 2-(1-fluoro-cyclopropyl)-6-[(2-hydroxy-ethyl)-methyl-amino]-quinazolin-4-ol (100 mg, 0.361 mmol) and 2-methoxy-1',2',3',4',5',6'-hexahydro-[3,4'] bipyridinyl (91 mg, 0.397 mmol) in MeCN (20 mL) were added BOP (240 mg, 0.542 mmol) and DBU (220 mg, 1.44 mmol). The resulting mixture was stirred at room temperature overnight. Then MeCN was removed in vacuum to give a residue, which was purified by Prep-HPLC with NH₄OH as additive to afford 2-{[2-(1-fluoro-cyclopropyl)-4-(2-methoxy-3',4',5',6'-tetrahydro-2'H-[3,4']bipyridinyl-1'-yl)-quinazolin-6-yl]-methyl-amino}-ethanol (31.6 mg, yield: 20%) as a yellow solid. ¹H NMR (400 MHz, CDCl₃): δ=8.05 (dd, J=5.6, 1.6 Hz, 1H), 7.87 (d, J=9.2 Hz, 1H), 7.46 (dd, J=7.2, 1.2 Hz, 1H), 7.39 (dd, J=9.6, 2.4 Hz, 1H), 6.95 (d, J=2.8 Hz, 1H), 6.88 (dd, J=7.6, 1.2 Hz, 1H), 4.34 (d, J=12.8 Hz, 2H), 3.98 (s, 3H), 3.88 (t, J=5.6 Hz, 2H), 3.58 (t, J=5.6 Hz, 2H), 3.19-3.08 (m, 3H), 3.07 (s, 3H), 2.03-1.78 (m, 5H), 1.54-1.46 (m, 4H). MS: m/z 452.2 (M+H⁺).

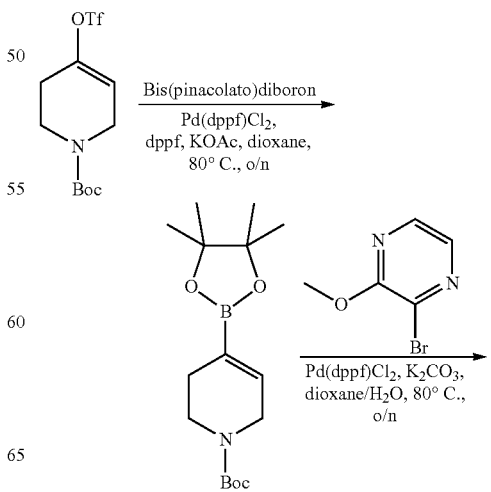

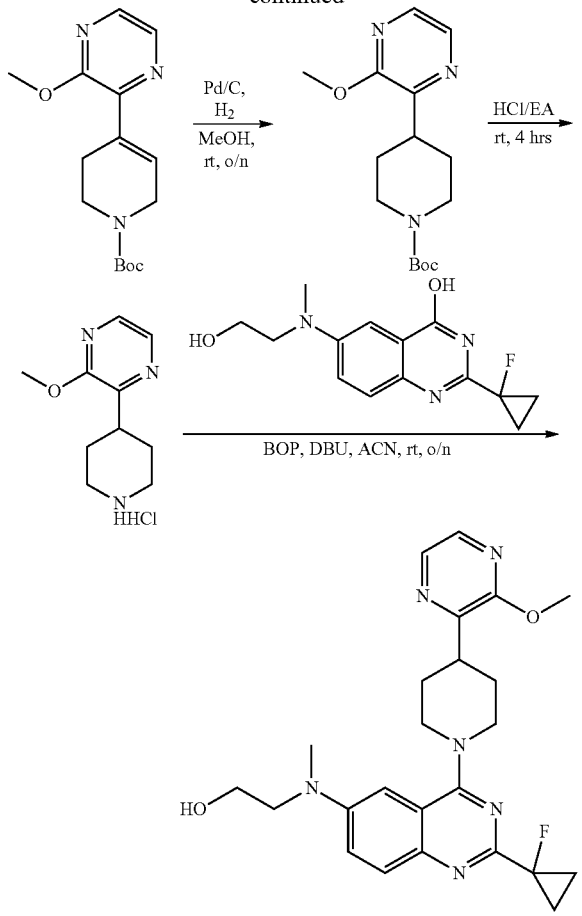

Example 208: Preparation of 2-({2-(1-Fluoro-cyclopropyl)-4-[4-(3-methoxy-pyrazin-2-yl)-piperidin-1-yl]-quinazolin-6-yl}-methyl-amino)-ethanol

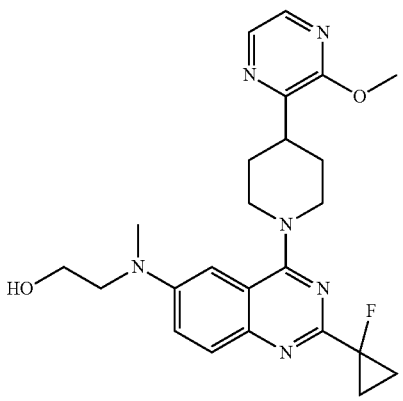 [SMILES: COc1nccnc1C1CCN(c2nc(C3(F)CC3)nc3ccc(N(C)CCO)cc23)CC1]

Step 1 To a solution of 4-trifluoromethanesulfonyloxy-3,6-dihydro-2H-pyridine-1-carboxylic acid tert-butyl ester (10.0 g, 30.2 mmol) and bis(pinacolato)diboron (9.2 g, 36.2 mmol) in dioxane (250 mL) were added Pd(dppf)Cl$_2$ (1.1 g, 1.5 mmol), dppf (0.84 g, 1.5 mmol) and KOAc (10.4 g, 106 mmol). The resulting mixture was stirred at 80° C. under N$_2$ overnight. Then the reaction mixture was poured into H$_2$O (100 mL) and extracted with EtOAc (50 mL×3). The extracts were washed with brine (50 mL×3), dried over Na$_2$SO$_4$ and concentrated in vacuum to give a residue, which was purified by a silica gel column (PE/EtOAc=50/1) to afford 4-(4,4,5,5-tetramethyl-[1,3,2]dioxaborolan-2-yl)-3,6-dihydro-2H-pyridine-1-carboxylic acid tert-butyl ester (6.8 g, yield: 73%) as a white solid. $^1$H NMR (400 MHz, CDCl$_3$): δ=6.46 (brs, 1H), 4.03-3.89 (m, 2H), 3.50-3.38 (m, 2H), 2.28-2.15 (m, 2H), 1.46 (s, 9H), 1.26 (m, 12H).

Step 2: To a solution of 4-(4,4,5,5-tetramethyl-[1,3,2]dioxaborolan-2-yl)-3,6-dihydro-2H-pyridine-1-carboxylic acid tert-butyl ester (1.0 g, 3.23 mmol) and 2-chloro-3-methoxy-pyrazine (425 mg, 2.94 mmol) in dioxane/H$_2$O (30 mL+10 mL) were added Pd(dppf)Cl$_2$ (108 mg, 0.15 mmol) and K$_2$CO$_3$ (1.62 g, 11.8 mmol). The resulting mixture was stirred at 80° C. under N$_2$ atmosphere overnight. Then the reaction mixture was poured into H$_2$O (100 mL) and extracted with EtOAc (20 mL×3). The extracts were washed with brine (20 mL×3), dried over Na$_2$SO$_4$ and concentrated in vacuum to give a residue, which was purified by a silica gel column (DCM/MeOH=50/1) to afford 4-(3-methoxy-pyrazin-2-yl)-3,6-dihydro-2H-pyridine-1-carboxylic acid tert-butyl ester (648 mg, yield: 76%) as a yellow oil. $^1$H NMR (400 MHz, CDCl$_3$): δ=8.11 (d, J=2.4 Hz, 1H), 7.95 (d, J=2.4 Hz, 1H), 6.97-6.71 (m, 1H), 4.23-4.10 (m, 2H), 4.00 (s, 3H), 3.70-3.54 (m, 2H), 2.76-2.59 (m, 2H), 1.49 (s, 9H).

Step 3: To a solution of 4-(3-methoxy-pyrazin-2-yl)-3,6-dihydro-2H-pyridine-1-carboxylic acid tert-butyl ester (648 mg, 2.22 mmol) in MeOH (20 mL) was added wet Pd/C (65 mg, 10% wt). The resulting mixture was stirred at room temperature under H$_2$ atmosphere overnight. Then Pd/C was filtered off and the filtrate was concentrated in vacuum to afford 4-(3-methoxy-pyrazin-2-yl)-piperidine-1-carboxylic acid tert-butyl ester (650 mg, yield: 100%) as a colorless oil, which was used for next step without further purification.

Step 4: To a solution of 4-(3-methoxy-pyrazin-2-yl)-piperidine-1-carboxylic acid tert-butyl ester (650 mg, 2.22 mmol) in EtOAc (20 mL) was added HCl/EtOAc (excess). The resulting mixture was stirred at room temperature for 4 hrs. The solid precipitated form the reaction mixture was collected by filtration. The cake was washed with EtOAc (60 mL), ether (60 mL) and air-dried to afford 2-methoxy-3-piperidin-4-yl-pyrazine (500 mg, yield: 98%) as a white solid. $^1$H NMR (400 MHz, DMSO-d6): δ=9.24 (brs, 1H), 9.04 (brs, 1H), 8.16 (d, J=2.4 Hz, 1H), 8.10 (d, J=2.4 Hz, 1H), 3.94 (s, 3H), 3.37-3.24 (m, 3H), 3.10-2.96 (m, 2H), 1.98-1.89 (m, 4H).

Step 5: To a mixture of 2-(1-fluoro-cyclopropyl)-6-[(2-hydroxy-ethyl)-methyl-amino]-quinazolin-4-ol (100 mg, 0.361 mmol) and 2-methoxy-3-piperidin-4-yl-pyrazine (92 mg, 0.397 mmol) in ACN (20 mL) were added BOP (240 mg, 0.542 mmol) and DBU (220 mg, 1.44 mmol). The resulting mixture was stirred at room temperature overnight. Then ACN was removed in vacuum to give a residue, which was purified by Prep-HPLC with NH$_4$OH as additive to afford 2-({2-(1-fluoro-cyclopropyl)-4-[4-(3-methoxy-pyrazin-2-yl)-piperidin-1-yl]-quinazolin-6-yl}-methyl-amino)-ethanol (36 mg, yield: 22%) as a yellow solid. $^1$H NMR (400 MHz, CDCl$_3$): δ=8.07 (d, J=2.8 Hz, 1H), 7.97 (d, J=3.2 Hz, 1H), 7.87 (d, J=9.6 Hz, 1H), 7.39 (dd, J=9.6, 2.4 Hz, 1H), 6.97 (d, J=2.8 Hz, 1H), 6.88 (dd, J=87.2, 4.8 Hz, 1H), 4.32 (d, J=12.4 Hz, 2H), 4.00 (s, 3H), 3.88 (t, J=5.6 Hz, 2H), 3.58 (t, J=5.6 Hz, 2H), 3.38-3.28 (m, 1H), 3.19-3.09 (m, 2H), 3.07 (s, 3H), 2.16-1.96 (m, 5H), 1.56-1.46 (m, 4H). MS: m/z 453.2 (M+H$^+$).

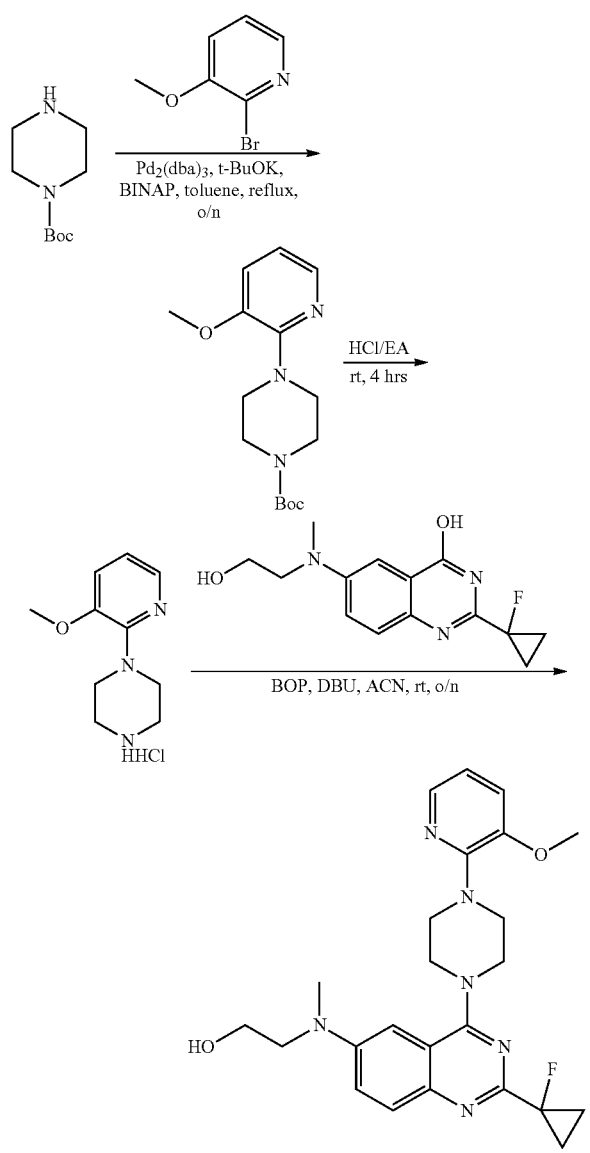

Example 209: Preparation of 2-({2-(1-Fluoro-cyclopropyl)-4-[4-(3-methoxy-pyridin-2-yl)-piperazin-1-yl]-quinazolin-6-yl}-methyl-amino)-ethanol

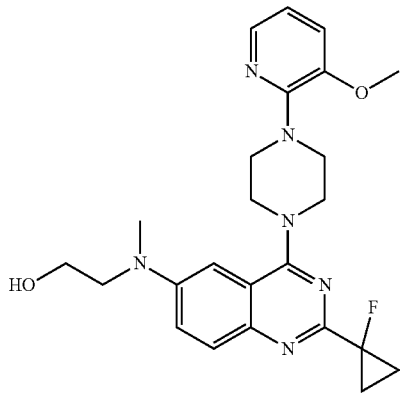

To a mixture of piperazine-1-carboxylic acid tert-butyl ester (500 mg, 2.68 mmol) and 2-bromo-3-methoxy-pyridine (500 mg, 2.68 mmol) in toluene (40 mL) were added $Pd_2(dba)_3$ (258 mg, 0.268 mmol), BINAP (250 mg, 0.40 mmol) and t-BuOK (450 mg, 4.03 mmol). The resulting mixture was stirred at 110° C. under $N_2$ atmosphere overnight. Then toluene was removed in vacuum to give a residue, which was purified by a silica gel column to afford 4-(3-Methoxy-pyridin-2-yl)-piperazine-1-carboxylic acid tert-butyl ester (574 mg, yield: 74.4%) as a yellow oil. $^1$H NMR (400 MHz, $CDCl_3$): δ=7.86 (dd, J=4.8, 1.2 Hz, 1H), 7.05 (d, J=7.6 Hz, 1H), 6.86 (dd, J=8.0, 4.8 Hz, 1H), 3.86 (s, 3H), 3.58 (t, J=4.8 Hz, 4H), 3.48 (t, J=4.8 Hz, 4H), 1.48 (s, 9H).

To a solution of 4-(3-methoxy-pyridin-2-yl)-piperazine-1-carboxylic acid tert-butyl ester (574 mg, 1.96 mmol) in EtOAc (10 mL) was added HCl/EtOAc (excess). The resulting mixture was stirred at room temperature for 4 hrs. Then the solid precipitated form the reaction mixture was filtered. The cake was washed with EtOAc (50 mL) and ether (50 mL) to afford 1-(3-Methoxy-pyridin-2-yl)-piperazine (448 mg, yield: 99%) as a yellow solid. $^1$H NMR (300 MHz, DMSO-d6): δ=9.64 (brs, 2H), 7.79 (dd, J=5.7, 1.2 Hz, 1H), 7.58 (d, J=8.1 Hz, 1H), 7.13 (dd, J=7.8, 5.4 Hz, 1H), 3.88 (s, 3H), 3.82-3.70 (m, 4H), 3.30-3.11 (m, 4H).

To a mixture of 2-(1-fluoro-cyclopropyl)-6-[(2-hydroxy-ethyl)-methyl-amino]-quinazolin-4-ol (100 mg, 0.361 mmol) and 1-(3-methoxy-pyridin-2-yl)-piperazine (92 mg, 0.397 mmol) in MeCN (20 mL) were added BOP (240 mg, 0.542 mmol) and DBU (220 mg, 1.44 mmol). The resulting mixture was stirred at room temperature overnight. Then MeCN was removed in vacuum to give a residue, which was purified by Prep-HPLC with $NH_4OH$ as additive to afford 2-({2-(1-fluoro-cyclopropyl)-4-[4-(3-methoxy-pyridin-2-yl)-piperazin-1-yl]-quinazolin-6-yl}-methyl-amino)-ethanol (36.7 mg, yield: 22.5%) as a yellow solid. $^1$H NMR (400 MHz, $CDCl_3$): δ=7.90 (dd, $J_1$=4.8 Hz, $J_2$=1.6 Hz, 1H), 7.87 (d, J=9.6 Hz, 1H), 7.40 (dd, J=9.6, 2.4 Hz, 1H), 7.09 (dd, J=8.0, 1.2 Hz, 1H), 6.98 (d, J=2.4 Hz, 1H), 6.90 (dd, J=8.0, 0.8 Hz, 1H), 3.93-3.86 (m, 5H), 3.75 (t, J=4.8 Hz, 4H), 3.61-3.55 (m, 6H), 3.07 (s, 3H), 1.56-1.46 (m, 4H). MS: m/z 453.2 (M+H$^+$).

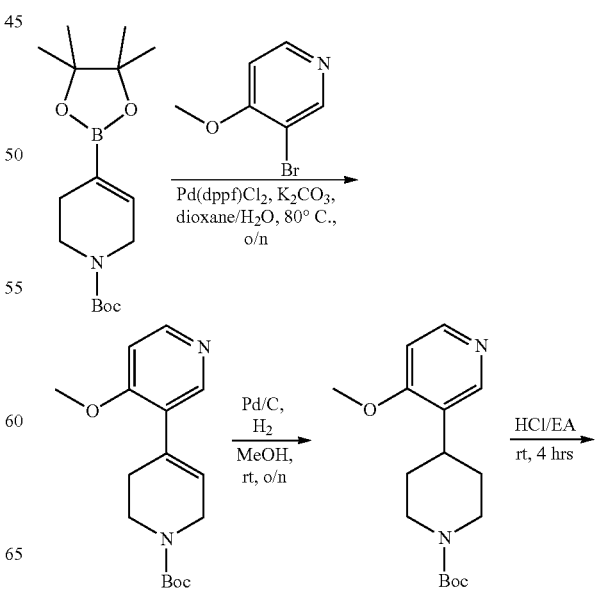

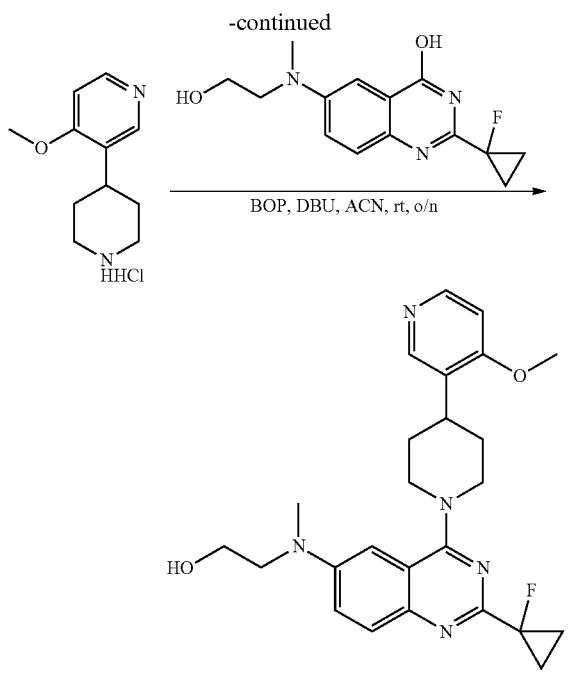

Example 210: Preparation of 2-{[2-(1-Fluoro-cyclopropyl)-4-(4-methoxy-3',4',5',6'-tetrahydro-2'H-[3,4']bipyridinyl-1'-yl)-quinazolin-6-yl]-methyl-amino}-ethanol

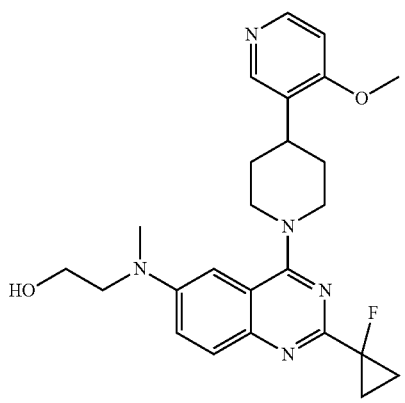 [SMILES: COc1ccncc1C1CCN(c2nc(C3(F)CC3)nc3ccc(N(C)CCO)cc23)CC1]

Step 1: To a solution of 4-(4,4,5,5-tetramethyl-[1,3,2]dioxaborolan-2-yl)-3,6-dihydro-2H-pyridine-1-carboxylic acid tert-butyl ester (1.0 g, 3.23 mmol) and 3-bromo-4-methoxy-pyridine (552 mg, 2.94 mmol) in dioxane/H₂O (30 mL+10 mL) were added Pd(dppf)Cl₂ (108 mg, 0.14 mmol) and K₂CO₃ (1.62 g, 11.8 mmol). The resulting mixture was stirred at 80° C. under N₂ atmosphere overnight. Then the reaction mixture was poured into H₂O (100 mL) and extracted with EtOAc (20 mL×3). The extracts were washed with brine (20 mL×3), dried over Na₂SO₄ and concentrated in vacuum to give a residue, which was purified by a silica gel column with DCM:MeOH=50:1 as eluent to afford 4-methoxy-3',6'-dihydro-2'H-[3,4']bipyridinyl-1'-carboxylic acid tert-butyl ester (721 mg, yield: 85%) as a yellow oil. $^1$H NMR (400 MHz, CDCl₃): δ=8.40 (d, J=5.2 Hz, 1H), 8.27 (s, 1H), 6.79 (d, J=4.8 Hz, 1H), 5.81 (s, 1H), 4.12-4.02 (m, 2H), 3.87 (s, 3H), 3.66-3.54 (m, 2H), 2.53-2.43 (m, 2H), 1.49 (s, 9H).

Step 2: To a solution of 4-methoxy-3',6'-dihydro-2'H-[3,4']bipyridinyl-1'-carboxylic acid tert-butyl ester (721 mg, 2.48 mmol) in MeOH (20 mL) was added wet Pd/C (72 mg, 10% wt). The resulting mixture was stirred at room temperature under H₂ atmosphere overnight. Then Pd/C was filtered off and the filtrate was concentrated in vacuum to afford 4-methoxy-3',4',5',6'-tetrahydro-2'H-[3,4']bipyridinyl-F-carboxylic acid tert-butyl ester (352 mg, yield: 48%) as a white solid, which was used for next step without further purification.

Step 3: To a solution of 4-methoxy-3',4',5',6'-tetrahydro-2'H-[3,4']bipyridinyl-1'-carboxylic acid tert-butyl ester (352 mg, 12.0 mmol) in EtOAc (20 mL) was added HCl/EtOAc (excess). The resulting mixture was stirred at room temperature for 4 hrs. The solid precipitated form the reaction mixture was collected by filtration. The cake was washed with EtOAc (60 mL), ether (60 mL) and air-dried to afford 4-methoxy-1',2',3',4',5',6'-hexahydro-[3,4']bipyridinyl (236 mg, yield: 86%) as a brown solid. $^1$H NMR (400 MHz, DMSO-d6): δ=9.37 (brs, 2H), 8.80 (s, 1H), 8.48 (s, 1H), 7.66 (s, 1H), 4.14 (s, 3H), 3.42-3.30 (m, 2H), 3.28-3.15 (m, 1H), 3.10-2.93 (m, 2H), 2.11-1.83 (m, 4H).

Step 4: To a mixture of 2-(1-fluoro-cyclopropyl)-6-[(2-hydroxy-ethyl)-methyl-amino]-quinazolin-4-ol (100 mg, 0.361 mmol) and 4-methoxy-1',2',3',4',5',6'-hexahydro-[3,4']bipyridinyl (91 mg, 0.397 mmol) in ACN (20 mL) were added BOP (240 mg, 0.542 mmol) and DBU (220 mg, 1.44 mmol). The resulting mixture was stirred at room temperature overnight. Then ACN was removed in vacuum to give a residue, which was purified by Prep-HPLC with NH₄OH as additive to afford 2-{[2-(1-fluoro-cyclopropyl)-4-(4-methoxy-3',4',5',6'-tetrahydro-2'H-[3,4']bipyridinyl-1'-yl)-quinazolin-6-yl]-methyl-amino}-ethanol (43.2 mg, yield: 27%) as a yellow solid. $^1$H NMR (400 MHz, CDCl₃): δ=8.39 (d, J=5.2 Hz, 1H), 8.35 (s, 1H), 7.85 (d, J=9.2 Hz, 1H), 7.38 (dd, J=9.6, 3.2 Hz, 1H), 6.95 (d, J=3.2 Hz, 1H), 6.80 (d, J=5.6 Hz, 1H), 4.37-4.27 (m, 2H), 3.93-3.85 (m, 5H), 3.59 (t, J=5.6 Hz, 2H), 3.23-3.14 (m, 1H), 3.13-3.05 (m, 5H), 2.04-1.92 (m, 5H), 1.55-1.45 (m, 4H). MS: m/z 452.2 (M+H⁺).

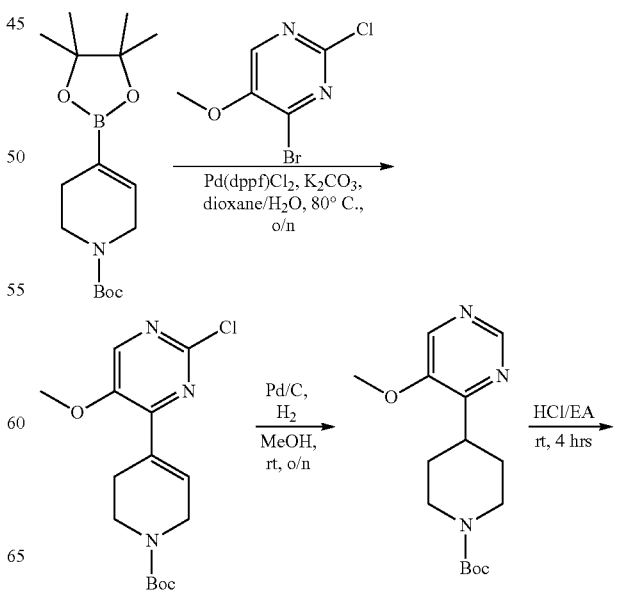

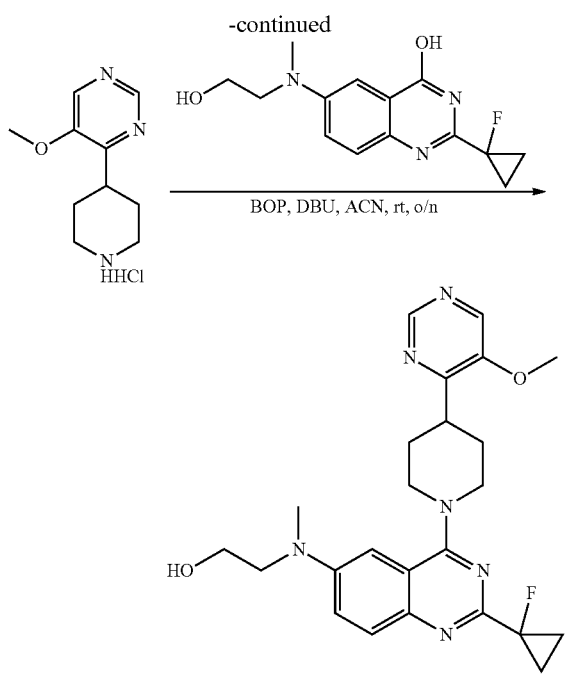

Example 211: Preparation of 2-({2-(1-Fluoro-cyclopropyl)-4-[4-(5-methoxy-pyrimidin-4-yl)-piperidin-1-yl]-quinazolin-6-yl}-methyl-amino)-ethanol

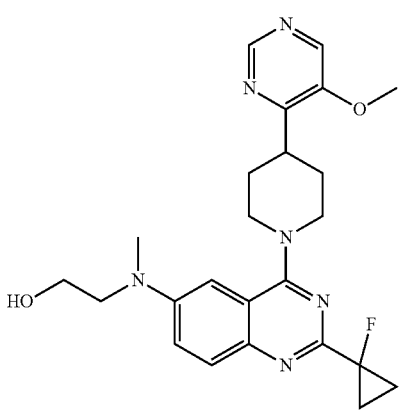 [SMILES: COc1cncnc1C1CCN(c2nc(C3(F)CC3)nc3ccc(N(C)CCO)cc23)CC1]

Step 1: To a solution of 4-(4,4,5,5-tetramethyl-[1,3,2]dioxaborolan-2-yl)-3,6-dihydro-2H-pyridine-1-carboxylic acid tert-butyl ester (1.0 g, 3.23 mmol) and 2,4-dichloro-5-methoxy-pyrimidine (526 mg, 2.94 mmol) in dioxane/H$_2$O (30 mL+10 mL) were added Pd(dppf)Cl$_2$ (108 mg, 0.14 mmol) and K$_2$CO$_3$ (1.62 g, 11.8 mmol). The resulting mixture was stirred at 80° C. under N$_2$ atmosphere overnight. Then the reaction mixture was poured into H$_2$O (100 mL) and extracted with EtOAc (20 mL×3). The extracts were washed with brine (20 mL×3), dried over Na$_2$SO$_4$ and concentrated in vacuum to give a residue, which was purified by a silica gel column (DCM/MeOH=50/1) to afford 4-(2-chloro-5-methoxy-pyrimidin-4-yl)-3,6-dihydro-2H-pyridine-1-carboxylic acid tert-butyl ester (900 mg, yield: 94%) as a yellow oil. $^1$H NMR (400 MHz, CDCl$_3$): δ=8.20 (s, 1H), 7.08-6.86 (m, 1H), 4.23-4.12 (m, 2H), 3.96 (s, 3H), 3.60 (t, J=5.6 Hz, 2H), 2.72-2.61 (m, 2H), 1.49 (s, 9H).

Step 2: To a solution of 4-(2-chloro-5-methoxy-pyrimidin-4-yl)-3,6-dihydro-2H-pyridine-1-carboxylic acid tert-butyl ester (900 g, 2.76 mmol) in MeOH (20 mL) was added wet Pd/C (90 mg, 10% wt). The resulting mixture was stirred at room temperature under H$_2$ atmosphere overnight. Then Pd/C was filtered off and the filtrate was concentrated in vacuum to afford 4-(5-methoxy-pyrimidin-4-yl)-piperidine-1-carboxylic acid tert-butyl ester (800 g, yield: 99%) as a white solid, which was used for next step without further purification.

Step 3: To a solution of 4-(5-methoxy-pyrimidin-4-yl)-piperidine-1-carboxylic acid tert-butyl ester (800 mg, 2.73 mmol) in EtOAc (20 mL) was added HCl/EtOAc (excess). The resulting mixture was stirred at room temperature for 4 hrs. The solid precipitated form the reaction mixture was collected by filtration. The cake was washed with EtOAc (60 mL), ether (60 mL) and air-dried to afford 5-methoxy-4-piperidin-4-yl-pyrimidine (620 mg, yield: 99%) as a white solid. $^1$H NMR (400 MHz, DMSO-d6): δ=9.24 (brs, 1H), 9.00 (brs, 1H), 8.78 (s, 1H), 8.54 (s, 1H), 3.95 (s, 3H), 3.42-3.26 (m, 3H), 3.09-2.95 (m, 2H), 2.04-1.82 (m, 4H).

Step 4: To a mixture of 2-(1-fluoro-cyclopropyl)-6-[(2-hydroxy-ethyl)-methyl-amino]-quinazolin-4-ol (100 mg, 0.361 mmol) and 5-methoxy-4-piperidin-4-yl-pyrimidine (92 mg, 0.397 mmol) in MeCN (20 mL) were added BOP (240 mg, 0.542 mmol) and DBU (220 mg, 1.44 mmol). The resulting mixture was stirred at room temperature overnight. Then MeCN was removed in vacuum to give a residue, which was purified by Prep-HPLC with NH$_4$OH as additive to afford 2-({2-(1-Fluoro-cyclopropyl)-4-[4-(5-methoxy-pyrimidin-4-yl)-piperidin-1-yl]-quinazolin-6-yl}-methyl-amino)-ethanol (36.3 mg, yield: 22%) as a yellow solid. $^1$H NMR (400 MHz, CDCl$_3$): δ=8.80 (s, 1H), 8.28 (s, 1H), 7.85 (d, J=9.2 Hz, 1H), 7.38 (dd, J=9.2, 2.8 Hz, 1H), 6.97 (d, J=2.8 Hz, 1H), 4.35-4.26 (m, 2H), 3.96 (s, 3H), 3.88 (t, J=5.6 Hz, 2H), 3.58 (t, J=5.6 Hz, 2H), 3.46-3.36 (m, 1H), 3.17-3.05 (m, 5H), 2.21-1.91 (m, 5H), 1.56-1.45 (m, 4H). MS: m/z 453.2 (M+H$^+$).

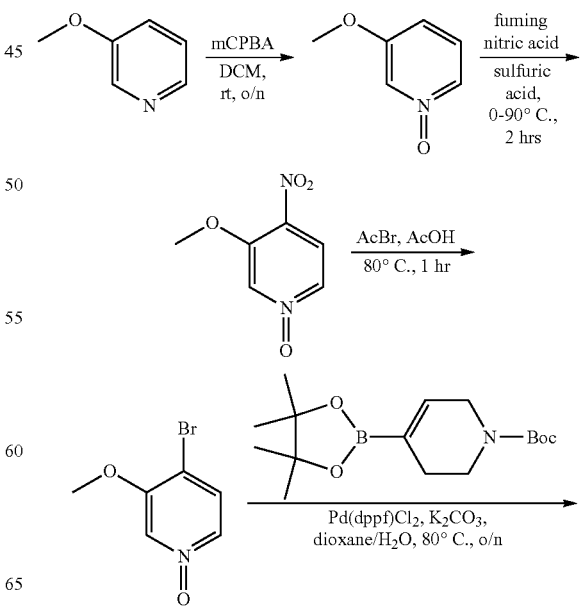

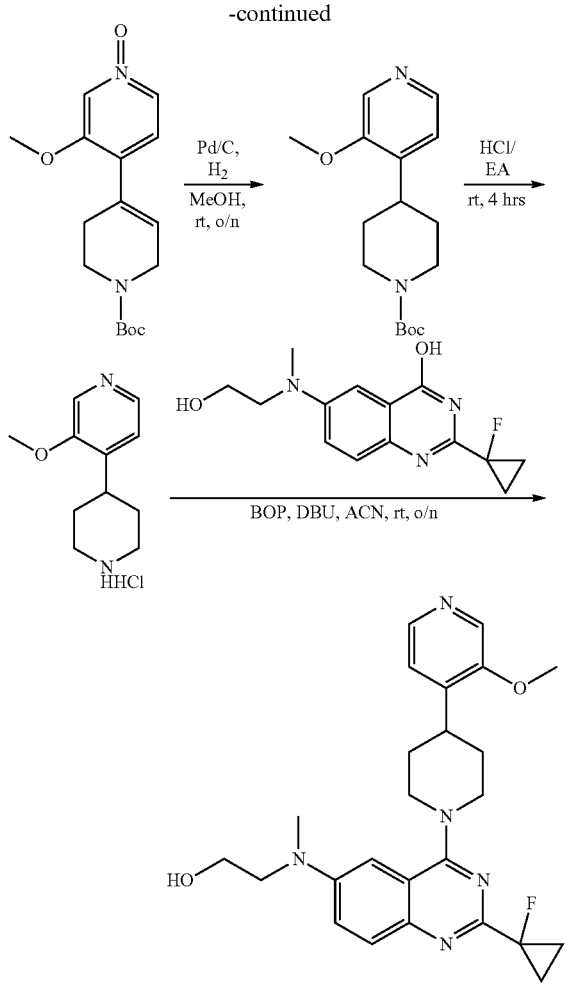

Example 212: Preparation of 2-{[2-(1-Fluoro-cyclopropyl)-4-(3'-methoxy-3,4,5,6-tetrahydro-2H-[4,4']bipyridinyl-1-yl)-quinazolin-6-yl]-methyl-amino}-ethanol

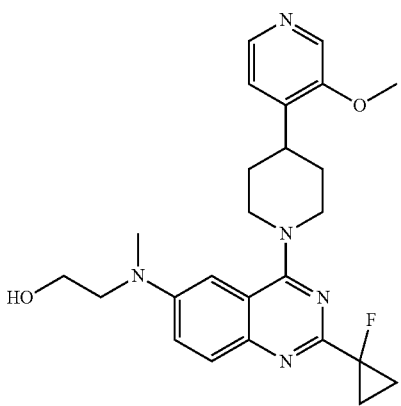 [SMILES: COc1cnccc1C1CCN(c2nc(C3(F)CC3)nc3ccc(N(C)CCO)cc23)CC1]

Step 1: To a solution of 3-methoxy-pyridine (5.0 g, 45.8 mmol) in DCM (100 mL) was added m-CPBA (15.0 g, 68.7 mmol). The resulting mixture was stirred at room temperature overnight. Then Na$_2$SO$_3$ (excess) was added into the reaction mixture and the mixture was stirred for 10 mins. The organic phase was collected and concentrated to give 3-methoxy-pyridine 1-oxide (4.2 g, yield: 73%) as a white solid, which was used for next step without further purification. NMR (400 MHz, CDCl$_3$): δ=7.98 (t, J=2.0 Hz, 1H), 7.93-7.87 (m, 1H), 7.16 (dd, J=8.4, 6.4 Hz, 1H), 6.88 (s, dd, J=8.8, 1.6 Hz, 1H), 3.85 (s, 3H).

Step 2: To a solution of 3-methoxy-pyridine 1-oxide (2.0 g, 16 mmol) in sulfuric acid (4 mL) was added fuming nitric acid (4 mL) at 0° C. dropwise. After addition of the nitric acid was completed, the reaction mixture was warmed to room temperature and then heated at 90° C. for 2 hrs. Then the reaction mixture was cooled in ice bath and adjusted to pH 10 with 2 M aqueous Na$_2$CO$_3$. The solution was extracted with DCM (50 mL×2). The extracts were collected and concentrated to give a residue, which was purified by a silica gel column (DCM/MeOH=50/1) to afford 3-methoxy-4-nitro-pyridine 1-oxide (1.5 g, yield: 55%) as a yellow solid. $^1$H NMR (400 MHz, CDCl$_3$): δ=7.98 (d, J=1.6 Hz, 1H), 7.97-7.85 (m, 2H), 4.03 (s, 3H).

Step 3: To a solution of 3-methoxy-4-nitro-pyridine 1-oxide (3.0 g, 17.6 mmol) in acetic AcOH (30 mL) was added AcBr (65.0 g, 529 mmol). The resulting mixture was stirred at 80° C. for 1 hr. Then the reaction mixture was neutralized with saturated aqueous NaOH till pH=8. The aqueous phase was extracted with EtOAc (60 mL×4). The extracts were washed with brine (60 mL×4), dried over Na$_2$SO$_4$ and concentrated to afford 4-bromo-3-methoxy-pyridine 1-oxide (3.2 g, yield: 89%) as a yellow solid, which was used for next step without further purification. MS: m/z 203.9 (M+H$^+$).

Step 4: To a solution of 4-bromo-3-methoxy-pyridine 1-oxide (1.0 g, 4.90 mmol) and 4-(4,4,5,5-Tetramethyl-[1,3,2]dioxaborolan-2-yl)-3,6-dihydro-2H-pyridine-1-carboxylic acid tert-butyl ester (1.82 g, 5.88 mmol) in dioxane/H$_2$O (30 mL+10 mL) were added Pd(dppf)Cl$_2$ (180 mg, 0.245 mmol) and K$_2$CO$_3$ (2.70 g, 19.6 mmol). The resulting mixture was stirred at 80° C. under N$_2$ atmosphere overnight. Then the reaction mixture was poured into H$_2$O (100 mL) and extracted with EtOAc (20 mL×3). The extracts were washed with brine (20 mL×3), dried over Na$_2$SO$_4$ and concentrated in vacuum to give a residue, which was purified by a silica gel column with DCM/MeOH=50/1 as eluent to afford 3'-methoxy-1'-oxy-3,6-dihydro-2H-[4,4']bipyridinyl-1-carboxylic acid tert-butyl ester (1.1 g, yield: 73%) as a yellow oil. $^1$H NMR (400 MHz, CDCl$_3$): δ=7.93 (d, J=1.6 Hz, 1H), 7.87 (dd, J=6.4, 1.6 Hz, 1H), 7.02 (d, J=6.8 Hz, 1H), 6.06 (brs, 1H), 4.13-4.02 (m, 2H), 3.87 (s, 3H), 3.60 (t, J=5.6 Hz, 2H), 2.54-2.39 (m, 2H), 1.49 (s, 9H).

Step 5: To a solution of 3'-methoxy-1'-oxy-3,6-dihydro-2H[4,4']bipyridinyl-1-carboxylic acid tert-butyl ester (1.1 g, 3.59 mmol) in MeOH (30 mL) was added wet Pd/C (110 mg, 10% wt). The resulting mixture was stirred at room temperature under H$_2$ atmosphere overnight. Then Pd/C was filtered off and the filtrate was concentrated in vacuum to afford 3'-methoxy-3,4,5,6-tetrahydro-2H-[4,4']bipyridinyl-1-carboxylic acid tert-butyl ester (950 mg, yield: 90.5%) as a green solid, which was used for next step without further purification.

Step 6: To a solution of 3'-methoxy-3,4,5,6-tetrahydro-2H[4,4']bipyridinyl-1-carboxylic acid tert-butyl ester (950 mg, 3.25 mmol) in MeOH (10 mL) was added HCl/EtOAc (excess). The resulting mixture was stirred at room temperature for 4 hrs. The solid precipitated form the reaction mixture was collected by filtration. The cake was washed with EtOAc (60 mL), ether (60 mL) and air-dried to afford 3'-methoxy-1,2,3,4,5,6-hexahydro[4,4']bipyridinyl (560 mg, yield: 75%) as a grey solid. ¹H NMR (400 MHz, DMSO-d6): δ=9.30 (brs, 1H), 9.22 (brs, 1H), 8.62 (s, 1H), 8.53 (d, J=5.6 Hz, 1H), 7.75 (d, J=5.6 Hz, 1H), 4.04 (s, 3H), 3.41-3.29 (m, 3H), 3.11-2.94 (m, 2H), 2.03-1.84 (m, 4H).

Step 7: To a mixture of 2-(1-fluoro-cyclopropyl)-6-[(2-hydroxy-ethyl)-methyl-amino]-quinazolin-4-ol (100 mg, 0.361 mmol) and 3'-methoxy-1,2,3,4,5,6-hexahydro[4,4']bipyridinyl (92 mg, 0.397 mmol) in MeCN (20 mL) were added BOP (240 mg, 0.542 mmol) and DBU (220 mg, 1.44 mmol). The resulting mixture was stirred at room temperature overnight. Then MeCN was removed in vacuum to give a residue, which was purified by Prep-HPLC with NH₄OH as additive to afford 2-{[2-(1-Fluoro-cyclopropyl)-4-(3'-methoxy-3,4,5,6-tetrahydro-2H[4,4']bipyridinyl-1-yl)-quinazolin-6-yl]-methyl-amino}-ethanol (33.2 mg, yield: 21%) as a yellow solid. ¹H NMR (400 MHz, CDCl₃): δ=8.24 (s, 2H), 7.87 (d, J=9.2 Hz, 1H), 7.40 (dd, J=9.6, 2.8 Hz, 1H), 7.14 (d, J=4.8 Hz, 1H), 6.95 (d, J=3.2 Hz, 1H), 4.38-4.29 (m, 2H), 3.95 (s, 3H), 3.89 (t, J=5.2 Hz, 2H), 3.58 (t, J=5.6 Hz, 2H), 3.31-3.19 (m, 1H), 3.18-3.08 (m, 2H), 3.07 (s, 3H), 2.04-1.80 (m, 5H), 1.55-1.46 (m, 4H). MS: m/z 452.2 (M+H⁺).

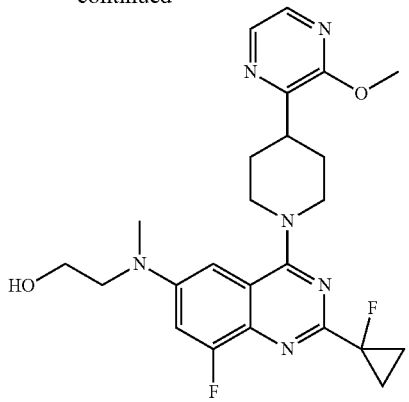

Example 213: Preparation of 2-({8-Fluoro-2-(1-fluoro-cyclopropyl)-4-[4-(3-methoxy-pyrazin-2-yl)-piperidin-1-yl]-quinazolin-6-yl}-methyl-amino)-ethanol

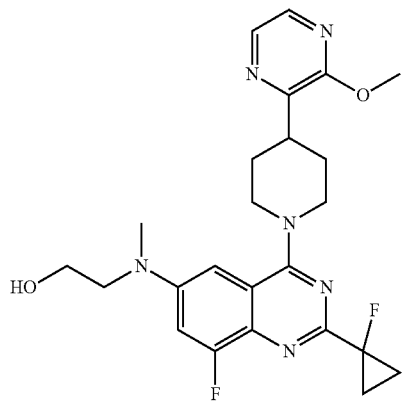 [SMILES: COc1nccnc1C1CCN(c2nc(C3(F)CC3)nc3c(F)cc(N(C)CCO)cc23)CC1]

Step 1: To a solution of 1-fluoro-cyclopropanecarboxylic acid (434 mg, 4.17 mmol) in dry DCM (10 mL) was added (COCl)₂ (644 mg, 5.0 mmol) and 2 drops of dry DMF. The resulting mixture was stirred at room temperature for 2 hrs. Then the mixture was added to a solution of 2-amino-3-fluoro-benzonitrile (900 mg, 4.17 mmol) in DCM (10 mL). The reaction mixture was stirred at room temperature for another 2 hrs. Then the mixture was washed with H₂O (100 mL), 1 N HCl (100 mL) and saturated NaHCO₃ (50 mL×2). The organic phase was concentrated to give a residue, which was purified by silica gel column with DCM as eluent to afford 1-fluoro-cyclopropanecarboxylic acid (4-bromo-2-cyano-6-fluoro-phenyl)-amide (1.08 g, yield: 85%) as a yellow solid. ¹H NMR (400 MHz, CDCl₃): δ=8.02 (brs, 1H), 7.65 (s, 1H), 7.60 (dd, J=8.8, 2.4 Hz, 1H), 1.61-1.43 (m, 4H).

Step 2: To a solution of 1-fluoro-cyclopropanecarboxylic acid (4-bromo-2-cyano-6-fluoro-phenyl)-amide (1.08 g, 3.58 mmol) in EtOH (30 mL) was added H₂O₂ (10 mL, 30% in H₂O) and NaOH (172 mg, 4.3 mmol). The resulting mixture was stirred at 85° C. overnight. Then the reaction mixture was concentrated to give only 10 mL suspension. The resulting solid was collected by filtration to afford 6-bromo-8-fluoro-2-(1-fluoro-cyclopropyl)-quinazolin-4-ol (702 mg, yield: 65%) as a white solid. ¹H NMR (400 MHz, DMSO-d6): δ=12.92 (brs, 1H), 8.04-7.98 (m, 2H), 1.66-1.46 (m, 4H).

Step 3: To a mixture of 6-bromo-8-fluoro-2-(1-fluoro-cyclopropyl)-quinazolin-4-ol (2.17 g, 7.21 mmol) and 2-amino-ethanol (0.66 mg, 10.8 mmol) in DMSO (20 mL)

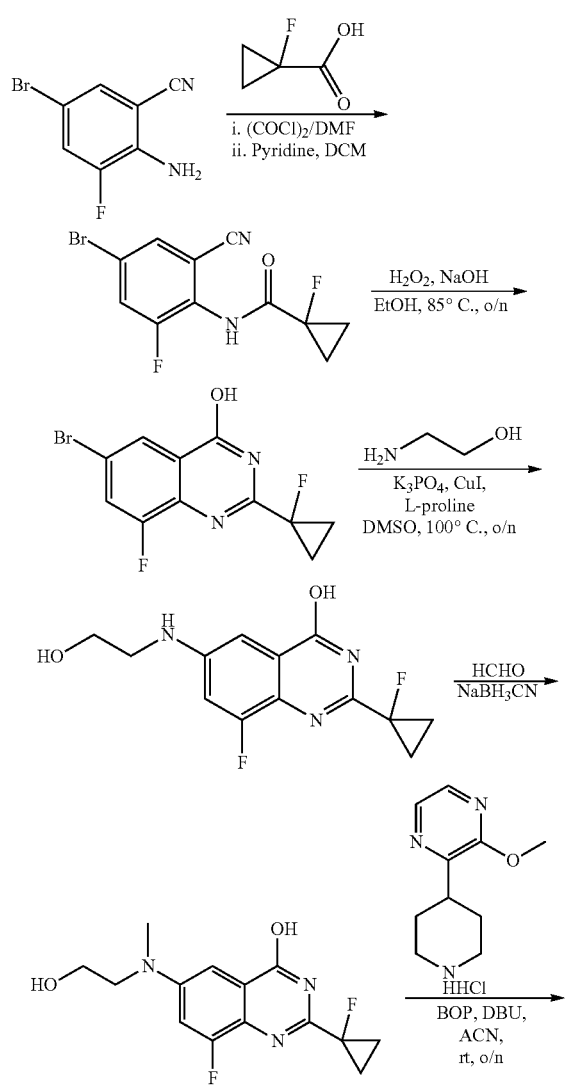

was added CuI (137 mg, 0.721 mmol), L-proline (166 mg, 1.44 mmol) and K₃PO₄ (3.06 g, 14.4 mmol). The resulting mixture was stirred at 100° C. under N₂ atmosphere overnight. Then DMSO was removed in vacuum to give a crude product 8-fluoro-2-(1-fluoro-cyclopropyl)-6-(2-hydroxy-ethylamino)-quinazolin-4-ol (4.0 g), which was used for next step without further purification. MS: m/z 281.9 (M+H⁺).

Step 4: To a solution of 8-fluoro-2-(1-fluoro-cyclopropyl)-6-(2-hydroxy-ethylamino)-quinazolin-4-ol (4.0 g, crude) in MeOH (100 mL) was added formaldehyde (20 mL, 37% in H₂O). The resulting mixture was stirred at room temperature for 2 hrs. Then NaBH(OAc)₃ (12.1 g, 56.8 mmol) and NaBH₃CN (3.58 g, 56.8 mmol) was added into the reaction mixture. The reaction mixture was stirred at room temperature overnight. Then the mixture was poured into water (100 mL) and extracted with EtOAc (60 mL×3). The organic layers were concentrated in vacuum to give a residue, which was purified by a silica gel column (DCM/MeOH=20/1) to afford 8-fluoro-2-(1-fluoro-cyclopropyl)-6-[(2-hydroxy-ethyl)-methyl-amino]-quinazolin-4-ol (1.85 g, two-step yield: 87%) as a yellow solid. ¹H NMR (400 MHz, DMSO-d6): δ=12.38 (brs, 1H), 7.16 (dd, J=14.4, 2.8 Hz, 1H), 7.00 (d, J=2.4 Hz, 1H), 4.75 (brs, 1H), 3.58 (t, J=5.6 Hz, 2H), 3.48 (t, J=5.6 Hz, 2H), 3.01 (s, 3H), 1.55-1.37 (m, 4H). MS: m/z 295.9 (M+H⁺).

Step 5: To a mixture of 8-fluoro-2-(1-fluoro-cyclopropyl)-6-[(2-hydroxy-ethyl)-methyl-amino]-quinazolin-4-ol (150 mg, 0.508 mmol) and 2-methoxy-3-piperidin-4-yl-pyrazine (128 mg, 0.558 mmol) in MeCN (20 mL) was added BOP (336 mg, 0.762 mmol) and DBU (309 mg, 2.03 mmol). The resulting mixture was stirred at room temperature overnight. Then MeCN was removed in vacuum to give a residue, which was purified by Prep-HPLC with NH₄OH as additive to afford 2-({8-fluoro-2-(1-fluoro-cyclopropyl)-4-[4-(3-methoxy-pyrazin-2-yl)-piperidin-1-yl]-quinazolin-6-yl}-methyl-amino)-ethanol (76 mg, yield: 32%) as a yellow solid. ¹H NMR (400 MHz, CDCl₃): δ=8.07 (d, J=2.8 Hz, 1H), 7.98 (d, J=2.8 Hz, 1H), 7.08 (dd, J=12.8, 2.8 Hz, 1H), 6.72 (d, J=2.0 Hz, 1H), 4.32 (d, J=13.2 Hz, 2H), 4.00 (s, 3H), 3.88 (t, J=5.6 Hz, 2H), 3.55 (t, J=5.6 Hz, 2H), 3.39-3.28 (m, 1H), 3.20-3.10 (m, 2H), 3.05 (s, 3H), 2.14-1.98 (m, 5H), 1.56-1.45 (m, 4H). MS: m/z 471.1 (M+H⁺).

Example 214: Preparation of 2-{[8-Fluoro-2-(1-fluoro-cyclopropyl)-4-(2-methoxy-3',4',5',6'-tetrahydro-2'H-[3,4']bipyridinyl-1'-yl)-quinazolin-6-yl]-methyl-amino}-ethanol

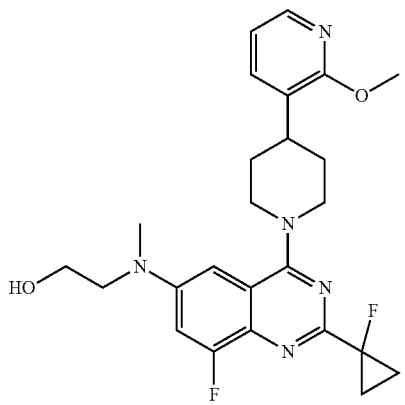 [SMILES: COc1ncccc1C1CCN(c2nc(C3(F)CC3)nc3c(F)cc(N(C)CCO)cc23)CC1]

The title compound was prepared as described in example 2-({8-fluoro-2-(1-fluoro-cyclopropyl)-4-[4-(3-methoxy-pyrazin-2-yl)-piperidin-1-yl]-quinazolin-6-yl}-methyl-amino)-ethanol. ¹H NMR (400 MHz, CDCl₃): δ=8.05 (dd, J=5.2, 1.6 Hz, 1H), 7.45 (dd, J=7.2, 1.6 Hz, 1H), 7.11 (dd, J=13.6, 2.4 Hz, 1H), 6.88 (dd, J=7.2, 4.8 Hz, 1H), 6.74 (s, 1H), 4.37 (d, J=12.8 Hz, 2H), 3.98 (s, 3H), 3.88 (t, J=5.6 Hz, 2H), 3.56 (t, J=5.6 Hz, 2H), 3.20-3.11 (m, 3H), 3.06 (s, 3H), 2.03-1.96 (m, 2H), 1.90-1.77 (m, 3H), 1.55-1.47 (m, 4H). MS: m/z 470.1 (M+H⁺).

Example 215: Preparation of 2-({8-Fluoro-2-(1-fluoro-cyclopropyl)-4-[4-(3-methoxy-pyridin-2-yl)-piperazin-1-yl]-quinazolin-6-yl}-methyl-amino)-ethanol

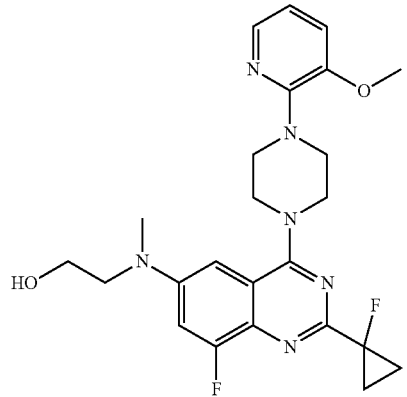 [SMILES: COc1cccnc1N1CCN(c2nc(C3(F)CC3)nc3c(F)cc(N(C)CCO)cc23)CC1]

The title compound was prepared as described in example 2-({8-fluoro-2-(1-fluoro-cyclopropyl)-4-[4-(3-methoxy-pyrazin-2-yl)-piperidin-1-yl]-quinazolin-6-yl}-methyl-amino)-ethanol. ¹H NMR (400 MHz, CDCl₃): δ=7.90 (d, J=4.0 Hz, 1H), 7.14-7.06 (m, 2H), 6.89 (dd, J=8.0, 4.8 Hz, 1H), 6.75 (s, 1H), 3.92-3.86 (m, 5H), 3.80-3.74 (m, 4H), 3.61-3.54 (m, 6H), 3.06 (s, 3H), 2.05-1.97 (m, 1H, active proton), 1.57-1.47 (m, 4H). MS: m/z 471.1 (M+H⁺).

Example 216: Preparation of 2-{[8-Fluoro-2-(1-fluoro-cyclopropyl)-4-(3-methoxy-3',4',5',6'-tetrahydro-2'H-[2,4']bipyridinyl-1'-yl)-quinazolin-6-yl]-methyl-amino}-ethanol

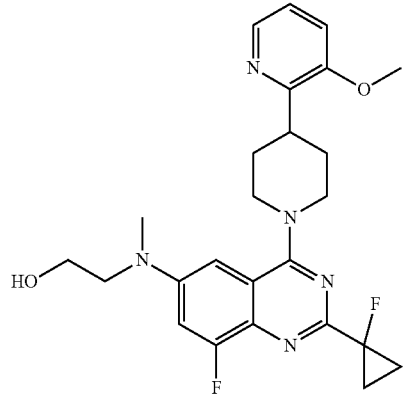 [SMILES: COc1cccnc1C1CCN(c2nc(C3(F)CC3)nc3c(F)cc(N(C)CCO)cc23)CC1]

The title compound was prepared as described in example 2-({8-fluoro-2-(1-fluoro-cyclopropyl)-4-[4-(3-methoxy-pyrazin-2-yl)-piperidin-1-yl]-quinazolin-6-yl}-methyl-amino)-ethanol. ¹H NMR (400 MHz, CDCl₃): δ=8.16 (t, J=3.2 Hz, 1H), 7.18-7.14 (m, 2H), 7.08 (dd, J=13.2, 2.8 Hz, 1H), 6.77 (d, J=2.0 Hz, 1H), 4.33 (d, J=13.6 Hz, 2H), 3.91-3.84 (m, 5H), 3.55 (t, J=5.6 Hz, 2H), 3.51-3.40 (m, 1H), 3.17-3.07 (m, 2H), 3.06 (s, 3H), 2.22-1.93 (m, 5H), 1.56-1.43 (m, 4H). MS: m/z 470.1 (M+H⁺).

Example 217: Preparation of 2-({8-Fluoro-2-(1-fluoro-cyclopropyl)-4-[4-(5-methoxy-pyrimidin-4-yl)-piperidin-1-yl]-quinazolin-6-yl}-methyl-amino)-ethanol

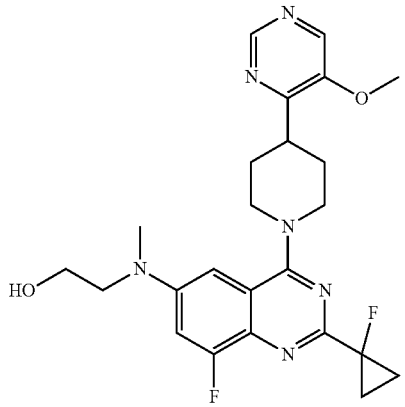 [SMILES: COc1cncnc1C1CCN(c2nc(C3(F)CC3)nc3c(F)cc(N(C)CCO)cc23)CC1]

The title compound was prepared as described in example 2-({8-fluoro-2-(1-fluoro-cyclopropyl)-4-[4-(3-methoxy-pyrazin-2-yl)-piperidin-1-yl]-quinazolin-6-yl}-methyl-amino)-ethanol. ¹H NMR (400 MHz, CDCl₃): δ=8.80 (s, 1H), 8.28 (s, 1H), 7.07 (dd, J=13.2, 1.6 Hz, 1H), 6.72 (s, 1H), 4.32 (d, J=13.2 Hz, 2H), 3.96 (s, 3H), 3.92-3.84 (m, 2H), 3.56 (t, J=5.6 Hz, 2H), 3.48-3.36 (m, 1H), 3.13 (t, J=12.0 Hz, 2H), 3.06 (s, 3H), 2.28-1.91 (m, 5H), 1.56-1.43 (m, 4H). MS: m/z 470.9 (M+H⁺).

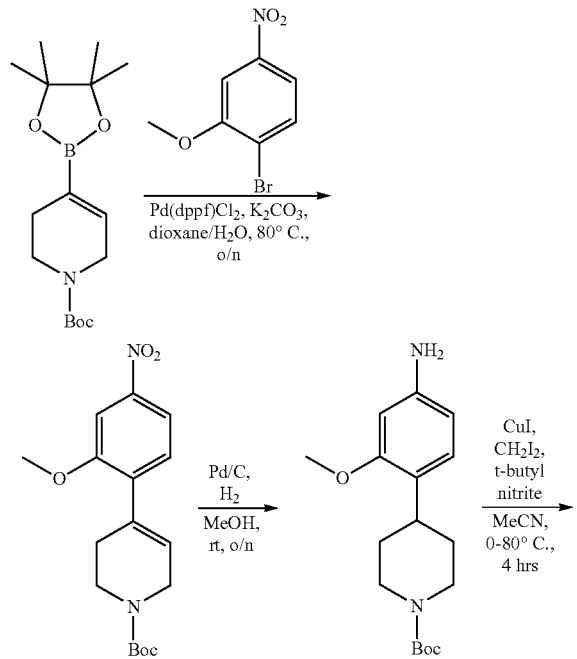

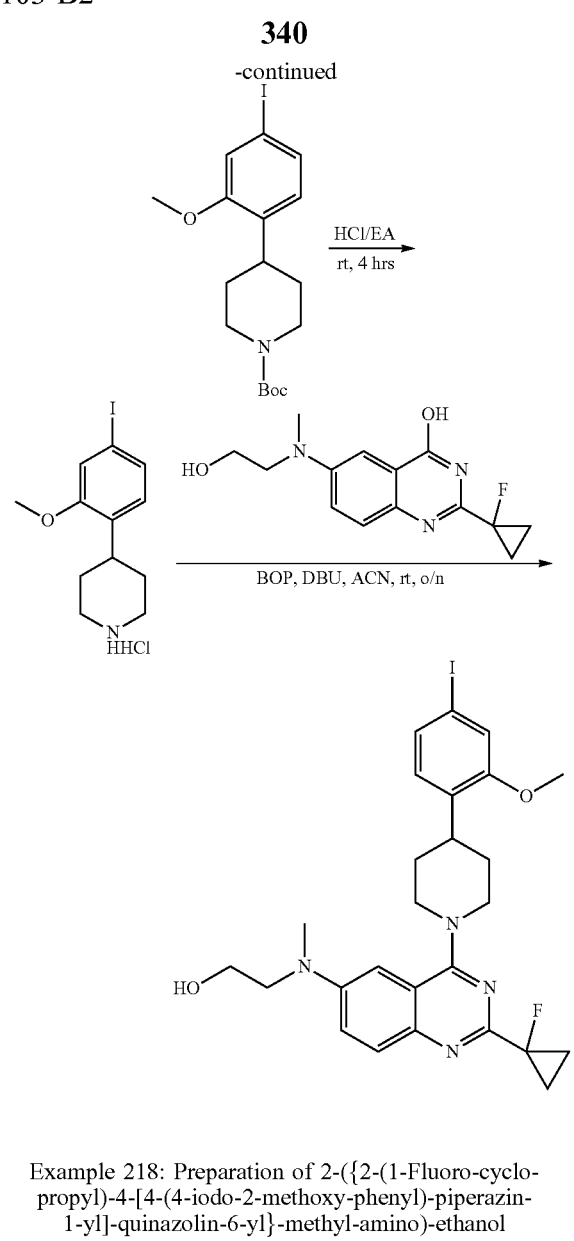

Example 218: Preparation of 2-({2-(1-Fluoro-cyclopropyl)-4-[4-(4-iodo-2-methoxy-phenyl)-piperazin-1-yl]-quinazolin-6-yl}-methyl-amino)-ethanol

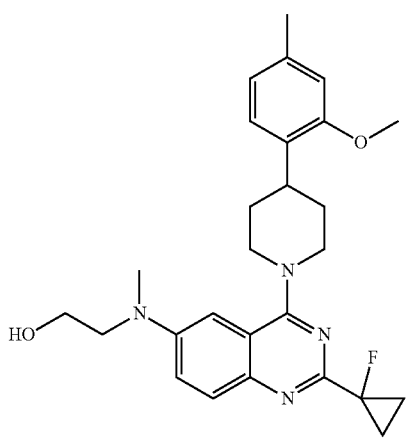 [SMILES: COc1cc(C)ccc1C1CCN(c2nc(C3(F)CC3)nc3ccc(N(C)CCO)cc23)CC1]

Step 1: To a solution of 4-(4,4,5,5-tetramethyl-[1,3,2]dioxaborolan-2-yl)-3,6-dihydro-2H-pyridine-1-carboxylic acid tert-butyl ester (7.34 g, 23.7 mmol) and 1-bromo-2-methoxy-4-nitro-benzene (5.0 g, 21.5 mmol) in dioxane/H₂O (240 mL+80 mL) were added Pd(dppf)Cl₂ (788 mg, 1.1 mmol) and K₂CO₃ (11.9 g, 86.2 mmol). The resulting mixture was stirred at 80° C. under N₂ atmosphere overnight. Then the reaction mixture was poured into H₂O (200 mL) and the aqueous phase was extracted with EtOAc (80 mL×2). The extracts were washed with brine (20 mL×3), dried over Na₂SO₄ and concentrated in vacuum to give a residue, which was purified by a silica gel column (PE/EtOAc=10/1) to afford 4-(2-methoxy-4-nitro-phenyl)-3,6-dihydro-2H-pyridine-1-carboxylic acid tert-butyl ester (7.1 g, yield: 98%) as a yellow solid. ¹H NMR (400 MHz, CDCl₃): δ=7.82 (dd, J=8.0, 2.4 Hz, 1H), 7.72 (d, J=2.0 Hz, 1H), 7.28 (d, J=8.4 Hz, 1H), 5.87 (brs, 1H), 4.10-4.06 (m, 2H), 3.92 (s, 3H), 3.61 (t, J=5.6 Hz, 2H), 2.52-2.47 (s, 2H), 1.50 (s, 9H).

Step 2: To a solution of 4-(2-methoxy-4-nitro-phenyl)-3,6-dihydro-2H-pyridine-1-carboxylic acid tert-butyl ester (7.1 g, 21.2 mmol) in MeOH (200 mL) was added wet Pd/C (710 mg, 10% wt). The resulting mixture was stirred at room temperature under H₂ atmosphere (50 psi) overnight. Then Pd/C was filtered off and the filtrate was concentrated in vacuum to afford 4-(4-amino-2-methoxy-phenyl)-piperidine-1-carboxylic acid tert-butyl ester (6.5 g, yield: 100%) as a white solid, which was used for next step without further purification. ¹H NMR (400 MHz, CDCl₃): δ=6.90 (d, J=8.4 Hz, 1H), 6.31-6.21 (m, 2H), 4.19 (brs, 2H), 3.77 (s, 3H), 3.65-3.55 (m, 2H), 2.99-2.89 (m, 1H), 2.87-2.72 (m, 2H), 1.78-1.69 (m, 2H), 1.58-1.49 (m, 2H), 1.48 (s, 9H).

Step 3: To a solution of 4-(4-amino-2-methoxy-phenyl)-piperidine-1-carboxylic acid tert-butyl ester (2.0 g, 6.53 mmol) in MeCN (50 mL) were added CuI (1.86 g, 9.8 mmol), CH₂I₂ (8.74 g, 32.6 mmol) and t-butyl nitrite (2.02 g, 19.6 mmol) at 0° C. The resulting mixture was stirred at 0° C. for 1 hr and then heated at at 80° C. for another 3 hrs. Later, MeCN was removed in vacuum to give a residue, which was purified by a silica gel column (PE/EtOAc=10/1) to afford 4-(4-iodo-2-methoxy-phenyl)-piperidine-1-carboxylic acid tert-butyl ester (805 mg, yield: 30%) as a yellow oil. ¹H NMR (400 MHz, CDCl₃): δ=7.26 (dd, J=8.4, 1.6 Hz, 1H), 7.10 (d, J=1.6 Hz, 1H), 6.85 (d, J=8.4 Hz, 1H), 4.37-4.08 (m, 2H), 3.81 (s, 3H), 3.07-2.96 (m, 1H), 2.90-2.70 (m, 2H), 1.81-1.68 (m, 2H), 1.56-1.49 (m, 2H), 1.48 (s, 9H).

Step 4: To a solution of 4-(4-iodo-2-methoxy-phenyl)-piperidine-1-carboxylic acid tert-butyl ester (800 mg, 1.92 mmol) in EtOAc (10 mL) was added HCl/EtOAc (excess). The resulting mixture was stirred at room temperature for 4 hrs. The solid precipitated form the reaction mixture was collected by filtration. The cake was washed with EtOAc (60 mL), ether (60 mL) and air-dried to afford 4-(4-iodo-2-methoxy-phenyl)-piperidine (586 mg, yield: 86%) as a white solid. ¹H NMR (400 MHz, DMSO-d6): δ=9.03 (brs, 2H), 7.32 (d, J=7.6 Hz, 1H), 7.29 (s, 1H), 6.91 (d, J=7.6 Hz, 1H), 3.80 (s, 3H), 3.38-3.26 (m, 2H), 3.17-3.05 (m, 1H), 3.04-2.91 (m, 2H), 1.89-1.76 (m, 4H).

Step 5: To a mixture of 2-(1-fluoro-cyclopropyl)-6-[(2-hydroxy-ethyl)-methyl-amino]-quinazolin-4-ol (250 mg, 0.902 mmol) and 4-(4-iodo-2-methoxy-phenyl)-piperidine (351 mg, 0.992 mmol) in MeCN (50 mL) were added BOP (600 mg, 1.35 mmol) and DBU (548 mg, 3.61 mmol). The resulting mixture was stirred at room temperature overnight. Then MeCN was removed in vacuum to give a residue, which was purified by Prep-HPLC with NH₄OH as additive to afford 2-{[2-(1-fluoro-cyclopropyl)-4-(4-methoxy-3',4',5',6'-tetrahydro-2'H-[3,4']bipyridinyl-1'-yl)-quinazolin-6-yl]-methyl-amino}-ethanol (278 mg, yield: 54%) as a yellow solid. ¹H NMR (400 MHz, CDCl₃): δ=7.90 (d, J=9.2 Hz, 1H), 7.40 (dd, J=9.2, 2.8 Hz, 1H), 7.29 (dd, J=8.0, 1.6 Hz, 1H), 7.17 (d, J=2.0 Hz, 1H), 6.97-6.91 (m, 2H), 4.34 (d, J=13.6 Hz, 2H), 3.88 (t, J=5.6 Hz, 2H), 3.83 (s, 3H), 3.58 (t, J=5.6 Hz, 2H), 3.25-3.17 (m, 1H), 3.16-3.08 (m, 2H), 3.06 (s, 3H), 1.96-1.78 (m, 5H), 1.54-1.47 (m, 4H). MS: m/z 577.1 (M+H⁺).

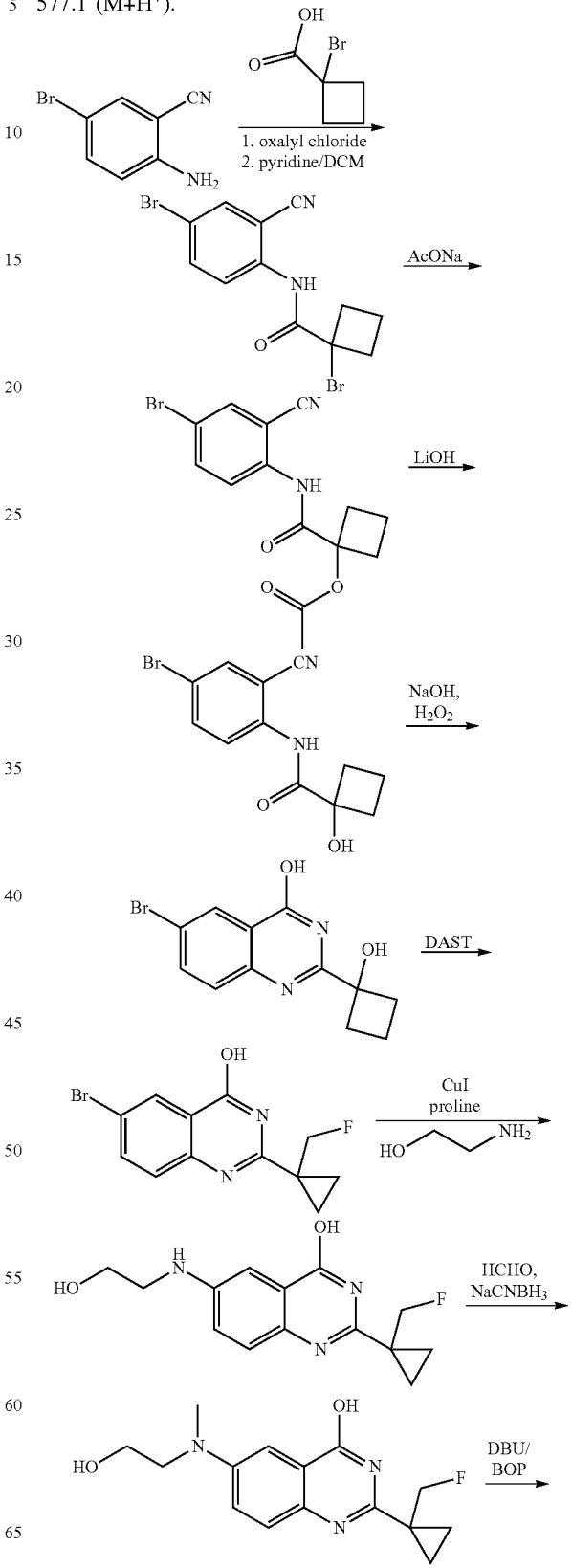

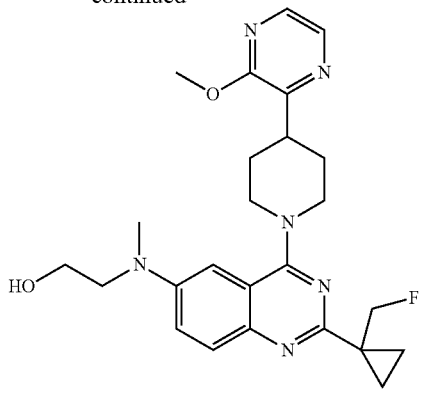

Example 219: Preparation of 2-({2-(1-Fluoromethyl-cyclopropyl)-4-[4-(3-methoxy-pyrazin-2-yl)-piperidin-1-yl]-quinazolin-6-yl}-methyl-amino)-ethanol

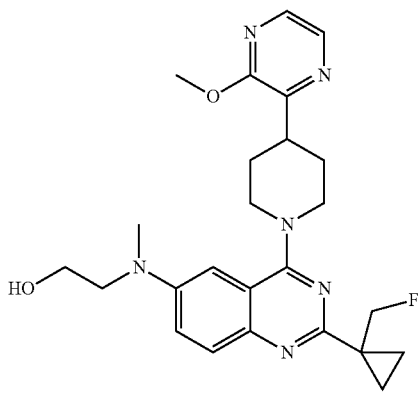 [SMILES: COc1nccnc1C1CCN(c2nc(C3(CF)CC3)nc3ccc(N(C)CCO)cc23)CC1]

Step 1: The procedure is similar to step 2 of 2-{[8-fluoro-4-[4-(3-methoxy-pyrazin-2-yl)-piperidin-1-yl]-2-(1-methyl-cyclopropyl)-quinazolin-6-yl]-methyl-amino}-ethanol.

Step 2: To a solution of 1-bromo-cyclobutanecarboxylic acid (4-bromo-2-cyano-phenyl)-amide (3 g, 8.4 mmol) in DMF (50 mL) was added AcONa (1.38 g, 16.8 mmol), and the mixture was then stirred at 90° C. overnight. Resultant was quenched with water (200 mL). The aqueous phase was extracted with EtOAc (100 mL×2). The organic layer was concentrated and purified by flash column (EtOAc in PE: 0 to 50%) to afford acetic acid 1-(4-bromo-2-cyano-phenyl-carbamoyl)-cyclobutyl ester (1.6 g, yield: 57%) as a white solid.

Step 3: To a solution of acetic acid 1-(4-bromo-2-cyano-phenylcarbamoyl)-cyclobutyl ester (1.6 g, 4.76 mmol) in THF/H$_2$O (5/1, 60 mL) was added LiOH (1.3 g, 23.8 mmol), it was then stirred at room temperature overnight. Resultant was evaporated to remove THF and the residue was diluted with water (100 mL). The mixture was acidified to pH to 2 with con. HCl and extracted with EA (100 mL×2). The extracts were dried over Na$_2$SO$_4$ and the solution was concentrated to afford 1-hydroxy-cyclobutanecarboxylic acid (4-bromo-2-cyano-phenyl)-amide (1.1 g, yield: 78%) as a white solid.

Step 4: The procedure is similar to step 3 of 2-{[8-fluoro-4-[4-(3-methoxy-pyrazin-2-yl)-piperidin-1-yl]-2-(1-methyl-cyclopropyl)-quinazolin-6-yl]-methyl-amino}-ethanol.

Step 5: To a solution of 6-bromo-2-(1-hydroxy-cyclobutyl)-quinazolin-4-ol (500 mg, 1.7 mmol) in DCM (50 mL) was added DAST (355 mg, 2.21 mmol), and the mixture was then stirred at room temperature for 1 h. Resultant was diluted with water (50 mL) the pH value was adjusted 8 with NaHCO$_3$. The organic layer was separated and concentrated to dryness. The residue was purified by flash column (C$_{18}$-silica; MeCN in water: 5% to 95%; 40 min) to afford 6-bromo-2-(1-fluoromethyl-cyclopropyl)-quinazolin-4-ol (280 mg, yield: 56%) as a pale solid.

Step 6: The procedure is similar to step 4 of 2-{[8-fluoro-4-[4-(3-methoxy-pyrazin-2-yl)-piperidin-1-yl]-2-(1-methyl-cyclopropyl)-quinazolin-6-yl]-methyl-amino}-ethanol.

Step 7: The procedure is similar to step 4 of 2-({2-Cyclopropylethynyl-4-[4-(2-methoxy-phenyl)-piperidin-1-yl]-quinazolin-6-yl}-methyl-amino)-ethanol.

Step 8: The procedure is similar to step 5 of 2-{[8-fluoro-4-[4-(3-methoxy-pyrazin-2-yl)-piperidin-1-yl]-2-(1-methyl-cyclopropyl)-quinazolin-6-yl]-methyl-amino}-ethanol and the target was obtained as a white solid. $^1$H NMR (400 MHz, DMSO-d6): δ=8.15 (d, J=3.2 Hz, 1H), 8.07 (d, J=2.8 Hz, 1H), 7.60 (d, J=9.2 Hz, 1H), 7.44 (dd, J=9.2, 2.4 Hz, 1H), 6.78 (d, J=2.4 Hz, 1H), 4.90 (d, J=48.4 Hz, 2H), 4.72 (t, J=4.8 Hz, 1H), 4.29-4.26 (m, 2H), 3.95 (s, 3H), 3.60-3.57 (m, 2H), 3.50-3.47 (m, 2H), 3.17-3.14 (m, 2H), 3.02 (s, 3H), 1.94-1.93 (m, 4H), 1.38-1.37 (m, 2H), 1.06-1.03 (m, 2H). MS: m/z 467.2 (M+H$^+$).

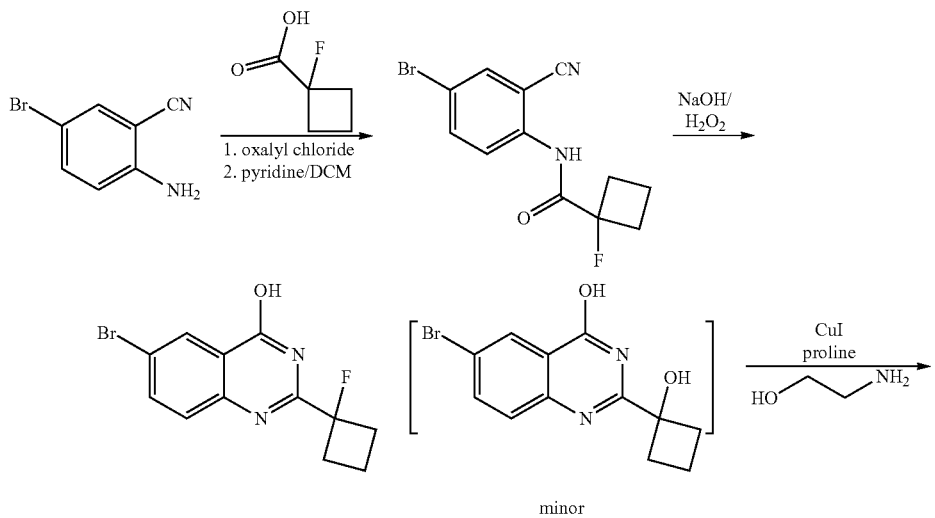

-continued

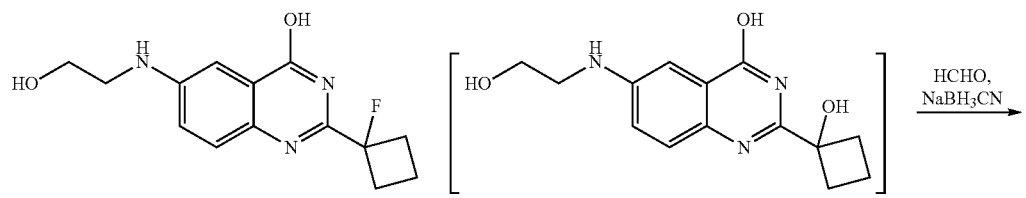

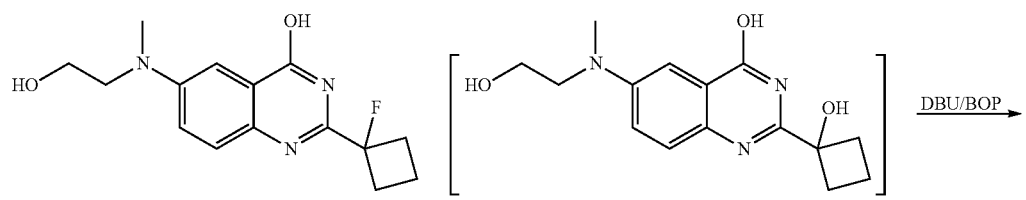

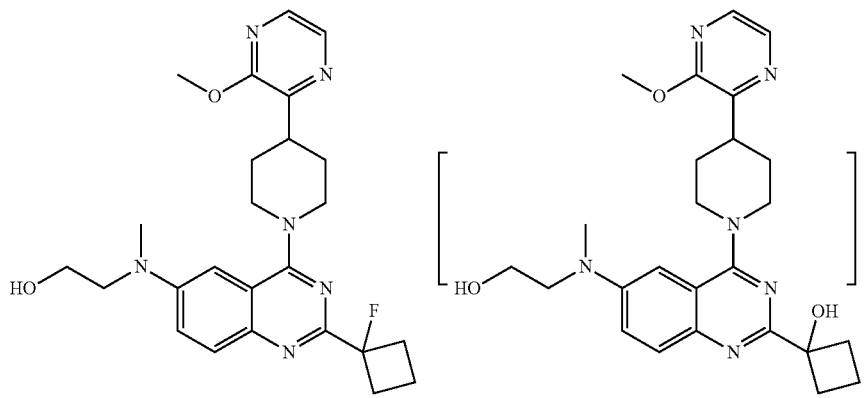

Example 220: Preparation of 2-({2-(1-Fluoro-cyclobutyl)-4-[4-(3-methoxy-pyrazin-2-yl)-piperidin-1-yl]-quinazolin-6-yl}-methyl-amino)-ethanol and Example 221: Preparation of 1-(6-((2-hydroxyethyl)(methyl)amino)-4-(4-(3-methoxypyrazin-2-yl)piperidin-1-yl)quinazolin-2-yl)cyclobutanol

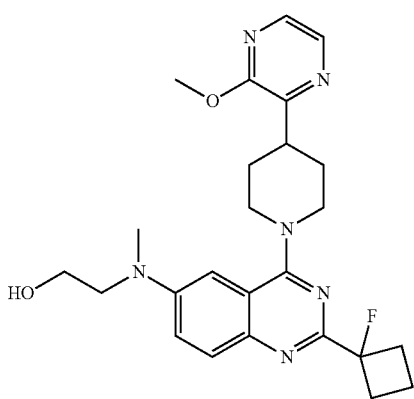

-continued

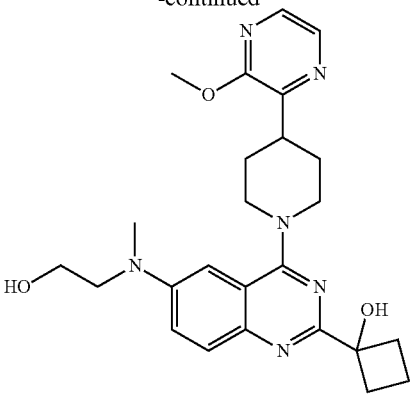

Step 1: The procedure is similar to step 2 of 2-{[8-fluoro-4-[4-(3-methoxy-pyrazin-2-yl)-piperidin-1-yl]-2-(1-methyl-cyclopropyl)-quinazolin-6-yl]-methyl-amino}-ethanol.

Step 2: To a solution of 1-fluoro-cyclobutanecarboxylic acid (4-bromo-2-cyano-phenyl)-amide (1.5 g, 5.07 mmol) in EtOH (50 mL) was added $H_2O_2$ (10 mL) and then NaOH (406 mg, 10.14 mmol), the mixture was then heated at reflux for 2 h. Resultant was cooled to room temperature and evaporated to remove EtOH. The residue was diluted with water (100 mL). The aqueous phase was acidified to 2 with con. HCl, and then extracted with EtOAc (100 mL×2). The organic layer was concentrated and the residue was purified by flash column (C$_{18}$-silica; MeCN in water: 5% to 95%; 40 min) to afford 6-bromo-2-(1-fluoro-cyclobutyl)-quinazolin-4-ol (1.1 g, yield: 73%) along with minor amount of 6-bromo-2-(1-hydroxy-cyclobutyl)-quinazolin-4-ol as a pale solid.

Step 3-4: The procedure is similar to step 3 and 4 of 2-({2-(1-fluoromethyl-cyclopropyl)-4-[4-(3-methoxy-pyrazin-2-yl)-piperidin-1-yl]-quinazolin-6-yl}-methyl-amino)-ethanol.

Step 5: To a solution of 2-(1-fluoro-cyclobutyl)-6-[(2-hydroxy-ethyl)-methyl-amino]-quinazolin-4-ol (100 mg, 0.34 mmol) in MeCN (50 mL) was added 2-methoxy-3-piperidin-4-yl-pyrazine (79 mg, 0.44 mmol), BOP (225 mg, 0.51 mmol) and DBU (0.2 mL), it was then stirred at room temperature overnight. Resultant was concentrated to dryness and the residue was purified directly by prep-HPLC to afford 2-({2-(1-fluoro-cyclobutyl)-4-[4-(3-methoxy-pyrazin-2-yl)-piperidin-1-yl]-quinazolin-6-yl}-methyl-amino)-ethanol (30 mg, yield: 18%) and 1-{6-[(2-hydroxy-ethyl)-methyl-amino]-4-[4-(3-methoxy-pyrazin-2-yl)-piperidin-1-yl]-quinazolin-2-yl}-cyclobutanol (10 mg, yield: 6%) as yellow solids. 2-({2-(1-Fluoro-cyclobutyl)-4-[4-(3-methoxy-pyrazin-2-yl)-piperidin-1-yl]-quinazolin-6-yl}-methyl-amino)-ethanol: $^1$H NMR (400 MHz, CD$_3$OD): δ=8.06 (d, J=2.4 Hz, 1H), 8.02 (d, J=3.2 Hz, 1H), 7.77 (d, J=9.2 Hz, 1H), 7.55 (dd, J=9.2, 2.8 Hz, 1H), 7.04 (d, J=2.4 Hz, 1H), 4.71-4.68 (m, 2H), 4.01 (s, 3H), 3.79 (t, J=6.0 Hz, 2H), 3.62 (t, J=5.6 Hz, 2H), 3.51-3.42 (m, 3H), 3.13 (s, 3H), 2.89-2.82 (m, 2H), 2.68-2.63 (m, 2H), 2.13-2.00 (m, 6H). MS: m/z 467.2 (M+H$^+$).

1-{6-[(2-hydroxy-ethyl)-methyl-amino]-4-[4-(3-methoxy-pyrazin-2-yl)-piperidin-1-yl]-quinazolin-2-yl}-cyclobutanol: $^1$H NMR (400 MHz, CD$_3$OD): δ=8.04 (d, J=2.8 Hz, 1H), 8.00 (d, J=2.8 Hz, 1H), 7.73 (d, J=9.2 Hz, 1H), 7.48 (dd, J=9.2, 2.4 Hz, 1H), 6.97 (d, J=2.4 Hz, 1H), 4.49-4.46 (m, 2H), 4.00 (s, 3H), 3.77 (t, J=6.0 Hz, 2H), 3.58 (t, J=6.0 Hz, 2H), 3.43-3.39 (m, 1H), 3.27-3.21 (m, 2H), 3.10 (s, 3H), 2.74-2.68 (m, 2H), 2.42-2.35 (m, 2H), 2.13-1.93 (m, 7H). MS: m/z 465.2 (M+H$^+$).

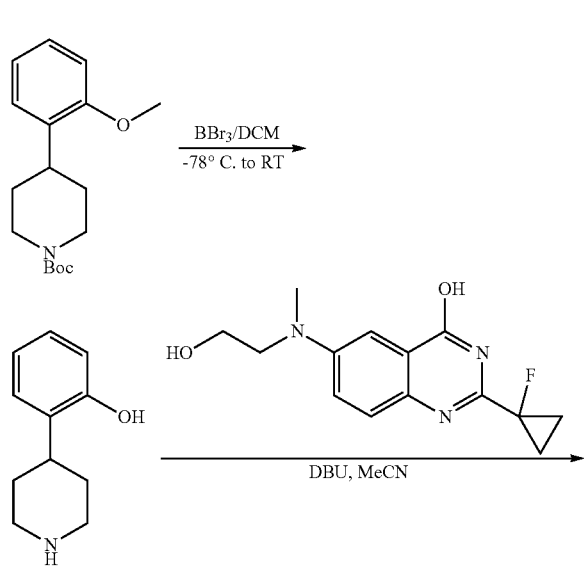

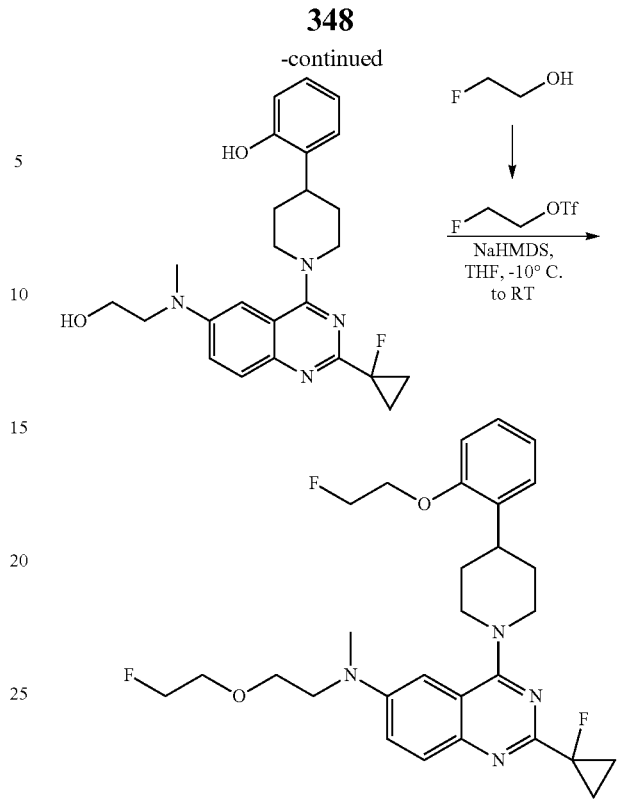

Example 222: Preparation of (2-(1-Fluoro-cyclopropyl)-4-{4-[2-(2-fluoro-ethoxy)-phenyl]-piperidin-1-yl}-quinazolin-6-yl)-[2-(2-fluoro-ethoxy)-ethyl]-methyl-amine

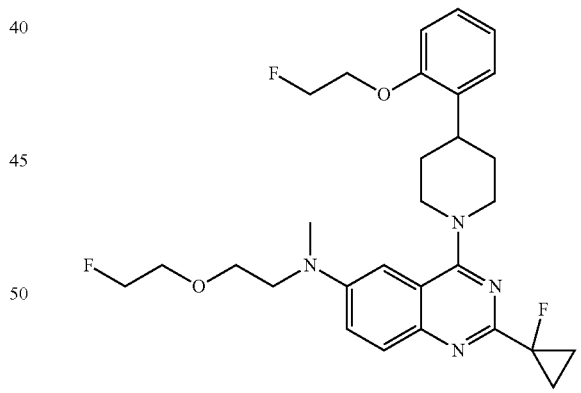

Step 1: To a solution of 4-(2-methoxy-phenyl)-piperidine-1-carboxylic acid tert-butyl ester (2.6 g, 8.9 mmol) in DCM (35 mL), was added BBr$_3$ (2.45 g, 9.8 mmol) slowly at −78° C. under N$_2$. The reaction was stirred at room temperature over weekend before quenched with NH$_4$OH. The mixture was separated between DCM (25 mL) and water (60 mL). The organic layer was dried over Na$_2$SO$_4$, concentrated to give 2-piperidin-4-yl-phenol (1 g, yield: 63%) as a white solid. $^1$H NMR (400 HMz, DMSO-d6): δ=9.30 (brs, 1H), 7.09-7.04 (m, 1H), 6.99-6.95 (m, 1H), 6.80-6.72 (m, 2H), 3.72-3.69 (m, 1H), 3.08-3.06 (m, 1H), 2.95-2.93 (m, 1H), 2.85-2.83 (m, 1H), 2.68-2.63 (m, 1H), 1.72-1.50 (m, 4H).

Step 2: To a suspension of 2-(1-fluoro-cyclopropyl)-6-[(2-hydroxy-ethyl)-methyl-amino]-quinazolin-4-ol (1 g, 3.61 mmol) and BOP (2.39 g, 5.41 mmol) in MeCN (30 mL) was added DBU (2.2 g, 14.44 mmol) and the mixture was stirred for 30 min. To the reaction, 2-piperidin-4-yl-phenol (639 mg, 3.61 mmol) was added. The reaction was stirred at room temperature overnight. The mixture was concentrated to dryness. The residue was taken up with water (60 mL) and the aqueous phase was extracted with EtOAc (60 mL). The organic layer was washed with brine (60 mL), dried over $Na_2SO_4$ and concentrated. The residue was purified by silica gel column (DCM/EA=1/1) to give 2-(1-{2-(1-fluoro-cyclopropyl)-6-[(2-hydroxy-ethyl)-methyl-amino}-quinazolin-4-yl]-piperidin-4-yl)-phenol (650 mg, yield: 41%) as a yellow solid. $^1H$ NMR (400 MHz, DMSO-d6): δ=9.40 (s, 1H), 7.79-7.76 (m, 1H), 7.55-7.53 (m, 1H), 7.13 (d, J=7.6 Hz, 1H), 7.04-7.00 (m, 1H), 6.91 (s, 1H), 6.81 (d, J=6.8 Hz, 1H), 6.75 (t, J=7.6 Hz, 1H), 4.59-4.58 (m, 1H), 4.57-4.53 (m, 2H), 3.61-3.60 (m, 2H), 3.54-3.52 (m, 2H), 3.26-3.21 (m, 3H), 3.05 (s, 3H), 1.98-1.80 (m, 4H), 1.66-1.53 (m, 4H). MS: m/z 437.2 (M+H$^+$).

Step 3: To a solution of 2-fluoro-ethanol (3.2 g, 50 mmol) in DCM (60 mL), was added $Tf_2O$ (15.5 g, 55 mmol) dropwise at −78° C. under $N_2$. The reaction was stirred at 10-20° C. for 1 h. The reaction solution was then washed with water (80 mL), saturated $NaHCO_3$ solution (60 mL) and brine (60 mL), then dried over $Na_2SO_4$ and concentrated to give trifluoro-methanesulfonic acid 2-fluoro-ethyl ester (7.9 g, yield: 81%) as a brown oil.

To a solution of 2-(1-{2-(1-fluoro-cyclopropyl)-6-[(2-hydroxy-ethyl)-methyl-amino]-quinazolin-4-yl}-piperidin-4-yl)-phenol (87 mg, 0.2 mmol) in THF (3 mL), was added 2N NaHMDS in THF (0.22 mL, 0.44 mmol) at −10° C. with stirring. After 15 min, trifluoro-methanesulfonic acid 2-fluoro-ethyl ester (98 mg, 0.5 mmol) was added at −10° C. The reaction was stirred at room temperature for 1 h. The reaction was separated between EtOAc (50 mL) and water (50 mL). The organic layer was dried over $Na_2SO_4$ and concentrated to dryness in vacuum. The residue was purified by prep-TLC (PE/EtOAc=1/1) to give (2-(1-fluoro-cyclopropyl)-4-{4-[2-(2-fluoro-ethoxy)-phenyl]-piperidin-1-yl]-quinazolin-6-yl)-[2-(2-fluoro-ethoxy)-ethyl]-methyl-amine (42 mg, yield: 40%) as a yellow solid. NMR (400 MHz, $CDCl_3$): δ=8.06-8.00 (m, 1H), 7.36 (dd, J=9.2, 2.8 Hz, 1H), 7.26-7.20 (m, 2H), 7.00 (t, J=7.6 Hz, 1H), 6.90-6.86 (m, 2H), 4.84 (t, J=4 Hz, 1H), 4.72 (t, J=4 Hz, 1H), 4.57 (t, J=4 Hz, 1H), 4.45-4.41 (m, 3H), 4.29 (t, J=4 Hz, 1H), 4.23-4.21 (m, 1H), 3.74-3.63 (m, 6H), 3.35-3.29 (m, 1H), 3.20-3.14 (m, 2H), 3.08 (s, 3H), 2.01-1.90 (m, 4H), 1.55-1.51 (m, 4H). MS: m/z 528.9 (M+H$^+$).

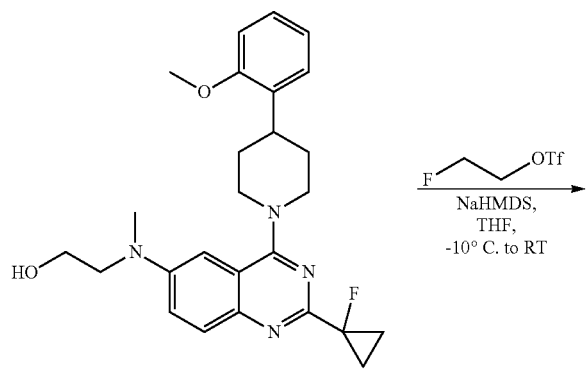

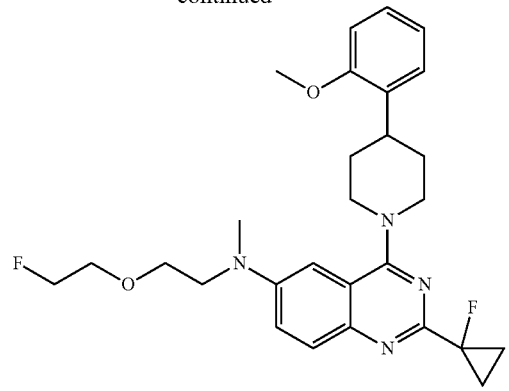

Example 223: Preparation of {2-(1-Fluoro-cyclopropyl)-4-[4-(2-methoxy-phenyl)-piperidin-1-yl]-quinazolin-6-yl}-[2-(2-fluoro-ethoxy)-ethyl]-methyl-amine

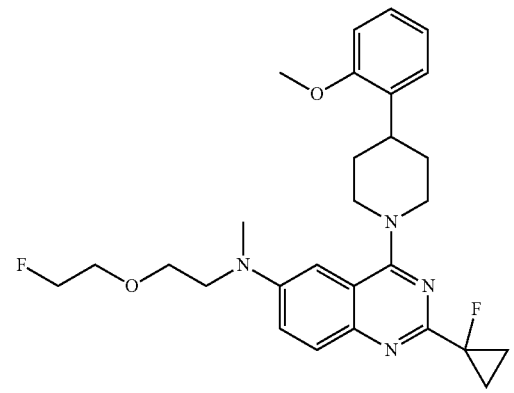 [SMILES: COc1ccccc1C1CCN(c2nc(C3(F)CC3)nc3ccc(N(C)CCOCCF)cc23)CC1]

To a solution of 2-({2-(1-fluoro-cyclopropyl)-4-[4-(2-methoxy-phenyl)-piperidin-1-yl]-quinazolin-6-yl}-methyl-amino)-ethanol (225 mg, 0.5 mmol) in THF (3 mL), was added 2N NaHMDS in THF (0.3 mL, 0.6 mmol) at −10° C. with stirring. After 15 min, trifluoro-methanesulfonic acid 2-fluoro-ethyl ester (147 mg, 0.75 mmol) was added at −10° C. The reaction was stirred at room temperature for 1 h. The reaction was separated between EtOAc (50 mL) and water (50 mL). The organic layer was dried over $Na_2SO_4$ and concentrated to dryness in vacuum. The residue was purified by prep-TLC (PE/EtOAc=1/1) to give {2-(1-fluoro-cyclopropyl)-4-[4-(2-methoxy-phenyl)-piperidin-1-yl]-quinazolin-6-yl}-[2-(2-fluoro-ethoxy)-ethyl]-methyl-amine (65 mg, yield: 52%) as a yellow solid. 1H NMR (400 MHz, $CDCl_3$): δ=8.10-8.06 (m, 1H), 7.37-7.35 (m, 1H), 7.26-7.21 (m, 2H), 6.98-6.89 (m, 3H), 4.5-4.55 (m, 1H), 4.44-4.42 (m, 3H), 3.86 (s, 3H), 3.72-3.65 (m, 6H), 3.33-3.28 (m, 1H), 3.21-3.15 (m, 2H), 3.08 (s, 3H), 2.00-1.85 (m, 4H), 1.55-1.49 (m, 4H). MS: m/z 496.9 (M+H$^+$).

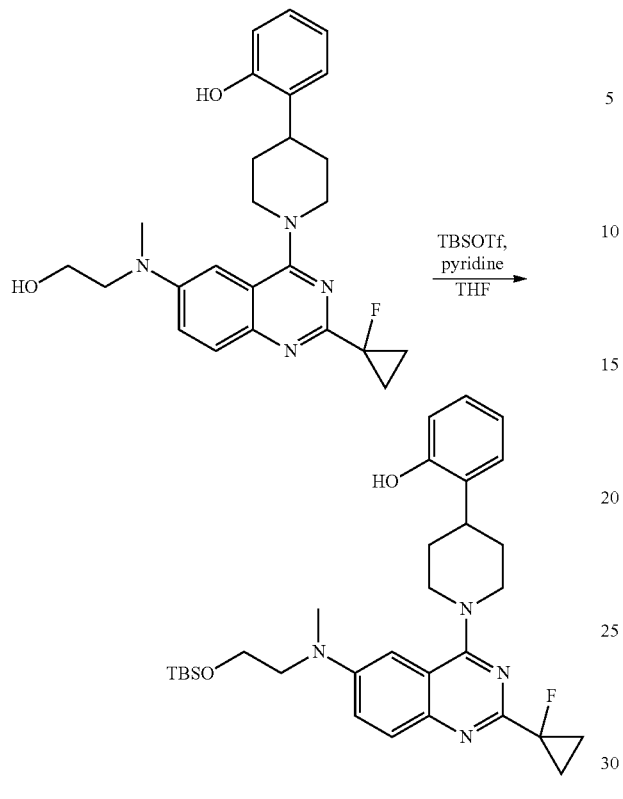

Example 224: Preparation of 2-{1-[6-{[2-(tert-Butyl-dimethyl-silanyloxy)-ethyl]-methyl-amino}-2-(1-fluoro-cyclopropyl)-quinazolin-4-yl]-piperidin-4-yl}-phenol

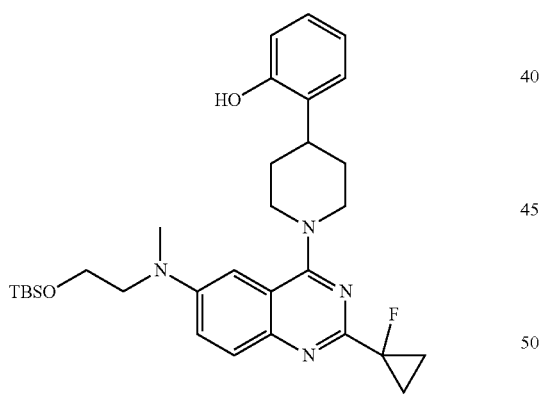

To a solution of 2-(1-{2-(1-fluoro-cyclopropyl)-6-[(2-hydroxy-ethyl)-methyl-amino]-quinazolin-4-yl}-piperidin-4-yl)-phenol (300 mg, 0.69 mmol) and pyridine (108 mg, 1.38 mmol) in THF (10 mL), was added TBSOTf (200 mg, 0.76 mmol) at −10° C. with stirring. After 10 min, the reaction was separated between EtOAc (50 mL) and water (70 mL). The organic layer was dried over Na$_2$SO$_4$ and concentrated. The residue was purified by silica gel column (PE/EtOAc=2/1) to give 2-{1-[6-{[2-(tert-butyl-dimethyl-silanyloxy)-ethyl]-methyl-amino}-2-(1-fluoro-cyclopropyl)-quinazolin-4-yl]-piperidin-4-yl}-phenol (350 mg, yield: 92%) as a yellow solid. 1H NMR (400 MHz, DMSO-d6): δ=9.35 (s, 1H), 7.65 (d, J=9.2 Hz, 1H), 7.48 (dd, J=9.2, 2.8 Hz, 1H), 7.14-7.12 (m, 1H), 7.03-6.99 (m, 1H), 6.85-6.73 (m, 3H), 4.33-4.30 (m, 2H), 3.80-3.77 (m, 2H), 3.60-3.57 (m, 2H), 3.21-3.08 (m, 3H), 3.04 (s, 3H), 1.98-1.80 (m, 4H), 1.47-1.40 (m, 4H), 0.78 (s, 9H), 0.00 (s, 6H). MS: m/z 551.2 (M+H$^+$).

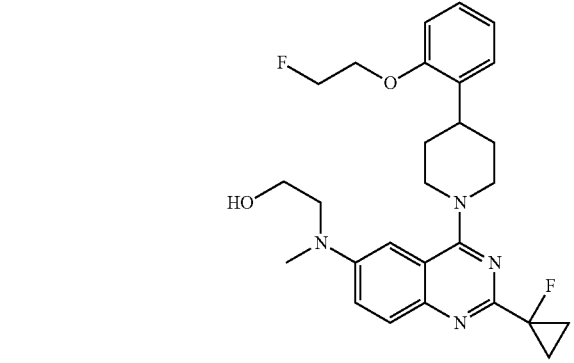

Example 225: Preparation of 2-[(2-(1-Fluoro-cyclopropyl)-4-{4-[2-(2-fluoro-ethoxy)-phenyl]-piperidin-1-yl}-quinazolin-6-yl)-methyl-amino]-ethanol

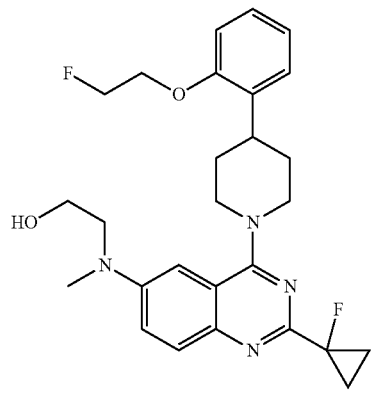 [SMILES: CN(CCO)c1ccc2nc(C3(F)CC3)nc(N3CCC(c4ccccc4OCCF)CC3)c2c1]

To a solution of 2-{1-[6-{[2-(tert-butyl-dimethyl-silanyloxy)-ethyl]-methyl-amino}-2-(1-fluoro-cyclopropyl)-quinazolin-4-yl]-piperidin-4-yl}-phenol (80 mg, 0.145 mmol) in THF (2 mL) was added 2N NaHMDS in THF (0.11 mL, 0.22 mmol) at −10° C. with stirring. After 10 min, trifluoromethanesulfonic acid 2-fluoro-ethyl ester (31 mg, 0.16 mmol) was added at −10° C. The reaction was stirred at room temperature for 10 min. 2N HCl (2 mL) was added to the reaction and stirred for 10 min. The mixture was then separated between EA (40 mL) and saturated $NaHCO_3$ solution (40 mL). The organic layer was washed with brine (40 mL), dried over $Na_2SO_4$ and concentrated to dryness in vacuum. The residue was purified by prep-TLC (EtOAc) to give 2-[(2-(1-fluoro-cyclopropyl)-4-{4-[2-(2-fluoro-ethoxy)-phenyl]-piperidin-1-yl}-quinazolin-6-yl)-methyl-amino]-ethanol (48 mg, yield: 69%) as a yellow solid. $^1$H NMR (400 MHz, $CDCl_3$): δ=8.10 (d, J=8.4 Hz, 1H), 7.41 (d, J=8.8 Hz, 1H), 7.26-7.20 (m, 2H), 7.01-6.97 (m, 2H), 6.87 (d, J=7.6 Hz, 1H), 4.84-4.83 (m, 1H), 4.72-4.71 (m, 1H), 4.48-4.44 (m, 2H), 4.30-4.29 (m, 1H), 4.22-4.21 (m, 1H), 3.89-3.87 (m, 2H), 3.60-3.57 (m, 2H), 3.32-3.16 (m, 3H), 3.07 (s, 3H), 2.04- 1.89 (m, 4H), 1.57-1.51 (m, 4H). MS: m/z 483.2 (M+H$^+$).

PHARMACEUTICAL COMPOSITION EXAMPLES

Example A1: Parenteral Composition

To prepare a parenteral pharmaceutical composition suitable for administration by injection, 100 mg of a water-soluble salt of a compound of Formula (I), (II), (III), (IV), (V), (VI), (VII) or (VIII), or pharmaceutically acceptable salt, N-oxide, racemate or stereoisomer thereof, is dissolved in 2% HPMC, 1% Tween 80 in DI water, pH 2.2 with MSA, q.s. to at least 20 mg/mL. The mixture is incorporated into a dosage unit form suitable for administration by injection.

Example A2: Oral Composition

To prepare a pharmaceutical composition for oral delivery, 100 mg of a compound of Formula (I), (II), (III), (IV), (V), (VI), (VII) or (VIII), or pharmaceutically acceptable salt, N-oxide, racemate or stereoisomer thereof, is mixed with 750 mg of starch. The mixture is incorporated into an oral dosage unit for, such as a hard gelatin capsule, which is suitable for oral administration.

BIOLOGY EXAMPLES

The cell lines utilized in the high-content imaging assays, which include the NTR1-, NTR2-, and GPR35-U2OS osteosarcomas, were obtained from the laboratory of Dr. Lawrence Barak at the Duke University Medical Center. The media used in the culture of the cell lines, as well as the assays themselves, consisted of Minimum Essential Medium (15-010-CM) and L-glutamine (25-005-CL) from Cellgro/Mediatech (Manassas, Va.), fetal bovine serum (SH30396.03) from Hyclone (Logan, Utah), penicillin-streptomycin solution (PS-20) from Omega Scientific in Tarzana, Calif., G418 (ant-gn-1) from Invivogen (San Diego, Calif.), and zeocin (R250-01) from Invitrogen (Carlsbad, Calif.). Cell lines were cultured in T225 tissue culture flasks (431082) supplied by Corning (Corning, N.Y.). Additional reagents employed include Dulbecco's Phosphate-Buffered Saline (DPBS) (21-031CV) from Cellgro/Mediatech, Trypsin-EDTA 0.05% (25300) from Invitrogen, paraformaldehyde (30528954) from Acros Organics (Geel, Belgium), Hoechst 33342 (H3570) from Invitrogen. The high-content assays were run in 1536-well plates (29326) supplied by Aurora Biotechnology (Poway, Calif.) and utilized aluminum plate seals (T592100) from E&K Scientific (Santa Clara, Calif.).

The neurotensin 1 peptide (N6383) from Sigma-Aldrich (St. Louis, Mo.) was used as a positive control in the NTR1 primary HCS assay. For the NTR2 selectivity assay, the non-specific, small molecule 3-(4-fluorophenyl)-7,8-dimethoxy-5-(4-methylbenzyl)-5H-pyrazolo[4,3-c]quinolone which was synthesized internally was used as a positive control. The GPR35 selectivity screen utilized zaprinast (ALX430-020-M010) from Alexis Biochemicals (Farmingdale, N.Y.) as a control.

The NTR1 β-Arrestin assays were performed using a PathHunter™ eXpress kit (93-0446E2) which contained the NTSR1 (NTR1) CHO cell line, OCC2 media (30-409), as well as the PathHunter Detection Reagents (93-0446E2). The kit was obtained from DiscoveRx (Fremont, Calif.). The assay employed the same neurotensin 1 peptide as a control as was used in the NTR1 primary assay. The assay was run in 1536-well, white, solid-bottom tissue culture plates (3727) from Corning.

The NTR1 $Ca^{2+}$ Flux assay was performed by ChanTest (Rockville, Md.). The assay used a CHO cell line, provided by ChanTest, which stably expressed the NTR1 receptor. The cells were grown and plated in Ham's F12 (11765) that was supplemented with fetal bovine serum (10437). Both were supplied by Gibco/Life Technologies (Carlsbad, Calif.). The DPBS (21-031CV) used in the assay was obtained from Cellgro/Mediatech and the G418 (ant-gn-1) was supplied by Invivogen. The Fluo-4 NW Dye (Invitrogen F36206) used to detect calcium mobilization was sourced by Invitrogen. The assay utilized 384-well, black, optical bottom assay plates (3683) and 384-well clear, non-binding plates (3640) as a compound source plate, both from Corning. The neurotensin 1 agonist control (1909) was obtained from Tocris (Bristol, U.K.).

NTR1 HTS
Primary Screen

The high-content imaging based NTR1 primary screen in 1536-well format was utilized to assay the MLSMR library of chemical entities in the following manner. On day one, 4 uL of a cell suspension containing 350,000 NTR1-U2OS cells per mL is added to each well of a 1536-well assay plate. Cells are plated in MEM medium containing 2.5% Fetal Bovine Serum, 1% Penicillin/Streptomycin solution, 1% L-Glutamine, 400 ug/mL G418, and 200 ug/mL Zeocin. The assay plates are then incubated overnight at 37° C., under 5% $CO_2$. Following the overnight incubation, a volume of 60 nL of the compounds at 2 mM in DMSO (final 20 μM, 1% DMSO) was transferred to columns 5-48 of the assay plates using a LabCyte Echo Liquid Handler. Next, 60 nL of DMSO were dispensed to columns 1-4, which served as the positive and neutral control wells. A volume of 2 μL of 300 nM neurotensin 1 (FAC=100 nM) peptide dissolved in DPBS was added to the positive control wells of columns 1 and 2, and 2 μL of DPBS only was transferred to the neutral control wells of columns 3 and 4 using a Kalypsys liquid handler (Kalypsys Systems). The assay plates were centrifuged on an Eppendorf 5810 centrifuge at 1000 rpm for 1 min to ensure even liquid levels in the wells of the assay plates. The assay plates were then returned to the incubator for 1 hour. Following the hour-long incubation at 37° C., the cells in each well were fixed with 4 μL of 6% paraformaldehyde added with a Multidrop Combi. The assay plates were centrifuged as before and incubated at room temperature for 1 hour. On the Kalypsys, plates were then aspirated down to 2.5 µL per well and washed twice with 11 µL per well of DPBS, followed by a final aspiration to 2.5 µL per well. On the Combi dispenser, 5 µL of 5 ug/mL Hoechst 33342 diluted in DPBS was added to each well of assay plates. The plates were again centrifuged as previously described, sealed, and incubated for at least 1 hour prior to being loaded on a PerkinElmer Opera QEHS.

Image acquisition was performed with a 45 plate capacity loader/stacker and the following settings: 40×0.6 NA air objective, acquisition camera set to 2-by-2 binning for an image size of 688 by 512 pixels, beta-arrestin-GFP acquired using 488 nm laser excitation and 540/75 nm emission filters, DAPI (nuclei) using 365 nm Xenon lamp excitation and 450/50 nm emission filters, 3 fields per well. Image analysis was performed using the Acapella Spot Detection Algorithm. For analysis settings and the metrics employed in the data analyses, please refer to supplemental information.

Compounds were selected as hits if they exhibited a percent activity of greater than or equal to 40 when compared to the neurotensin 1 control in the "Ratio of Spot Intensity to Cytoplasmic Intensity" metric. Compounds were excluded from the hit set if the "CellCount" was less than or equal to 20 which was indicative of cellular toxicity.

NTR1 Single Concentration Hit Confirmation

Hits from the primary screen were ordered and received from the MLSMR as 10 mM solutions in DMSO. The hit confirmation assays were performed in an identical manner as the primary screen with the exception of the source plate compound concentration, and therefore the volume transferred to the assay plate to achieve the same concentration as in the primary screen. A volume of 12.5 nL of test compounds at 10 mM in DMSO (final 20 µM, 0.2% DMSO) was delivered. Compounds were screened in quadruplicate and those with an average activity with regards to the "Ratio of Spot Intensity to Cytoplasmic Intensity" metric of greater than or equal to 40% were identified as being "confirmed".

NTR1 Dose Response

Compounds that were successfully confirmed in quadruplicate at 20 µM were then run in dose response in the primary assay. As with the single concentration hit confirmation, the assay was performed in an identical manner as the primary screen with the following modifications. For the initial hit confirmation in dose response, 40, 20, 10, 5, and 2.5 nL of 6 mM and 188 µM test compound in DMSO were transferred from source well to assay wells to achieve the final assay concentrations ranging from 40 to 0.078 µM. Test compound wells and control wells were backfilled with DMSO to achieve a final volume of DMSO of 40 nL or a final assay concentration of 0.5%. $EC_{50}$ values for this assay and the following dose response assays were calculated in the CBIS database (Cheminnovation) using the same analysis parameters and metrics as in the primary assay. All subsequent dose response assays followed the same basic protocol.

NTR2 Dose Response

The operating procedure used for the NTR1 dose response assay was adapted to the development of the NTR2 assay which was used to assess receptor selectivity. The protocol put to use for the NTR2 dose response assays was identical to that used in the NTR1 dose response experiments with a few deviations. Firstly, the NTR2-U2OS cell line was used for the assay, but cell densities as well as cell media in the assay remained the same. Secondly, because the response of the NTR2 cell line to the neurotensin 1 peptide was low relative to the primary NTR1 cell line, a non-specific, small molecule 3-(4-fluorophenyl)-7,8-dimethoxy-5-(4-methylbenzyl)-5H-pyrazolo[4,3-c]quinoline was used at a saturating concentration of 10 µM to generate a more robust signal window.

GPR35 Dose Response

The GPR35 dose response assay was used to assess selectivity against an unrelated GPCR. It utilized a very similar protocol to the NTR1 and NTR2 dose response assays with a few modifications. The GPR35-U2OS cells were plated at the same density and in the same media as the other two assays. Zaprinast was added to control wells in the same volume and in the same manner as the NTR1 primary assay to yield a final concentration of 40 µM.

NTR1β-Arrestin Dose Response

On day one of the assay, 5 µL of a cell suspension containing 120,000 NTSR1 (NTR1) CHO-K1 cells per mL in OCC2 media is added to each well of a 1536-well assay plate using a Multidrop Combi. The assay plates are then incubated for 48 hours at 37° C., under 5% $CO_2$. Following the two day incubation, a volume of 20, 10, and 5 nL of 10 and 1.2 mM test compounds in DMSO were transferred from source wells to test compound wells in assay plates with a LabCyte Echo to achieve final assay concentrations ranging from 33 to 1.03 µM for each test sample. Test compound wells and control wells were backfilled with DMSO to achieve a final volume of DMSO of 20 nL or a final assay concentration of 0.33%. Next, 1 µL of 120 nM neurotensin 1 peptide (FAC=20 nM) control diluted in assay media is dispensed with a Multidrop Combi to the positive control wells followed by 1 µL of assay media only to the neutral control and test compound wells. The assay plates were centrifuged on an Eppendorf 5810 centrifuge at 1000 rpm for 1 minute. The assay plates were then incubated in the dark at room temperature for 90 minutes. During the incubation, the detection reagent was prepared according to manufacturer's instructions. After 90 minutes, 3 µL of the detection reagent is delivered to all wells of each assay plate. Plates are again centrifuged as previously described then incubated at room temperature for 1 hour before being read on the PerkinElmer using a luminescent protocol.

NTR1 $Ca^{2+}$ Flux Dose Response

NTSR1 (NTR1) CHO cells are plated in 20 µL of assay media containing Ham's F12 supplemented with 10% fetal bovine serum and 0.4 mg/mL G418 at a concentration of $1.0 \times 10^6$ cells per mL into black, 384-well assay plates with clear bottoms using a Multidrop liquid handler. Assay plates are incubated at 37° C. in 5% $CO_2$. The next day, the assay plates are aspirated to remove growth media and washed once with 20 µL of DPBS. The DPBS is then aspirated from the assay plate and replaced with 25 µL of Fluo-4 NW calcium dye prepared according to the manufacturer's recommendations then the plates are incubated for 1 hour at 37° C. Following the incubation in the presence of dye, the assay is run on a Molecular Devices FlexStation-III using 494 excitation and 516 emission wavelengths set to read for 90 seconds with the addition at 18 seconds of 5 µL of 6× final concentration of test compounds and peptide control diluted in assay media containing 0.1% BSA and no more than 9% DMSO to yield a maximum final DMSO concentration of 1.5%. Percent activation is calculated based on the maximum response minus the minimum value over the time course relative to the neurotensin 1 control peptide at 100 µM. $EC_{50}$ values were calculated for those compounds tested in 8-point dose dependent response.

Representative biological data is presented in Table 1.

TABLE 1

| Ex. | Chemical name | Structure | EC$_{50}$ |
|---|---|---|---|
| 1 | {4-[4-(2-azetidin-1-yl-phenyl)-piperazin-1-yl]-2-cyclopropyl-quinazolin-6-yl}-dimethyl-amine | 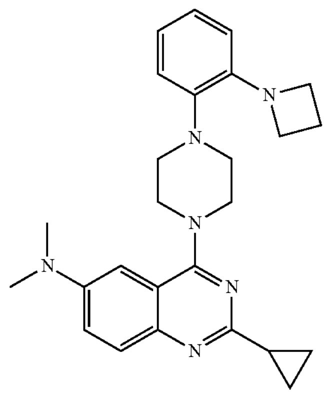 | B |
| 2 | {4-[4-(2-azetidin-1-yl-phenyl)-piperazin-1-yl]-2-cyclopropyl-quinazolin-6-yl}-ethyl-methyl-amine | 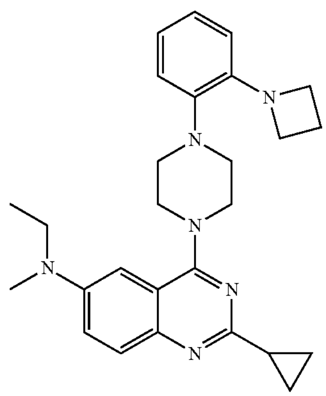 [SMILES: CCN(C)c1ccc2nc(C3CC3)nc(N3CCN(c4ccccc4N4CCC4)CC3)c2c1] | B |
| 3 | 4-[4-(2-azetidin-1-yl-phenyl)-piperidin-1-yl]-2-cyclopropyl-quinazolin-6-yl}-dimethyl-amine | 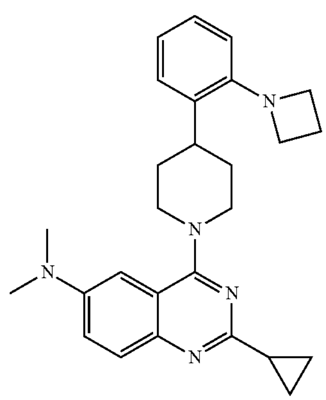 | D |
| 4 | {4-[4-(2-azetidin-1-yl-phenyl)-piperidin-1-yl]-2-cyclopropyl-quinazolin-6-yl}-ethyl-methyl-amine | 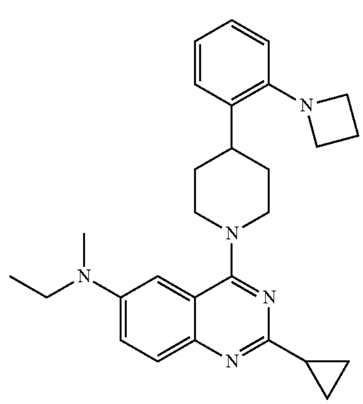 [SMILES: CCN(C)c1ccc2nc(C3CC3)nc(N3CCC(c4ccccc4N4CCC4)CC3)c2c1] | D |

TABLE 1-continued

| Ex. | Chemical name | Structure | EC$_{50}$ |
|---|---|---|---|
| 5 | N-{4-[4-(2-azetidin-1-yl-phenyl)-piperidin-1-yl]-2-cyclopropyl-quinazolin-6-yl}-N,N',N'-trimethyl-ethane-1,2-diamine | 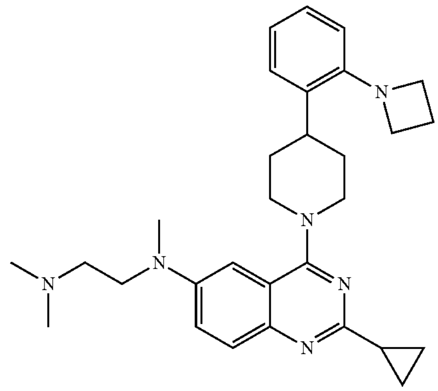 [SMILES: CN(C)CCN(C)c1ccc2nc(C3CC3)nc(N3CCC(c4ccccc4N4CCC4)CC3)c2c1] | C |
| 6 | 2-({4-[4-(2-azetidin-1-yl-phenyl)-piperidin-1-yl]-2-cyclopropyl-quinazolin-6-yl}-methyl-amino)-ethanol | 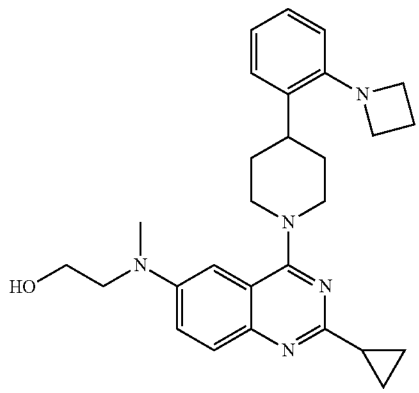 [SMILES: CN(CCO)c1ccc2nc(C3CC3)nc(N3CCC(c4ccccc4N4CCC4)CC3)c2c1] | B |
| 7 | {4-[4-(2-azetidin-1-yl-phenyl)-piperidin-1-yl]-2-cyclopropyl-quinazolin-6-yl}-(2-methoxy-ethyl)-methyl-amine | 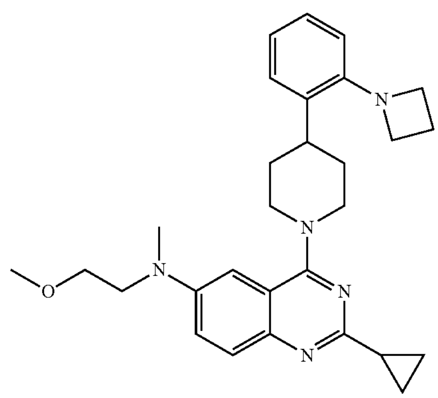 [SMILES: COCCN(C)c1ccc2nc(C3CC3)nc(N3CCC(c4ccccc4N4CCC4)CC3)c2c1] | C |
| 8 | {4-[4-(2-azetidin-1-yl-phenyl)-piperidin-1-yl]-2-cyclopropyl-quinazolin-6-yl}-methyl-(2-morpholin-4-yl-ethyl)-amine | 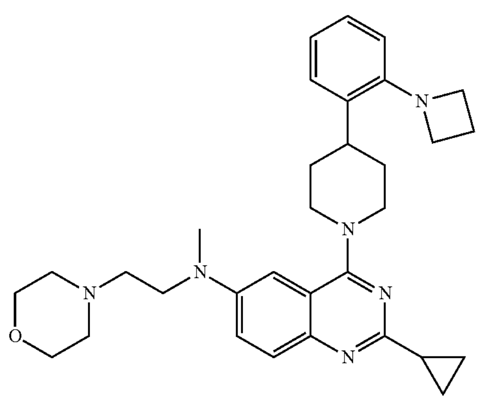 [SMILES: CN(CCN1CCOCC1)c1ccc2nc(C3CC3)nc(N3CCC(c4ccccc4N4CCC4)CC3)c2c1] | B |

TABLE 1-continued

| Ex. | Chemical name | Structure | EC$_{50}$ |
|---|---|---|---|
| 9 | {4-[4-(2-azetidin-1-yl-phenyl)-piperidin-1-yl]-2-cyclopropyl-quinazolin-6-yl}-methyl-(2-pyrrolidin-1-yl-ethyl)-amine | 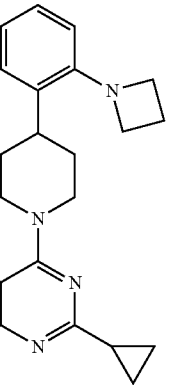 | D |
| 10 | 2-({2-cyclopropyl-4-[4-(2-dimethylamino-phenyl)-piperidin-1-yl]-quinazolin-6-yl}-methyl-amino)-ethanol | 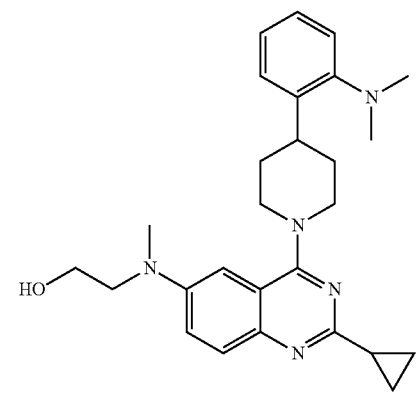 [SMILES: CN(C)c1ccccc1C1CCN(c2nc(C3CC3)nc3ccc(N(C)CCO)cc23)CC1] | C |
| 11 | {2-cyclopropyl-4-[4-(2-dimethylamino-phenyl)-piperidin-1-yl]-quinazolin-6-yl}-(2-methoxy-ethyl)-methyl-amine | 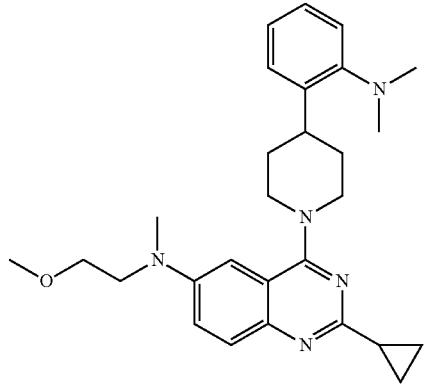 | C |
| 12 | {2-Cyclopropyl-4-[4-(2-dimethylamino-phenyl)-piperidin-1-yl]-quinazolin-6-yl}-methyl-(2-morpholin-4-yl-ethyl)-amine | 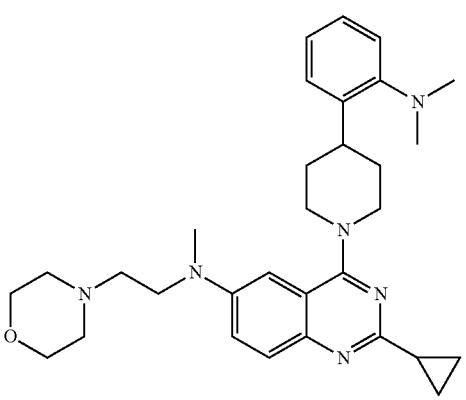 [SMILES: CN(C)c1ccccc1C1CCN(c2nc(C3CC3)nc3ccc(N(C)CCN4CCOCC4)cc23)CC1] | C |

TABLE 1-continued

| Ex. | Chemical name | Structure | EC$_{50}$ |
|---|---|---|---|
| 13 | {2-cyclopropyl-4-[4-(2-dimethylamino-phenyl)-piperidin-1-yl]-quinazolin-6-yl}-methyl-(2-pyrrolidin-1-yl-ethyl)-amine | 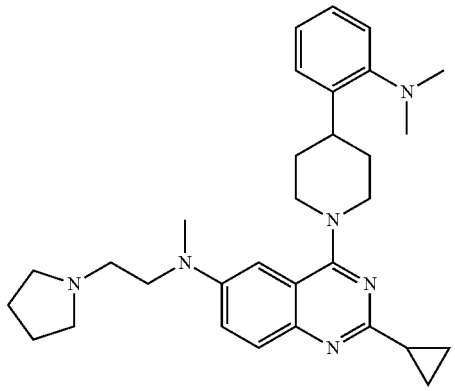 | C |
| 14 | N-{2-cyclopropyl-4-[4-(2-dimethylamino-phenyl)-piperidin-1-yl]-quinazolin-6-yl}-N,N',N'-trimethyl-ethane-1,2-diamine | 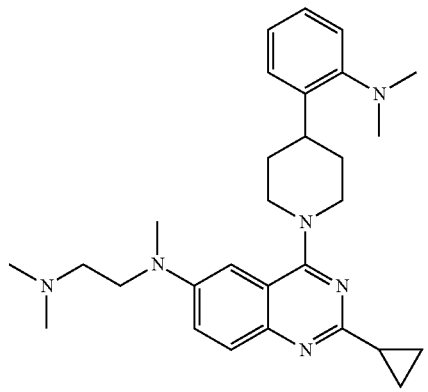 [SMILES: CN(C)CCN(C)c1ccc2nc(C3CC3)nc(N3CCC(c4ccccc4N(C)C)CC3)c2c1] | C |
| 15 | 2-({2-(1-Fluoro-cyclopropyl)-4-[4-(2-methoxy-phenyl)-piperidin-1-yl]-quinazolin-6-yl}-methyl-amino)-ethanol | 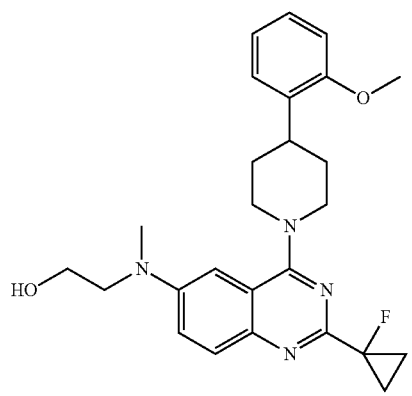 [SMILES: COc1ccccc1C1CCN(c2nc(C3(F)CC3)nc3ccc(N(C)CCO)cc23)CC1] | A |
| 16 | {2-(1-fluoro-cyclopropyl)-4-[4-(2-methoxy-phenyl)-piperidin-1-yl]-quinazolin-6-yl}-(2-methoxy-ethyl)-methyl-amine | 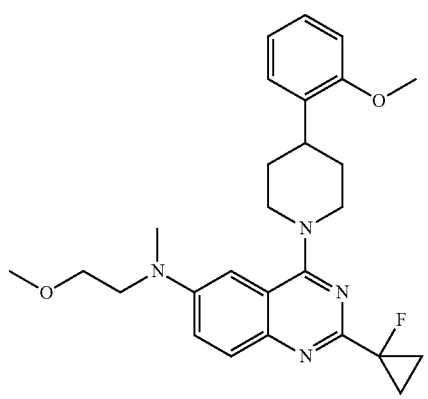 [SMILES: COCCN(C)c1ccc2nc(C3(F)CC3)nc(N3CCC(c4ccccc4OC)CC3)c2c1] | B |

TABLE 1-continued

| Ex. | Chemical name | Structure | EC$_{50}$ |
|---|---|---|---|
| 17 | {2-(1-fluoro-cyclopropyl)-4-[4-(2-methoxy-phenyl)-piperidin-1-yl]-quinazolin-6-yl}-methyl-(2-morpholin-4-yl-ethyl)-amine | 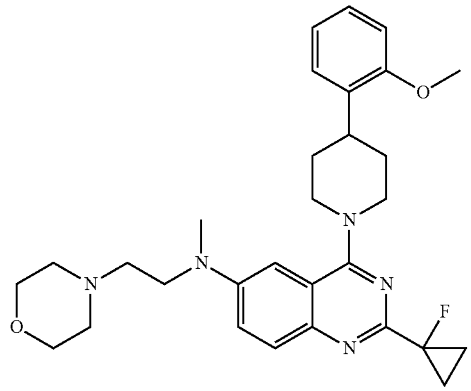 [SMILES: COc1ccccc1C1CCN(c2nc(C3(F)CC3)nc3ccc(N(C)CCN4CCOCC4)cc23)CC1] | B |
| 18 | {2-(1-fluoro-cyclopropyl)-4-[4-(2-methoxy-phenyl)-piperidin-1-yl]-quinazolin-6-yl}-dimethyl-amine | 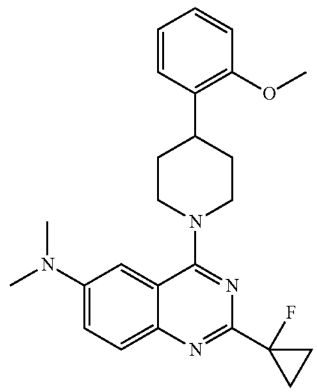 [SMILES: COc1ccccc1C1CCN(c2nc(C3(F)CC3)nc3ccc(N(C)C)cc23)CC1] | B |
| 19 | {2-(1-dimethylamino-cyclopropyl)-4-[4-(2-methoxy-phenyl)-piperidin-1-yl]-quinazolin-6-yl}-dimethyl-amine | 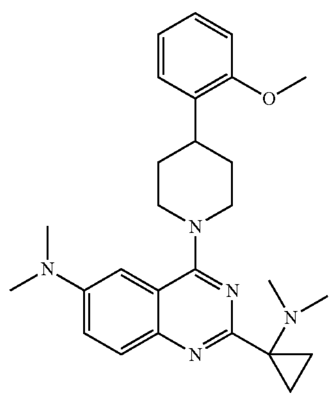 | D |
| 20 | {2-(1-fluoro-cyclopropyl)-4-[4-(2-methoxy-phenyl)-piperidin-1-yl]-quinazolin-6-yl}-methyl-propyl-amine | 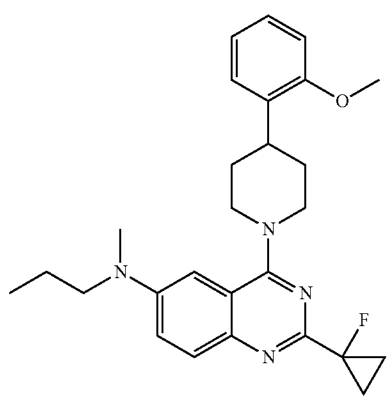 [SMILES: CCCN(C)c1ccc2nc(C3(F)CC3)nc(N3CCC(c4ccccc4OC)CC3)c2c1] | B |

TABLE 1-continued

| Ex. | Chemical name | Structure | EC$_{50}$ |
|---|---|---|---|
| 21 | {4-[4-(2-methoxy-phenyl)-piperidin-1-yl]-2-[1-(methyl-propyl-amino)-cyclopropyl]-quinazolin-6-yl}-methyl-propyl-amine | 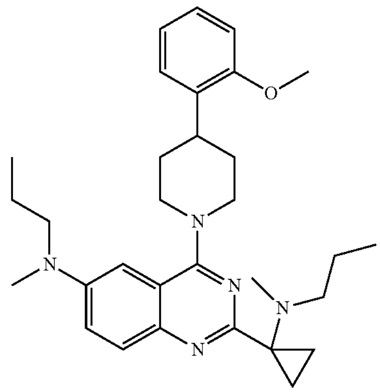 [SMILES: CCCN(C)c1ccc2nc(C3(N(C)CCC)CC3)nc(N3CCC(c4ccccc4OC)CC3)c2c1] | D |
| 22 | 2-{[4-[4-(2-methoxy-phenyl)-piperidin-1-yl]-2-(1-methyl-cyclopropyl)-quinazolin-6-yl]-methyl-amino}-ethanol | 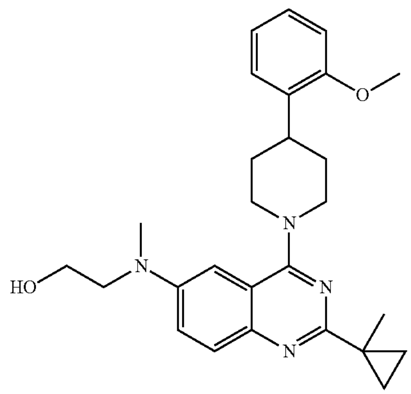 [SMILES: COc1ccccc1C1CCN(c2nc(C3(C)CC3)nc3ccc(N(C)CCO)cc23)CC1] | A |
| 23 | N-[4-[4-(2-methoxy-phenyl)-piperidin-1-yl]-2-(1-methyl-cyclopropyl)-quinazolin-6-yl]-N,N',N'-trimethyl-ethane-1,2-diamine | 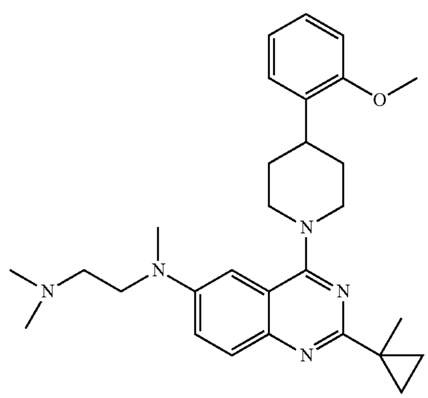 [SMILES: COc1ccccc1C1CCN(c2nc(C3(C)CC3)nc3ccc(N(C)CCN(C)C)cc23)CC1] | D |
| 24 | [4-[4-(2-methoxy-phenyl)-piperidin-1-yl]-2-(1-methyl-cyclopropyl)-quinazolin-6-yl]-methyl-(2-pyrrolidin-1-yl-ethyl)-amine | 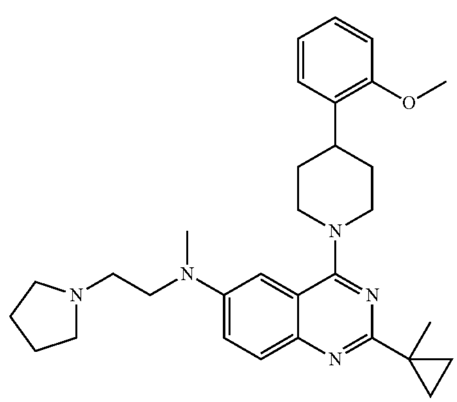 [SMILES: COc1ccccc1C1CCN(c2nc(C3(C)CC3)nc3ccc(N(C)CCN4CCCC4)cc23)CC1] | C |

TABLE 1-continued

| Ex. | Chemical name | Structure | $EC_{50}$ |
|---|---|---|---|
| 25 | 2-{[4-[4-(2-dimethylamino-phenyl)-piperidin-1-yl]-2-(1-methyl-cyclopropyl)-quinazolin-6-yl]-methyl-amino}-ethanol | 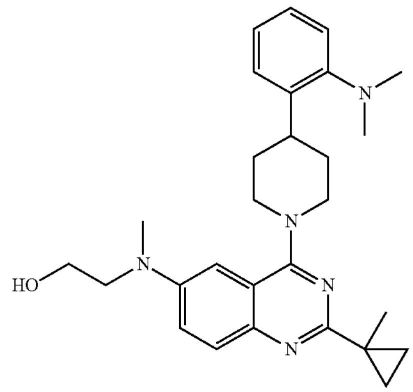 [SMILES: CN(C)c1ccccc1C1CCN(c2nc(C3(C)CC3)nc3ccc(N(C)CCO)cc23)CC1] | C |
| 26 | [4-[4-(2-dimethylamino-phenyl)-piperidin-1-yl]-2-(1-methyl-cyclopropyl)-quinazolin-6-yl]-(2-methoxy-ethyl)-methyl-amine | 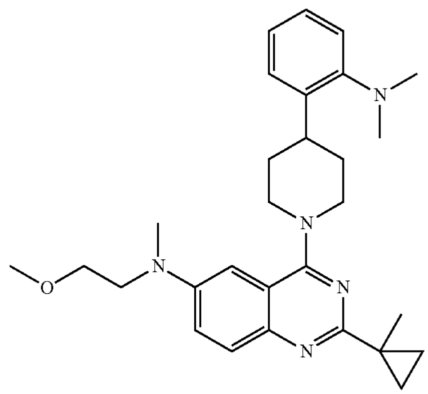 [SMILES: COCCN(C)c1ccc2nc(C3(C)CC3)nc(N3CCC(c4ccccc4N(C)C)CC3)c2c1] | D |
| 27 | [4-[4-(2-dimethylamino-1-vinyl-propenyl)-piperidin-1-yl]-2-(1-methyl-cyclopropyl)-quinazolin-6-yl]-methyl-(2-morpholin-4-yl-ethyl)-amine | 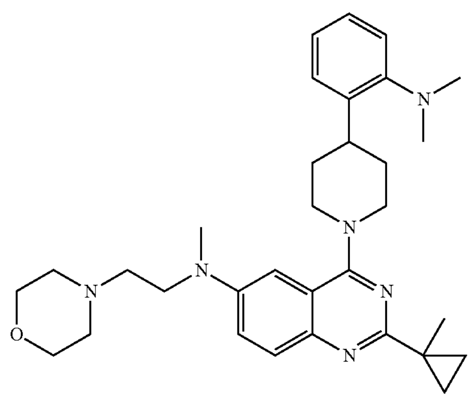 [SMILES: CN(C)c1ccccc1C1CCN(c2nc(C3(C)CC3)nc3ccc(N(C)CCN4CCOCC4)cc23)CC1] | D |
| 28 | N-[4-[4-(2-dimethylamino-phenyl)-piperidin-1-yl]-2-(1-methyl-cyclopropyl)-quinazolin-6-yl]-N,N',N'-trimethyl-ethane-1,2-diamine | 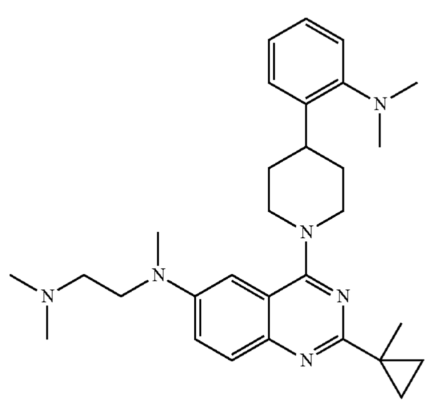 [SMILES: CN(C)CCN(C)c1ccc2nc(C3(C)CC3)nc(N3CCC(c4ccccc4N(C)C)CC3)c2c1] | D |

TABLE 1-continued

| Ex. | Chemical name | Structure | EC₅₀ |
|---|---|---|---|
| 29 | [4-[4-(2-dimethylamino-phenyl)-piperidin-1-yl]-2-(1-methyl-cyclopropyl)-quinazolin-6-yl]-methyl-(2-pyrrolidin-1-yl-ethyl)-amine | 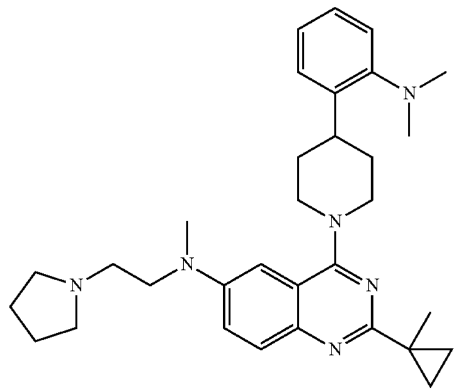 | D |
| 30 | 2-{[4-[4-(2-azetidin-1-yl-phenyl)-piperidin-1-yl]-2-(1-methyl-cyclopropyl)-quinazolin-6-yl]-methyl-amino}-ethanol | 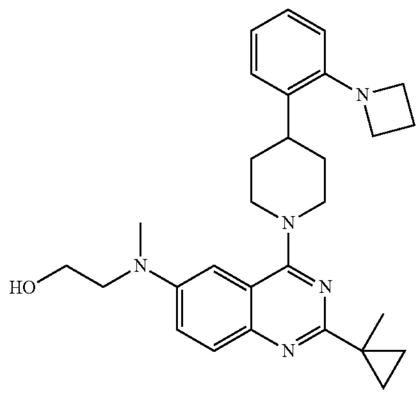 [SMILES: CN(CCO)c1ccc2nc(C3(C)CC3)nc(N3CCC(c4ccccc4N4CCC4)CC3)c2c1] | C |
| 31 | [4-[4-(2-azetidin-1-yl-phenyl)-piperidin-1-yl]-2-(1-methyl-cyclopropyl)-quinazolin-6-yl]-(2-methoxy-ethyl)-methyl-amine | 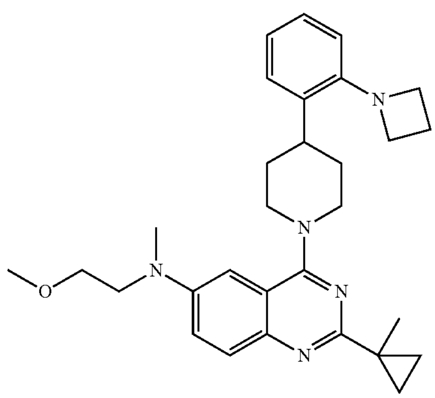 [SMILES: COCCN(C)c1ccc2nc(C3(C)CC3)nc(N3CCC(c4ccccc4N4CCC4)CC3)c2c1] | D |
| 32 | [4-[4-(2-azetidin-1-yl-phenyl)-piperidin-1-yl]-2-(1-methyl-cyclopropyl)-quinazolin-6-yl]-methyl-(2-morpholin-4-yl-ethyl)-amine | 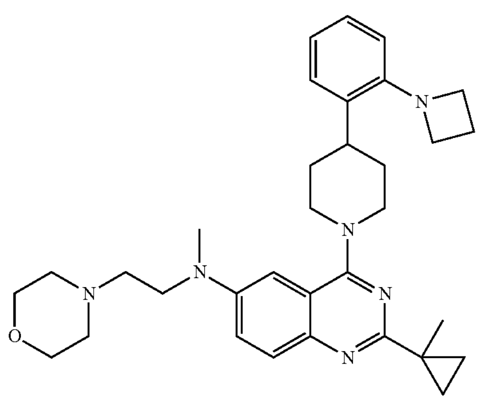 [SMILES: CN(CCN1CCOCC1)c1ccc2nc(C3(C)CC3)nc(N3CCC(c4ccccc4N4CCC4)CC3)c2c1] | D |

TABLE 1-continued

| Ex. | Chemical name | Structure | EC$_{50}$ |
|---|---|---|---|
| 33 | N-(2-methoxyethyl)-4-(4-(2-methoxyphenyl)piperidin-1-yl)-N-methyl-2-(1-methylcyclopropyl)quinazolin-6-amine | 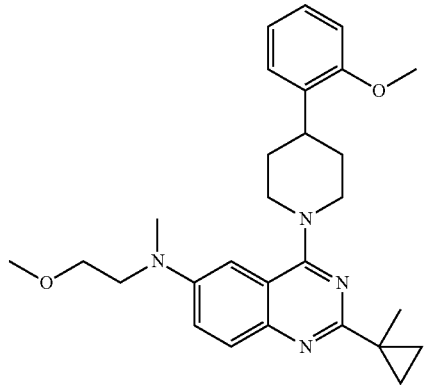 [SMILES: COCCN(C)c1ccc2nc(C3(C)CC3)nc(N3CCC(c4ccccc4OC)CC3)c2c1] | C |
| 34 | 4-(4-(2-methoxyphenyl)piperidin-1-yl)-N-methyl-2-(1-methylcyclopropyl)-N-(2-morpholinoethyl)quinazolin-6-amine | 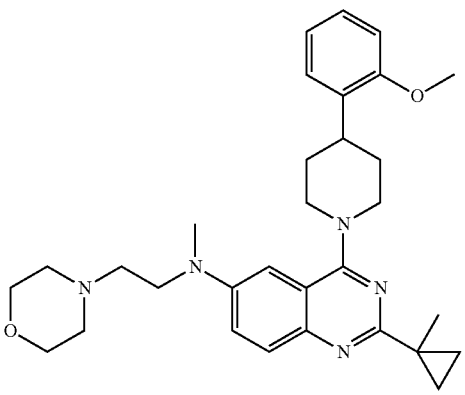 [SMILES: COc1ccccc1C1CCN(c2nc(C3(C)CC3)nc3ccc(N(C)CCN4CCOCC4)cc23)CC1] | C |
| 35 | N-[4-[4-(2-azetidin-1-yl-phenyl)-piperidin-1-yl]-2-(1-methyl-cyclopropyl)-quinazolin-6-yl]-N,N',N'-trimethyl-ethane-1,2-diamine | 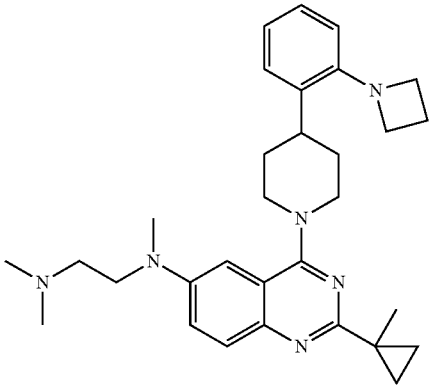 [SMILES: CN(C)CCN(C)c1ccc2nc(C3(C)CC3)nc(N3CCC(c4ccccc4N4CCC4)CC3)c2c1] | D |
| 36 | [4-[4-(2-azetidin-1-yl-phenyl)-piperidin-1-yl]-2-(1-methyl-cyclopropyl)-quinazolin-6-yl]-methyl-(2-pyrrolidin-1-yl-ethyl)-amine | 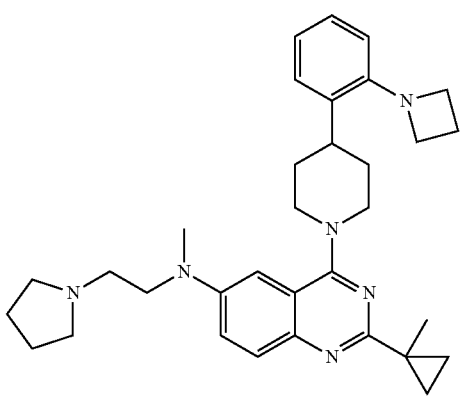 | D |

TABLE 1-continued

| Ex. | Chemical name | Structure | EC$_{50}$ |
|---|---|---|---|
| 37 | {2-cyclopentyl-4-[4-(2-methoxy-phenyl)-piperidin-1-yl]-quinazolin-6-yl}-dimethyl-amine | 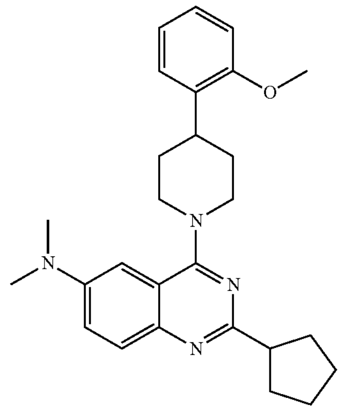 [SMILES: COc1ccccc1C1CCN(c2nc(C3CCCC3)nc3ccc(N(C)C)cc23)CC1] | D |
| 38 | 2-({2-cyclopentyl-4-[4-(2-methoxy-phenyl)-piperidin-1-yl]-quinazolin-6-yl}-methyl-amino)-ethanol | 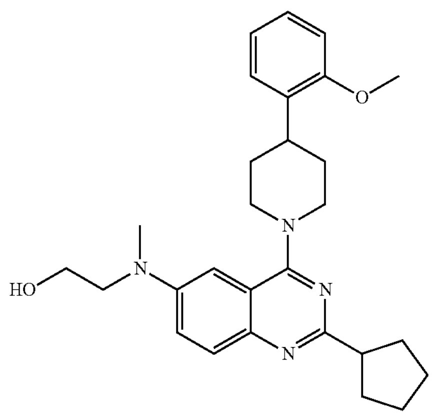 [SMILES: COc1ccccc1C1CCN(c2nc(C3CCCC3)nc3ccc(N(C)CCO)cc23)CC1] | C |
| 39 | {2-cyclopentyl-4-[4-(2-methoxy-phenyl)-piperidin-1-yl]-quinazolin-6-yl}-(2-methoxy-ethyl)-methyl-amine | 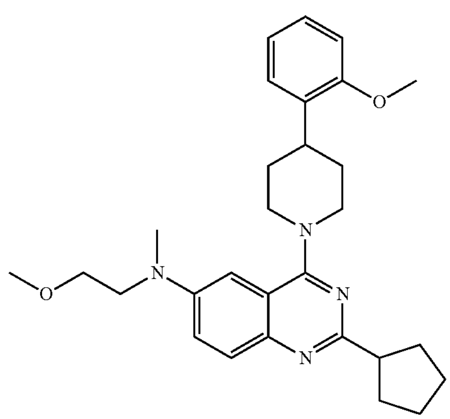 [SMILES: COCCN(C)c1ccc2nc(C3CCCC3)nc(N3CCC(c4ccccc4OC)CC3)c2c1] | D |

TABLE 1-continued

| Ex. | Chemical name | Structure | EC$_{50}$ |
|---|---|---|---|
| 40 | 2-cyclopentyl-4-[4-(2-methoxy-phenyl)-piperidin-1-yl]-quinazolin-6-yl}-methyl-propyl-amine | 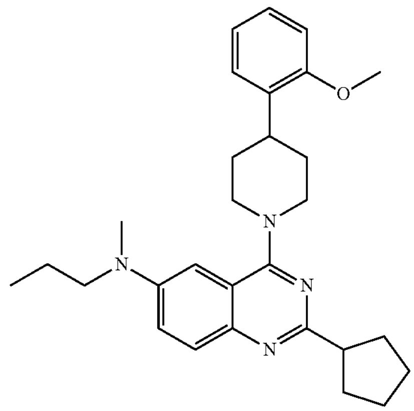 [SMILES: CCCN(C)c1ccc2nc(C3CCCC3)nc(N3CCC(c4ccccc4OC)CC3)c2c1] | D |
| 41 | 2-cyclopentyl-4-[4-(2-methoxy-phenyl)-piperidin-1-yl]-quinazolin-6-yl}-methyl-(2-morpholin-4-yl-ethyl)-amine | 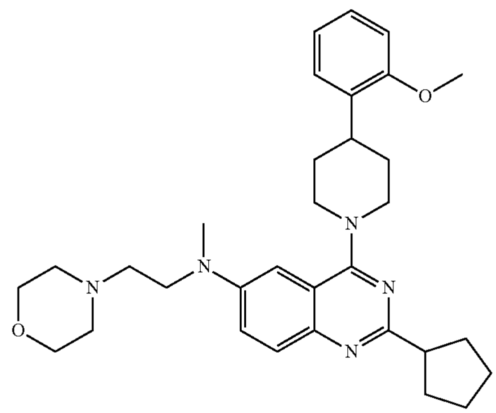 [SMILES: COc1ccccc1C1CCN(c2nc(C3CCCC3)nc3ccc(N(C)CCN4CCOCC4)cc23)CC1] | D |
| 42 | {2-cyclobutyl-4-[4-(2-methoxy-phenyl)-piperidin-1-yl]-quinazolin-6-yl}-dimethyl-amine | 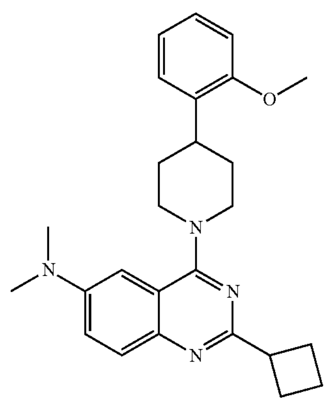 [SMILES: COc1ccccc1C1CCN(c2nc(C3CCC3)nc3ccc(N(C)C)cc23)CC1] | C or D |
| 43 | 2-({2-cyclobutyl-4-[4-(2-methoxy-phenyl)-piperidin-1-yl]-quinazolin-6-yl}-methyl-amino)-ethanol | 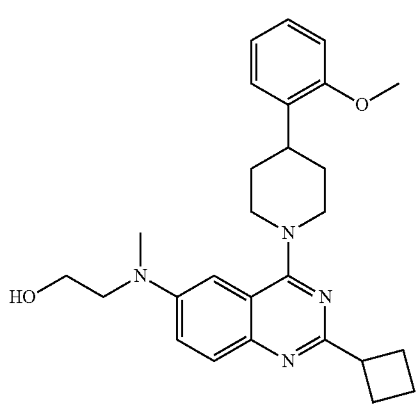 [SMILES: COc1ccccc1C1CCN(c2nc(C3CCC3)nc3ccc(N(C)CCO)cc23)CC1] | B |

TABLE 1-continued

| Ex. | Chemical name | Structure | EC$_{50}$ |
|---|---|---|---|
| 44 | 2-cyclobutyl-4-[4-(2-methoxy-phenyl)-piperidin-1-yl]-quinazolin-6-yl}-(2-methoxy-ethyl)-methyl-amine | 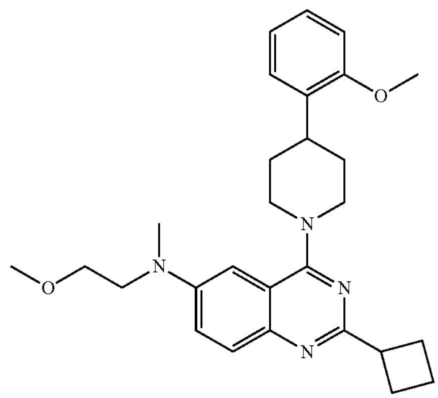 [SMILES: COCCN(C)c1ccc2nc(C3CCC3)nc(N3CCC(c4ccccc4OC)CC3)c2c1] | C |
| 45 | {2-cyclobutyl-4-[4-(2-methoxy-phenyl)-piperidin-1-yl]-quinazolin-6-yl}-methyl-propyl-amine | 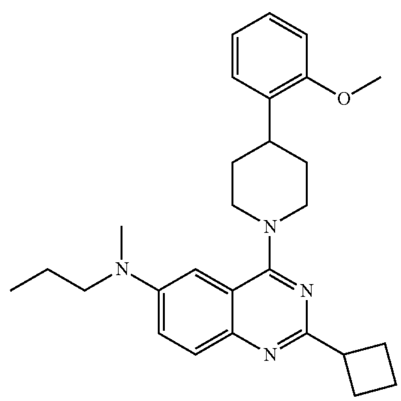 [SMILES: CCCN(C)c1ccc2nc(C3CCC3)nc(N3CCC(c4ccccc4OC)CC3)c2c1] | D |
| 46 | {2-cyclobutyl-4-[4-(2-methoxy-phenyl)-piperidin-1-yl]-quinazolin-6-yl}-methyl-(2-morpholin-4-yl-ethyl)-amine | 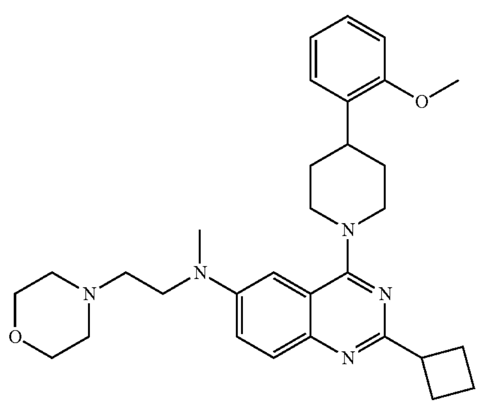 [SMILES: COc1ccccc1C1CCN(c2nc(C3CCC3)nc3ccc(N(C)CCN4CCOCC4)cc23)CC1] | C |
| 47 | 2-{[4-[4-(2-methoxy-phenyl)-piperidin-1-yl]-2-(1-trifluoromethyl-cyclopropyl)-quinazolin-6-yl]-methyl-amino}-ethanol | 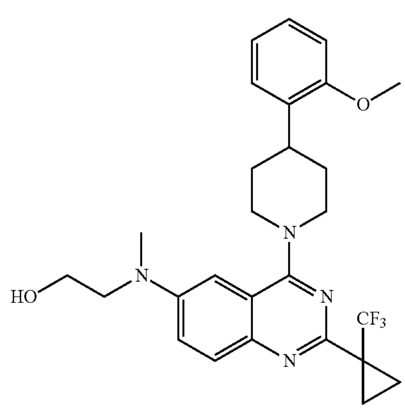 [SMILES: COc1ccccc1C1CCN(c2nc(C3(C(F)(F)F)CC3)nc3ccc(N(C)CCO)cc23)CC1] | A |

TABLE 1-continued

| Ex. | Chemical name | Structure | EC$_{50}$ |
|---|---|---|---|
| 48 | [4-(2-methoxy-phenyl)-piperidin-1-yl]-2-(1-trifluoromethyl-cyclopropyl)-quinazolin-6-yl]-methyl-(2-morpholin-4-yl-ethyl)-amine | 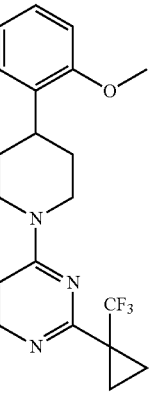 | C |
| 49 | 2-{[4-[4-(2-dimethylamino-phenyl)-piperidin-1-yl]-2-(1-trifluoromethyl-cyclopropyl)-quinazolin-6-yl]-methyl-amino}-ethanol | 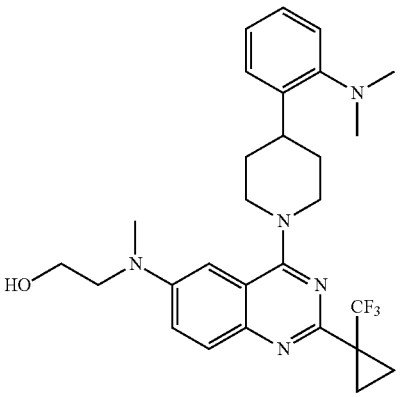 [SMILES: CN(C)c1ccccc1C1CCN(c2nc(C3(C(F)(F)F)CC3)nc3ccc(N(C)CCO)cc23)CC1] | B |
| 50 | [4-[4-(2-dimethylamino-phenyl)-piperidin-1-yl]-2-(1-trifluoromethyl-cyclopropyl)-quinazolin-6-yl]-methyl-(2-morpholin-4-yl-ethyl)-amine | 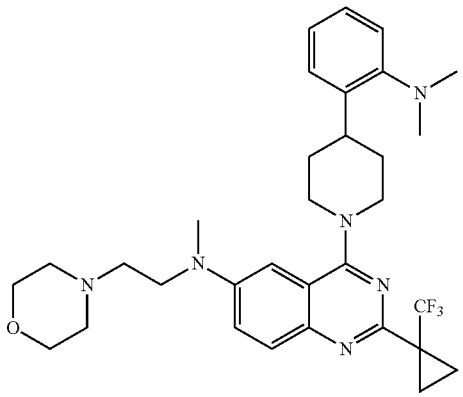 [SMILES: CN(C)c1ccccc1C1CCN(c2nc(C3(C(F)(F)F)CC3)nc3ccc(N(C)CCN4CCOCC4)cc23)CC1] | D |

TABLE 1-continued
| Ex. | Chemical name | Structure | EC$_{50}$ |
|---|---|---|---|
| 51 | 2-{[4-[4-(2-methoxy-phenyl)-piperidin-1-yl]-2-(1-methyl-cyclopentyl)-quinazolin-6-yl]-methyl-amino}-ethanol | 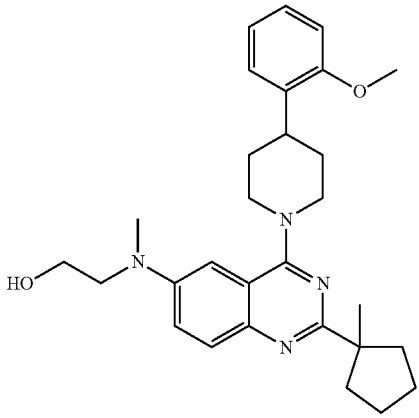 [SMILES: COc1ccccc1C1CCN(c2nc(C3(C)CCCC3)nc3ccc(N(C)CCO)cc23)CC1] | C |
| 52 | 4-[4-(2-methoxy-phenyl)-piperidin-1-yl]-2-(1-methyl-cyclopentyl)-quinazolin-6-yl]-methyl-(2-morpholin-4-yl-ethyl)-amine | 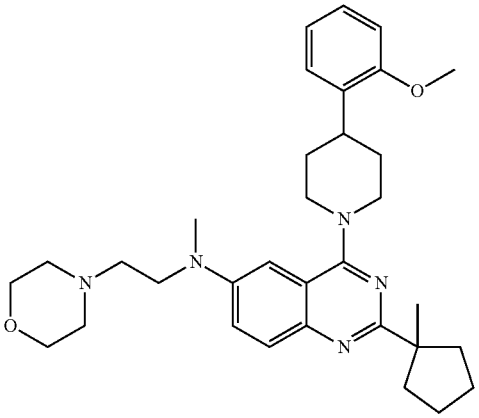 [SMILES: COc1ccccc1C1CCN(c2nc(C3(C)CCCC3)nc3ccc(N(C)CCN4CCOCC4)cc23)CC1] | C |
| 53 | {[4-[4-(2-Dimethylamino-phenyl)-piperidin-1-yl]-2-(1-methyl-cyclopentyl)-quinazolin-6-yl]-methyl-amino}-ethanol | 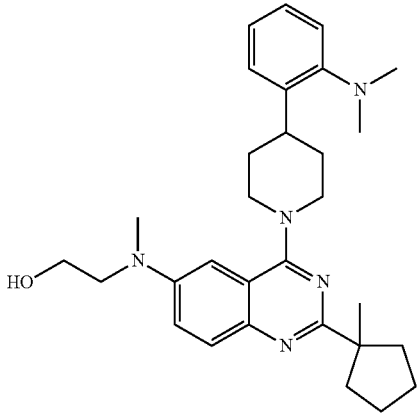 [SMILES: CN(C)c1ccccc1C1CCN(c2nc(C3(C)CCCC3)nc3ccc(N(C)CCO)cc23)CC1] | C |

TABLE 1-continued

| Ex. | Chemical name | Structure | EC$_{50}$ |
|---|---|---|---|
| 54 | [4-[4-(2-dimethylamino-phenyl)-piperidin-1-yl]-2-(1-methyl-cyclopentyl)-quinazolin-6-yl]-methyl-(2-morpholin-4-yl-ethyl)-amine | 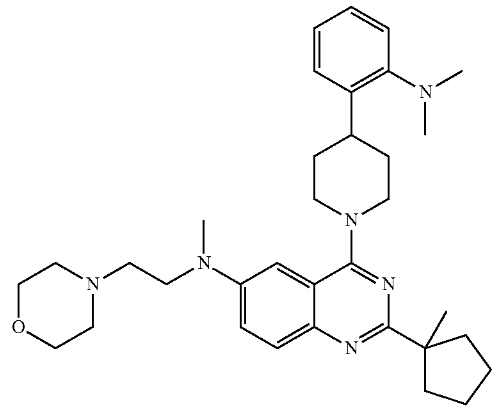 | C |
| 55 | 2-{[4-[4-(2-methoxy-phenyl)-piperidin-1-yl]-2-(1-trifluoromethyl-cyclopentyl)-quinazolin-6-yl]-methyl-amino}-ethanol | 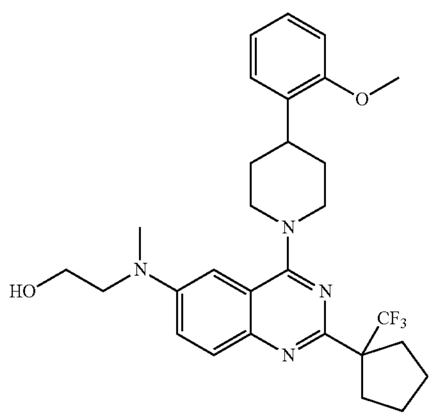 | C |
| 56 | [4-[4-(2-methoxy-phenyl)-piperidin-1-yl]-2-(1-trifluoromethyl-cyclopentyl)-quinazolin-6-yl]-methyl-(2-morpholin-4-yl-ethyl)-amine | 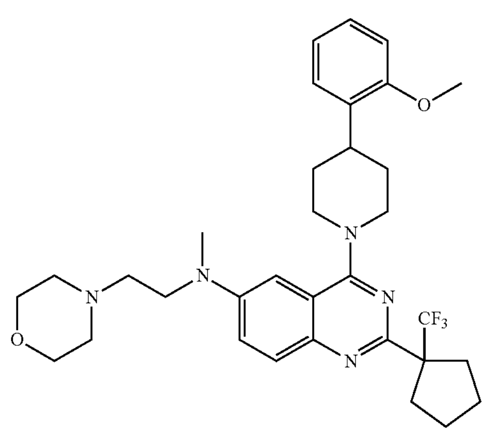 [SMILES: COc1ccccc1C1CCN(c2nc(C3(C(F)(F)F)CCCC3)nc3ccc(N(C)CCN4CCOCC4)cc23)CC1] | C |

TABLE 1-continued

| Ex. | Chemical name | Structure | EC$_{50}$ |
|---|---|---|---|
| 57 | 2-{[4-[4-(2-dimethylamino-phenyl)-piperidin-1-yl]-2-(1-trifluoromethyl-cyclopentyl)-quinazolin-6-yl]-methyl-amino}-ethanol | 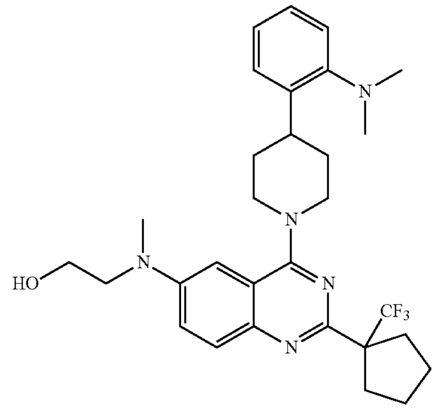 [SMILES: CN(C)c1ccccc1C1CCN(c2nc(C3(C(F)(F)F)CCCC3)nc3ccc(N(C)CCO)cc23)CC1] | B |
| 58 | [4-[4-(2-dimethylamino-phenyl)-piperidin-1-yl]-2-(1-trifluoromethyl-cyclopentyl)-quinazolin-6-yl]-methyl-(2-morpholin-4-yl-ethyl)-amine | 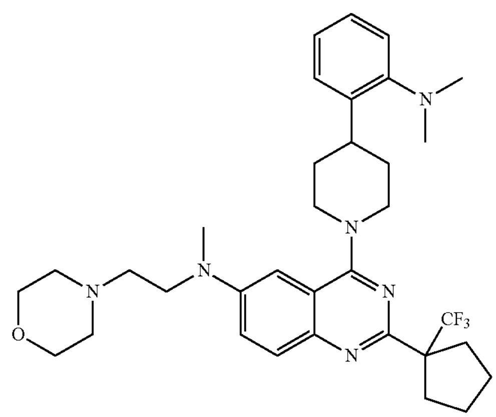 [SMILES: CN(C)c1ccccc1C1CCN(c2nc(C3(C(F)(F)F)CCCC3)nc3ccc(N(C)CCN4CCOCC4)cc23)CC1] | C |
| 59 | 2-({2-(1-fluoro-cyclobutyl)-4-[4-(2-methoxy-phenyl)-piperidin-1-yl]-quinazolin-6-yl}-methyl-amino)-ethanol | 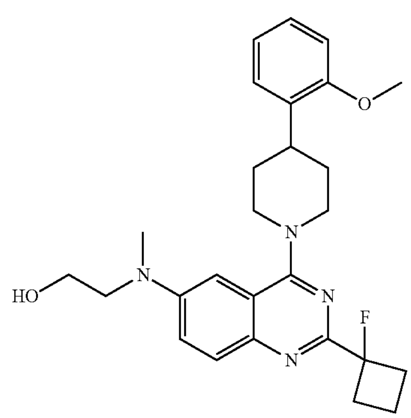 [SMILES: COc1ccccc1C1CCN(c2nc(C3(F)CCC3)nc3ccc(N(C)CCO)cc23)CC1] | A |

TABLE 1-continued

| Ex. | Chemical name | Structure | EC₅₀ |
|---|---|---|---|
| 60 | {2-(1-fluoro-cyclobutyl)-4-[4-(2-methoxy-phenyl)-piperidin-1-yl]-quinazolin-6-yl}-methyl-(2-morpholin-4-yl-ethyl)-amine | 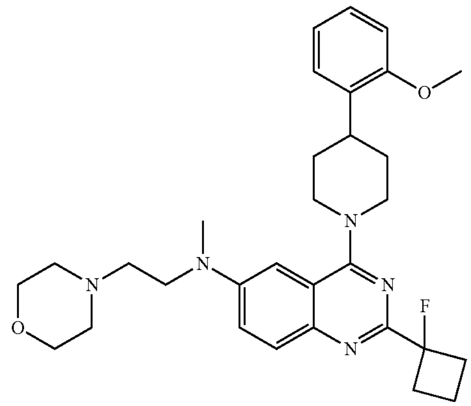 [SMILES: COc1ccccc1C1CCN(c2nc(C3(F)CCC3)nc3ccc(N(C)CCN4CCOCC4)cc23)CC1] | A |
| 61 | 2-{[4-[4-(2-dimethylamino-phenyl)-piperidin-1-yl]-2-(1-fluoro-cyclobutyl)-quinazolin-6-yl]-methyl-amino}-ethanol | 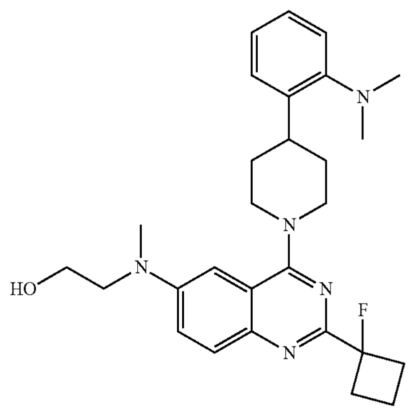 [SMILES: CN(C)c1ccccc1C1CCN(c2nc(C3(F)CCC3)nc3ccc(N(C)CCO)cc23)CC1] | A |
| 62 | [4-[4-(2-dimethylamino-phenyl)-piperidin-1-yl]-2-(1-fluoro-cyclobutyl)-quinazolin-6-yl]-methyl-(2-morpholin-4-yl-ethyl)-amine | 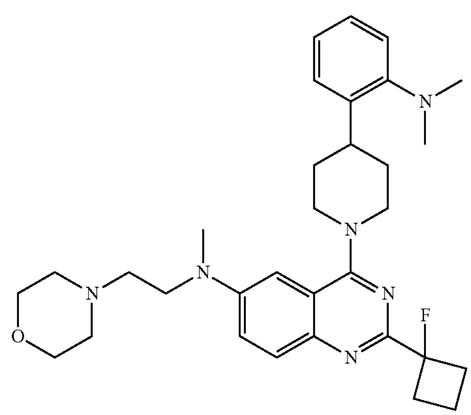 [SMILES: CN(C)c1ccccc1C1CCN(c2nc(C3(F)CCC3)nc3ccc(N(C)CCN4CCOCC4)cc23)CC1] | B |

TABLE 1-continued

| Ex. | Chemical name | Structure | EC$_{50}$ |
|---|---|---|---|
| 63 | 2-{[4-[4-(2-methoxy-phenyl)-piperidin-1-yl]-2-(1-trifluoromethyl-cyclobutyl)-quinazolin-6-yl]-methyl-amino}-ethanol | 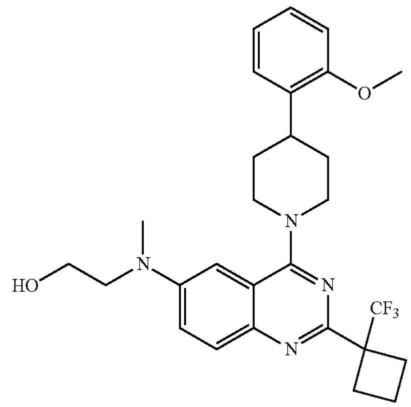 [SMILES: COc1ccccc1C1CCN(c2nc(C3(C(F)(F)F)CCC3)nc3ccc(N(C)CCO)cc23)CC1] | B |
| 64 | [4-[4-(2-methoxy-phenyl)-piperidin-1-yl]-2-(1-trifluoromethyl-cyclobutyl)-quinazolin-6-yl]-methyl-(2-morpholin-4-yl-ethyl)-amine | 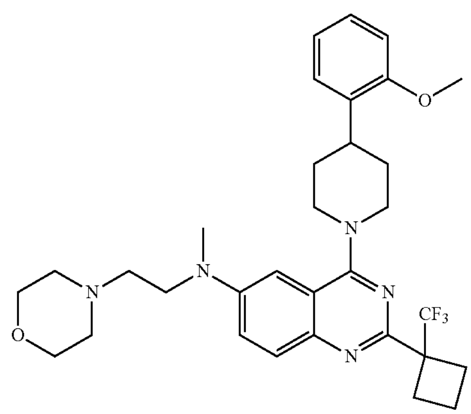 [SMILES: COc1ccccc1C1CCN(c2nc(C3(C(F)(F)F)CCC3)nc3ccc(N(C)CCN4CCOCC4)cc23)CC1] | D |
| 65 | 2-{[4-[4-(2-Dimethylamino-phenyl)-piperidin-1-yl]-2-(1-trifluoromethyl-cyclobutyl)-quinazolin-6-yl]-methyl-amino}-ethanol | 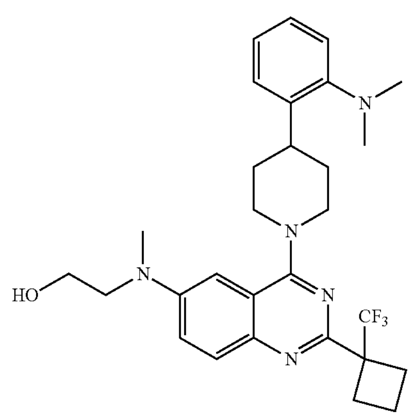 [SMILES: CN(C)c1ccccc1C1CCN(c2nc(C3(C(F)(F)F)CCC3)nc3ccc(N(C)CCO)cc23)CC1] | C |

TABLE 1-continued

| Ex. | Chemical name | Structure | EC$_{50}$ |
|---|---|---|---|
| 66 | Preparation of [4-[4-(2-dimethylamino-phenyl)-piperidin-1-yl]-2-(1-trifluoromethyl-cyclobutyl)-quinazolin-6-yl]-methyl-(2-morpholin-4-yl-ethyl)-amine | 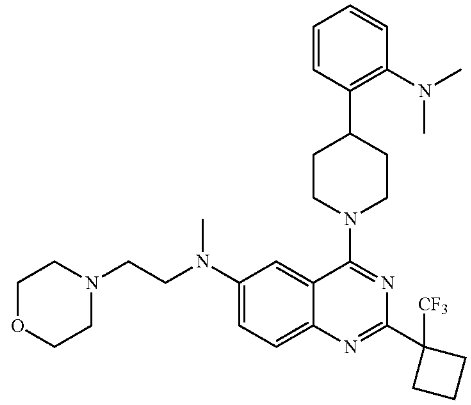 [SMILES: CN(C)c1ccccc1C1CCN(c2nc(C3(C(F)(F)F)CCC3)nc3ccc(N(C)CCN4CCOCC4)cc23)CC1] | D |
| 67 | [4-[4-(2-dimethylamino-phenyl)-piperidin-1-yl]-2-(1-methyl-cyclobutyl)-quinazolin-6-yl]-methyl-(2-morpholin-4-yl-ethyl)-amine | 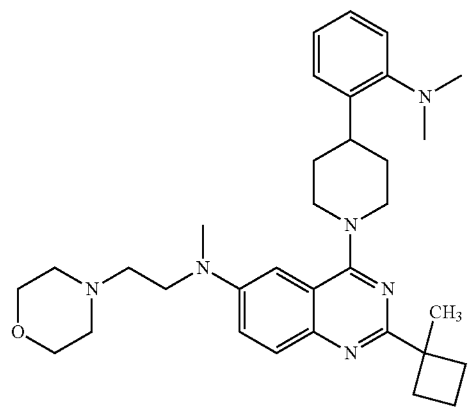 [SMILES: CN(C)c1ccccc1C1CCN(c2nc(C3(C)CCC3)nc3ccc(N(C)CCN4CCOCC4)cc23)CC1] | D |
| 68 | 2-{[4-[4-(2-dimethylamino-phenyl)-piperidin-1-yl]-2-(1-methyl-cyclobutyl)-quinazolin-6-yl]-methyl-amino}-ethanol | 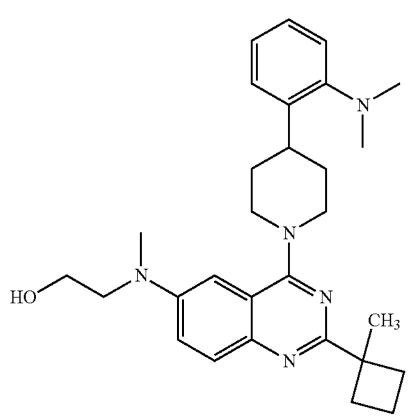 [SMILES: CN(C)c1ccccc1C1CCN(c2nc(C3(C)CCC3)nc3ccc(N(C)CCO)cc23)CC1] | B |

TABLE 1-continued

| Ex. | Chemical name | Structure | $EC_{50}$ |
|---|---|---|---|
| 69 | [4-[4-(2-methoxy-phenyl)-piperidin-1-yl]-2-(1-methyl-cyclobutyl)-quinazolin-6-yl]-methyl-(2-morpholin-4-yl-ethyl)-amine | 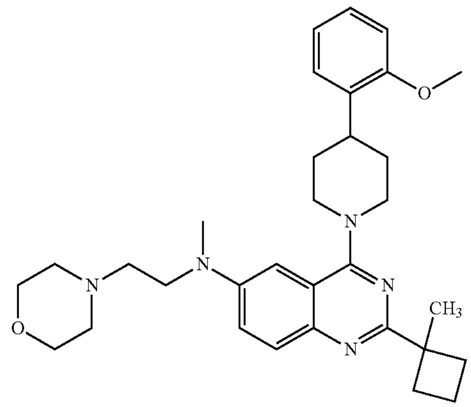 [SMILES: COc1ccccc1C1CCN(c2nc(C3(C)CCC3)nc3ccc(N(C)CCN4CCOCC4)cc23)CC1] | B |
| 70 | 2-{[4-[4-(2-Methoxy-phenyl)-piperidin-1-yl]-2-(1-methyl-cyclobutyl)-quinazolin-6-yl]-methyl-amino}-ethanol | 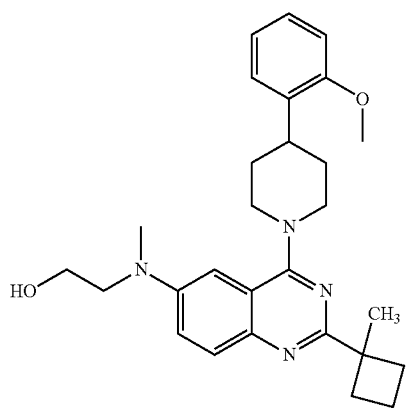 [SMILES: COc1ccccc1C1CCN(c2nc(C3(C)CCC3)nc3ccc(N(C)CCO)cc23)CC1] | B |
| 71 | {2-(1fluoro-cyclopentyl)-4-[4-(2-methoxy-phenyl)-piperidin-1-yl]-quinazolin-6-yl}-methyl-(2-morpholin-4-yl-ethyl)-amine | 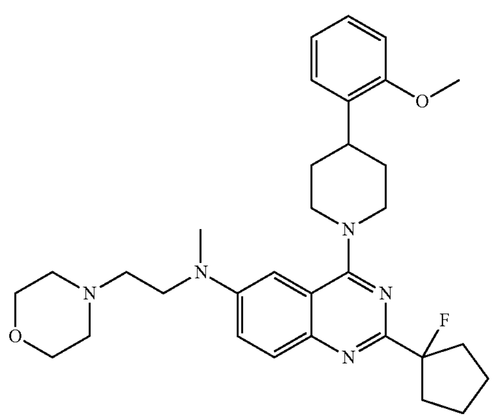 [SMILES: COc1ccccc1C1CCN(c2nc(C3(F)CCCC3)nc3ccc(N(C)CCN4CCOCC4)cc23)CC1] | C |

TABLE 1-continued

| Ex. | Chemical name | Structure | EC$_{50}$ |
|---|---|---|---|
| 72 | 2-({2-(1-fluoro-cyclopentyl)-4-[4-(2-methoxy-phenyl)-piperidin-1-yl]-quinazolin-6-yl}-methyl-amino)-ethanol | 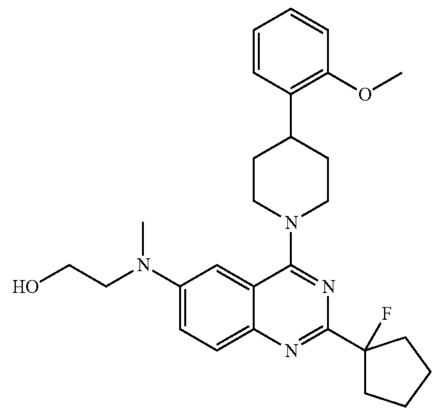 [SMILES: COc1ccccc1C1CCN(c2nc(C3(F)CCCC3)nc3ccc(N(C)CCO)cc23)CC1] | B |
| 73 | [4-[4-(2-dimethylamino-phenyl)-piperidin-1-yl]-2-(1-fluoro-cyclopentyl)-quinazolin-6-yl]-methyl-(2-morpholin-4-yl-ethyl)-amine | 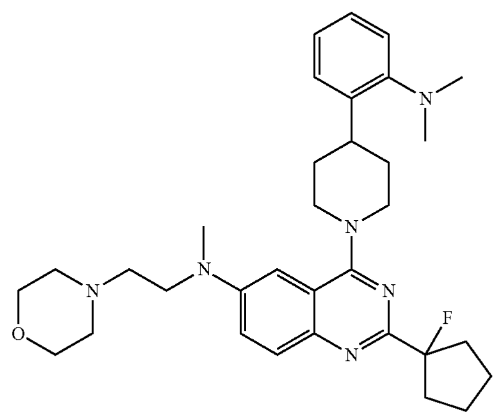 [SMILES: CN(C)c1ccccc1C1CCN(c2nc(C3(F)CCCC3)nc3ccc(N(C)CCN4CCOCC4)cc23)CC1] | C |
| 74 | {2-cyclopentyl-4-[4-(2-dimethylamino-phenyl)-piperidin-1-yl]-quinazolin-6-yl}-methyl-(2-morpholin-4-yl-ethyl)-amine | 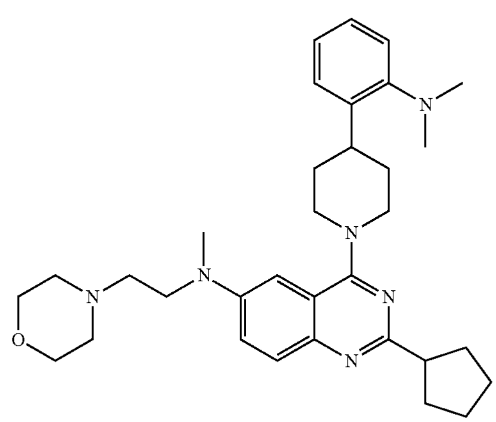 [SMILES: CN(C)c1ccccc1C1CCN(c2nc(C3CCCC3)nc3ccc(N(C)CCN4CCOCC4)cc23)CC1] | C |

TABLE 1-continued

| Ex. | Chemical name | Structure | EC$_{50}$ |
|---|---|---|---|
| 75 | 2-{[4-[4-(2-dimethylamino-phenyl)-piperidin-1-yl]-2-(1-fluoro-cyclopentyl)-quinazolin-6-yl]-methyl-amino}-ethanol | 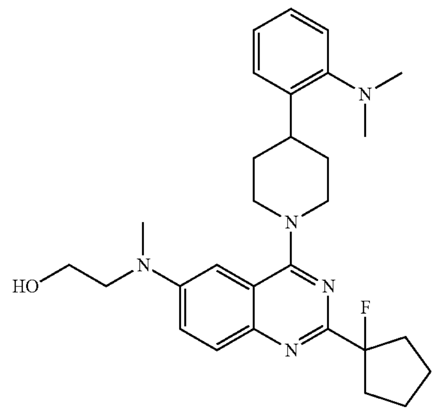 [SMILES: CN(C)c1ccccc1C1CCN(c2nc(C3(F)CCCC3)nc3ccc(N(C)CCO)cc23)CC1] | C |
| 76 | 1-{2-cyclopropyl-4-[4-(2-methoxy-phenyl)-piperidin-1-yl]-quinazolin-6-yl}-piperidin-4-ol | 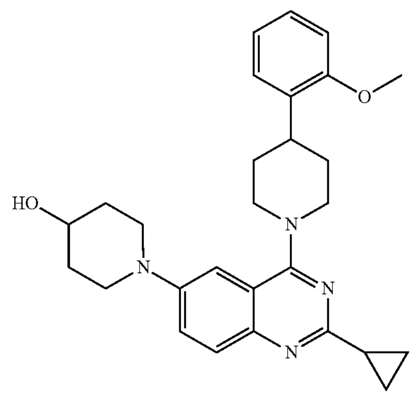 [SMILES: COc1ccccc1C1CCN(c2nc(C3CC3)nc3ccc(N4CCC(O)CC4)cc23)CC1] | C |
| 77 | {2-cyclopropyl-4-[4-(2-methoxy-phenyl)-piperidin-1-yl]-6-(4-methoxy-piperidin-1-yl)-quinazoline | 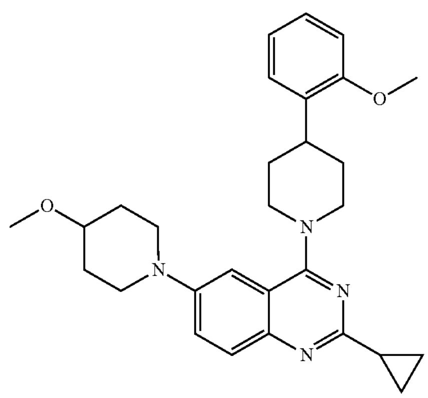 [SMILES: COc1ccccc1C1CCN(c2nc(C3CC3)nc3ccc(N4CCC(OC)CC4)cc23)CC1] | C |
| 78 | (1-{2-cyclopropyl-4-[4-(2-methoxy-phenyl)-piperidin-1-yl]-quinazolin-6-yl}-piperidin-4-yl)-dimethyl-amine | 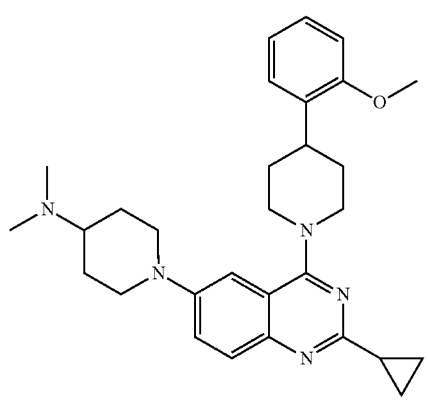 [SMILES: COc1ccccc1C1CCN(c2nc(C3CC3)nc3ccc(N4CCC(N(C)C)CC4)cc23)CC1] | D |

TABLE 1-continued

| Ex. | Chemical name | Structure | $EC_{50}$ |
|---|---|---|---|
| 79 | 1-{2-cyclopropyl-4-[4-(2-methoxy-phenyl)-piperidin-1-yl]-quinazolin-6-yl}-pyrrolidin-3-ol | 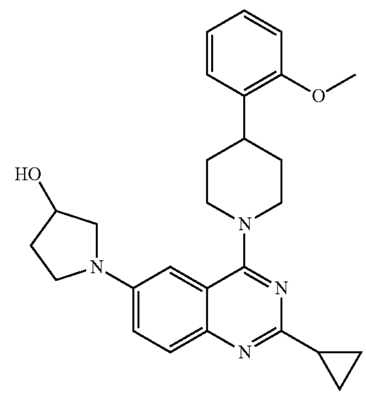 [SMILES: COc1ccccc1C1CCN(c2nc(C3CC3)nc3ccc(N4CCC(O)C4)cc23)CC1] | B |
| 80 | 2-cyclopropyl-4-[4-(2-methoxy-phenyl)-piperidin-1-yl]-6-(3-methoxy-pyrrolidin-1-yl)-quinazoline | 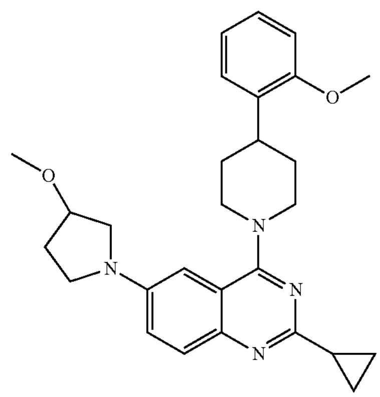 [SMILES: COc1ccccc1C1CCN(c2nc(C3CC3)nc3ccc(N4CCC(OC)C4)cc23)CC1] | B |
| 81 | (R)-1-{2-cyclopropyl-4-[4-(2-methoxy-phenyl)-piperidin-1-yl]-quinazolin-6-yl}-pyrrolidin-3-ol, HCl salt | 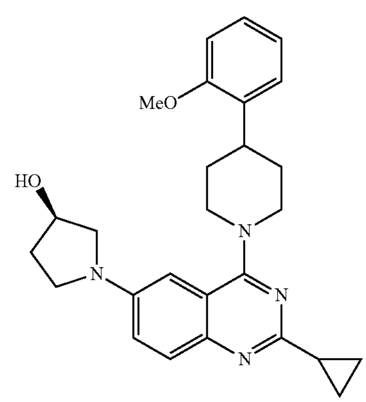 [SMILES: COc1ccccc1C1CCN(c2nc(C3CC3)nc3ccc(N4CC[C@@H](O)C4)cc23)CC1] | A |
| 82 | (S)-1-(2-cyclopropyl-4-(4-(2-methoxyphenyl)piperidin-1-yl)quinazolin-6-yl)pyrrolidin-3-ol | 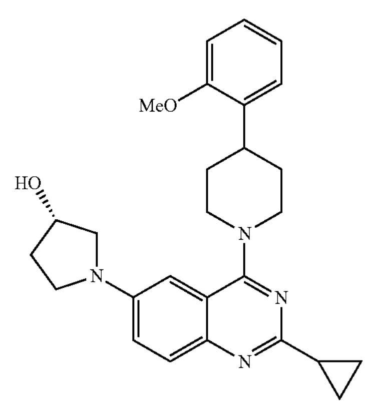 [SMILES: COc1ccccc1C1CCN(c2nc(C3CC3)nc3ccc(N4CC[C@H](O)C4)cc23)CC1] | B |

TABLE 1-continued

| Ex. | Chemical name | Structure | EC$_{50}$ |
|---|---|---|---|
| 83 | (R)-2-cyclopropyl-4-(4-(2-methoxyphenyl)piperidin-1-yl)-6-(3-methoxypyrrolidin-1-yl)quinazoline, HCl salt | 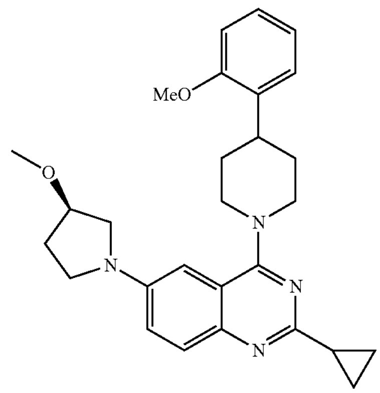 [SMILES: COc1ccccc1C1CCN(c2nc(C3CC3)nc3ccc(N4CC[C@@H](OC)C4)cc23)CC1] | A |
| 84 | (S)-2-cyclopropyl-4-(4-(2-methoxyphenyl)piperidin-1-yl)-6-(3-methoxypyrrolidin-1-yl)quinazoline | 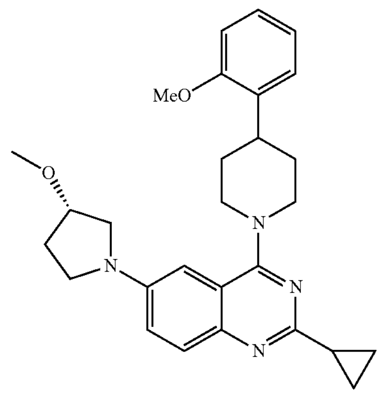 [SMILES: COc1ccccc1C1CCN(c2nc(C3CC3)nc3ccc(N4CC[C@H](OC)C4)cc23)CC1] | B |
| 85 | {2-cyclopropyl-4-[4-(2-methoxy-phenyl)-piperidin-1-yl]-quinazolin-6-ylmethyl}-methyl-propyl-amine | 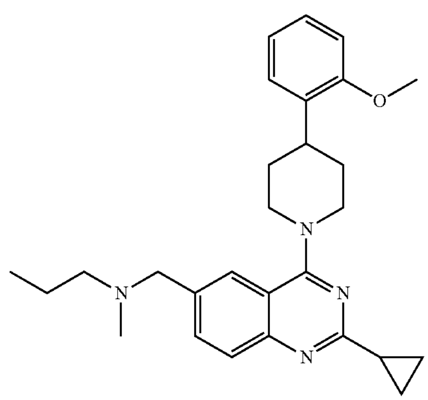 [SMILES: CCCN(C)Cc1ccc2nc(C3CC3)nc(N3CCC(c4ccccc4OC)CC3)c2c1] | D |
| 86 | {2-cyclopropyl-4-[4-(2-methoxy-phenyl)-piperidin-1-yl]-quinazolin-6-ylmethyl}-dimethyl-amine | 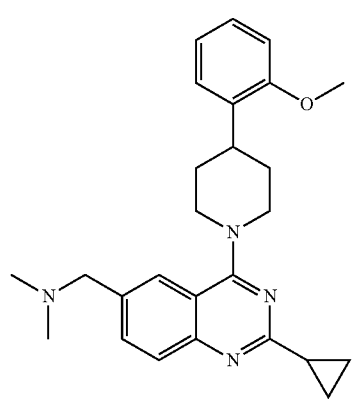 [SMILES: COc1ccccc1C1CCN(c2nc(C3CC3)nc3ccc(CN(C)C)cc23)CC1] | D |

TABLE 1-continued

| Ex. | Chemical name | Structure | $EC_{50}$ |
|---|---|---|---|
| 87 | {2-cyclopropyl-4-[4-(2-methoxy-phenyl)-piperidin-1-yl]-quinazolin-6-ylmethyl}-(2-methoxy-ethyl)-methyl-amine | 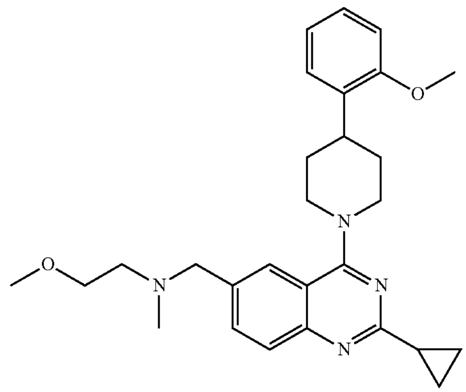 [SMILES: COCCN(C)Cc1ccc2nc(C3CC3)nc(N3CCC(c4ccccc4OC)CC3)c2c1] | C |
| 88 | {2-cyclopropyl-4-[4-(2-methoxy-phenyl)-piperidin-1-yl]-quinazolin-6-ylmethyl}-methyl-(2-morpholin-4-yl-ethyl)-amine | 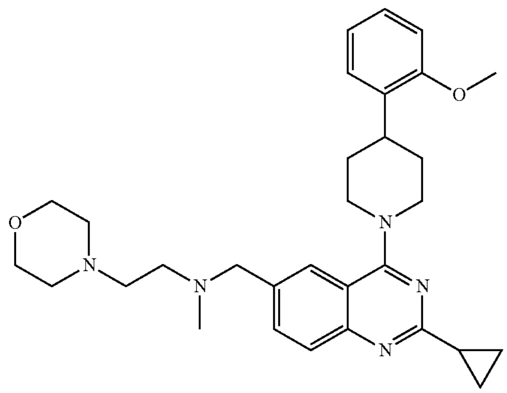 [SMILES: COc1ccccc1C1CCN(c2nc(C3CC3)nc3ccc(CN(C)CCN4CCOCC4)cc23)CC1] | D |
| 89 | 2-({2-cyclopropyl-4-[4-(2-methoxy-phenyl)-piperidin-1-yl]-quinazolin-6-ylmethyl}-methyl-amino)-ethanol | 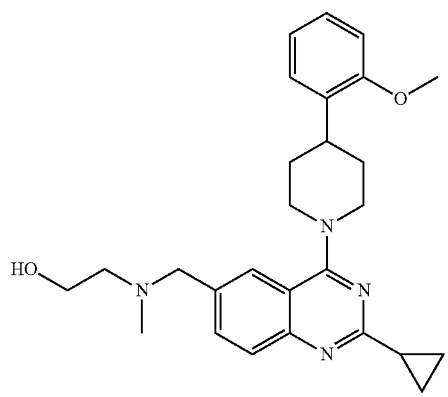 [SMILES: COc1ccccc1C1CCN(c2nc(C3CC3)nc3ccc(CN(C)CCO)cc23)CC1] | D |
| 90 | ({2-cyclopropyl-4-[4-(2-methoxy-phenyl)-piperidin-1-yl]-quinazolin-6-yl}-methyl-amino)-acetic acid ethyl ester | 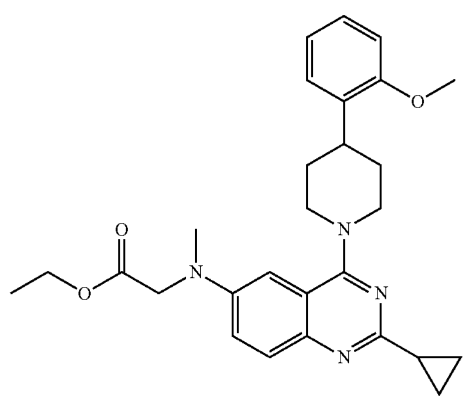 [SMILES: CCOC(=O)CN(C)c1ccc2nc(C3CC3)nc(N3CCC(c4ccccc4OC)CC3)c2c1] | D |

TABLE 1-continued

| Ex. | Chemical name | Structure | EC$_{50}$ |
|---|---|---|---|
| 91 | (1-{2-cyclopropyl-4-[4-(2-methoxy-phenyl)-piperidin-1-yl]-quinazolin-6-yl}-pyrrolidin-3-yl)-dimethyl-amine | 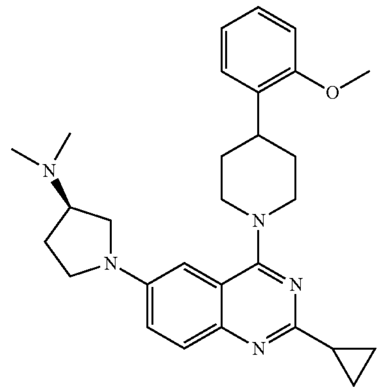 [SMILES: COc1ccccc1C1CCN(c2nc(C3CC3)nc3ccc(N4CC[C@@H](N(C)C)C4)cc23)CC1] | C |
| 92 | (1-{2-cyclopropyl-4-[4-(2-methoxy-phenyl)-piperidin-1-yl]-quinazolin-6-yl}-piperidin-4-yl)-ethoxycarbonylmethyl-amino]-acetic acid ethyl ester | 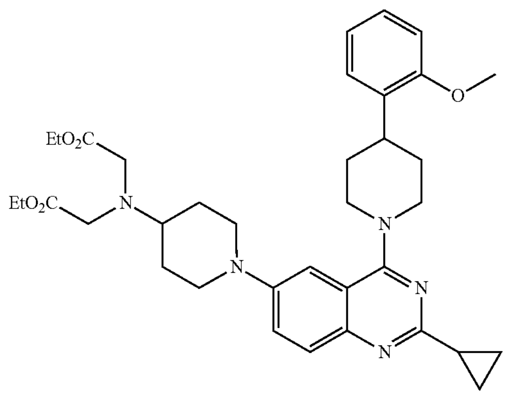 [SMILES: CCOC(=O)CN(CC(=O)OCC)C1CCN(c2ccc3nc(C4CC4)nc(N4CCC(c5ccccc5OC)CC4)c3c2)CC1] | D |
| 93 | [(1-{2-cyclopropyl-4-[4-(2-methoxy-phenyl)-piperidin-1-yl]-quinazolin-6-yl}-piperidin-4-yl)-methyl-amino]-acetic acid ethyl ester | 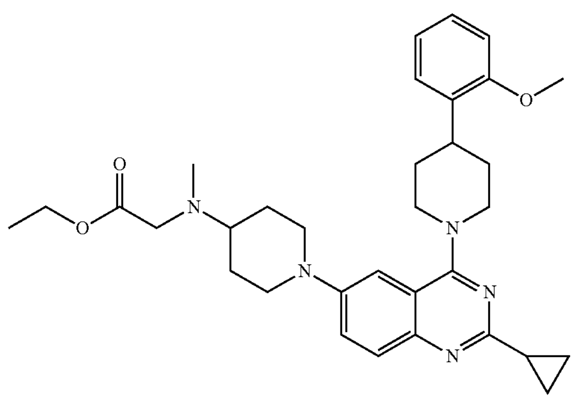 [SMILES: CCOC(=O)CN(C)C1CCN(c2ccc3nc(C4CC4)nc(N4CCC(c5ccccc5OC)CC4)c3c2)CC1] | D |
| 94 | 2-{2-Dimethylamino-4-[4-(2-methoxy-phenyl)-piperidin-1-yl]-quinazolin-6-ylamino}-ethanol | 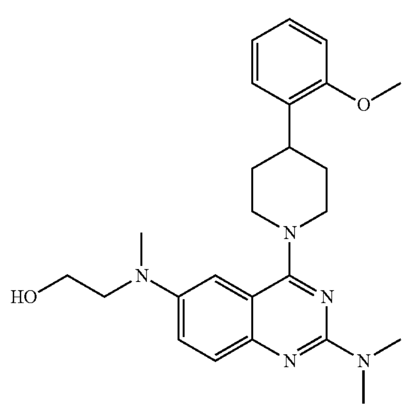 [SMILES: COc1ccccc1C1CCN(c2nc(N(C)C)nc3ccc(N(C)CCO)cc23)CC1] | B |

TABLE 1-continued

| Ex. | Chemical name | Structure | EC$_{50}$ |
|---|---|---|---|
| 95 | 4-(4-(2-methoxyphenyl)piperidin-1-yl)-N2,N2,N6-trimethyl-N6-propylquinazoline-2,6-diamine | 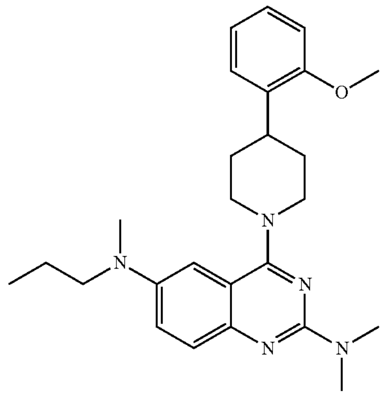 [SMILES: CCCN(C)c1ccc2nc(N(C)C)nc(N3CCC(c4ccccc4OC)CC3)c2c1] | D |
| 96 | 4-(4-(2-methoxyphenyl)piperidin-1-yl)-N2,N2-dimethyl-N6,N6-dipropylquinazoline-2,6-diamine | 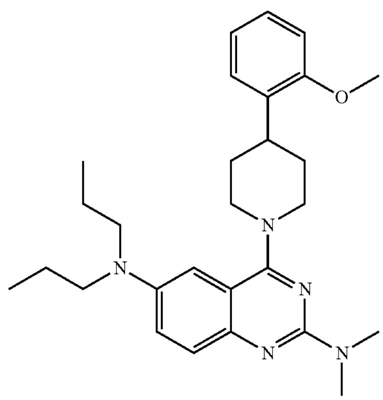 [SMILES: CCCN(CCC)c1ccc2nc(N(C)C)nc(N3CCC(c4ccccc4OC)CC3)c2c1] | D |
| 97 | N2-Cyclobutyl-4-[4-(2-methoxy-phenyl)-piperidin-1-yl]-N6-methyl-N6-propyl-quinazoline-2,6-diamine | 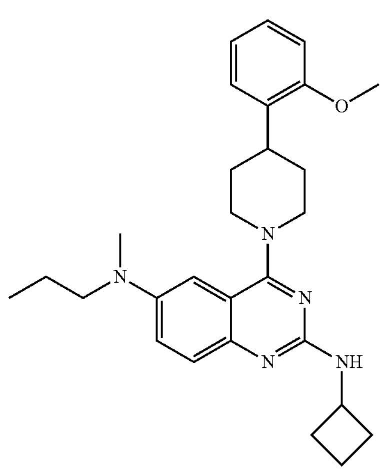 [SMILES: CCCN(C)c1ccc2nc(NC3CCC3)nc(N3CCC(c4ccccc4OC)CC3)c2c1] | D |

TABLE 1-continued
| Ex. | Chemical name | Structure | EC$_{50}$ |
|---|---|---|---|
| 98 | 2-((2-(cyclobutylamino)-4-(4-(2-methoxyphenyl)piperidin-1-yl)quinazolin-6-yl)(methyl)amino)ethanol | 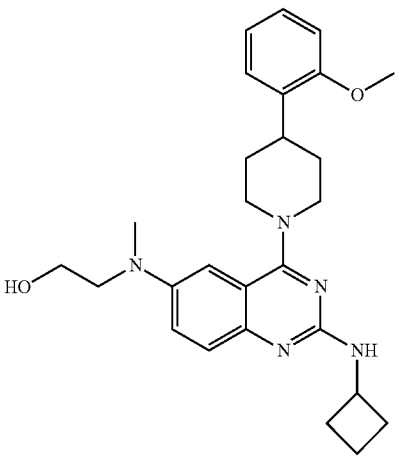 [SMILES: COc1ccccc1C1CCN(c2nc(NC3CCC3)nc3ccc(N(C)CCO)cc23)CC1] | D |
| 99 | 2-({2-cyclopropyl-4-[6-(2-methoxy-phenyl)-2,6-diaza-spiro[3.3]hept-2-yl]-quinazolin-6-yl}-methyl-amino)-ethanol | 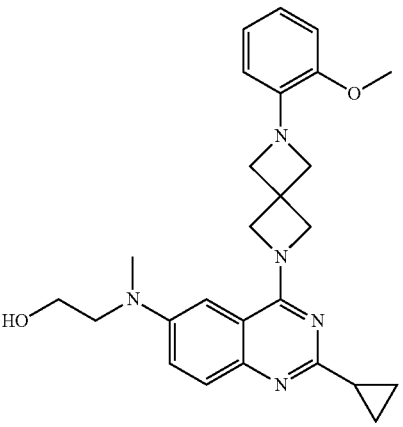 [SMILES: COc1ccccc1N1CC2(C1)CN(c1nc(C3CC3)nc3ccc(N(C)CCO)cc13)C2] | C |
| 100 | {2-cyclopropyl-4-[6-(2-methoxy-phenyl)-2,6-diaza-spiro[3.3]hept-2-yl]-quinazolin-6-yl}-methyl-propyl-amine | 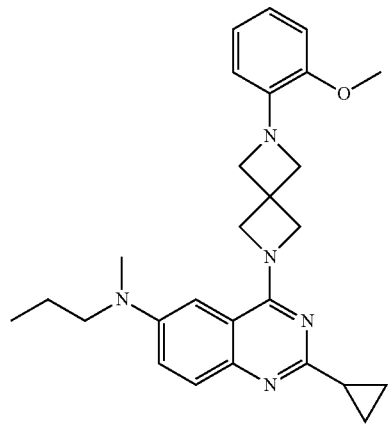 [SMILES: CCCN(C)c1ccc2nc(C3CC3)nc(N3CC4(CN(c5ccccc5OC)C4)C3)c2c1] | C |

TABLE 1-continued

| Ex. | Chemical name | Structure | EC$_{50}$ |
|---|---|---|---|
| 101 | {2-cyclopropyl-4-[6-(2-methoxy-phenyl)-2,6-diaza-spiro[3.3]hept-2-yl]-quinazolin-6-yl}-methyl-(2-morpholin-4-yl-ethyl)-amine | 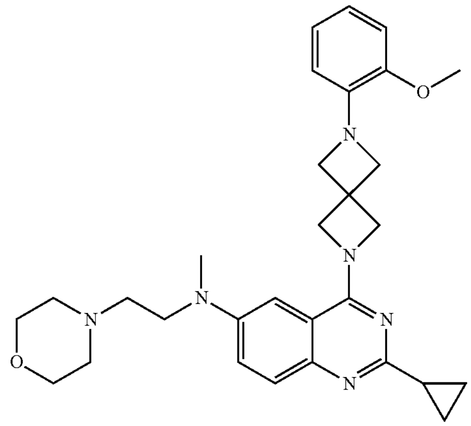 [SMILES: COc1ccccc1N1CC2(C1)CN(c1nc(C3CC3)nc3ccc(N(C)CCN4CCOCC4)cc13)C2] | D |
| 102 | 1-[2-cyclopropyl-6-(methyl-propyl-amino)-quinazolin-4-yl]-4-(2-methoxy-phenyl)-piperidin-2-one | 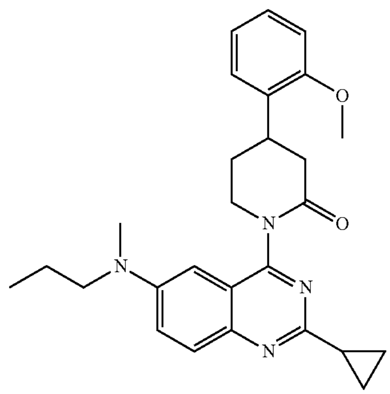 [SMILES: CCCN(C)c1ccc2nc(C3CC3)nc(N3CCC(c4ccccc4OC)CC3=O)c2c1] | D |
| 103 | 2-({5-chloro-2-cyclopropyl-4-[4-(2-methoxy-phenyl)-piperidin-1-yl]-quinazolin-6-yl}-methyl-amino)-ethanol | 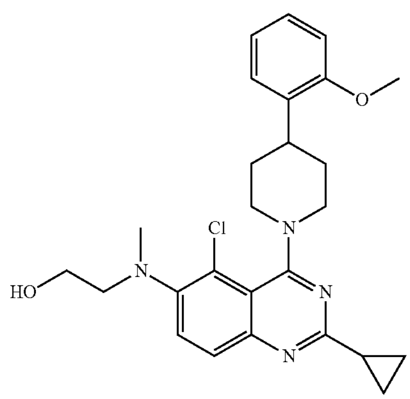 [SMILES: COc1ccccc1C1CCN(c2nc(C3CC3)nc3ccc(N(C)CCO)c(Cl)c23)CC1] | A |
| 104 | {7-chloro-2-cyclopropyl-4-[4-(2-methoxy-phenyl)-piperidin-1-yl]-quinazolin-6-yl}-methyl-propyl-amine | 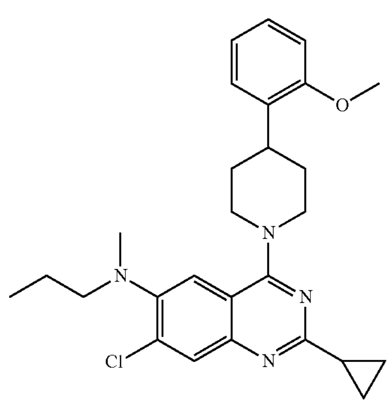 [SMILES: CCCN(C)c1cc2c(N3CCC(c4ccccc4OC)CC3)nc(C3CC3)nc2cc1Cl] | D |

TABLE 1-continued
| Ex. | Chemical name | Structure | EC$_{50}$ |
|---|---|---|---|
| 105 | {2-cyclopropyl-7-fluoro-4-[4-(2-methoxy-phenyl)-piperidin-1-yl]-quinazolin-6-yl}-methyl-propyl-amine | 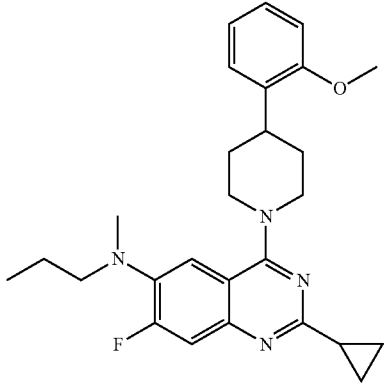 | C |
| 106 | {4-[4-(2-azetidin-1-yl-phenyl)-piperidin-1-yl]-2-cyclopropyl-7-fluoro-quinazolin-6-yl}-methyl-propyl-amine | 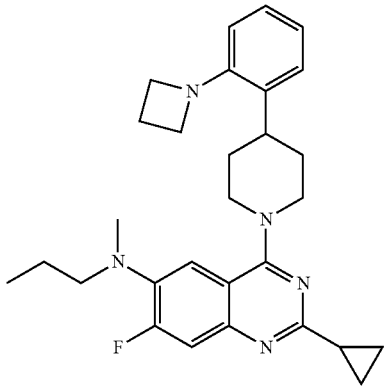 [SMILES: CCCN(C)c1cc2c(N3CCC(c4ccccc4N4CCC4)CC3)nc(C3CC3)nc2cc1F] | D |
| 107 | 2-({7-chloro-2-cyclopropyl-4-[4-(2-methoxy-phenyl)-piperidin-1-yl]-quinazolin-6-yl}-methyl-amino)-ethanol | 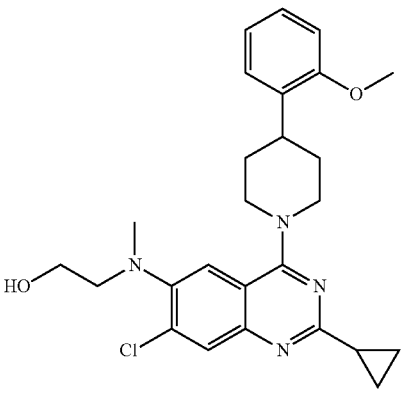 [SMILES: COc1ccccc1C1CCN(c2nc(C3CC3)nc3cc(Cl)c(N(C)CCO)cc23)CC1] | B |

TABLE 1-continued

| Ex. | Chemical name | Structure | EC$_{50}$ |
|---|---|---|---|
| 108 | 2-({2-cyclopropyl-4-[4-(4-fluoro-2-methoxy-phenyl)-piperidin-1-yl]-quinazolin-6-yl}-methyl-amino)-ethanol | 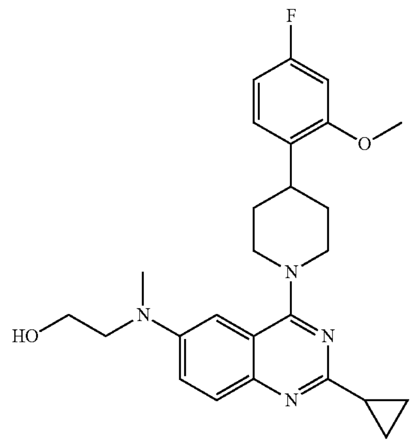 [SMILES: COc1cc(F)ccc1C1CCN(c2nc(C3CC3)nc3ccc(N(C)CCO)cc23)CC1] | B |
| 109 | 2-({2-cyclopropyl-4-[4-(5-fluoro-2-methoxy-phenyl)-piperidin-1-yl]-quinazolin-6-yl}-methyl-amino)-ethanol | 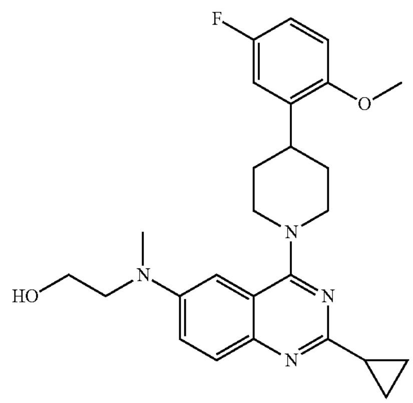 [SMILES: COc1ccc(F)cc1C1CCN(c2nc(C3CC3)nc3ccc(N(C)CCO)cc23)CC1] | B |
| 110 | 2-({2-cyclopropyl-7-fluoro-4-[4-(4-fluoro-2-methoxy-phenyl)-piperidin-1-yl]-quinazolin-6-yl}-methyl-amino)-ethanol | 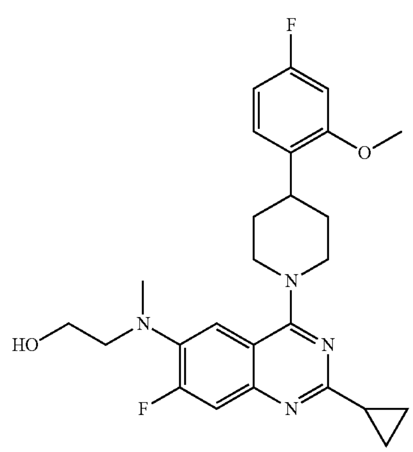 [SMILES: COc1cc(F)ccc1C1CCN(c2nc(C3CC3)nc3cc(F)c(N(C)CCO)cc23)CC1] | B |

TABLE 1-continued

| Ex. | Chemical name | Structure | EC$_{50}$ |
|---|---|---|---|
| 111 | 2-({2-cyclopropyl-7-fluoro-4-[4-(5-fluoro-2-methoxy-phenyl)-piperidin-1-yl]-quinazolin-6-yl}-methyl-amino)-ethanol | 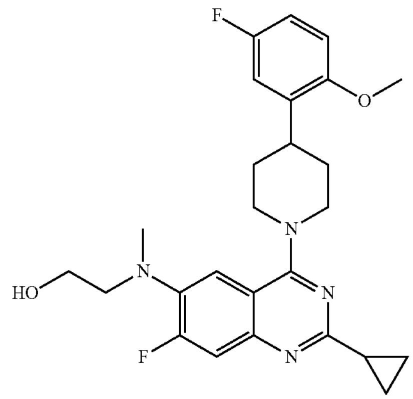 [SMILES: COc1ccc(F)cc1C1CCN(c2nc(C3CC3)nc3cc(F)c(N(C)CCO)cc23)CC1] | B |
| 112 | 2-({7-chloro-2-cyclopropyl-4-[4-(4-fluoro-2-methoxy-phenyl)-piperidin-1-yl]-quinazolin-6-yl}-methyl-amino)-ethanol | 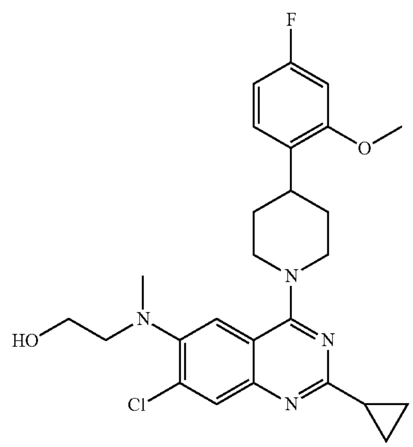 [SMILES: COc1cc(F)ccc1C1CCN(c2nc(C3CC3)nc3cc(Cl)c(N(C)CCO)cc23)CC1] | D |
| 113 | 2-({7-chloro-2-cyclopropyl-4-[4-(5-fluoro-2-methoxy-phenyl)-piperidin-1-yl]-quinazolin-6-yl}-methyl-amino)-ethanol | 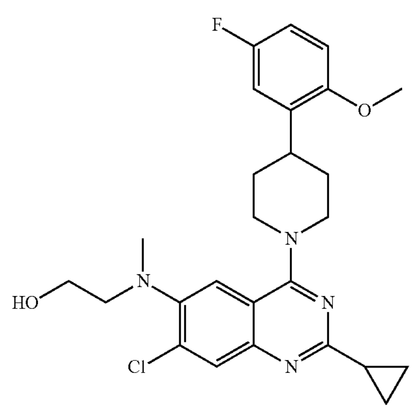 | C |

TABLE 1-continued

| Ex. | Chemical name | Structure | EC$_{50}$ |
|---|---|---|---|
| 114 | 2-({2-cyclopropyl-4-[4-(4-fluoro-2-methoxy-phenyl)-piperidin-1-yl]-7-methyl-quinazolin-6-yl}-methyl-amino)-ethanol | 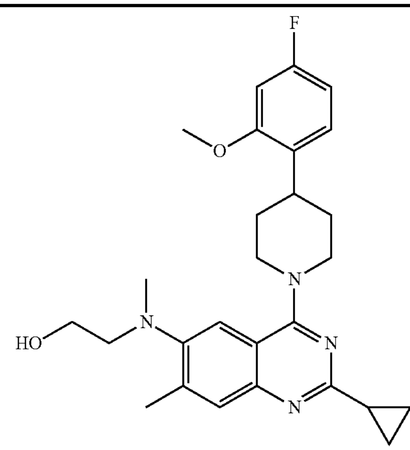 | C |
| 115 | 2-({2-cyclopropyl-4-[4-(5-fluoro-2-methoxy-phenyl)-piperidin-1-yl]-7-methyl-quinazolin-6-yl}-methyl-amino)-ethanol | 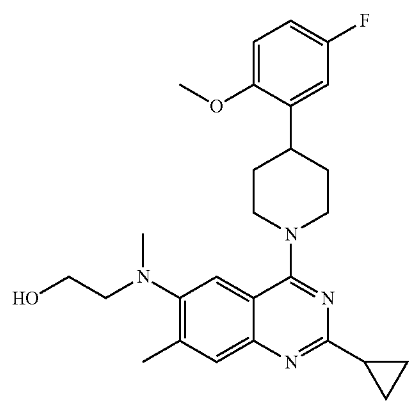 [SMILES: COc1ccc(F)cc1C1CCN(c2nc(C3CC3)nc3cc(C)c(N(C)CCO)cc23)CC1] | C |
| 116 | 2-({2-cyclopropyl-4-[4-(2-dimethylamino-phenyl)-piperidin-1-yl]-7-methyl-quinazolin-6-yl}-methyl-amino)-ethanol | 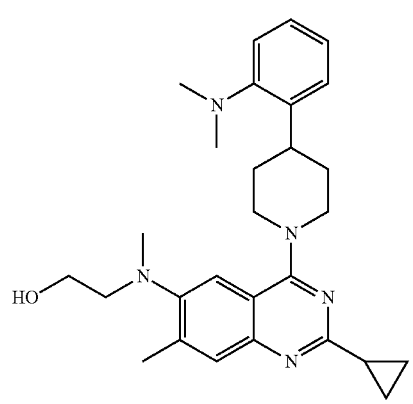 | B |

TABLE 1-continued

| Ex. | Chemical name | Structure | $EC_{50}$ |
|---|---|---|---|
| 117 | 2-({2-cyclopropyl-4-[4-(2-methoxy-phenyl)-piperidin-1-yl]-7-methyl-quinazolin-6-yl}-methyl-amino)-ethanol | 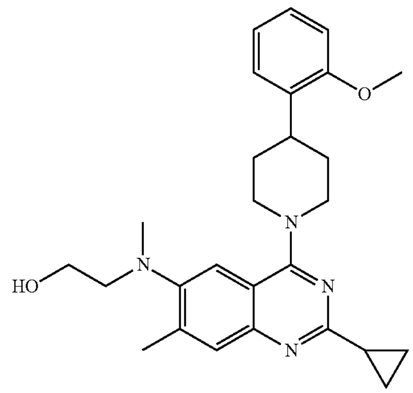 [SMILES: COc1ccccc1C1CCN(c2nc(C3CC3)nc3cc(C)c(N(C)CCO)cc23)CC1] | A |
| 118 | 2-({7-chloro-2-cyclopropyl-4-[4-(2-dimethylamino-phenyl)-piperidin-1-yl]-quinazolin-6-yl}-methyl-amino)-ethanol | 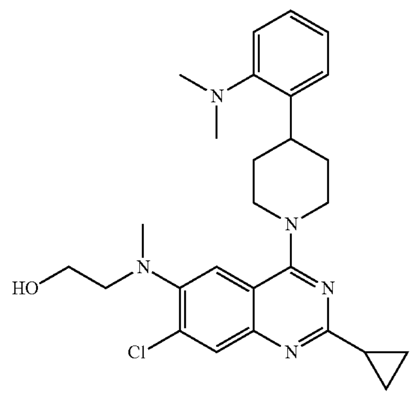 [SMILES: CN(C)c1ccccc1C1CCN(c2nc(C3CC3)nc3cc(Cl)c(N(C)CCO)cc23)CC1] | C |
| 119 | 2-({4-[4-(2-azetidin-1-yl-phenyl)-piperidin-1-yl]-7-chloro-2-cyclopropyl-quinazolin-6-yl}-methyl-amino)-ethanol | 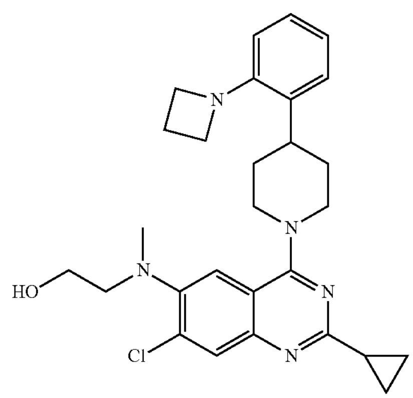 [SMILES: CN(CCO)c1cc2c(N3CCC(c4ccccc4N4CCC4)CC3)nc(C3CC3)nc2cc1Cl] | C |
| 120 | 2-({2-cyclopropyl-4-[4-(2-dimethylamino-phenyl)-piperidin-1-yl]-7-fluoro-quinazolin-6-yl}-methyl-amino)-ethanol | 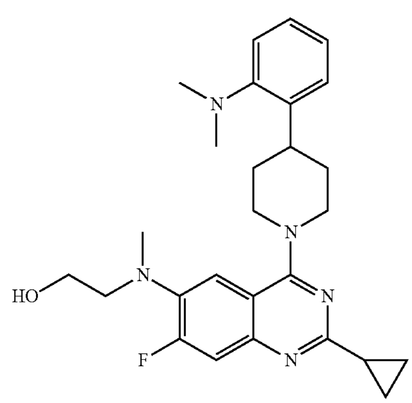 | A |

TABLE 1-continued

| Ex. | Chemical name | Structure | EC$_{50}$ |
|---|---|---|---|
| 121 | 2-({4-[4-(2-azetidin-1-yl-phenyl)-piperidin-1-yl]-2-cyclopropyl-7-methyl-quinazolin-6-yl}-methyl-amino)-ethanol | 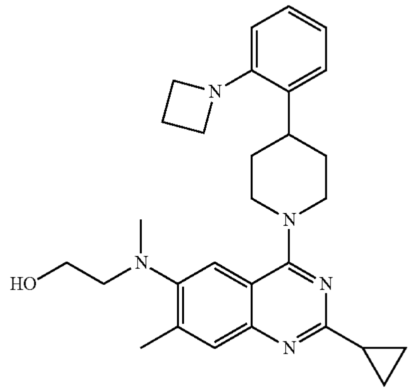 [SMILES: Cc1cc2nc(C3CC3)nc(N3CCC(c4ccccc4N4CCC4)CC3)c2cc1N(C)CCO] | B |
| 122 | {2-cyclopropyl-4-[4-(2-methoxy-phenyl)-piperidin-1-yl]-7-methyl-quinazolin-6-yl}-methyl-propyl-amine | 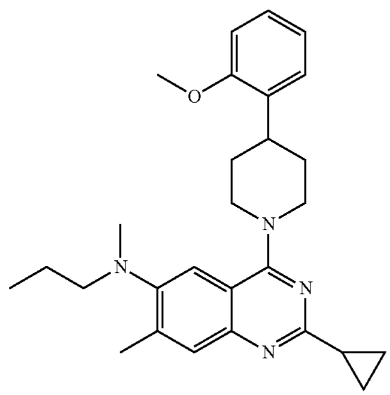 [SMILES: CCCN(C)c1cc2c(N3CCC(c4ccccc4OC)CC3)nc(C3CC3)nc2cc1C] | B |
| 123 | {2-cyclopropyl-4-[4-(5-fluoro-2-methoxy-phenyl)-piperidin-1-yl]-7-methyl-quinazolin-6-yl}-methyl-propyl-amine | 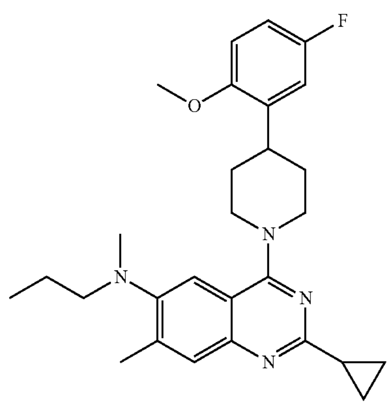 [SMILES: CCCN(C)c1cc2c(N3CCC(c4cc(F)ccc4OC)CC3)nc(C3CC3)nc2cc1C] | D |
| 124 | 2-({2-cyclopropyl-7-fluoro-4-[4-(2-methoxy-phenyl)-piperidin-1-yl]-quinazolin-6-yl}-methyl-amino)-ethanol | 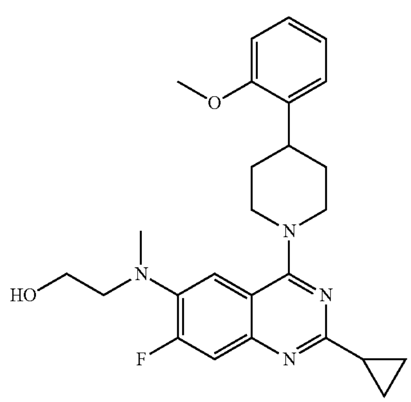 [SMILES: COc1ccccc1C1CCN(c2nc(C3CC3)nc3cc(F)c(N(C)CCO)cc23)CC1] | A |

TABLE 1-continued
| Ex. | Chemical name | Structure | EC₅₀ |
|---|---|---|---|
| 125 | 2-({2-cyclopropyl-4-[4-(2-methoxy-phenyl)-piperidin-1-yl]-8-methyl-quinazolin-6-yl}-methyl-amino)-ethanol | 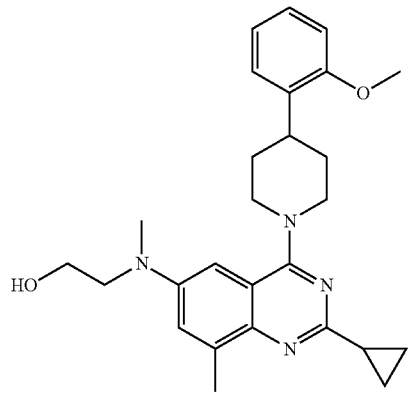 [SMILES: COc1ccccc1C1CCN(c2nc(C3CC3)nc3c(C)cc(N(C)CCO)cc23)CC1] | A |
| 126 | 2-({2-cyclopropyl-4-[4-(2-methoxy-phenyl)-piperidin-1-yl]-5-methyl-quinazolin-6-yl}-methyl-amino)-ethanol | 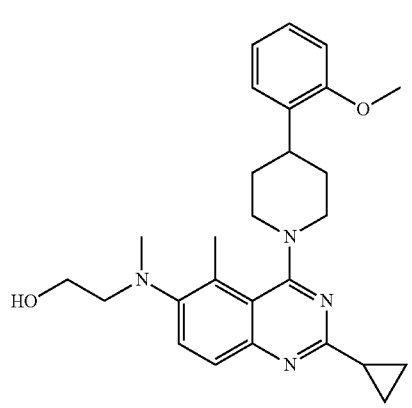 [SMILES: COc1ccccc1C1CCN(c2nc(C3CC3)nc3ccc(N(C)CCO)c(C)c23)CC1] | B |
| 127 | 2-({2-cyclopropyl-4-[4-(2-methoxy-phenyl)-piperidin-1-yl]-quinazolin-8-yl}-methyl-amino)-ethanol | 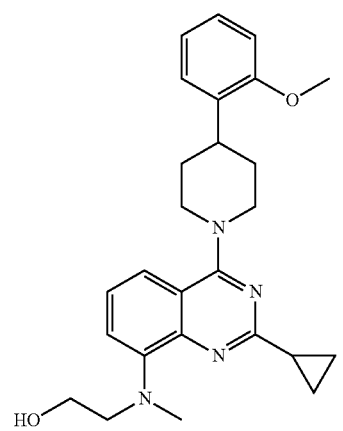 [SMILES: COc1ccccc1C1CCN(c2nc(C3CC3)nc3c(N(C)CCO)cccc23)CC1] | D |

TABLE 1-continued

| Ex. | Chemical name | Structure | EC$_{50}$ |
|---|---|---|---|
| 128 | {2-cyclopropyl-4-[4-(2-methoxy-phenyl)-piperidin-1-yl]-quinazolin-8-yl}-methyl-propyl-amine | 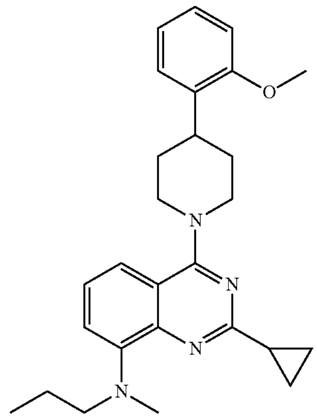 [SMILES: CCCN(C)c1cccc2c(N3CCC(c4ccccc4OC)CC3)nc(C3CC3)nc12] | D |
| 129 | {2-cyclopropyl-4-[4-(2-methoxy-phenyl)-piperidin-1-yl]-quinazolin-8-yl}-methyl-(2-morpholin-4-yl-ethyl)-amine | 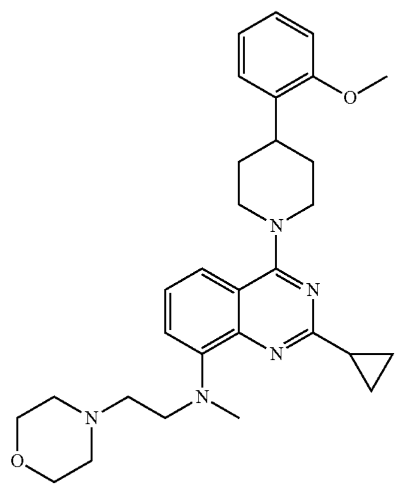 [SMILES: COc1ccccc1C1CCN(c2nc(C3CC3)nc3c(N(C)CCN4CCOCC4)cccc23)CC1] | D |
| 130 | 2-({8-chloro-2-cyclopropyl-4-[4-(2-methoxy-phenyl)-piperidin-1-yl]-quinazolin-6-yl}-methyl-amino)-ethanol | 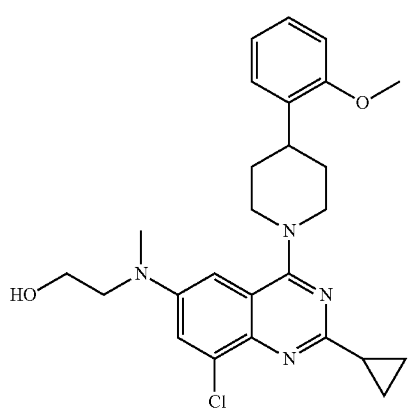 | A |

TABLE 1-continued

| Ex. | Chemical name | Structure | EC$_{50}$ |
|---|---|---|---|
| 131 | {2-cyclopropyl-4-[4-(2-methoxy-phenyl)-piperidin-1-yl]-quinazolin-5-yl}-methyl-propyl-amine | 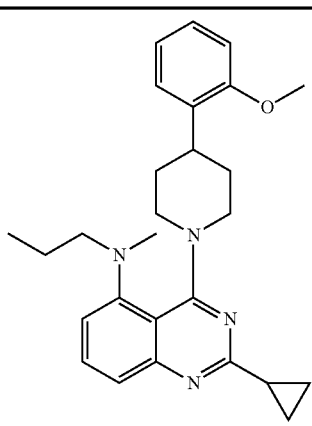 | C |
| 132 | 2-((2-cyclopropyl-5-fluoro-4-(4-(2-methoxyphenyl)piperidin-1-yl)quinazolin-6-yl)(methyl)amino)ethanol | 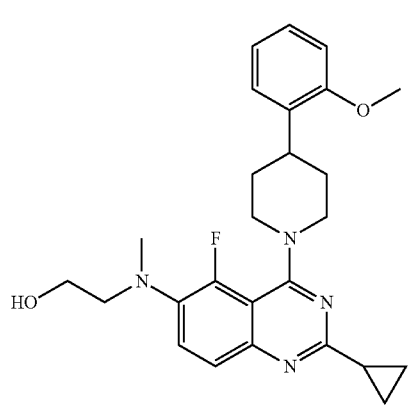 | B |
| 133 | 2-((2-cyclopropyl-8-fluoro-4-(4-(2-methoxyphenyl)piperidin-1-yl)quinazolin-6-yl)(methyl)amino)ethanol | 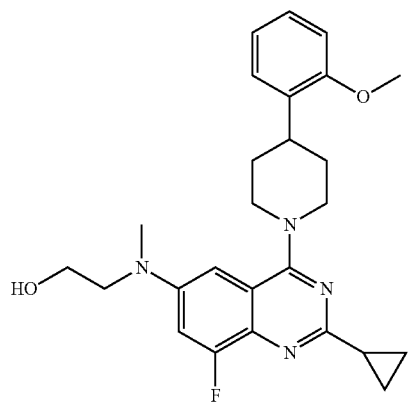 | A |
| 134 | 2-cyclopropyl-4-(4-(2-methoxyphenyl)piperidin-1-yl)-N-methyl-N-(2-morpholinoethyl)pyrido[3,4-d]pyrimidin-6-amine | 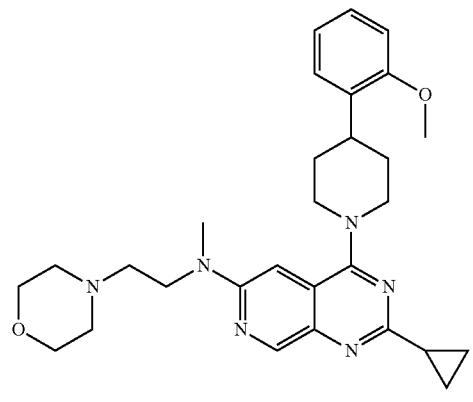 [SMILES: COc1ccccc1C1CCN(c2nc(C3CC3)nc3cnc(N(C)CCN4CCOCC4)cc23)CC1] | B |

TABLE 1-continued

| Ex. | Chemical name | Structure | EC$_{50}$ |
|---|---|---|---|
| 135 | 2-cyclopropyl-4-(4-(2-methoxyphenyl)piperidin-1-yl)-N-methyl-N-propylquinazolin-7-amine | 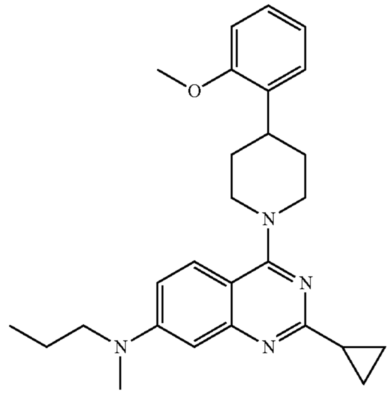 [SMILES: CCCN(C)c1ccc2c(N3CCC(c4ccccc4OC)CC3)nc(C3CC3)nc2c1] | D |
| 136 | 2-((2-(cyclopropylethynyl)-4-(4-(2-methoxyphenyl)piperidin-1-yl)quinazolin-6-yl)(methyl)amino)ethanol | 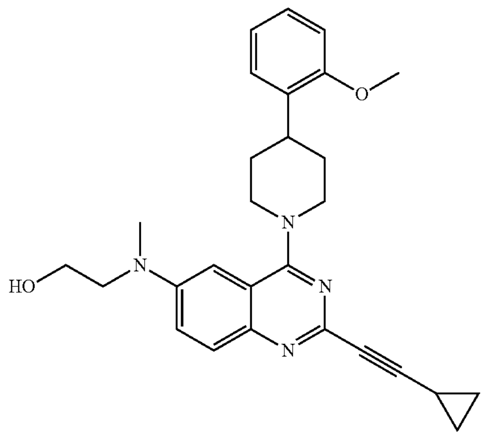 [SMILES: COc1ccccc1C1CCN(c2nc(C#CC3CC3)nc3ccc(N(C)CCO)cc23)CC1] | C |
| 137 | 2-({2-cyclopropyl-4-[4-(2-methoxy-phenyl)-piperidin-1-yl]-pyrido[3,4-d]pyrimidin-6-yl}-methyl-amino)-ethanol | 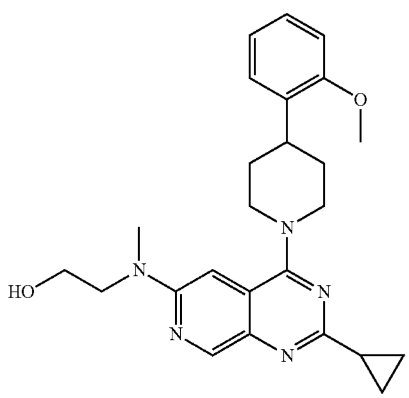 [SMILES: COc1ccccc1C1CCN(c2nc(C3CC3)nc3cnc(N(C)CCO)cc23)CC1] | A |
| 138 | 2-((2-cyclopropyl-4-(4-(3-methoxythiophen-2-yl)piperidin-1-yl)quinazolin-6-yl)(methyl)amino)ethanol | 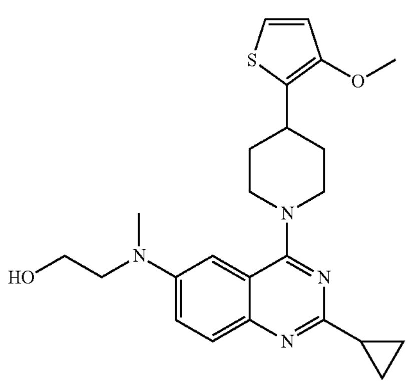 [SMILES: COc1ccsc1C1CCN(c2nc(C3CC3)nc3ccc(N(C)CCO)cc23)CC1] | B |

TABLE 1-continued

| Ex. | Chemical name | Structure | $EC_{50}$ |
|---|---|---|---|
| 139 | 2-((4-(4-cyclohexylpiperidin-1-yl)-2-(1-fluorocyclopropyl)quinazolin-6-yl)(methyl)amino)ethanol | 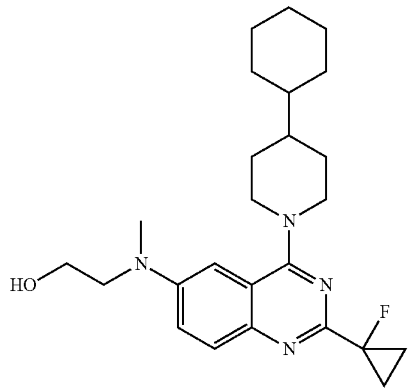 [SMILES: CN(CCO)c1ccc2nc(C3(F)CC3)nc(N3CCC(C4CCCCC4)CC3)c2c1] | D |
| 140 | 2-(4-{2-cyclopropyl-6-[(2-hydroxy-ethyl)-methyl-amino]-quinazolin-4-yl}-piperazin-1-yl)-cyclopentanol | 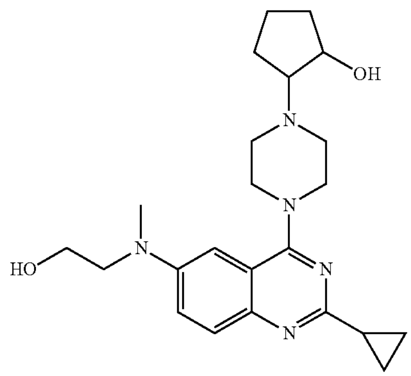 [SMILES: CN(CCO)c1ccc2nc(C3CC3)nc(N3CCN(C4CCCC4O)CC3)c2c1] | D |
| 141 | 2-{4-[2-cyclopropyl-6-(methyl-propyl-amino)-quinazolin-4-yl]-piperazin-1-yl}-cyclopentanol | 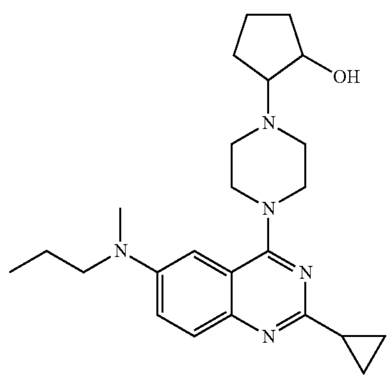 [SMILES: CCCN(C)c1ccc2nc(C3CC3)nc(N3CCN(C4CCCC4O)CC3)c2c1] | D |
| 142 | 2-(4-{2-cyclopropyl-6-[methyl-(2-morpholin-4-yl-ethyl)-amino]-quinazolin-4-yl}-piperazin-1-yl)-cyclopentanol | 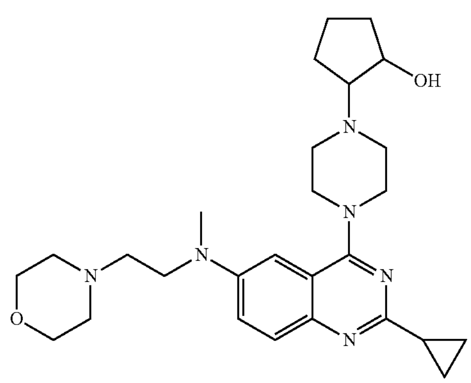 [SMILES: CN(CCN1CCOCC1)c1ccc2nc(C3CC3)nc(N3CCN(C4CCCC4O)CC3)c2c1] | D |

TABLE 1-continued

| Ex. | Chemical name | Structure | EC$_{50}$ |
|---|---|---|---|
| 143 | 4-[4-(2-methoxy-phenyl)-piperidin-1-yl]-2-phenyl-quinazolin-6-yl}-dimethyl-amine | 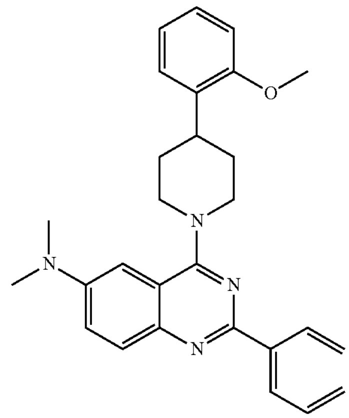 [SMILES: C=C/C=C(\C=C)c1nc(N2CCC(c3ccccc3OC)CC2)c2cc(N(C)C)ccc2n1] | D |
| 144 | 2-({4-[4-(2-methoxy-phenyl)-piperidin-1-yl]-2-phenyl-quinazolin-6-yl}-methyl-amino)-ethanol | 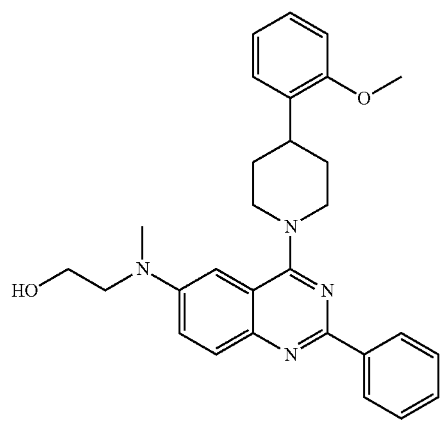 [SMILES: COc1ccccc1C1CCN(c2nc(-c3ccccc3)nc3ccc(N(C)CCO)cc23)CC1] | C |
| 145 | (2-methoxy-ethyl)-{4-[4-(2-methoxy-phenyl)-piperidin-1-yl]-2-phenyl-quinazolin-6-yl}-methyl-amine | 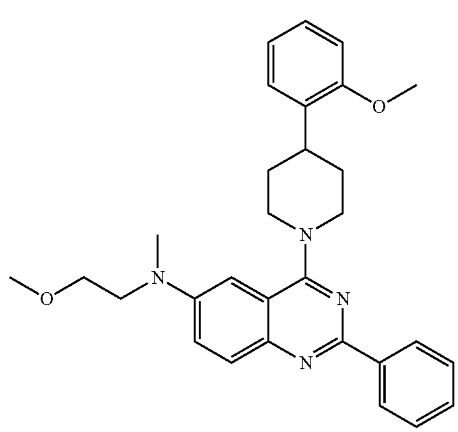 [SMILES: COCCN(C)c1ccc2nc(-c3ccccc3)nc(N3CCC(c4ccccc4OC)CC3)c2c1] | D |

TABLE 1-continued

| Ex. | Chemical name | Structure | EC$_{50}$ |
|---|---|---|---|
| 146 | {4-[4-(2-methoxy-phenyl)-piperidin-1-yl]-2-phenyl-quinazolin-6-yl}-methyl-propyl-amine | 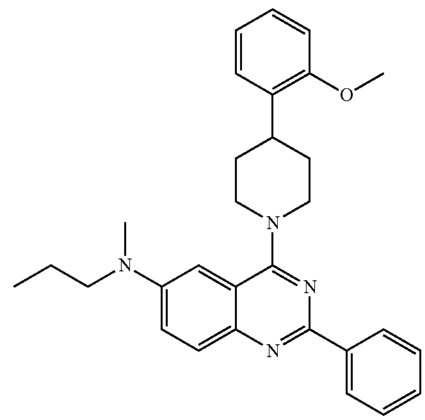 [SMILES: CCCN(C)c1ccc2nc(-c3ccccc3)nc(N3CCC(c4ccccc4OC)CC3)c2c1] | D |
| 147 | {4-[4-(2-methoxy-phenyl)-piperidin-1-yl]-2-phenyl-quinazolin-6-yl}-methyl-(2-morpholin-4-yl-ethyl)-amine | 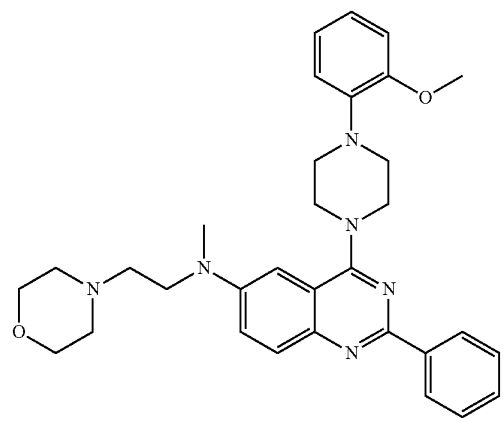 [SMILES: COc1ccccc1N1CCN(c2nc(-c3ccccc3)nc3ccc(N(C)CCN4CCOCC4)cc23)CC1] | D |
| 148 | {[2-cyclopropyl-4-(5-methoxy-3,4-dihydro-1H-isoquinolin-2-yl)-quinazolin-6-yl]-methyl-amino}-ethanol | 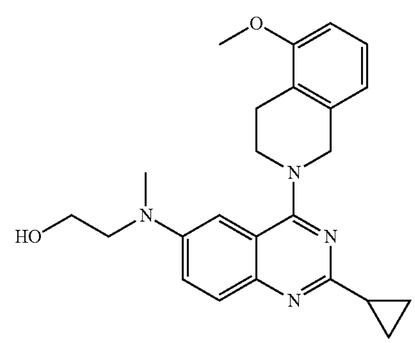 [SMILES: COc1cccc2c1CCN(c1nc(C3CC3)nc3ccc(N(C)CCO)cc13)C2] | D |
| 149 | 2-{[2-cyclopropyl-4-(4-methoxy-1,3-dihydro-isoindol-2-yl)-quinazolin-6-yl]-methyl-amino}-ethanol | 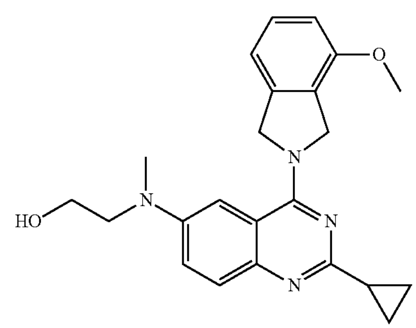 [SMILES: COc1cccc2c1CN(c1nc(C3CC3)nc3ccc(N(C)CCO)cc13)C2] | D |

TABLE 1-continued

| Ex. | Chemical name | Structure | EC$_{50}$ |
|---|---|---|---|
| 150 | 2-{[2-cyclopropyl-4-(6-methoxy-1,2,4,5-tetrahydro-benzo[d]azepin-3-yl)-quinazolin-6-yl]-methyl-amino}-ethanol | 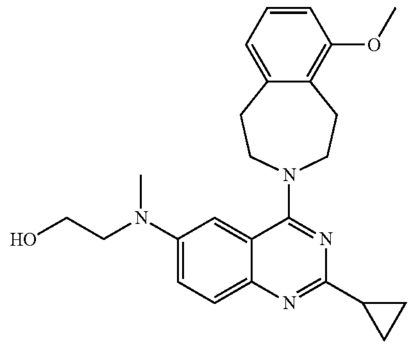 [SMILES: COc1cccc2c1CCN(c1nc(C3CC3)nc3ccc(N(C)CCO)cc13)CC2] | D |
| 151 | 2-[(2-cyclopropyl-4-{2-[(2-methoxy-phenyl)-methyl-amino]-cyclopentylamino}-quinazolin-6-yl)-methyl-amino]-ethanol | 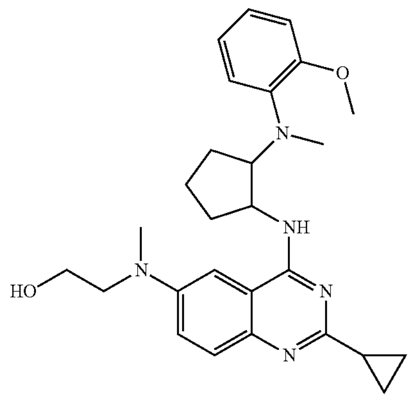 [SMILES: COc1ccccc1N(C)C1CCCC1Nc1nc(C2CC2)nc2ccc(N(C)CCO)cc12] | D |
| 152 | 2-cyclopropyl-N4-{2-[(2-methoxy-phenyl)-methyl-amino]-cyclopentyl}-N6-methyl-N6-propyl-quinazoline-4,6-diamine | 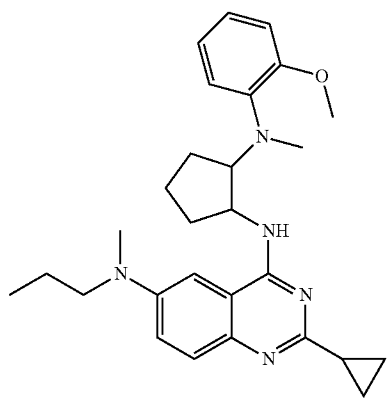 [SMILES: CCCN(C)c1ccc2nc(C3CC3)nc(NC3CCCC3N(C)c3ccccc3OC)c2c1] | D |
| 153 | 2-({2-cyclopropyl-4-[3-(2-methoxy-phenylamino)-pyrrolidin-1-yl]-quinazolin-6-yl}-methyl-amino)-ethanol | 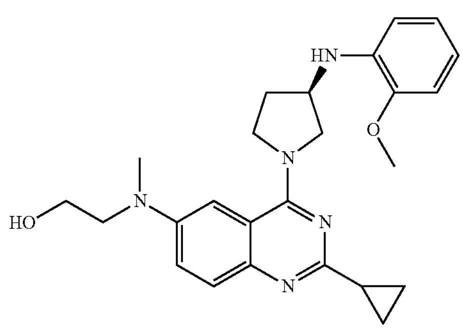 [SMILES: COc1ccccc1N[C@@H]1CCN(c2nc(C3CC3)nc3ccc(N(C)CCO)cc23)C1] | D |

TABLE 1-continued

| Ex. | Chemical name | Structure | EC$_{50}$ |
|---|---|---|---|
| 154 | 2-((2-cyclopropyl-4-((1-(2-methoxyphenyl)pyrrolidin-3-yl)amino)quinazolin-6-yl)(methyl)amino)ethanol | 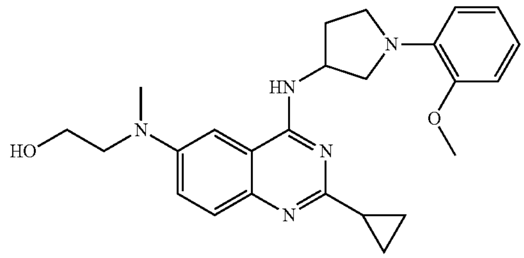 [SMILES: COc1ccccc1N1CCC(Nc2nc(C3CC3)nc3ccc(N(C)CCO)cc23)C1] | D |
| 155 | 2-cyclopropyl-N4-(1-(2-methoxyphenyl)pyrrolidin-3-yl)-N6-methyl-N6-propylquinazoline-4,6-diamine | 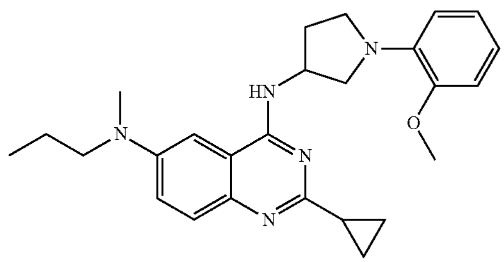 [SMILES: CCCN(C)c1ccc2nc(C3CC3)nc(NC3CCN(c4ccccc4OC)C3)c2c1] | D |
| 156 | Methyl 2-(2-cyclopropyl-4-(4-(2-methoxyphenyl)piperidin-1-yl)-6-methylpyrimidin-5-yl)acetate | 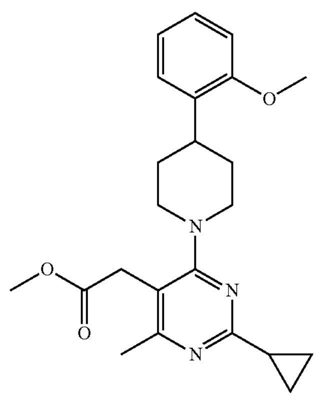 [SMILES: COC(=O)Cc1c(C)nc(C2CC2)nc1N1CCC(c2ccccc2OC)CC1] | D |
| 157 | 2-{2-cyclopropyl-4-[4-(2-methoxy-phenyl)-piperidin-1-yl]-6-methyl-pyrimidin-5-yl}-N,N-dimethyl-acetamide | 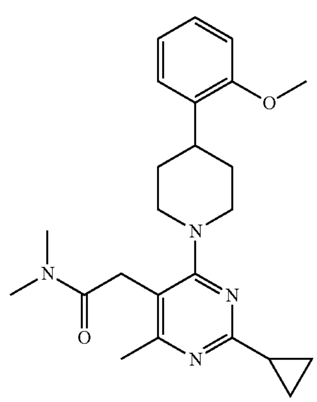 [SMILES: COc1ccccc1C1CCN(c2nc(C3CC3)nc(C)c2CC(=O)N(C)C)CC1] | D |

TABLE 1-continued

| Ex. | Chemical name | Structure | EC$_{50}$ |
|---|---|---|---|
| 158 | 2-{2-cyclopropyl-4-[4-(2-methoxy-phenyl)-piperidin-1-yl]-6-methyl-pyrimidin-5-yl}-N-methyl-N-propyl-acetamide | 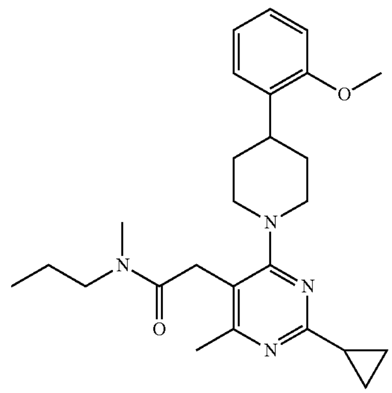 [SMILES: CCCN(C)C(=O)Cc1c(C)nc(C2CC2)nc1N1CCC(c2ccccc2OC)CC1] | D |
| 159 | 2-{2-cyclopropyl-4-[4-(2-methoxy-phenyl)-piperidin-1-yl]-6-methyl-pyrimidin-5-yl}-N-(2-hydroxy-ethyl)-N-methyl-acetamide | 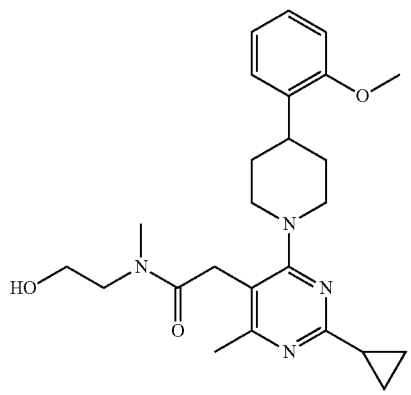 [SMILES: COc1ccccc1C1CCN(c2nc(C3CC3)nc(C)c2CC(=O)N(C)CCO)CC1] | D |
| 160 | 2-{2-cyclopropyl-4-[4-(2-methoxy-phenyl)-piperidin-1-yl]-6-methyl-pyrimidin-5-yl}-1-phenyl-ethanone | 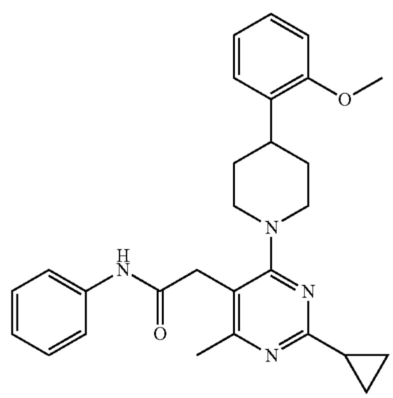 [SMILES: COc1ccccc1C1CCN(c2nc(C3CC3)nc(C)c2CC(=O)Nc2ccccc2)CC1] | D |
| 161 | {4-cyclopropyl-2-[4-(2-methoxy-phenyl)-piperidin-1-yl]-6-methyl-pyrimidin-5-yl}-acetic acid methyl ester | 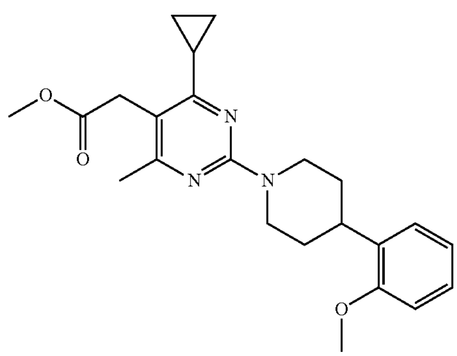 [SMILES: COC(=O)Cc1c(C)nc(N2CCC(c3ccccc3OC)CC2)nc1C1CC1] | D |

TABLE 1-continued

| Ex. | Chemical name | Structure | EC$_{50}$ |
|---|---|---|---|
| 162 | 2-{4-cyclopropyl-2-[4-(2-methoxy-phenyl)-piperidin-1-yl]-6-methyl-pyrimidin-5-yl}-N-methyl-N-propyl-acetamide | 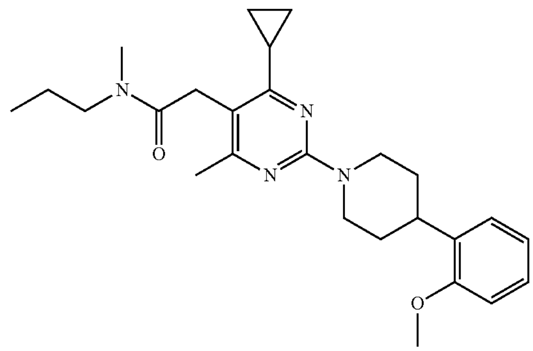 [SMILES: CCCN(C)C(=O)Cc1c(C)nc(N2CCC(c3ccccc3OC)CC2)nc1C1CC1] | D |
| 163 | 2-{4-cyclopropyl-2-[4-(2-methoxy-phenyl)-piperidin-1-yl]-6-methyl-pyrimidin-5-yl}-N-(2-hydroxy-ethyl)-N-methyl-acetamide | 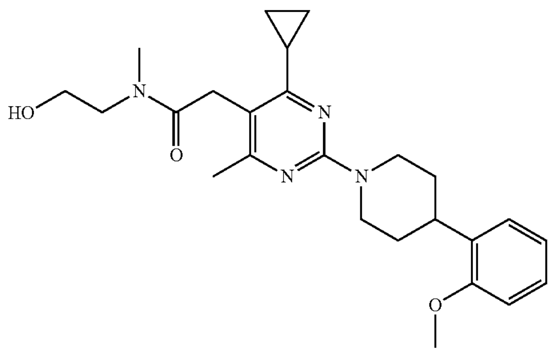 [SMILES: COc1ccccc1C1CCN(c2nc(C)c(CC(=O)N(C)CCO)c(C3CC3)n2)CC1] | D |
| 164 | 2-{2-cyclopropyl-4-[4-(2-methoxy-phenyl)-piperidin-1-yl]-6-methyl-pyrimidin-5-yl}-N-methyl-N-propyl-acetamide | 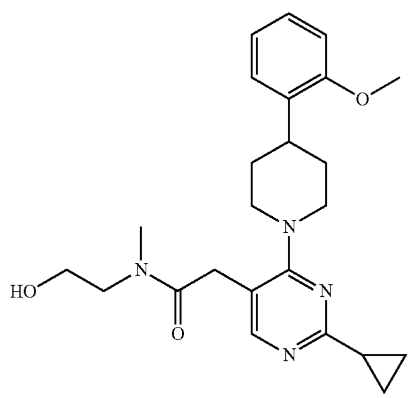 [SMILES: COc1ccccc1C1CCN(c2nc(C3CC3)ncc2CC(=O)N(C)CCO)CC1] | D |
| 165 | 2-{2-cyclopropyl-4-[4-(2-methoxy-phenyl)-piperidin-1-yl]-pyrimidin-5-yl}-N-methyl-N-propyl-acetamide | 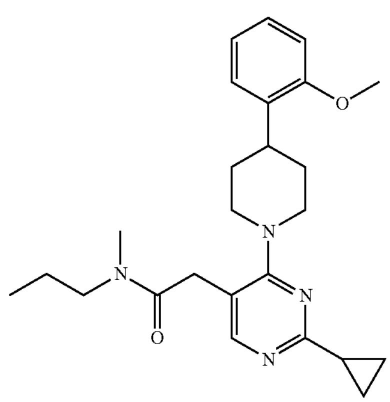 [SMILES: CCCN(C)C(=O)Cc1cnc(C2CC2)nc1N1CCC(c2ccccc2OC)CC1] | D |

TABLE 1-continued

| Ex. | Chemical name | Structure | EC$_{50}$ |
|---|---|---|---|
| 166 | 2-({2-Cyclopropyl-8-fluoro-4-[4-(2-methoxy-phenyl)-piperidin-1-yl]-quinazolin-6-yl}-methyl-amino)-ethanol | 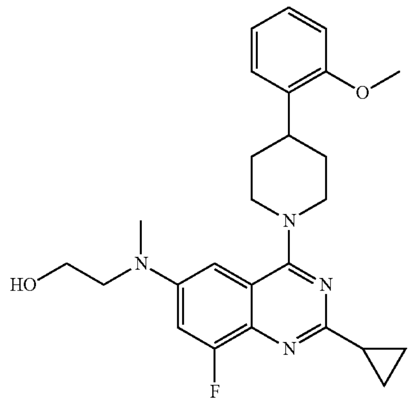 [SMILES: COc1ccccc1C1CCN(c2nc(C3CC3)nc3c(F)cc(N(C)CCO)cc23)CC1] | A |
| 167 | 2-({2-Cyclopropyl-5-fluoro-4-[4-(2-methoxy-phenyl)-piperidin-1-yl]-quinazolin-6-yl}-methyl-amino)-ethanol | 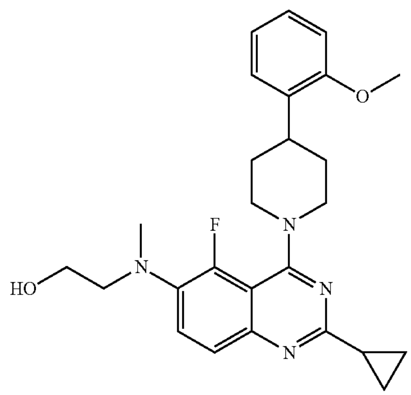 [SMILES: COc1ccccc1C1CCN(c2nc(C3CC3)nc3ccc(N(C)CCO)c(F)c23)CC1] | B |
| 168 | 2-({2-Cyclopropyl-4-[4-(2-methoxy-phenyl)-piperidin-1-yl]-quinazolin-5-yl}-methyl-amino)-ethanol | 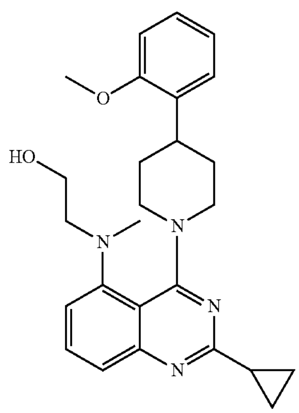 [SMILES: COc1ccccc1C1CCN(c2nc(C3CC3)nc3cccc(N(C)CCO)c23)CC1] | D |
| 169 | 2-({2-Cyclopropyl-4-[4-(2-methoxy-phenyl)-piperidin-1-yl]-quinazolin-7-yl}-methyl-amino)-ethanol | 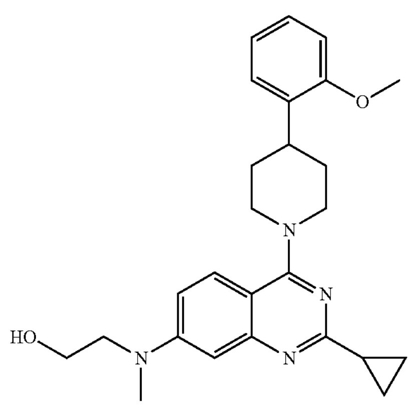 [SMILES: COc1ccccc1C1CCN(c2nc(C3CC3)nc3cc(N(C)CCO)ccc23)CC1] | C |

TABLE 1-continued

| Ex. | Chemical name | Structure | EC$_{50}$ |
|---|---|---|---|
| 170 | {2-Cyclopropyl-4-[4-(2-methoxy-phenyl)-piperidin-1-yl]-quinazolin-7-yl}-methyl-propyl-amine | 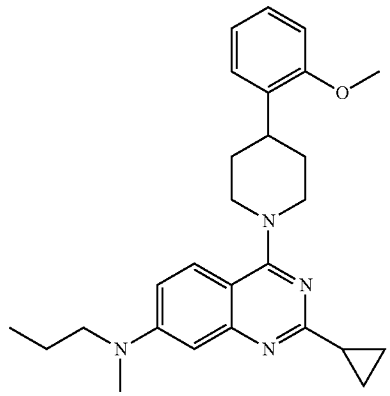 [SMILES: CCCN(C)c1ccc2c(N3CCC(c4ccccc4OC)CC3)nc(C3CC3)nc2c1] | C |
| 171 | (1-Fluoro-cyclopropyl)-{7-fluoro-6-[(2-hydroxy-ethyl)-methyl-amino]-4-[4-(2-methoxy-phenyl)-piperidin-1-yl]-quinazolin-2-yl}-methanone | 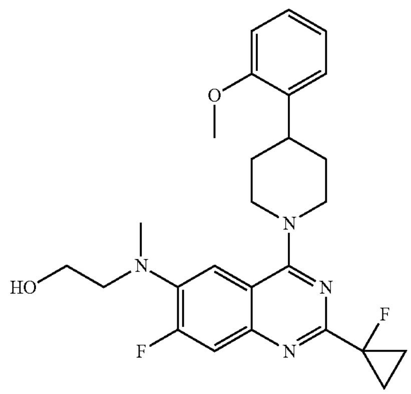 [SMILES: COc1ccccc1C1CCN(c2nc(C3(F)CC3)nc3cc(F)c(N(C)CCO)cc23)CC1] | A |
| 172 | {7-Chloro-6-[(2-hydroxy-ethyl)-methyl-amino]-4-[4-(2-methoxy-phenyl)-piperidin-1-yl]-quinazolin-2-yl}-(1-fluoro-cyclopropyl)-methanone | 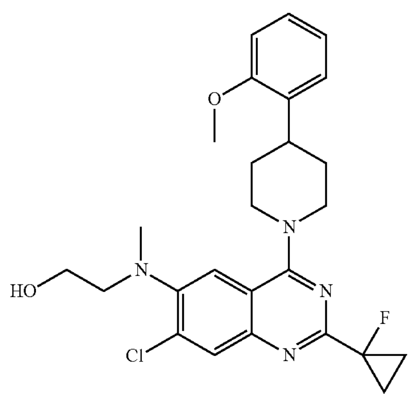 | B |
| 173 | (S)-1-(2-cyclopropyl-4-(4-(2-methoxyphenyl)piperidin-1-yl)quinazolin-6-yl)pyrrolidin-3-ol | 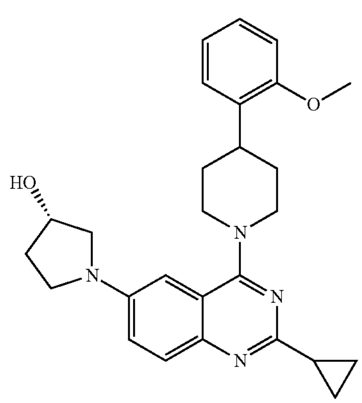 [SMILES: COc1ccccc1C1CCN(c2nc(C3CC3)nc3ccc(N4CC[C@H](O)C4)cc23)CC1] | B |

TABLE 1-continued

| Ex. | Chemical name | Structure | EC$_{50}$ |
|---|---|---|---|
| 174 | (S)-2-cyclopropyl-4-(4-(2-methoxyphenyl)piperidin-1-yl)-6-(3-methoxypyrrolidin-1-yl)quinazoline | 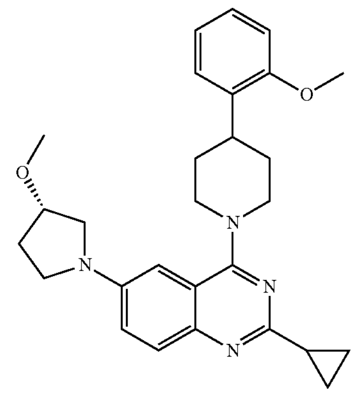 [SMILES: COc1ccccc1C1CCN(c2nc(C3CC3)nc3ccc(N4CC[C@H](OC)C4)cc23)CC1] | B |
| 175 | (R)-1-{2-cyclopropyl-4-[4-(2-methoxy-phenyl)-piperidin-1-yl]-quinazolin-6-yl}-pyrrolidin-3-ol | 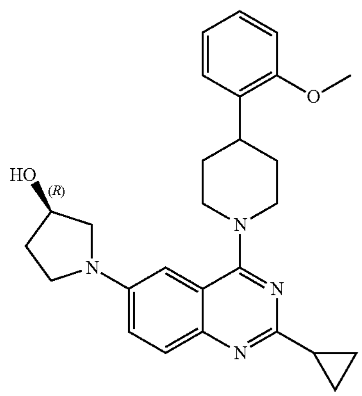 | B |
| 176 | (R)-2-cyclopropyl-4-[4-(2-methoxy-phenyl)-piperidin-1-yl]-6-(3-methoxy-pyrrolidin-1-yl)-quinazoline | 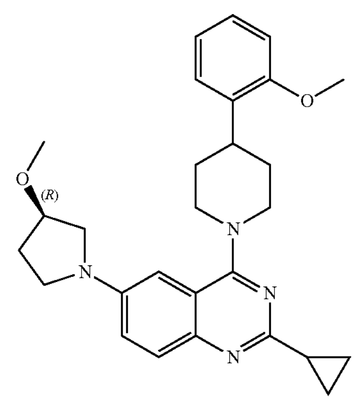 | B |
| 177 | (S)-1-{2-(1-Fluoro-cyclopropyl)-4-[4-(2-methoxy-phenyl)-piperidin-1-yl]-quinazolin-6-yl}-pyrrolidin-3-ol | 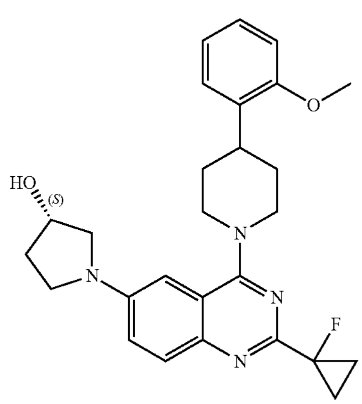 | B |

TABLE 1-continued

| Ex. | Chemical name | Structure | EC$_{50}$ |
|---|---|---|---|
| 178 | (R)-1-{2-(1-Fluoro-cyclopropyl)-4-[4-(2-methoxy-phenyl)-piperidin-1-yl]-quinazolin-6-yl}-pyrrolidin-3-ol | 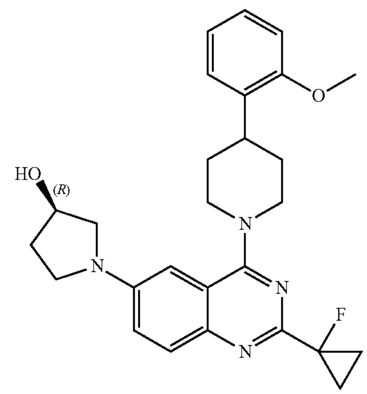 | B |
| 179 | ({2-Cyclopropyl-4-[4-(2-methoxy-phenyl)-piperidin-1-yl]-quinazolin-6-yl}-methyl-amino)-acetic acid | 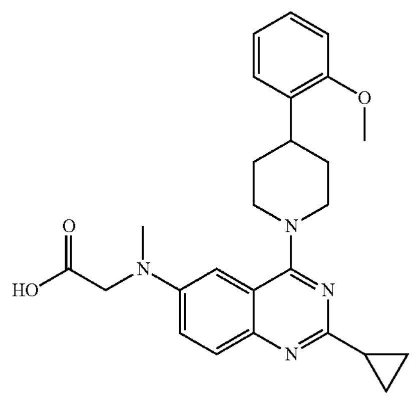 [SMILES: COc1ccccc1C1CCN(c2nc(C3CC3)nc3ccc(N(C)CC(=O)O)cc23)CC1] | A |
| 180 | 2-((2-(1-fluorocyclopropyl)-4-(4-(2-methoxyphenyl)piperidin-1-yl)quinazolin-6-yl)(methyl)amino)acetic acid | 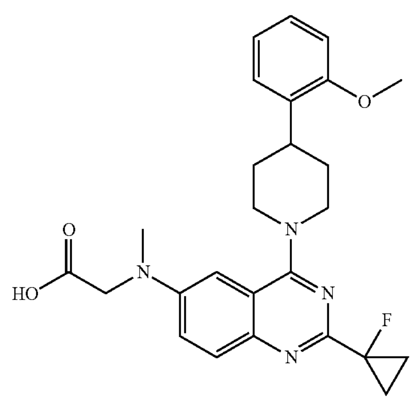 [SMILES: COc1ccccc1C1CCN(c2nc(C3(F)CC3)nc3ccc(N(C)CC(=O)O)cc23)CC1] | C |
| 181 | 2-((8-chloro-2-(1-fluorocyclobutyl)-4-(4-(2-methoxyphenyl)piperidin-1-yl)quinazolin-6-yl)(methyl)amino)ethanol | 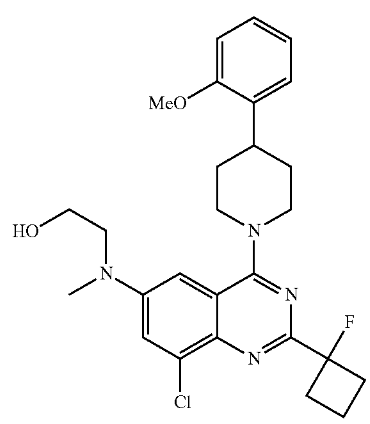 [SMILES: COc1ccccc1C1CCN(c2nc(C3(F)CCC3)nc3c(Cl)cc(N(C)CCO)cc23)CC1] | B |

TABLE 1-continued

| Ex. | Chemical name | Structure | EC$_{50}$ |
|---|---|---|---|
| 182 | 3-{8-Chloro-2-(1-fluoro-cyclobutyl)-4-[4-(2-methoxy-phenyl)-piperidin-1-yl]-quinazolin-6-yl}-cyclopentanol | 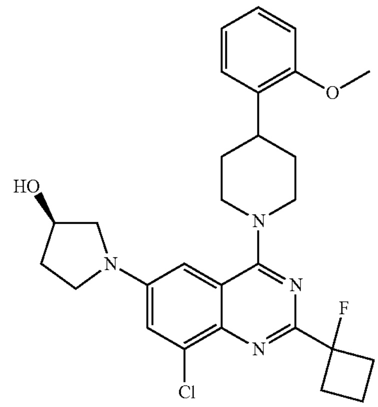 [SMILES: COc1ccccc1C1CCN(c2nc(C3(F)CCC3)nc3c(Cl)cc(N4CC[C@@H](O)C4)cc23)CC1] | C |
| 183 | 3-{8-Chloro-2-(1-fluoro-cyclobutyl)-4-[4-(2-methoxy-phenyl)-piperidin-1-yl]-quinazolin-6-yl}-cyclopentanol | 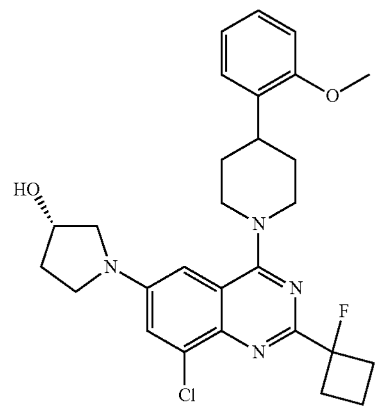 [SMILES: COc1ccccc1C1CCN(c2nc(C3(F)CCC3)nc3c(Cl)cc(N4CC[C@H](O)C4)cc23)CC1] | C |
| 184 | 2-({2-Cyclopropyl-4-[4-(2-methoxy-cyclopentyl)-piperazin-1-yl]-quinazolin-6-yl}-methyl-amino)-ethanol | 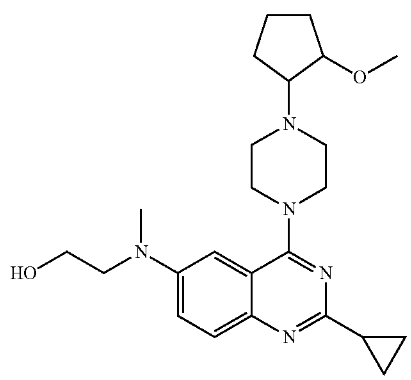 [SMILES: COC1CCCC1N1CCN(c2nc(C3CC3)nc3ccc(N(C)CCO)cc23)CC1] | D |
| 185 | 2-cyclopropyl-4-(4-(2-methoxycyclopentyl)piperazin-1-yl)-N-methyl-N-propylquinazolin-6-amine | 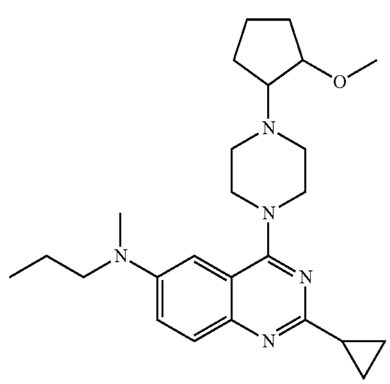 [SMILES: CCCN(C)c1ccc2nc(C3CC3)nc(N3CCN(C4CCCC4OC)CC3)c2c1] | D |

TABLE 1-continued

| Ex. | Chemical name | Structure | EC$_{50}$ |
|---|---|---|---|
| 186 | 2-({2-Cyclopropyl-4-[1-(2-methoxy-phenyl)-pyrrolidin-3-ylamino]-quinazolin-6-yl}-methyl-amino)-ethanol | 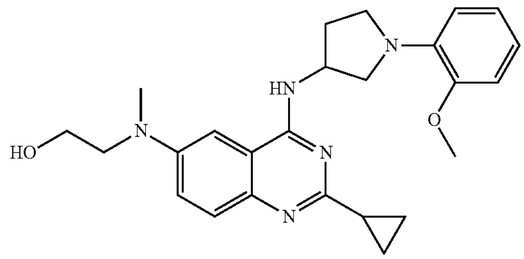 [SMILES: COc1ccccc1N1CCC(Nc2nc(C3CC3)nc3ccc(N(C)CCO)cc23)C1] | D |
| 187 | 2-Cyclopropyl-N4-[1-(2-methoxy-phenyl)-pyrrolidin-3-yl]-N6-methyl-N6-propyl-quinazoline-4,6-diamine | 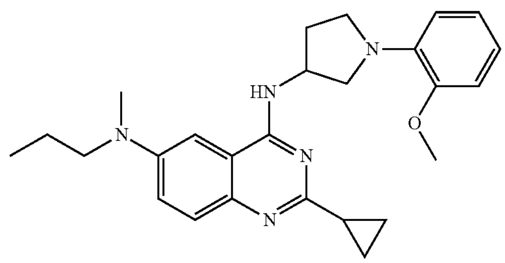 [SMILES: CCCN(C)c1ccc2nc(C3CC3)nc(NC3CCN(c4ccccc4OC)C3)c2c1] | D |
| 188 | 2-{[4-(4-Cyclohexyl-piperidin-1-yl)-2-(1-fluoro-cyclopropyl)-quinazolin-6-yl]-methyl-amino}-ethanol | 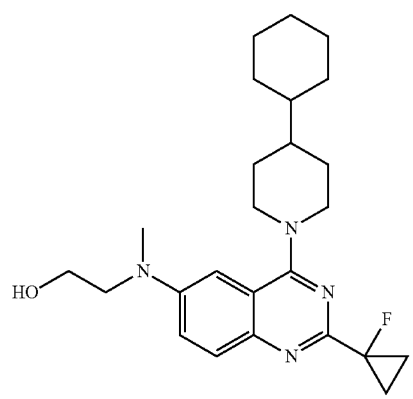 [SMILES: CN(CCO)c1ccc2nc(C3(F)CC3)nc(N3CCC(C4CCCCC4)CC3)c2c1] | D |
| 189 | 2-({2-(1-Fluoro-cyclopropyl)-4-[4-(2-methoxy-cyclohexyl)-piperidin-1-yl]-quinazolin-6-yl}-methyl-amino)-ethanol | 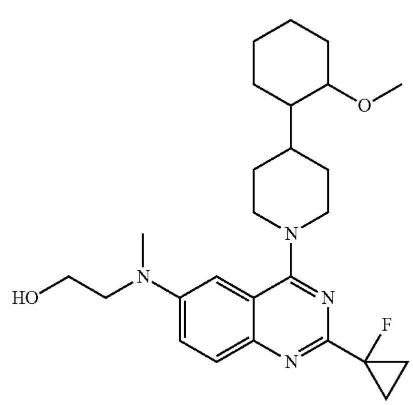 [SMILES: COC1CCCCC1C1CCN(c2nc(C3(F)CC3)nc3ccc(N(C)CCO)cc23)CC1] | D |

TABLE 1-continued

| Ex. | Chemical name | Structure | EC$_{50}$ |
|---|---|---|---|
| 190 | 2-({2-Cyclopropyl-4-[4-(3-methoxy-thiophen-2-yl)-piperidin-1-yl]-quinazolin-6-yl}-methyl-amino)-ethanol | 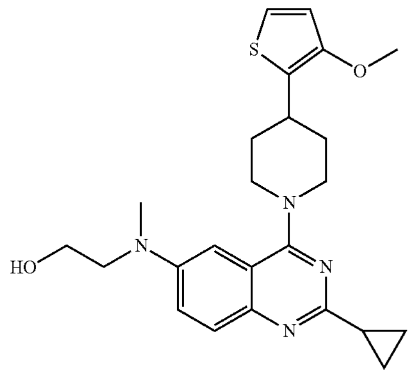 [SMILES: COc1ccsc1C1CCN(c2nc(C3CC3)nc3ccc(N(C)CCO)cc23)CC1] | C |
| 191 | 2-({2-Cyclopropylethynyl-4-[4-(2-methoxy-phenyl)-piperidin-1-yl]-quinazolin-6-yl}-methyl-amino)-ethanol | 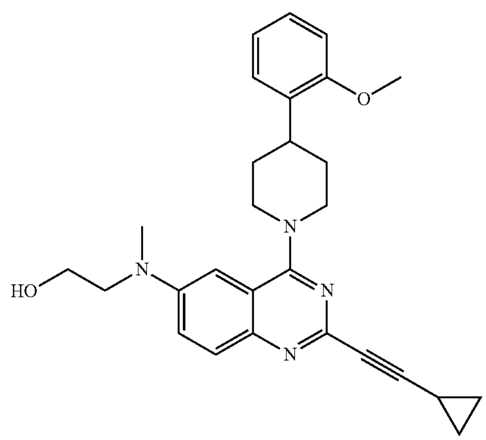 [SMILES: COc1ccccc1C1CCN(c2nc(C#CC3CC3)nc3ccc(N(C)CCO)cc23)CC1] | C |
| 192 | 2-({2-Ethynyl-4-[4-(2-methoxy-phenyl)-piperidin-1-yl]-quinazolin-6-yl}-methyl-amino)-ethanol | 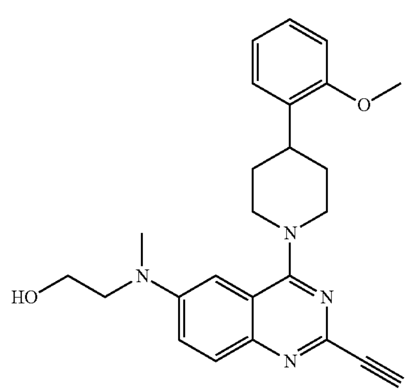 [SMILES: C#Cc1nc(N2CCC(c3ccccc3OC)CC2)c2cc(N(C)CCO)ccc2n1] | et |

TABLE 1-continued

| Ex. | Chemical name | Structure | EC$_{50}$ |
|---|---|---|---|
| 193 | 2-((2-cyclobutoxy-4-(4-(2-methoxyphenyl)piperidin-1-yl)quinazolin-6-yl)(methyl)amino)ethanol | 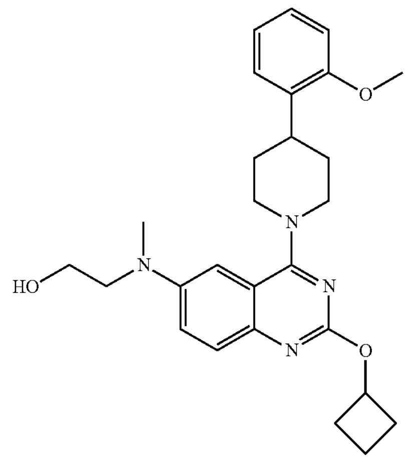 [SMILES: COc1ccccc1C1CCN(c2nc(OC3CCC3)nc3ccc(N(C)CCO)cc23)CC1] | B |
| 194 | 2-cyclopropyl-4-(4-(2-methoxyphenyl)piperidin-1-yl)-N-methyl-N-(2-morpholinoethyl)pyrido[3,4-d]pyrimidin-6-amine | 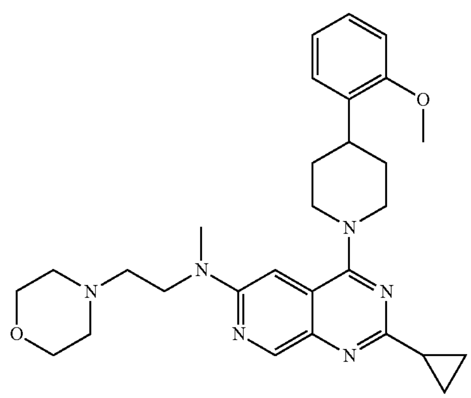 [SMILES: COc1ccccc1C1CCN(c2nc(C3CC3)nc3cnc(N(C)CCN4CCOCC4)cc23)CC1] | B |
| 195 | 2-({2-(1-Fluoro-cyclopropyl)-4-[4-(2-methoxy-phenyl)-piperidin-1-yl]-pyrido[3,4-d]pyrimidin-6-yl}-methyl-amino)-ethanol | 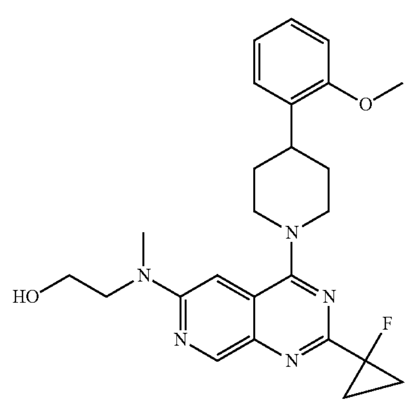 [SMILES: COc1ccccc1C1CCN(c2nc(C3(F)CC3)nc3cnc(N(C)CCO)cc23)CC1] | A |

TABLE 1-continued

| Ex. | Chemical name | Structure | EC$_{50}$ |
|---|---|---|---|
| 196 | 1-{2-(1-Fluoro-cyclopropyl)-4-[4-(2-methoxy-phenyl)-piperidin-1-yl]-pyrido[3,4-d]pyrimidin-6-yl}-pyrrolidin-3-ol | 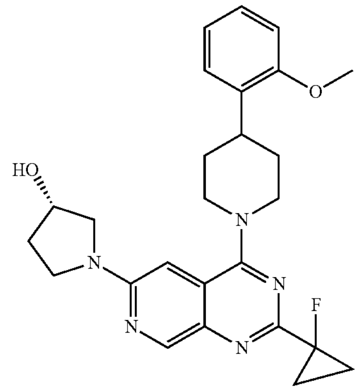 [SMILES: COc1ccccc1C1CCN(c2nc(C3(F)CC3)nc3cnc(N4CC[C@H](O)C4)cc23)CC1] | B |
| 197 | 1-{2-(1-Fluoro-cyclopropyl)-4-[4-(2-methoxy-phenyl)-piperidin-1-yl]-pyrido[3,4-d]pyrimidin-6-yl}-pyrrolidin-3-ol | 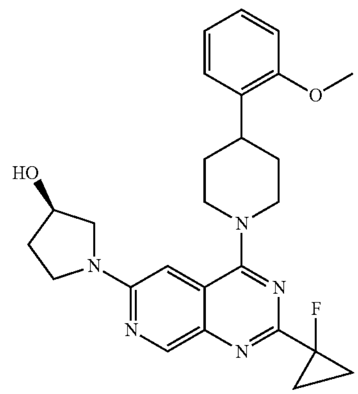 [SMILES: COc1ccccc1C1CCN(c2nc(C3(F)CC3)nc3cnc(N4CC[C@@H](O)C4)cc23)CC1] | B |
| 198 | 2-({2-(1-Fluoro-cyclobutyl)-4-[4-(2-methoxy-phenyl)-piperidin-1-yl]-pyrido[3,4-d]pyrimidin-6-yl}-methyl-amino)-ethanol | 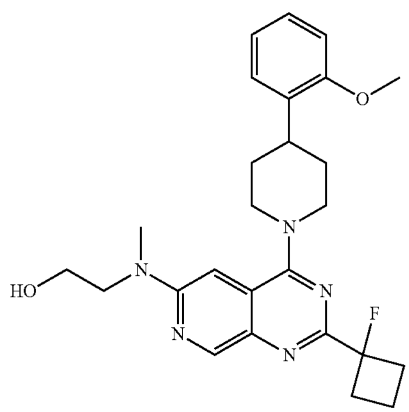 [SMILES: COc1ccccc1C1CCN(c2nc(C3(F)CCC3)nc3cnc(N(C)CCO)cc23)CC1] | C |
| 199 | 1-{2-(1-Fluoro-cyclobutyl)-4-[4-(2-methoxy-phenyl)-piperidin-1-yl]-pyrido[3,4-d]pyrimidin-6-yl}-pyrrolidin-3-ol | 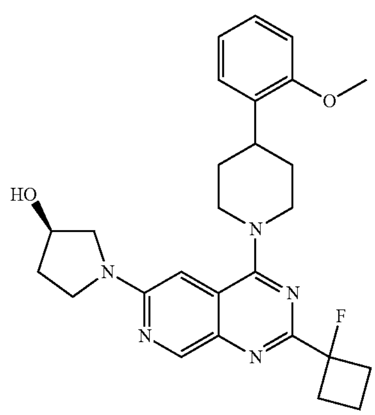 [SMILES: COc1ccccc1C1CCN(c2nc(C3(F)CCC3)nc3cnc(N4CC[C@@H](O)C4)cc23)CC1] | C |

TABLE 1-continued

| Ex. | Chemical name | Structure | EC$_{50}$ |
|---|---|---|---|
| 200 | 1-{2-(1-Fluoro-cyclobutyl)-4-[4-(2-methoxy-phenyl)-piperidin-1-yl]-pyrido[3,4-d]pyrimidin-6-yl}-pyrrolidin-3-ol | 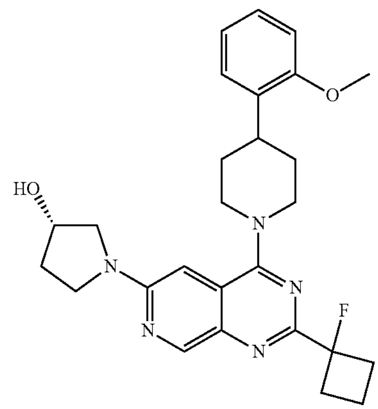 [SMILES: COc1ccccc1C1CCN(c2nc(C3(F)CCC3)nc3cnc(N4CC[C@H](O)C4)cc23)CC1] | C |
| 201 | 2-({8-Chloro-2-(1-fluoro-cyclopropyl)-4-[4-(2-methoxy-phenyl)-piperidin-1-yl]-quinazolin-6-yl}-methyl-amino)-ethanol | 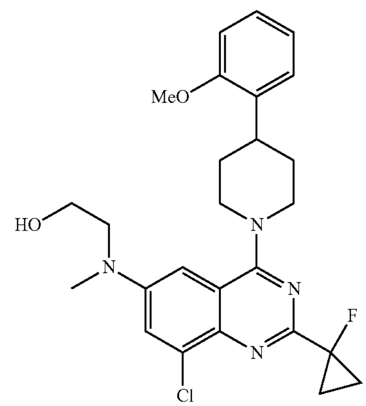 [SMILES: COc1ccccc1C1CCN(c2nc(C3(F)CC3)nc3c(Cl)cc(N(C)CCO)cc23)CC1] | A |
| 202 | 1-{8-Chloro-2-(1-fluoro-cyclopropyl)-4-[4-(2-methoxy-phenyl)-piperidin-1-yl]-quinazolin-6-yl}-pyrrolidin-3-ol | 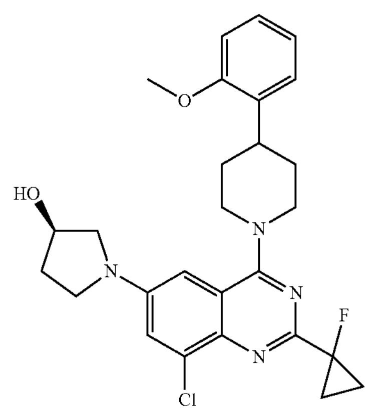 [SMILES: COc1ccccc1C1CCN(c2nc(C3(F)CC3)nc3c(Cl)cc(N4CC[C@@H](O)C4)cc23)CC1] | B |
| 203 | 1-{8-Chloro-2-(1-fluoro-cyclopropyl)-4-[4-(2-methoxy-phenyl)-piperidin-1-yl]-quinazolin-6-yl}-pyrrolidin-3-ol | 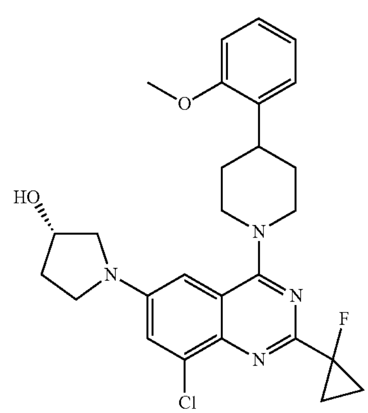 [SMILES: COc1ccccc1C1CCN(c2nc(C3(F)CC3)nc3c(Cl)cc(N4CC[C@H](O)C4)cc23)CC1] | C |

TABLE 1-continued

| Ex. | Chemical name | Structure | EC₅₀ |
|---|---|---|---|
| 204 | 2-{[8-Fluoro-4-[4-(3-methoxy-pyrazin-2-yl)-piperidin-1-yl]-2-(1-methyl-cyclopropyl)-quinazolin-6-yl]-methyl-amino}-ethanol | 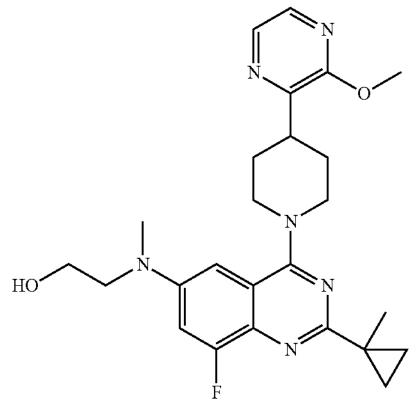 [SMILES: COc1nccnc1C1CCN(c2nc(C3(C)CC3)nc3c(F)cc(N(C)CCO)cc23)CC1] | B |
| 205 | 2-{[4-[4-(3-Methoxy-pyrazin-2-yl)-piperidin-1-yl]-2-(1-methyl-cyclopropyl)-quinazolin-6-yl]-methyl-amino}-ethanol | 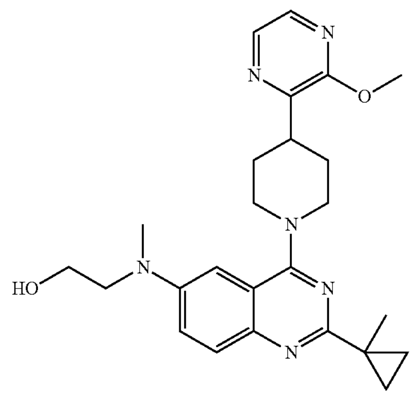 [SMILES: COc1nccnc1C1CCN(c2nc(C3(C)CC3)nc3ccc(N(C)CCO)cc23)CC1] | B |
| 206 | 2-{[2-(1-Fluoro-cyclopropyl)-4-(3-methoxy-3',4',5',6'-tetrahydro-2'H-[2,4']bipyridinyl-1'-yl)-quinazolin-6-yl]-methyl-amino}-ethanol | 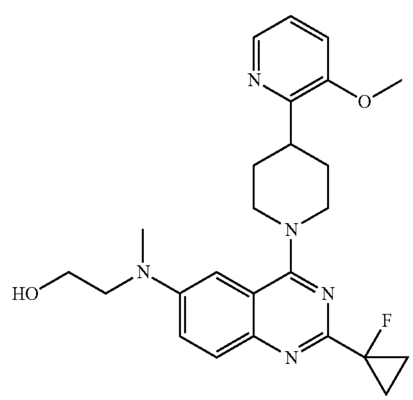 [SMILES: COc1cccnc1C1CCN(c2nc(C3(F)CC3)nc3ccc(N(C)CCO)cc23)CC1] | B |
| 207 | 2-{[2-(1-Fluoro-cyclopropyl)-4-(2-methoxy-3',4',5',6'-tetrahydro-2'H-[3,4']bipyridinyl-1'-yl)-quinazolin-6-yl]-methyl-amino}-ethanol | 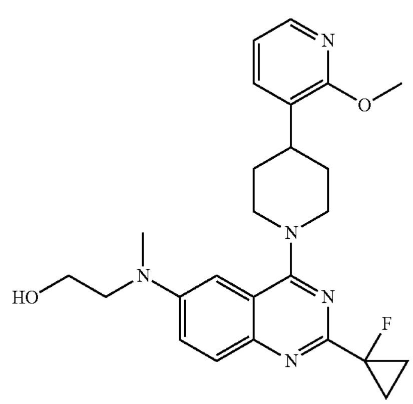 [SMILES: COc1ncccc1C1CCN(c2nc(C3(F)CC3)nc3ccc(N(C)CCO)cc23)CC1] | B |

TABLE 1-continued

| Ex. | Chemical name | Structure | EC$_{50}$ |
|---|---|---|---|
| 208 | 2-({2-(1-Fluoro-cyclopropyl)-4-[4-(3-methoxy-pyrazin-2-yl)-piperidin-1-yl]-quinazolin-6-yl}-methyl-amino)-ethanol. | 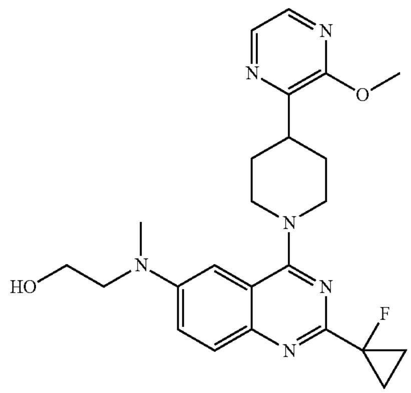 [SMILES: COc1nccnc1C1CCN(c2nc(C3(F)CC3)nc3ccc(N(C)CCO)cc23)CC1] | B |
| 209 | 2-({2-(1-Fluoro-cyclopropyl)-4-[4-(3-methoxy-pyridin-2-yl)-piperazin-1-yl]-quinazolin-6-yl}-methyl-amino)-ethanol | 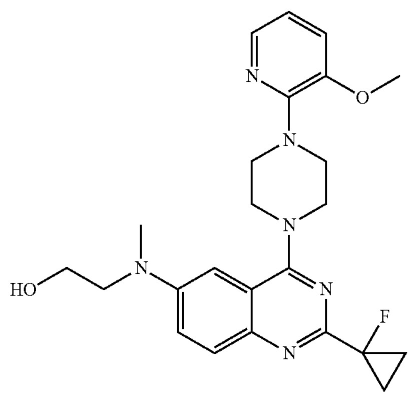 | C |
| 210 | 2-{[2-(1-Fluoro-cyclopropyl)-4-(4-methoxy-3',4',5',6'-tetrahydro-2'H-[3,4']bipyridinyl-1'-yl)-quinazolin-6-yl]-methyl-amino}-ethanol | 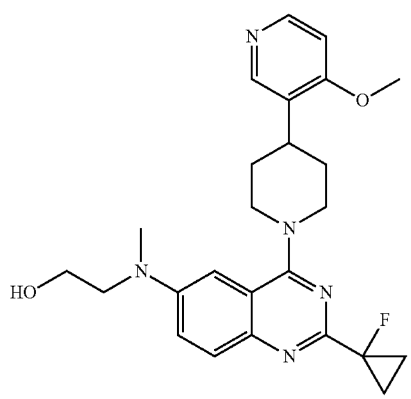 [SMILES: COc1ccncc1C1CCN(c2nc(C3(F)CC3)nc3ccc(N(C)CCO)cc23)CC1] | C |
| 211 | 2-({2-(1-Fluoro-cyclopropyl)-4-[4-(5-methoxy-pyrimidin-4-yl)-piperidin-1-yl]-quinazolin-6-yl}-methyl-amino)-ethanol | 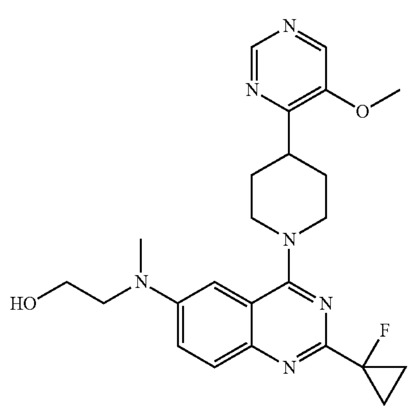 [SMILES: COc1cncnc1C1CCN(c2nc(C3(F)CC3)nc3ccc(N(C)CCO)cc23)CC1] | D |

TABLE 1-continued

| Ex. | Chemical name | Structure | EC$_{50}$ |
|---|---|---|---|
| 212 | 2-{[2-(1-Fluoro-cyclopropyl)-4-(3'-methoxy-3',4',5',6'-tetrahydro-2H-[4,4']bipyridinyl-1-yl)-quinazolin-6-yl]-methyl-amino}-ethanol | 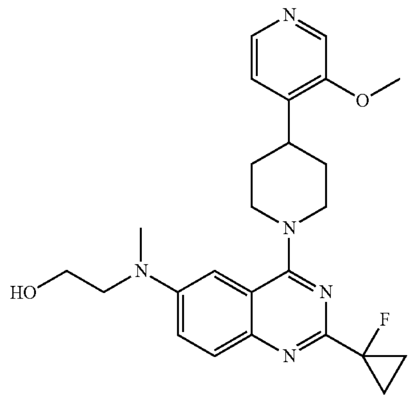 [SMILES: COc1cnccc1C1CCN(c2nc(C3(F)CC3)nc3ccc(N(C)CCO)cc23)CC1] | D |
| 213 | 2-({8-Fluoro-2-(1-fluoro-cyclopropyl)-4-[4-(3-methoxy-pyrazin-2-yl)-piperidin-1-yl]-quinazolin-6-yl}-methyl-amino)-ethanol | 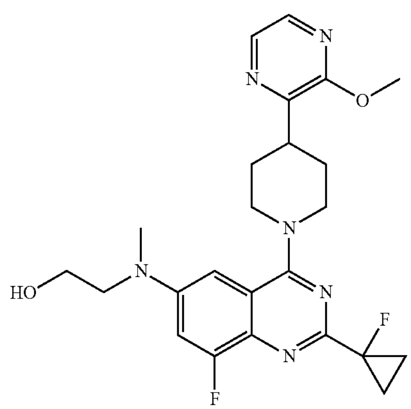 [SMILES: COc1nccnc1C1CCN(c2nc(C3(F)CC3)nc3c(F)cc(N(C)CCO)cc23)CC1] | B |
| 214 | 2-{[8-Fluoro-2-(1-fluoro-cyclopropyl)-4-(2-methoxy-3',4',5',6'-tetrahydro-2'H-[3,4']bipyridinyl-1'-yl)-quinazolin-6-yl]-methyl-amino}-ethanol | 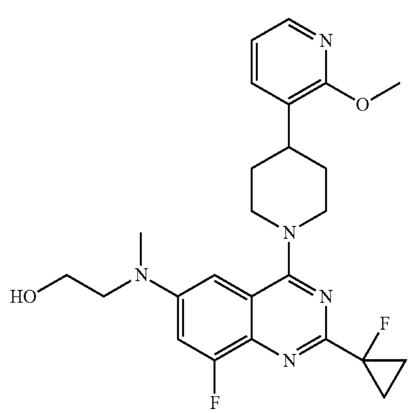 | B |

TABLE 1-continued

| Ex. | Chemical name | Structure | EC$_{50}$ |
|---|---|---|---|
| 215 | 2-({8-Fluoro-2-(1-fluoro-cyclopropyl)-4-[4-(3-methoxy-pyridin-2-yl)-piperazin-1-yl]-quinazolin-6-yl}-methyl-amino)-ethanol | 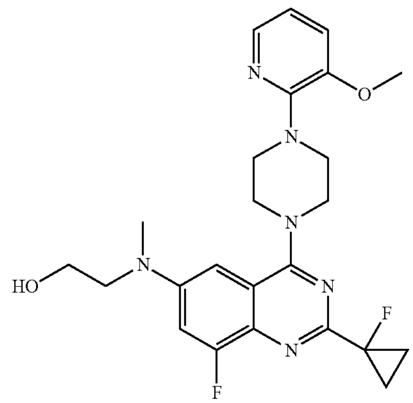 [SMILES: COc1cccnc1N1CCN(c2nc(C3(F)CC3)nc3c(F)cc(N(C)CCO)cc23)CC1] | B |
| 216 | 2-{[8-Fluoro-2-(1-fluoro-cyclopropyl)-4-(3-methoxy-3',4',5',6'-tetrahydro-2'H-[2,4']bipyridinyl-1'-yl)-quinazolin-6-yl]-methyl-amino}-ethanol | 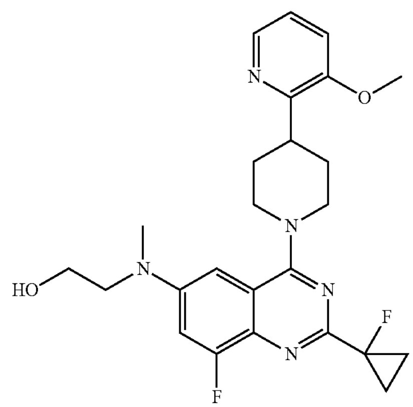 [SMILES: COc1cccnc1C1CCN(c2nc(C3(F)CC3)nc3c(F)cc(N(C)CCO)cc23)CC1] | C |
| 217 | 2-({8-Fluoro-2-(1-fluoro-cyclopropyl)-4-[4-(5-methoxy-pyrimidin-4-yl)-piperidin-1-yl]-quinazolin-6-yl}-methyl-amino)-ethanol | 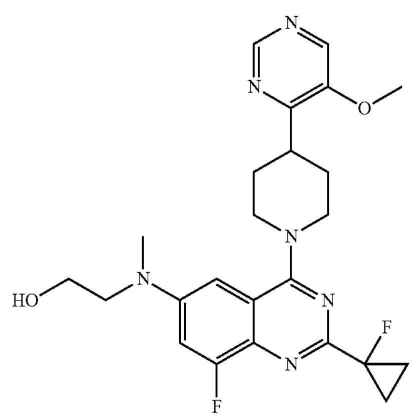 [SMILES: COc1cncnc1C1CCN(c2nc(C3(F)CC3)nc3c(F)cc(N(C)CCO)cc23)CC1] | D |

TABLE 1-continued

| Ex. | Chemical name | Structure | $EC_{50}$ |
|---|---|---|---|
| 218 | 2-({2-(1-Fluoro-cyclopropyl)-4-[4-(4-iodo-2-methoxy-phenyl)-piperazin-1-yl]-quinazolin-6-yl}-methyl-amino)-ethanol. | 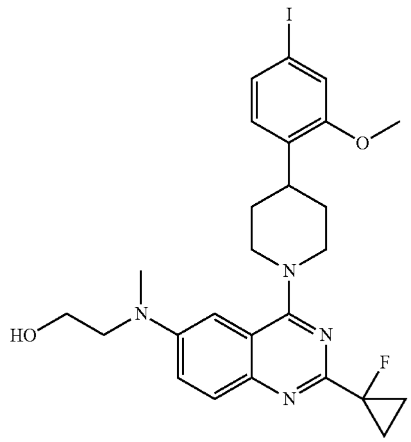 [SMILES: COc1cc(I)ccc1C1CCN(c2nc(C3(F)CC3)nc3ccc(N(C)CCO)cc23)CC1] | D |
| 219 | 2-({2-(1-Fluoromethyl-cyclopropyl)-4-[4-(3-methoxy-pyrazin-2-yl)-piperidin-1-yl]-quinazolin-6-yl}-methyl-amino)-ethanol | 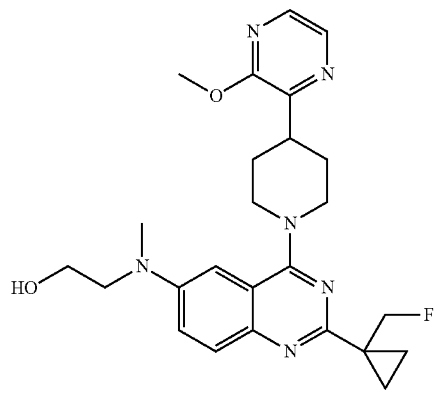 [SMILES: COc1nccnc1C1CCN(c2nc(C3(CF)CC3)nc3ccc(N(C)CCO)cc23)CC1] | B |
| 221 | 1-(6-((2-hydroxyethyl)(methyl)amino)-4-(4-(3-methoxypyrazin-2-yl)piperidin-1-yl)quinazolin-2-yl)cyclobutanol | 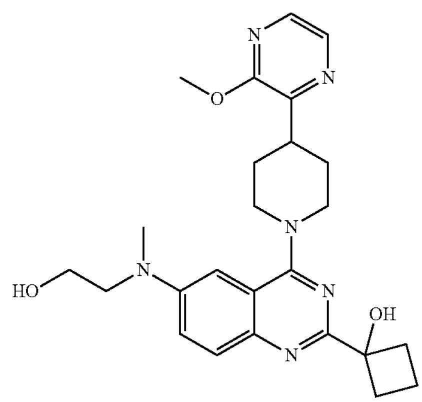 [SMILES: COc1nccnc1C1CCN(c2nc(C3(O)CCC3)nc3ccc(N(C)CCO)cc23)CC1] | D |
| 222 | (2-(1-Fluoro-cyclopropyl)-4-{4-[2-(2-fluoro-ethoxy)-phenyl]-piperidin-1-yl}-quinazolin-6-yl)-[2-(2-fluoro-ethoxy)-ethyl]-methyl-amine | 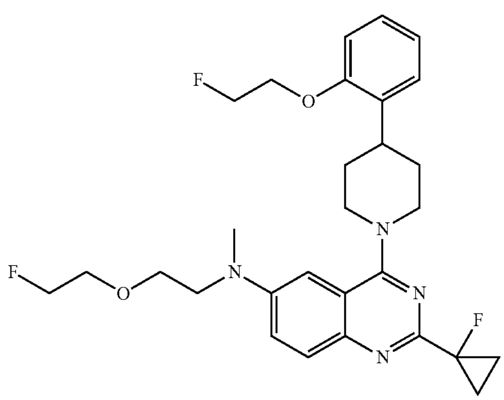 [SMILES: CN(CCOCCF)c1ccc2nc(C3(F)CC3)nc(N3CCC(c4ccccc4OCCF)CC3)c2c1] | C |

TABLE 1-continued

| Ex. | Chemical name | Structure | EC$_{50}$ |
|---|---|---|---|
| 223 | {2-(1-Fluoro-cyclopropyl)-4-[4-(2-methoxy-phenyl)-piperidin-1-yl]-quinazolin-6-yl}-[2-(2-fluoro-ethoxy)-ethyl]-methyl-amine | 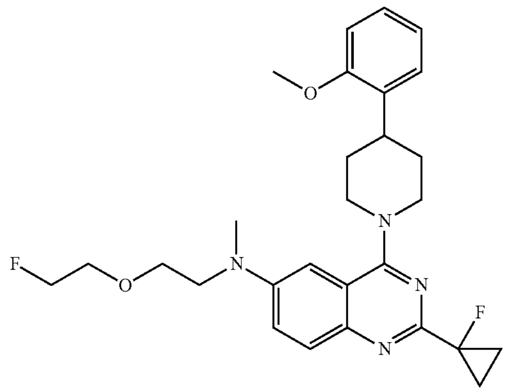 [SMILES: COc1ccccc1C1CCN(c2nc(C3(F)CC3)nc3ccc(N(C)CCOCCF)cc23)CC1] | B |
| 224 | 2-{1-[6-{[2-(tert-Butyl-dimethyl-silanyloxy)-ethyl]-methyl-amino}-2-(1-fluoro-cyclopropyl)-quinazolin-4-yl]-piperidin-4-yl}-phenol | 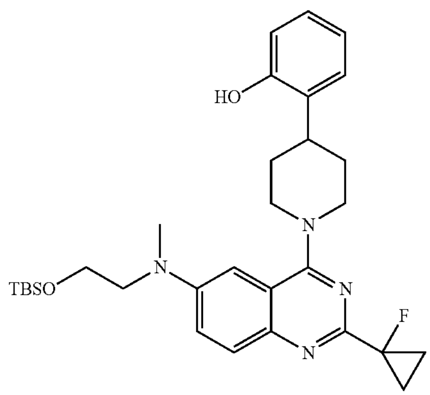 [SMILES: CN(CCO[Si](C)(C)C(C)(C)C)c1ccc2nc(C3(F)CC3)nc(N3CCC(c4ccccc4O)CC3)c2c1] | C |
| 225 | 2-[(2-(1-Fluoro-cyclopropyl)-4-{4-[2-(2-fluoro-ethoxy)-phenyl]-piperidin-1-yl}-quinazolin-6-yl)-methyl-amino]-ethanol | 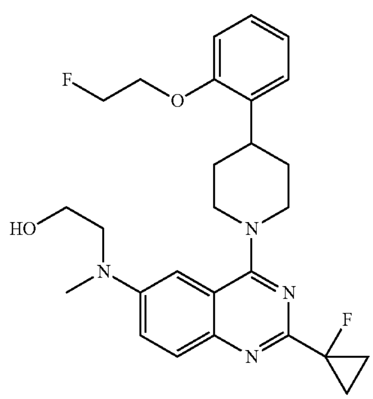 [SMILES: CN(CCO)c1ccc2nc(C3(F)CC3)nc(N3CCC(c4ccccc4OCCF)CC3)c2c1] | B |

A is <0.5 uM;
B is 0.5-2 uM;
C is 2-10 uM;
D is >10 uM.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating substance abuse in a subject comprising administering to the subject in need thereof a therapeutically effective amount of a compound of Formula (I), or a pharmaceutically acceptable salt, or solvate, thereof:

Formula (I)

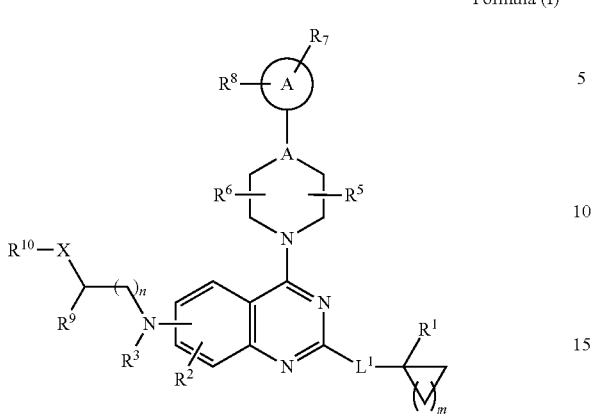

wherein,
ring A is phenyl, $C_3$-$C_6$cycloalkyl, $C_2$-$C_6$heterocycloalkyl, or monocyclic heteroaryl;
A is CH or N;
$R^1$ is halogen, $C_1$-$C_4$alkyl, $C_1$-$C_4$alkoxy, $C_1$-$C_4$haloalkyl, $C_1$-$C_4$haloalkoxy, or —N($R^a$)$_2$; and $R^3$ is hydrogen, $C_1$-$C_4$alkyl, or $C_1$-$C_4$haloalkyl;
or
$R^1$ is hydrogen, halogen, $C_1$-$C_4$alkyl, $C_1$-$C_4$alkoxy, $C_1$-$C_4$haloalkyl, $C_1$-$C_4$haloalkoxy, or —N($R^a$)$_2$; and $R^3$ and $R^9$ are taken together with the intervening atoms to form an optionally substituted $C_2$-$C_6$heterocycloalkyl;
each $R^a$ is independently selected from the group consisting of hydrogen, $C_1$-$C_4$ alkyl, —C(=O)$R^{11}$, —C(=O)—O—$R^{11}$, and —S(=O)$_2R^{11}$, or 2 $R^a$ taken together with the nitrogen to which they are attached form an optionally substituted $C_2$-$C_6$heterocycloalkyl;
$L^1$ is absent, $C_1$-$C_4$alkylene, $C_1$-$C_4$alkenylene, $C_1$-$C_4$alkynylene, or —N($R^b$)—;
$R^b$ is hydrogen, $C_1$-$C_4$alkyl, $C_1$-$C_4$haloalkyl, —C(=O)—O—$R^{11}$, —S(=O)$_2R^{11}$, or —C(=O)$R^{11}$;
$R^2$ is hydrogen, halogen, —CN, —OH, —NO$_2$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, and optionally substituted 5- or 6-membered heteroaryl;
$R^5$ and $R^6$ are each independently selected from hydrogen, halogen, —OH, and $C_1$-$C_4$alkyl, or when on the same carbon, $R^5$ and $R^6$ taken together form an oxo;
$R^7$ is hydrogen, halogen, —CN, —OH, —NO$_2$, —N($R^{12}$)—$R^{13}$, —C(=O)—N($R^{12}$)—$R^{13}$, —N$R^{12}$C(=O)$R^{11}$, —C(=O)—O—$R^{11}$, —O—C(=O)—$R^{11}$, —S$R^{12}$, —S(=O)$R^{11}$, —S(=O)$_2R^{11}$, —N($R^{12}$)S(=O)$_2R^{11}$, —S(=O)$_2$—N($R^{12}$)—$R^{13}$, —C(=O)$R^{11}$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, or optionally substituted 5- or 6-membered heteroaryl;
$R^8$ is hydrogen, —OH, $C_1$-$C_4$alkyl, $C_1$-$C_4$fluoroalkyl, $C_1$-$C_4$alkoxy, $C_1$-$C_4$fluoroalkoxy, or —N($R^a$)$_2$;

$R^9$ is hydrogen, $C_1$-$C_4$alkyl, or $C_1$-$C_4$fluoroalkyl;
X is —O— or —N($R^b$)—;
$R^{10}$ is hydrogen, $C_1$-$C_4$alkyl, $C_1$-$C_4$fluoroalkyl, —C(=O)—O—$R^{11}$, —C(=O)N($R^{12}$)$R^{13}$, —S(=O)$_2R^{11}$, or —C(=O)$R^{11}$;
each $R^{11}$ is independently selected from the group consisting of optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl;
each of $R^{12}$ and $R^{13}$ is independently selected from the group consisting of hydrogen, optionally substituted $C_1$-$C_4$alkyl, optionally substituted $C_1$-$C_4$fluoroalkyl, optionally substituted $C_3$-$C_6$cycloalkyl, optionally substituted $C_2$-$C_6$heterocycloalkyl, optionally substituted phenyl, and optionally substituted 5- or 6-membered heteroaryl; or $R^{12}$ and $R^{13}$, when on the same nitrogen atom, are taken together with the nitrogen atom to which they are attached to form an optionally substituted $C_2$-$C_6$heterocycloalkyl;
n is 1, 2, or 3; and
m is 1, 2, 3, or 4.

2. The method of claim 1, wherein:
the substance abused is an amphetamine, an opioid, a cannabinoid, a barbiturate, a benzodiazepine, nicotine, alcohol, a hallucinogen, cocaine, or combinations thereof.

3. The method of claim 1, wherein:
the substance abused is a psychostimulant.

4. The method of claim 1, wherein:
the compound of Formula (I), or a pharmaceutically acceptable salt, or solvate thereof, has the following structure of Formula (Ia), or a pharmaceutically acceptable salt, or solvate thereof:

Formula (Ia)

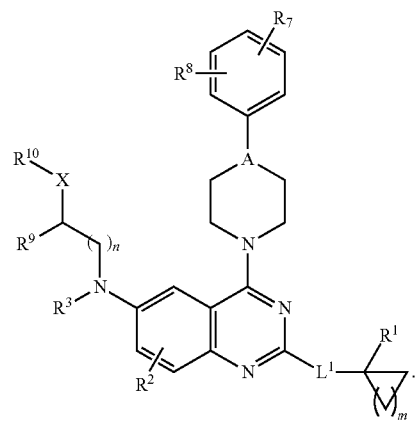

5. The method of claim 4, wherein:
$R^1$ is halogen, $C_1$-$C_4$alkyl, $C_1$-$C_4$alkoxy, $C_1$-$C_4$haloalkyl, $C_1$-$C_4$haloalkoxy, or —N($R^a$)$_2$; and
$R^3$ is hydrogen or $C_1$-$C_4$alkyl.

6. The method of claim 4, wherein:
$R^1$ is hydrogen, halogen, $C_1$-$C_4$alkyl, $C_1$-$C_4$alkoxy, $C_1$-$C_4$haloalkyl, $C_1$-$C_4$haloalkoxy, or —N($R^a$)$_2$; and
$R^3$ and $R^9$ are taken together with the intervening atoms to form an optionally substituted $C_2$-$C_6$heterocycloalkyl.

7. The method of claim 1, wherein the compound of Formula (I), or a pharmaceutically acceptable salt, or solvate thereof, has the following structure of Formula (Ib), or a pharmaceutically acceptable salt, or solvate thereof:

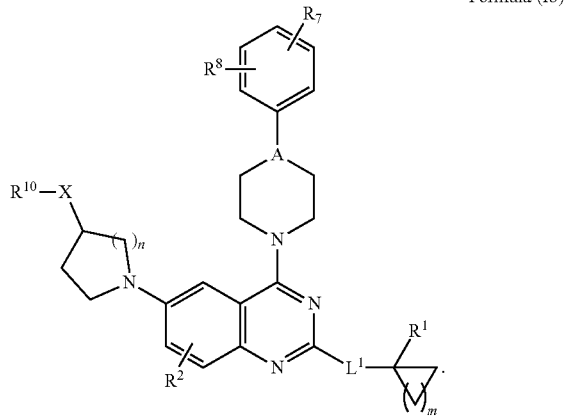

Formula (Ib)

8. The method of claim 7, wherein the compound of Formula (Ib), or a pharmaceutically acceptable salt, or solvate thereof, has one of the following structures, or a pharmaceutically acceptable salt, or solvate thereof:

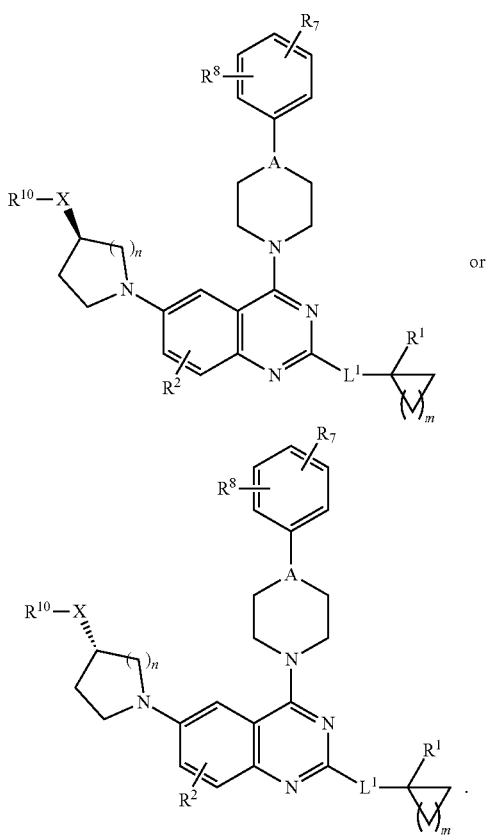

9. The method of claim 7, wherein:
A is CH;
$R^7$ is hydrogen, halogen, —CN, —OH, $C_1$-$C_4$alkyl, $C_1$-$C_4$alkoxy, $C_1$-$C_4$haloalkyl, or $C_1$-$C_4$haloalkoxy;
$R^8$ is $C_1$-$C_4$alkoxy or —N($R^a$)$_2$;
$R^{10}$ is hydrogen or $C_1$-$C_4$alkyl;
m is 1 or 2; and
n is 1 or 2.

10. The method of claim 7, wherein:
A is N;
$R^7$ is hydrogen, halogen, —CN, —OH, $C_1$-$C_4$alkyl, $C_1$-$C_4$alkoxy, $C_1$-$C_4$haloalkyl, or $C_1$-$C_4$haloalkoxy;
$R^8$ is $C_1$-$C_4$alkoxy or —N($R^a$)$_2$;
$R^{10}$ is hydrogen or $C_1$-$C_4$alkyl;
m is 1 or 2; and
n is 1 or 2, 11. A method for treating substance abuse in a subject comprising administering to the subject in need thereof a therapeutically effective amount of a compound of Formula (VI), or a pharmaceutically acceptable salt, or solvate, thereof:

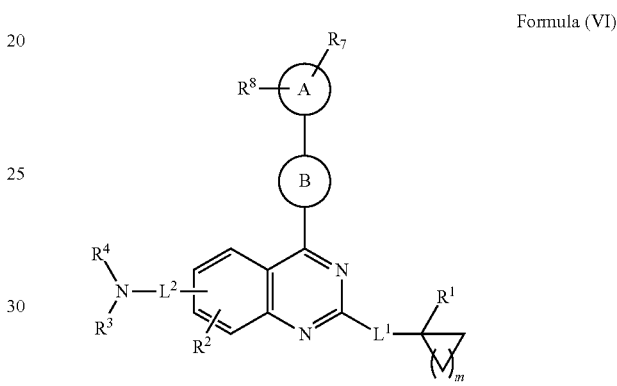

Formula (VI)

wherein,
ring A is $C_3$-$C_6$cycloalkyl, $C_2$-$C_6$heterocycloalkyl, or monocyclic heteroaryl;
ring B is an optionally substituted hetereocycloalkyl, wherein if ring B is substituted then it is substituted with $R^5$ and $R^6$;
$R^1$ is hydrogen, halogen, $C_1$-$C_4$alkyl, $C_1$-$C_4$alkoxy, $C_1$-$C_4$haloalkyl, $C_1$-$C_4$haloalkoxy, or —N($R^a$)$_2$;
each $R^a$ is independently selected from the group consisting of hydrogen, $C_1$-$C_4$ alkyl, —C(=O)$R^{11}$, —C(=O)—O—$R^{11}$, and —S(=O)$_2R^{11}$, or 2 $R^a$ taken together with the nitrogen to which they are attached form an optionally substituted $C_2$-$C_6$heterocycloalkyl;
$L^1$ is absent, $C_1$-$C_4$alkylene, $C_1$-$C_4$alkenylene, $C_1$-$C_4$alkynylene, —O—, or —N($R^b$)—;
$R^b$ is hydrogen, $C_1$-$C_4$alkyl, $C_1$-$C_4$haloalkyl, —C(=O)—O—$R^{11}$, —S(=O)$_2R^{11}$, or —C(=O)$R^{11}$;
$R^2$ is hydrogen, halogen, —CN, —OH, —NO$_2$, optionally substituted $C_1$-$C_4$alkyl, optionally substituted $C_1$-$C_4$alkoxy, optionally substituted $C_1$-$C_4$haloalkyl, optionally substituted $C_1$-$C_4$haloalkoxy, optionally substituted $C_3$-$C_6$cycloalkyl, optionally substituted $C_2$-$C_6$heterocycloalkyl, optionally substituted phenyl, or optionally substituted 5- or 6-membered heteroaryl;
$L^2$ is absent or an optionally substituted $C_1$-$C_4$alkylene;
$R^3$ is hydrogen, $C_1$-$C_4$alkyl, or $C_1$-$C_4$haloalkyl;
$R^4$ is hydrogen, optionally substituted $C_1$-$C_4$ alkyl, —$C_1$-$C_4$ alkylene-C(=O)$R^{11}$, —$C_1$-$C_4$ alkylene-OR$^{10}$, or —$C_1$-$C_4$ alkylene-N($R^b$)($R^{10}$);
$R^{10}$ is hydrogen, $C_1$-$C_4$alkyl, $C_1$-$C_4$fluoroalkyl, —C(=O)—O—$R^{11}$, —C(=O)N($R^{12}$)$R^{13}$, —S(=O)$_2$R$^{11}$, or —C(=O)R$^{11}$; or R$^{10}$ and R$^b$ are taken together with the N atom to which they are attached to form a C$_2$-C$_6$heterocycle;

or R$^3$ and R$^4$ taken together with the nitrogen to which they are attached form an optionally substituted C$_2$-C$_6$heterocycloalkyl;

R$^5$ and R$^6$ are each independently selected from hydrogen, halogen, —OH, and C$_1$-C$_4$alkyl, or when on the same carbon, R$^5$ and R$^6$ taken together form an oxo;

R$^7$ is hydrogen, halogen, —CN, —OH, —NO$_2$, —N(R$^{12}$)—R$^{13}$, —C(=O)—N(R$^{12}$)—R$^{13}$, —NR$^{12}$C(=O)R$^{11}$, —C(=O)—O—R$^{11}$, —O—C(=O)—R$^{11}$, —SR$^{12}$, —S(=O)R$^{11}$, —S(=O)$_2$R$^{11}$, —N(R$^{12}$)S(=O)$_2$R$^{11}$, —S(=O)$_2$—N(R$^{12}$)—R$^{13}$, —C(=O)R$^{11}$, optionally substituted C$_1$-C$_4$alkyl, optionally substituted C$_1$-C$_4$alkoxy, optionally substituted C$_1$-C$_4$haloalkyl, optionally substituted C$_1$-C$_4$haloalkoxy, optionally substituted C$_3$-C$_6$cycloalkyl, optionally substituted C$_2$-C$_6$heterocycloalkyl, optionally substituted phenyl, or optionally substituted 5- or 6-membered heteroaryl;

R$^8$ is hydrogen, —OH, C$_1$-C$_4$alkyl, C$_1$-C$_4$fluoroalkyl, C$_1$-C$_4$alkoxy, C$_1$-C$_4$fluoroalkoxy, or —N(R$^a$)$_2$;

each R$^{11}$ is independently selected from the group consisting of optionally substituted C$_1$-C$_4$alkyl, optionally substituted C$_1$-C$_4$fluoroalkyl, optionally substituted C$_3$-C$_6$cycloalkyl, optionally substituted C$_2$-C$_6$heterocycloalkyl, optionally substituted phenyl, and optionally substituted 5- or 6-membered heteroaryl;

each of R$^{12}$ and R$^{13}$ is independently selected from the group consisting of hydrogen, optionally substituted C$_1$-C$_4$alkyl, optionally substituted C$_1$-C$_4$fluoroalkyl, optionally substituted C$_3$-C$_6$cycloalkyl, optionally substituted C$_2$-C$_6$heterocycloalkyl, optionally substituted phenyl, and optionally substituted 5- or 6-membered heteroaryl; or R$^{12}$ and R$^{13}$, when on the same nitrogen atom, are taken together with the nitrogen atom to which they are attached to form an optionally substituted C$_2$-C$_6$heterocycloalkyl; and m is 1, 2, 3 or 4.

12. The method of claim 11, wherein:
the substance abused is an amphetamine, an opioid, a cannabinoid, a barbiturate, a benzodiazepine, nicotine, alcohol, a hallucinogen, cocaine, or combinations thereof.

13. The method of claim 11, wherein:
the substance abused is a psychostimulant.

14. The method of claim 11, wherein:
ring A is monocyclic heteroaryl;
R$^1$ is hydrogen, halogen, C$_1$-C$_4$alkyl, C$_1$-C$_4$haloalkyl, or —N(R$^a$)$_2$;
L$^1$ is absent;
L$^2$ is absent or —CH$_2$—;
R$^3$ is hydrogen or C$_1$-C$_4$alkyl;
R$^4$ is C$_1$-C$_4$ alkyl, —C$_1$-C$_4$ alkylene-OR$^{10}$, or —C$_1$-C$_4$ alkylene-N(R$^b$)(R$^{10}$);
or R$^3$ and R$^4$ taken together with the nitrogen to which they are attached form an optionally substituted C$_2$-C$_5$heterocycloalkyl;
R$^7$ is hydrogen, halogen, —CN, —OH, C$_1$-C$_4$alkyl, C$_1$-C$_4$alkoxy, C$_1$-C$_4$haloalkyl, or C$_1$-C$_4$haloalkoxy; and
m is 1 or 2.

15. The method of claim 11, wherein:
ring A is C$_3$-C$_6$cycloalkyl;
R$^1$ is hydrogen, halogen, C$_1$-C$_4$alkyl, C$_1$-C$_4$haloalkyl, or —N(R$^a$)$_2$;
L$^1$ is absent;
L$^2$ is absent or —CH$_2$—;
R$^3$ is hydrogen or C$_1$-C$_4$alkyl;
R$^4$ is C$_1$-C$_4$ alkyl, —C$_1$-C$_4$ alkylene-OR$^{10}$, or —C$_1$-C$_4$ alkylene-N(R$^b$)(R$^{10}$);
or R$^3$ and R$^4$ taken together with the nitrogen to which they are attached form an optionally substituted C$_2$-C$_5$heterocycloalkyl;
R$^7$ is hydrogen, halogen, —CN, —OH, C$_1$-C$_4$alkyl, C$_1$-C$_4$alkoxy, C$_1$-C$_4$haloalkyl, or C$_1$-C$_4$haloalkoxy; and
m is 1 or 2.

16. The method of claim 11, wherein:
ring B is an N-containing optionally substituted monocyclic heterocycloalkyl.

17. The method of claim 11, wherein:
ring B is an N-containing optionally substituted bicyclic heterocycloalkyl or an N-containing optionally substituted tricyclic heterocycloalkyl.

18. A method for treating substance abuse in a subject comprising administering to the subject in need thereof a therapeutically effective amount of a compound that is:

2-({2-(1-Fluoro-cyclopropyl)-4-[4-(2-methoxy-phenyl)-piperidin-1-yl]-quinazolin-6-yl}-methyl-amino)-ethanol;

{2-(1-fluoro-cyclopropyl)-4-[4-(2-methoxy-phenyl)-piperidin-1-yl]-quinazolin-6-yl}-(2-methoxy-ethyl)-methyl-amine;

{2-(1-fluoro-cyclopropyl)-4-[4-(2-methoxy-phenyl)-piperidin-1-yl]-quinazolin-6-yl}-methyl-propyl-amine;

{4-[4-(2-methoxy-phenyl)-piperidin-1-yl]-2-[1-(methyl-propyl-amino)-cyclopropyl]-quinazolin-6-yl}-methyl-propyl-amine;

2-{[4-[4-(2-methoxy-phenyl)-piperidin-1-yl]-2-(1-methyl-cyclopropyl)-quinazolin-6-yl]-methyl-amino}-ethanol;

N-[4-[4-(2-methoxy-phenyl)-piperidin-1-yl]-2-(1-methyl-cyclopropyl)-quinazolin-6-yl]-N,N',N'-trimethyl-ethane-1,2-diamine;

2-{[4-[4-(2-dimethylamino-phenyl)-piperidin-1-yl]-2-(1-methyl-cyclopropyl)-quinazolin-6-yl]-methyl-amino}-ethanol;

[4-[4-(2-dimethylamino-phenyl)-piperidin-1-yl]-2-(1-methyl-cyclopropyl)-quinazolin-6-yl]-(2-methoxy-ethyl)-methyl-amine;

N-[4-[4-(2-dimethylamino-phenyl)-piperidin-1-yl]-2-(1-methyl-cyclopropyl)-quinazolin-6-yl]-N,N',N'-trimethyl-ethane-1,2-diamine;

2-{[4-[4-(2-azetidin-1-yl-phenyl)-piperidin-1-yl]-2-(1-methyl-cyclopropyl)-quinazolin-6-yl]-methyl-amino}-ethanol;

[4-[4-(2-azetidin-1-yl-phenyl)-piperidin-1-yl]-2-(1-methyl-cyclopropyl)-quinazolin-6-yl]-(2-methoxy-ethyl)-methyl-amine;

N-(2-methoxyethyl)-4-(4-(2-methoxyphenyl)piperidin-1-yl)-N-methyl-2-(1-methylcyclopropyl)quinazolin-6-amine;

2-{[4-[4-(2-methoxy-phenyl)-piperidin-1-yl]-2-(1-trifluoromethyl-cyclopropyl)-quinazolin-6-yl]-methyl-amino}-ethanol;

2-{[4-[4-(2-dimethylamino-phenyl)-piperidin-1-yl]-2-(1-trifluoromethyl-cyclopropyl)-quinazolin-6-yl]-methyl-amino}-ethanol;

2-{[4-[4-(2-methoxy-phenyl)-piperidin-1-yl]-2-(1-methyl-cyclopentyl)-quinazolin-6-yl]-methyl-amino}-ethanol;
{[4-[4-(2-Dimethylamino-phenyl)-piperidin-1-yl]-2-(1-methyl-cyclopentyl)-quinazolin-6-yl]-methyl-amino}-ethanol;
2-{[4-[4-(2-methoxy-phenyl)-piperidin-1-yl]-2-(1-trifluoromethyl-cyclopentyl)-quinazolin-6-yl]-methyl-amino}-ethanol;
2-{[4-[4-(2-dimethylamino-phenyl)-piperidin-1-yl]-2-(1-trifluoromethyl-cyclopentyl)-quinazolin-6-yl]-methyl-amino}-ethanol;
2-({2-(1-fluoro-cyclobutyl)-4-[4-(2-methoxy-phenyl)-piperidin-1-yl]-quinazolin-6-yl}-methyl-amino)-ethanol;
2-{[4-[4-(2-dimethylamino-phenyl)-piperidin-1-yl]-2-(1-fluoro-cyclobutyl)-quinazolin-6-yl]-methyl-amino}-ethanol;
2-{[4-[4-(2-methoxy-phenyl)-piperidin-1-yl]-2-(1-trifluoromethyl-cyclobutyl)-quinazolin-6-yl]-methyl-amino}-ethanol;
2-{[4-[4-(2-Dimethylamino-phenyl)-piperidin-1-yl]-2-(1-trifluoromethyl-cyclobutyl)-quinazolin-6-yl]-methyl-amino}-ethanol;
2-{[4-[4-(2-dimethylamino-phenyl)-piperidin-1-yl]-2-(1-methyl-cyclobutyl)-quinazolin-6-yl]-methyl-amino}-ethanol;
2-{[4-[4-(2-Methoxy-phenyl)-piperidin-1-yl]-2-(1-methyl-cyclobutyl)-quinazolin-6-yl]-methyl-amino}-ethanol;
2-({2-(1-fluoro-cyclopentyl)-4-[4-(2-methoxy-phenyl)-piperidin-1-yl]-quinazolin-6-yl}-methyl-amino)-ethanol;
2-{[4-[4-(2-dimethylamino-phenyl)-piperidin-1-yl]-2-(1-fluoro-cyclopentyl)-quinazolin-6-yl]-methyl-amino}-ethanol;
1-{2-cyclopropyl-4-[4-(2-methoxy-phenyl)-piperidin-1-yl]-quinazolin-6-yl}-piperidin-4-ol;
{2-cyclopropyl-4-[4-(2-methoxy-phenyl)-piperidin-1-yl]-6-(4-methoxy-piperidin-1-yl)-quinazoline;
(1-{2-cyclopropyl-4-[4-(2-methoxy-phenyl)-piperidin-1-yl]-quinazolin-6-yl}-piperidin-4-yl)-dimethyl-amine;
1-{2-cyclopropyl-4-[4-(2-methoxy-phenyl)-piperidin-1-yl]-quinazolin-6-yl}-pyrrolidin-3-ol;
2-cyclopropyl-4-[4-(2-methoxy-phenyl)-piperidin-1-yl]-6-(3-methoxy-pyrrolidin-1-yl)-quinazoline;
(R)-1-{2-cyclopropyl-4-[4-(2-methoxy-phenyl)-piperidin-1-yl]-quinazolin-6-yl}-pyrrolidin-3-ol;
(S)-1-(2-cyclopropyl-4-(4-(2-methoxyphenyl)piperidin-1-yl)quinazolin-6-yl)pyrrolidin-3-ol;
(R)-2-cyclopropyl-4-(4-(2-methoxyphenyl)piperidin-1-yl)-6-(3-methoxypyrrolidin-1-yl)quinazoline;
(S)-2-cyclopropyl-4-(4-(2-methoxyphenyl)piperidin-1-yl)-6-(3-methoxypyrrolidin-1-yl)quinazoline;
[(1-{2-cyclopropyl-4-[4-(2-methoxy-phenyl)-piperidin-1-yl]-quinazolin-6-yl)}-piperidin-4-yl)-methyl-amino]-acetic acid ethyl ester;
4-(4-(2-methoxyphenyl)piperidin-1-yl)-N2,N2,N6-trimethyl-N6-propylquinazoline-2,6-diamine;
4-(4-(2-methoxyphenyl)piperidin-1-yl)-N2,N2-dimethyl-N6,N6-dipropylquinazoline-2,6-diamine;
N2-Cyclobutyl-4-[4-(2-methoxy-phenyl)-piperidin-1-yl]-N6-methyl-N6-propyl-quinazoline-2,6-diamine;
2-((2-(cyclobutylamino)-4-(4-(2-methoxyphenyl)piperidin-1-yl) quinazolin-6-yl)(methyl)amino)ethanol;
2-({2-cyclopropyl-4-[6-(2-methoxy-phenyl)-2,6-diazaspiro[3.3]hept-2-yl]-quinazolin-6-yl}-methyl-amino)-ethanol;
2-((2-cyclopropyl-4-(4-(3-methoxythiophen-2-yl)piperidin-1-yl)quinazolin-6-yl)(methyl)amino)ethanol;
2-((4-(4-cyclohexylpiperidin-1-yl)-2-(1-fluorocyclopropyl)quinazolin-6-yl)(methyl)amino)ethanol;
2-(4-{2-cyclopropyl-6-[(2-hydroxy-ethyl)-methyl-amino]-quinazolin-4-yl}-piperazin-1-yl)-cyclopentanol;
2-{4-[2-cyclopropyl-6-(methyl-propyl-amino)-quinazolin-4-yl]-piperazin-1-yl}-cyclopentanol;
2-(4-{2-cyclopropyl-6-[methyl-(2-morpholin-4-yl-ethyl)-amino]-quinazolin-4-yl}-piperazin-1-yl)-cyclopentanol;
(1-Fluoro-cyclopropyl)-{7-fluoro-6-[(2-hydroxy-ethyl)-methyl-amino]-4-[4-(2-methoxy-phenyl)-piperidin-1-yl]-quinazolin-2-yl}-methanone;
{7-Chloro-6-[(2-hydroxy-ethyl)-methyl-amino]-4-[4-(2-methoxy-phenyl)-piperidin-1-yl]-quinazolin-2-yl}-(1-fluoro-cyclopropyl)-methanone;
(S)-1-(2-cyclopropyl-4-(4-(2-methoxyphenyl)piperidin-1-yl)quinazolin-6-yl)pyrrolidin-3-ol;
(S)-2-cyclopropyl-4-(4-(2-methoxyphenyl)piperidin-1-yl)-6-(3-methoxypyrrolidin-1-yl)quinazoline;
(R)-1-{2-cyclopropyl-4-[4-(2-methoxy-phenyl)-piperidin-1-yl]-quinazolin-6-yl})-pyrrolidin-3-ol;
(R)-2-cyclopropyl-4-[4-(2-methoxy-phenyl)-piperidin-1-yl]-6-(3-methoxy-pyrrolidin-1-yl)-quinazoline;
(S)-1-{2-(1-Fluoro-cyclopropyl)-4-[4-(2-methoxy-phenyl)-piperidin-1-yl]-quinazolin-6-yl}-pyrrolidin-3-ol;
(R)-1-{2-(1-Fluoro-cyclopropyl)-4-[4-(2-methoxy-phenyl)-piperidin-1-yl]-quinazolin-6-yl}-pyrrolidin-3-ol;
2-((2-(1-fluorocyclopropyl)-4-(4-(2-methoxyphenyl)piperidin-1-yl)quinazolin-6-yl)(methyl)amino)acetic acid;
2-((8-chloro-2-(1-fluorocyclobutyl)-4-(4-(2-methoxyphenyl)piperidin-1-yl)quinazolin-6-yl)(methyl)amino) ethanol;
3-{8-Chloro-2-(1-fluoro-cyclobutyl)-4-[4-(2-methoxyphenyl)-piperidin-1-yl]-quinazolin-6-yl)}-cyclopentanol;
3-{8-Chloro-2-(1-fluoro-cyclobutyl)-4-[4-(2-methoxyphenyl)-piperidin-1-yl]-quinazolin-6-yl)}-cyclopentanol;
2-({2-Cyclopropyl-4-[4-(2-methoxy-cyclopentyl)-piperazin-1-yl]-quinazolin-6-yl)}-methyl-amino)-ethanol;
2-cyclopropyl-4-(4-(2-methoxycyclopentyl)piperazin-1-yl)-N-methyl-N-propylquinazolin-6-amine
2-{[4-(4-Cyclohexyl-piperidin-1-yl)-2-(1-fluoro-cyclopropyl)-quinazolin-6-yl]-methyl-amino}-ethanol
2-({2-(1-Fluoro-cyclopropyl)-4-[4-(2-methoxy-cyclohexyl)-piperidin-1-yl]-quinazolin-6-yl}-methyl-amino)-ethanol;
2-({2-Cyclopropyl-4-[4-(3-methoxy-thiophen-2-yl)-piperidin-1-yl]-quinazolin-6-yl}-methyl-amino)-ethanol;
2-({2-(1-Fluoro-cyclopropyl)-4-[4-(2-methoxy-phenyl)-piperidin-1-yl]-pyrido[3,4-d]pyrimidin-6-yl}-methyl-amino)-ethanol;
1-{2-(1-Fluoro-cyclopropyl)-4-[4-(2-methoxy-phenyl)-piperidin-1-yl]-pyrido[3,4-d]pyrimidin-6-yl}-pyrrolidin-3-ol;
1-{2-(1-Fluoro-cyclopropyl)-4-[4-(2-methoxy-phenyl)-piperidin-1-yl]-pyrido[3,4-d]pyrimidin-6-yl}-pyrrolidin-3-ol;
2-({2-(1-Fluoro-cyclobutyl)-4-[4-(2-methoxy-phenyl)-piperidin-1-yl]-pyrido[3,4-d]pyrimidin-6-yl}-methyl-amino)-ethanol;
1-{2-(1-Fluoro-cyclobutyl)-4-[4-(2-methoxy-phenyl)-piperidin-1-yl]-pyrido[3,4-d]pyrimidin-6-yl}-pyrrolidin-3-ol;

1-{2-(1-Fluoro-cyclobutyl)-4-[4-(2-methoxy-phenyl)-piperidin-1-yl]-pyrido[3,4-d]pyrimidin-6-yl}-pyrrolidin-3-ol;

2-({8-Chloro-2-(1-fluoro-cyclopropyl)-4-[4-(2-methoxy-phenyl)-piperidin-1-yl]-quinazolin-6-yl}-methyl-amino)-ethanol;

1-{8-Chloro-2-(1-fluoro-cyclopropyl)-4-[4-(2-methoxy-phenyl)-piperidin-1-yl]-quinazolin-6-yl}-pyrrolidin-3-ol;

1-{8-Chloro-2-(1-fluoro-cyclopropyl)-4-[4-(2-methoxy-phenyl)-piperidin-1-yl]-quinazolin-6-yl}-pyrrolidin-3-ol;

2-{[8-Fluoro-4-[4-(3-methoxy-pyrazin-2-yl)-piperidin-1-yl]-2-(1-methyl-cyclopropyl)-quinazolin-6-yl]-methyl-amino}-ethanol;

2-{[4-[4-(3-Methoxy-pyrazin-2-yl)-piperidin-1-yl]-2-(1-methyl-cyclopropyl)-quinazolin-6-yl]-methyl-amino}-ethanol;

2-{[2-(1-Fluoro-cyclopropyl)-4-(3-methoxy-3',4',5',6'-tetrahydro-2'H-[2,4']bipyridinyl-1'-yl)-quinazolin-6-yl]-methyl-amino}-ethanol;

2-{[2-(1-Fluoro-cyclopropyl)-4-(2-methoxy-3',4',5',6'-tetrahydro-2'H-[3,4']bipyridinyl-1'-yl)-quinazolin-6-yl]-methyl-amino}-ethanol;

2-({2-(1-Fluoro-cyclopropyl)-4-[4-(3-methoxy-pyrazin-2-yl)-piperidin-1-yl]-quinazolin-6-yl}-methyl-amino)-ethanol;

2-({2-(1-Fluoro-cyclopropyl)-4-[4-(3-methoxy-pyridin-2-yl)-piperazin-1-yl]-quinazolin-6-yl}-methyl-amino)-ethanol;

2-{[2-(1-Fluoro-cyclopropyl)-4-(4-methoxy-3',4',5',6'-tetrahydro-2'H-[3,4']bipyridinyl-1'-yl)-quinazolin-6-yl]-methyl-amino}-ethanol;

2-({2-(1-Fluoro-cyclopropyl)-4-[4-(5-methoxy-pyrimidin-4-yl)-piperidin-1-yl]-quinazolin-6-yl}-methyl-amino)-ethanol;

2-{[2-(1-Fluoro-cyclopropyl)-4-(3'-methoxy-3,4,5,6-tetrahydro-2H-[4,4']bipyridinyl-1-yl)-quinazolin-6-yl]-methyl-amino}-ethanol;

2-({8-Fluoro-2-(1-fluoro-cyclopropyl)-4-[4-(3-methoxy-pyrazin-2-yl)-piperidin-1-yl]-quinazolin-6-yl}-methyl-amino)-ethanol;

2-{[8-Fluoro-2-(1-fluoro-cyclopropyl)-4-(2-methoxy-3',4',5',6'-tetrahydro-2'H-[3,4']bipyridinyl-1'-yl)-quinazolin-6-yl]-methyl-amino}-ethanol;

2-({8-Fluoro-2-(1-fluoro-cyclopropyl)-4-[4-(3-methoxy-pyridin-2-yl)-piperazin-1-yl]-quinazolin-6-yl}-methyl-amino)-ethanol;

2-{[8-Fluoro-2-(1-fluoro-cyclopropyl)-4-(3-methoxy-3',4',5',6'-tetrahydro-2'H-[2,4']bipyridinyl-1'-yl)-quinazolin-6-yl]-methyl-amino}-ethanol;

2-({8-Fluoro-2-(1-fluoro-cyclopropyl)-4-[4-(5-methoxy-pyrimidin-4-yl)-piperidin-1-yl]-quinazolin-6-yl}-methyl-amino)-ethanol;

2-({2-(1-Fluoro-cyclopropyl)-4-[4-(4-iodo-2-methoxy-phenyl)-piperazin-1-yl]-quinazolin-6-yl}-methyl-amino)-ethanol;

2-({2-(1-Fluoromethyl-cyclopropyl)-4-[4-(3-methoxy-pyrazin-2-yl)-piperidin-1-yl]-quinazolin-6-yl}-methyl-amino)-ethanol;

2-({2-(1-Fluoro-cyclobutyl)-4-[4-(3-methoxy-pyrazin-2-yl)-piperidin-1-yl]-quinazolin-6-yl}-methyl-amino)-ethanol;

1-(6-((2-hydroxyethyl)(methyl)amino)-4-(4-(3-methoxy-pyrazin-2-yl)piperidin-1-yl)quinazolin-2-yl)cyclobutanol;

(2-(1-Fluoro-cyclopropyl)-4-{4-[2-(2-fluoro-ethoxy)-phenyl]-piperidin-1-yl}-quinazolin-6-yl)-[2-(2-fluoro-ethoxy)-ethyl]-methyl-amine;

{2-(1-Fluoro-cyclopropyl)-4-[4-(2-methoxy-phenyl)-piperidin-1-yl]-quinazolin-6-yl}-[2-(2-fluoro-ethoxy)-ethyl]-methyl-amine;

2-{1-[6-{[2-(tert-Butyl-dimethyl-silanyloxy)-ethyl]-methyl-amino}-2-(1-fluoro-cyclopropyl)-quinazolin-4-yl]-piperidin-4-yl}-phenol; or 2-[(2-(1-Fluoro-cyclopropyl)-4-{4-[2-(2-fluoro-ethoxy)-phenyl]-piperidin-1-yl}-quinazolin-6-yl)-methyl-amino]-ethanol;

or a pharmaceutically acceptable salt, or solvate thereof.

19. The method of claim 18, wherein:

the substance abused is an amphetamine, an opioid, a cannabinoid, a barbiturate, a benzodiazepine, nicotine, alcohol, a hallucinogen, cocaine, or combinations thereof.

20. The method of claim 18, wherein:

the substance abused is a psychostimulant.

\* \* \* \* \*

UNITED STATES PATENT AND TRADEMARK OFFICE
CERTIFICATE OF CORRECTION

| | |
|---|---|
| PATENT NO. | : 10,584,103 B2 |
| APPLICATION NO. | : 16/140363 |
| DATED | : March 10, 2020 |
| INVENTOR(S) | : Anthony B. Pinkerton et al. |

Page 1 of 4

It is certified that error appears in the above-identified patent and that said Letters Patent is hereby corrected as shown below:

Claim 1; Column 481, Lines 54-56; delete:
"$R^7$ is hydrogen, halogen, -CN, -OH, -NO$_2$, -N($R^{12}$)-$R^{13}$, -C(=O)-N($R^{12}$)-$R^{13}$, -N$R^{12}$C(=O)$R^{11}$, -C(=O)-O-$R^1$"
And replace with:
-- $R^7$ is hydrogen, halogen, -CN, -OH, -NO$_2$, -N($R^{12}$)-$R^{13}$, -C(=O)-N($R^{12}$)-$R^{13}$, -N$R^{12}$C(=O)$R^{11}$, -C(=O)-O-$R^{11}$ --

Claim 4; Column 482, Lines 38-57; delete the following structure:

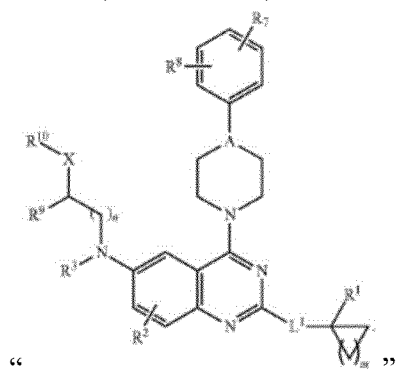

"

And replace with:

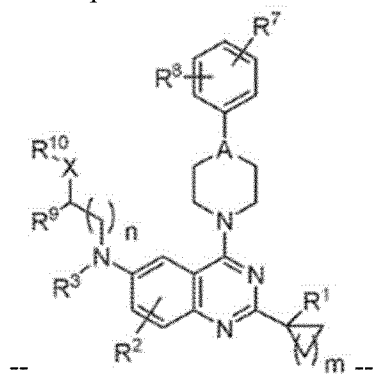

--

Signed and Sealed this
Ninth Day of June, 2020

Andrei Iancu
*Director of the United States Patent and Trademark Office*

Claim 7; Column 483, Lines 5-23; delete the following structure:
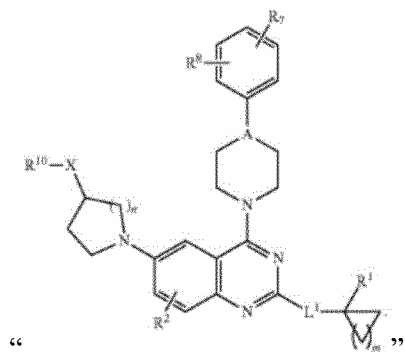
"
And replace with:
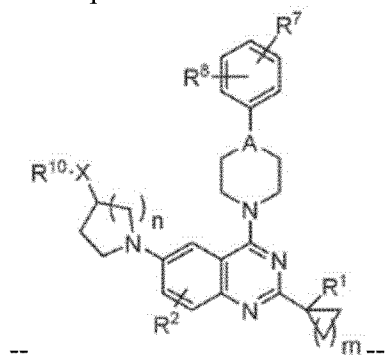
--
Claim 8; Column 483, Lines 30-45; delete the following structure:
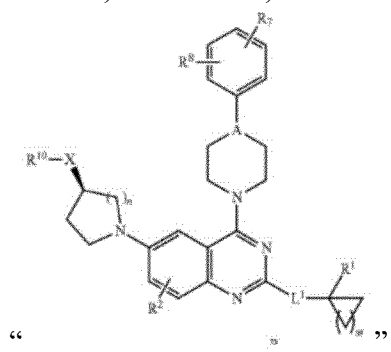
"
And replace with:
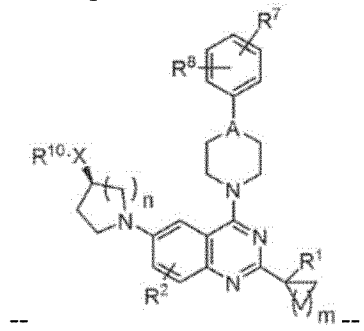
--

CERTIFICATE OF CORRECTION (continued)
U.S. Pat. No. 10,584,103 B2

Claim 8; Column 483, Lines 46-61; delete the following structure:

"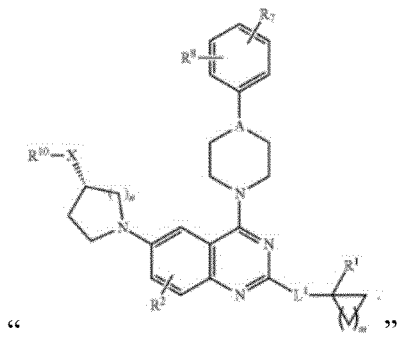"

And replace with:

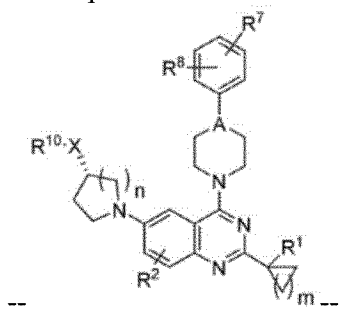

--

Claim 18; Column 488, Lines 44-45; delete:
"2-({2-Cyclopropyl-4-[4-(2-methoxycyclopentyl)piperazin-1-yl)-N-methyl-N-propylquinazolin-6-amine"
And replace with:
-- 2-({2-Cyclopropyl-4-[4-(2-methoxycyclopentyl)piperazin-1-yl)-N-methyl-N-propylquinazolin-6-amine; --

Claim 18; Column 488, Lines 46-47; delete:
"2-{[4-(4-Cyclohexyl-piperidin-1-yl)-2-(1-fluoro-cyclopropyl)-quinazolin-6-yl]-methyl-amino}-ethanol"
And replace with:
-- 2-{[4-(4-Cyclohexyl-piperidin-1-yl)-2-(1-fluoro-cyclopropyl)-quinazolin-6-yl]-methyl-amino}-ethanol; --

Claim 18; Column 488, Lines 56-61; delete:
"1-{2-1-Fluoro-cycplopropyl)-4-[4-(2-methoxy-phenyl)-piperidin-1-yl]-pyrido[3,4-d]pyrimidin-6-yl}-pyrrolidin-3-ol; 1-{2-1-Fluoro-cycplopropyl)-4-[4-(2-methoxy-phenyl)-piperidin-1-yl]-pyrido[3,4-d]pyrimidin-6-yl}-pyrrolidin-3-ol;"
And replace with:
-- 1-{2-1-Fluoro-cycplopropyl)-4-[4-(2-methoxy-phenyl)-piperidin-1-yl]-pyrido[3,4-d]pyrimidin-6-yl}-pyrrolidin-3-ol; --

Claim 18; Column 488, Lines 65-67 and Column 489, Lines 1-3; delete:
"1-{2-(1-Fluoro-cyclobutyl)-4-[4-(2-methoxy-phenyl)-piperidin-1-yl]-pyrido[3,4-d]pyrimidin-6-yl}-pyrrolidin-3-ol; 1-{2-(1-Fluoro-cyclobutyl)-4-[4-(2-methoxy-phenyl)-piperidin-1-yl]-pyrido[3,4-

CERTIFICATE OF CORRECTION (continued)
U.S. Pat. No. 10,584,103 B2 d]pyrimidin-6-yl}-pyrrolidin-3-ol;"
And replace with:
-- 1-{2-(1-Fluoro-cyclobutyl)-4-[4-(2-methoxy-phenyl)-piperidin-1-yl]-pyrido[3,4-d]pyrimidin-6-yl}-pyrrolidin-3-ol; --

Claim 18; Column 489, Lines 7-12; delete:
"1-{8-Chloro-2-(1-fluoro-cyclopropyl)-4-[4-(2-methoxy-phenyl)-piperidin-1-yl]-quinazolin-6-yl}-pyrrolidin-3-ol; 1-{8-Chloro-2-(1-fluoro-cyclopropyl)-4-[4-(2-methoxy-phenyl)-piperidin-1-yl]-quinazolin-6-yl}-pyrrolidin-3-ol;"
And replace with:
-- 1-{8-Chloro-2-(1-fluoro-cyclopropyl)-4-[4-(2-methoxy-phenyl)-piperidin-1-yl]-quinazolin-6-yl}-pyrrolidin-3-ol; --